US010633685B2

(12) United States Patent
Houghton-Larsen et al.

(10) Patent No.: US 10,633,685 B2
(45) **Date of Patent: *Apr. 28, 2020**

(54) METHODS AND MATERIALS FOR BIOSYNTHESIS OF MOGROSIDE COMPOUNDS

(71) Applicant: Evolva SA, Reinach (CH)

(72) Inventors: Jens Houghton-Larsen, Birkerod (DK); Katarzyna Krzystanek, Reinach (CH); Angelika Semmler, Copenhagen (DK); Iver Klavs Riishede Hansen, Copenhagen (DK); Soren Damkiaer, Reinach (CH); Yaoquan Liu, Palo Alto, CA (US); Jorgen Hansen, Frederiksberg (DK); Sathish Kumar, Tamil Nadu (IN); Muthuswamy Panchapagesa Murali, Chennai (IN); Nina Nicoline Rasmussen, Hvidovre (DK)

(73) Assignee: EVOLVA SA, Reinach (CH)

( * ) Notice: Subject to any disclaimer, the term of this patent is extended or adjusted under 35 U.S.C. 154(b) by 244 days.

This patent is subject to a terminal disclaimer.

(21) Appl. No.: 15/511,565

(22) PCT Filed: Sep. 30, 2015

(86) PCT No.: PCT/EP2015/072645

§ 371 (c)(1),
(2) Date: Mar. 15, 2017

(87) PCT Pub. No.: WO2016/050890

PCT Pub. Date: Apr. 7, 2016

(65) Prior Publication Data

US 2017/0247735 A1 Aug. 31, 2017

Related U.S. Application Data

(63) Continuation of application No. 14/504,109, filed on Oct. 1, 2014, now Pat. No. 10,011,859, which is a continuation of application No. PCT/EP2013/075510, filed on Dec. 4, 2013.

(60) Provisional application No. 61/733,220, filed on Dec. 4, 2012, provisional application No. 62/059,136, filed on Oct. 2, 2014, provisional application No. 62/087,726, filed on Dec. 4, 2014, provisional application No. 62/090,836, filed on Dec. 11, 2014, provisional application No. 62/091,895, filed on Dec. 15, 2014, provisional application No. 62/199,115, filed on Jul. 30, 2015.

(51) Int. Cl.

| | |
|---|---|
| ***C12P 33/00*** | (2006.01) |
| ***C12P 19/56*** | (2006.01) |
| ***C12P 19/18*** | (2006.01) |
| ***C12N 9/14*** | (2006.01) |
| ***C12N 9/10*** | (2006.01) |
| ***C12N 9/06*** | (2006.01) |
| ***C12N 9/90*** | (2006.01) |
| ***C12N 9/02*** | (2006.01) |
| ***A23L 27/30*** | (2016.01) |
| ***C07H 1/06*** | (2006.01) |
| ***C12N 15/00*** | (2006.01) |

(52) U.S. Cl.

CPC .............. *C12P 33/00* (2013.01); *A23L 27/36* (2016.08); *C07H 1/06* (2013.01); *C12N 9/0014* (2013.01); *C12N 9/0042* (2013.01); *C12N 9/0071* (2013.01); *C12N 9/0073* (2013.01); *C12N 9/1051* (2013.01); *C12N 9/14* (2013.01); *C12N 9/90* (2013.01); *C12N 15/00* (2013.01); *C12P 19/18* (2013.01); *C12P 19/56* (2013.01); *A23V 2002/00* (2013.01)

(58) Field of Classification Search

CPC combination set(s) only.
See application file for complete search history.

(56) References Cited

U.S. PATENT DOCUMENTS

| | | | |
|---|---|---|---|
| 8,257,948 | B1 | 9/2012 | Markosyan |
| 10,011,859 | B2 | 7/2018 | Liu et al. |
| 2007/0039067 | A1 | 2/2007 | Feldmann et al. |
| 2007/0118916 | A1 | 5/2007 | Puzio et al. |
| 2015/0322473 | A1 | 11/2015 | Liu et al. |

FOREIGN PATENT DOCUMENTS

| | | |
|---|---|---|
| EP | 1510573 | 3/2005 |
| EP | 1897951 | 12/2010 |
| RU | 2008123244 | 12/2009 |
| WO | 2001/012845 | 2/2001 |
| WO | WO 0112845 | 2/2001 |
| WO | WO 2007/061753 | 5/2007 |
| WO | 2008/062165 | 5/2008 |
| WO | 2008/065370 | 5/2008 |
| WO | 2010/106318 | 9/2010 |
| WO | 2011/153378 | 12/2011 |

(Continued)

OTHER PUBLICATIONS

Guo et al., "Protein tolerance to random amino acid change," Proc Natl Acad Sci U 22;101(25):9205-10 (2004).

Nilsson et al., "Chemical synthesis of proteins," Annu Rev Biophys Biomol Struct. 34: 91-118 (2005).

Poppenberger et al., "Heterologous expression of *Arabidopsis* UDP-glucosyltransferases in *Saccharomyces cerevisiae* for production of zearalenone-4-O-glucoside," Appl Environ Microbiol. 72(6):4404-10 (2006).

Shao et al., "Crysal structures of a multifunctional triterpene/flavonoid glycosyltransferase from Medicago truncatula," Plant Cell. 17(11):3141-54 (2005).

(Continued)

*Primary Examiner* — Kagnew H Gebreyesus
(74) *Attorney, Agent, or Firm* — McDonnell Boehnen Hulbert & Berghoff LLP

(57) ABSTRACT

Methods for recombinant and enzymatic production of mogroside compounds and compositions containing mogroside compounds are provided by this invention.

29 Claims, 28 Drawing Sheets

Specification includes a Sequence Listing.

(56) References Cited

FOREIGN PATENT DOCUMENTS

| | | |
|---|---|---|
| WO | 2013/076577 | 5/2013 |
| WO | WO 2014/086842 | 6/2014 |

OTHER PUBLICATIONS

Xiong et al., "Biosynthesis of triterpene glycoside in Lo Han Kuo," Guangdong Pharmaceutical University 27(5):544-5 (2011). English abstract provided.
Wikipedia: "Mogroside," Internet Archive Wayback Machine Jan. 9, 2014 (Jan. 9, 2014), retrieved from the Internet: URL:https://web.archive.org/web/20140109130110/http://en.wikipedia.org/wiki/Mogroside [retrieved on Apr. 14, 2016] (pp. 1-2).
UniProt Database Accession No. AT223684, "Stevia rebaudiana protein SEQ ID No. 10008," Feb. 3, 2011 (1 page).
GenBank Accession No. XP_008442743; last accessed Apr. 28, 2016 (pp. 1-2).
GenBank Accession No. XP_008450117; last accessed Apr. 28, 2016 (p. 1-2).
GenBank Accession No. XP_008454322; last accessed Apr. 21, 2016 (pp. 1-2).
UniProt Accession No. F6GXH0; last accessed Apr. 21, 2016 (pp. 1-2).
UniProt Accession No. F6HIX7; last accessed Apr. 28, 2016 (pp. 1-2).
UniProt Accession No. K7NBR2; last accessed Apr. 29, 2016 (p. 1).
UniProt Accession No. K7NBZ9; last accessed Apr. 21, 2016 (p. 1).
UniProt Accession No. W7PH03; last accessed Apr. 28, 2016 (p. 1).
UniProt Accession No. W9SCC7; last accessed Apr. 21, 2016 (p. 1).
UniProt Accession No. K7NBX0; last accessed Nov. 29, 2016 (pp. 1-4).
Non-Final Office Action for U.S. Appl. No. 14/356,782, dated Oct. 30, 2015 (pp. 1-12).
Final Office Action for U.S. Appl. No. 14/356,782,dated Jul. 18, 2016, pp. 1-16.
Response to Non-Final Office Action for U.S. Appl. No. 14/356,782, filed Mar. 22, 2016 (pp. 1-10).
Non-Final Office Action for U.S. Appl. No. 14/504,109, dated Jun. 29, 2016, pp. 1-13.
Final Office Action for U.S. Appl. No. 14/504,109, dated Sep. 8, 2016, pp. 1-18.
International Search Report and Written Opinion of the International Searching Authority for International Application No. PCT/EP2015/072645, dated May 20, 2016 (pp. 1-39).
International Preliminary Report on Patentability issued by the International Preliminary Examining Authority for International Application No. PCT/EP2015/072645, dated Apr. 4, 2017 (pp. 1-28).
Written Opinion of the International Preliminary Examining Authority for International Application No. PCT/EP2013/075510, dated May 5, 2015 (pp. 1-15).
Frankel et al., "Characterization of diphtheria fusion proteins targeted to the human interleukin-3 receptor", Protein Eng., v.13, No. 8, p. 575-581 abstract, p. 579-580 (2000).
Poppenberger et al., "Detoxification of the Fusarium mycotoxin deoxynivalenol by a UDP-glucosyltransferase from *Arabidopsis thaliana*," J Biol Chem. 278(48):47905-14 (Epub 2003).
Non-Final Office Action for U.S. Appl. No. 14/356,782, dated Jun. 1, 2017 (pp. 1-15).
Non-Final Office Action for U.S. Appl. No. 14/442,694, dated May 16, 2017, pp. 1-13.
Pakula et al., "Genetic analysis of protein stability and function," Anna. Rev. Genet. v.23, 289-310 (p. 305-306) (1989).
UniProt Accession No. A7VJN1 (pp. 1-5).
UniProt Accession No. B5AID3 (pp. 1-4).
UniProt Accession No. B5AID4 (pp. 1-4).
UniProt Accession No. B5AID5 (pp. 1-4).
UniProt Accession No. B9R6V0 (pp. 1-5).
UniProt Accession No. B9RHC3 (pp. 1-6).
UniProt Accession No. B9S6Y2 (pp. 1-5).
UniProt Accession No. B9S7T0 (pp. 1-5).
UniProt Accession No. B9S7W5 (pp. 1-5).
UniProt Accession No. B9SX91 (pp. 1-6).
UniProt Accession No. B9T0Y3 (pp. 1-5).
UniProt Accession No. B9WZW7 (pp. 1-5).
UniProt Accession No. C4P9M2 (pp. 1-5).
UniProt Accession No. C4P9M3 (pp. 1-5).
UniProt Accession No. C6KE07 (pp. 1-5).
UniProt Accession No. C6KE08 (pp. 1-5).
UniProt Accession No. C7EDC9 (pp. 1-5).
UniProt Accession No. C7EDD0 (pp. 1-5).
UniProt Accession No. D6QX35 (pp. 1-5).
UniProt Accession No. D6QX37 (pp. 1-5).
UniProt Accession No. D6QX38 (pp. 1-5).
UniProt Accession No. D6QX39 (pp. 1-5).
UniProt Accession No. D6QX40 (pp. 1-5).
UniProt Accession No. D6QX41 (pp. 1-5).
UniProt Accession No. D6QX42 (pp. 1-5).
UniProt Accession No. D6QX43 (pp. 1-5).
UniProt Accession No. D6QX44 (pp. 1-5).
UniProt Accession No. D6QX45 (pp. 1-5).
UniProt Accession No. D6QX47 (pp. 1-5).
UniProt Accession No. D6QX53 (pp. 1-5).
UniProt Accession No. D6QX55 (pp. 1-5).
UniProt Accession No. O65402 (pp. 1-9).
UniProt Accession No. O65403 (pp. 1-10).
UniProt Accession No. O65404 (pp. 1-10).
UniProt Accession No. O65726 (pp. 1-7).
UniProt Accession No. O65727 (pp. 1-7).
UniProt Accession No. O81000 (pp. 1-9).
UniProt Accession No. Q42760 (pp. 1-5).
UniProt Accession No. Q42761 (pp. 1-5).
UniProt Accession No. Q84LE3 (pp. 1-5).
UniProt Accession No. Q8GSL6 (pp. 1-6).
UniProt Accession No. Q8GSM8 (pp. 1-5).
UniProt Accession No. Q8GSM9 (pp. 1-5).
UniProt Accession No. Q9SM02 (pp. 1-11).
UniProt Accession No. Q9T064 (Q8VYH2) (pp. 1-10).
Non-Final Office Action for U.S. Appl. No. 14/504,109, dated Aug. 31, 2017 pp. 1-22.
Bateman et al., "Pfam 3.1: 1313 multiple alignments and profile HMMs match the majority of proteins," Nucl Acids Res. 27(1):260-2 (1999).
Bowles et al., "Glycosyltransferases: manages of small molecules," Curr Opin Plant Biol. 8(3):254-63 (2005).
Brochado et al., "Improved vanillin production in baker's yeast through in silico design," Microb Cell Fact. 9:84 (2010).
Chatuvedula & Prakash, "Cucurbitane glycosides from Siraitia grosvenorii," J Carbohydrate Chem. 30(1):16-26 (2011).
Chiu et al., "Biotransformation of mogrosides from Siraitia grosvenorii Swingle by *Saccharomyces cerevisiae*," J Agric Food Chem. 61(29):7127-34 (2013).
Donald et al., "Effects of overproduction of the catalytic domain of 3-hydroxy-3-methylglutaryl coenzyme A reductase on squalene synthesis in *Saccharomyces cerevisiae*," Appl Environ Microbiol. 63(9):3341-4 (1997).
Hamberger & Bak, "Plant P450s as versatile drivers for evolution of species-specific chemical diversity," Philos Trans R Soc Lond B Biol Sci. 368(1612):20120426 (2013).
Jia & Yang, "A minor, sweet cucurbitane glycoside from Siraitia grosvenorii," Nat Prod Commun. 4(6):769-72 (2009).
Kasai et al., "Sweet cucurbitane glycosides from fruits of Siraitia siamensis (chi-zi luo-han-guo), a Chinese folk medicine," Agric Biol Chem. 53(12):3347-9 (1989).
Kirby et al., "Engineering triterpene production in *Saccharomyces cerevisiae*-beta-amyrin synthase from Artemisia annua," FEBS J. 275(8):1852-9 (2008).
Li et al. "Cucurbitane glycosides from unripe fruits of Lo Han Kuo (Siraiitia grosvenori)," Chem Pharm Bull (Tokyo) 54 (10):1425-8 (2006).

(56) References Cited

OTHER PUBLICATIONS

Matsumoto, "Minor cucurbitane-glycosides from fruits of Siraitia grosvenorii (Cucurbitaceae)," Chem Pharm Bull. 38 (7):2030-2 (1990).
Richman, Functional genomics uncovers three glucosyltransferases involved in the synthesis of the major sweet glucosides of Stevia rebaudiana, Plant J. 41(1):56-67 (2005).
Seki, Licorice beta-amyrin 11-oxidase, a cytochrome P450 with a key role in the biosynthesis of the triterpene sweetener glycyrrhizin, Proc Natl Acad Sci U S A. 105(37):14204-9 (2008).
Shibuya et al., "Cucurbitadienol synthase, the first committed enzyme for cucurbitacin biosynthesis, is a distinct enzyme from cycloartenol synthase for phytosterol biosynthesis," Tetrahedron 60(33):6995-7003 (2004).
Sonnhammer et al., "Pfam: a comprehensive database of protein domain families based on seed alignments," Proteins 28(3):405-20 (1997).
Sonnhammer et al., "Pfam: multiple sequence alignments and HMM-profiles of protein domains," Nucl Acids Res. 26(1):320-2 (1998).
Takemoto et al., "Studies on the constituents of Fructus Momordicae. I. On the sweet principle," Yakugaku Zasshi 103(11):1151-4 (1983).
Takemoto et al., "Studies on the constituents of Fructus Momordicae. II. Structure of sapogenin," Yakugaku Zasshi 103(11):1155-66 (1983).
Takemoto et al., "Studies on the constituents of Fructus Momordicae. III. Structures of mogrosides," Yakugaku Zasshi 103(11):1167-73 (1983).
Tang et al., "An efficient approach to finding Siraitia grosvenorii triterpene biosynthetic genes by RNA-seq and digital gene expression analysis," BMC Genomics 12:343 (2011).
Thompson et al., "Clustal W: improving the sensitivity of progressive multiple sequence alignment through sequence weighting, position-specific gap penalties and weight matrix choice," Nucleic Acids Res. 22(22):4673-80 (1994).
Ukiya et al., "Inhibitory effects of cucurbitane glycosides and other triterpenoids from the fruit of Momordica grosvenori on epstein-barr virus early antigen induced by tumor promoter 12-O-tetradecanoylphorbol-13-acetate," J Agric Food Chem. 50(23):6710-5 (2002).
International Search Report issued by the International Searching Authority for International Application No. PCT/EP2013/075510, dated May 4, 2015 (pp. 1-7).
Written Opinion of the International Searching Authority for International Application No. PCT/EP2013/075510, dated Apr. 23, 2014 (pp. 1-14).
Written Opinion of the International Preliminary Examining Authority for International Application No. PCT/EP2013/075510, dated Feb. 4, 2015 (pp. 1-14).
International Search Report issued by the International Searching Authority for International Application No. PCT/IB2012/002857, dated May 14, 2013 (pp. 1-6).
Written Opinion of the International Searching Authority for International Application No. PCT/IB2012/002857, dated May 14, 2013 (pp. 1-7).
International Preliminary Report on Patentability issued by the International Preliminary Examining Authority for International Application No. PCT/IB2012/002857, dated Jan. 9, 2014 (pp. 1-13).
GenBank Accession No. AAS01524 (pp. 1-2).
GenBank Accession No. ADC84219 (pp. 1-2).
GenBank Accession No. BAA33460 (pp. 1-2).
GenBank Accession No. BAA76902 (pp. 1-2).
GenBank Accession No. BAB83085 (pp. 1-2).
GenBank Accession No. BAB83086 (pp. 1-2).
GenBank Accession No. BAD34645.1 (pp. 1-2).
GenBank Accession No. BAE53431 (pp. 1-2).
GenBank Accession No. XP_002264289 (pp. 1-2).
GenBank Accession No. XP_002310905 (pp. 1-2).
Qiao et al., "Identification of a Novel Specific Cucurbitadienol Synthase Allele in Siraitia grosvenorii Correlates with High Catalytic Efficiency," Molecules. 24(3) (2019).

Mogroside V

Mogroside IV

Siamenoside I

11-Oxo-Mogroside V

Mogrol

Mogroside IA$_1$

Mogroside IE$_1$

Mogroside II E

Mogroside IIIA$_2$

Mogroside III

Mogroside IV A

Mogroside V

*See Figure 4 description for non-limiting examples of UGTa-g.

Mogrol

Mogroside V

Mogroside IIA1

Mogroside III

Mogroside IIE

Mogroside IA1

Mogroside IVA

Mogroside III

Mogroside IE1 cucurbitadienol 11-oxo-mogrol mogrol cucurbitadienol mogrol 11-oxo-mogrol mogrol Mogroside I A1

Mogroside II A

Mogroside III A1

Mogroside II E
Mogroside II A
Mogroside I E1
Mogroside I A1

Mogroside II E
Mogroside II A
Mogroside I A1

UGT1576 + UGT430 + UGT98 + UGT11789

UGT1576 + UGT430 + UGT11789

Mogroside V

Mogroside II A2

$^1$H NMR (700 MHz, DMSO-$d_6$) δ ppm 0.78 (s, 3 H) 0.83 (s, 3 H) 0.88 (br d, J=6.24 Hz, 3 H) 0.95 - 1.00 (m, 3 H) 0.98 (s, 3 H) 1.00 - 1.06 (m, 6 H) 1.05 (br s, 1 H) 1.11 (s, 3 H) 1.13 - 1.20 (m, 1 H) 1.14 - 1.20 (m, 2 H) 1.15 - 1.20 (m, 1 H) 1.22 - 1.28 (m, 1 H) 1.23 - 1.28 (m, 1 H) 1.32 - 1.44 (m, 1 H) 1.34 - 1.41 (m, 1 H) 1.38 - 1.44 (m, 1 H) 1.46 - 1.52 (m, 1 H) 1.58 (br d, J=7.74 Hz, 1 H) 1.63 - 1.75 (m, 1 H) 1.65 - 1.73 (m, 1 H) 1.68 - 1.74 (m, 1 H) 1.75 - 1.87 (m, 1 H) 1.80 - 1.87 (m, 1 H) 2.25 (br d, J=9.50 Hz, 1 H) 2.31 (br dd, J=18.28, 6.67 Hz, 1 H) 2.37 (br d, J=11.63 Hz, 1 H) 2.92 - 3.06 (m, 2 H) 2.92 - 2.96 (m, 1 H) 2.99 - 3.06 (m, 2 H) 3.01 - 3.03 (m, 1 H) 3.07 - 3.11 (m, 1 H) 3.12 (br dd, J=9.03, 4.95 Hz, 1 H) 3.27 - 3.30 (m, 1 H) 3.36 - 3.37 (m, 1 H) 3.39 - 3.46 (m, 1 H) 3.58 (br dd, J=12.15, 6.99 Hz, 1 H) 3.64 - 3.71 (m, 2 H) 3.91 (br d, J=11.40 Hz, 1 H) 3.96 - 4.05 (m, 1 H) 4.12 - 4.20 (m, 2 H) 4.29 - 4.34 (m, 2 H) 4.48 (t, J=5.81 Hz, 1 H) 4.76 (d, J=5.16 Hz, 1 H) 4.81 (d, J=4.30 Hz, 1 H) 4.89 (dt, J=9.47, 4.73 Hz, 3 H) 4.94 (d, J=5.38 Hz, 1 H) 5.35 (br d, J=5.81 Hz, 1 H)

$^{13}$C NMR (176 MHz, DMSO-$d_6$) δ ppm 143.9 (1C), 117.6 (1C), 105.3 (1C), 103.3 (1C), 86.1 (1C), 77.9 (1C), 77.4 (1C), 77.1 (1C), 77.0 (2C), 76.3 (1C), 74.1 (1C), 73.9 (1C), 72.0 (1C), 70.4 (1C), 70.3 (1C), 68.4 (1C), 61.4 (1C), 50.4 (1C), 49.3 (1C), 46.8 (1C), 43.0 (1C), 41.8 (1C), 40.5 (1C), 39.3 (1C), 35.8 (1C), 35.4 (1C), 34.2 (1C), 33.4 (1C), 28.7 (1C), 28.0 (1C), 27.7 (1C), 27.6 (1C), 26.6 (1C), 26.0 (2C), 25.7 (1C), 25.0 (1C), 24.2 (1C), 18.9 (1C), 18.8 (1C), 16.7 (1C).

Figure 18C

Mogroside IV A

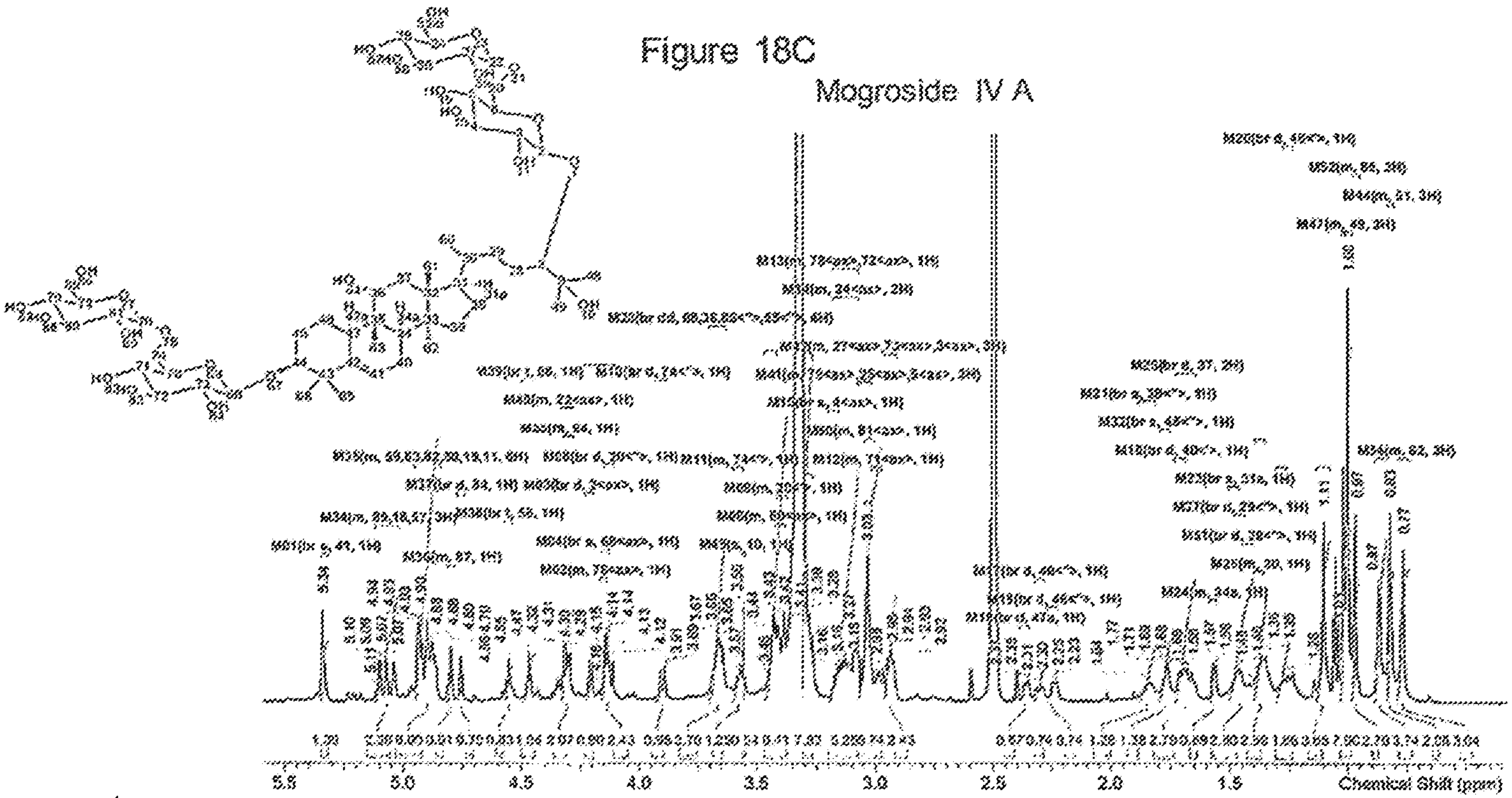

1H NMR (700 MHz, DMSO-$d_6$) δ ppm 0.74 - 0.78 (m, 3 H) 0.81 - 0.84 (m, 3 H) 0.84 - 0.89 (m, 3 H) 0.96 - 0.99 (m, 3 H) 0.99 - 1.03 (m, 6 H) 0.99 - 1.03 (m, 1 H) 1.01 - 1.02 (m, 3 H) 1.11 (br s, 4 H) 1.26 (br d, J=10.76 Hz, 1 H) 1.26 - 1.31 (m, 1 H) 1.35 (br s, 2 H) 1.35 - 1.40 (m, 1 H) 1.36 - 1.40 (m, 1 H) 1.42 (br d, J=10.11 Hz, 1 H) 1.46 (br d, J=7.53 Hz, 1 H) 1.48 (br s, 1 H) 1.56 - 1.59 (m, 1 H) 1.67 (br d, J=13.98 Hz, 2 H) 1.70 (br d, J=11.40 Hz, 1 H) 1.77 (br s, 1 H) 1.84 (br s, 1 H) 2.24 (br d, J=9.47 Hz, 1 H) 2.30 (br d, J=11.40 Hz, 1 H) 2.34 (br d, J=11.40 Hz, 1 H) 2.91 - 2.97 (m, 3 H) 2.97 - 3.02 (m, 1 H) 3.01 - 3.05 (m, 1 H) 3.02 - 3.07 (m, 3 H) 3.02 - 3.05 (m, 2 H) 3.07 - 3.18 (m, 3 H) 3.07 - 3.18 (m, 1 H) 3.13 (br s, 1 H) 3.27 (br d, J=9.47 Hz, 1 H) 3.27 - 3.31 (m, 1 H) 3.38 - 3.42 (m, 1 H) 3.38 - 3.42 (m, 1 H) 3.42 - 3.47 (m, 2 H) 3.50 (s, 1 H) 3.56 - 3.69 (m, 1 H) 3.66 (br dd, J=10.86, 4.84 Hz, 4 H) 3.90 (br d, J=11.19 Hz, 1 H) 4.12 (br d, J=8.39 Hz, 1 H) 4.13 (br s, 1 H) 4.13 - 4.17 (m, 1 H) 4.20 (br d, J=7.74 Hz, 1 H) 4.28 - 4.32 (m, 1 H) 4.28 - 4.33 (m, 1 H) 4.47 (br t, J=5.81 Hz, 1 H) 4.55 (br t, J=6.02 Hz, 1 H) 4.76 (br d, J=5.16 Hz, 1 H) 4.76 - 4.81 (m, 1 H) 4.84 - 4.93 (m, 8 H) 5.02 - 5.12 (m, 3 H) 5.34 (br s, 1 H)

13C NMR (176 MHz, DMSO-$d_6$) δ ppm 143.6 (1C), 117.0 (1C), 105.1 (1C), 104.3 (1C), 103.1 (1C), 103.0 (1C), 90.6 (1C), 85.8 (1C), 77.0 (1C), 76.7 (3C), 76.6 (2C), 76.3 (1C), 76.2 (1C), 74.8 (1C), 73.7 (3C), 73.6 (1C), 71.7 (1C), 70.2 (1C), 70.1 (3C), 69.2 (1C), 68.2 (1C), 61.1 (2C), 50.2 (1C), 49.0 (1C), 46.5 (1C), 42.7 (1C), 41.5 (1C), 40.0 (1C), 39.1 (1C), 35.4 (1C), 35.3 (1C), 33.9 (1C), 31.8 (1C), 28.4 (1C), 28.3 (1C), 27.4 (1C), 27.2 (1C), 25.8 (2C), 25.7 (1C), 23.5 (1C), 24.2 (1C), 23.9 (1C), 18.7 (1C), 18.4 (1C), 16.5 (1C)

Mogroside I E1

$^1$H NMR (700 MHz, *DMSO-d$_6$*) δ ppm 0.79 (s, 3 H) 0.83 (s, 3 H) 0.88 (br d, *J*=6.24 Hz, 3 H) 0.97 - 1.04 (m, 13 H) 1.08 - 1.20 (m, 2 H) 1.10 - 1.12 (m, 3 H) 1.15 - 1.20 (m, 1 H) 1.31 - 1.31 (m, 1 H) 1.23 - 1.27 (m, 1 H) 1.33 - 1.44 (m, 3 H) 1.49 (q, *J*=8.89 Hz, 1 H) 1.58 (br d, *J*=7.31 Hz, 1 H) 1.63 - 1.79 (m, 4 H) 1.82 - 1.86 (m, 1 H) 1.82 - 1.86 (m, 1 H) 2.24 (br d, *J*=9.68 Hz, 1 H) 2.31 (br dd, *J*=18.50, 6.88 Hz, 1 H) 2.37 (br d, *J*=12.05 Hz, 1 H) 2.93 (td, *J*=8.28, 5.38 Hz, 1 H) 3.00 - 3.05 (m, 1 H) 3.00 - 3.03 (m, 1 H) 3.02 - 3.05 (m, 1 H) 3.06 - 3.12 (m, 1 H) 3.26 - 3.39 (m, 1 H) 3.39 - 3.45 (m, 1 H) 3.61 - 3.71 (m, 2 H) 4.00 (s, 1 H) 4.12 (d, *J*=7.74 Hz, 1 H) 4.18 (d, *J*=5.81 Hz, 1 H) 4.22 - 4.35 (m, 2 H) 4.71 (d, *J*=5.38 Hz, 1 H) 4.82 (t, *J*=4.41 Hz, 2 H) 5.35 (br d, *J*=6.02 Hz, 1 H)

SEQUENCE LISTING

<160> NUMBER OF SEQ ID NOS: 105

<210> SEQ ID NO 1
<211> LENGTH: 764
<212> TYPE: PRT
<213> ORGANISM: Cucurbita pepo

<400> SEQUENCE: 1

-continued

```
Met Trp Arg Leu Lys Val Gly Ala Glu Ser Val Gly Glu Glu Asp Glu
1               5                   10                  15

Lys Trp Val Lys Ser Val Ser Asn His Leu Gly Arg Gln Val Trp Glu
            20                  25                  30

Phe Cys Ala Asp Ala Ala Ala Asp Thr Pro His Gln Leu Leu Gln Ile
        35                  40                  45

Gln Asn Ala Arg Asn His Phe His His Asn Arg Phe His Arg Lys Gln
    50                  55                  60

Ser Ser Asp Leu Phe Leu Ala Ile Gln Tyr Glu Lys Glu Ile Ala Lys
65                  70                  75                  80

Gly Ala Lys Gly Gly Ala Val Lys Val Lys Glu Gly Glu Glu Val Gly
                85                  90                  95

Lys Glu Ala Val Lys Ser Thr Leu Glu Arg Ala Leu Gly Phe Tyr Ser
            100                 105                 110

Ala Val Gln Thr Arg Asp Gly Asn Trp Ala Ser Asp Leu Gly Gly Pro
        115                 120                 125

Leu Phe Leu Leu Pro Gly Leu Val Ile Ala Leu His Val Thr Gly Val
    130                 135                 140

Leu Asn Ser Val Leu Ser Lys His His Arg Val Glu Met Cys Arg Tyr
145                 150                 155                 160

Leu Tyr Asn His Gln Asn Glu Asp Gly Gly Trp Gly Leu His Ile Glu
                165                 170                 175

Gly Thr Ser Thr Met Phe Gly Ser Ala Leu Asn Tyr Val Ala Leu Arg
            180                 185                 190

Leu Leu Gly Glu Asp Ala Asp Gly Gly Asp Gly Gly Ala Met Thr Lys
        195                 200                 205

Ala Arg Ala Trp Ile Leu Glu Arg Gly Gly Ala Thr Ala Ile Thr Ser
    210                 215                 220

Trp Gly Lys Leu Trp Leu Ser Val Leu Gly Val Tyr Glu Trp Ser Gly
225                 230                 235                 240

Asn Asn Pro Leu Pro Pro Glu Phe Trp Leu Leu Pro Tyr Ser Leu Pro
                245                 250                 255

Phe His Pro Gly Arg Met Trp Cys His Cys Arg Met Val Tyr Leu Pro
            260                 265                 270

Met Ser Tyr Leu Tyr Gly Lys Arg Phe Val Gly Pro Ile Thr Pro Lys
        275                 280                 285

Val Leu Ser Leu Arg Gln Glu Leu Tyr Thr Ile Pro Tyr His Glu Ile
    290                 295                 300

Asp Trp Asn Lys Ser Arg Asn Thr Cys Ala Lys Glu Asp Leu Tyr Tyr
305                 310                 315                 320

Pro His Pro Lys Met Gln Asp Ile Leu Trp Gly Ser Ile Tyr His Val
                325                 330                 335

Tyr Glu Pro Leu Phe Thr Arg Trp Pro Gly Lys Arg Leu Arg Glu Lys
            340                 345                 350

Ala Leu Gln Ala Ala Met Lys His Ile His Tyr Glu Asp Glu Asn Ser
        355                 360                 365

Arg Tyr Ile Cys Leu Gly Pro Val Asn Lys Val Leu Asn Met Leu Cys
    370                 375                 380

Cys Trp Val Glu Asp Pro Tyr Ser Asp Ala Phe Lys Leu His Leu Gln
385                 390                 395                 400

Arg Val His Asp Tyr Leu Trp Val Ala Glu Asp Gly Met Arg Met Gln
                405                 410                 415

Gly Tyr Asn Gly Ser Gln Leu Trp Asp Thr Ala Phe Ser Ile Gln Ala
```

-continued

```
            420                 425                 430

Ile Val Ala Thr Lys Leu Val Asp Ser Tyr Ala Pro Thr Leu Arg Lys
        435                 440                 445

Ala His Asp Phe Val Lys Asp Ser Gln Ile Gln Glu Asp Cys Pro Gly
    450                 455                 460

Asp Pro Asn Val Trp Phe Arg His Ile His Lys Gly Ala Trp Pro Leu
465                 470                 475                 480

Ser Thr Arg Asp His Gly Trp Leu Ile Ser Asp Cys Thr Ala Glu Gly
                485                 490                 495

Leu Lys Ala Ser Leu Met Leu Ser Lys Leu Pro Ser Thr Met Val Gly
            500                 505                 510

Glu Pro Leu Glu Lys Asn Arg Leu Cys Asp Ala Val Asn Val Leu Leu
        515                 520                 525

Ser Leu Gln Asn Asp Asn Gly Gly Phe Ala Ser Tyr Glu Leu Thr Arg
    530                 535                 540

Ser Tyr Pro Trp Leu Glu Leu Ile Asn Pro Ala Glu Thr Phe Gly Asp
545                 550                 555                 560

Ile Val Ile Asp Tyr Pro Tyr Val Glu Cys Thr Ala Ala Thr Met Glu
                565                 570                 575

Ala Leu Thr Leu Phe Lys Lys Leu His Pro Gly His Arg Thr Lys Glu
            580                 585                 590

Ile Asp Thr Ala Ile Gly Lys Ala Ala Asn Phe Leu Glu Lys Met Gln
        595                 600                 605

Arg Ala Asp Gly Ser Trp Tyr Gly Cys Trp Gly Val Cys Phe Thr Tyr
    610                 615                 620

Ala Gly Trp Phe Gly Ile Lys Gly Leu Val Ala Ala Gly Arg Thr Tyr
625                 630                 635                 640

Asn Ser Cys Leu Ala Ile Arg Lys Ala Cys Glu Phe Leu Leu Ser Lys
                645                 650                 655

Glu Leu Pro Gly Gly Gly Trp Gly Glu Ser Tyr Leu Ser Cys Gln Asn
            660                 665                 670

Lys Val Tyr Thr Asn Leu Glu Gly Asn Lys Pro His Leu Val Asn Thr
        675                 680                 685

Ala Trp Val Leu Met Ala Leu Ile Glu Ala Gly Gln Gly Glu Arg Asp
    690                 695                 700

Pro Ala Pro Leu His Arg Ala Ala Arg Leu Leu Met Asn Ser Gln Leu
705                 710                 715                 720

Glu Asn Gly Asp Phe Val Gln Gln Glu Ile Met Gly Val Phe Asn Lys
                725                 730                 735

Asn Cys Met Ile Thr Tyr Ala Ala Tyr Arg Asn Ile Phe Pro Ile Trp
            740                 745                 750

Ala Leu Gly Glu Tyr Cys His Arg Val Leu Thr Glu
        755                 760


<210> SEQ ID NO 2
<211> LENGTH: 250
<212> TYPE: PRT
<213> ORGANISM: Siraitia grosvenorii

<400> SEQUENCE: 2

Leu Glu Arg Asn Arg Leu Cys Asp Ala Val Asn Val Leu Leu Ser Leu
1               5                   10                  15

Gln Asn Asp Asn Gly Gly Phe Ala Ser Tyr Glu Leu Thr Arg Ser Tyr
            20                  25                  30
```

```
Pro Trp Leu Glu Leu Ile Asn Pro Ala Glu Thr Phe Gly Asp Ile Val
        35                  40                  45

Ile Asp Tyr Pro Tyr Val Glu Cys Thr Ser Ala Thr Met Glu Ala Leu
    50                  55                  60

Thr Leu Phe Lys Lys Leu His Pro Gly His Arg Thr Lys Glu Ile Asp
65                  70                  75                  80

Thr Ala Ile Val Arg Ala Ala Asn Phe Leu Glu Asn Met Gln Arg Thr
                85                  90                  95

Asp Gly Ser Trp Tyr Gly Cys Trp Gly Val Cys Phe Thr Tyr Ala Gly
            100                 105                 110

Trp Phe Gly Ile Lys Gly Leu Val Ala Ala Gly Arg Thr Tyr Asn Asn
        115                 120                 125

Cys Leu Ala Ile Arg Lys Ala Cys Asp Phe Leu Leu Ser Lys Glu Leu
    130                 135                 140

Pro Gly Gly Gly Trp Gly Glu Ser Tyr Leu Ser Cys Gln Asn Lys Val
145                 150                 155                 160

Tyr Thr Asn Leu Glu Gly Asn Arg Pro His Leu Val Asn Thr Ala Trp
                165                 170                 175

Val Leu Met Ala Leu Ile Glu Ala Gly Gln Ala Glu Arg Asp Pro Thr
            180                 185                 190

Pro Leu His Arg Ala Ala Arg Leu Leu Ile Asn Ser Gln Leu Glu Asn
        195                 200                 205

Gly Asp Phe Pro Gln Gln Glu Ile Met Gly Val Phe Asn Lys Asn Cys
    210                 215                 220

Met Ile Thr Tyr Ala Ala Tyr Arg Asn Ile Phe Pro Ile Trp Ala Leu
225                 230                 235                 240

Gly Glu Tyr Cys His Arg Val Leu Thr Glu
                245                 250
```

<210> SEQ ID NO 3
<211> LENGTH: 1572
<212> TYPE: DNA
<213> ORGANISM: Siraitia grosvenorii

<400> SEQUENCE: 3

```
atggaactct tctctaccaa aactgcagcc gagatcatcg ctgttgtctt gtttttctac      60

gctctcatcc ggctattatc tggaagattc agctctcaac agaagagact gccacctgaa     120

gccggtggcg cctggccact gatcggccat ctccatctcc taggtgggtc ggaacctgca     180

cataaaacct tggcgaacat ggcggacgcc tacggaccag tttttacgtt gaaactgggc     240

atgcatacag ctttggttat gagcagttgg gaaatagcga gagagtgctt tactaaaaac     300

gacagaatct ttgcctcccg ccccatagtc actgcctcaa agcttctcac ctataaccat     360

accatgtttg ggttcagcca atatggtcca ttctggcgcc atatgcgcaa aatagccacg     420

cttcaactcc tctcaaacca ccgcctcgag cagctccaac acatcagaat atcggaggtc     480

cagacttcga ttaagaaact gtacgagttg tgggtcaaca gcagaaataa tggaggcgag     540

aaagtgttgg tggagatgaa gacgtggttc ggaggcataa ccttgaacac catattcagg     600

atggtggtcg gaaagcgatt ctcgactgct ttcgaaggca gtggtggcga acggtatcgg     660

aaggcgttga gggattctct tgaatggttt ggggcattcg ttccgtcaga ttcattcccg     720

tttttaagat ggttggattt gggaggatat gagaaggcga tgaagaagac ggcgagtgtg     780

ctggacgagg tgcttgataa atggctcaaa gagcatcagc agaggagaaa ctccggtgaa     840

ctggagacgg aggagcacga cttcatgcac gtgatgctgt ctattgttaa ggatgatgaa     900
```

gaactatccg gctacgatgc cgatacagtc acaaaagcta catgtttgaa tttaatagtt 960
ggtggattcg acactacaca agtaactatg acatgggctc tttctttgct tctcaacaat 1020
gaagaggtat taaaaaaggc ccaacttgaa ctagacgaac aagttggaag agagaggttt 1080
gtggaagagt ccgatgttaa aaatctgtta tatctccagg ccatcgtgaa ggaaactttg 1140
cgtttgtacc cttcagcgcc aatctcgaca tttcatgagg ccatggaaga ttgcactgtt 1200
tctggctacc acatcttttc agggacgcgt ttgatggtga atcttcaaaa gcttcaaaga 1260
gatccacttg catgggagga tccatgtgac tttcgaccgg agagatttct gacaactcat 1320
aaggatttcg atcttagagg acatagtcct caattgatac catttgggag tggtcgaaga 1380
atatgccctg gcatctcgtt tgccattcaa gttttgcatc ttacgcttgc aaatctactt 1440
catgggtttg acattggaag gccatctcat gaaccaatcg atatgcagga gagtaaagga 1500
ctaacgagta ttaaaacaac tccacttgag gttgttttag ctccacgcct tgctgctcaa 1560
gtttatgagt ga 1572

<210> SEQ ID NO 4
<211> LENGTH: 1497
<212> TYPE: DNA
<213> ORGANISM: Siraitia grosvenorii

<400> SEQUENCE: 4
atgccgatcg cagaaggtgc agtctctgat ttgtttggtc gcccactctt ctttgcacta 60
tatgattggt tcttagagca tggatctgtt tataaacttg cctttggacc aaaagccttt 120
gttgttgtat cagatcccat tgtggcaaga tatattcttc gagaaaatgc atttggttat 180
gacaagggag tgcttgctga tattttagaa ccgataatgg gtaaaggact aataccagct 240
gaccttggca cttggaagca gaggagacga gttattgctc caggattcca tgccttgtac 300
ttggaagcta tgaccaaagt atttgccaat tgttcagaac gatcaatatt gaaattggag 360
aagcttctag gagaaggtga actacaggag aataaaacca ttgagttgga tatggaagca 420
gagttttcaa gtttggctct tgatatcatt ggactcggtg ttttcaacta tgattttggt 480
tctgtaacca aagaatctcc ggtgattaag gctgtatatg ggactctttt tgaagcagag 540
catagatcga ctttctatat cccatattgg aaagtacctt tggcaaggtg gatagtccca 600
aggcagcgta aattccatgg tgaccttaag gttattaatg agtgtcttga tggcctaata 660
cgcaacgcaa gagaaacccg agacgaaacg gatgttgaga aattgcagca aagggactac 720
ttaaatctca aggatgccag tcttttgcgt ttcttagttg atatgcgggg agctgatgtt 780
gatgatcgcc agcttaggga cgatctgatg acgatgctta ttgctggcca tgaaacaact 840
gctgctgtgc ttacatgggc tgttttttg cttgcacaaa atccttcaaa aatgaaaaaa 900
gcgcaagcag agattgattt ggttcttggc atggggaggc caacttttga atcatttaaa 960
gcattgaagt acatcagact tatcgttgca gagactcttc gtttgtttcc tcagcctcca 1020
ttgctgataa gacgagctct caaatcagat atattaccag gaggatacaa tggtgacaaa 1080
actggatatg caattcctgc agggactgac atcttcatct ctgtttacaa tctccacaga 1140
tctccctact tctgggataa tcctcaagaa tttgaaccag agagatttca agtaaagagg 1200
gcaagcgagg gaattgaagg atgggatggt ttcgacccat ctagaagccc tggagctcta 1260
tacccgaatg agattgtagc agacttttcc ttcttaccat ttggtggagg ccctagaaaa 1320
tgtgtgggag atcaatttgc tctaatggag tcaactatag cattggccat gttactgcag 1380

```
aagtttgatg tggagctaaa aggaagtcca gaatctgtag aactagttac tggagccaca   1440

atacatacca aaagtgggtt gtggtgcaaa ctgagaagaa gatcacaagt aaactga      1497
```

<210> SEQ ID NO 5
<211> LENGTH: 1563
<212> TYPE: DNA
<213> ORGANISM: Artificial Sequence
<220> FEATURE:
<223> OTHER INFORMATION: Codon-optimized DNA sequence encoding CYP1798

<400> SEQUENCE: 5

```
atggaaatgt cctcaagtgt cgcagccaca atcagtatct ggatggtcgt cgtatgtatc     60

gtaggtgtag gttggagagt cgtaaattgg gtttggttga gaccaaagaa attggaaaag    120

agattgagag aacaaggttt ggccggtaat tcttacagat tgttgttcgg tgacttgaag    180

gaaagagctg caatggaaga acaagcaaat tcaaagccta taaacttctc ccatgacatc    240

ggtccaagag ttttcccttc aatgtacaag accatccaaa actacggtaa aaactcctac    300

atgtggttag gtccataccc tagagtccac atcatggatc cacaacaatt gaagaccgtt    360

tttactttgg tctacgacat tcaaaagcca aatttgaacc ctttgattaa attcttgtta    420

gatggtatcg ttacacatga aggtgaaaag tgggctaagc acagaaagat tattaaccca    480

gcattccatt tggaaaagtt gaaggatatg atacctgctt tctttcactc atgtaatgaa    540

atcgtcaacg aatgggaaag attgatttca aaagaaggtt cctgcgaatt ggatgtaatg    600

ccttatttgc aaaatttggc cgctgacgcc atttcaagaa ccgcttttgg ttcttcatac    660

gaagaaggta aaatgatctt ccaattgttg aaggaattga ctgatttggt tgtcaaggta    720

gcttttggtg tttatattcc aggttggaga ttcttgccta caaagagtaa caacaaaatg    780

aaggaaatta atagaaaaat caagtctttg ttgttgggta tcattaacaa gagacaaaag    840

gcaatggaag aaggtgaagc cggtcaatct gatttgttgg gtatattaat ggaaagtaat    900

tctaacgaaa tccaaggtga aggtaataac aaggaagatg gcatgtctat tgaagacgtc    960

atcgaagagt gtaaggtatt ttatataggt ggtcaagaaa ctacagcaag attattgatc   1020

tggactatga tattgttgtc cagtcataca gaatggcaag aaagagccag aaccgaagtc   1080

ttgaaggtat ttggtaataa gaaaccagat ttcgacggtt tgtcaagatt gaaggtagtt   1140

actatgatct tgaacgaagt tttaagattg tacccacctg cttccatgtt gacaagaatc   1200

atccaaaagg aaacaagagt tggtaaatta accttgccag caggtgttat cttgataatg   1260

cctatcatct tgatacatag agatcacgac ttgtggggtg aagatgctaa cgagtttaaa   1320

ccagaaagat tcagtaaagg tgtttctaag gcagccaaag tccaaccagc ctttttccct   1380

tttggttggg gtcctagaat ttgcatgggt caaaacttcg ctatgatcga agctaagatg   1440

gcattgagtt tgatcttgca aagattttct ttcgaattgt cttcatccta cgttcatgca   1500

ccaactgtcg tcttcactac acaaccacaa cacggtgccc acatcgtttt gagaaagtta   1560

tga                                                                 1563
```

<210> SEQ ID NO 6
<211> LENGTH: 1602
<212> TYPE: DNA
<213> ORGANISM: Siraitia grosvenorii

<400> SEQUENCE: 6

```
atggaaccac aaccaagtgc ggaattcaac tggaatcaca gcctaagcac cgtcgctatc     60

ggtgtcattg ccattatttt cttccgtttt ctcgtcaaaa gagtcaccgg cgccggtgag    120
```

```
cgaaagggtc cgaagccgcc aaaagtagcc ggagggtggc ctctaattgg ccacctccct    180
ctcctcggag gacctgaact gccccatgtc aaactgggtg gtttggctga taaatatggt    240
ccaatcttct cgatccggct gggtgtccac tccgccgtcg tgataaacag ttgggaggcg    300
gcgaaacagt tattaaccaa ccatgacgtc gccgtctctt cccgccccca aatgctcggc    360
ggaaaactcc tgggctacaa ctacgccgtg tttggtttcg gaccctacgg ctcttactgg    420
cgcaacatgc gcaagataac cacgcaagag cttctatcca atagcagaat ccagctccta    480
agagacgttc gagcgtcaga agtgaaccaa ggcataaaag agctctacca gcactggaaa    540
gaaagaagag acggtcacga ccaagccttg gtggaactgc agcagtgggt cggggacttg    600
actatgaatc tgattctcgg agtcatcgcc gggaaaaggt tctttggagc tgcagcaacg    660
gtagacgagg aagaggcgcg acggagccat aaagcattga aggagttgtt acattatatg    720
gggctttttc tactgggtga tgctgttcca tatctaggat ggttggacgt cggcggccat    780
gtgaaggcga tgaagaaaac ttcaaaagaa ttggaccgta tgttaacaca gtggttggag    840
gagcacaaga aggaaggacc caagaaagat cataaagact tcatggacgt gatgctttca    900
gttctcaatg aaacatccga tgttctttca gataagaccc atggcttcga tgctgatacc    960
atcatcaaag ctacatgtat gacgatggtt ttaggaggga gtgatacgac ggcggtggtt   1020
gtgatatggg caatctcgct gctgctgaat aatcgccctg cgttgagaaa agtgcaagaa   1080
gaactggaag cccatatcgg ccgagacaga gaactggagg aatcggatct cggtaagcta   1140
gtgtatttgc aggcagtcgt gaaggagaca ttgcggctgt acggagccgg aggccttttc   1200
tttcgtgaaa ccacagagga tgtcaccatc gacggattcc atgtcgagaa agggacatgg   1260
ctgttcgtga acgtggggaa gatccacaga gatgggaagg tgtggccgga gccaacggag   1320
ttcaaaccgg agaggtttct gacgacccac aaagattttg atctgaaggg ccagcggttt   1380
gagctcatcc ctttcggggg aggaagaaga tcgtgccctg gaatgtcttt tgggctccaa   1440
atgctacagc ttattttggg taaactgctt caggcttttg atatatcgac gccgggggac   1500
gccgccgttg atatgaccgg atccattgga ctgacgaaca tgaaagccac tccattggaa   1560
gtgctcatca ccccgcgctt gcctctttcg ctttacgatt ga                      1602
```

<210> SEQ ID NO 7
<211> LENGTH: 1236
<212> TYPE: DNA
<213> ORGANISM: Siraitia grosvenorii

<400> SEQUENCE: 7

```
atggagactc ttcttcttca tcttcaatcg ttatttcatc caatttcctt cactggtttc     60
gttgtcctct ttagcttcct gttcctgctc cagaaatggt tactgacacg tccaaactct    120
tcatcagaag cctcaccccc ttctccacca aagcttccca tcttcggaca ccttctaaac    180
ctgggtctgc atccccacat caccctcgga gcctacgctc gccgctatgg ccctctcttc    240
ctcctccact tcggcagcaa gcccaccatc gtcgtctctt ctgccgaaat cgctcgcgat    300
atcatgaaga cccacgacct cgtcttcgcc aaccgtccta aatcaagcat cagcgaaaag    360
attctttacg gctccaaaga tttagccgca tctccttacg gcgaatactg gaggcagatg    420
aaaagcgttg gcgtgcttca tcttttgagc aacaaaaggg ttcaatcctt tcgctctgtc    480
agagaagaag aagtcgaact gatgatccag aagatccaac agaacccccct atcagttaat    540
ttaagcgaaa tattctctgg actgacgaac gacatagttt gcagggtggc tttagggaga    600
```

-continued

```
aagtatggcg tgggagaaga cggaaagaag ttccggtctc ttctgctgga gtttggggaa     660

gtattgggaa gtttcagtac gagagacttc atcccgtggc tgggttggat tgatcgtatc     720

agtgggctgg acgccaaagc cgagagggta gccaaagagc tcgatgcttt ctttgacaga     780

gtgatcgaag atcacatcca tctaaacaag agagagaata atcccgatga gcagaaggac     840

ttggtggatg tgctgctttg tgtacagaga gaagactcca tcgggtttcc ccttgagatg     900

gatagcataa aagctttaat cttggacatg tttgctgcag gcacagacac gacatacacg     960

gtgttggagt gggcaatgtc ccaactgttg agacacccag aagcgatgaa gaaactgcag    1020

agggaggtca gagaaatagc aggtgagaaa gaacacgtaa gtgaggatga tttagaaaag    1080

atgcattact tgaaggcagt aatcaaagaa acgctgcggc tacacccacc aatcccactc    1140

ctcgtcccca gagaatcaac ccaagacatc aggttgaggg ggtacgatat cagaggcggc    1200

acccgggtta tgatcaatgc atgggccatc ggaaga                              1236
```

<210> SEQ ID NO 8
<211> LENGTH: 1614
<212> TYPE: DNA
<213> ORGANISM: Siraitia grosvenorii

<400> SEQUENCE: 8

```
atgtcgatga gtagtgaaat tgaaagcctc tgggttttcg cgctggcttc taaatgctct      60

gctttaacta aagaaaacat cctctggtct ttactcttct ttttcctaat ctgggtttct     120

gtttccattc tccactgggc ccatccgggc ggcccggctt ggggccgcta ctggtggcgc     180

cgccgccgca gcaattccac cgccgctgct attcccggcc cgagaggcct ccccctcgtc     240

ggcagcatgg gcttgatggc cgacttggcc caccaccgga ttgccgccgt ggctgactcc     300

ttaaacgcca cccgcctcat ggccttttcg ctcggcgaca ctcgcgtgat cgtcacatgc     360

aaccccgacg tcgccaaaga gattctcaac agctccctct tcgccgaccg ccccgttaag     420

gagtccgctt actccttgat gttcaaccgc gccattgggt tcgcccccta tggcctttac     480

tggcggaccc tccgccgcat cgcttcccac cacctcttct gccccaagca aatcaagtcc     540

tcccagtccc agcgccgcca aatcgcttcc caaatggtcg caatgttcgc aaaccgcgat     600

gccacacaga gcctctgcgt tcgcgactct ctcaagcggg cttctctcaa caacatgatg     660

ggctctgttt tcggccgagt ttacgacctc tctgactcgg ctaacaatga cgtccaagaa     720

ctccagagcc tcgtcgacga aggctacgac ttgctgggcc tcctcaactg gtccgaccat     780

ctcccatggc tcgccgactt cgactctcag aaaatccggt tcagatgctc ccgactcgtc     840

cccaaggtga accacttcgt cggccggatc atcgccgaac accgcgccaa atccgacaac     900

caagtcctag atttcgtcga cgttttgctc tctctccaag aagccgacaa actctctgac     960

tccgatatga tcgccgttct ttgggaaatg atttttcgtg ggacggacac ggtggcagtt    1020

ttaatcgagt ggatactggc caggatggta cttcacaacg atatccaaag gaaagttcaa    1080

gaggagctag ataacgtggt tgggagtaca cgcgccgtcg cggaatccga cattccgtcg    1140

ctggtgtatc taacggctgt ggttaaggaa gttctgaggt tacatccgcc gggcccactc    1200

ctgtcgtggg cccgcctagc catcactgat acaatcatcg atgggcatca cgtgccccgg    1260

gggaccaccg ctatggttaa catgtggtcg atagcgcggg acccacaggt ctggtcggac    1320

ccactcgaat ttatgcccca gaggtttgtg tccgaccccg gtgacgtgga gttctcggtc    1380

atgggttcgg atctccggct ggctccgttc gggtcgggca gaaggacctg ccccgggaag    1440

gccttcgcct ggacaactgt caccttctgg gtggccacgc ttttacacga cttcaaatgg    1500
```

```
tcgccgtccg atcaaaacga cgccgtcgac ttgtcggagg tcctcaagct ctcctgcgag   1560

atggccaatc ccctcaccgt taaagtacac ccaaggcgca gtttaagctt ttaa         1614
```

<210> SEQ ID NO 9
<211> LENGTH: 1506
<212> TYPE: DNA
<213> ORGANISM: Siraitia grosvenorii

<400> SEQUENCE: 9

```
atggatggtt ttcttccaac agtggcggcg agcgtgcctg tgggagtggg tgcaatattg     60

ttcacggcgt tgtgcgtcgt cgtgggaggg gttttggttt atttctatgg accttactgg    120

ggagtgagaa gggtgcctgg tccaccagct attccactgg tcggacatct tcccttgctg    180

gctaagtacg gcccagacgt tttctctgtc cttgccaccc aatatggccc tatcttcagg    240

ttccatatgg gtaggcagcc attgataatt atagcagacc ctgagctttg taaagaagct    300

ggtattaaga aattcaagga catcccaaat agaagtgtcc cttctccaat atcagcttcc    360

cctcttcatc agaagggtct tttcttcaca agggatgcaa gatggtcgac aatgcggaac    420

acgatattat cggtctatca gtcctcccat ctagcgagac taatacctac tatgcaatca    480

atcattgaaa ctgcaactca aaatctccat tcctctgtcc aggaagacat ccctttctcc    540

aatctctccc tcaaattgac caccgatgtg attggaacag cagccttcgg tgtcaacttt    600

gggctctcta atccacaggc aaccaaaact tgtgctacca acggccaaga caacaaaaat    660

gacgaagttt cagacttcat caatcaacac atctactcca caacgcagct caagatggat    720

ttatcaggtt ccttctcaat catacttgga ctgcttgtcc ctatactcca agaaccattt    780

agacaagtcc taaagagaat accattcacc atggactgga aagtggaccg gacaaatcag    840

aaattaagtg gtcggcttaa tgagattgtg gagaagagaa tgaagtgtaa cgatcaaggt    900

tcaaaagact tcttatcgct cattttgaga gcaagagagt cagagacagt atcaaggaat    960

gtcttcactc cagactacat cagtgcagtt acgtatgaac acctacttgc tgggtcggct   1020

accacggcgt ttacgttgtc ttctattgta tatttagttg ctgggcatcc agaagtcgag   1080

aagaagttgc tagaagagat tgacaacttt ggtccatccg atcagatacc aacagctaat   1140

gatcttcatc agaagtttcc atatcttgat caggtgatta aagaggctat gaggttctac   1200

actgtttccc ctctagtagc cagagaaaca gctaaagatg tggagattgg tggatatctt   1260

cttccaaagg ggacatgggt ttggttagca cttggagttc ttgccaagga tccaaagaac   1320

tttccagaac cagataaatt caaaccagag aggtttgatc caaatgaaga agaggagaaa   1380

caaaggcatc cttatgcttt aatccccttt ggaattggtc ctcgagcatg cattggtaaa   1440

aaattcgccc ttcaggagtt gaagctctcg ttgattcatt tgtacaggaa gtttgtattt   1500

cggcat                                                              1506
```

<210> SEQ ID NO 10
<211> LENGTH: 1566
<212> TYPE: DNA
<213> ORGANISM: Siraitia grosvenorii

<400> SEQUENCE: 10

```
atggaaatca ttttatcata tctcaacagc tccatagctg gactcttcct cttgcttctc     60

ttctcgtttt ttgttttgaa aaaggctaga acctgtaaac gcagacagcc tcctgaagca    120

gccggcggat ggccgatcat cggccacctg agactgctcg gggttcgca acttccccat     180
```

gaaaccttgg gagccatggc cgacaagtat ggaccaatct tcagcatccg agttggtgtc 240
cacccatctc ttgttataag cagttgggaa gtggctaaag agtgctacac caccctcgac 300
tcagttgtct cttctcgtcc caagagtttg ggtggaaagt tgttgggcta caacttcgcc 360
gcttttgggt tcaggcctta tgattccttt taccggagta tccgcaaaac catagcctcc 420
gaggtgctgt cgaaccgccg tctggagttg cagagacaca ttcgagtttc tgaggtgaag 480
agatcggtga aggagcttta caatctgtgg acgcagagag aggaaggctc agaccacata 540
cttattgatg cggatgaatg gattggtaat attaatttga acgtgattct gatgatggtt 600
tgtgggaagc ggtttcttgg cggttctgcc agcgatgaga aggagatgag gcggtgtctc 660
aaagtctcga gagatttctt cgatttgaca gggcagttta cggtgggaga tgccattcct 720
ttcctgcgat ggctggattt gggtggatat gcgaaggcga tgaagaaaac tgcaaaagaa 780
atggactgtc tcgttgagga atggctggaa gaacaccgcc ggaagagaga ctccggcgcc 840
accgacggtg aacgtgactt catggatgtg atgctttcga ttcttgaaga gatggacctt 900
gctggctacg acgctgacac agtcaacaaa gccacatgcc tgagcattat ttctggggga 960
atcgatacta taacgctaac tctgacatgg gcgatctcgt tattgctgaa caatcgagag 1020
gcactgcgaa gggttcaaga ggaggtggac atccatgtcg gaaacaaaag gcttgtggat 1080
gaatcagact tgagcaagct ggtgtatctc caagccgtcg tgaaagagac attaaggttg 1140
tacccagcag ggccgctgtc gggagctcga gagttcagtc gggactgcac ggtcggaggg 1200
tatgacgtgg ccgccggcac acggctcatc acaaaccttt ggaagataca gacggaccct 1260
cgggtgtggc cggagccact tgagttcagg ccggagaggt ttctgagcag ccaccagcag 1320
ttggatgtga agggccagaa ctttgaactg gccccatttg gttgtggaag aagagtgtgc 1380
cctggggcgg ggcttggggt tcagatgacg cagttggtgc tggcgagtct gattcattcg 1440
gtggaacttg gaactcgctc cgatgaagcg gtggacatgg ctgctaagtt tggactcaca 1500
atgtacagag ccacccctct tcaggctctc gtcaagccac gcctccaagc cggtgcttat 1560
tcatga 1566

<210> SEQ ID NO 11
<211> LENGTH: 1425
<212> TYPE: DNA
<213> ORGANISM: Siraitia grosvenorii

<400> SEQUENCE: 11
atgggtgtat tgtccatttt attattcaga tattccgtca agaagaagcc attaagatgc 60
ggtcacgatc aaagaagtac cacagatagt ccacctggtt caagaggttt gccattgata 120
ggtgaaactt tgcaattcat ggctgctatt aattctttga acggtgtata cgatttcgtt 180
agaataagat gtttgagata cggtagatgc tttaagacaa gaatcttcgg tgaaacccat 240
gtttttgtct caactacaga atccgctaag ttgatcttga aggatggtgg tgaaaaattc 300
accaaaaagt acatcagatc aatcgctgaa ttggttggtg acagaagttt gttatgtgca 360
tctcatttgc aacacaagag attgagaggt ttgttgacta atttgttttc tgccacattc 420
ttggcttctt tcgtaactca attcgatgaa caaatcgttg aagcttttag atcatgggaa 480
tccggtagta ccataatcgt tttgaacgaa gcattgaaga tcacttgtaa ggccatgtgc 540
aaaatggtca tgtccttaga aagagaaaac gaattggaag ctttgcaaaa ggaattgggt 600
catgtttgtg aagctatgtt ggcatttcca tgcagattcc ctggtacaag atttcacaat 660
ggtttgaagg caagaagaag aatcattaaa gttgtcgaaa tggccattag agaaagaaga 720
agatctgaag ctcctagaga agatttcttg caaagattgt tgacagaaga aaaggaagaa 780
gaagacggtg gtggtgtttt aagtgatgcc gaaattggtg acaacatatt gacaatgatg 840
atcgcaggtc aagataccac tgcctctgct attacctgga tggtcaagtt tttggaagaa 900
aaccaagatg tattgcaaaa cttaagagac gaacaattcg aaatcatggg taaacaagaa 960
ggttgtggtt catgcttctt gacattagaa gatttgggta atatgtccta tggtgcaaaa 1020
gtagttaagg aatcattgag attagcctcc gtcgtaccat ggtttcctag attggtttta 1080
caagattctt tgatccaagg ttacaaaatt aaaaagggtt ggaacgtcaa catagacgta 1140
agatctttac attcagatcc atccttgtat aatgacccaa caaagtttaa ccctagtaga 1200
ttcgatgacg aagctaaacc ttactcattt ttggcattcg gtatgggtgg tagacaatgt 1260
ttgggtatga acatggcaaa ggccatgatg ttggttttct tgcacagatt ggtcacctca 1320
ttcagatgga aggttataga ttccgactct tcaatcgaaa aatgggcttt gttctctaag 1380
ttgaagtcag gttgccctat cgtagttacc cacatcggtt cctaa 1425

<210> SEQ ID NO 12
<211> LENGTH: 1509
<212> TYPE: DNA
<213> ORGANISM: Siraitia grosvenorii

<400> SEQUENCE: 12
atggatttct actggatctg tgttcttctg ctttgcttcg catggttttc cattttatcc 60
cttcactcga gaacaaacag cagcggcact tccaaacttc ctcccggacc gaaacccttg 120
ccgatcatcg gaagcctttt ggctctcggc cacgagcccc acaagtcttt ggctaatctc 180
gctaaatctc atggccctct tatgacctta aagctcggcc aaatcaccac cgtcgtagtt 240
tcctccgctg ccatggctaa gcaagttctc caaacgcacg accagtttct gtccagcagg 300
accgttccag acgcaatgac ctctcacaac cacgatgctt tcgcactccc atggattccg 360
gtttcacccc tctggcgaaa ccttcgacga atatgcaaca accagttgtt tgccggcaag 420
attctcgacg ccaacgagaa tctccggcga accaaagtgg ccgagctcgt atccgatatc 480
tcgagaagtg cattgaaagg tgagatggtg gattttggaa acgtggtgtt cgtcacttcg 540
ctcaatctgc tttccaatac gattttctcg gtggatttct tcgacccaaa ttctgaaatt 600
gggaaagagt tcaggcacgc agtacgaggc ctcatggaag aagctgccaa accaaatttg 660
ggggattatt tccctctgct gaagaagata gatcttcaag gaataaagag gagacagacc 720
acttacttcg atcgggtttt taatgttttg gagcacatga tcgaccagcg tcttcagcag 780
cagaagacga cgtctggttc tacctccaac aacaacaacg acttactgca ctaccttctc 840
aacctcagca acgaaaatag cgacatgaaa ttggggaaac ttgagctgaa acacttctta 900
ttggtgctat tcgtcgctgg gactgaaacg agttctgcaa cactgcaatg ggcaatggca 960
gaactactaa gaaacccaga aaagttagca aaagctcaag cggagaccag gcgggtgatt 1020
gggaaaggga acccaattga agaatcagac atttcgaggc tgccttatct gcaagcagtg 1080
gtgaaagaaa ctttcagatt gcacacacca gcgccatttc tactgccgcg caaagcacta 1140
caggacgtgg aaattgcagg tttcacagtc ccaaaggacg ctcaggtact ggtaaattta 1200
tgggctatga gcagagattc aagcatctgg gagaacccag agtggttcga gccagaaagg 1260
tttttggagt cggagctgga cgttagaggg agagattttg agctgatccc gttcggcggt 1320
gggcggagga tttgccccgg tctgccgttg gcgatgagaa tgttgcattt gattttgggt 1380
tctctcatcc acttctttga ttggaagctt gaagatgggt gtcggccgga agacgtgaaa 1440
atggacgaaa agcttggcct cactctggag ttggcttttc ccctcacagc cttgcctgtc 1500
cttgtctaa 1509

<210> SEQ ID NO 13
<211> LENGTH: 1734
<212> TYPE: DNA
<213> ORGANISM: Siraitia grosvenorii

<400> SEQUENCE: 13
atgtcctcct gcggtggtcc aactcctttg aatgttatcg gtatcttatt acaatcagaa 60
tcctccagag cctgcaactc agacgaaaac tcaagaattt tgagagattt cgtaacaaga 120
gaagttaacg ctttcttatg gttgtccttg atcactatca cagcagtttt gatcagtaaa 180
gttgtcggtt tgtttagatt gtggtctaag gcaaagcaat tgagaggtcc accttgtcca 240
tcattctacg gtcattctaa gatcatctca agacaaaatt tgactgattt gttatatgac 300
tcccacaaaa agtacggtcc agtagttaaa ttgtggttag gtcctatgca attgttagtc 360
tccgtaaagg aaccaagttt gttgaaggaa atattggtta aagctgagga taagttgcct 420
ttaacaggta gagcctttag attggctttc ggtagatctt cattatttgc atccagtttc 480
gaaaaggttc aaaacagaag acaaagattg gccgaaaagt tgaataagat cgcattccaa 540
agagccaaca tcattccaga aaaggccgta gcttgtttca tgggtagagt tcaagatttg 600
atgatagaag aatctgtcga ctgtaataag gtttctcaac atttggcttt tactttgtta 660
ggttgcacat tgtttggtga cgccttctta ggttggtcta aggctacaat ctatgaagaa 720
ttgttgatga tgatcgctaa ggacgcatcc ttttgggcta gttatagagt taccccaatc 780
tggaagcaag gtttctggag ataccaaaga ttgtgtatga agttgaagtg cttgactcaa 840
gatatcgttc aacaatacag aaagcattac aagttgtttt ctcactcaca aaaccaaaac 900
ttacacaacg aaaccaagtc aactggtgtt gaagtcgctt ttgatattcc accttgtcct 960
gctgcagacg ttagaaattc ttgctttttc tacggtttga acgatcatgt taacccaaac 1020
gaagaacctt gtggtaatat tatgggtgtc atgtttcacg gttgcttgac tacaacctct 1080
ttgatcgcat caatcttgga aagattggcc actaacccag aaatccaaga aaagattaat 1140
tctgaattga acttagttca aaagggtcca gtcaaggatc atagaaagaa tgttgacaac 1200
atgcctttgt tattggcaac aatctatgaa tcagctagat tattgccagc aggtccttta 1260
ttgcaaagat gtcctttgaa gcaagatttg gttttgaaaa caggtatcac cattccagct 1320
ggtaccttgg tcgtagttcc tattaaattg gttcaaatgg atgactcttc atggggttca 1380
gatgccaatg agtttaatcc atacagattc ttgtccatgg cttgtaatgg tattgacatg 1440
atacaaagaa ccccttttagc tggtgaaaac attggtgacc aaggtgaagg ttcatttgtc 1500
ttgaatgacc caattggtaa cgtaggtttc ttacctttttg gtttcggtgc aagagcctgc 1560
gttggtcaaa agtttataat ccaaggtgtc gctactttgt tcgcaagttt gttggcccat 1620
tacgaaatta aattgcaatc cgagagtaag aatgattcta aaccatccag taacacctct 1680
gccagtcaaa tcgtcccaaa ctcaaaaatc gtattcgtaa gaagaaactc ataa 1734

<210> SEQ ID NO 14
<211> LENGTH: 1422
<212> TYPE: DNA
<213> ORGANISM: Siraitia grosvenorii

<400> SEQUENCE: 14
atgtggactg tcgtgctcgg tttggcgacg ctgtttgtcg cctactacat ccattggatt 60
aacaaatgga gagattccaa gttcaacgga gttctgccgc cgggcaccat gggtttgccg 120
ctcatcggag agacgattca actgagtcga cccagtgact ccctcgacgt tcaccctttc 180
atccagaaaa aagttgaaag atacgggccg atcttcaaaa catgtctggc cggaaggccg 240
gtggtggtgt cggcggacgc agagttcaac aactacataa tgctgcagga aggaagagca 300
gtggaaatgt ggtatttgga tacgctctcc aaatttttcg gcctcgacac cgagtggctc 360
aaagctctgg gcctcatcca caagtacatc agaagcatta ctctcaatca cttcggcgcc 420
gaggccctgc gggagagatt tcttcctttt attgaagcat cctccatgga agcccttcac 480
tcctggtcta ctcaacctag cgtcgaagtc aaaaatgcct ccgctctcat ggtttttagg 540
acctcggtga ataagatgtt cggtgaggat gcgaagaagc tatcgggaaa tatccctggg 600
aagttcacga agcttctagg aggatttctc agtttaccac tgaattttcc cggcaccacc 660
taccacaaat gcttgaagga tatgaaggaa atccagaaga agctaagaga ggttgtagac 720
gatagattgg ctaatgtggg ccctgatgtg gaagatttct tggggcaagc ccttaaagat 780
aaggaatcag agaagttcat ttcagaggag ttcatcatcc aactgttgtt ttctatcagt 840
tttgctagct ttgagtccat ctccaccact cttactttga ttctcaagct ccttgatgaa 900
cacccagaag tagtgaaaga gttggaagct gaacacgagg cgattcgaaa agctagagca 960
gatccagatg gaccaattac ttgggaagaa tacaaatcca tgacttttac attacaagtc 1020
atcaatgaaa ccctaaggtt ggggagtgtc acacctgcct tgttgaggaa aacagttaaa 1080
gatcttcaag taaaaggata cataatcccg gaaggatgga caataatgct tgtcaccgct 1140
tcacgtcaca gagacccaaa agtctataag gaccctcata tcttcaatcc atggcgttgg 1200
aaggacttgg actcaattac catccaaaag aacttcatgc cttttggggg aggcttaagg 1260
cattgtgctg gtgctgagta ctctaaagtc tacttgtgca ccttcttgca catcctctgt 1320
accaaatacc gatggaccaa acttggggga ggaaggattg caagagctca tatattgagt 1380
tttgaagatg ggttacatgt gaagttcaca cccaaggaat ga 1422

<210> SEQ ID NO 15
<211> LENGTH: 1374
<212> TYPE: DNA
<213> ORGANISM: Siraitia grosvenorii

<400> SEQUENCE: 15
atgaagatga agatggaatc catgcgcacc tccctggata tctccgacca tgacatactt 60
ccaagggttt atcctcatgt tcacctatgg atcaacaaat atgggaaaaa cttcattcag 120
tggaatggca acgtagctca gttgattgtt tcggatcctg acacgatcaa ggagatactc 180
caaaaccgag aacaagctgt tcccaaaata gatctcagcg gagatgcacg gaggatattc 240
gggaatgggc tttcgacttc tgacggtgaa aaatgggcta aggctcgaag aatcgctgat 300
tacgctttcc acggggatct cctaagaaat atgggggccaa ccatggtttc ctgtgctgag 360
gcaatggtgg aaaagtggaa gcatcatcaa ggcaaagagc ttgatttgtt cgaagagttt 420
aaggtgctca cttcagatat cattgcacat acagcctttg gaagcagtta tttggaaggg 480
aaagttattt ttcagactct aagtaagctg agcatgatat tatttaagaa tcagttcaaa 540
cgaaggattc ctgttatcag caagttcttc agatcaaagg atgcgaggga gggagaggag 600
ctggaaagaa ggttgaaaaa ttccataatt tcaataatgg aaaagagaga agagaaggtg 660

```
ataagtggtg aagcagataa ctatggtaat gattttcttg gattactttt gaaggcaaag     720

aatgagcctg accagaggca gaggatttct gttgatgatg tagtggatga atgcaaaaca     780

gtttacttcg ctgggcaaga aactacaagt gttttgcttg cttggaccgc ctttctttta     840

gcaactcatg agcattggca agaagaagca agaaaggaag tgctgaatat gtttggcaac     900

aagaatccaa ctttagaagg catcacaaaa ttaaagatta tgagcatgat catcaaggaa     960

tctctaagat tatatcctcc agccccgccc atgtcaagga aggttaaaaa ggaagtcaga    1020

ttggggaagc tggttctccc ccccaacatt caagtaagca tctcaactat tgcagttcat    1080

catgatactg caatatgggg tgaagatgcc catgtattca aaccagaaag attttctgaa    1140

ggaacagcta aagatatccc atcagctgca tacatcccat ttggctttgg tcctcgaaac    1200

tgcatcggca atatcttggc catcaacgaa actaagattg cactgtcgat gattctacaa    1260

cgattttctt tcaccatctc cccggcctac gtccacgcac ctttccagtt cctcactatc    1320

tgcccccaac acggggttca ggtaaagctt cagtccctat taagtgaaag gtga          1374
```

<210> SEQ ID NO 16
<211> LENGTH: 1590
<212> TYPE: DNA
<213> ORGANISM: Siraitia grosvenorii

<400> SEQUENCE: 16

```
atggaagctg aatttggtgc cggtgctact atggtattat ccgttgtcgc aatcgtcttc      60

tttttcacat ttttacactt gtttgaatct ttctttttga agccagatag attgagatct     120

aagttgagaa agcaaggtat tggtggtcca tctccttcat tttgttgggg taatttgtca     180

gaaattaaat ccatcagagc tttgtcttca caagctaaga acgcagaaga tgcctctgct     240

ggtggtggtg gtggttccgc cagtatagct catggttgga cttcaaattt gtttcctcac     300

ttagaacaat ggagaaacag atatggtcca attttcgtat actccagtgg tacaatccaa     360

atcttgtgta tcacagaaat ggaaaccgtt aaggaaatct ctttgtcaac ctccttgagt     420

ttaggtaaac ctgctcattt gtctaaggat agaggtccat tgttaggttt gggtatctta     480

gcctcttcag gtcctatttg ggttcaccaa agaaagatca tcgctccaca attgtatttg     540

gataaagtaa agggtatgac ctcattgatg gttgaaagtg caaattctat gttaagatcc     600

tgggaaacta aagttgaaaa tcatggtggt caagccgaaa ttaacgtcga tggtgacttg     660

agagcattaa gtgccgatat catttctaag gcttgctttg gttcaaacta ttccgaaggt     720

gaagaaattt tcttgaagtt gagagcattg caagttgtca tgagtaaggg ttctattggt     780

atacctggtt ttagatacat accaactaaa aataacagag aaatgtggaa gttggaaaag     840

gaaatcgaat caatgatctt gaaggttgcc aacgaaagaa cacaacattc cagtcacgaa     900

caagatttgt tgcaaatgat tttggaaggt gcaaagtctt tgggtgaaga caataagagt     960

atgaacatat caagagacaa gtttattgtt gacaattgta agaacatcta tttcgctggt    1020

catgaaacta cagctataac cgcatcttgg tgcttgatgt tgttagctgc acaccctgat    1080

tggcaagcaa gagccagatc tgaagtttta caatgttgcg atgacagacc aatcgatgca    1140

gacacagtca aaaatatgaa gaccttgact atggtaattc aagaaacttt gagattgtac    1200

ccacctgctg tattcgttac aagacaagca ttagaagata tcagattcaa aaacatcaca    1260

ataccaaagg gtatgaactt tcatatacca atccctatgt tgcaacaaga cttccactta    1320

tggggtcctg atgcttgttc atttgaccca caaagattct ccaatggtgt cttaggtgca    1380

tgcaaaaacc cacaagccta tatgcctttt ggtgttggtc caagagtctg tgccggtcaa    1440
```

catttcgcta tgatcgaatt gaaagtcatc gtatcattgg ttttgtccag attcgaattt 1500
tctttgtcac cttcctacaa gcattcacca gccttcagat tagttgtcga accagaaaac 1560
ggtgtcatat tgcatgtcag aaagttgtga 1590

<210> SEQ ID NO 17
<211> LENGTH: 1554
<212> TYPE: DNA
<213> ORGANISM: Siraitia grosvenorii

<400> SEQUENCE: 17
atggaagtgg atatcaatat cttcaccgtc ttttccttcg tattatgcac agtcttcctc 60
ttctttctat ccttcttgat cctcctcctc ctccgaacgc tcgccggaaa atccataacg 120
agctccgagt acacgccagt gtacggcacc gtctacggtc aggctttcta tttcaacaac 180
ctgtacgatc atctaacgga ggtggccaag agacatcgaa ccttccggct gcttgcgccg 240
gcatacagcg agatatacac gaccgatccg agaaacatcg agcatatgtt gaagacgaaa 300
ttcgataagt attcgaaagg aagcaaggat caagaaatcg ttggggatct gtttggagag 360
gggatatttg cagtcgatgg agataagtgg aagcagcaga ggaagctggc tagctatgaa 420
ttctcgacga ggattcttag ggattttagc tgctcggttt tcagacgaag tgctgctaaa 480
cttgttggag ttgtttcgga gttttccagc atgggtcggg tttttgatat ccaggatttg 540
ctaatgcggt gcgctttgga ctccattttc aaagtggggt tcggggttga tttgaattgc 600
ttggaggaat caagcaaaga agggagcgat ttcatgaaag ccttcgatga ttctagcgct 660
cagatttttt ggcgctatat cgatcccttc tggaaattga agagattgct taacatcggt 720
tccgaagctt cgtttaggaa caacataaaa accatagatg cttttgtgca ccagttgatc 780
agagacaaga gaaaattgct tcagcaaccg aatcacaaga atgacaaaga ggacatactt 840
tggaggtttc tgatggaaag tgagaaggat ccaacaagaa tgaatgatca atatctaagg 900
gatatagtcc tcaatttcat gttggctggc aaagattcaa gtggaggaac tctgtcctgg 960
ttcttctaca tgctatgcaa gaacccttta atacaggaaa aagttgcaga agaagtgagg 1020
caaattgttg cgtttgaagg ggaagaagtt gacatcaatt tgttcataca aaacttaact 1080
gattcagctc ttgacaaaat gcattatctt catgcagcat tgaccgagac tctgaggcta 1140
tatcctgcag tccctttgga tggaaggact gcagaaatag atgacattct tcctgatggc 1200
tataaactaa gaaaagggga tggagtatac tacatggcct attccatggg caggatgtcc 1260
tccctttggg gagaagatgc tgaagatttt aaacccgaaa gatggcttga aagtggaact 1320
tttcaacccg aatcaccttt caaattcatc gcttttcatg cgggtcctcg aatgtgtttg 1380
ggaaaagagt ttgcttatcg acaaatgaag atagtatctg ctgctttgct tcaatttttt 1440
cgattcaaag tagctgatac aacgaggaat gtgacttata ggatcatgct tacccttcac 1500
attgatggag gtctccctct tcttgcaatt ccgagaatta gaaaatttac ctaa 1554

<210> SEQ ID NO 18
<211> LENGTH: 1686
<212> TYPE: DNA
<213> ORGANISM: Siraitia grosvenorii

<400> SEQUENCE: 18
ttggatagtg gagttaaaag agtgaaacgg ctagttgaag agaaacggcg agcagaattg 60
tctgcccgga ttgcctctgg agaattcaca gtcgaaaaag ctggttttcc atctgtattg 120
aggagtggct tatcaaagat gggtgttccc agtgagattc tggacatatt atttggtttc 180
gttgatgctc aagaagaata tcccaagatt cccgaagcaa aaggatcagt aaatgcaatt 240
cgtagtgagg ccttcttcat acctctctat gagctttatc tcacatatgg tggaatattt 300
aggttgactt ttgggccaaa gtcattcttg atagtttctg atccttccat tgctaaacat 360
atactgaagg ataatccgag gaattattct aagggtatct tagctgaaat tctagagttt 420
gtcatgggga agggacttat accagctgac gagaagatat ggcgtgtacg aaggcgggct 480
atagtcccat ctttgcatct gaagtatgta ggtgctatga ttaatctttt tggagaagct 540
gcagataggc tttgcaagaa gctagatgct gcagcatctg atggggttga tgtggaaatg 600
gagtccctgt tctcccgttt gactttagat atcattggca aggcagtttt taactatgac 660
tttgattcac ttacaaatga cactggcata gttgaggctg tttacactgt gctaagagaa 720
gcagaggatc gcagtgttgc accaattcca gtatgggaaa ttccaatttg gaaggatatt 780
tcaccacggc aaaaaaaggt ctctaaagcc ctcaaattga tcaacgacac cctcgatcaa 840
ctaattgcta tatgcaagag gatggttgat gaggaggagc tgcagtttca tgaggaatac 900
atgaatgagc aagatccaag catccttcat ttccttttgg catcaggaga tgatgtttca 960
agcaagcagc ttcgtgatga cttgatgact atgcttatag ctgggcatga aacatctgct 1020
gcagttttaa catggacctt ttatcttctt tccaaggagc cgaggatcat gtccaagctc 1080
caggaggagg ttgattcagt ccttggggat cggtttccaa ctattgaaga tatgaagaac 1140
ctcaaatatg ccacacgaat aattaacgaa tccttgaggc tttacccaca gccaccagtt 1200
ttaatacgtc gatctcttga caatgatatg ctcgggaagt accccattaa aaagggtgag 1260
gacatattca tttctgtttg gaacttgcat cgcagtccaa aactctggga tgatgcggat 1320
aaatttaatc ctgaaaggtg gcctctggat ggacccaatc caaatgagac aaatcaaaat 1380
ttcagatatt taccttttgg tggcggacca cggaaatgtg tgggagacat gtttgcttcg 1440
tacgagactg ttgtagcact tgcaatgctt gttcggcgat ttgacttcca aatggcactt 1500
ggagcacctc ctgtaaaaat gacaactgga gctacaattc acacaacaga tggattgaaa 1560
atgacagtta cacgaagaat gagacctcca atcataccca cattagagat gcctgcagtg 1620
gtcgttgact cgtctgtcgt ggactcgtcc gtcgccattt tgaaagaaga aacacaaatt 1680
ggttag 1686

<210> SEQ ID NO 19
<211> LENGTH: 1299
<212> TYPE: DNA
<213> ORGANISM: Siraitia grosvenorii

<400> SEQUENCE: 19
cagttcctct cctggtcctc ccagtttggc aagaggttca tcttctggaa tgggatcgag 60
cccagaatgt gcctcaccga gaccgatttg atcaaagagc ttctctctaa gtacagcgcc 120
gtctccggta agtcatggct tcagcaacag ggctccaagc acttcatcgg ccgcggtctc 180
ttaatggcca acggccaaaa ctggtaccac cagcgtcaca tcgtcgcgcc ggccttcatg 240
ggagacagac tcaagagtta cgccgggtac atggtggaat gcacaaagga gatgcttcag 300
tcaattgaaa acgaggtcaa ctcggggcga tccgagttcg aaatcggtga gtatatgacc 360
agactcaccg ccgatataat atcacgaacc gagttcgaaa gcagctacga aaagggaaag 420
caaattttcc atttgctcac cgttttacag catctctgcg ctcaggcgag ccgccacctc 480
tgccttcctg gaagccggtt ttttccgagt aaatacaaca gagagataaa ggcattgaag 540
acgaaggtgg aggggttgtt aatggagata atacagagca gaagagactg tgtggaggtg 600
gggaggagca gttcgtatgg aaatgatctg ttgggaatgt tgctgaatga gatgcagaag 660
aagaaagatg ggaatgggtt gagcttgaat ttgcagatta taatggatga atgcaagacc 720
ttcttcttcg ccggccatga aaccactgct cttttgctca cttggactgt aatgttattg 780
gccagcaacc cttcttggca acacaaggtt cgagccgaag ttatggccgt ctgcaatgga 840
ggaactctct ctcttgaaca tctctccaag ctctctctgt tgagtatggt gataaatgaa 900
tcgttgaggc tatacccgcc agcaagtatt cttccaagaa tggcatttga agatataaag 960
ctgggagatc ttgagatccc aaaagggctg tcgatatgga tcccagtgct tgcaattcac 1020
cacagtgaag agctatgggg caaagatgca aatgagttca acccagaaag atttgcaaat 1080
tcaaaagcct tcacttcggg gagattcatt ccctttgctt ctggccctcg caactgcgtt 1140
ggccaatcat ttgctctcat ggaaaccaag atcattttgg ctatgctcat ctccaagttt 1200
tccttcacca tctctgacaa ttatcgccat gcacccgtgg tcgtcctcac tataaaaccc 1260
aaatacggag tccaagtttg cttgaagcct ttcaattaa 1299

<210> SEQ ID NO 20
<211> LENGTH: 1506
<212> TYPE: DNA
<213> ORGANISM: Siraitia grosvenorii

<400> SEQUENCE: 20
atggaagaca ccttcctact ctatccttcc ctctctcttc tctttcttct ttttgctttc 60
aagctcatcc gtcgatccgg aggagttcgc aggaacttac cgccgagtcc gccctctctt 120
ccggttatcg gccacctcca tctcttgaaa aagccactcc accggacttt ccagaaactt 180
tccgccaaat atggtcctgt tatgtccctc cgcctcgggt ctcgcctcgc agtcattgta 240
tcgtcgtcgt cggcggtgga cgagtgtttc actaaaaacg acgtcgtgct cgccaaccgt 300
cctcgtttgc taattggcaa acacctcggc tacaactaca ctaccatggt tggggctccc 360
tacggcgacc actggcgtag cctccgccgc atcggtgccc tcgaaatctt ctcttcatct 420
cgcctcaaca aattcgccga catccgaagg gatgaagtag agggattgct tcgcaaactc 480
tcacgcaatt cgctccatca attctcgaaa gtggaagttc aatcggcctt gtcggagctg 540
acgttcaaca tctcgatgag aatggcggca gggaaacggt attacggaga tgacgtgacg 600
gacgaggaag aggcgagaaa gttcagagag ttaattaaac agatagtggc gctgggcgga 660
gtatcaaatc caggggattt cgtcccgatt ctgaattgga ttccgaacgg tttcgagagg 720
aagttgatcg agtgtgggaa gaagacggat gcgttcttgc aggggctgat cgaggaccac 780
cggagaaaga aggaagaggg taggaacacg atgatcgatc acctgctctc tctgcaagaa 840
tcggagcctg ctcactacgg agaccaaata atcaaaggat ttatactggt gttactgacg 900
gcggggaccg atacatcggc cgtgacaatg gagtgggcgc tatctcatct cctgaacaat 960
cctgaagtgc taaagaaggc aagagatgag gtcgacactg aaattggaca agaacgactt 1020
gtcgaagaat cagacgtagt atctaagtta ccctatcttc aagggatcat ctccgagact 1080
ctccggctga atcccgccgc tccgatgttg ttgccccatt acgcctcgga cgactgcacg 1140
atatgtggat acgacgtgcc acgtgacaca atcgtaatgg tcaatgcatg ggccatacat 1200
agggatccaa acgaatggga ggagcccacg tgtttcagac cagaacgata tgaaaagtcg 1260
tcgtcggaag cggaggtaca caagtcggtg agtttcgggg tgggaaggcg agcttgtcct 1320

-continued gggtctggca tggcgcagag ggtgatgggc ttgactttgg cggcactggt tcagtgcttc 1380
gagtgggaga gagttggaga agaagaagtg gacatgaacg aaggctcagg tgccacaatg 1440
cccaagatgg tgccattgga ggccatgtgc agagctcgtc ccatcgtcca caaccttctt 1500
tactga 1506

<210> SEQ ID NO 21
<211> LENGTH: 496
<212> TYPE: PRT
<213> ORGANISM: Arabidopsis thaliana

<400> SEQUENCE: 21

Met Ala Thr Glu Lys Thr His Gln Phe His Pro Ser Leu His Phe Val
1 5 10 15

Leu Phe Pro Phe Met Ala Gln Gly His Met Ile Pro Met Ile Asp Ile
20 25 30

Ala Arg Leu Leu Ala Gln Arg Gly Val Thr Ile Thr Ile Val Thr Thr
35 40 45

Pro His Asn Ala Ala Arg Phe Lys Asn Val Leu Asn Arg Ala Ile Glu
50 55 60

Ser Gly Leu Ala Ile Asn Ile Leu His Val Lys Phe Pro Tyr Gln Glu
65 70 75 80

Phe Gly Leu Pro Glu Gly Lys Glu Asn Ile Asp Ser Leu Asp Ser Thr
85 90 95

Glu Leu Met Val Pro Phe Phe Lys Ala Val Asn Leu Leu Glu Asp Pro
100 105 110

Val Met Lys Leu Met Glu Glu Met Lys Pro Arg Pro Ser Cys Leu Ile
115 120 125

Ser Asp Trp Cys Leu Pro Tyr Thr Ser Ile Ile Ala Lys Asn Phe Asn
130 135 140

Ile Pro Lys Ile Val Phe His Gly Met Gly Cys Phe Asn Leu Leu Cys
145 150 155 160

Met His Val Leu Arg Arg Asn Leu Glu Ile Leu Glu Asn Val Lys Ser
165 170 175

Asp Glu Glu Tyr Phe Leu Val Pro Ser Phe Pro Asp Arg Val Glu Phe
180 185 190

Thr Lys Leu Gln Leu Pro Val Lys Ala Asn Ala Ser Gly Asp Trp Lys
195 200 205

Glu Ile Met Asp Glu Met Val Lys Ala Glu Tyr Thr Ser Tyr Gly Val
210 215 220

Ile Val Asn Thr Phe Gln Glu Leu Glu Pro Pro Tyr Val Lys Asp Tyr
225 230 235 240

Lys Glu Ala Met Asp Gly Lys Val Trp Ser Ile Gly Pro Val Ser Leu
245 250 255

Cys Asn Lys Ala Gly Ala Asp Lys Ala Glu Arg Gly Ser Lys Ala Ala
260 265 270

Ile Asp Gln Asp Glu Cys Leu Gln Trp Leu Asp Ser Lys Glu Glu Gly
275 280 285

Ser Val Leu Tyr Val Cys Leu Gly Ser Ile Cys Asn Leu Pro Leu Ser
290 295 300

Gln Leu Lys Glu Leu Gly Leu Gly Leu Glu Glu Ser Arg Arg Ser Phe
305 310 315 320

Ile Trp Val Ile Arg Gly Ser Glu Lys Tyr Lys Glu Leu Phe Glu Trp
325 330 335

-continued

```
Met Leu Glu Ser Gly Phe Glu Glu Arg Ile Lys Glu Arg Gly Leu Leu
            340                 345                 350

Ile Lys Gly Trp Ala Pro Gln Val Leu Ile Leu Ser His Pro Ser Val
        355                 360                 365

Gly Gly Phe Leu Thr His Cys Gly Trp Asn Ser Thr Leu Glu Gly Ile
    370                 375                 380

Thr Ser Gly Ile Pro Leu Ile Thr Trp Pro Leu Phe Gly Asp Gln Phe
385                 390                 395                 400

Cys Asn Gln Lys Leu Val Val Gln Val Leu Lys Ala Gly Val Ser Ala
                405                 410                 415

Gly Val Glu Glu Val Met Lys Trp Gly Glu Glu Asp Lys Ile Gly Val
            420                 425                 430

Leu Val Asp Lys Glu Gly Val Lys Lys Ala Val Glu Glu Leu Met Gly
        435                 440                 445

Asp Ser Asp Asp Ala Lys Glu Arg Arg Arg Arg Val Lys Glu Leu Gly
    450                 455                 460

Glu Leu Ala His Lys Ala Val Glu Lys Gly Gly Ser Ser His Ser Asn
465                 470                 475                 480

Ile Thr Leu Leu Leu Gln Asp Ile Met Gln Leu Ala Gln Phe Lys Asn
                485                 490                 495


<210> SEQ ID NO 22
<211> LENGTH: 495
<212> TYPE: PRT
<213> ORGANISM: Arabidopsis thaliana

<400> SEQUENCE: 22

Met Val Ser Glu Thr Thr Lys Ser Ser Pro Leu His Phe Val Leu Phe
1               5                   10                  15

Pro Phe Met Ala Gln Gly His Met Ile Pro Met Val Asp Ile Ala Arg
            20                  25                  30

Leu Leu Ala Gln Arg Gly Val Ile Ile Thr Ile Val Thr Thr Pro His
        35                  40                  45

Asn Ala Ala Arg Phe Lys Asn Val Leu Asn Arg Ala Ile Glu Ser Gly
    50                  55                  60

Leu Pro Ile Asn Leu Val Gln Val Lys Phe Pro Tyr Leu Glu Ala Gly
65                  70                  75                  80

Leu Gln Glu Gly Gln Glu Asn Ile Asp Ser Leu Asp Thr Met Glu Arg
                85                  90                  95

Met Ile Pro Phe Phe Lys Ala Val Asn Phe Leu Glu Glu Pro Val Gln
            100                 105                 110

Lys Leu Ile Glu Glu Met Asn Pro Arg Pro Ser Cys Leu Ile Ser Asp
        115                 120                 125

Phe Cys Leu Pro Tyr Thr Ser Lys Ile Ala Lys Lys Phe Asn Ile Pro
    130                 135                 140

Lys Ile Leu Phe His Gly Met Gly Cys Phe Cys Leu Leu Cys Met His
145                 150                 155                 160

Val Leu Arg Lys Asn Arg Glu Ile Leu Asp Asn Leu Lys Ser Asp Lys
                165                 170                 175

Glu Leu Phe Thr Val Pro Asp Phe Pro Asp Arg Val Glu Phe Thr Arg
            180                 185                 190

Thr Gln Val Pro Val Glu Thr Tyr Val Pro Ala Gly Asp Trp Lys Asp
        195                 200                 205

Ile Phe Asp Gly Met Val Glu Ala Asn Glu Thr Ser Tyr Gly Val Ile
    210                 215                 220
```

```
Val Asn Ser Phe Gln Glu Leu Glu Pro Ala Tyr Ala Lys Asp Tyr Lys
225                 230                 235                 240

Glu Val Arg Ser Gly Lys Ala Trp Thr Ile Gly Pro Val Ser Leu Cys
                245                 250                 255

Asn Lys Val Gly Ala Asp Lys Ala Glu Arg Gly Asn Lys Ser Asp Ile
            260                 265                 270

Asp Gln Asp Glu Cys Leu Lys Trp Leu Asp Ser Lys Lys His Gly Ser
        275                 280                 285

Val Leu Tyr Val Cys Leu Gly Ser Ile Cys Asn Leu Pro Leu Ser Gln
    290                 295                 300

Leu Lys Glu Leu Gly Leu Gly Leu Glu Glu Ser Gln Arg Pro Phe Ile
305                 310                 315                 320

Trp Val Ile Arg Gly Trp Glu Lys Tyr Lys Glu Leu Val Glu Trp Phe
                325                 330                 335

Ser Glu Ser Gly Phe Glu Asp Arg Ile Gln Asp Arg Gly Leu Leu Ile
            340                 345                 350

Lys Gly Trp Ser Pro Gln Met Leu Ile Leu Ser His Pro Ser Val Gly
        355                 360                 365

Gly Phe Leu Thr His Cys Gly Trp Asn Ser Thr Leu Glu Gly Ile Thr
    370                 375                 380

Ala Gly Leu Pro Leu Leu Thr Trp Pro Leu Phe Ala Asp Gln Phe Cys
385                 390                 395                 400

Asn Glu Lys Leu Val Val Glu Val Leu Lys Ala Gly Val Arg Ser Gly
                405                 410                 415

Val Glu Gln Pro Met Lys Trp Gly Glu Glu Glu Lys Ile Gly Val Leu
            420                 425                 430

Val Asp Lys Glu Gly Val Lys Lys Ala Val Glu Glu Leu Met Gly Glu
        435                 440                 445

Ser Asp Asp Ala Lys Glu Arg Arg Arg Arg Ala Lys Glu Leu Gly Asp
    450                 455                 460

Ser Ala His Lys Ala Val Glu Glu Gly Gly Ser Ser His Ser Asn Ile
465                 470                 475                 480

Ser Phe Leu Leu Gln Asp Ile Met Glu Leu Ala Glu Pro Asn Asn
                485                 490                 495


<210> SEQ ID NO 23
<211> LENGTH: 495
<212> TYPE: PRT
<213> ORGANISM: Arabidopsis thaliana

<400> SEQUENCE: 23

Met Ala Phe Glu Lys Asn Asn Glu Pro Phe Pro Leu His Phe Val Leu
1               5                   10                  15

Phe Pro Phe Met Ala Gln Gly His Met Ile Pro Met Val Asp Ile Ala
            20                  25                  30

Arg Leu Leu Ala Gln Arg Gly Val Leu Ile Thr Ile Val Thr Thr Pro
        35                  40                  45

His Asn Ala Ala Arg Phe Lys Asn Val Leu Asn Arg Ala Ile Glu Ser
    50                  55                  60

Gly Leu Pro Ile Asn Leu Val Gln Val Lys Phe Pro Tyr Gln Glu Ala
65                  70                  75                  80

Gly Leu Gln Glu Gly Gln Glu Asn Met Asp Leu Leu Thr Thr Met Glu
                85                  90                  95

Gln Ile Thr Ser Phe Phe Lys Ala Val Asn Leu Leu Lys Glu Pro Val
```

-continued

```
            100                 105                 110

Gln Asn Leu Ile Glu Glu Met Ser Pro Arg Pro Ser Cys Leu Ile Ser
        115                 120                 125

Asp Met Cys Leu Ser Tyr Thr Ser Glu Ile Ala Lys Lys Phe Lys Ile
    130                 135                 140

Pro Lys Ile Leu Phe His Gly Met Gly Cys Phe Cys Leu Leu Cys Val
145                 150                 155                 160

Asn Val Leu Arg Lys Asn Arg Glu Ile Leu Asp Asn Leu Lys Ser Asp
                165                 170                 175

Lys Glu Tyr Phe Ile Val Pro Tyr Phe Pro Asp Arg Val Glu Phe Thr
            180                 185                 190

Arg Pro Gln Val Pro Val Glu Thr Tyr Val Pro Ala Gly Trp Lys Glu
        195                 200                 205

Ile Leu Glu Asp Met Val Glu Ala Asp Lys Thr Ser Tyr Gly Val Ile
    210                 215                 220

Val Asn Ser Phe Gln Glu Leu Glu Pro Ala Tyr Ala Lys Asp Phe Lys
225                 230                 235                 240

Glu Ala Arg Ser Gly Lys Ala Trp Thr Ile Gly Pro Val Ser Leu Cys
                245                 250                 255

Asn Lys Val Gly Val Asp Lys Ala Glu Arg Gly Asn Lys Ser Asp Ile
            260                 265                 270

Asp Gln Asp Glu Cys Leu Glu Trp Leu Asp Ser Lys Glu Pro Gly Ser
        275                 280                 285

Val Leu Tyr Val Cys Leu Gly Ser Ile Cys Asn Leu Pro Leu Ser Gln
    290                 295                 300

Leu Leu Glu Leu Gly Leu Gly Leu Glu Glu Ser Gln Arg Pro Phe Ile
305                 310                 315                 320

Trp Val Ile Arg Gly Trp Glu Lys Tyr Lys Glu Leu Val Glu Trp Phe
                325                 330                 335

Ser Glu Ser Gly Phe Glu Asp Arg Ile Gln Asp Arg Gly Leu Leu Ile
            340                 345                 350

Lys Gly Trp Ser Pro Gln Met Leu Ile Leu Ser His Pro Ser Val Gly
        355                 360                 365

Gly Phe Leu Thr His Cys Gly Trp Asn Ser Thr Leu Glu Gly Ile Thr
    370                 375                 380

Ala Gly Leu Pro Met Leu Thr Trp Pro Leu Phe Ala Asp Gln Phe Cys
385                 390                 395                 400

Asn Glu Lys Leu Val Val Gln Ile Leu Lys Val Gly Val Ser Ala Glu
                405                 410                 415

Val Lys Glu Val Met Lys Trp Gly Glu Glu Glu Lys Ile Gly Val Leu
            420                 425                 430

Val Asp Lys Glu Gly Val Lys Lys Ala Val Glu Glu Leu Met Gly Glu
        435                 440                 445

Ser Asp Asp Ala Lys Glu Arg Arg Arg Arg Ala Lys Glu Leu Gly Glu
    450                 455                 460

Ser Ala His Lys Ala Val Glu Glu Gly Gly Ser Ser His Ser Asn Ile
465                 470                 475                 480

Thr Phe Leu Leu Gln Asp Ile Met Gln Leu Ala Gln Ser Asn Asn
                485                 490                 495
```

<210> SEQ ID NO 24
<211> LENGTH: 495
<212> TYPE: PRT
<213> ORGANISM: Stevia rebaudiana

<400> SEQUENCE: 24

```
Met Ser Pro Lys Met Val Ala Pro Pro Thr Asn Leu His Phe Val Leu
1               5                   10                  15

Phe Pro Leu Met Ala Gln Gly His Leu Val Pro Met Val Asp Ile Ala
            20                  25                  30

Arg Ile Leu Ala Gln Arg Gly Ala Thr Val Thr Ile Ile Thr Thr Pro
        35                  40                  45

Tyr His Ala Asn Arg Val Arg Pro Val Ile Ser Arg Ala Ile Ala Thr
    50                  55                  60

Asn Leu Lys Ile Gln Leu Leu Glu Leu Gln Leu Arg Ser Thr Glu Ala
65                  70                  75                  80

Gly Leu Pro Glu Gly Cys Glu Ser Phe Asp Gln Leu Pro Ser Phe Glu
                85                  90                  95

Tyr Trp Lys Asn Ile Ser Thr Ala Ile Asp Leu Leu Gln Gln Pro Ala
            100                 105                 110

Glu Asp Leu Leu Arg Glu Leu Ser Pro Pro Pro Asp Cys Ile Ile Ser
        115                 120                 125

Asp Phe Leu Phe Pro Trp Thr Thr Asp Val Ala Arg Arg Leu Asn Ile
    130                 135                 140

Pro Arg Leu Val Phe Asn Gly Pro Gly Cys Phe Tyr Leu Leu Cys Ile
145                 150                 155                 160

His Val Ala Ile Thr Ser Asn Ile Leu Gly Glu Asn Glu Pro Val Ser
                165                 170                 175

Ser Asn Thr Glu Arg Val Val Leu Pro Gly Leu Pro Asp Arg Ile Glu
            180                 185                 190

Val Thr Lys Leu Gln Ile Val Gly Ser Ser Arg Pro Ala Asn Val Asp
        195                 200                 205

Glu Met Gly Ser Trp Leu Arg Ala Val Glu Ala Glu Lys Ala Ser Phe
    210                 215                 220

Gly Ile Val Val Asn Thr Phe Glu Glu Leu Glu Pro Glu Tyr Val Glu
225                 230                 235                 240

Glu Tyr Lys Thr Val Lys Asp Lys Lys Met Trp Cys Ile Gly Pro Val
                245                 250                 255

Ser Leu Cys Asn Lys Thr Gly Pro Asp Leu Ala Glu Arg Gly Asn Lys
            260                 265                 270

Ala Ala Ile Thr Glu His Asn Cys Leu Lys Trp Leu Asp Glu Arg Lys
        275                 280                 285

Leu Gly Ser Val Leu Tyr Val Cys Leu Gly Ser Leu Ala Arg Ile Ser
    290                 295                 300

Ala Ala Gln Ala Ile Glu Leu Gly Leu Gly Leu Glu Ser Ile Asn Arg
305                 310                 315                 320

Pro Phe Ile Trp Cys Val Arg Asn Glu Thr Asp Glu Leu Lys Thr Trp
                325                 330                 335

Phe Leu Asp Gly Phe Glu Glu Arg Val Arg Asp Arg Gly Leu Ile Val
            340                 345                 350

His Gly Trp Ala Pro Gln Val Leu Ile Leu Ser His Pro Thr Ile Gly
        355                 360                 365

Gly Phe Leu Thr His Cys Gly Trp Asn Ser Thr Ile Glu Ser Ile Thr
    370                 375                 380

Ala Gly Val Pro Met Ile Thr Trp Pro Phe Phe Ala Asp Gln Phe Leu
385                 390                 395                 400

Asn Glu Ala Phe Ile Val Glu Val Leu Lys Ile Gly Val Arg Ile Gly
```

-continued

```
                405                 410                 415

Val Glu Arg Ala Cys Leu Phe Gly Glu Glu Asp Lys Val Gly Val Leu
            420                 425                 430

Val Lys Lys Glu Asp Val Lys Lys Ala Val Glu Cys Leu Met Asp Glu
        435                 440                 445

Asp Glu Asp Gly Asp Gln Arg Arg Lys Arg Val Ile Glu Leu Ala Lys
    450                 455                 460

Met Ala Lys Ile Ala Met Ala Glu Gly Gly Ser Ser Tyr Glu Asn Val
465                 470                 475                 480

Ser Ser Leu Ile Arg Asp Val Thr Glu Thr Val Arg Ala Pro His
                485                 490                 495


<210> SEQ ID NO 25
<211> LENGTH: 481
<212> TYPE: PRT
<213> ORGANISM: Stevia rebaudiana

<400> SEQUENCE: 25

Met Asp Ala Met Ala Thr Thr Glu Lys Lys Pro His Val Ile Phe Ile
1               5                   10                  15

Pro Phe Pro Ala Gln Ser His Ile Lys Ala Met Leu Lys Leu Ala Gln
            20                  25                  30

Leu Leu His His Lys Gly Leu Gln Ile Thr Phe Val Asn Thr Asp Phe
        35                  40                  45

Ile His Asn Gln Phe Leu Glu Ser Ser Gly Pro His Cys Leu Asp Gly
    50                  55                  60

Ala Pro Gly Phe Arg Phe Glu Thr Ile Pro Asp Gly Val Ser His Ser
65                  70                  75                  80

Pro Glu Ala Ser Ile Pro Ile Arg Glu Ser Leu Leu Arg Ser Ile Glu
                85                  90                  95

Thr Asn Phe Leu Asp Arg Phe Ile Asp Leu Val Thr Lys Leu Pro Asp
            100                 105                 110

Pro Pro Thr Cys Ile Ile Ser Asp Gly Phe Leu Ser Val Phe Thr Ile
        115                 120                 125

Asp Ala Ala Lys Lys Leu Gly Ile Pro Val Met Met Tyr Trp Thr Leu
    130                 135                 140

Ala Ala Cys Gly Phe Met Gly Phe Tyr His Ile His Ser Leu Ile Glu
145                 150                 155                 160

Lys Gly Phe Ala Pro Leu Lys Asp Ala Ser Tyr Leu Thr Asn Gly Tyr
                165                 170                 175

Leu Asp Thr Val Ile Asp Trp Val Pro Gly Met Glu Gly Ile Arg Leu
            180                 185                 190

Lys Asp Phe Pro Leu Asp Trp Ser Thr Asp Leu Asn Asp Lys Val Leu
        195                 200                 205

Met Phe Thr Thr Glu Ala Pro Gln Arg Ser His Lys Val Ser His His
    210                 215                 220

Ile Phe His Thr Phe Asp Glu Leu Glu Pro Ser Ile Ile Lys Thr Leu
225                 230                 235                 240

Ser Leu Arg Tyr Asn His Ile Tyr Thr Ile Gly Pro Leu Gln Leu Leu
                245                 250                 255

Leu Asp Gln Ile Pro Glu Glu Lys Lys Gln Thr Gly Ile Thr Ser Leu
            260                 265                 270

His Gly Tyr Ser Leu Val Lys Glu Glu Pro Glu Cys Phe Gln Trp Leu
        275                 280                 285
```

```
Gln Ser Lys Glu Pro Asn Ser Val Val Tyr Val Asn Phe Gly Ser Thr
    290                 295                 300

Thr Val Met Ser Leu Glu Asp Met Thr Glu Phe Gly Trp Gly Leu Ala
305                 310                 315                 320

Asn Ser Asn His Tyr Phe Leu Trp Ile Ile Arg Ser Asn Leu Val Ile
                325                 330                 335

Gly Glu Asn Ala Val Leu Pro Pro Glu Leu Glu Glu His Ile Lys Lys
            340                 345                 350

Arg Gly Phe Ile Ala Ser Trp Cys Ser Gln Glu Lys Val Leu Lys His
        355                 360                 365

Pro Ser Val Gly Gly Phe Leu Thr His Cys Gly Trp Gly Ser Thr Ile
    370                 375                 380

Glu Ser Leu Ser Ala Gly Val Pro Met Ile Cys Trp Pro Tyr Ser Trp
385                 390                 395                 400

Asp Gln Leu Thr Asn Cys Arg Tyr Ile Cys Lys Glu Trp Glu Val Gly
                405                 410                 415

Leu Glu Met Gly Thr Lys Val Lys Arg Asp Glu Val Lys Arg Leu Val
            420                 425                 430

Gln Glu Leu Met Gly Glu Gly Gly His Lys Met Arg Asn Lys Ala Lys
        435                 440                 445

Asp Trp Lys Glu Lys Ala Arg Ile Ala Ile Ala Pro Asn Gly Ser Ser
    450                 455                 460

Ser Leu Asn Ile Asp Lys Met Val Lys Glu Ile Thr Val Leu Ala Arg
465                 470                 475                 480

Asn


<210> SEQ ID NO 26
<211> LENGTH: 1380
<212> TYPE: DNA
<213> ORGANISM: Siraitia grosvenorii

<400> SEQUENCE: 26

atggatgccc agcgaggtca caccaccacc attttgatgc ttccatgggt cggctacggc     60

catctcttgc ctttcctcga gctggccaaa agcctctcca ggaggaaatt attccacatc    120

tacttctgtt caacgtctgt tagcctcgac gccattaaac caaagcttcc tccttctatc    180

tcttctgatg attccatcca acttgtggaa cttcgtctcc cttcttctcc tgagttacct    240

cctcatcttc acacaaccaa cggccttccc tctcacctca tgcccgctct ccaccaagcc    300

ttcgtcatgg ccgcccaaca ctttcaggtc attttacaaa cacttgcccc gcatctcctc    360

atttatgaca ttctccaacc ttgggctcct caagtggctt catccctcaa cattccagcc    420

atcaacttca gtactaccgg agcttcaatg ctttctcgaa cgcttcaccc tactcactac    480

ccaagttcta aattcccaat ctcagagttt gttcttcaca atcactggag agccatgtac    540

accaccgccg atggggctct tacagaagaa ggccacaaaa ttgaagaaac acttgcgaat    600

tgcttgcata cttcttgcgg ggtagttttg gtcaatagtt tcagagagct tgagacgaaa    660

tatatcgatt atctctctgt tctcttgaac aagaaagttg ttccggtcgg tcctttggtt    720

tacgaaccga atcaagaagg ggaagatgaa ggttattcaa gcatcaaaaa ttggcttgac    780

aaaaaggaac cgtcctcaac cgtcttcgtt tcatttggaa ccgaatactt cccgtcaaag    840

gaagaaatgg aagagatagc gtatgggtta gagctgagcg aggttaattt catctgggtc    900

cttagatttc ctcaaggaga cagcaccagc accattgaag acgccttgcc gaaggggttt    960

ctggagagag cgggagagag ggcgatggtg gtgaagggtt gggctcctca ggcgaagata   1020
```

ctgaagcatt ggagcacagg ggggcttgtg agtcactgtg gatggaactc gatgatggag 1080
ggcatgatgt ttggcgtacc cataatagcg gtcccgatgc atctggacca gccctttaac 1140
gccggactct tggaagaagc tggcgtcggc gtggaagcca agcgaggttc ggacggcaaa 1200
attcaaagag aagaagttgc aaagtcgatc aaagaagtgg tgattgagaa aaccagggaa 1260
gacgtgagga agaaagcaag agaaatgggt gagattttga ggagtaaagg agatgagaaa 1320
attgatgagt tggtggctga aatttctctt ttgcgcaaaa aggctccatg ttcaatttaa 1380

<210> SEQ ID NO 27
<211> LENGTH: 1434
<212> TYPE: DNA
<213> ORGANISM: Siraitia grosvenorii

<400> SEQUENCE: 27
atgcttccat ggctggctca cggccatgtc tccccttct tcgagctcgc caagttgctc 60
gccgctagaa acttccacat attcttctgc tccaccgccg taaacctccg ctccgtcgaa 120
ccaaaactct ctcagaagct ctcctcccac gtggagctgg tggagctcaa cctaccgccc 180
tcgccggagc tccctccgca ccgccacacc accgccggcc ttccaccgca cctcatgttc 240
tcgctcaagc gagctttcga catggccgct cccgccttcg ccgccatcct ccgcgacctg 300
aacccggact tgctcatcta cgacttcctg cagccgtggg cggcggcgga ggctctgtcg 360
gcggatattc cggccgtgat gttcaaaagc acgggtgcgc tcatggcggc catggtcgcg 420
tacgagctga cgtttccgaa ctctgatttt ttctcgcttt tccctgagat tcgtctctcc 480
gagtgcgaga ttaaacagct gaagaacttg tttcaatgtt ctgtgaatga tgcgaaagac 540
aagcaaagga ttaagggatg ttatgagaga tcttgcggca tgattttggt gaaatctttc 600
agagaaatcg aaggcaaata tattgatttt ctctctactc tgctgggcaa gaaggttgtt 660
ccagttggtc cacttgttca acaaacagaa gacgacgtcg tatcaggaag ttttgacgaa 720
tggctaaatg gaaaagatag atcgtcttcc atactcgtgt ctttcggaag cgagttctac 780
ctgtccagag aagacatgga agagatcgcg catggcttag agctgagcca ggtgaacttc 840
atatgggtcg tcaggtttcc ggcgggagga gagagaaaca cgacaaaggt ggaagaagaa 900
ctgccaaaag ggtttctaga gagagttaga gagagaggga tggtggtgga gggctgggcg 960
ccgcaggctc agatcttgaa acatccaagc gtcggcggat tcctcagcca ctgcgggtgg 1020
agctccgtcg tggagagcat gaaattcggc gttccgatca tcgccatgcc gatgcacctc 1080
gaccagccgc tgaattcccg gctggtcgag cggctcggcg tcggcgtagt ggtggagaga 1140
gacggccgcc tccggggaga ggtggagaga gttgtcagag aggtggtggt ggagaaaagt 1200
ggagagagag tgaggaagaa ggtggaggag tttgcagaga tcatgaagaa gaaaaaagac 1260
aatgaagaga tggacgtagt cgtggaagag ttggtgacgc tctgcaggaa gaagaagaag 1320
gaggaggatt tacagagtaa ttattggtgc agaaccgcca ttgatgacca ttgttctgaa 1380
gtcgtgaaga ttgaagatgc tgcagcagcc gacgaggagc ctctttgcaa ataa 1434

<210> SEQ ID NO 28
<211> LENGTH: 1383
<212> TYPE: DNA
<213> ORGANISM: Siraitia grosvenorii

<400> SEQUENCE: 28
atggctgtca cttacagcct gcacatagca atgtaccctt ggtttgcttt cggccacttg 60
actccatttc tccaagtctc caacaagctt gccaaggaag gccacaaaat ctccttcttc 120
atcccaacga aaacgctaac caaattgcag cctttcaatc tctttccaga tctcattacc 180
tttgtcccca tcactgttcc tcatgttgat ggtctccctc ttggagctga gactactgct 240
gatgtttctc acccttcaca gctcagtctc atcatgactg ctatggattg cacccaaccc 300
gaaatcgagt gtcttcttcg agacataaaa cctgatgcca tcttcttcga tttcgcgcac 360
tgggtgccaa aattggcatg tggattgggc attaagtcga ttgattacag tgtctgttct 420
gcagtatcaa ttggttatgt tttgccccta ttaaggaaag tttgtggaca agatttatta 480
actgaagatg attttatgca gccatctcct ggctacccga gttccaccat caatcttcaa 540
gctcatgagg ctcgatattt tgcatctctg agccgctgga ggtttggcag tgatgtccct 600
ttctttagtc gccatcttac tgcacttaat gaatgcaatg ctttagcatt caggtcatgt 660
agggagattg aagggccttt tatagactat ccagaaagtg aattaaaaaa gcctgtgttg 720
ctttccggag cagtggatct acaaccgcca accacaactg tagaagaaag atgggcaaaa 780
tggctatcag ggttcaacac cgactcggtc gtatattgtg catttggaag tgagtgtacc 840
ttagcaaaag accaattcca agaactgctg ttgggttttg agctttcaaa tatgccattc 900
tttgctgcac ttaaaccacc ttttggtgtt gactcggttg aagcagcctt gcctgaaggt 960
tttgaacaga gagttcaggg aagaggggtg gtctatgggg gatgggtcca acagcagctc 1020
attttggagc acccatcaat tggatgcttt gttacacatt gtggatcagg ctccttatca 1080
gaggcgttag tgaagaagtg tcaattagtg ttgttacctc gtatcggtga ccactttttc 1140
cgagcaagaa tgttgagcaa ttatttgaaa gttggtgtgg aggtagagaa aggagaagga 1200
gatggatctt ttacaaagga aagtgtgtgg aaggcagtga agacagtgat ggatgaagag 1260
aatgaaactg ggaaagagtt cagagcgaac cgtgccaaga taagagagct attgctcgac 1320
gaagatctcg aggagtctta tatcaacaat ttcatccaca gcctgcatac tttgaatgca 1380
tga 1383

<210> SEQ ID NO 29
<211> LENGTH: 174
<212> TYPE: DNA
<213> ORGANISM: Artificial sequence
<220> FEATURE:
<223> OTHER INFORMATION: Partial nucleotide sequence from Siraitia grosvenorii

<400> SEQUENCE: 29
atggcggatc ggaaagagag cgttgtgatg ttcccgttca tggggcaggg ccatatcatc 60
ccttttctag ctttggccct ccagattgag cacagaaaca gaaactacgc catatacttg 120
gtaaatactc ctctcaacgt taagaaaatg agatcttctc tccctccaga ttga 174

<210> SEQ ID NO 30
<211> LENGTH: 1347
<212> TYPE: DNA
<213> ORGANISM: Siraitia grosvenorii

<400> SEQUENCE: 30
atggaagcta agaactgcaa aaaggttctg atgttcccat ggctggcgca tggtcacata 60
tcaccatttg tagagctggc caagaagctc acagacaaca acttcgccgt ttttctatgt 120
tcttcccctg caaatcttca aaacgtcaag ccaaaactcc cccatcacta ctctgattcc 180
attgaactcg tggagctcaa ccttccatcg tcgccggagc ttccccctca tatgcacacc 240

-continued

```
accaatggcc tccctttgca tttagttccc accctcgttg acgccttgga catggccgct    300
ccgcacttct ccgccatttt acaggaactg aatccagatt ttctcatatt cgacatcttc    360
caaccctggg cggctgaaat cgcttcctcc ttcggcgttc ctgctatttt gttgcttatc    420
gttggatctg ctataaccgc tttaggggtt cattttgtcc ggagctccgg tacggaattc    480
ccctttcccg agcttactaa atcattcaag aaggaggacg accgaaaacc tccaggagat    540
tccggcaacg atagaggaaa acggctattc aaatgtctgc tggacctgga acattcttca    600
gagactattt tggtgaacag ttttacagag atagagggca aatatatgga ctatctctcg    660
gtcttactga agaagaagat ccttccgatt ggtcctttgg ttcagaaaat tggctccgat    720
gacgatgaat cgggaatcct ccggtggctt gacaagaaga aaccgaattc aactgtgtac    780
gtttcgttcg ggagtgagta ctatttgagc aaagaagaca tagcagagct tgcgcatggt    840
ctggaaatca gcggcgtcaa tttcatctgg attgttcggt ttccaaaggg agagaaaatc    900
gccattgaag aggcattacc agatgaattt cttgaaagag tcggagagag aggcgtcgtc    960
gttgatggat gggcgccgca gatgaaaata ttagggcatt cgagcgtcgg cgggtttctg   1020
tctcactgcg gatggaactc tgtgctggag agtctggtgc tcggcgtgcc gatcatatcc   1080
ctgccgatac acctcgaaca gccgtggaac gccttggtag cggagcacgt cggcgtttgt   1140
gtgagggcga agagagacga cggaggaaat cttcaaagag agttggtggc ggaggccatt   1200
aaagaagtgg tggttgagga aacaggagcg gaactgagaa gcaaagcaag agtaattagt   1260
gaaatcttga aaaataaaga agctgaaaca atacaagatt tggtggctga gcttcaccgg   1320
ctttctgacg caagaagagc ttgttga                                       1347
```

<210> SEQ ID NO 31
<211> LENGTH: 1389
<212> TYPE: DNA
<213> ORGANISM: Siraitia grosvenorii

<400> SEQUENCE: 31

```
atggaaaaaa atcttcacat agtgatgctt ccatggtcgg cgttcggcca tctcatacca     60
ttttttcacc tctccatagc cttagccaaa gccaaagttt atatctcctt cgtctccact    120
ccaagaaata ttcagagact ycccccaaatc ccgccggact tagcttcttt catagatttg    180
gtggccattc ccttgccgag actcgacgac gatctgttgc tagaatctgc agaggccact    240
tctgatattc cgatcgacaa gattcagtat ttgaagcgag ccgtcgacct cctccgccac    300
cccttcaaga agtttgtcgc cgaacaatcg ccggactggg tcgtcgttga ttttcatgct    360
tattgggccg gcgagatcta ccaggagttt caagttcccg tcgcctactt ctgtattttc    420
tcggccatct gtttgcttta tcttggacct ccagacgtgt attcgaagga tcctcagatc    480
atggcacgaa tatctcccgt taccatgacg gtgccgccgg agtgggtcgg ttttccgtcc    540
gccgtagcct acaacttgca tgaggcgacg gtcatgtact ctgctctcta tgaaacaaat    600
gggtctggaa taagcgactg cgagaggatt cgccggctcg tcctttcctg tcaagccgtg    660
gccattcgaa gctgcgagga gattgaaggc gaatacctta ggttatgtaa gaaactgatt    720
ccaccgcagg ggattgccgt cggcttgctt ccgccggaaa agccaccaaa atcagatcac    780
gagctcatca aatggcttga cgagcaaaag ctccgattcg tcgtgtacgt gacattcggc    840
agcgaatgca acctgacgaa ggaccaagtt cacgagatag cccacgggct ggaactgtcg    900
gagctgccat ttttatgggc actgaggaaa cccagctggg cagctgagga agacgatggg    960
ctgccgtctg ggtttcgtga gagaacgtcc gggagagggg tggtgagcat ggagtgggtg   1020
```

ccgcagttgg agattctggc gcaccaggcc atcggcgtct ctttagttca cgggggctgg 1080
ggctctatta tcgagtcgct acaagctggg cactgtctgg ttgtgctgcc gtttatcatc 1140
gaccagccgc tgaactcaaa gcttttggtg gagaaaggga tggcgcttga gatcagaagg 1200
aacggttctg atggatggtt tagtagagaa gacatcgccg gaactttgag agaagctatg 1260
cggtcgtctg aggaaggcgg gcagctgagg agccgtgcaa aagaggcggc ggccatcgtt 1320
ggagatgaga agctgcagtg ggaacaatac ttcggcgcgt tcgtacagtt tctgagggac 1380
aagtcttga 1389

<210> SEQ ID NO 32
<211> LENGTH: 1395
<212> TYPE: DNA
<213> ORGANISM: Siraitia grosvenorii

<400> SEQUENCE: 32
atgtccgagg agaaaggcag agggcacagc tcgtcgacgg agagacacac tgctgccgcc 60
atgaacgccg agaaacgaag caccaaaatc ttgatgctcc catggctggc tcacggccac 120
atatctccat acttcgagct cgccaagagg ctcaccaaga aaaactgcca cgtttacttg 180
tgttcttcgc ctgtaaatct ccaaggcatc aagccgaaac tctctgaaaa ttactcttcc 240
tccattgaac ttgtggagct tcatcttcca tctctccccg accttcctcc ccatatgcac 300
acgaccaaag gcatccctct acatctacaa tccaccctca tcaaagcctt cgacatggcc 360
gcccctgatt tttccgacct gttgcagaaa ctcgagccgg atctcgtcat ttccgatctc 420
ttccagccat gggcagttca attagcgtcg tctcggaaca ttcccgtcgt caatttcgtt 480
gtcaccggag tcgctgttct tagtcgtttg gctcacgtgt tttgcaactc cgttaaggaa 540
ttccctttcc cggaactcga tctaaccgac cattggatct ccaagagccg ccgcaaaacg 600
tccgacgaat taggtcgcga gtgcgcgatg cgatttttca actgcatgaa acaatcttca 660
aacatcactc tagccaacac tttccccgag ttcgaagaaa aatacatcga ttatctctct 720
tcctcgttta agaaaaagat tcttccggtt gctcctctag ttcctgaaat cgacgcagac 780
gacgagaaat cggaaattat cgagtggctt gacaagaaga aaccgaaatc gactgtttac 840
gtttcgtttg ggagtgagta ttatctgacg aaagaagaca gggaagagct cgcccatggc 900
ttagaaaaga gcggcgtgaa tttcatctgg gttattaggt ttccaaaggg cgagaagatc 960
accattgaag aggctttacc agaaggattt ctcgagagag taggggacag gggagtgatt 1020
atcgacgggt gggcgccgca gttgaaaata ttgaggcatt caagcgtggg cgggttcgtg 1080
tgccactgcg ggtggaactc tgtggtggag agcgtggtgt ttggggtgcc gatcatagcc 1140
ttgccgatgc agctcgatca gccatggcat gcgaaggtgg cggaggacgg cggcgtctgt 1200
gcggaggcga agagagacgt tgaagggagc gttcagagag aagaggtggc gaaggccatt 1260
aaagaggtgg tgtttgagaa gaagggggggg gttctgagtg gaaaagcaag agagatcagc 1320
gaggccttga gaaagaggga aggggaaatc atagaggaat tggttgctga gtttcaccag 1380
ctctgtgaag cttga 1395

<210> SEQ ID NO 33
<211> LENGTH: 1242
<212> TYPE: DNA
<213> ORGANISM: Artificial sequence
<220> FEATURE:
<223> OTHER INFORMATION: Partial nucleotide sequence from Siraitia grosvenorii

<400> SEQUENCE: 33
ttctgctcca cgcctgtaaa tttggaagcc attaaaccaa agctttccaa aagctactct 60
gattcgatcc aactaatgga ggttcctctc gaatcgacgc cggagcttcc tcctcactat 120
catacagcca aaggccttcc gccgcattta atgcccaaac tcatgaatgc ctttaaaatg 180
gttgctccca atctcgaatc gatcctaaaa accctaaacc cagatctgct catcgtcgac 240
attctccttc catggatgct tccactcgct tcatcgctca aaattccgat ggttttcttc 300
actattttcg gtgccatggc catctccttt atgatttata atcgaaccgt ctcgaacgag 360
cttccatttc cagaatttga acttcacgag tgctggaaat cgaagtgccc ctatttgttc 420
aaggaccaag cggaaagtca atcgttctta gaatacttgg atcaatcttc aggcgtaatt 480
ttgatcaaaa cttccagaga gattgaggct aagtatgtag actttctcac ttcgtcgttt 540
acgaagaagg ttgtgaccac cggtcccctg gttcagcaac cttcttccgg cgaagacgag 600
aagcagtact ccgatatcat cgaatggcta gacaagaagg agccgttatc gacggtgctc 660
gtttcgtttg ggagcgagta ttatctgtca aaggaagaga tggaagaaat cgcctacggg 720
ctggagagcg ccagcgaggt gaatttcatc tggattgtta ggtttccgat gggacaggaa 780
acggaggtcg aggcggcgct gccggagggg ttcatccaga gggcaggaga gagagggaaa 840
gtggtcgagg gctgggctcc gcaggcgaaa atattggcgc atccgagcac cggcggccat 900
gtgagccaca acgggtggag ctcgattgtg gagtgcttga tgtccggtgt accggtgatc 960
ggcgcgccga tgcaacttga cgggccaatc gtcgcaaggc tggtggagga gatcggcgtg 1020
ggtttggaaa tcaagagaga tgaggaaggg agaatcacga ggggcgaagt tgccgatgca 1080
atcaagacgg tggcggtggg caaaaccggg gaagatttta gaaggaaagc aaaaaaaatc 1140
agcagcattt tgaagatgaa agatgaagaa gaggttgaca ctttggcaat ggaattagtg 1200
aggttatgcc aaatgaaaag agggcaggag tctcaggact aa 1242

<210> SEQ ID NO 34
<211> LENGTH: 912
<212> TYPE: DNA
<213> ORGANISM: Artificial sequence
<220> FEATURE:
<223> OTHER INFORMATION: Partial nucleotide sequence from Siraitia grosvenorii

<400> SEQUENCE: 34
tcccggtcaa cggtagagga cttcacggag cttcgagagt ggatgccttc tggatcgaac 60
atggtctacc ggtaccacga gattaaaaaa tccttagatg gagcaaccgg caacgaatcg 120
gggacgtctg attcggtccg attcggaatt gtgattgagg agagtgttgc tgtggctgta 180
agaagctccc ctgaactgga accggaatgg ttcgatttgc tcgcgaagct ttaccagaag 240
ccagttgttc cggtaggatt tctacctcca gtaattgaag atgcggaaga attgagcagc 300
gatatcaagg aatggttaga caaacagagc tcaaactcgg tcctttacgt cgcattcggg 360
accgaggcga ctctgagtca agatgacgtc actgagttag ccatggggct tgagcaatct 420
gggataccat ttttctgggt actgagaacc tcacctcggg acgagtcaga catgttaccg 480
gccgggttca aggagcgagt cgaaggtcga ggaagtgttc acgtgggatg ggtctcgcag 540
gtgaagatac tgagtcacga ctcggttggc ggttgtttga cacactgtgg atggaactcg 600
atcatagagg ggctcggatt cgggcgcgtt atggtattgt ttccagtcgt gaacgaccag 660
ggattgaacg ctagattgtt gggggagaag aagctcggga tagagataga aagggacgag 720

-continued cgagatggat cgttcacacg cgactcggtg tcggaatcgg tgaggtcggc aatggcggaa 780
agttcaggcg aggccttgag agtgagggcc agggaaatga aggggttgtt tggaaacgga 840
gatgagaacg agcatcaact gaacaagttt gtacaatttc tcgaggcaaa caggaatagg 900
cagtccgagt aa 912

<210> SEQ ID NO 35
<211> LENGTH: 1125
<212> TYPE: DNA
<213> ORGANISM: Artificial sequence
<220> FEATURE:
<223> OTHER INFORMATION: Partial nucleotide sequence from Siraitia grosvenorii

<400> SEQUENCE: 35
ctgctgccga ttccgctgcc gaaaccggcc gccgatctct tgccggaagg tgcagaggcg 60
acggtggata ttccgtccga caagattccg tatctgaaat tggccctcga tctcgccgag 120
cagccgtttc ggaagttcgt cgttgatcgt ccgccggatt ggatgatcgt cgattttaat 180
gctacttggg tctgcgatat ttctcgggag cttcaaatcc caatcgtttt ctttcgtgtt 240
ctttcgcctg gatttcttgc tttctttgcg catgttcttg ggagtggtct gccgctgtcg 300
gagatcgaaa gcctgatgac tccgccggtg atcgacgggt cgacggtggc gtaccgccgg 360
catgaagctg ccgttatttg tgctgggttt tttgagaaga acgcttctgg tatgagtgat 420
cgcgatcggg taaccaaaat tctctctgcc agtcaagcaa tcgcagttcg ttcttgctac 480
gaatttgacg ttgagtattt gaaattgtac gagaaatatt gtggaaaaag agtgattcct 540
ctagggtttc tccctccaga aaagccccaa aagtccgagt tcgccgccga ttcgccatgg 600
aaaccgacct tcgagtggct tgacaaacaa aagccccgat cagtggtgtt cgtcggattc 660
ggcagcgaat gcaaactcac gaaagatgat gtttacgaga tagcgcgcgg ggtggagctg 720
tcggagctgc catttttgtg ggctctgaga aaaccgatct gggcggcggc ggacgattcc 780
gacgctctgc ctgccggatt cctcgagcgg acggcggaga gagggattgt gagcatgggg 840
tgggcgccgc agatggagat tttaacgcac ccgtcgattg gcggctctct gtttcacgcc 900
gggtggggat ccgccattga agctctgcaa ttcgggcatt gccttgttct gttgccattc 960
atcgtggatc agccactgaa tgcaaggctt ctggtggaga agggtgttgc agtcgaagtt 1020
ggaagaaagg aagacgggtc ttttagtgga gaagacatag ctaaagctct gagagaagct 1080
atggtttcag aagaaggtga gcagatgagg aggcaagcga gaaag 1125

<210> SEQ ID NO 36
<211> LENGTH: 486
<212> TYPE: DNA
<213> ORGANISM: Artificial sequence
<220> FEATURE:
<223> OTHER INFORMATION: Partial nucleotide sequence from Siraitia grosvenorii

<400> SEQUENCE: 36
atggaaaacg acggcgtttt gcacgtggtg gtattcccat ggctagcctt gggtcatctc 60
attcctttcg ctcgactcgc cacctgctta gcccacaagg gtctcagggt ttcgttcgta 120
tcaaccacaa ggaacctgag cagaattccc aaaataccccc cacatctctc ctcctccgtc 180
aacctcgtcg gctttcctct gccccacgtc gacggccttc cggacgccgc cgaggcttcc 240
tccgacgtgc cttacaacaa gcaacagtta ctgaagaagg ccttcgactc tctggaatca 300

```
ccgctcgccg atttgcttcg tgatttgaat cccgattgga ttatctacga ttacgcctct    360

cattggcttc cgcagctcgc ggcggagctc cgtatctcgt ctgttttctt cagcctcttc    420

accgcggcgt ttcttgcttt tcttggccca ccgtcggcgt tgtccggcga cggcagttcc    480

cggtga                                                               486


<210> SEQ ID NO 37
<211> LENGTH: 954
<212> TYPE: DNA
<213> ORGANISM: Artificial Sequence
<220> FEATURE:
<223> OTHER INFORMATION: Codon-optimized nucleotide sequence encoding
      Epoxide Hydrolase 1

<400> SEQUENCE: 37

atggacgcga ttgaacatag aaccgtaagt gttaatggta tcaatatgca tgtggcagaa     60

aagggagagg gacctgtcgt gttgttgctt catggtttcc cagaattgtg gtacagttgg    120

agacatcaaa tattggctct ttcctcttta ggttacagag ctgtcgcacc agacttacga    180

ggctacgggg atacagatgc cccagggtca atttcatcat acacatgctt tcacatcgta    240

ggagatctcg tggctctagt tgagtctctg ggtatggaca gggtttttgt tgtagcccac    300

gattggggtg ccatgatcgc ttggtgtttg tgtctgttta gacctgaaat ggttaaagct    360

tttgtttgtc tctccgtccc attcagacag agaaacccta agatgaaacc agttcaaagt    420

atgagagcct tttcggcga tgattactat atttgcagat ttcaaaatcc tggggaaatc    480

gaagaggaga tggctcaagt gggtgcaagg gaagtcttaa gaggaattct aacatctcgt    540

cgtcctggac caccaatctt accaaaaggg caagctttta gagcaagacc aggagcatcc    600

actgcattgc catcttggct atctgaaaaa gatctgtcat tttcgcttc taagtatgat    660

caaaagggct ttacaggccc actaaactac tacagagcca tggatcttaa ttgggaattg    720

actgcgtcat ggactggtgt ccaagttaaa gtacctgtca aatacatcgt gggtgacgtt    780

gacatggttt ttacgactcc tggtgtaaag gaatatgtca acggcggtgg tttcaaaaag    840

gacgttccat ttttacagga agtggtaatc atggaaggcg ttggtcattt cattaatcag    900

gaaaaacctg aggagatttc atctcatata cacgatttca taagcaaatt ctaa          954


<210> SEQ ID NO 38
<211> LENGTH: 317
<212> TYPE: PRT
<213> ORGANISM: Siraitia grosvenorii

<400> SEQUENCE: 38

Met Asp Ala Ile Glu His Arg Thr Val Ser Val Asn Gly Ile Asn Met
1               5                   10                  15

His Val Ala Glu Lys Gly Glu Gly Pro Val Val Leu Leu Leu His Gly
            20                  25                  30

Phe Pro Glu Leu Trp Tyr Ser Trp Arg His Gln Ile Leu Ala Leu Ser
        35                  40                  45

Ser Leu Gly Tyr Arg Ala Val Ala Pro Asp Leu Arg Gly Tyr Gly Asp
    50                  55                  60

Thr Asp Ala Pro Gly Ser Ile Ser Ser Tyr Thr Cys Phe His Ile Val
65                  70                  75                  80

Gly Asp Leu Val Ala Leu Val Glu Ser Leu Gly Met Asp Arg Val Phe
                85                  90                  95

Val Val Ala His Asp Trp Gly Ala Met Ile Ala Trp Cys Leu Cys Leu
            100                 105                 110
```

-continued

```
Phe Arg Pro Glu Met Val Lys Ala Phe Val Cys Leu Ser Val Pro Phe
        115                 120                 125

Arg Gln Arg Asn Pro Lys Met Lys Pro Val Gln Ser Met Arg Ala Phe
    130                 135                 140

Phe Gly Asp Asp Tyr Tyr Ile Cys Arg Phe Gln Asn Pro Gly Glu Ile
145                 150                 155                 160

Glu Glu Glu Met Ala Gln Val Gly Ala Arg Glu Val Leu Arg Gly Ile
                165                 170                 175

Leu Thr Ser Arg Arg Pro Gly Pro Pro Ile Leu Pro Lys Gly Gln Ala
            180                 185                 190

Phe Arg Ala Arg Pro Gly Ala Ser Thr Ala Leu Pro Ser Trp Leu Ser
        195                 200                 205

Glu Lys Asp Leu Ser Phe Phe Ala Ser Lys Tyr Asp Gln Lys Gly Phe
    210                 215                 220

Thr Gly Pro Leu Asn Tyr Tyr Arg Ala Met Asp Leu Asn Trp Glu Leu
225                 230                 235                 240

Thr Ala Ser Trp Thr Gly Val Gln Val Lys Val Pro Val Lys Tyr Ile
                245                 250                 255

Val Gly Asp Val Asp Met Val Phe Thr Thr Pro Gly Val Lys Glu Tyr
            260                 265                 270

Val Asn Gly Gly Gly Phe Lys Lys Asp Val Pro Phe Leu Gln Glu Val
        275                 280                 285

Val Ile Met Glu Gly Val Gly His Phe Ile Asn Gln Glu Lys Pro Glu
    290                 295                 300

Glu Ile Ser Ser His Ile His Asp Phe Ile Ser Lys Phe
305                 310                 315
```

<210> SEQ ID NO 39
<211> LENGTH: 951
<212> TYPE: DNA
<213> ORGANISM: Artificial Sequence
<220> FEATURE:
<223> OTHER INFORMATION: Codon-optimized nucleotide sequence encoding Epoxide Hydrolase 2

<400> SEQUENCE: 39

```
atggatgaaa tcgaacatat taccatcaat acaaatggaa tcaaaatgca tattgcgtca      60

gtcggcacag gaccagttgt tctcttgcta cacggctttc cagaattatg gtactcttgg     120

agacaccaac tactttacct gtcctccgtt gggtacagag caatagctcc agatttgaga     180

ggctatggcg atactgacag tccagctagt cctacctctt atactgctct tcatattgta     240

ggtgacctgg tcggcgcatt agacgaattg ggaatagaaa aggtcttttt agtgggtcat     300

gactggggtg ctattatcgc atggtacttt tgtttgttta gaccagatag aattaaagca     360

cttgtgaatt tgtctgtcca gtttatccca cgtaacccag caatacctttt tatagaaggt     420

ttcagaacag cttttggtga tgacttctac atttgtagat ttcaagtacc tggggaagct     480

gaagaggatt tcgcgtctat cgatactgct caattgttta aaacttcatt atgcaataga     540

agctcagccc ctccttgttt gcctaaagag attggtttta gggctatccc accaccagaa     600

aatctgccat cttggctcac agaggaagat atcaacttct acgcagccaa gtttaaacaa     660

actggtttta ctggtgccct taactattat agagcattcg acttgacatg ggaattaaca     720

gccccatgga caggagccca gatccaagtt cctgtaaagt tcatagttgg tgattcagat     780

ctcacgtacc atttccctgg tgctaaggaa tacatccaca acggagggtt taaaagagat     840
```

```
gtgccactat tagaggaagt tgttgtggta aaagatgcct gccacttcat taaccaagag     900

cgaccacaag agattaatgc tcatattcat gacttcatca ataagttcta a              951


<210> SEQ ID NO 40
<211> LENGTH: 316
<212> TYPE: PRT
<213> ORGANISM: Siraitia grosvenorii

<400> SEQUENCE: 40

Met Asp Glu Ile Glu His Ile Thr Ile Asn Thr Asn Gly Ile Lys Met
1               5                   10                  15

His Ile Ala Ser Val Gly Thr Gly Pro Val Val Leu Leu Leu His Gly
            20                  25                  30

Phe Pro Glu Leu Trp Tyr Ser Trp Arg His Gln Leu Leu Tyr Leu Ser
        35                  40                  45

Ser Val Gly Tyr Arg Ala Ile Ala Pro Asp Leu Arg Gly Tyr Gly Asp
    50                  55                  60

Thr Asp Ser Pro Ala Ser Pro Thr Ser Tyr Thr Ala Leu His Ile Val
65                  70                  75                  80

Gly Asp Leu Val Gly Ala Leu Asp Glu Leu Gly Ile Glu Lys Val Phe
                85                  90                  95

Leu Val Gly His Asp Trp Gly Ala Ile Ile Ala Trp Tyr Phe Cys Leu
            100                 105                 110

Phe Arg Pro Asp Arg Ile Lys Ala Leu Val Asn Leu Ser Val Gln Phe
        115                 120                 125

Ile Pro Arg Asn Pro Ala Ile Pro Phe Ile Glu Gly Phe Arg Thr Ala
    130                 135                 140

Phe Gly Asp Asp Phe Tyr Ile Cys Arg Phe Gln Val Pro Gly Glu Ala
145                 150                 155                 160

Glu Glu Asp Phe Ala Ser Ile Asp Thr Ala Gln Leu Phe Lys Thr Ser
                165                 170                 175

Leu Cys Asn Arg Ser Ser Ala Pro Pro Cys Leu Pro Lys Glu Ile Gly
            180                 185                 190

Phe Arg Ala Ile Pro Pro Pro Glu Asn Leu Pro Ser Trp Leu Thr Glu
        195                 200                 205

Glu Asp Ile Asn Phe Tyr Ala Ala Lys Phe Lys Gln Thr Gly Phe Thr
    210                 215                 220

Gly Ala Leu Asn Tyr Tyr Arg Ala Phe Asp Leu Thr Trp Glu Leu Thr
225                 230                 235                 240

Ala Pro Trp Thr Gly Ala Gln Ile Gln Val Pro Val Lys Phe Ile Val
                245                 250                 255

Gly Asp Ser Asp Leu Thr Tyr His Phe Pro Gly Ala Lys Glu Tyr Ile
            260                 265                 270

His Asn Gly Gly Phe Lys Arg Asp Val Pro Leu Leu Glu Glu Val Val
        275                 280                 285

Val Val Lys Asp Ala Cys His Phe Ile Asn Gln Glu Arg Pro Gln Glu
    290                 295                 300

Ile Asn Ala His Ile His Asp Phe Ile Asn Lys Phe
305                 310                 315


<210> SEQ ID NO 41
<211> LENGTH: 1461
<212> TYPE: DNA
<213> ORGANISM: Siraitia grosvenorii

<400> SEQUENCE: 41
```

```
gtggggccgt cgtctgttga agctcctcag cggacgattt cgaagcctga acagagggag     60
ctaccgttga ggaagattcc cggggactat gggccgccgt tgttgggtcc gattaaggac    120
cgacaagact atttttacaa tcaggggagg gaggagttcc tgagatcacg catgaacagg    180
tacgaatcaa ctgtgtacag aactaatatg ccaccaggtc cctttatctc ctccgattct    240
cgtgtcatcg ttttactcga cggcaagagc ttccctgtac tcttcgacgt ttctaaagtt    300
ctgaaacaag acgtcttcac cggaacttat atgcccttaa cggagctcac tggcggctac    360
cgagttcttt cttatctcga cccctccgag cccgatcacg agaagcttaa acagttcctc    420
ttctacctcc tcaagtaccg tcgcgacaag attctgccgg agtttcactc taccttttcg    480
gagctgtttg agactctgga gaaggaggtg gctgccgccg gtagagcaga ttataatgat    540
cccggtgaac aggcggcgtt taacttcttg gctcggtctc tgttcggcgc caacccgccc    600
gacaccaaac tgggaaacga cgctccgagt ttaatatcca aatgggtgct gttccagctg    660
ggtccggttc tcactcttgg tcttcccaag cctgtcgagg agcttctcct gcgaaccgtc    720
cggctgccac cggcgcttgt gaaatcggat taccagcggc tgtacgattt cttttacgag    780
gcgtcggagg ctgtgtttgc ggaggcggat agattgggca ttgcgagaga ggaagcgtgt    840
cacaacttgg tcttcgccac gtgcttcaat tccttcggag ggatgaagat cctcttcccc    900
aatatgataa aatggatcgg acgtgccgga gtgaatctcc atacggagct cgcacgggag    960
ataagatccg ccgtcaaagc ccacggcggc aagatcacga tggcggctat ggaacagatg   1020
ccgctgatga agtccgtagt gtacgaaacg ctcagaatcg aacccccggt tcctgcgcaa   1080
tacgggcgag cgaaggagga cctggtgatc gagagccacg acgccgcttt cgagatcaaa   1140
gaaggggaaa tgttgtgtgg gtaccagcca ttcgccacta gagatccgaa aatattcgag   1200
agatccgaag aattcgtacc ggatcggttc accggcgacg gcgaggagtt gctgaagcac   1260
gtgctctggt caaacggacc ggagactcaa tccccaaccg ttaaagacaa gcagtgcgct   1320
ggcaaagact tcatagtctt cgtctcccgc ctcctcgtcg tcgaactctt cctccgatac   1380
gactccttcg acattgaagt cgcagcttcg ccgttgggcg ccgccgtcac cataacttcc   1440
ctgaagaagg caagctttta a                                             1461
```

<210> SEQ ID NO 42
<211> LENGTH: 2280
<212> TYPE: DNA
<213> ORGANISM: Artificial Sequence
<220> FEATURE:
<223> OTHER INFORMATION: Codon-optimized nucleotide sequence encoding cucurbitadienol synthase

<400> SEQUENCE: 42

```
atgtggagat tgaaagtagg tgctgaatcc gtaggtgaaa acgacgaaaa gtggttgaaa     60
agtataagta atcatttggg tagacaagtc tgggaatttt gtccagatgc aggtacacaa    120
caacaattgt tgcaagtaca taaggctaga aaggcatttc atgatgacag attccacaga    180
aagcaatctt cagatttgtt catcaccatc caatacggca aggaagtaga aaacggtggc    240
aagactgctg gtgttaaatt gaaggaaggt gaagaagtta gaaaagaagc agttgaatcc    300
agtttggaaa gagccttgtc tttctactct tcaatccaaa cctctgatgg taattgggca    360
tcagacttgg gtggtccaat gttcttgtta cctggtttgg tcattgcctt gtacgtaact    420
ggtgttttga actctgtatt gtcaaagcat cacagacaag aaatgtgtag atacgtttac    480
aaccatcaaa acgaagatgg tggttggggt ttgcacattg aaggtccatc cactatgttt    540
```

ggtagtgcat tgaattatgt cgccttaaga ttgttaggtg aagatgcaaa cgccggtgct 600
atgcctaagg caagagcctg gatattagac catggtggtg ctactggtat cacatcctgg 660
ggtaaattgt ggttaagtgt cttaggtgta tatgaatggt ctggtaataa cccattgcca 720
cctgaatttt ggttgttccc ttactttttta ccattccatc ctggtagaat gtggtgtcac 780
tgcagaatgg tttacttgcc aatgtcttac ttgtacggca agagattcgt tggtccaata 840
acacctatcg tcttgtcatt gagaaaggaa ttgtacgcag ttccttacca tgaaatcgat 900
tggaacaagt ccagaaacac ctgtgctaag gaagatttgt attacccaca ccctaaaatg 960
caagacattt tgtggggtag tttacatcac gtttacgaac cattatttac tagatggcct 1020
gctaaaagat tgagagaaaa ggcattacaa acagccatgc aacatatcca ctacgaagat 1080
gaaaacacca gatacatctg cttgggtcca gttaacaagg tcttgaactt gttgtgttgc 1140
tgggttgaag atccttattc tgacgctttc aagttgcatt tgcaaagagt acacgattac 1200
ttgtgggttg cagaagacgg tatgaaaatg caaggttaca atggttcaca attgtgggat 1260
acagcttttt ccattcaagc aatagtcagt actaagttgg tagataacta cggtccaaca 1320
ttaagaaaag ctcatgactt cgtaaagtcc agtcaaatac aacaagattg tccaggtgac 1380
cctaatgttt ggtatagaca tatccacaaa ggtgcatggc cattttctac cagagatcat 1440
ggttggttga tttcagactg tactgctgaa ggtttgaagg ctgcattgat gttgtctaag 1500
ttgccatcag aaactgttgg tgaatccttg gaaagaaata gattatgcga tgccgttaac 1560
gtcttgttga gtttgcaaaa cgacaacggt ggtttcgctt cttacgaatt gactagatca 1620
tacccatggt tggaattaat taatcctgct gaaacattcg gtgatatcgt cattgactat 1680
ccatacgtag aatgtacctc cgctactatg gaagcattga ccttgttcaa gaagttgcat 1740
cctggtcaca gaacaaagga aatcgatacc gcaattgtta gagccgctaa tttcttggaa 1800
aacatgcaaa gaacagacgg ttcttggtat ggttgttggg gtgtttgctt tacctacgct 1860
ggttggttcg gtattaaagg tttagtcgca gccggtagaa catacaataa ctgtttggcc 1920
ataagaaaag cttgcgattt cttgttatct aaggaattac caggtggtgg ttggggtgaa 1980
tcctacttga gttgtcaaaa caaggtttac actaatttgg aaggcaacag acctcattta 2040
gttaacacag cctgggtctt gatggcttta atcgaagccg gtcaagctga aagagatcca 2100
actcctttgc atagagctgc aagattgttg atcaactcac aattggaaaa cggtgatttt 2160
ccacaacaag aaatcatggg tgttttcaac aagaactgca tgataacata tgccgcttac 2220
agaaacattt ttcctatatg ggctttgggt gaatactgcc acagagtctt gaccgaataa 2280

<210> SEQ ID NO 43
<211> LENGTH: 759
<212> TYPE: PRT
<213> ORGANISM: Siraitia grosvenorii

<400> SEQUENCE: 43

Met Trp Arg Leu Lys Val Gly Ala Glu Ser Val Gly Glu Asn Asp Glu
1 5 10 15

Lys Trp Leu Lys Ser Ile Ser Asn His Leu Gly Arg Gln Val Trp Glu
20 25 30

Phe Cys Pro Asp Ala Gly Thr Gln Gln Gln Leu Leu Gln Val His Lys
35 40 45

Ala Arg Lys Ala Phe His Asp Asp Arg Phe His Arg Lys Gln Ser Ser
50 55 60

-continued

```
Asp Leu Phe Ile Thr Ile Gln Tyr Gly Lys Glu Val Glu Asn Gly Gly
65                  70                  75                  80

Lys Thr Ala Gly Val Lys Leu Lys Glu Gly Glu Glu Val Arg Lys Glu
                85                  90                  95

Ala Val Glu Ser Ser Leu Glu Arg Ala Leu Ser Phe Tyr Ser Ser Ile
            100                 105                 110

Gln Thr Ser Asp Gly Asn Trp Ala Ser Asp Leu Gly Gly Pro Met Phe
        115                 120                 125

Leu Leu Pro Gly Leu Val Ile Ala Leu Tyr Val Thr Gly Val Leu Asn
    130                 135                 140

Ser Val Leu Ser Lys His His Arg Gln Glu Met Cys Arg Tyr Val Tyr
145                 150                 155                 160

Asn His Gln Asn Glu Asp Gly Gly Trp Gly Leu His Ile Glu Gly Pro
                165                 170                 175

Ser Thr Met Phe Gly Ser Ala Leu Asn Tyr Val Ala Leu Arg Leu Leu
            180                 185                 190

Gly Glu Asp Ala Asn Ala Gly Ala Met Pro Lys Ala Arg Ala Trp Ile
        195                 200                 205

Leu Asp His Gly Gly Ala Thr Gly Ile Thr Ser Trp Gly Lys Leu Trp
    210                 215                 220

Leu Ser Val Leu Gly Val Tyr Glu Trp Ser Gly Asn Asn Pro Leu Pro
225                 230                 235                 240

Pro Glu Phe Trp Leu Phe Pro Tyr Phe Leu Pro Phe His Pro Gly Arg
                245                 250                 255

Met Trp Cys His Cys Arg Met Val Tyr Leu Pro Met Ser Tyr Leu Tyr
            260                 265                 270

Gly Lys Arg Phe Val Gly Pro Ile Thr Pro Ile Val Leu Ser Leu Arg
        275                 280                 285

Lys Glu Leu Tyr Ala Val Pro Tyr His Glu Ile Asp Trp Asn Lys Ser
    290                 295                 300

Arg Asn Thr Cys Ala Lys Glu Asp Leu Tyr Tyr Pro His Pro Lys Met
305                 310                 315                 320

Gln Asp Ile Leu Trp Gly Ser Leu His His Val Tyr Glu Pro Leu Phe
                325                 330                 335

Thr Arg Trp Pro Ala Lys Arg Leu Arg Glu Lys Ala Leu Gln Thr Ala
            340                 345                 350

Met Gln His Ile His Tyr Glu Asp Glu Asn Thr Arg Tyr Ile Cys Leu
        355                 360                 365

Gly Pro Val Asn Lys Val Leu Asn Leu Leu Cys Cys Trp Val Glu Asp
    370                 375                 380

Pro Tyr Ser Asp Ala Phe Lys Leu His Leu Gln Arg Val His Asp Tyr
385                 390                 395                 400

Leu Trp Val Ala Glu Asp Gly Met Lys Met Gln Gly Tyr Asn Gly Ser
                405                 410                 415

Gln Leu Trp Asp Thr Ala Phe Ser Ile Gln Ala Ile Val Ser Thr Lys
            420                 425                 430

Leu Val Asp Asn Tyr Gly Pro Thr Leu Arg Lys Ala His Asp Phe Val
        435                 440                 445

Lys Ser Ser Gln Ile Gln Gln Asp Cys Pro Gly Asp Pro Asn Val Trp
    450                 455                 460

Tyr Arg His Ile His Lys Gly Ala Trp Pro Phe Ser Thr Arg Asp His
465                 470                 475                 480

Gly Trp Leu Ile Ser Asp Cys Thr Ala Glu Gly Leu Lys Ala Ala Leu
```

485 490 495

Met Leu Ser Lys Leu Pro Ser Glu Thr Val Gly Glu Ser Leu Glu Arg
500 505 510

Asn Arg Leu Cys Asp Ala Val Asn Val Leu Leu Ser Leu Gln Asn Asp
515 520 525

Asn Gly Gly Phe Ala Ser Tyr Glu Leu Thr Arg Ser Tyr Pro Trp Leu
530 535 540

Glu Leu Ile Asn Pro Ala Glu Thr Phe Gly Asp Ile Val Ile Asp Tyr
545 550 555 560

Pro Tyr Val Glu Cys Thr Ser Ala Thr Met Glu Ala Leu Thr Leu Phe
565 570 575

Lys Lys Leu His Pro Gly His Arg Thr Lys Glu Ile Asp Thr Ala Ile
580 585 590

Val Arg Ala Ala Asn Phe Leu Glu Asn Met Gln Arg Thr Asp Gly Ser
595 600 605

Trp Tyr Gly Cys Trp Gly Val Cys Phe Thr Tyr Ala Gly Trp Phe Gly
610 615 620

Ile Lys Gly Leu Val Ala Ala Gly Arg Thr Tyr Asn Asn Cys Leu Ala
625 630 635 640

Ile Arg Lys Ala Cys Asp Phe Leu Leu Ser Lys Glu Leu Pro Gly Gly
645 650 655

Gly Trp Gly Glu Ser Tyr Leu Ser Cys Gln Asn Lys Val Tyr Thr Asn
660 665 670

Leu Glu Gly Asn Arg Pro His Leu Val Asn Thr Ala Trp Val Leu Met
675 680 685

Ala Leu Ile Glu Ala Gly Gln Ala Glu Arg Asp Pro Thr Pro Leu His
690 695 700

Arg Ala Ala Arg Leu Leu Ile Asn Ser Gln Leu Glu Asn Gly Asp Phe
705 710 715 720

Pro Gln Gln Glu Ile Met Gly Val Phe Asn Lys Asn Cys Met Ile Thr
725 730 735

Tyr Ala Ala Tyr Arg Asn Ile Phe Pro Ile Trp Ala Leu Gly Glu Tyr
740 745 750

Cys His Arg Val Leu Thr Glu
755

<210> SEQ ID NO 44
<211> LENGTH: 473
<212> TYPE: PRT
<213> ORGANISM: Siraitia grosvenorii

<400> SEQUENCE: 44

Met Trp Thr Val Val Leu Gly Leu Ala Thr Leu Phe Val Ala Tyr Tyr
1 5 10 15

Ile His Trp Ile Asn Lys Trp Arg Asp Ser Lys Phe Asn Gly Val Leu
20 25 30

Pro Pro Gly Thr Met Gly Leu Pro Leu Ile Gly Glu Thr Ile Gln Leu
35 40 45

Ser Arg Pro Ser Asp Ser Leu Asp Val His Pro Phe Ile Gln Lys Lys
50 55 60

Val Glu Arg Tyr Gly Pro Ile Phe Lys Thr Cys Leu Ala Gly Arg Pro
65 70 75 80

Val Val Val Ser Ala Asp Ala Glu Phe Asn Asn Tyr Ile Met Leu Gln
85 90 95

-continued

```
Glu Gly Arg Ala Val Glu Met Trp Tyr Leu Asp Thr Leu Ser Lys Phe
            100                 105                 110

Phe Gly Leu Asp Thr Glu Trp Leu Lys Ala Leu Gly Leu Ile His Lys
        115                 120                 125

Tyr Ile Arg Ser Ile Thr Leu Asn His Phe Gly Ala Glu Ala Leu Arg
    130                 135                 140

Glu Arg Phe Leu Pro Phe Ile Glu Ala Ser Ser Met Glu Ala Leu His
145                 150                 155                 160

Ser Trp Ser Thr Gln Pro Ser Val Glu Val Lys Asn Ala Ser Ala Leu
                165                 170                 175

Met Val Phe Arg Thr Ser Val Asn Lys Met Phe Gly Glu Asp Ala Lys
            180                 185                 190

Lys Leu Ser Gly Asn Ile Pro Gly Lys Phe Thr Lys Leu Leu Gly Gly
        195                 200                 205

Phe Leu Ser Leu Pro Leu Asn Phe Pro Gly Thr Thr Tyr His Lys Cys
    210                 215                 220

Leu Lys Asp Met Lys Glu Ile Gln Lys Lys Leu Arg Glu Val Val Asp
225                 230                 235                 240

Asp Arg Leu Ala Asn Val Gly Pro Asp Val Glu Asp Phe Leu Gly Gln
                245                 250                 255

Ala Leu Lys Asp Lys Glu Ser Glu Lys Phe Ile Ser Glu Glu Phe Ile
            260                 265                 270

Ile Gln Leu Leu Phe Ser Ile Ser Phe Ala Ser Phe Glu Ser Ile Ser
        275                 280                 285

Thr Thr Leu Thr Leu Ile Leu Lys Leu Leu Asp Glu His Pro Glu Val
    290                 295                 300

Val Lys Glu Leu Glu Ala Glu His Glu Ala Ile Arg Lys Ala Arg Ala
305                 310                 315                 320

Asp Pro Asp Gly Pro Ile Thr Trp Glu Glu Tyr Lys Ser Met Thr Phe
                325                 330                 335

Thr Leu Gln Val Ile Asn Glu Thr Leu Arg Leu Gly Ser Val Thr Pro
            340                 345                 350

Ala Leu Leu Arg Lys Thr Val Lys Asp Leu Gln Val Lys Gly Tyr Ile
        355                 360                 365

Ile Pro Glu Gly Trp Thr Ile Met Leu Val Thr Ala Ser Arg His Arg
    370                 375                 380

Asp Pro Lys Val Tyr Lys Asp Pro His Ile Phe Asn Pro Trp Arg Trp
385                 390                 395                 400

Lys Asp Leu Asp Ser Ile Thr Ile Gln Lys Asn Phe Met Pro Phe Gly
                405                 410                 415

Gly Gly Leu Arg His Cys Ala Gly Ala Glu Tyr Ser Lys Val Tyr Leu
            420                 425                 430

Cys Thr Phe Leu His Ile Leu Cys Thr Lys Tyr Arg Trp Thr Lys Leu
        435                 440                 445

Gly Gly Gly Arg Ile Ala Arg Ala His Ile Leu Ser Phe Glu Asp Gly
    450                 455                 460

Leu His Val Lys Phe Thr Pro Lys Glu
465                 470
```

<210> SEQ ID NO 45
<211> LENGTH: 2106
<212> TYPE: DNA
<213> ORGANISM: Siraitia grosvenorii

<400> SEQUENCE: 45

-continued

```
atgaaggtct ctccatttga gttcatgtcg gcaataatta agggcaggat ggacccgtcc      60
aattcttcat ttgagtcgac tggcgaggtt gcctcagtta ttttcgagaa ccgtgagctg     120
gttgcgatct taaccacctc gatcgccgtc atgattggct gcttcgttgt tctcatgtgg     180
cgaagagccg gcagtcggaa agttaagaac gtggagctac ctaagccgtt gattgtgcac     240
gagccggagc ccgaagttga agacggcaag aagaaggttt caatcttctt cggtacacag     300
acaggcaccg ccgaaggatt tgcaaaggct ctagctgacg aggcgaaagc acgatacgag     360
aaggccacat ttagagttgt tgatttggat gattatgcag ctgatgacga tcagtatgaa     420
gagaagttga agaacgagtc tttcgctgtc ttcttattgg caacgtatgg cgatggagag     480
cccactgata atgccgcaag attctataaa tggttcgcgg aggggaaaga gagaggggag     540
tggcttcaga accttcatta tgcggtcttt ggccttggca accgacagta cgagcatttt     600
aataagattg caaaggtggc agatgagctg cttgaggcac agggaggcaa ccgccttgtt     660
aaagttggtc ttggagatga cgatcagtgc atagaggatg acttcagtgc ctggagagaa     720
tcattgtggc ctgagttgga tatgttgctt cgagatgagg atgatgcaac aacagtgacc     780
accccttaca cagctgccgt attagaatat cgagttgtat tccatgattc tgcagatgta     840
gctgctgagg acaagagctg gatcaatgca aacggtcatg ctgtacatga tgctcagcat     900
cccttcagat ctaatgtggt tgtgaggaag gagctccata cgtccgcatc tgatcgctcc     960
tgtagtcatc tagaatttaa tatttctggg tctgcactca attatgaaac aggggatcat    1020
gtcggtgttt actgtgaaaa cttaactgag actgtggacg aggcactaaa cttattgggt    1080
ttgtctcctg aaacgtattt ctccatatat actgataacg aggatggcac tccacttggt    1140
ggaagctctt taccacctcc ttttccatcc tgcaccctca gaacagcatt gactcgatat    1200
gcagatctct tgaattcacc caagaagtca gctttgcttg cattagcagc acatgcttca    1260
aatccagtag aggctgaccg attaagatat cttgcatcac ctgccgggaa ggatgaatac    1320
gcccagtctg tgattggtag ccagaaaagc cttcttgagg tcatggctga atttccttct    1380
gccaagcccc cacttggtgt cttcttcgca gctgttgcac cgcgcttgca gcctcgattc    1440
tactccatat catcatctcc aaggatggct ccatctagaa ttcatgttac ttgtgcttta    1500
gtctatgaca aaatgccaac aggacgtatt cataaaggag tgtgctcaac ttggatgaag    1560
aattctgtgc ccatggagaa aagccatgaa tgcagttggg ctccaatttt cgtgagacaa    1620
tcaaacttca agcttcctgc agagagtaaa gtgcccatta tcatggttgg tcctggaact    1680
ggattggctc ctttcagagg tttcttacag gaaagattag ctttgaagga atctggagta    1740
gaattggggc cttccatatt gttctttgga tgcagaaacc gtaggatgga ttacatatac    1800
gaggatgagc tgaacaactt tgttgagact ggtgctctct ctgagttggt tattgccttc    1860
tcacgcgaag ggccaactaa ggaatatgtg cagcataaaa tggcagagaa ggcttcggat    1920
atctggaatt tgatatcaga aggggcttac ttatatgtat gtggtgatgc aaagggcatg    1980
gctaaggatg tccaccgaac tctccatact atcatgcaag agcagggatc tcttgacagc    2040
tcaaaagctg agagcatggt gaagaatctg caaatgaatg gaaggtatct gcgtgatgtc    2100
tggtga                                                                2106
```

<210> SEQ ID NO 46
<211> LENGTH: 701
<212> TYPE: PRT
<213> ORGANISM: Siraitia grosvenorii

<400> SEQUENCE: 46

Met Lys Val Ser Pro Phe Glu Phe Met Ser Ala Ile Ile Lys Gly Arg
1               5                   10                  15

Met Asp Pro Ser Asn Ser Ser Phe Glu Ser Thr Gly Glu Val Ala Ser
            20                  25                  30

Val Ile Phe Glu Asn Arg Glu Leu Val Ala Ile Leu Thr Thr Ser Ile
        35                  40                  45

Ala Val Met Ile Gly Cys Phe Val Val Leu Met Trp Arg Arg Ala Gly
    50                  55                  60

Ser Arg Lys Val Lys Asn Val Glu Leu Pro Lys Pro Leu Ile Val His
65                  70                  75                  80

Glu Pro Glu Pro Glu Val Glu Asp Gly Lys Lys Lys Val Ser Ile Phe
                85                  90                  95

Phe Gly Thr Gln Thr Gly Thr Ala Glu Gly Phe Ala Lys Ala Leu Ala
            100                 105                 110

Asp Glu Ala Lys Ala Arg Tyr Glu Lys Ala Thr Phe Arg Val Val Asp
        115                 120                 125

Leu Asp Asp Tyr Ala Ala Asp Asp Asp Gln Tyr Glu Glu Lys Leu Lys
    130                 135                 140

Asn Glu Ser Phe Ala Val Phe Leu Leu Ala Thr Tyr Gly Asp Gly Glu
145                 150                 155                 160

Pro Thr Asp Asn Ala Ala Arg Phe Tyr Lys Trp Phe Ala Glu Gly Lys
                165                 170                 175

Glu Arg Gly Glu Trp Leu Gln Asn Leu His Tyr Ala Val Phe Gly Leu
            180                 185                 190

Gly Asn Arg Gln Tyr Glu His Phe Asn Lys Ile Ala Lys Val Ala Asp
        195                 200                 205

Glu Leu Leu Glu Ala Gln Gly Gly Asn Arg Leu Val Lys Val Gly Leu
    210                 215                 220

Gly Asp Asp Asp Gln Cys Ile Glu Asp Asp Phe Ser Ala Trp Arg Glu
225                 230                 235                 240

Ser Leu Trp Pro Glu Leu Asp Met Leu Leu Arg Asp Glu Asp Asp Ala
                245                 250                 255

Thr Thr Val Thr Thr Pro Tyr Thr Ala Ala Val Leu Glu Tyr Arg Val
            260                 265                 270

Val Phe His Asp Ser Ala Asp Val Ala Ala Glu Asp Lys Ser Trp Ile
        275                 280                 285

Asn Ala Asn Gly His Ala Val His Asp Ala Gln His Pro Phe Arg Ser
    290                 295                 300

Asn Val Val Val Arg Lys Glu Leu His Thr Ser Ala Ser Asp Arg Ser
305                 310                 315                 320

Cys Ser His Leu Glu Phe Asn Ile Ser Gly Ser Ala Leu Asn Tyr Glu
                325                 330                 335

Thr Gly Asp His Val Gly Val Tyr Cys Glu Asn Leu Thr Glu Thr Val
            340                 345                 350

Asp Glu Ala Leu Asn Leu Leu Gly Leu Ser Pro Glu Thr Tyr Phe Ser
        355                 360                 365

Ile Tyr Thr Asp Asn Glu Asp Gly Thr Pro Leu Gly Gly Ser Ser Leu
    370                 375                 380

Pro Pro Pro Phe Pro Ser Cys Thr Leu Arg Thr Ala Leu Thr Arg Tyr
385                 390                 395                 400

Ala Asp Leu Leu Asn Ser Pro Lys Lys Ser Ala Leu Leu Ala Leu Ala
                405                 410                 415

-continued

```
Ala His Ala Ser Asn Pro Val Glu Ala Asp Arg Leu Arg Tyr Leu Ala
            420                 425                 430

Ser Pro Ala Gly Lys Asp Glu Tyr Ala Gln Ser Val Ile Gly Ser Gln
        435                 440                 445

Lys Ser Leu Leu Glu Val Met Ala Glu Phe Pro Ser Ala Lys Pro Pro
    450                 455                 460

Leu Gly Val Phe Phe Ala Ala Val Ala Pro Arg Leu Gln Pro Arg Phe
465                 470                 475                 480

Tyr Ser Ile Ser Ser Ser Pro Arg Met Ala Pro Ser Arg Ile His Val
                485                 490                 495

Thr Cys Ala Leu Val Tyr Asp Lys Met Pro Thr Gly Arg Ile His Lys
            500                 505                 510

Gly Val Cys Ser Thr Trp Met Lys Asn Ser Val Pro Met Glu Lys Ser
        515                 520                 525

His Glu Cys Ser Trp Ala Pro Ile Phe Val Arg Gln Ser Asn Phe Lys
    530                 535                 540

Leu Pro Ala Glu Ser Lys Val Pro Ile Ile Met Val Gly Pro Gly Thr
545                 550                 555                 560

Gly Leu Ala Pro Phe Arg Gly Phe Leu Gln Glu Arg Leu Ala Leu Lys
                565                 570                 575

Glu Ser Gly Val Glu Leu Gly Pro Ser Ile Leu Phe Phe Gly Cys Arg
            580                 585                 590

Asn Arg Arg Met Asp Tyr Ile Tyr Glu Asp Glu Leu Asn Asn Phe Val
        595                 600                 605

Glu Thr Gly Ala Leu Ser Glu Leu Val Ile Ala Phe Ser Arg Glu Gly
    610                 615                 620

Pro Thr Lys Glu Tyr Val Gln His Lys Met Ala Glu Lys Ala Ser Asp
625                 630                 635                 640

Ile Trp Asn Leu Ile Ser Glu Gly Ala Tyr Leu Tyr Val Cys Gly Asp
                645                 650                 655

Ala Lys Gly Met Ala Lys Asp Val His Arg Thr Leu His Thr Ile Met
            660                 665                 670

Gln Glu Gln Gly Ser Leu Asp Ser Ser Lys Ala Glu Ser Met Val Lys
        675                 680                 685

Asn Leu Gln Met Asn Gly Arg Tyr Leu Arg Asp Val Trp
    690                 695                 700
```

<210> SEQ ID NO 47
<211> LENGTH: 1491
<212> TYPE: DNA
<213> ORGANISM: Siraitia grosvenorii

<400> SEQUENCE: 47

```
atggcttctc ctcgccacac tcctcacttt ctgctcttcc ctttcatggc tcaaggccac      60

atgatcccca tgattgacct tgccaggctt ctggctcagc gaggagttat catcactatt     120

atcaccacgc cccacaatgc tgctcgctac cactctgttc ttgctcgcgc catcgattct     180

gggttacaca tccatgtcct ccaactgcag tttccatgta aggaaggtgg gctgccagaa     240

gggtgcgaga atgtggactt gctaccttca cttgcttcca tacccagatt ctacagagca     300

gcaagtgatc tcctttacga accatctgaa aaactgtttg aggaactcat cccccggccg     360

acctgcataa tctccgatat gtgcctgccc tggaccatgc gaattgctct gaaatatcac     420

gtcccaaggc tcgttttcta cagtttgagc tgcttctttc ttctctgtat gcggagttta     480
```

-continued

```
aaaaacaatc tagcgcttat aagctccaag tctgattctg agttcgtaac tttctctgac    540

ttgcctgatc cagtcgagtt tctcaagtcg gagctaccta aatccaccga tgaagacttg    600

gtgaagttta gttatgaaat gggggaggcc gatcggcagt catacggcgt tattttaaat    660

ctatttgagg agatggaacc aaagtatctt gcagaatatg aaaaggaaag agaatcgccg    720

gaaagagtct ggtgcgtcgg cccagtttcg ctttgcaacg acaacaaact cgacaaagct    780

gaaagaggca acaaagcctc catcgacgaa tacaaatgca tcaggtggct cgacgggcag    840

cagccatctt cggtggttta cgtctcttta ggaagcttgt gcaatctggt gacggcgcag    900

atcatagagc tgggtttggg tttggaggca tcaaagaaac ccttcatttg ggtcataaga    960

agaggaaaca taacagagga gttacagaaa tggcttgtgg agtacgattt cgaggagaaa   1020

attaaaggga gagggctggt gattcttggc tgggctcccc aagttctgat actgtcacac   1080

cctgcaatcg gatgcttttt gacgcactgc ggttggaact caagcatcga agggatatcg   1140

gccggcgtgc caatggtcac ctggccgctt tttgcggatc aagtcttcaa cgagaagcta   1200

attgtacaaa tactcagaat cggcgtaagt gtaggcacgg aaactactat gaactgggga   1260

gaggaagagg agaaaggggt ggttgtgaag agagagaaag tgagggaagc catagaaata   1320

gtgatggatg gagatgagag agaagagagg agagagagat gcaaagagct tgctgaaacg   1380

gcgaagagag ctatagaaga agggggctcg tctcaccgga acctcacgat gttgattgaa   1440

gatataattc atggaggagg tttgagttat gagaaaggaa gttgtcgctg a            1491
```

```
<210> SEQ ID NO 48
<211> LENGTH: 496
<212> TYPE: PRT
<213> ORGANISM: Siraitia grosvenorii

<400> SEQUENCE: 48

Met Ala Ser Pro Arg His Thr Pro His Phe Leu Leu Phe Pro Phe Met
1               5                   10                  15

Ala Gln Gly His Met Ile Pro Met Ile Asp Leu Ala Arg Leu Leu Ala
            20                  25                  30

Gln Arg Gly Val Ile Ile Thr Ile Ile Thr Thr Pro His Asn Ala Ala
        35                  40                  45

Arg Tyr His Ser Val Leu Ala Arg Ala Ile Asp Ser Gly Leu His Ile
    50                  55                  60

His Val Leu Gln Leu Gln Phe Pro Cys Lys Glu Gly Gly Leu Pro Glu
65                  70                  75                  80

Gly Cys Glu Asn Val Asp Leu Leu Pro Ser Leu Ala Ser Ile Pro Arg
                85                  90                  95

Phe Tyr Arg Ala Ala Ser Asp Leu Leu Tyr Glu Pro Ser Glu Lys Leu
            100                 105                 110

Phe Glu Glu Leu Ile Pro Arg Pro Thr Cys Ile Ile Ser Asp Met Cys
        115                 120                 125

Leu Pro Trp Thr Met Arg Ile Ala Leu Lys Tyr His Val Pro Arg Leu
    130                 135                 140

Val Phe Tyr Ser Leu Ser Cys Phe Phe Leu Leu Cys Met Arg Ser Leu
145                 150                 155                 160

Lys Asn Asn Leu Ala Leu Ile Ser Ser Lys Ser Asp Ser Glu Phe Val
                165                 170                 175

Thr Phe Ser Asp Leu Pro Asp Pro Val Glu Phe Leu Lys Ser Glu Leu
            180                 185                 190

Pro Lys Ser Thr Asp Glu Asp Leu Val Lys Phe Ser Tyr Glu Met Gly
```

```
        195                 200                 205

Glu Ala Asp Arg Gln Ser Tyr Gly Val Ile Leu Asn Leu Phe Glu Glu
    210                 215                 220

Met Glu Pro Lys Tyr Leu Ala Glu Tyr Glu Lys Glu Arg Glu Ser Pro
225                 230                 235                 240

Glu Arg Val Trp Cys Val Gly Pro Val Ser Leu Cys Asn Asp Asn Lys
                245                 250                 255

Leu Asp Lys Ala Glu Arg Gly Asn Lys Ala Ser Ile Asp Glu Tyr Lys
            260                 265                 270

Cys Ile Arg Trp Leu Asp Gly Gln Gln Pro Ser Ser Val Val Tyr Val
        275                 280                 285

Ser Leu Gly Ser Leu Cys Asn Leu Val Thr Ala Gln Ile Ile Glu Leu
    290                 295                 300

Gly Leu Gly Leu Glu Ala Ser Lys Lys Pro Phe Ile Trp Val Ile Arg
305                 310                 315                 320

Arg Gly Asn Ile Thr Glu Glu Leu Gln Lys Trp Leu Val Glu Tyr Asp
                325                 330                 335

Phe Glu Glu Lys Ile Lys Gly Arg Gly Leu Val Ile Leu Gly Trp Ala
            340                 345                 350

Pro Gln Val Leu Ile Leu Ser His Pro Ala Ile Gly Cys Phe Leu Thr
        355                 360                 365

His Cys Gly Trp Asn Ser Ser Ile Glu Gly Ile Ser Ala Gly Val Pro
    370                 375                 380

Met Val Thr Trp Pro Leu Phe Ala Asp Gln Val Phe Asn Glu Lys Leu
385                 390                 395                 400

Ile Val Gln Ile Leu Arg Ile Gly Val Ser Val Gly Thr Glu Thr Thr
                405                 410                 415

Met Asn Trp Gly Glu Glu Glu Glu Lys Gly Val Val Val Lys Arg Glu
            420                 425                 430

Lys Val Arg Glu Ala Ile Glu Ile Val Met Asp Gly Asp Glu Arg Glu
        435                 440                 445

Glu Arg Arg Glu Arg Cys Lys Glu Leu Ala Glu Thr Ala Lys Arg Ala
    450                 455                 460

Ile Glu Glu Gly Gly Ser Ser His Arg Asn Leu Thr Met Leu Ile Glu
465                 470                 475                 480

Asp Ile Ile His Gly Gly Gly Leu Ser Tyr Glu Lys Gly Ser Cys Arg
                485                 490                 495
```

<210> SEQ ID NO 49
<211> LENGTH: 1380
<212> TYPE: DNA
<213> ORGANISM: Siraitia grosvenorii

<400> SEQUENCE: 49

```
atggatgccc agcgaggtca caccaccacc atttgatgc ttccatgggt cggctacggc      60

catctcttgc ctttcctcga gctggccaaa agcctctcca ggaggaaatt attccacatc    120

tacttctgtt caacgtctgt tagcctcgac gccattaaac caaagcttcc tccttctatc    180

tcttctgatg attccatcca acttgtggaa cttcgtctcc cttcttctcc tgagttacct    240

cctcatcttc acacaaccaa cggccttccc tctcacctca tgcccgctct ccaccaagcc    300

ttcgtcatgg ccgcccaaca ctttcaggtc attttacaaa cacttgcccc gcatctcctc    360

atttatgaca ttctccaacc ttgggctcct caagtggctt catccctcaa cattccagcc    420

atcaacttca gtactaccgg agcttcaatg ctttctcgaa cgcttcaccc tactcactac    480
```

```
ccaagttcta aattcccaat ctcagagttt gttcttcaca atcactggag agccatgtac    540

accaccgccg atggggctct tacagaagaa ggccacaaaa ttgaagaaac acttgcgaat    600

tgcttgcata cttcttgcgg ggtagttttg gtcaatagtt tcagagagct tgagacgaaa    660

tatatcgatt atctctctgt tctcttgaac aagaaagttg ttccggtcgg tcctttggtt    720

tacgaaccga atcaagaagg ggaagatgaa ggttattcaa gcatcaaaaa ttggcttgac    780

aaaaaggaac cgtcctcaac cgtcttcgtt tcatttggaa ccgaatactt cccgtcaaag    840

gaagaaatgg aagagatagc gtatgggtta gagctgagcg aggttaattt catctgggtc    900

cttagatttc ctcaaggaga cagcaccagc accattgaag acgccttgcc gaaggggttt    960

ctggagagag cgggagagag ggcgatggtg gtgaagggtt gggctcctca ggcgaagata   1020

ctgaagcatt ggagcacagg ggggcttgtg agtcactgtg gatggaactc gatgatggag   1080

ggcatgatgt ttggcgtacc cataatagcg gtcccgatgc atctggacca gccctttaac   1140

gccggactct tggaagaagc tggcgtcggc gtggaagcca agcgaggttc ggacggcaaa   1200

attcaaagag aagaagttgc aaagtcgatc aaagaagtgg tgattgagaa aaccagggaa   1260

gacgtgagga agaaagcaag agaaatgggt gagattttga ggagtaaagg agatgagaaa   1320

attgatgagt tggtggctga aatttctctt ttgcgcaaaa aggctccatg ttcaatttaa   1380
```

```
<210> SEQ ID NO 50
<211> LENGTH: 459
<212> TYPE: PRT
<213> ORGANISM: Siraitia grosvenorii

<400> SEQUENCE: 50

Met Asp Ala Gln Arg Gly His Thr Thr Thr Ile Leu Met Leu Pro Trp
1               5                   10                  15

Val Gly Tyr Gly His Leu Leu Pro Phe Leu Glu Leu Ala Lys Ser Leu
            20                  25                  30

Ser Arg Arg Lys Leu Phe His Ile Tyr Phe Cys Ser Thr Ser Val Ser
        35                  40                  45

Leu Asp Ala Ile Lys Pro Lys Leu Pro Pro Ser Ile Ser Ser Asp Asp
    50                  55                  60

Ser Ile Gln Leu Val Glu Leu Arg Leu Pro Ser Ser Pro Glu Leu Pro
65                  70                  75                  80

Pro His Leu His Thr Thr Asn Gly Leu Pro Ser His Leu Met Pro Ala
                85                  90                  95

Leu His Gln Ala Phe Val Met Ala Ala Gln His Phe Gln Val Ile Leu
            100                 105                 110

Gln Thr Leu Ala Pro His Leu Leu Ile Tyr Asp Ile Leu Gln Pro Trp
        115                 120                 125

Ala Pro Gln Val Ala Ser Ser Leu Asn Ile Pro Ala Ile Asn Phe Ser
    130                 135                 140

Thr Thr Gly Ala Ser Met Leu Ser Arg Thr Leu His Pro Thr His Tyr
145                 150                 155                 160

Pro Ser Ser Lys Phe Pro Ile Ser Glu Phe Val Leu His Asn His Trp
                165                 170                 175

Arg Ala Met Tyr Thr Thr Ala Asp Gly Ala Leu Thr Glu Glu Gly His
            180                 185                 190

Lys Ile Glu Glu Thr Leu Ala Asn Cys Leu His Thr Ser Cys Gly Val
        195                 200                 205

Val Leu Val Asn Ser Phe Arg Glu Leu Glu Thr Lys Tyr Ile Asp Tyr
```

```
    210                 215                 220

Leu Ser Val Leu Leu Asn Lys Lys Val Val Pro Val Gly Pro Leu Val
225                 230                 235                 240

Tyr Glu Pro Asn Gln Glu Gly Glu Asp Glu Gly Tyr Ser Ser Ile Lys
                245                 250                 255

Asn Trp Leu Asp Lys Lys Glu Pro Ser Ser Thr Val Phe Val Ser Phe
            260                 265                 270

Gly Thr Glu Tyr Phe Pro Ser Lys Glu Glu Met Glu Glu Ile Ala Tyr
        275                 280                 285

Gly Leu Glu Leu Ser Glu Val Asn Phe Ile Trp Val Leu Arg Phe Pro
    290                 295                 300

Gln Gly Asp Ser Thr Ser Thr Ile Glu Asp Ala Leu Pro Lys Gly Phe
305                 310                 315                 320

Leu Glu Arg Ala Gly Glu Arg Ala Met Val Val Lys Gly Trp Ala Pro
                325                 330                 335

Gln Ala Lys Ile Leu Lys His Trp Ser Thr Gly Gly Leu Val Ser His
            340                 345                 350

Cys Gly Trp Asn Ser Met Met Glu Gly Met Met Phe Gly Val Pro Ile
        355                 360                 365

Ile Ala Val Pro Met His Leu Asp Gln Pro Phe Asn Ala Gly Leu Leu
    370                 375                 380

Glu Glu Ala Gly Val Gly Val Glu Ala Lys Arg Gly Ser Asp Gly Lys
385                 390                 395                 400

Ile Gln Arg Glu Glu Val Ala Lys Ser Ile Lys Glu Val Val Ile Glu
                405                 410                 415

Lys Thr Arg Glu Asp Val Arg Lys Lys Ala Arg Glu Met Gly Glu Ile
            420                 425                 430

Leu Arg Ser Lys Gly Asp Glu Lys Ile Asp Glu Leu Val Ala Glu Ile
        435                 440                 445

Ser Leu Leu Arg Lys Lys Ala Pro Cys Ser Ile
    450                 455
```

<210> SEQ ID NO 51
<211> LENGTH: 1377
<212> TYPE: DNA
<213> ORGANISM: Siraitia grosvenorii

<400> SEQUENCE: 51

```
atggatgccc agcgaggtca caccacaacc attttgatgt ttccatggct cggctatggc      60

catctttcgg ctttcctaga gttggccaaa agcctctcaa ggaggaactt ccatatctac     120

ttctgttcaa cctctgttaa cctcgacgcc attaaaccaa agcttccttc ttcttcctct     180

tctgattcca tccaacttgt ggaactttgt cttccatctt ctcctgatca gctccctcct     240

catcttcaca caaccaacgc cctccccccct cacctcatgc ccactctcca ccaagccttc     300

tccatggctg cccaacactt tgctgccatt ttacacacac ttgctccgca tctcctcatt     360

tacgactctt tccaaccttg ggctcctcaa ctagcttcat ccctcaacat tccagccatc     420

aacttcaata ctacgggagc ttcagtcctg acccgaatgc ttcacgctac tcactaccca     480

agttctaaat tcccaatttc agagtttgtt ctccacgatt attggaaagc catgtacagc     540

gccgccggtg ggctgttac aaaaaaagac cacaaaattg gagaaacact tgcgaattgc     600

ttgcatgctt cttgtagtgt aattctaatc aatagtttca gagagctcga ggagaaatat     660

atggattatc tctccgttct cttgaacaag aaagttgttc cggttggtcc tttggtttac     720
```

gaaccgaatc aagacgggga agatgaaggt tattcaagca tcaaaaattg gcttgacaaa 780
aaggaaccgt cctccaccgt cttcgtttca tttggaagcg aatacttccc gtcaaaggaa 840
gaaatggaag agatagccca tgggttagag gcgagcgagg ttcatttcat ctgggtcgtt 900
aggtttcctc aaggagacaa caccagcgcc attgaagatg ccttgccgaa ggggtttctg 960
gagagggtgg gagagagagg gatggtggtg aagggttggg ctcctcaggc gaagatactg 1020
aagcattgga gcacaggggg attcgtgagc cactgtggat ggaactcggt gatggaaagc 1080
atgatgtttg gcgttcccat aataggggtt ccgatgcatc tggaccagcc ctttaacgcc 1140
ggactcgcgg aagaagctgg cgtcggcgtg gaagccaagc gagattcgga cggcaaaatt 1200
caaagagaag aagttgcaaa gtcgatcaaa gaagtggtga ttgagaaaac cagggaagac 1260
gtgaggaaga aagcaagaga aatgggtgag attttgagga gtaaaggaga tgagaaaatt 1320
gatgagttgg tggctgaaat ttctcttttg cgcaaaaagg ctccatgttc aatttaa 1377

<210> SEQ ID NO 52
<211> LENGTH: 1377
<212> TYPE: DNA
<213> ORGANISM: Artificial Sequence
<220> FEATURE:
<223> OTHER INFORMATION: Codon-optimized nucleotide sequence encoding UGT98

<400> SEQUENCE: 52
atggatgctc aaagaggtca taccactacc attttgatgt ttccatggtt gggttacggt 60
catttgtctg ctttttgga attggccaag tccttgtcta gaagaaactt ccatatctac 120
ttttgctcca cctccgttaa tttggatgct attaagccaa agttgccatc ctcttcatcc 180
tccgattcta ttcaattggt tgaattgtgc ttgccatctt ccccagatca attgccacca 240
cacttgcata caactaatgc tttaccacca catttgatgc caacattgca tcaagctttt 300
tctatggctg ctcaacattt tgctgctatc ttgcatactt tggctcctca tttgttgatc 360
tacgattctt ttcaaccatg ggctccacaa ttggcttcat ctttgaatat tccagccatc 420
aacttcaaca ctactggtgc ttcagttttg accagaatgt tgcatgctac tcattaccca 480
tcttccaagt tcccaatttc tgaattcgtc ttgcatgatt actggaaggc tatgtattct 540
gctgctggtg gtgctgttac aaaaaaggat cataagattg gtgaaacctt ggccaactgt 600
ttacatgctt cttgctctgt tatcttgatc aactccttca gagaattgga agaaaagtac 660
atggactact tgtccgtctt gttgaacaaa aaggttgttc cagttggtcc attggtctac 720
gaacctaatc aagatggtga agatgaaggt tactcctcca ttaagaattg gttggacaag 780
aaagaaccat cctctaccgt tttgtttcc ttcggttctg aatacttccc atccaaagaa 840
gaaatggaag aaatcgctca tggtttggaa gcttcagaag ttcatttcat ctgggttgtt 900
agattccctc aaggtgataa cacttccgct attgaagatg ctttgccaaa aggtttcttg 960
gaaagagtcg gtgaaagagg tatggttgtt aagggttggg ctcctcaagc taagattttg 1020
aaacattggt caaccggtgg tttcgtttct cattgtggtt ggaattctgt catggaatct 1080
atgatgttcg gtgttccaat tattggtgtc ccaatgcatt tggatcaacc attcaatgct 1140
ggtttggctg aagaagctgg tgttggtgtt gaagctaaaa gagattctga cggtaagatc 1200
caaagagaag aagttgccaa gtccatcaaa gaagttgtta tcgaaaagac cagagaagat 1260
gtcagaaaga aagctagaga aatgggtgaa atcttgagat ctaaaggtga cgaaaagatc 1320
gatgaattgg tcgccgaaat ttccttgttg agaaaaaaag ctccatgctc tatttga 1377

<210> SEQ ID NO 53
<211> LENGTH: 458
<212> TYPE: PRT
<213> ORGANISM: Siraitia grosvenorii

<400> SEQUENCE: 53

Met Asp Ala Gln Arg Gly His Thr Thr Thr Ile Leu Met Phe Pro Trp
1 5 10 15

Leu Gly Tyr Gly His Leu Ser Ala Phe Leu Glu Leu Ala Lys Ser Leu
20 25 30

Ser Arg Arg Asn Phe His Ile Tyr Phe Cys Ser Thr Ser Val Asn Leu
35 40 45

Asp Ala Ile Lys Pro Lys Leu Pro Ser Ser Ser Ser Ser Asp Ser Ile
50 55 60

Gln Leu Val Glu Leu Cys Leu Pro Ser Ser Pro Asp Gln Leu Pro Pro
65 70 75 80

His Leu His Thr Thr Asn Ala Leu Pro Pro His Leu Met Pro Thr Leu
85 90 95

His Gln Ala Phe Ser Met Ala Ala Gln His Phe Ala Ala Ile Leu His
100 105 110

Thr Leu Ala Pro His Leu Leu Ile Tyr Asp Ser Phe Gln Pro Trp Ala
115 120 125

Pro Gln Leu Ala Ser Ser Leu Asn Ile Pro Ala Ile Asn Phe Asn Thr
130 135 140

Thr Gly Ala Ser Val Leu Thr Arg Met Leu His Ala Thr His Tyr Pro
145 150 155 160

Ser Ser Lys Phe Pro Ile Ser Glu Phe Val Leu His Asp Tyr Trp Lys
165 170 175

Ala Met Tyr Ser Ala Ala Gly Gly Ala Val Thr Lys Lys Asp His Lys
180 185 190

Ile Gly Glu Thr Leu Ala Asn Cys Leu His Ala Ser Cys Ser Val Ile
195 200 205

Leu Ile Asn Ser Phe Arg Glu Leu Glu Glu Lys Tyr Met Asp Tyr Leu
210 215 220

Ser Val Leu Leu Asn Lys Lys Val Val Pro Val Gly Pro Leu Val Tyr
225 230 235 240

Glu Pro Asn Gln Asp Gly Glu Asp Glu Gly Tyr Ser Ser Ile Lys Asn
245 250 255

Trp Leu Asp Lys Lys Glu Pro Ser Ser Thr Val Phe Val Ser Phe Gly
260 265 270

Ser Glu Tyr Phe Pro Ser Lys Glu Glu Met Glu Glu Ile Ala His Gly
275 280 285

Leu Glu Ala Ser Glu Val His Phe Ile Trp Val Val Arg Phe Pro Gln
290 295 300

Gly Asp Asn Thr Ser Ala Ile Glu Asp Ala Leu Pro Lys Gly Phe Leu
305 310 315 320

Glu Arg Val Gly Glu Arg Gly Met Val Val Lys Gly Trp Ala Pro Gln
325 330 335

Ala Lys Ile Leu Lys His Trp Ser Thr Gly Gly Phe Val Ser His Cys
340 345 350

Gly Trp Asn Ser Val Met Glu Ser Met Met Phe Gly Val Pro Ile Ile
355 360 365

Gly Val Pro Met His Leu Asp Gln Pro Phe Asn Ala Gly Leu Ala Glu
370 375 380

```
Glu Ala Gly Val Gly Val Glu Ala Lys Arg Asp Ser Asp Gly Lys Ile
385                 390                 395                 400

Gln Arg Glu Glu Val Ala Lys Ser Ile Lys Glu Val Val Ile Glu Lys
                405                 410                 415

Thr Arg Glu Asp Val Arg Lys Lys Ala Arg Glu Met Gly Glu Ile Leu
            420                 425                 430

Arg Ser Lys Gly Asp Glu Lys Ile Asp Glu Leu Val Ala Glu Ile Ser
        435                 440                 445

Leu Leu Arg Lys Lys Ala Pro Cys Ser Ile
    450                 455


<210> SEQ ID NO 54
<211> LENGTH: 496
<212> TYPE: PRT
<213> ORGANISM: Saccharomyces cerevisiae

<400> SEQUENCE: 54

Met Ser Ala Val Asn Val Ala Pro Glu Leu Ile Asn Ala Asp Asn Thr
1               5                   10                  15

Ile Thr Tyr Asp Ala Ile Val Ile Gly Ala Gly Val Ile Gly Pro Cys
            20                  25                  30

Val Ala Thr Gly Leu Ala Arg Lys Gly Lys Lys Val Leu Ile Val Glu
        35                  40                  45

Arg Asp Trp Ala Met Pro Asp Arg Ile Val Gly Glu Leu Met Gln Pro
    50                  55                  60

Gly Gly Val Arg Ala Leu Arg Ser Leu Gly Met Ile Gln Ser Ile Asn
65                  70                  75                  80

Asn Ile Glu Ala Tyr Pro Val Thr Gly Tyr Thr Val Phe Phe Asn Gly
                85                  90                  95

Glu Gln Val Asp Ile Pro Tyr Pro Tyr Lys Ala Asp Ile Pro Lys Val
            100                 105                 110

Glu Lys Leu Lys Asp Leu Val Lys Asp Gly Asn Asp Lys Val Leu Glu
        115                 120                 125

Asp Ser Thr Ile His Ile Lys Asp Tyr Glu Asp Asp Glu Arg Glu Arg
    130                 135                 140

Gly Val Ala Phe Val His Gly Arg Phe Leu Asn Asn Leu Arg Asn Ile
145                 150                 155                 160

Thr Ala Gln Glu Pro Asn Val Thr Arg Val Gln Gly Asn Cys Ile Glu
                165                 170                 175

Ile Leu Lys Asp Glu Lys Asn Glu Val Val Gly Ala Lys Val Asp Ile
            180                 185                 190

Asp Gly Arg Gly Lys Val Glu Phe Lys Ala His Leu Thr Phe Ile Cys
        195                 200                 205

Asp Gly Ile Phe Ser Arg Phe Arg Lys Glu Leu His Pro Asp His Val
    210                 215                 220

Pro Thr Val Gly Ser Ser Phe Val Gly Met Ser Leu Phe Asn Ala Lys
225                 230                 235                 240

Asn Pro Ala Pro Met His Gly His Val Ile Leu Gly Ser Asp His Met
                245                 250                 255

Pro Ile Leu Val Tyr Gln Ile Ser Pro Glu Glu Thr Arg Ile Leu Cys
            260                 265                 270

Ala Tyr Asn Ser Pro Lys Val Pro Ala Asp Ile Lys Ser Trp Met Ile
        275                 280                 285

Lys Asp Val Gln Pro Phe Ile Pro Lys Ser Leu Arg Pro Ser Phe Asp
```

```
    290                 295                 300

Glu Ala Val Ser Gln Gly Lys Phe Arg Ala Met Pro Asn Ser Tyr Leu
305                 310                 315                 320

Pro Ala Arg Gln Asn Asp Val Thr Gly Met Cys Val Ile Gly Asp Ala
                325                 330                 335

Leu Asn Met Arg His Pro Leu Thr Gly Gly Gly Met Thr Val Gly Leu
            340                 345                 350

His Asp Val Val Leu Leu Ile Lys Lys Ile Gly Asp Leu Asp Phe Ser
        355                 360                 365

Asp Arg Glu Lys Val Leu Asp Glu Leu Leu Asp Tyr His Phe Glu Arg
    370                 375                 380

Lys Ser Tyr Asp Ser Val Ile Asn Val Leu Ser Val Ala Leu Tyr Ser
385                 390                 395                 400

Leu Phe Ala Ala Asp Ser Asp Asn Leu Lys Ala Leu Gln Lys Gly Cys
                405                 410                 415

Phe Lys Tyr Phe Gln Arg Gly Gly Asp Cys Val Asn Lys Pro Val Glu
            420                 425                 430

Phe Leu Ser Gly Val Leu Pro Lys Pro Leu Gln Leu Thr Arg Val Phe
        435                 440                 445

Phe Ala Val Ala Phe Tyr Thr Ile Tyr Leu Asn Met Glu Glu Arg Gly
    450                 455                 460

Phe Leu Gly Leu Pro Met Ala Leu Leu Glu Gly Ile Met Ile Leu Ile
465                 470                 475                 480

Thr Ala Ile Arg Val Phe Thr Pro Phe Leu Phe Gly Glu Leu Ile Gly
                485                 490                 495


<210> SEQ ID NO 55
<211> LENGTH: 731
<212> TYPE: PRT
<213> ORGANISM: Saccharomyces cerevisiae

<400> SEQUENCE: 55

Met Thr Glu Phe Tyr Ser Asp Thr Ile Gly Leu Pro Lys Thr Asp Pro
1               5                   10                  15

Arg Leu Trp Arg Leu Arg Thr Asp Glu Leu Gly Arg Glu Ser Trp Glu
            20                  25                  30

Tyr Leu Thr Pro Gln Gln Ala Ala Asn Asp Pro Pro Ser Thr Phe Thr
        35                  40                  45

Gln Trp Leu Leu Gln Asp Pro Lys Phe Pro Gln Pro His Pro Glu Arg
    50                  55                  60

Asn Lys His Ser Pro Asp Phe Ser Ala Phe Asp Ala Cys His Asn Gly
65                  70                  75                  80

Ala Ser Phe Phe Lys Leu Leu Gln Glu Pro Asp Ser Gly Ile Phe Pro
                85                  90                  95

Cys Gln Tyr Lys Gly Pro Met Phe Met Thr Ile Gly Tyr Val Ala Val
            100                 105                 110

Asn Tyr Ile Ala Gly Ile Glu Ile Pro Glu His Glu Arg Ile Glu Leu
        115                 120                 125

Ile Arg Tyr Ile Val Asn Thr Ala His Pro Val Asp Gly Gly Trp Gly
    130                 135                 140

Leu His Ser Val Asp Lys Ser Thr Val Phe Gly Thr Val Leu Asn Tyr
145                 150                 155                 160

Val Ile Leu Arg Leu Leu Gly Leu Pro Lys Asp His Pro Val Cys Ala
                165                 170                 175
```

-continued

```
Lys Ala Arg Ser Thr Leu Leu Arg Leu Gly Gly Ala Ile Gly Ser Pro
            180                 185                 190

His Trp Gly Lys Ile Trp Leu Ser Ala Leu Asn Leu Tyr Lys Trp Glu
        195                 200                 205

Gly Val Asn Pro Ala Pro Pro Glu Thr Trp Leu Leu Pro Tyr Ser Leu
    210                 215                 220

Pro Met His Pro Gly Arg Trp Trp Val His Thr Arg Gly Val Tyr Ile
225                 230                 235                 240

Pro Val Ser Tyr Leu Ser Leu Val Lys Phe Ser Cys Pro Met Thr Pro
                245                 250                 255

Leu Leu Glu Glu Leu Arg Asn Glu Ile Tyr Thr Lys Pro Phe Asp Lys
            260                 265                 270

Ile Asn Phe Ser Lys Asn Arg Asn Thr Val Cys Gly Val Asp Leu Tyr
        275                 280                 285

Tyr Pro His Ser Thr Thr Leu Asn Ile Ala Asn Ser Leu Val Val Phe
    290                 295                 300

Tyr Glu Lys Tyr Leu Arg Asn Arg Phe Ile Tyr Ser Leu Ser Lys Lys
305                 310                 315                 320

Lys Val Tyr Asp Leu Ile Lys Thr Glu Leu Gln Asn Thr Asp Ser Leu
                325                 330                 335

Cys Ile Ala Pro Val Asn Gln Ala Phe Cys Ala Leu Val Thr Leu Ile
            340                 345                 350

Glu Glu Gly Val Asp Ser Glu Ala Phe Gln Arg Leu Gln Tyr Arg Phe
        355                 360                 365

Lys Asp Ala Leu Phe His Gly Pro Gln Gly Met Thr Ile Met Gly Thr
    370                 375                 380

Asn Gly Val Gln Thr Trp Asp Cys Ala Phe Ala Ile Gln Tyr Phe Phe
385                 390                 395                 400

Val Ala Gly Leu Ala Glu Arg Pro Glu Phe Tyr Asn Thr Ile Val Ser
                405                 410                 415

Ala Tyr Lys Phe Leu Cys His Ala Gln Phe Asp Thr Glu Cys Val Pro
            420                 425                 430

Gly Ser Tyr Arg Asp Lys Arg Lys Gly Ala Trp Gly Phe Ser Thr Lys
        435                 440                 445

Thr Gln Gly Tyr Thr Val Ala Asp Cys Thr Ala Glu Ala Ile Lys Ala
    450                 455                 460

Ile Ile Met Val Lys Asn Ser Pro Val Phe Ser Glu Val His His Met
465                 470                 475                 480

Ile Ser Ser Glu Arg Leu Phe Glu Gly Ile Asp Val Leu Leu Asn Leu
                485                 490                 495

Gln Asn Ile Gly Ser Phe Glu Tyr Gly Ser Phe Ala Thr Tyr Glu Lys
            500                 505                 510

Ile Lys Ala Pro Leu Ala Met Glu Thr Leu Asn Pro Ala Glu Val Phe
        515                 520                 525

Gly Asn Ile Met Val Glu Tyr Pro Tyr Val Glu Cys Thr Asp Ser Ser
    530                 535                 540

Val Leu Gly Leu Thr Tyr Phe His Lys Tyr Phe Asp Tyr Arg Lys Glu
545                 550                 555                 560

Glu Ile Arg Thr Arg Ile Arg Ile Ala Ile Glu Phe Ile Lys Lys Ser
                565                 570                 575

Gln Leu Pro Asp Gly Ser Trp Tyr Gly Ser Trp Gly Ile Cys Phe Thr
            580                 585                 590

Tyr Ala Gly Met Phe Ala Leu Glu Ala Leu His Thr Val Gly Glu Thr
```

```
        595                 600                 605

Tyr Glu Asn Ser Ser Thr Val Arg Lys Gly Cys Asp Phe Leu Val Ser
    610                 615                 620

Lys Gln Met Lys Asp Gly Gly Trp Gly Glu Ser Met Lys Ser Ser Glu
625                 630                 635                 640

Leu His Ser Tyr Val Asp Ser Glu Lys Ser Leu Val Val Gln Thr Ala
                645                 650                 655

Trp Ala Leu Ile Ala Leu Leu Phe Ala Glu Tyr Pro Asn Lys Glu Val
            660                 665                 670

Ile Asp Arg Gly Ile Asp Leu Leu Lys Asn Arg Gln Glu Glu Ser Gly
        675                 680                 685

Glu Trp Lys Phe Glu Ser Val Glu Gly Val Phe Asn His Ser Cys Ala
    690                 695                 700

Ile Glu Tyr Pro Ser Tyr Arg Phe Leu Phe Pro Ile Lys Ala Leu Gly
705                 710                 715                 720

Met Tyr Ser Arg Ala Tyr Glu Thr His Thr Leu
                725                 730


<210> SEQ ID NO 56
<211> LENGTH: 496
<212> TYPE: PRT
<213> ORGANISM: Arabidopsis thaliana

<400> SEQUENCE: 56

Met Ala Thr Glu Lys Thr His Gln Phe His Pro Ser Leu His Phe Val
1               5                   10                  15

Leu Phe Pro Phe Met Ala Gln Gly His Met Ile Pro Met Ile Asp Ile
            20                  25                  30

Ala Arg Leu Leu Ala Gln Arg Gly Val Thr Ile Thr Ile Val Thr Thr
        35                  40                  45

Pro His Asn Ala Ala Arg Phe Lys Asn Val Leu Asn Arg Ala Ile Glu
    50                  55                  60

Ser Gly Leu Ala Ile Asn Ile Leu His Val Lys Phe Pro Tyr Gln Glu
65                  70                  75                  80

Phe Gly Leu Pro Glu Gly Lys Glu Asn Ile Asp Ser Leu Asp Ser Thr
                85                  90                  95

Glu Leu Met Val Pro Phe Phe Lys Ala Val Asn Leu Leu Glu Asp Pro
            100                 105                 110

Val Met Lys Leu Met Glu Glu Met Lys Pro Arg Pro Ser Cys Leu Ile
        115                 120                 125

Ser Asp Trp Cys Leu Pro Tyr Thr Ser Ile Ile Ala Lys Asn Phe Asn
    130                 135                 140

Ile Pro Lys Ile Val Phe His Gly Met Gly Cys Phe Asn Leu Leu Cys
145                 150                 155                 160

Met His Val Leu Arg Arg Asn Leu Glu Ile Leu Glu Asn Val Lys Ser
                165                 170                 175

Asp Glu Glu Tyr Phe Leu Val Pro Ser Phe Pro Asp Arg Val Glu Phe
            180                 185                 190

Thr Lys Leu Gln Leu Pro Val Lys Ala Asn Ala Ser Gly Asp Trp Lys
        195                 200                 205

Glu Ile Met Asp Glu Met Val Lys Ala Glu Tyr Thr Ser Tyr Gly Val
    210                 215                 220

Ile Val Asn Thr Phe Gln Glu Leu Glu Pro Pro Tyr Val Lys Asp Tyr
225                 230                 235                 240
```

-continued

```
Lys Glu Ala Met Asp Gly Lys Val Trp Ser Ile Gly Pro Val Ser Leu
                245                 250                 255

Cys Asn Lys Ala Gly Ala Asp Lys Ala Glu Arg Gly Ser Lys Ala Ala
            260                 265                 270

Ile Asp Gln Asp Glu Cys Leu Gln Trp Leu Asp Ser Lys Glu Glu Gly
        275                 280                 285

Ser Val Leu Tyr Val Cys Leu Gly Ser Ile Cys Asn Leu Pro Leu Ser
    290                 295                 300

Gln Leu Lys Glu Leu Gly Leu Gly Leu Glu Glu Ser Arg Arg Ser Phe
305                 310                 315                 320

Ile Trp Val Ile Arg Gly Ser Glu Lys Tyr Lys Glu Leu Phe Glu Trp
                325                 330                 335

Met Leu Glu Ser Gly Phe Glu Glu Arg Ile Lys Glu Arg Gly Leu Leu
            340                 345                 350

Ile Lys Gly Trp Ala Pro Gln Val Leu Ile Leu Ser His Pro Ser Val
        355                 360                 365

Gly Gly Phe Leu Thr His Cys Gly Trp Asn Ser Thr Leu Glu Gly Ile
    370                 375                 380

Thr Ser Gly Ile Pro Leu Ile Thr Trp Pro Leu Phe Gly Asp Gln Phe
385                 390                 395                 400

Cys Asn Gln Lys Leu Val Val Gln Val Leu Lys Ala Gly Val Ser Ala
                405                 410                 415

Gly Val Glu Glu Val Met Lys Trp Gly Glu Glu Asp Lys Ile Gly Val
            420                 425                 430

Leu Val Asp Lys Glu Gly Val Lys Lys Ala Val Glu Glu Leu Met Gly
        435                 440                 445

Asp Ser Asp Asp Ala Lys Glu Arg Arg Arg Arg Val Lys Glu Leu Gly
    450                 455                 460

Glu Leu Ala His Lys Ala Val Glu Lys Gly Gly Ser Ser His Ser Asn
465                 470                 475                 480

Ile Thr Leu Leu Leu Gln Asp Ile Met Gln Leu Ala Gln Phe Lys Asn
                485                 490                 495
```

<210> SEQ ID NO 57
<211> LENGTH: 495
<212> TYPE: PRT
<213> ORGANISM: Arabidopsis thaliana

<400> SEQUENCE: 57

```
Met Val Ser Glu Thr Thr Lys Ser Ser Pro Leu His Phe Val Leu Phe
1               5                   10                  15

Pro Phe Met Ala Gln Gly His Met Ile Pro Met Val Asp Ile Ala Arg
            20                  25                  30

Leu Leu Ala Gln Arg Gly Val Ile Ile Thr Ile Val Thr Thr Pro His
        35                  40                  45

Asn Ala Ala Arg Phe Lys Asn Val Leu Asn Arg Ala Ile Glu Ser Gly
    50                  55                  60

Leu Pro Ile Asn Leu Val Gln Val Lys Phe Pro Tyr Leu Glu Ala Gly
65                  70                  75                  80

Leu Gln Glu Gly Gln Glu Asn Ile Asp Ser Leu Asp Thr Met Glu Arg
                85                  90                  95

Met Ile Pro Phe Phe Lys Ala Val Asn Phe Leu Glu Glu Pro Val Gln
            100                 105                 110

Lys Leu Ile Glu Glu Met Asn Pro Arg Pro Ser Cys Leu Ile Ser Asp
        115                 120                 125
```

```
Phe Cys Leu Pro Tyr Thr Ser Lys Ile Ala Lys Lys Phe Asn Ile Pro
    130                 135                 140

Lys Ile Leu Phe His Gly Met Gly Cys Phe Cys Leu Leu Cys Met His
145                 150                 155                 160

Val Leu Arg Lys Asn Arg Glu Ile Leu Asp Asn Leu Lys Ser Asp Lys
                165                 170                 175

Glu Leu Phe Thr Val Pro Asp Phe Pro Asp Arg Val Glu Phe Thr Arg
            180                 185                 190

Thr Gln Val Pro Val Glu Thr Tyr Val Pro Ala Gly Asp Trp Lys Asp
        195                 200                 205

Ile Phe Asp Gly Met Val Glu Ala Asn Glu Thr Ser Tyr Gly Val Ile
    210                 215                 220

Val Asn Ser Phe Gln Glu Leu Glu Pro Ala Tyr Ala Lys Asp Tyr Lys
225                 230                 235                 240

Glu Val Arg Ser Gly Lys Ala Trp Thr Ile Gly Pro Val Ser Leu Cys
                245                 250                 255

Asn Lys Val Gly Ala Asp Lys Ala Glu Arg Gly Asn Lys Ser Asp Ile
            260                 265                 270

Asp Gln Asp Glu Cys Leu Lys Trp Leu Asp Ser Lys Lys His Gly Ser
        275                 280                 285

Val Leu Tyr Val Cys Leu Gly Ser Ile Cys Asn Leu Pro Leu Ser Gln
    290                 295                 300

Leu Lys Glu Leu Gly Leu Gly Leu Glu Glu Ser Gln Arg Pro Phe Ile
305                 310                 315                 320

Trp Val Ile Arg Gly Trp Glu Lys Tyr Lys Glu Leu Val Glu Trp Phe
                325                 330                 335

Ser Glu Ser Gly Phe Glu Asp Arg Ile Gln Asp Arg Gly Leu Leu Ile
            340                 345                 350

Lys Gly Trp Ser Pro Gln Met Leu Ile Leu Ser His Pro Ser Val Gly
        355                 360                 365

Gly Phe Leu Thr His Cys Gly Trp Asn Ser Thr Leu Glu Gly Ile Thr
    370                 375                 380

Ala Gly Leu Pro Leu Leu Thr Trp Pro Leu Phe Ala Asp Gln Phe Cys
385                 390                 395                 400

Asn Glu Lys Leu Val Val Glu Val Leu Lys Ala Gly Val Arg Ser Gly
                405                 410                 415

Val Glu Gln Pro Met Lys Trp Gly Glu Glu Glu Lys Ile Gly Val Leu
            420                 425                 430

Val Asp Lys Glu Gly Val Lys Lys Ala Val Glu Glu Leu Met Gly Glu
        435                 440                 445

Ser Asp Asp Ala Lys Glu Arg Arg Arg Arg Ala Lys Glu Leu Gly Asp
    450                 455                 460

Ser Ala His Lys Ala Val Glu Glu Gly Gly Ser Ser His Ser Asn Ile
465                 470                 475                 480

Ser Phe Leu Leu Gln Asp Ile Met Glu Leu Ala Glu Pro Asn Asn
                485                 490                 495
```

<210> SEQ ID NO 58
<211> LENGTH: 495
<212> TYPE: PRT
<213> ORGANISM: Arabidopsis thaliana

<400> SEQUENCE: 58

```
Met Ala Phe Glu Lys Asn Asn Glu Pro Phe Pro Leu His Phe Val Leu
```

-continued 1 5 10 15
Phe Pro Phe Met Ala Gln Gly His Met Ile Pro Met Val Asp Ile Ala
20 25 30
Arg Leu Leu Ala Gln Arg Gly Val Leu Ile Thr Ile Val Thr Thr Pro
35 40 45
His Asn Ala Ala Arg Phe Lys Asn Val Leu Asn Arg Ala Ile Glu Ser
50 55 60
Gly Leu Pro Ile Asn Leu Val Gln Val Lys Phe Pro Tyr Gln Glu Ala
65 70 75 80
Gly Leu Gln Glu Gly Gln Glu Asn Met Asp Leu Leu Thr Thr Met Glu
85 90 95
Gln Ile Thr Ser Phe Phe Lys Ala Val Asn Leu Leu Lys Glu Pro Val
100 105 110
Gln Asn Leu Ile Glu Glu Met Ser Pro Arg Pro Ser Cys Leu Ile Ser
115 120 125
Asp Met Cys Leu Ser Tyr Thr Ser Glu Ile Ala Lys Lys Phe Lys Ile
130 135 140
Pro Lys Ile Leu Phe His Gly Met Gly Cys Phe Cys Leu Leu Cys Val
145 150 155 160
Asn Val Leu Arg Lys Asn Arg Glu Ile Leu Asp Asn Leu Lys Ser Asp
165 170 175
Lys Glu Tyr Phe Ile Val Pro Tyr Phe Pro Asp Arg Val Glu Phe Thr
180 185 190
Arg Pro Gln Val Pro Val Glu Thr Tyr Val Pro Ala Gly Trp Lys Glu
195 200 205
Ile Leu Glu Asp Met Val Glu Ala Asp Lys Thr Ser Tyr Gly Val Ile
210 215 220
Val Asn Ser Phe Gln Glu Leu Glu Pro Ala Tyr Ala Lys Asp Phe Lys
225 230 235 240
Glu Ala Arg Ser Gly Lys Ala Trp Thr Ile Gly Pro Val Ser Leu Cys
245 250 255
Asn Lys Val Gly Val Asp Lys Ala Glu Arg Gly Asn Lys Ser Asp Ile
260 265 270
Asp Gln Asp Glu Cys Leu Glu Trp Leu Asp Ser Lys Glu Pro Gly Ser
275 280 285
Val Leu Tyr Val Cys Leu Gly Ser Ile Cys Asn Leu Pro Leu Ser Gln
290 295 300
Leu Leu Glu Leu Gly Leu Gly Leu Glu Glu Ser Gln Arg Pro Phe Ile
305 310 315 320
Trp Val Ile Arg Gly Trp Glu Lys Tyr Lys Glu Leu Val Glu Trp Phe
325 330 335
Ser Glu Ser Gly Phe Glu Asp Arg Ile Gln Asp Arg Gly Leu Leu Ile
340 345 350
Lys Gly Trp Ser Pro Gln Met Leu Ile Leu Ser His Pro Ser Val Gly
355 360 365
Gly Phe Leu Thr His Cys Gly Trp Asn Ser Thr Leu Glu Gly Ile Thr
370 375 380
Ala Gly Leu Pro Met Leu Thr Trp Pro Leu Phe Ala Asp Gln Phe Cys
385 390 395 400
Asn Glu Lys Leu Val Val Gln Ile Leu Lys Val Gly Val Ser Ala Glu
405 410 415
Val Lys Glu Val Met Lys Trp Gly Glu Glu Glu Lys Ile Gly Val Leu
420 425 430

```
Val Asp Lys Glu Gly Val Lys Lys Ala Val Glu Glu Leu Met Gly Glu
        435                 440                 445

Ser Asp Asp Ala Lys Glu Arg Arg Arg Arg Ala Lys Glu Leu Gly Glu
    450                 455                 460

Ser Ala His Lys Ala Val Glu Glu Gly Gly Ser Ser His Ser Asn Ile
465                 470                 475                 480

Thr Phe Leu Leu Gln Asp Ile Met Gln Leu Ala Gln Ser Asn Asn
                485                 490                 495


<210> SEQ ID NO 59
<211> LENGTH: 495
<212> TYPE: PRT
<213> ORGANISM: Stevia rebaudiana

<400> SEQUENCE: 59

Met Ser Pro Lys Met Val Ala Pro Pro Thr Asn Leu His Phe Val Leu
1               5                   10                  15

Phe Pro Leu Met Ala Gln Gly His Leu Val Pro Met Val Asp Ile Ala
            20                  25                  30

Arg Ile Leu Ala Gln Arg Gly Ala Thr Val Thr Ile Ile Thr Thr Pro
        35                  40                  45

Tyr His Ala Asn Arg Val Arg Pro Val Ile Ser Arg Ala Ile Ala Thr
    50                  55                  60

Asn Leu Lys Ile Gln Leu Leu Glu Leu Gln Leu Arg Ser Thr Glu Ala
65                  70                  75                  80

Gly Leu Pro Glu Gly Cys Glu Ser Phe Asp Gln Leu Pro Ser Phe Glu
                85                  90                  95

Tyr Trp Lys Asn Ile Ser Thr Ala Ile Asp Leu Leu Gln Gln Pro Ala
            100                 105                 110

Glu Asp Leu Leu Arg Glu Leu Ser Pro Pro Pro Asp Cys Ile Ile Ser
        115                 120                 125

Asp Phe Leu Phe Pro Trp Thr Thr Asp Val Ala Arg Arg Leu Asn Ile
    130                 135                 140

Pro Arg Leu Val Phe Asn Gly Pro Gly Cys Phe Tyr Leu Leu Cys Ile
145                 150                 155                 160

His Val Ala Ile Thr Ser Asn Ile Leu Gly Glu Asn Glu Pro Val Ser
                165                 170                 175

Ser Asn Thr Glu Arg Val Val Leu Pro Gly Leu Pro Asp Arg Ile Glu
            180                 185                 190

Val Thr Lys Leu Gln Ile Val Gly Ser Ser Arg Pro Ala Asn Val Asp
        195                 200                 205

Glu Met Gly Ser Trp Leu Arg Ala Val Glu Ala Glu Lys Ala Ser Phe
    210                 215                 220

Gly Ile Val Val Asn Thr Phe Glu Glu Leu Glu Pro Glu Tyr Val Glu
225                 230                 235                 240

Glu Tyr Lys Thr Val Lys Asp Lys Lys Met Trp Cys Ile Gly Pro Val
                245                 250                 255

Ser Leu Cys Asn Lys Thr Gly Pro Asp Leu Ala Glu Arg Gly Asn Lys
            260                 265                 270

Ala Ala Ile Thr Glu His Asn Cys Leu Lys Trp Leu Asp Glu Arg Lys
        275                 280                 285

Leu Gly Ser Val Leu Tyr Val Cys Leu Gly Ser Leu Ala Arg Ile Ser
    290                 295                 300

Ala Ala Gln Ala Ile Glu Leu Gly Leu Gly Leu Glu Ser Ile Asn Arg
```

305 310 315 320

Pro Phe Ile Trp Cys Val Arg Asn Glu Thr Asp Glu Leu Lys Thr Trp
325 330 335

Phe Leu Asp Gly Phe Glu Glu Arg Val Arg Asp Arg Gly Leu Ile Val
340 345 350

His Gly Trp Ala Pro Gln Val Leu Ile Leu Ser His Pro Thr Ile Gly
355 360 365

Gly Phe Leu Thr His Cys Gly Trp Asn Ser Thr Ile Glu Ser Ile Thr
370 375 380

Ala Gly Val Pro Met Ile Thr Trp Pro Phe Phe Ala Asp Gln Phe Leu
385 390 395 400

Asn Glu Ala Phe Ile Val Glu Val Leu Lys Ile Gly Val Arg Ile Gly
405 410 415

Val Glu Arg Ala Cys Leu Phe Gly Glu Glu Asp Lys Val Gly Val Leu
420 425 430

Val Lys Lys Glu Asp Val Lys Lys Ala Val Glu Cys Leu Met Asp Glu
435 440 445

Asp Glu Asp Gly Asp Gln Arg Arg Lys Arg Val Ile Glu Leu Ala Lys
450 455 460

Met Ala Lys Ile Ala Met Ala Glu Gly Gly Ser Ser Tyr Glu Asn Val
465 470 475 480

Ser Ser Leu Ile Arg Asp Val Thr Glu Thr Val Arg Ala Pro His
485 490 495

<210> SEQ ID NO 60
<211> LENGTH: 481
<212> TYPE: PRT
<213> ORGANISM: Stevia rebaudiana

<400> SEQUENCE: 60

Met Asp Ala Met Ala Thr Thr Glu Lys Lys Pro His Val Ile Phe Ile
1 5 10 15

Pro Phe Pro Ala Gln Ser His Ile Lys Ala Met Leu Lys Leu Ala Gln
20 25 30

Leu Leu His His Lys Gly Leu Gln Ile Thr Phe Val Asn Thr Asp Phe
35 40 45

Ile His Asn Gln Phe Leu Glu Ser Ser Gly Pro His Cys Leu Asp Gly
50 55 60

Ala Pro Gly Phe Arg Phe Glu Thr Ile Pro Asp Gly Val Ser His Ser
65 70 75 80

Pro Glu Ala Ser Ile Pro Ile Arg Glu Ser Leu Leu Arg Ser Ile Glu
85 90 95

Thr Asn Phe Leu Asp Arg Phe Ile Asp Leu Val Thr Lys Leu Pro Asp
100 105 110

Pro Pro Thr Cys Ile Ile Ser Asp Gly Phe Leu Ser Val Phe Thr Ile
115 120 125

Asp Ala Ala Lys Lys Leu Gly Ile Pro Val Met Met Tyr Trp Thr Leu
130 135 140

Ala Ala Cys Gly Phe Met Gly Phe Tyr His Ile His Ser Leu Ile Glu
145 150 155 160

Lys Gly Phe Ala Pro Leu Lys Asp Ala Ser Tyr Leu Thr Asn Gly Tyr
165 170 175

Leu Asp Thr Val Ile Asp Trp Val Pro Gly Met Glu Gly Ile Arg Leu
180 185 190

-continued

```
Lys Asp Phe Pro Leu Asp Trp Ser Thr Asp Leu Asn Asp Lys Val Leu
        195                 200                 205

Met Phe Thr Thr Glu Ala Pro Gln Arg Ser His Lys Val Ser His His
    210                 215                 220

Ile Phe His Thr Phe Asp Glu Leu Glu Pro Ser Ile Ile Lys Thr Leu
225                 230                 235                 240

Ser Leu Arg Tyr Asn His Ile Tyr Thr Ile Gly Pro Leu Gln Leu Leu
                245                 250                 255

Leu Asp Gln Ile Pro Glu Glu Lys Lys Gln Thr Gly Ile Thr Ser Leu
            260                 265                 270

His Gly Tyr Ser Leu Val Lys Glu Glu Pro Glu Cys Phe Gln Trp Leu
        275                 280                 285

Gln Ser Lys Glu Pro Asn Ser Val Val Tyr Val Asn Phe Gly Ser Thr
    290                 295                 300

Thr Val Met Ser Leu Glu Asp Met Thr Glu Phe Gly Trp Gly Leu Ala
305                 310                 315                 320

Asn Ser Asn His Tyr Phe Leu Trp Ile Ile Arg Ser Asn Leu Val Ile
                325                 330                 335

Gly Glu Asn Ala Val Leu Pro Pro Glu Leu Glu Glu His Ile Lys Lys
            340                 345                 350

Arg Gly Phe Ile Ala Ser Trp Cys Ser Gln Glu Lys Val Leu Lys His
        355                 360                 365

Pro Ser Val Gly Gly Phe Leu Thr His Cys Gly Trp Gly Ser Thr Ile
    370                 375                 380

Glu Ser Leu Ser Ala Gly Val Pro Met Ile Cys Trp Pro Tyr Ser Trp
385                 390                 395                 400

Asp Gln Leu Thr Asn Cys Arg Tyr Ile Cys Lys Glu Trp Glu Val Gly
                405                 410                 415

Leu Glu Met Gly Thr Lys Val Lys Arg Asp Glu Val Lys Arg Leu Val
            420                 425                 430

Gln Glu Leu Met Gly Glu Gly Gly His Lys Met Arg Asn Lys Ala Lys
        435                 440                 445

Asp Trp Lys Glu Lys Ala Arg Ile Ala Ile Ala Pro Asn Gly Ser Ser
    450                 455                 460

Ser Leu Asn Ile Asp Lys Met Val Lys Glu Ile Thr Val Leu Ala Arg
465                 470                 475                 480

Asn
```

<210> SEQ ID NO 61
<211> LENGTH: 1410
<212> TYPE: DNA
<213> ORGANISM: Siraitia grosvenorii

<400> SEQUENCE: 61

```
atggagcaag ctcatgatct tcttcacgtc ctccttttc cgtatccggc gaagggccac      60

atcaagccct tcctctgcct cgccgagctc ctctgcaacg ccggtctcaa cgtcaccttc    120

ctcaacaccg actacaacca ccgccgcctc cacaatctcc atctcctcgc cgcctgcttt    180

ccctctcttc atttcgagtc catttccgac ggcctccagc ccgatcagcc tcgagatata    240

ctggaccca agttttatat atccatctgt caagtcacta aacccctttt ccgggagctc    300

ctcctttcct acaaacgaac ttccagtgtc cagaccggcc gcccgccaat aacttgcgtt    360

attacagatg tgatttttcg ttttccgatc gacgtagctg aagaactgga tattcctgtg    420

tttagtttct gtactttcag tgcccgtttc atgtttcttt acttctggat tcccaagctc    480
```

-continued

```
attgaagatg gccagcttcc atacccaaac ggcaatatca accagaaact ctacggtgtt    540

gctcctgagg cggaaggcct tttaagatgt aaagatttgc cgggacattg ggctttcgca    600

gacgaactaa aagatgatca acttaacttt gtggaccaga caacggcgtc acttcgatcc    660

tccggtctca ttctcaacac attcgacgac ctcgaagctc catttctggg gcgtctctcc    720

accatcttta agaaaatcta cgccgttgga cccatccacg ctctgttgaa ctcccaccac    780

tgtggtcttt ggaaagaaga tcacagttgc ctggcgtggc tcgactcccg ggcggcgaga    840

tccgtcgtgt tcgtcagctt cgggagcttg gtgaagataa caagtaggca gctgatggag    900

ttttggcatg gcttgctcaa cagtggaacg tcgttcctct tcgtgttgag atctgacgta    960

gttgagggcg atggtgaaaa acaagtcgtc aaagaaattt acgagacgaa ggcagagggg   1020

aaatggttgg ttgtggggtg ggctccgcaa gagaaggtgt tagcccatga agctgttggt   1080

ggatttctga cccattcggg ctggaactcc attttagaga gcattgctgc tggggttcct   1140

atgatctcct gccccaaaat tggagaccag tccagtaact gtacgtggat cagtaaagta   1200

tggaaaattg ggctcgaaat ggaggaccaa tacgaccggg ccacggtcga ggcaatggtt   1260

aggtctataa tgaaacatga aggagaaaaa attcaaaaga caattgcaga gttagcaaaa   1320

cgagccaagt ataaagttag taaagatggg acatcgtatc gaaatttaga aattttaatt   1380

gaggatatta aaaaaattaa accaaattaa                                    1410
```

<210> SEQ ID NO 62
<211> LENGTH: 469
<212> TYPE: PRT
<213> ORGANISM: Siraitia grosvenorii

<400> SEQUENCE: 62

```
Met Glu Gln Ala His Asp Leu Leu His Val Leu Leu Phe Pro Tyr Pro
1               5                   10                  15

Ala Lys Gly His Ile Lys Pro Phe Leu Cys Leu Ala Glu Leu Leu Cys
            20                  25                  30

Asn Ala Gly Leu Asn Val Thr Phe Leu Asn Thr Asp Tyr Asn His Arg
        35                  40                  45

Arg Leu His Asn Leu His Leu Leu Ala Ala Cys Phe Pro Ser Leu His
    50                  55                  60

Phe Glu Ser Ile Ser Asp Gly Leu Gln Pro Asp Gln Pro Arg Asp Ile
65                  70                  75                  80

Leu Asp Pro Lys Phe Tyr Ile Ser Ile Cys Gln Val Thr Lys Pro Leu
                85                  90                  95

Phe Arg Glu Leu Leu Leu Ser Tyr Lys Arg Thr Ser Ser Val Gln Thr
            100                 105                 110

Gly Arg Pro Pro Ile Thr Cys Val Ile Thr Asp Val Ile Phe Arg Phe
        115                 120                 125

Pro Ile Asp Val Ala Glu Glu Leu Asp Ile Pro Val Phe Ser Phe Cys
    130                 135                 140

Thr Phe Ser Ala Arg Phe Met Phe Leu Tyr Phe Trp Ile Pro Lys Leu
145                 150                 155                 160

Ile Glu Asp Gly Gln Leu Pro Tyr Pro Asn Gly Asn Ile Asn Gln Lys
                165                 170                 175

Leu Tyr Gly Val Ala Pro Glu Ala Glu Gly Leu Leu Arg Cys Lys Asp
            180                 185                 190

Leu Pro Gly His Trp Ala Phe Ala Asp Glu Leu Lys Asp Asp Gln Leu
        195                 200                 205
```

Asn Phe Val Asp Gln Thr Thr Ala Ser Leu Arg Ser Ser Gly Leu Ile
    210                 215                 220

Leu Asn Thr Phe Asp Asp Leu Glu Ala Pro Phe Leu Gly Arg Leu Ser
225                 230                 235                 240

Thr Ile Phe Lys Lys Ile Tyr Ala Val Gly Pro Ile His Ala Leu Leu
                245                 250                 255

Asn Ser His His Cys Gly Leu Trp Lys Glu Asp His Ser Cys Leu Ala
            260                 265                 270

Trp Leu Asp Ser Arg Ala Ala Arg Ser Val Val Phe Val Ser Phe Gly
        275                 280                 285

Ser Leu Val Lys Ile Thr Ser Arg Gln Leu Met Glu Phe Trp His Gly
    290                 295                 300

Leu Leu Asn Ser Gly Thr Ser Phe Leu Phe Val Leu Arg Ser Asp Val
305                 310                 315                 320

Val Glu Gly Asp Gly Glu Lys Gln Val Val Lys Glu Ile Tyr Glu Thr
                325                 330                 335

Lys Ala Glu Gly Lys Trp Leu Val Val Gly Trp Ala Pro Gln Glu Lys
            340                 345                 350

Val Leu Ala His Glu Ala Val Gly Gly Phe Leu Thr His Ser Gly Trp
        355                 360                 365

Asn Ser Ile Leu Glu Ser Ile Ala Ala Gly Val Pro Met Ile Ser Cys
    370                 375                 380

Pro Lys Ile Gly Asp Gln Ser Ser Asn Cys Thr Trp Ile Ser Lys Val
385                 390                 395                 400

Trp Lys Ile Gly Leu Glu Met Glu Asp Gln Tyr Asp Arg Ala Thr Val
                405                 410                 415

Glu Ala Met Val Arg Ser Ile Met Lys His Glu Gly Glu Lys Ile Gln
            420                 425                 430

Lys Thr Ile Ala Glu Leu Ala Lys Arg Ala Lys Tyr Lys Val Ser Lys
        435                 440                 445

Asp Gly Thr Ser Tyr Arg Asn Leu Glu Ile Leu Ile Glu Asp Ile Lys
    450                 455                 460

Lys Ile Lys Pro Asn
465

<210> SEQ ID NO 63
<211> LENGTH: 1347
<212> TYPE: DNA
<213> ORGANISM: Saccharomyces cerevisiae

<400> SEQUENCE: 63
atgctttcgc ttaaaacgtt actgtgtacg ttgttgactg tgtcatcagt actcgctacc 60
ccagtccctg caagagaccc ttcttccatt caatttgttc atgaggagaa caagaaaaga 120
tactacgatt atgaccacgg ttccctcgga gaaccaatcc gtggtgtcaa cattggtggt 180
tggttacttc ttgaaccata cattactcca tctttgttcg aggctttccg tacaaatgat 240
gacaacgacg aaggaattcc tgtcgacgaa tatcacttct gtcaatattt aggtaaggat 300
ttggctaaaa gccgtttaca gagccattgg tctactttct accaagaaca agatttcgct 360
aatattgctt cccaaggttt caaccttgtc agaattccta tcggttactg ggctttccaa 420
actttggacg atgatcctta tgttagcggc ctacaggaat cttacctaga ccaagccatc 480
ggttgggcta gaaacaacag cttgaaagtt tgggttgatt tgcatggtgc cgctggttcg 540
cagaacgggt ttgataactc tggtttgaga gattcataca agtttttgga agacagcaat 600

```
ttggccgtta ctacaaatgt cttgaactac atattgaaaa aatactctgc ggaggaatac    660

ttggacactg ttattggtat cgaattgatt aatgagccat tgggtcctgt tctagacatg    720

gataaaatga agaatgacta cttggcacct gcttacgaat acttgagaaa caacatcaag    780

agtgaccaag ttatcatcat ccatgacgct ttccaaccat acaattattg ggatgacttc    840

atgactgaaa acgatggcta ctggggtgtc actatcgacc atcatcacta ccaagtcttt    900

gcttctgatc aattggaaag atccattgat gaacatatta aagtagcttg tgaatggggt    960

accggagttt tgaatgaatc ccactggact gtttgtggtg agtttgctgc cgctttgact   1020

gattgtacaa aatggttgaa tagtgttggc ttcggcgcta gatacgacgg ttcttgggtc   1080

aatggtgacc aaacatcttc ttacattggc tcttgtgcta acaacgatga tatagcttac   1140

tggtctgacg aaagaaagga aaacacaaga cgttatgtgg aggcacaact agatgccttt   1200

gaaatgagag gggttggat tatctggtgt tacaagacag aatctagttt ggaatgggat   1260

gctcaaagat tgatgttcaa tggtttattc cctcaaccat tgactgacag aaagtatcca   1320

aaccaatgtg gcacaatttc taactaa                                        1347
```

<210> SEQ ID NO 64
<211> LENGTH: 448
<212> TYPE: PRT
<213> ORGANISM: Saccharomyces cerevisiae

<400> SEQUENCE: 64

```
Met Leu Ser Leu Lys Thr Leu Leu Cys Thr Leu Leu Thr Val Ser Ser
1               5                   10                  15

Val Leu Ala Thr Pro Val Pro Ala Arg Asp Pro Ser Ser Ile Gln Phe
            20                  25                  30

Val His Glu Glu Asn Lys Lys Arg Tyr Tyr Asp Tyr Asp His Gly Ser
        35                  40                  45

Leu Gly Glu Pro Ile Arg Gly Val Asn Ile Gly Gly Trp Leu Leu Leu
    50                  55                  60

Glu Pro Tyr Ile Thr Pro Ser Leu Phe Glu Ala Phe Arg Thr Asn Asp
65                  70                  75                  80

Asp Asn Asp Glu Gly Ile Pro Val Asp Glu Tyr His Phe Cys Gln Tyr
                85                  90                  95

Leu Gly Lys Asp Leu Ala Lys Ser Arg Leu Gln Ser His Trp Ser Thr
            100                 105                 110

Phe Tyr Gln Glu Gln Asp Phe Ala Asn Ile Ala Ser Gln Gly Phe Asn
        115                 120                 125

Leu Val Arg Ile Pro Ile Gly Tyr Trp Ala Phe Gln Thr Leu Asp Asp
    130                 135                 140

Asp Pro Tyr Val Ser Gly Leu Gln Glu Ser Tyr Leu Asp Gln Ala Ile
145                 150                 155                 160

Gly Trp Ala Arg Asn Asn Ser Leu Lys Val Trp Val Asp Leu His Gly
                165                 170                 175

Ala Ala Gly Ser Gln Asn Gly Phe Asp Asn Ser Gly Leu Arg Asp Ser
            180                 185                 190

Tyr Lys Phe Leu Glu Asp Ser Asn Leu Ala Val Thr Thr Asn Val Leu
        195                 200                 205

Asn Tyr Ile Leu Lys Lys Tyr Ser Ala Glu Glu Tyr Leu Asp Thr Val
    210                 215                 220

Ile Gly Ile Glu Leu Ile Asn Glu Pro Leu Gly Pro Val Leu Asp Met
225                 230                 235                 240
```

```
Asp Lys Met Lys Asn Asp Tyr Leu Ala Pro Ala Tyr Glu Tyr Leu Arg
                245                 250                 255

Asn Asn Ile Lys Ser Asp Gln Val Ile Ile Ile His Asp Ala Phe Gln
            260                 265                 270

Pro Tyr Asn Tyr Trp Asp Asp Phe Met Thr Glu Asn Asp Gly Tyr Trp
        275                 280                 285

Gly Val Thr Ile Asp His His His Tyr Gln Val Phe Ala Ser Asp Gln
    290                 295                 300

Leu Glu Arg Ser Ile Asp Glu His Ile Lys Val Ala Cys Glu Trp Gly
305                 310                 315                 320

Thr Gly Val Leu Asn Glu Ser His Trp Thr Val Cys Gly Glu Phe Ala
                325                 330                 335

Ala Ala Leu Thr Asp Cys Thr Lys Trp Leu Asn Ser Val Gly Phe Gly
            340                 345                 350

Ala Arg Tyr Asp Gly Ser Trp Val Asn Gly Asp Gln Thr Ser Ser Tyr
        355                 360                 365

Ile Gly Ser Cys Ala Asn Asn Asp Asp Ile Ala Tyr Trp Ser Asp Glu
    370                 375                 380

Arg Lys Glu Asn Thr Arg Arg Tyr Val Glu Ala Gln Leu Asp Ala Phe
385                 390                 395                 400

Glu Met Arg Gly Gly Trp Ile Ile Trp Cys Tyr Lys Thr Glu Ser Ser
                405                 410                 415

Leu Glu Trp Asp Ala Gln Arg Leu Met Phe Asn Gly Leu Phe Pro Gln
            420                 425                 430

Pro Leu Thr Asp Arg Lys Tyr Pro Asn Gln Cys Gly Thr Ile Ser Asn
        435                 440                 445
```

<210> SEQ ID NO 65
<211> LENGTH: 1689
<212> TYPE: DNA
<213> ORGANISM: Saccharomyces cerevisiae

<400> SEQUENCE: 65

```
atgcctttga agtcgttttt tttttcagca tttctagttt tatgcctgtc taaattcacg     60

caaggcgttg gcaccacaga gaaggaagaa tcgttatcgc ctttggaact aaatatttta    120

caaaacaaat tcgcctccta ctatgcaaac gacactatca ccgtgaaagg tattactatt    180

ggcggctggc tagtaacaga accttatatc acgccatcat tatatcgtaa tgctacgtca    240

ctggcaaaac agcaaaactc ttccagcaat atctccattg tcgacgaatt tactctttgt    300

aaaaccttag gatataacac ctctctaact ttattggata atcacttcaa aacttggatt    360

acagaggatg attttgaaca aatcaaaacc aacggtttca atttagttag gatccccatc    420

ggatattggg cgtggaaaca aaatactgat aaaaacttgt acatcgataa cataactttc    480

aatgatccat acgtaagtga tggattacaa ctgaaatatt taaataatgc tctcgaatgg    540

gcgcaaaagt acgaactaaa tgtatggtta gatctacatg gtgctcctgg atcccagaat    600

ggattcgata attccggtga aagaatactc tatggcgatt taggctggtt aaggttgaat    660

aatactaaag aactgactct ggctatttgg agagatatgt tccagacatt tttaaataaa    720

ggtgacaaaa gtcctgtggt gggtattcaa atcgtcaacg aaccgcttgg tggcaaaatc    780

gatgtttcag acataacgga gatgtattac gaagcatttg acttgctcaa gaaaaatcag    840

aattcgagtg acaacactac gtttgttatt catgacggtt ttcaaggaat cggtcactgg    900

aacttggagc taaacccaac ctaccagaat gtatcgcatc attatttcaa tttgactggt    960
```

```
gcaaattaca gctctcaaga tatattggtc gaccatcatc attatgaagt gtttactgat   1020

gcgcaattgg ccgaaactca gtttgcacgt attgaaaaca ttatcaatta tggggactct   1080

atccacaaag aactttcttt tcacccagca gtagtcggag aatggtcagg cgctattact   1140

gattgtgcaa cctggctaaa tggtgttggg gtgggtgcac gttacgatgg atcatactac   1200

aatacaacgt tgtttaccac caacgacaag ccagttggaa catgtatatc ccaaaatagc   1260

ttagctgatt ggacgcaaga ttaccgtgac cgtgtgagac aattcattga ggcacagcta   1320

gccacttatt cgtcaaaaac aacgggatgg attttttgga attggaagac cgaagacgcc   1380

gtagaatggg attatttgaa gctaaaagaa gctaaccttt tcccttcccc tttcgacaac   1440

tacacgtact tcaaagcaga tggatctatc gaagaaaaat tctcatcctc tttatcagca   1500

caggcatttc caagaacaac gtcatcggtt ttgtcctcca ctacgacttc caggaagagt   1560

aagaatgctg caatttctaa taaactaaca acttcgcagc tattaccaat caaaaatatg   1620

agtttgacct ggaaagcgag cgtatgcgca ctcgctatca ccattgccgc tctttgcgct   1680

tctctttaa                                                           1689
```

<210> SEQ ID NO 66
<211> LENGTH: 562
<212> TYPE: PRT
<213> ORGANISM: Saccharomyces cerevisiae

<400> SEQUENCE: 66

```
Met Pro Leu Lys Ser Phe Phe Phe Ser Ala Phe Leu Val Leu Cys Leu
1               5                   10                  15

Ser Lys Phe Thr Gln Gly Val Gly Thr Thr Glu Lys Glu Glu Ser Leu
            20                  25                  30

Ser Pro Leu Glu Leu Asn Ile Leu Gln Asn Lys Phe Ala Ser Tyr Tyr
        35                  40                  45

Ala Asn Asp Thr Ile Thr Val Lys Gly Ile Thr Ile Gly Gly Trp Leu
    50                  55                  60

Val Thr Glu Pro Tyr Ile Thr Pro Ser Leu Tyr Arg Asn Ala Thr Ser
65                  70                  75                  80

Leu Ala Lys Gln Gln Asn Ser Ser Ser Asn Ile Ser Ile Val Asp Glu
                85                  90                  95

Phe Thr Leu Cys Lys Thr Leu Gly Tyr Asn Thr Ser Leu Thr Leu Leu
            100                 105                 110

Asp Asn His Phe Lys Thr Trp Ile Thr Glu Asp Asp Phe Glu Gln Ile
        115                 120                 125

Lys Thr Asn Gly Phe Asn Leu Val Arg Ile Pro Ile Gly Tyr Trp Ala
    130                 135                 140

Trp Lys Gln Asn Thr Asp Lys Asn Leu Tyr Ile Asp Asn Ile Thr Phe
145                 150                 155                 160

Asn Asp Pro Tyr Val Ser Asp Gly Leu Gln Leu Lys Tyr Leu Asn Asn
                165                 170                 175

Ala Leu Glu Trp Ala Gln Lys Tyr Glu Leu Asn Val Trp Leu Asp Leu
            180                 185                 190

His Gly Ala Pro Gly Ser Gln Asn Gly Phe Asp Asn Ser Gly Glu Arg
        195                 200                 205

Ile Leu Tyr Gly Asp Leu Gly Trp Leu Arg Leu Asn Asn Thr Lys Glu
    210                 215                 220

Leu Thr Leu Ala Ile Trp Arg Asp Met Phe Gln Thr Phe Leu Asn Lys
225                 230                 235                 240
```

```
Gly Asp Lys Ser Pro Val Val Gly Ile Gln Ile Val Asn Glu Pro Leu
                245                 250                 255

Gly Gly Lys Ile Asp Val Ser Asp Ile Thr Glu Met Tyr Tyr Glu Ala
            260                 265                 270

Phe Asp Leu Leu Lys Lys Asn Gln Asn Ser Ser Asp Asn Thr Thr Phe
        275                 280                 285

Val Ile His Asp Gly Phe Gln Gly Ile Gly His Trp Asn Leu Glu Leu
    290                 295                 300

Asn Pro Thr Tyr Gln Asn Val Ser His His Tyr Phe Asn Leu Thr Gly
305                 310                 315                 320

Ala Asn Tyr Ser Ser Gln Asp Ile Leu Val Asp His His His Tyr Glu
                325                 330                 335

Val Phe Thr Asp Ala Gln Leu Ala Glu Thr Gln Phe Ala Arg Ile Glu
            340                 345                 350

Asn Ile Ile Asn Tyr Gly Asp Ser Ile His Lys Glu Leu Ser Phe His
        355                 360                 365

Pro Ala Val Val Gly Glu Trp Ser Gly Ala Ile Thr Asp Cys Ala Thr
    370                 375                 380

Trp Leu Asn Gly Val Gly Val Gly Ala Arg Tyr Asp Gly Ser Tyr Tyr
385                 390                 395                 400

Asn Thr Thr Leu Phe Thr Thr Asn Asp Lys Pro Val Gly Thr Cys Ile
                405                 410                 415

Ser Gln Asn Ser Leu Ala Asp Trp Thr Gln Asp Tyr Arg Asp Arg Val
            420                 425                 430

Arg Gln Phe Ile Glu Ala Gln Leu Ala Thr Tyr Ser Ser Lys Thr Thr
        435                 440                 445

Gly Trp Ile Phe Trp Asn Trp Lys Thr Glu Asp Ala Val Glu Trp Asp
    450                 455                 460

Tyr Leu Lys Leu Lys Glu Ala Asn Leu Phe Pro Ser Pro Phe Asp Asn
465                 470                 475                 480

Tyr Thr Tyr Phe Lys Ala Asp Gly Ser Ile Glu Glu Lys Phe Ser Ser
                485                 490                 495

Ser Leu Ser Ala Gln Ala Phe Pro Arg Thr Thr Ser Ser Val Leu Ser
            500                 505                 510

Ser Thr Thr Thr Ser Arg Lys Ser Lys Asn Ala Ala Ile Ser Asn Lys
        515                 520                 525

Leu Thr Thr Ser Gln Leu Leu Pro Ile Lys Asn Met Ser Leu Thr Trp
    530                 535                 540

Lys Ala Ser Val Cys Ala Leu Ala Ile Thr Ile Ala Ala Leu Cys Ala
545                 550                 555                 560

Ser Leu
```

<210> SEQ ID NO 67
<211> LENGTH: 1425
<212> TYPE: DNA
<213> ORGANISM: Siraitia grosvenorii

<400> SEQUENCE: 67

```
atggtgcaac ctcgggtact gctgtttcct ttcccggcac tgggccacgt gaagcccttc      60

ttatcactgg cggagctgct ttccgacgcc ggcatagacg tcgtcttcct cagcaccgag     120

tataaccacc gtcggatctc caacactgaa gccctagcct cccgcttccc gacgcttcat     180

ttcgaaacta taccggatgg cctgccgcct aatgagtcgc gcgctcttgc cgacggccca     240
```

-continued

```
ctgtatttct ccatgcgtga gggaactaaa ccgagattcc ggcaactgat tcaatctctt    300

aacgacggtc gttggcccat cacctgcatt atcactgaca tcatgttatc ttctccgatt    360

gaagtagcgg aagaatttgg gattccagta attgccttct gcccctgcag tgctcgctac    420

ttatcgattc actttttat accgaagctc gttgaggaag gtcaaattcc atacgcagat    480

gacgatccga ttggagagat ccagggggtg cccttgttcg aaggtctttt gcgacggaat    540

catttgcctg gttcttggtc tgataaatct gcagatatat ctttctcgca tggcttgatt    600

aatcagaccc ttgcagctgg tcgagcctcg gctcttatac tcaacacctt cgacgagctc    660

gaagctccat ttctgaccca tctctcttcc attttcaaca aaatctacac cattggaccc    720

ctccatgctc tgtccaaatc aaggctcggc gactcctcct cctccgcttc tgccctctcc    780

ggattctgga aagaggatag agcctgcatg tcctggctcg actgtcagcc gccgagatct    840

gtggttttcg tcagtttcgg gagtacgatg aagatgaaag ccgatgaatt gagagagttc    900

tggtatgggt tggtgagcag cgggaaaccg ttcctctgcg tgttgagatc cgacgttgtt    960

tccggcggag aagcggcgga attgatcgaa cagatggcgg aggaggaggg agctggaggg   1020

aagctgggaa tggtagtgga gtgggcagcg caagagaagg tcctgagcca ccctgccgtc   1080

ggtgggtttt tgacgcactg cgggtggaac tcaacggtgg aaagcattgc cgcgggagtt   1140

ccgatgatgt gctggccgat tctcggcgac caacccagca acgccacttg gatcgacaga   1200

gtgtggaaaa ttggggttga aaggaacaat cgtgaatggg acaggttgac ggtggagaag   1260

atggtgagag cattgatgga aggccaaaag agagtggaga ttcagagatc aatggagaag   1320

ctttcaaagt tggcaaatga gaaggttgtc aggggtgggt tgtcttttga taacttggaa   1380

gttctcgttg aagacatcaa aaaattgaaa ccatataaat tttaa                   1425


<210> SEQ ID NO 68
<211> LENGTH: 474
<212> TYPE: PRT
<213> ORGANISM: Siratia grosvenorii

<400> SEQUENCE: 68

Met Val Gln Pro Arg Val Leu Leu Phe Pro Phe Pro Ala Leu Gly His
1               5                   10                  15

Val Lys Pro Phe Leu Ser Leu Ala Glu Leu Leu Ser Asp Ala Gly Ile
            20                  25                  30

Asp Val Val Phe Leu Ser Thr Glu Tyr Asn His Arg Arg Ile Ser Asn
        35                  40                  45

Thr Glu Ala Leu Ala Ser Arg Phe Pro Thr Leu His Phe Glu Thr Ile
    50                  55                  60

Pro Asp Gly Leu Pro Pro Asn Glu Ser Arg Ala Leu Ala Asp Gly Pro
65                  70                  75                  80

Leu Tyr Phe Ser Met Arg Glu Gly Thr Lys Pro Arg Phe Arg Gln Leu
                85                  90                  95

Ile Gln Ser Leu Asn Asp Gly Arg Trp Pro Ile Thr Cys Ile Ile Thr
            100                 105                 110

Asp Ile Met Leu Ser Ser Pro Ile Glu Val Ala Glu Glu Phe Gly Ile
        115                 120                 125

Pro Val Ile Ala Phe Cys Pro Cys Ser Ala Arg Tyr Leu Ser Ile His
    130                 135                 140

Phe Phe Ile Pro Lys Leu Val Glu Glu Gly Gln Ile Pro Tyr Ala Asp
145                 150                 155                 160

Asp Asp Pro Ile Gly Glu Ile Gln Gly Val Pro Leu Phe Glu Gly Leu
```

-continued

```
                165                 170                 175

Leu Arg Arg Asn His Leu Pro Gly Ser Trp Ser Asp Lys Ser Ala Asp
            180                 185                 190

Ile Ser Phe Ser His Gly Leu Ile Asn Gln Thr Leu Ala Ala Gly Arg
        195                 200                 205

Ala Ser Ala Leu Ile Leu Asn Thr Phe Asp Glu Leu Glu Ala Pro Phe
    210                 215                 220

Leu Thr His Leu Ser Ser Ile Phe Asn Lys Ile Tyr Thr Ile Gly Pro
225                 230                 235                 240

Leu His Ala Leu Ser Lys Ser Arg Leu Gly Asp Ser Ser Ser Ser Ala
                245                 250                 255

Ser Ala Leu Ser Gly Phe Trp Lys Glu Asp Arg Ala Cys Met Ser Trp
            260                 265                 270

Leu Asp Cys Gln Pro Pro Arg Ser Val Val Phe Val Ser Phe Gly Ser
        275                 280                 285

Thr Met Lys Met Lys Ala Asp Glu Leu Arg Glu Phe Trp Tyr Gly Leu
    290                 295                 300

Val Ser Ser Gly Lys Pro Phe Leu Cys Val Leu Arg Ser Asp Val Val
305                 310                 315                 320

Ser Gly Gly Glu Ala Ala Glu Leu Ile Glu Gln Met Ala Glu Glu Glu
                325                 330                 335

Gly Ala Gly Gly Lys Leu Gly Met Val Val Glu Trp Ala Ala Gln Glu
            340                 345                 350

Lys Val Leu Ser His Pro Ala Val Gly Gly Phe Leu Thr His Cys Gly
        355                 360                 365

Trp Asn Ser Thr Val Glu Ser Ile Ala Ala Gly Val Pro Met Met Cys
    370                 375                 380

Trp Pro Ile Leu Gly Asp Gln Pro Ser Asn Ala Thr Trp Ile Asp Arg
385                 390                 395                 400

Val Trp Lys Ile Gly Val Glu Arg Asn Asn Arg Glu Trp Asp Arg Leu
                405                 410                 415

Thr Val Glu Lys Met Val Arg Ala Leu Met Glu Gly Gln Lys Arg Val
            420                 425                 430

Glu Ile Gln Arg Ser Met Glu Lys Leu Ser Lys Leu Ala Asn Glu Lys
        435                 440                 445

Val Val Arg Gly Gly Leu Ser Phe Asp Asn Leu Glu Val Leu Val Glu
    450                 455                 460

Asp Ile Lys Lys Leu Lys Pro Tyr Lys Phe
465                 470
```

<210> SEQ ID NO 69
<211> LENGTH: 1359
<212> TYPE: DNA
<213> ORGANISM: Siraitia grosvenorii

<400> SEQUENCE: 69

```
atggatgcaa aagaagaaag cttgaaagtt tttatgcttc catggttggc ccatggtcat      60

atatcgccct acctagagct agccaagagg cttgcaaaga gaaaatttct tgtttatttc     120

tgctccacgc ctgtaaattt ggaagccatt aaaccaaagc tttccaaaag ctactctgat     180

tcgatccaac taatggaggt tcctctcgaa tcgacgccgg agcttcctcc tcactatcat     240

acagccaaag gccttccgcc gcatttaatg cccaaactca tgaatgcctt taaaatggtt     300

gctcccaatc tcgaatcgat cctaaaaacc ctaaacccag atctgctcat cgtcgacatt     360
```

```
ctccttccat ggatgcttcc actcgcttca tcgctcaaaa ttccgatggt tttcttcact    420

attttcggtg ccatggccat ctcctttatg atttataatc gaaccgtctc gaacgagctt    480

ccatttccag aatttgaact tcacgagtgc tggaaatcga agtgccccta tttgttcaag    540

gaccaagcgg aaagtcaatc gttcttagaa tacttggatc aatcttcagg cgtaattttg    600

atcaaaactt ccagagagat tgaggctaag tatgtagact ttctcacttc gtcgtttacg    660

aagaaggttg tgaccaccgg tcccctggtt cagcaacctt cttccggcga agacgagaag    720

cagtactccg atatcatcga atggctagac aagaaggagc cgttatcgac ggtgctcgtt    780

tcgtttggga gcgagtatta tctgtcaaag gaagagatgg aagaaatcgc ctacgggctg    840

gagagcgcca gcgaggtgaa tttcatctgg attgttaggt ttccgatggg acaggaaacg    900

gaggtcgagg cggcgctgcc ggaggggttc atccagaggg caggagagag agggaaagtg    960

gtcgagggct gggctccgca ggcgaaaata ttggcgcatc cgagcaccgg cggccatgtg   1020

agccacaacg ggtggagctc gattgtggag tgcttgatgt ccggtgtacc ggtgatcggc   1080

gcgccgatgc aacttgacgg gccaatcgtc gcaaggctgg tggaggagat cggcgtgggt   1140

ttggaaatca agagagatga ggaagggaga atcacgaggg gcgaagttgc cgatgcaatc   1200

aagacggtgg cggtgggcaa aaccggggaa gattttagaa ggaaagcaaa aaaaatcagc   1260

agcattttga agatgaaaga tgaagaagag gttgacactt tggcaatgga attagtgagg   1320

ttatgccaaa tgaaaagagg gcaggagtct caggactaa                          1359
```

```
<210> SEQ ID NO 70
<211> LENGTH: 1359
<212> TYPE: DNA
<213> ORGANISM: Artificial Sequence
<220> FEATURE:
<223> OTHER INFORMATION: Codon-optimized nucleotide sequence A encoding
      UGT11789

<400> SEQUENCE: 70

atggacgcca aagaagaatc cttgaaggtt tttatgttgc catggttggc tcatggtcat     60

atttctccat atttggaatt ggctaagaga ttggccaaga gaaagttctt ggtttacttc    120

tgttctaccc cagttaactt ggaagctatt aagccaaagt tgtccaagtc ctactccgat    180

tctattcaat tgatggaagt cccattggaa tccactccag aattgccacc acattatcat    240

actgctaaag gtttgccacc tcatttgatg ccaaaattga tgaacgcttt caagatggtt    300

gctccaaact tggaatcaat cttgaaaacc ttgaacccag acttgttgat cgttgatatt    360

ttgttgcctt ggatgttgcc tttggcctcc tctttgaaaa ttcctatggt tttcttcacc    420

atcttcggtg ctatggctat ttctttcatg atctacaaca gaaccgtttc caacgaattg    480

ccatttccag aatttgaatt gcacgaatgc tggaagtcta agtgtccata cttgtttaag    540

gatcaagccg aatcccaatc cttcttggaa tatttggatc aatcctccgg tgtcattttg    600

atcaagacct ctagagaaat tgaagccaag tacgttgatt tcttgacctc ttcattcacc    660

aagaaggttg ttactactgg tccattggtt caacaaccat catctggtga agatgaaaag    720

caatactccg atatcattga atggttggac aagaaagaac cattgtccac tgttttggtt    780

tctttcggtt ccgaatatta cttgtctaaa gaagaaatgg aagaaatcgc ctacggtttg    840

gaatctgctt ctgaagttaa tttcatctgg atcgtcagat tcccaatggg tcaagaaact    900

gaagttgaag ctgctttgcc agaaggtttt attcaaagag ctggtgaaag aggtaaagtt    960

gttgaaggtt gggctccaca agctaagatt ttggctcatc catctactgg tggtcacgtt   1020
```

```
tctcataatg gttggtcatc tatcgttgaa tgcttgatgt ctggtgttcc agttattggt   1080

gctccaatgc aattggatgg tccaatagtt gctagattgg tcgaagaaat tggtgttggt   1140

ttggaaatca agagagatga agaaggtaga atcaccagag gtgaagttgc tgatgctatt   1200

aagactgttg ctgttggtaa aaccggtgaa gattttagaa gaaaggccaa gaagatctcc   1260

tccattttaa agatgaagga cgaagaagaa gttgacacct tggctatgga attggttaga   1320

ttgtgtcaaa tgaagagagg tcaagaatcc caagactga                          1359
```

<210> SEQ ID NO 71
<211> LENGTH: 1359
<212> TYPE: DNA
<213> ORGANISM: Artificial Sequence
<220> FEATURE:
<223> OTHER INFORMATION: Codon-optimized nucleotide sequence B encoding UGT11789

<400> SEQUENCE: 71

```
atggatgcta aggaagaatc tttgaaagtc tttatgctgc cttggttggc tcacggtcat     60

atttccccgt atttggaatt ggcaaaaaga ctggccaaga gaaaattctt agtgtatttc    120

tgttcaactc cagtgaattt ggaagccatc aaaccaaaat tgtctaagtc atattctgac    180

tctatacaac tgatggaagt tcctttggaa agtacaccgg aactgccacc ccattatcat    240

acagctaaag ggttaccccc acacttgatg cccaagctaa tgaatgcatt taagatggtc    300

gcaccaaatc tggaaagtat acttaagacg ctaaaccctg atttattaat tgtagatatc    360

cttctaccat ggatgttgcc cttagcttca tctttaaaaa ttccgatggt ttttttcact    420

atctttggag ccatggcaat ttcctttatg atttacaata gaacagtctc aaatgagtta    480

cctttcccag agtttgaatt acatgaatgc tggaaatcta aatgtccata tttgttcaaa    540

gaccaagcag aatcccaatc tttcttagaa tacttagatc agagttccgg agttatcttg    600

atcaagacat ctagggaaat tgaagcaaag tatgtggact tttgacctc cagttttact     660

aagaaagtcg taacaacggg tcctctagtc caacaaccta gttcaggaga ggatgagaaa    720

caatatagcg atataatcga atggttagat aaaaaagagc cattgagtac cgttctagtg    780

tcctttggtt cagaatatta tttgtctaaa gaagagatgg aagagattgc ctacggctta    840

gaatcagctt ccgaagtaaa ctttatatgg attgtcagat ttcccatggg acaagaaacc    900

gaggtcgaag cagctttgcc cgaaggtttt attcaacgtg ccggcgaaag aggaaaagta    960

gtggaaggtt gggctccaca agccaaaatt ctagctcacc cgtccactgg tggtcatgtc   1020

tctcataacg gatggagttc aattgttgaa tgtttgatga gtggtgttcc agtgatagga   1080

gctcctatgc agctggacgg tccaatagtc gccaggttag tcgaagaaat tggtgttggt   1140

ttagaaataa agagagacga agaaggtaga attactagag gtgaagtagc agatgcaatt   1200

aaaactgttg ctgtcggcaa gactggagag gattttcgta gaaaagccaa aaaaatatca   1260

tctatactaa aaatgaaaga cgaagaggag gttgatacgc tggcgatgga actagttaga   1320

ttgtgtcaga tgaagcgtgg tcaggaaagt caagactaa                          1359
```

<210> SEQ ID NO 72
<211> LENGTH: 452
<212> TYPE: PRT
<213> ORGANISM: Siraitia grosvenorii

<400> SEQUENCE: 72

```
Met Asp Ala Lys Glu Glu Ser Leu Lys Val Phe Met Leu Pro Trp Leu
1               5                   10                  15
```

-continued

```
Ala His Gly His Ile Ser Pro Tyr Leu Glu Leu Ala Lys Arg Leu Ala
            20                  25                  30

Lys Arg Lys Phe Leu Val Tyr Phe Cys Ser Thr Pro Val Asn Leu Glu
        35                  40                  45

Ala Ile Lys Pro Lys Leu Ser Lys Ser Tyr Ser Asp Ser Ile Gln Leu
    50                  55                  60

Met Glu Val Pro Leu Glu Ser Thr Pro Glu Leu Pro Pro His Tyr His
65                  70                  75                  80

Thr Ala Lys Gly Leu Pro Pro His Leu Met Pro Lys Leu Met Asn Ala
                85                  90                  95

Phe Lys Met Val Ala Pro Asn Leu Glu Ser Ile Leu Lys Thr Leu Asn
            100                 105                 110

Pro Asp Leu Leu Ile Val Asp Ile Leu Leu Pro Trp Met Leu Pro Leu
        115                 120                 125

Ala Ser Ser Leu Lys Ile Pro Met Val Phe Phe Thr Ile Phe Gly Ala
    130                 135                 140

Met Ala Ile Ser Phe Met Ile Tyr Asn Arg Thr Val Ser Asn Glu Leu
145                 150                 155                 160

Pro Phe Pro Glu Phe Glu Leu His Glu Cys Trp Lys Ser Lys Cys Pro
                165                 170                 175

Tyr Leu Phe Lys Asp Gln Ala Glu Ser Gln Ser Phe Leu Glu Tyr Leu
            180                 185                 190

Asp Gln Ser Ser Gly Val Ile Leu Ile Lys Thr Ser Arg Glu Ile Glu
        195                 200                 205

Ala Lys Tyr Val Asp Phe Leu Thr Ser Ser Phe Thr Lys Lys Val Val
    210                 215                 220

Thr Thr Gly Pro Leu Val Gln Gln Pro Ser Ser Gly Glu Asp Glu Lys
225                 230                 235                 240

Gln Tyr Ser Asp Ile Ile Glu Trp Leu Asp Lys Lys Glu Pro Leu Ser
                245                 250                 255

Thr Val Leu Val Ser Phe Gly Ser Glu Tyr Tyr Leu Ser Lys Glu Glu
            260                 265                 270

Met Glu Glu Ile Ala Tyr Gly Leu Glu Ser Ala Ser Glu Val Asn Phe
        275                 280                 285

Ile Trp Ile Val Arg Phe Pro Met Gly Gln Glu Thr Glu Val Glu Ala
    290                 295                 300

Ala Leu Pro Glu Gly Phe Ile Gln Arg Ala Gly Glu Arg Gly Lys Val
305                 310                 315                 320

Val Glu Gly Trp Ala Pro Gln Ala Lys Ile Leu Ala His Pro Ser Thr
                325                 330                 335

Gly Gly His Val Ser His Asn Gly Trp Ser Ser Ile Val Glu Cys Leu
            340                 345                 350

Met Ser Gly Val Pro Val Ile Gly Ala Pro Met Gln Leu Asp Gly Pro
        355                 360                 365

Ile Val Ala Arg Leu Val Glu Glu Ile Gly Val Gly Leu Glu Ile Lys
    370                 375                 380

Arg Asp Glu Glu Gly Arg Ile Thr Arg Gly Glu Val Ala Asp Ala Ile
385                 390                 395                 400

Lys Thr Val Ala Val Gly Lys Thr Gly Glu Asp Phe Arg Arg Lys Ala
                405                 410                 415

Lys Lys Ile Ser Ser Ile Leu Lys Met Lys Asp Glu Glu Glu Val Asp
            420                 425                 430
```

```
Thr Leu Ala Met Glu Leu Val Arg Leu Cys Gln Met Lys Arg Gly Gln
        435                 440                 445

Glu Ser Gln Asp
    450
```

<210> SEQ ID NO 73
<211> LENGTH: 1563
<212> TYPE: DNA
<213> ORGANISM: Siraitia grosvenorii

<400> SEQUENCE: 73

```
atggaaatgt cgtcgtctgt tgcagctacg atttcaatat ggatggttgt ggtgtgcata      60

gtgggagtgg gatggagagt tgtgaactgg gtttggttga ggccgaagaa gcttgagaag     120

cggctgagag agcaaggcct cgccggaaac tcttaccggc ttctgttcgg agacttgaag     180

gagagggcgg cgatggagga gcaggccaac tccaagccca tcaacttctc ccatgatatc     240

ggaccacgtg tcttcccctc catgtacaaa accatccaga attatggtaa gaattcgtac     300

atgtggcttg gcccatatcc aagagtgcac atcatggacc ctcagcaact taaaactgtt     360

tttactctag tctatgatat ccaaaagcca aatttgaacc cccttatcaa gtttcttttg     420

gatggaatag taactcatga aggagaaaaa tgggctaaac acagaaagat aatcaaccct     480

gcatttcatt tggaaaagtt gaaggatatg ataccagcat tctttcatag ttgtaatgag     540

atagttaacg aatgggaaag attaatctcg aaagagggtt cgtgtgagtt ggatgttatg     600

ccatatctgc aaaatttggc agctgatgcc atttctcgaa ctgcatttgg gagtagctat     660

gaagaaggaa aaatgatctt ccaactttta aaagaactaa ctgatttggt ggttaaagtt     720

gcatttggag tttatattcc cggatggagg tttctaccaa ctaagtcaaa caataaaatg     780

aaagaaataa atagaaaaat taaaagtttg cttttgggta ttataaacaa aaggcaaaag     840

gctatggaag aaggtgaagc tggacaaagt gatttattag gcattctcat ggaatccaat     900

tcaaacgaaa ttcaaggaga aggaaacaat aaagaagatg gaatgagcat agaagatgtt     960

attgaagaat gcaaggtttt ctatattggt ggccaagaaa ccacagccag attactgatt    1020

tggaccatga ttttgttgag ttcacacacg gaatggcaag agcgagcaag aactgaggta    1080

ttaaaagtat ttggtaacaa gaagccagat tttgatggtt tgagtcgact aaaagttgta    1140

actatgattt tgaacgaggt tctcaggtta tacccaccag caagtatgct tactcgtatt    1200

attcaaaagg aaacaagagt tggaaaattg actctaccag ctggtgtgat attgatcatg    1260

ccaattattc ttatccatcg tgatcatgac ctatggggtg aagatgcaaa cgaatttaaa    1320

ccagaaagat tttctaaggg agtctctaaa gcagcaaaag ttcaacccgc tttcttccca    1380

tttggatggg gtcctcgaat atgcatgggg cagaactttg cgatgattga agcaaaaatg    1440

gcattatcat taattctaca acgcttctca tttgagcttt cttcgtcgta tgttcatgct    1500

cctaccgtcg ttttcactac tcaacctcaa catggagctc atatcgtcct gcgcaaactg    1560

tag                                                                  1563
```

<210> SEQ ID NO 74
<211> LENGTH: 520
<212> TYPE: PRT
<213> ORGANISM: Siraitia grosvenorii

<400> SEQUENCE: 74

```
Met Glu Met Ser Ser Ser Val Ala Ala Thr Ile Ser Ile Trp Met Val
1               5                   10                  15
```

```
Val Val Cys Ile Val Gly Val Gly Trp Arg Val Val Asn Trp Val Trp
            20                  25                  30

Leu Arg Pro Lys Lys Leu Glu Lys Arg Leu Arg Glu Gln Gly Leu Ala
        35                  40                  45

Gly Asn Ser Tyr Arg Leu Leu Phe Gly Asp Leu Lys Glu Arg Ala Ala
    50                  55                  60

Met Glu Glu Gln Ala Asn Ser Lys Pro Ile Asn Phe Ser His Asp Ile
65                  70                  75                  80

Gly Pro Arg Val Phe Pro Ser Met Tyr Lys Thr Ile Gln Asn Tyr Gly
                85                  90                  95

Lys Asn Ser Tyr Met Trp Leu Gly Pro Tyr Pro Arg Val His Ile Met
            100                 105                 110

Asp Pro Gln Gln Leu Lys Thr Val Phe Thr Leu Val Tyr Asp Ile Gln
        115                 120                 125

Lys Pro Asn Leu Asn Pro Leu Ile Lys Phe Leu Leu Asp Gly Ile Val
    130                 135                 140

Thr His Glu Gly Glu Lys Trp Ala Lys His Arg Lys Ile Ile Asn Pro
145                 150                 155                 160

Ala Phe His Leu Glu Lys Leu Lys Asp Met Ile Pro Ala Phe Phe His
                165                 170                 175

Ser Cys Asn Glu Ile Val Asn Glu Trp Glu Arg Leu Ile Ser Lys Glu
            180                 185                 190

Gly Ser Cys Glu Leu Asp Val Met Pro Tyr Leu Gln Asn Leu Ala Ala
        195                 200                 205

Asp Ala Ile Ser Arg Thr Ala Phe Gly Ser Ser Tyr Glu Glu Gly Lys
    210                 215                 220

Met Ile Phe Gln Leu Leu Lys Glu Leu Thr Asp Leu Val Val Lys Val
225                 230                 235                 240

Ala Phe Gly Val Tyr Ile Pro Gly Trp Arg Phe Leu Pro Thr Lys Ser
                245                 250                 255

Asn Asn Lys Met Lys Glu Ile Asn Arg Lys Ile Lys Ser Leu Leu Leu
            260                 265                 270

Gly Ile Ile Asn Lys Arg Gln Lys Ala Met Glu Glu Gly Glu Ala Gly
        275                 280                 285

Gln Ser Asp Leu Leu Gly Ile Leu Met Glu Ser Asn Ser Asn Glu Ile
    290                 295                 300

Gln Gly Glu Gly Asn Asn Lys Glu Asp Gly Met Ser Ile Glu Asp Val
305                 310                 315                 320

Ile Glu Glu Cys Lys Val Phe Tyr Ile Gly Gly Gln Glu Thr Thr Ala
                325                 330                 335

Arg Leu Leu Ile Trp Thr Met Ile Leu Leu Ser Ser His Thr Glu Trp
            340                 345                 350

Gln Glu Arg Ala Arg Thr Glu Val Leu Lys Val Phe Gly Asn Lys Lys
        355                 360                 365

Pro Asp Phe Asp Gly Leu Ser Arg Leu Lys Val Val Thr Met Ile Leu
    370                 375                 380

Asn Glu Val Leu Arg Leu Tyr Pro Pro Ala Ser Met Leu Thr Arg Ile
385                 390                 395                 400

Ile Gln Lys Glu Thr Arg Val Gly Lys Leu Thr Leu Pro Ala Gly Val
                405                 410                 415

Ile Leu Ile Met Pro Ile Ile Leu Ile His Arg Asp His Asp Leu Trp
            420                 425                 430

Gly Glu Asp Ala Asn Glu Phe Lys Pro Glu Arg Phe Ser Lys Gly Val
```

```
        435                 440                 445

Ser Lys Ala Ala Lys Val Gln Pro Ala Phe Phe Pro Phe Gly Trp Gly
    450                 455                 460

Pro Arg Ile Cys Met Gly Gln Asn Phe Ala Met Ile Glu Ala Lys Met
465                 470                 475                 480

Ala Leu Ser Leu Ile Leu Gln Arg Phe Ser Phe Glu Leu Ser Ser Ser
                485                 490                 495

Tyr Val His Ala Pro Thr Val Val Phe Thr Thr Gln Pro Gln His Gly
            500                 505                 510

Ala His Ile Val Leu Arg Lys Leu
        515                 520
```

<210> SEQ ID NO 75
<211> LENGTH: 675
<212> TYPE: DNA
<213> ORGANISM: Saccharomyces cerevisiae

<400> SEQUENCE: 75

```
atgtctgtta ttaatttcac aggtagttct ggtccattgg tgaaagtttg cggcttgcag      60

agcacagagg ccgcagaatg tgctctagat tccgatgctg acttgctggg tattatatgt     120

gtgcccaata gaaagagaac aattgacccg gttattgcaa ggaaaatttc aagtcttgta     180

aaagcatata aaaatagttc aggcactccg aaatacttgg ttggcgtgtt tcgtaatcaa     240

cctaaggagg atgttttggc tctggtcaat gattacggca ttgatatcgt ccaactgcat     300

ggagatgagt cgtggcaaga ataccaagag ttcctcggtt tgccagttat taaaagactc     360

gtatttccaa aagactgcaa catactactc agtgcagctt cacagaaacc tcattcgttt     420

attcccttgt ttgattcaga agcaggtggg acaggtgaac ttttggattg gaactcgatt     480

tctgactggg ttggaaggca agagagcccc gaaagcttac attttatgtt agctggtgga     540

ctgacgccag aaaatgttgg tgatgcgctt agattaaatg gcgttattgg tgttgatgta     600

agcggaggtg tggagacaaa tggtgtaaaa gactctaaca aaatagcaaa tttcgtcaaa     660

aatgctaaga aatag                                                      675
```

<210> SEQ ID NO 76
<211> LENGTH: 224
<212> TYPE: PRT
<213> ORGANISM: Saccharomyces cerevisiae

<400> SEQUENCE: 76

```
Met Ser Val Ile Asn Phe Thr Gly Ser Ser Gly Pro Leu Val Lys Val
1               5                   10                  15

Cys Gly Leu Gln Ser Thr Glu Ala Ala Glu Cys Ala Leu Asp Ser Asp
            20                  25                  30

Ala Asp Leu Leu Gly Ile Ile Cys Val Pro Asn Arg Lys Arg Thr Ile
        35                  40                  45

Asp Pro Val Ile Ala Arg Lys Ile Ser Ser Leu Val Lys Ala Tyr Lys
    50                  55                  60

Asn Ser Ser Gly Thr Pro Lys Tyr Leu Val Gly Val Phe Arg Asn Gln
65                  70                  75                  80

Pro Lys Glu Asp Val Leu Ala Leu Val Asn Asp Tyr Gly Ile Asp Ile
                85                  90                  95

Val Gln Leu His Gly Asp Glu Ser Trp Gln Glu Tyr Gln Glu Phe Leu
            100                 105                 110

Gly Leu Pro Val Ile Lys Arg Leu Val Phe Pro Lys Asp Cys Asn Ile
```

-continued

```
        115                 120                 125

Leu Leu Ser Ala Ala Ser Gln Lys Pro His Ser Phe Ile Pro Leu Phe
    130                 135                 140

Asp Ser Glu Ala Gly Gly Thr Gly Glu Leu Leu Asp Trp Asn Ser Ile
145                 150                 155                 160

Ser Asp Trp Val Gly Arg Gln Glu Ser Pro Glu Ser Leu His Phe Met
                165                 170                 175

Leu Ala Gly Gly Leu Thr Pro Glu Asn Val Gly Asp Ala Leu Arg Leu
            180                 185                 190

Asn Gly Val Ile Gly Val Asp Val Ser Gly Gly Val Glu Thr Asn Gly
        195                 200                 205

Val Lys Asp Ser Asn Lys Ile Ala Asn Phe Val Lys Asn Ala Lys Lys
    210                 215                 220


<210> SEQ ID NO 77
<211> LENGTH: 1584
<212> TYPE: DNA
<213> ORGANISM: Saccharomyces cerevisiae

<400> SEQUENCE: 77

atggcagctg accaattggt gaaaactgaa gtcaccaaga agtcttttac tgctcctgta      60

caaaaggctt ctacaccagt tttaaccaat aaaacagtca tttctggatc gaaagtcaaa     120

agtttatcat ctgcgcaatc gagctcatca ggaccttcat catctagtga ggaagatgat     180

tcccgcgata ttgaaagctt ggataagaaa atacgtcctt tagaagaatt agaagcatta     240

ttaagtagtg gaaatacaaa acaattgaag aacaaagagg tcgctgcctt ggttattcac     300

ggtaagttac ctttgtacgc tttggagaaa aaattaggtg atactacgag agcggttgcg     360

gtacgtagga aggctctttc aattttggca gaagctcctg tattagcatc tgatcgttta     420

ccatataaaa attatgacta cgaccgcgta tttggcgctt gttgtgaaaa tgttataggt     480

tacatgcctt tgcccgttgg tgttataggc cccttggtta tcgatggtac atcttatcat     540

ataccaatgg caactacaga gggttgtttg gtagcttctg ccatgcgtgg ctgtaaggca     600

atcaatgctg gcggtggtgc aacaactgtt ttaactaagg atggtatgac aagaggccca     660

gtagtccgtt tcccaacttt gaaaagatct ggtgcctgta agatatggtt agactcagaa     720

gagggacaaa acgcaattaa aaaagctttt aactctacat caagatttgc acgtctgcaa     780

catattcaaa cttgtctagc aggagattta ctcttcatga gatttagaac aactactggt     840

gacgcaatgg gtatgaatat gatttctaaa ggtgtcgaat actcattaaa gcaaatggta     900

gaagagtatg gctgggaaga tatggaggtt gtctccgttt ctggtaacta ctgtaccgac     960

aaaaaaccag ctgccatcaa ctggatcgaa ggtcgtggta agagtgtcgt cgcagaagct    1020

actattcctg gtgatgttgt cagaaaagtg ttaaaaagtg atgtttccgc attggttgag    1080

ttgaacattg ctaagaattt ggttggatct gcaatggctg ggtctgttgg tggatttaac    1140

gcacatgcag ctaatttagt gacagctgtt ttcttggcat taggacaaga tcctgcacaa    1200

aatgttgaaa gttccaactg tataacattg atgaaagaag tggacggtga tttgagaatt    1260

tccgtatcca tgccatccat cgaagtaggt accatcggtg gtggtactgt tctagaacca    1320

caaggtgcca tgttggactt attaggtgta agaggcccgc atgctaccgc tcctggtacc    1380

aacgcacgtc aattagcaag aatagttgcc tgtgccgtct tggcaggtga attatcctta    1440

tgtgctgccc tagcagccgg ccatttggtt caaagtcata tgacccacaa caggaaacct    1500

gctgaaccaa caaaacctaa caatttggac gccactgata taaatcgttt gaaagatggg    1560
```

```
tccgtcacct gcattaaatc ctaa                                        1584


<210> SEQ ID NO 78
<211> LENGTH: 527
<212> TYPE: PRT
<213> ORGANISM: Saccharomyces cerevisiae

<400> SEQUENCE: 78

Met Ala Ala Asp Gln Leu Val Lys Thr Glu Val Thr Lys Lys Ser Phe
1               5                   10                  15

Thr Ala Pro Val Gln Lys Ala Ser Thr Pro Val Leu Thr Asn Lys Thr
            20                  25                  30

Val Ile Ser Gly Ser Lys Val Lys Ser Leu Ser Ser Ala Gln Ser Ser
        35                  40                  45

Ser Ser Gly Pro Ser Ser Ser Ser Glu Glu Asp Asp Ser Arg Asp Ile
    50                  55                  60

Glu Ser Leu Asp Lys Lys Ile Arg Pro Leu Glu Glu Leu Glu Ala Leu
65                  70                  75                  80

Leu Ser Ser Gly Asn Thr Lys Gln Leu Lys Asn Lys Glu Val Ala Ala
                85                  90                  95

Leu Val Ile His Gly Lys Leu Pro Leu Tyr Ala Leu Glu Lys Lys Leu
            100                 105                 110

Gly Asp Thr Thr Arg Ala Val Ala Val Arg Arg Lys Ala Leu Ser Ile
        115                 120                 125

Leu Ala Glu Ala Pro Val Leu Ala Ser Asp Arg Leu Pro Tyr Lys Asn
    130                 135                 140

Tyr Asp Tyr Asp Arg Val Phe Gly Ala Cys Cys Glu Asn Val Ile Gly
145                 150                 155                 160

Tyr Met Pro Leu Pro Val Gly Val Ile Gly Pro Leu Val Ile Asp Gly
                165                 170                 175

Thr Ser Tyr His Ile Pro Met Ala Thr Thr Glu Gly Cys Leu Val Ala
            180                 185                 190

Ser Ala Met Arg Gly Cys Lys Ala Ile Asn Ala Gly Gly Gly Ala Thr
        195                 200                 205

Thr Val Leu Thr Lys Asp Gly Met Thr Arg Gly Pro Val Val Arg Phe
    210                 215                 220

Pro Thr Leu Lys Arg Ser Gly Ala Cys Lys Ile Trp Leu Asp Ser Glu
225                 230                 235                 240

Glu Gly Gln Asn Ala Ile Lys Lys Ala Phe Asn Ser Thr Ser Arg Phe
                245                 250                 255

Ala Arg Leu Gln His Ile Gln Thr Cys Leu Ala Gly Asp Leu Leu Phe
            260                 265                 270

Met Arg Phe Arg Thr Thr Thr Gly Asp Ala Met Gly Met Asn Met Ile
        275                 280                 285

Ser Lys Gly Val Glu Tyr Ser Leu Lys Gln Met Val Glu Glu Tyr Gly
    290                 295                 300

Trp Glu Asp Met Glu Val Val Ser Val Ser Gly Asn Tyr Cys Thr Asp
305                 310                 315                 320

Lys Lys Pro Ala Ala Ile Asn Trp Ile Glu Gly Arg Gly Lys Ser Val
                325                 330                 335

Val Ala Glu Ala Thr Ile Pro Gly Asp Val Val Arg Lys Val Leu Lys
            340                 345                 350

Ser Asp Val Ser Ala Leu Val Glu Leu Asn Ile Ala Lys Asn Leu Val
        355                 360                 365
```

```
Gly Ser Ala Met Ala Gly Ser Val Gly Gly Phe Asn Ala His Ala Ala
    370                 375                 380

Asn Leu Val Thr Ala Val Phe Leu Ala Leu Gly Gln Asp Pro Ala Gln
385                 390                 395                 400

Asn Val Glu Ser Ser Asn Cys Ile Thr Leu Met Lys Glu Val Asp Gly
                405                 410                 415

Asp Leu Arg Ile Ser Val Ser Met Pro Ser Ile Glu Val Gly Thr Ile
            420                 425                 430

Gly Gly Gly Thr Val Leu Glu Pro Gln Gly Ala Met Leu Asp Leu Leu
        435                 440                 445

Gly Val Arg Gly Pro His Ala Thr Ala Pro Gly Thr Asn Ala Arg Gln
    450                 455                 460

Leu Ala Arg Ile Val Ala Cys Ala Val Leu Ala Gly Glu Leu Ser Leu
465                 470                 475                 480

Cys Ala Ala Leu Ala Ala Gly His Leu Val Gln Ser His Met Thr His
                485                 490                 495

Asn Arg Lys Pro Ala Glu Pro Thr Lys Pro Asn Asn Leu Asp Ala Thr
            500                 505                 510

Asp Ile Asn Arg Leu Lys Asp Gly Ser Val Thr Cys Ile Lys Ser
        515                 520                 525
```

<210> SEQ ID NO 79
<211> LENGTH: 951
<212> TYPE: DNA
<213> ORGANISM: Siraitia grosvenorii

<400> SEQUENCE: 79

```
atggacgaga ttgagcatat caccatcaac accaatggca tcaaaatgca cattgcctct     60

gtagggacgg gcccagtagt tcttcttctc catggcttcc cggagctctg gtactcatgg    120

cgccaccagc ttctgtatct ttcttccgta ggatatcgag ctattgcgcc ggacctccgc    180

ggctatggcg acacggactc gccggcgtct cctacctcct acaccgcgct ccacatcgtc    240

ggcgatttgg ttggggctct ggacgagctt gggatcgaga aggtgttcct ggtcggacat    300

gactgggggg cgatcatcgc ctggtacttt tgcttgttca ggcccgatag aatcaaggcg    360

ctggtgaatc tgagcgtcca gttcataccc agaaacccag cgattccttt catcgagggt    420

ttcagaactg cgttcggtga tgacttctat atttgcaggt ttcaggttcc aggagaggca    480

gaagaagatt ttgcctccat cgacacagct cagctgttca agacatcatt atgtaataga    540

agttctgcac ctccatgctt gcctaaagaa attggatttc gtgcgatccc acctccagag    600

aaccttcctt cttggctgac agaagaagat atcaactttt atgctgccaa atttaagcag    660

acaggcttca ccggagcgtt gaactactat cgagcttttg acctaacttg ggagctcacg    720

gcgccatgga cgggagcaca gattcaggta ccggtgaagt tcatcgtcgg ggattcggat    780

ctaacttacc attttccggg agccaaggaa tatatccata atggcggatt caaaagggac    840

gtgccgttgc tggaggaagt agttgtagta aaagatgctt gtcacttcat caaccaagaa    900

aggccacaag aaatcaatgc tcacatccat gacttcatca ataaattctg a             951
```

<210> SEQ ID NO 80
<211> LENGTH: 2280
<212> TYPE: DNA
<213> ORGANISM: Siraitia grosvenorii

<400> SEQUENCE: 80

```
atgtggaggt taaaggtcgg agcagaaagc gttggggaga atgatgagaa atggttgaag     60
agcataagca atcacttggg acgccaggtg tgggagttct gtccggatgc cggcacccaa    120
caacagctct tgcaagtcca caaagctcgt aaagctttcc acgatgaccg tttccaccga    180
aagcaatctt ccgatctctt tatcactatt cagtatggaa aggaagtaga aaatggtgga    240
aagacagcgg gagtgaaatt gaaagaaggg gaagaggtga ggaaagaggc agtagagagt    300
agcttagaga gggcattaag tttctactca agcatccaga caagcgatgg gaactgggct    360
tcggatcttg gggggcccat gtttttactt ccgggtctgg tgattgccct ctacgttaca    420
ggcgtcttga attctgtttt atccaagcac caccggcaag agatgtgcag atatgtttac    480
aatcaccaga atgaagatgg ggggtggggt ctccacatcg agggcccaag caccatgttt    540
ggttccgcac tgaattatgt tgcactcagg ctgcttggag aagacgccaa cgccggggca    600
atgccaaaag cacgtgcttg gatcttggac cacggtggcg ccaccggaat cacttcctgg    660
ggcaaattgt ggctttctgt acttggagtc tacgaatgga gtggcaataa tcctcttcca    720
cccgaatttt ggttatttcc ttacttccta ccatttcatc caggaagaat gtggtgccat    780
tgtcgaatgg tttatctacc aatgtcatac ttatatggaa agagatttgt tgggccaatc    840
acacccatag ttctgtctct cagaaaagaa ctctacgcag ttccatatca tgaaatagac    900
tggaataaat ctcgcaatac atgtgcaaag gaggatctgt actatccaca tcccaagatg    960
caagatattc tgtggggatc tctccaccac gtgtatgagc ccttgtttac tcgttggcct   1020
gccaaacgcc tgagagaaaa ggctttgcag actgcaatgc aacatattca ctatgaagat   1080
gagaataccc gatatatatg ccttggccct gtcaacaagg tactcaatct gctttgttgt   1140
tgggttgaag atccctactc cgacgccttc aaacttcatc ttcaacgagt ccatgactat   1200
ctctgggttg ctgaagatgg catgaaaatg cagggttata atgggagcca gttgtgggac   1260
actgctttct ccatccaagc aatcgtatcc accaaacttg tagacaacta tggcccaacc   1320
ttaagaaagg cacacgactt cgttaaaagt tctcagattc agcaggactg tcctggggat   1380
cctaatgttt ggtaccgtca cattcataaa ggtgcatggc cattttcaac tcgagatcat   1440
ggatggctca tctctgactg tacagcagag ggattaaagg ctgctttgat gttatccaaa   1500
cttccatccg aaacagttgg ggaatcatta gaacggaatc gcctttgcga tgctgtaaac   1560
gttctccttt ctttgcaaaa cgataatggt ggctttgcat catatgagtt gacaagatca   1620
taccttggt tggagttgat caaccccgca gaaacgtttg gagatattgt cattgattat   1680
ccgtatgtgg agtgcacctc agccacaatg gaagcactga cgttgtttaa gaaattacat   1740
cccggccata ggaccaaaga aattgatact gctattgtca gggcggccaa cttccttgaa   1800
aatatgcaaa ggacggatgg ctcttggtat ggatgttggg gggtttgctt cacgtatgcg   1860
gggtggtttg gcataaaggg attggtggct gcaggaagga catataataa ttgccttgcc   1920
attcgcaagg cttgcgattt tttactatct aaagagctgc ccggcggtgg atggggagag   1980
agttaccttt catgtcagaa taaggtatac acaaatcttg aaggaaacag accgcacctg   2040
gttaacacgg cctgggtttt aatggccctc atagaagctg gccaggctga gagagaccca   2100
acaccattgc atcgtgcagc aaggttgtta atcaattccc agttggagaa tggtgatttc   2160
ccccaacagg agatcatggg agtctttaat aaaaattgca tgatcacata tgctgcatac   2220
cgaaacattt ttcccatttg ggctcttgga gagtattgcc atcgggtttt gactgaataa   2280
```

<210> SEQ ID NO 81
<211> LENGTH: 1422

<212> TYPE: DNA
<213> ORGANISM: Artificial Sequence
<220> FEATURE:
<223> OTHER INFORMATION: Codon-optimized nucleotide sequence encoding CYP5491

<400> SEQUENCE: 81
atgtggactg ttgttttggg tttggctact ttgtttgttg cctactacat tcactggatc 60
aacaagtgga gagactctaa gtttaatggt gttttgccac caggtactat gggtttgcca 120
ttgattggtg aaaccatcca attgtcaaga ccatccgatt ctttggatgt tcatccattc 180
atccaaaaaa aggtcgaaag atacggtcca atcttcaaga cttgtttggc tggtagacca 240
gttgttgttt ctgctgatgc tgaatttaac aactacatca tgttgcaaga aggtagagct 300
gttgaaatgt ggtacttgga tactttgtct aagttcttcg gtttggatac cgaatggttg 360
aaggctttgg gtttaatcca taagtacatc agatccatca ccttgaatca ttttggtgct 420
gaagccttga gagaaagatt cttgcctttt attgaagcct cttctatgga agccttgcat 480
tcttggtcta ctcaaccatc tgttgaagtt aagaatgctt ccgctttgat ggttttcaga 540
acctctgtta acaagatgtt tggtgaagat gccaagaagt tgtctggtaa tattccaggt 600
aagttcacca agttgttggg tggtttttttg tctttgcctt tgaatttccc aggtacaacc 660
taccataagt gcttgaaaga tatgaaggaa atccaaaaga agttgagaga agtcgttgat 720
gatagattgg ctaatgttgg tccagatgtc gaagattttt tgggtcaagc cttgaaggac 780
aaagaatccg aaaagttcat ctccgaagaa tttatcattc aattgttgtt ctctatctcc 840
ttcgcctcct tcgaatctat ttctactact ttgaccttga tcttgaagtt gttagacgaa 900
catccagaag tcgtcaaaga attggaagct gaacatgaag ctattagaaa ggctagagct 960
gatccagatg gtccaattac ttgggaagaa tacaagtcta tgaccttcac cttgcaagtt 1020
atcaacgaaa ctttgagatt gggttctgtt actccagctt tgttgagaaa aactgtcaag 1080
gacttacaag tcaagggtta cattattcct gaaggttgga ccattatgtt ggttactgct 1140
tcaagacata gagatccaaa ggtttacaaa gacccacata ttttcaatcc ttggagatgg 1200
aaggatttgg actccattac tattcaaaag aacttcatgc cattcggtgg tggtttgaga 1260
cattgtgctg gtgcagaata ctctaaggtt tacttgtgta ctttcttgca catcttgtgc 1320
actaagtaca gatggacaaa attgggtggt ggtagaattg ctagagccca tattttgtca 1380
ttcgaagatg gtttacatgt caagttcacc ccaaaagaat ga 1422

<210> SEQ ID NO 82
<211> LENGTH: 2106
<212> TYPE: DNA
<213> ORGANISM: Artificial Sequence
<220> FEATURE:
<223> OTHER INFORMATION: Codon-optimized nucleotide sequence encoding CYP4497

<400> SEQUENCE: 82
atgaaggtca gtccattcga attcatgtcc gctattatca agggtagaat ggacccatct 60
aactcctcat ttgaatctac tggtgaagtt gcctccgtta tctttgaaaa cagagaattg 120
gttgccatct tgaccacttc tattgctgtt atgattggtt gcttcgttgt cttgatgtgg 180
agaagagctg gttctagaaa ggttaagaat gtcgaattgc caaagccatt gattgtccat 240
gaaccagaac ctgaagttga agatggtaag aagaaggttt ccatcttctt cggtactcaa 300
actggtactg ctgaaggttt tgctaaggct ttggctgatg aagctaaagc tagatacgaa 360

-continued aaggctacct tcagagttgt tgatttggat gattatgctg ccgatgatga ccaatacgaa 420
gaaaaattga agaacgaatc cttcgccgtt ttcttgttgg ctacttatgg tgatggtgaa 480
cctactgata atgctgctag attttacaag tggttcgccg aaggtaaaga aagaggtgaa 540
tggttgcaaa acttgcacta tgctgttttt ggtttgggta acagacaata cgaacacttc 600
aacaagattg ctaaggttgc cgacgaatta ttggaagctc aaggtggtaa tagattggtt 660
aaggttggtt taggtgatga cgatcaatgc atcgaagatg atttttctgc ttggagagaa 720
tctttgtggc cagaattgga tatgttgttg agagatgaag atgatgctac tactgttact 780
actccatata ctgctgctgt cttggaatac agagttgtct ttcatgattc tgctgatgtt 840
gctgctgaag ataagtcttg gattaacgct aatggtcatg ctgttcatga tgctcaacat 900
ccattcagat ctaacgttgt cgtcagaaaa gaattgcata cttctgcctc tgatagatcc 960
tgttctcatt tggaattcaa catttccggt tccgctttga attacgaaac tggtgatcat 1020
gttggtgtct actgtgaaaa cttgactgaa actgttgatg aagccttgaa cttgttgggt 1080
ttgtctccag aaacttactt ctctatctac accgataacg aagatggtac tccattgggt 1140
ggttcttcat tgccaccacc atttccatca tgtactttga gaactgcttt gaccagatac 1200
gctgatttgt tgaactctcc aaaaaagtct gctttgttgg ctttagctgc tcatgcttct 1260
aatccagttg aagctgatag attgagatac ttggcttctc cagctggtaa agatgaatat 1320
gcccaatctg ttatcggttc ccaaaagtct ttgttggaag ttatggctga attcccatct 1380
gctaaaccac cattaggtgt ttttttgct gctgttgctc caagattgca acctagattc 1440
tactccattt catcctctcc aagaatggct ccatctagaa tccatgttac ttgtgctttg 1500
gtttacgata agatgccaac tggtagaatt cataagggtg tttgttctac ctggatgaag 1560
aattctgttc caatggaaaa gtcccatgaa tgttcttggg ctccaatttt cgttagacaa 1620
tccaatttta agttgccagc cgaatccaag gttccaatta tcatggttgg tccaggtact 1680
ggtttggctc cttttagagg ttttttacaa gaaagattgg ccttgaaaga atccggtgtt 1740
gaattgggtc catccatttt gtttttcggt tgcagaaaca gaagaatgga ttacatctac 1800
gaagatgaat tgaacaactt cgttgaaacc ggtgctttgt ccgaattggt tattgctttt 1860
tctagagaag gtcctaccaa agaatacgtc caacataaga tggctgaaaa ggcttctgat 1920
atctggaact tgatttctga aggtgcttac ttgtacgttt gtggtgatgc taaaggtatg 1980
gctaaggatg ttcatagaac cttgcatacc atcatgcaag aacaaggttc tttggattct 2040
tccaaagctg aatccatggt caagaacttg caaatgaatg gtagatactt aagagatgtt 2100
tggtaa 2106

<210> SEQ ID NO 83
<211> LENGTH: 1491
<212> TYPE: DNA
<213> ORGANISM: Artificial Sequence
<220> FEATURE:
<223> OTHER INFORMATION: Codon-optimized nucleotide sequence encoding
UGT1576

<400> SEQUENCE: 83
atggcgtcac ctagacatac tcctcatttc ttgttatttc catttatggc tcaaggacat 60
atgataccta tgattgatct ggctaggcta ctagcacaaa gaggtgttat tatcactatt 120
attactactc cacataatgc agctcgttat catagtgttt tagctcgtgc cattgactct 180
ggtttacata tccacgtttt acaactacaa ttcccttgca aagaaggcgg actaccggaa 240

```
ggttgtgaga acgtagactt acttccatcc ttagcgagca ttccaagatt ttacagagct    300

gcctctgatc tactatatga acctagcgaa aaacttttcg aagagttgat accgagacca    360

acttgtatca tttctgatat gtgtttacca tggactatga gaattgcctt aaagtatcat    420

gtgcccagac ttgttttcta ctctttgtct tgcttttttc tgctgtgcat gagaagctta    480

aagaacaatt tagcattaat ttctagcaag tcagattccg agttcgtaac tttctctgat    540

ttacccgatc cagttgaatt tttgaagtct gagcttccta agtccacaga cgaagacttg    600

gttaaatttt catatgaaat gggtgaggca gacagacaat catatggcgt tatactaaac    660

ttgtttgaag aaatggagcc caaatatttg gcagagtatg aaaaagaaag agaaagtccc    720

gaaagagttt ggtgtgttgg tccagtatct ttgtgcaacg ataacaaatt agataaagca    780

gagaggggta acaaagcatc aattgacgaa tataagtgta ttagatggtt agatgggcaa    840

caacctagca gtgttgttta tgttagtctt ggatcattat gcaacttggt tactgctcaa    900

attattgaat tggggttggg gttggaagct tctaaaaagc cattcatttg ggttattagg    960

aggggcaaca taacagaaga actacaaaaa tggctggttg aatatgactt tgaggagaag   1020

attaagggac gtggattagt catattaggg tgggcgcccc aagtacttat tctatctcat   1080

ccagctattg gttgcttctt aactcattgc ggttggaatt cctctatcga aggtatttcc   1140

gccggtgttc ctatggttac ctggcctcta tttgcagatc aggttttcaa cgaaaaatta   1200

atagttcaaa tcttgagaat cggagttagc gttggtacag aaacaaccat gaactggggt   1260

gaggaagaag aaaaaggtgt ggtggtcaaa agggagaaag tgagagaggc gatagagatc   1320

gtaatggatg gcgacgaaag agaagaaaga agagaaaggt gtaaagaact agcagaaact   1380

gccaaacgtg ctatcgagga aggtggtagc agtcatagaa atttgaccat gctaattgaa   1440

gatattatcc acggtggtgg cttatcttac gagaaagggt cctgcaggta g            1491
```

<210> SEQ ID NO 84
<211> LENGTH: 1410
<212> TYPE: DNA
<213> ORGANISM: Artificial Sequence
<220> FEATURE:
<223> OTHER INFORMATION: Codon-optimized nucleotide sequence encoding UGT430

<400> SEQUENCE: 84

```
atggaacaag cccacgattt gctgcatgtt ttactttttc catatccagc taaagggcat     60

attaagccct ttttgtgtct tgcggaactt ttatgcaacg caggtcttaa tgttacgttt    120

ttgaataccg attataatca cagaagatta cacaatctgc acctattagc ggcttgtttt    180

cctagtttgc attttgaaag tatcagtgat ggtttgcagc cagatcaacc tagagatatc    240

ttggacccaa agttttacat ctctatttgc caagttacca agccattatt cagagaattg    300

ttattatcct ataaaaggac atcctcagta caaaccggca ggccgccaat aacttgtgtt    360

ataacagatg ttatatttcg ttttccaatc gatgtagccg aggaattaga tatccctgtt    420

ttttctttct gtacttttag cgcgcgtttt atgtttcttt acttctggat cccaaagctt    480

atcgaggatg ggcaattgcc ttacccaaac ggtaacataa atcagaaact gtatggtgtt    540

gcacctgaag cagaaggatt attaaggtgt aaggatttac cgggacactg ggctttcgct    600

gatgagttaa aagacgatca gttgaacttt gttgatcaaa ctaccgccag tttgagatca    660

tctggtttga tcttaaacac tttcgacgat ttggaagctc cattcctggg acgtttgtca    720

acaatattta agaagatcta cgctgttggg ccaatacatg cgttgctaaa cagtcaccat    780
```

tgcggtttat ggaaagaaga ccacagctgt ttggcctggt tagatagtag agcggcacgt 840
tctgtcgtgt tcgtcagttt cggttctttg gttaagatca cttctaggca attgatggaa 900
ttctggcatg gattgttgaa tagcgggaca agctttttgt ttgtcttgag aagtgatgtt 960
gtagaaggtg atggggaaaa gcaagttgtc aaagaaatct acgaaacgaa agcagagggt 1020
aaatggttag ttgttggttg ggctccacaa gaaaaagtat tggcacatga agccgttgga 1080
ggtttcttaa ctcattccgg ttggaactca atcttagagt ctatagccgc aggtgtacct 1140
atgataagtt gcccaaaaat aggagaccaa tcttctaatt gtacctggat tagtaaagtt 1200
tggaagattg gtttagaaat ggaagaccag tatgacagag caactgtgga agctatggtg 1260
agatcaatta tgaaacacga aggtgagaag atacaaaaga ctattgcgga acttgcaaaa 1320
agagcaaaat ataaagtttc caaggacggc acttcatata gaaatctgga aattttgatc 1380
gaagatatca agaagatcaa gccgaattag 1410

<210> SEQ ID NO 85
<211> LENGTH: 1425
<212> TYPE: DNA
<213> ORGANISM: Artificial Sequence
<220> FEATURE:
<223> OTHER INFORMATION: Codon-optimized nucleotide sequence encoding UGT1697

<400> SEQUENCE: 85
atggttcaac ctagggtctt attgtttccc ttccctgctt tgggacatgt caaacccttt 60
ctgtcactgg cagaattact ttccgatgct gggatagacg ttgtatttct tagtacagaa 120
tacaatcata ggaggattag taacacggag gctctggcct caagatttcc aaccttgcat 180
tttgaaacaa taccagatgg tcttccacct aacgagagca gggctttggc agacggccct 240
ttgtacttta gcatgcgtga ggggacaaaa cccagattca gacagctgat acagagcctg 300
aacgatggca gatggcctat cacgtgtatc attaccgata tcatgttgag tagcccccatc 360 gaagtagctg aggagtttgg aattccagta attgcctttt gtccctgctc cgctagatac 420
ttgtctattc attttttcat acccaagttg gttgaagagg gtcagatccc ttatgcagat 480
gatgatccaa tcggtgaaat tcaaggtgtg ccacttttcg aagggcttct gaggagaaat 540
catttgccag gcagctggag tgataagtct gcagacatct cattttccca tggtttgatc 600
aaccaaacat tagcagccgg tagagcttct gcattaatct tgaatacgtt tgatgagttg 660
gaagctccat ttctgactca tctttctagt atttttaata agatttatac aattggtcct 720
ttgcatgcct tatctaagtc aaggttagga gactcctcat ctagtgctag tgcacttagt 780
ggattctgga aggaagatag ggcttgtatg tcttggttgg attgtcaacc tcctagatct 840
gttgttttcg tctcttttgg cagtactatg aaaatgaagg cggacgaact aagagaattt 900
tggtatggat tagtatcttc aggaaaacca tttttatgcg ttttaagatc cgatgtagtc 960
tcaggcggag aagctgcgga gttaattgaa caaatggcag aagaggaagg tgccgggggt 1020
aagttgggca tggttgttga atgggcagct caggagaagg tacttagcca tccagcggtt 1080
ggtggatttt tgacgcattg cgggtggaat agcactgtgg aaagtatagc agcaggggtc 1140
ccgatgatgt gttggccaat cttgggagat caaccatcca acgcgacctg gatcgataga 1200
gtttggaaaa tcggtgtaga aagaaataat agagaatggg atagattaac tgttgaaaaa 1260
atggttagag ccttgatgga aggacagaaa agagttgaaa ttcagcgttc aatggaaaag 1320
ctatcaaagt tggccaatga aaaagtagtt aggggggtc tttcatttga taatcttgaa 1380

```
gttcttgtcg aagatattaa aaagttaaag ccgtacaagt tttaa                1425


<210> SEQ ID NO 86
<211> LENGTH: 1563
<212> TYPE: DNA
<213> ORGANISM: Artificial Sequence
<220> FEATURE:
<223> OTHER INFORMATION: Codon-optimized nucleotide sequence encoding
      CYP1798

<400> SEQUENCE: 86

atggaaatgt cctcttctgt tgctgccacc atttctattt ggatggttgt tgtatgtatc     60

gttggtgttg gttggagagt tgttaattgg gtttggttaa gaccaaagaa gttggaaaag    120

agattgagag aacaaggttt ggctggtaac tcttacagat tgttgttcgg tgacttgaaa    180

gaaagagctg ctatggaaga acaagctaac tctaagccaa tcaacttctc ccatgatatt    240

ggtccaagag ttttcccatc tatgtacaag accattcaaa actacggtaa gaactcctat    300

atgtggttgg gtccataccc aagagttcat attatggatc cacaacaatt gaaaaccgtc    360

tttaccttgg tttacgacat ccaaaagcca aacttgaacc cattgatcaa gttcttgttg    420

gatggtattg tcacccatga aggtgaaaaa tgggctaaac atagaaagat tatcaaccca    480

gccttccact tggaaaagtt gaaagatatg attccagcct tcttccactc ttgcaacgaa    540

atagttaatg aatgggaaag attgatctcc aaagaaggtt cttgcgaatt ggatgttatg    600

ccatacttgc aaaatttggc tgctgatgct atttctagaa ctgcttttgg ttcctcttac    660

gaagaaggta agatgatctt ccaattattg aaagaattga ccgacttggt tgttaaggtt    720

gctttcggtg tttacattcc aggttggaga tttttgccaa ctaagtccaa caacaagatg    780

aaggaaatca acagaaagat caagtctttg ttgttaggta tcatcaacaa gagacaaaag    840

gccatggaag aaggtgaagc tggtcaatct gatttgttgg gtattttgat ggaatccaac    900

tccaacgaaa ttcaaggtga aggtaacaac aaagaagatg gtatgtccat cgaagatgtt    960

atcgaagaat gcaaggtttt ctacatcggt ggtcaagaaa ctaccgccag attattgatt   1020

tggaccatga tcttgttgag ttcccatact gaatggcaag aaagagcaag aactgaagtc   1080

ttgaaggttt tcggtaacaa aaagccagat ttcgacggtt tgtctagatt gaaggttgtc   1140

accatgattt tgaacgaagt tttgagatta tacccaccag cttctatgtt gaccagaatc   1200

attcaaaaag aaaccagagt cggtaagttg actttgccag ctggtgttat tttgatcatg   1260

ccaatcatct tgatccacag agatcatgat ttgtggggtg aagatgctaa tgaattcaag   1320

ccagaaagat tctccaaggg tgtttctaaa gctgctaaag ttcaaccagc tttctttcca   1380

tttggttggg gtccaagaat atgtatgggt caaaatttcg ctatgatcga agctaagatg   1440

gccttgtctt tgatcttgca aagattttcc ttcgaattgt cctcctcata tgttcatgct   1500

ccaactgttg ttttcaccac tcaaccacaa catggtgctc atatcgtttt gagaaagttg   1560

taa                                                                 1563


<210> SEQ ID NO 87
<211> LENGTH: 444
<212> TYPE: PRT
<213> ORGANISM: Saccharomyces cerevisiae

<400> SEQUENCE: 87

Met Gly Lys Leu Leu Gln Leu Ala Leu His Pro Val Glu Met Lys Ala
1               5                   10                  15

Ala Leu Lys Leu Lys Phe Cys Arg Thr Pro Leu Phe Ser Ile Tyr Asp
```

```
            20                  25                  30

Gln Ser Thr Ser Pro Tyr Leu Leu His Cys Phe Glu Leu Leu Asn Leu
        35                  40                  45

Thr Ser Arg Ser Phe Ala Ala Val Ile Arg Glu Leu His Pro Glu Leu
    50                  55                  60

Arg Asn Cys Val Thr Leu Phe Tyr Leu Ile Leu Arg Ala Leu Asp Thr
65                  70                  75                  80

Ile Glu Asp Asp Met Ser Ile Glu His Asp Leu Lys Ile Asp Leu Leu
                85                  90                  95

Arg His Phe His Glu Lys Leu Leu Leu Thr Lys Trp Ser Phe Asp Gly
            100                 105                 110

Asn Ala Pro Asp Val Lys Asp Arg Ala Val Leu Thr Asp Phe Glu Ser
        115                 120                 125

Ile Leu Ile Glu Phe His Lys Leu Lys Pro Glu Tyr Gln Glu Val Ile
    130                 135                 140

Lys Glu Ile Thr Glu Lys Met Gly Asn Gly Met Ala Asp Tyr Ile Leu
145                 150                 155                 160

Asp Glu Asn Tyr Asn Leu Asn Gly Leu Gln Thr Val His Asp Tyr Asp
                165                 170                 175

Val Tyr Cys His Tyr Val Ala Gly Leu Val Gly Asp Gly Leu Thr Arg
            180                 185                 190

Leu Ile Val Ile Ala Lys Phe Ala Asn Glu Ser Leu Tyr Ser Asn Glu
        195                 200                 205

Gln Leu Tyr Glu Ser Met Gly Leu Phe Leu Gln Lys Thr Asn Ile Ile
    210                 215                 220

Arg Asp Tyr Asn Glu Asp Leu Val Asp Gly Arg Ser Phe Trp Pro Lys
225                 230                 235                 240

Glu Ile Trp Ser Gln Tyr Ala Pro Gln Leu Lys Asp Phe Met Lys Pro
                245                 250                 255

Glu Asn Glu Gln Leu Gly Leu Asp Cys Ile Asn His Leu Val Leu Asn
            260                 265                 270

Ala Leu Ser His Val Ile Asp Val Leu Thr Tyr Leu Ala Gly Ile His
        275                 280                 285

Glu Gln Ser Thr Phe Gln Phe Cys Ala Ile Pro Gln Val Met Ala Ile
    290                 295                 300

Ala Thr Leu Ala Leu Val Phe Asn Asn Arg Glu Val Leu His Gly Asn
305                 310                 315                 320

Val Lys Ile Arg Lys Gly Thr Thr Cys Tyr Leu Ile Leu Lys Ser Arg
                325                 330                 335

Thr Leu Arg Gly Cys Val Glu Ile Phe Asp Tyr Tyr Leu Arg Asp Ile
            340                 345                 350

Lys Ser Lys Leu Ala Val Gln Asp Pro Asn Phe Leu Lys Leu Asn Ile
        355                 360                 365

Gln Ile Ser Lys Ile Glu Gln Phe Met Glu Glu Met Tyr Gln Asp Lys
    370                 375                 380

Leu Pro Pro Asn Val Lys Pro Asn Glu Thr Pro Ile Phe Leu Lys Val
385                 390                 395                 400

Lys Glu Arg Ser Arg Tyr Asp Asp Glu Leu Val Pro Thr Gln Gln Glu
                405                 410                 415

Glu Glu Tyr Lys Phe Asn Met Val Leu Ser Ile Ile Leu Ser Val Leu
            420                 425                 430

Leu Gly Phe Tyr Tyr Ile Tyr Thr Leu His Arg Ala
        435                 440
```

<210> SEQ ID NO 88
<211> LENGTH: 525
<212> TYPE: PRT
<213> ORGANISM: Gynostemma pentaphyllum

<400> SEQUENCE: 88

```
Met Val Asp Gln Phe Ser Leu Ala Phe Ile Phe Ala Ser Val Leu Gly
1               5                   10                  15

Ala Val Ala Phe Tyr Tyr Leu Phe Leu Arg Asn Arg Ile Phe Arg Val
            20                  25                  30

Ser Arg Glu Pro Arg Arg Glu Ser Leu Lys Asn Ile Ala Thr Thr Asn
        35                  40                  45

Gly Glu Cys Lys Ser Ser Tyr Ser Asp Gly Asp Ile Ile Ile Val Gly
    50                  55                  60

Ala Gly Val Ala Gly Ser Ala Leu Ala Tyr Thr Leu Gly Lys Asp Gly
65                  70                  75                  80

Arg Arg Val His Val Ile Glu Arg Asp Leu Thr Glu Pro Asp Arg Thr
                85                  90                  95

Val Gly Glu Leu Leu Gln Pro Gly Gly Tyr Leu Lys Leu Thr Glu Leu
            100                 105                 110

Gly Leu Glu Asp Cys Val Asn Glu Ile Asp Ala Gln Arg Val Tyr Gly
        115                 120                 125

Tyr Ala Leu Phe Lys Asp Gly Lys Asp Thr Lys Leu Ser Tyr Pro Leu
    130                 135                 140

Glu Lys Phe His Ser Asp Val Ser Gly Arg Ser Phe His Asn Gly Arg
145                 150                 155                 160

Phe Ile Gln Arg Met Arg Glu Lys Ala Ala Thr Leu Pro Asn Val Arg
                165                 170                 175

Leu Glu Gln Gly Thr Val Thr Ser Leu Leu Glu Glu Asn Gly Ile Ile
            180                 185                 190

Lys Gly Val Gln Tyr Lys Ser Lys Thr Gly Gln Glu Met Thr Ala Tyr
        195                 200                 205

Ala Pro Leu Thr Ile Val Cys Asp Gly Cys Phe Ser Asn Leu Arg Arg
    210                 215                 220

Ser Leu Cys Asn Pro Lys Val Asp Val Pro Ser Cys Phe Val Ala Leu
225                 230                 235                 240

Val Leu Glu Asn Cys Glu Leu Pro His Ala Asn Tyr Gly His Val Ile
                245                 250                 255

Leu Ala Asp Pro Ser Pro Ile Leu Phe Tyr Pro Ile Ser Ser Thr Glu
            260                 265                 270

Val Arg Cys Leu Val Asp Val Pro Gly Gln Lys Val Pro Ser Ile Ser
        275                 280                 285

Asn Gly Glu Met Ala Asn Tyr Leu Lys Ser Val Val Ala Pro Gln Ile
    290                 295                 300

Pro Pro Gln Ile Tyr Asp Ala Leu Arg Ser Cys Tyr Asp Lys Gly Asn
305                 310                 315                 320

Ile Arg Thr Met Pro Asn Arg Ser Met Pro Ala Asp Pro Tyr Pro Thr
                325                 330                 335

Pro Gly Ala Leu Leu Met Gly Asp Ala Phe Asn Met Arg His Pro Leu
            340                 345                 350

Thr Gly Gly Gly Met Thr Val Ala Leu Ser Asp Ile Val Val Leu Arg
        355                 360                 365

Asp Leu Leu Lys Pro Leu Arg Asp Leu His Asp Ala Pro Ile Leu Ser
```

```
    370                 375                 380

Asn Tyr Leu Glu Ala Phe Tyr Thr Leu Arg Lys Pro Val Ala Ser Thr
385                 390                 395                 400

Ile Asn Thr Leu Ala Gly Ala Leu Tyr Lys Val Phe Cys Ala Ser Pro
                405                 410                 415

Asp Gln Ala Arg Arg Glu Met Arg Gln Ala Cys Phe Asp Tyr Leu Ser
            420                 425                 430

Leu Gly Gly Val Phe Ser Asn Gly Pro Val Ser Leu Leu Ser Gly Leu
        435                 440                 445

Asn Pro Arg Pro Leu Ser Leu Val Leu His Phe Phe Ala Val Ala Ile
    450                 455                 460

Tyr Gly Val Gly Arg Leu Leu Ile Pro Phe Pro Ser Pro Arg Arg Val
465                 470                 475                 480

Trp Ile Gly Ala Arg Leu Ile Ser Gly Ala Ser Gly Ile Ile Phe Pro
                485                 490                 495

Ile Ile Lys Ala Glu Gly Val Arg Gln Ile Phe Phe Pro Ala Thr Leu
            500                 505                 510

Pro Ala Tyr Tyr Arg Ala Pro Pro Leu Val Arg Gly Arg
        515                 520                 525


<210> SEQ ID NO 89
<211> LENGTH: 531
<212> TYPE: PRT
<213> ORGANISM: Arabidopsis thaliana

<400> SEQUENCE: 89

Met Glu Ser Gln Leu Trp Asn Trp Ile Leu Pro Leu Leu Ile Ser Ser
1               5                   10                  15

Leu Leu Ile Ser Phe Val Ala Phe Tyr Gly Phe Phe Val Lys Pro Lys
            20                  25                  30

Arg Asn Gly Leu Arg His Asp Arg Lys Thr Val Ser Thr Val Thr Ser
        35                  40                  45

Asp Val Gly Ser Val Asn Ile Thr Gly Asp Thr Val Ala Asp Val Ile
    50                  55                  60

Val Val Gly Ala Gly Val Ala Gly Ser Ala Leu Ala Tyr Thr Leu Gly
65                  70                  75                  80

Lys Asp Lys Arg Arg Val His Val Ile Glu Arg Asp Leu Ser Glu Pro
                85                  90                  95

Asp Arg Ile Val Gly Glu Leu Leu Gln Pro Gly Gly Tyr Leu Lys Leu
            100                 105                 110

Leu Glu Leu Gly Ile Glu Asp Cys Val Glu Glu Ile Asp Ala Gln Arg
        115                 120                 125

Val Tyr Gly Tyr Ala Leu Phe Lys Asn Gly Lys Arg Ile Arg Leu Ala
    130                 135                 140

Tyr Pro Leu Glu Lys Phe His Glu Asp Val Ser Gly Arg Ser Phe His
145                 150                 155                 160

Asn Gly Arg Phe Ile Gln Arg Met Arg Glu Lys Ala Ala Ser Leu Pro
                165                 170                 175

Asn Val Gln Leu Glu Gln Gly Thr Val Leu Ser Leu Leu Glu Glu Asn
            180                 185                 190

Gly Thr Ile Lys Gly Val Arg Tyr Lys Asn Lys Ala Gly Glu Glu Gln
        195                 200                 205

Thr Ala Phe Ala Ala Leu Thr Ile Val Cys Asp Gly Cys Phe Ser Asn
    210                 215                 220
```

```
Leu Arg Arg Ser Leu Cys Asn Pro Gln Val Glu Val Pro Ser Cys Phe
225                 230                 235                 240

Val Gly Leu Val Leu Glu Asn Cys Asn Leu Pro Tyr Ala Asn His Gly
                245                 250                 255

His Val Val Leu Ala Asp Pro Ser Pro Ile Leu Met Tyr Pro Ile Ser
            260                 265                 270

Ser Thr Glu Val Arg Cys Leu Val Asp Val Pro Gly Gln Lys Val Pro
        275                 280                 285

Ser Ile Ala Asn Gly Glu Met Lys Asn Tyr Leu Lys Thr Val Val Ala
    290                 295                 300

Pro Gln Met Pro His Glu Val Tyr Asp Ser Phe Ile Ala Ala Val Asp
305                 310                 315                 320

Lys Gly Asn Ile Lys Ser Met Pro Asn Arg Ser Met Pro Ala Ser Pro
                325                 330                 335

Tyr Pro Thr Pro Gly Ala Leu Leu Met Gly Asp Ala Phe Asn Met Arg
            340                 345                 350

His Pro Leu Thr Gly Gly Gly Met Thr Val Ala Leu Ala Asp Ile Val
        355                 360                 365

Val Leu Arg Asn Leu Leu Arg Pro Leu Arg Asp Leu Ser Asp Gly Ala
    370                 375                 380

Ser Leu Cys Lys Tyr Leu Glu Ser Phe Tyr Thr Leu Arg Lys Pro Val
385                 390                 395                 400

Ala Ala Thr Ile Asn Thr Leu Ala Asn Ala Leu Tyr Gln Val Phe Cys
                405                 410                 415

Ser Ser Glu Asn Glu Ala Arg Asn Glu Met Arg Glu Ala Cys Phe Asp
            420                 425                 430

Tyr Leu Gly Leu Gly Gly Met Cys Thr Ser Gly Pro Val Ser Leu Leu
        435                 440                 445

Ser Gly Leu Asn Pro Arg Pro Leu Thr Leu Val Cys His Phe Phe Ala
    450                 455                 460

Val Ala Val Tyr Gly Val Ile Arg Leu Leu Ile Pro Phe Pro Ser Pro
465                 470                 475                 480

Lys Arg Ile Trp Leu Gly Ala Lys Leu Ile Ser Gly Ala Ser Gly Ile
                485                 490                 495

Ile Phe Pro Ile Ile Lys Ala Glu Gly Val Arg Gln Met Phe Phe Pro
            500                 505                 510

Ala Thr Val Pro Ala Tyr Tyr Tyr Lys Ala Pro Thr Val Gly Glu Thr
        515                 520                 525

Lys Cys Ser
    530
```

<210> SEQ ID NO 90
<211> LENGTH: 516
<212> TYPE: PRT
<213> ORGANISM: Arabidopsis thaliana

<400> SEQUENCE: 90

```
Met Thr Tyr Ala Trp Leu Trp Thr Leu Leu Ala Phe Val Leu Thr Trp
1               5                   10                  15

Met Val Phe His Leu Ile Lys Met Lys Lys Ala Ala Thr Gly Asp Leu
            20                  25                  30

Glu Ala Glu Ala Glu Ala Arg Arg Asp Gly Ala Thr Asp Val Ile Ile
        35                  40                  45

Val Gly Ala Gly Val Ala Gly Ala Ser Leu Ala Tyr Ala Leu Ala Lys
    50                  55                  60
```

```
Asp Gly Arg Arg Val His Val Ile Glu Arg Asp Leu Lys Glu Pro Gln
65                  70                  75                  80

Arg Phe Met Gly Glu Leu Met Gln Ala Gly Gly Arg Phe Met Leu Ala
                85                  90                  95

Gln Leu Gly Leu Glu Asp Cys Leu Glu Asp Ile Asp Ala Gln Glu Ala
            100                 105                 110

Lys Ser Leu Ala Ile Tyr Lys Asp Gly Lys His Ala Thr Leu Pro Phe
        115                 120                 125

Pro Asp Asp Lys Ser Phe Pro His Glu Pro Val Gly Arg Leu Leu Arg
    130                 135                 140

Asn Gly Arg Leu Val Gln Arg Leu Arg Gln Lys Ala Ala Ser Leu Ser
145                 150                 155                 160

Asn Val Gln Leu Glu Glu Gly Thr Val Lys Ser Leu Ile Glu Glu Glu
                165                 170                 175

Gly Val Val Lys Gly Val Thr Tyr Lys Asn Ser Ala Gly Glu Glu Ile
            180                 185                 190

Thr Ala Phe Ala Pro Leu Thr Val Val Cys Asp Gly Cys Tyr Ser Asn
        195                 200                 205

Leu Arg Arg Ser Leu Val Asp Asn Thr Glu Glu Val Leu Ser Tyr Met
    210                 215                 220

Val Gly Tyr Val Thr Lys Asn Ser Arg Leu Glu Asp Pro His Ser Leu
225                 230                 235                 240

His Leu Ile Phe Ser Lys Pro Leu Val Cys Val Ile Tyr Gln Ile Thr
                245                 250                 255

Ser Asp Glu Val Arg Cys Val Ala Glu Val Pro Ala Asp Ser Ile Pro
            260                 265                 270

Ser Ile Ser Asn Gly Glu Met Ser Thr Phe Leu Lys Lys Ser Met Ala
        275                 280                 285

Pro Gln Ile Pro Glu Thr Gly Asn Leu Arg Glu Ile Phe Leu Lys Gly
    290                 295                 300

Ile Glu Glu Gly Leu Pro Glu Ile Lys Ser Thr Ala Thr Lys Ser Met
305                 310                 315                 320

Ser Ser Arg Leu Cys Asp Lys Arg Gly Val Ile Val Leu Gly Asp Ala
                325                 330                 335

Phe Asn Met Arg His Pro Ile Ile Ala Ser Gly Met Met Val Ala Leu
            340                 345                 350

Ser Asp Ile Cys Ile Leu Arg Asn Leu Leu Lys Pro Leu Pro Asn Leu
        355                 360                 365

Ser Asn Thr Lys Lys Val Ser Asp Leu Val Lys Ser Phe Tyr Ile Ile
    370                 375                 380

Arg Lys Pro Met Ser Ala Thr Val Asn Thr Leu Ala Ser Ile Phe Ser
385                 390                 395                 400

Gln Val Leu Val Ala Thr Thr Asp Glu Ala Arg Glu Gly Met Arg Gln
                405                 410                 415

Gly Cys Phe Asn Tyr Leu Ala Arg Gly Asp Phe Lys Thr Arg Gly Leu
            420                 425                 430

Met Thr Ile Leu Gly Gly Met Asn Pro His Pro Leu Thr Leu Val Leu
        435                 440                 445

His Leu Val Ala Ile Thr Leu Thr Ser Met Gly His Leu Leu Ser Pro
    450                 455                 460

Phe Pro Ser Pro Arg Arg Phe Trp His Ser Leu Arg Ile Leu Ala Trp
465                 470                 475                 480
```

```
Ala Leu Gln Met Leu Gly Ala His Leu Val Asp Glu Gly Phe Lys Glu
                485                 490                 495

Met Leu Ile Pro Thr Asn Ala Ala Ala Tyr Arg Arg Asn Tyr Ile Ala
            500                 505                 510

Thr Thr Thr Val
        515


<210> SEQ ID NO 91
<211> LENGTH: 517
<212> TYPE: PRT
<213> ORGANISM: Arabidopsis thaliana

<400> SEQUENCE: 91

Met Ala Phe Thr His Val Cys Leu Trp Thr Leu Val Ala Phe Val Leu
1               5                   10                  15

Thr Trp Thr Val Phe Tyr Leu Thr Asn Met Lys Lys Lys Ala Thr Asp
            20                  25                  30

Leu Ala Asp Thr Val Ala Glu Asp Gln Lys Asp Gly Ala Ala Asp Val
        35                  40                  45

Ile Ile Val Gly Ala Gly Val Gly Gly Ser Ala Leu Ala Tyr Ala Leu
    50                  55                  60

Ala Lys Asp Gly Arg Arg Val His Val Ile Glu Arg Asp Met Arg Glu
65                  70                  75                  80

Pro Glu Arg Met Met Gly Glu Phe Met Gln Pro Gly Gly Arg Leu Met
                85                  90                  95

Leu Ser Lys Leu Gly Leu Gln Asp Cys Leu Glu Asp Ile Asp Ala Gln
            100                 105                 110

Lys Ala Thr Gly Leu Ala Val Tyr Lys Asp Gly Lys Glu Ala Asp Ala
        115                 120                 125

Pro Phe Pro Val Asp Asn Asn Asn Phe Ser Tyr Glu Pro Ser Ala Arg
    130                 135                 140

Ser Phe His Asn Gly Arg Phe Val Gln Gln Leu Arg Arg Lys Ala Phe
145                 150                 155                 160

Ser Leu Ser Asn Val Arg Leu Glu Glu Gly Thr Val Lys Ser Leu Leu
                165                 170                 175

Glu Glu Lys Gly Val Val Lys Gly Val Thr Tyr Lys Asn Lys Glu Gly
            180                 185                 190

Glu Glu Thr Thr Ala Leu Ala Pro Leu Thr Val Val Cys Asp Gly Cys
        195                 200                 205

Tyr Ser Asn Leu Arg Arg Ser Leu Asn Asp Asp Asn Asn Ala Glu Ile
    210                 215                 220

Met Ser Tyr Ile Val Gly Tyr Ile Ser Lys Asn Cys Arg Leu Glu Glu
225                 230                 235                 240

Pro Glu Lys Leu His Leu Ile Leu Ser Lys Pro Ser Phe Thr Met Val
                245                 250                 255

Tyr Gln Ile Ser Ser Thr Asp Val Arg Cys Gly Phe Glu Val Leu Pro
            260                 265                 270

Glu Asn Phe Pro Ser Ile Ala Asn Gly Glu Met Ser Thr Phe Met Lys
        275                 280                 285

Asn Thr Ile Val Pro Gln Val Pro Pro Lys Leu Arg Lys Ile Phe Leu
    290                 295                 300

Lys Gly Ile Asp Glu Gly Ala His Ile Lys Val Val Pro Ala Lys Arg
305                 310                 315                 320

Met Thr Ser Thr Leu Ser Lys Lys Lys Gly Val Ile Val Leu Gly Asp
                325                 330                 335
```

```
Ala Phe Asn Met Arg His Pro Val Val Ala Ser Gly Met Met Val Leu
            340                 345                 350

Leu Ser Asp Ile Leu Ile Leu Arg Arg Leu Leu Gln Pro Leu Ser Asn
        355                 360                 365

Leu Gly Asp Ala Asn Lys Val Ser Glu Val Ile Asn Ser Phe Tyr Asp
    370                 375                 380

Ile Arg Lys Pro Met Ser Ala Thr Val Asn Thr Leu Gly Asn Ala Phe
385                 390                 395                 400

Ser Gln Val Leu Ile Gly Ser Thr Asp Glu Ala Lys Glu Ala Met Arg
                405                 410                 415

Gln Gly Val Tyr Asp Tyr Leu Cys Ser Gly Gly Phe Arg Thr Ser Gly
            420                 425                 430

Met Met Ala Leu Leu Gly Gly Met Asn Pro Arg Pro Leu Ser Leu Val
        435                 440                 445

Tyr His Leu Cys Ala Ile Thr Leu Ser Ser Ile Gly Gln Leu Leu Ser
    450                 455                 460

Pro Phe Pro Ser Pro Leu Arg Ile Trp His Ser Leu Lys Leu Phe Gly
465                 470                 475                 480

Leu Ala Met Lys Met Leu Val Pro Asn Leu Lys Ala Glu Gly Val Ser
                485                 490                 495

Gln Met Leu Phe Pro Ala Asn Ala Ala Ala Tyr His Lys Ser Tyr Met
            500                 505                 510

Ala Ala Thr Thr Leu
        515


<210> SEQ ID NO 92
<211> LENGTH: 516
<212> TYPE: PRT
<213> ORGANISM: Arabidopsis thaliana

<400> SEQUENCE: 92

Met Ala Phe Thr Asn Val Cys Leu Trp Thr Leu Leu Ala Phe Met Leu
1               5                   10                  15

Thr Trp Thr Val Phe Tyr Val Thr Asn Arg Gly Lys Lys Ala Thr Gln
            20                  25                  30

Leu Ala Asp Ala Val Val Glu Glu Arg Glu Asp Gly Ala Thr Asp Val
        35                  40                  45

Ile Ile Val Gly Ala Gly Val Gly Gly Ser Ala Leu Ala Tyr Ala Leu
    50                  55                  60

Ala Lys Asp Gly Arg Arg Val His Val Ile Glu Arg Asp Leu Arg Glu
65                  70                  75                  80

Pro Glu Arg Ile Met Gly Glu Phe Met Gln Pro Gly Gly Arg Leu Met
                85                  90                  95

Leu Ser Lys Leu Gly Leu Glu Asp Cys Leu Glu Gly Ile Asp Ala Gln
            100                 105                 110

Lys Ala Thr Gly Met Thr Val Tyr Lys Asp Gly Lys Glu Ala Val Ala
        115                 120                 125

Ser Phe Pro Val Asp Asn Asn Asn Phe Pro Phe Asp Pro Ser Ala Arg
    130                 135                 140

Ser Phe His Asn Gly Arg Phe Val Gln Arg Leu Arg Gln Lys Ala Ser
145                 150                 155                 160

Ser Leu Pro Asn Val Arg Leu Glu Glu Gly Thr Val Lys Ser Leu Ile
                165                 170                 175

Glu Glu Lys Gly Val Ile Lys Gly Val Thr Tyr Lys Asn Ser Ala Gly
```

```
            180                 185                 190

Glu Glu Thr Thr Ala Leu Ala Pro Leu Thr Val Val Cys Asp Gly Cys
        195                 200                 205

Tyr Ser Asn Leu Arg Arg Ser Leu Asn Asp Asn Asn Ala Glu Val Leu
    210                 215                 220

Ser Tyr Gln Val Gly Phe Ile Ser Lys Asn Cys Gln Leu Glu Glu Pro
225                 230                 235                 240

Glu Lys Leu Lys Leu Ile Met Ser Lys Pro Ser Phe Thr Met Leu Tyr
                245                 250                 255

Gln Ile Ser Ser Thr Asp Val Arg Cys Val Phe Glu Val Leu Pro Asn
            260                 265                 270

Asn Ile Pro Ser Ile Ser Asn Gly Glu Met Ala Thr Phe Val Lys Asn
        275                 280                 285

Thr Ile Ala Pro Gln Val Pro Leu Lys Leu Arg Lys Ile Phe Leu Lys
    290                 295                 300

Gly Ile Asp Glu Gly Glu His Ile Lys Ala Met Pro Thr Lys Lys Met
305                 310                 315                 320

Thr Ala Thr Leu Ser Glu Lys Lys Gly Val Ile Leu Leu Gly Asp Ala
                325                 330                 335

Phe Asn Met Arg His Pro Ala Ile Ala Ser Gly Met Met Val Leu Leu
            340                 345                 350

Ser Asp Ile Leu Ile Leu Arg Arg Leu Leu Gln Pro Leu Ser Asn Leu
        355                 360                 365

Gly Asn Ala Gln Lys Ile Ser Gln Val Ile Lys Ser Phe Tyr Asp Ile
    370                 375                 380

Arg Lys Pro Met Ser Ala Thr Val Asn Thr Leu Gly Asn Ala Phe Ser
385                 390                 395                 400

Gln Val Leu Val Ala Ser Thr Asp Glu Ala Lys Glu Ala Met Arg Gln
                405                 410                 415

Gly Cys Tyr Asp Tyr Leu Ser Ser Gly Gly Phe Arg Thr Ser Gly Met
            420                 425                 430

Met Ala Leu Leu Gly Gly Met Asn Pro Arg Pro Ile Ser Leu Ile Tyr
        435                 440                 445

His Leu Cys Ala Ile Thr Leu Ser Ser Ile Gly His Leu Leu Ser Pro
    450                 455                 460

Phe Pro Ser Pro Leu Arg Ile Trp His Ser Leu Arg Leu Phe Gly Leu
465                 470                 475                 480

Ala Met Lys Met Leu Val Pro His Leu Lys Ala Glu Gly Val Ser Gln
                485                 490                 495

Met Leu Phe Pro Val Asn Ala Ala Ala Tyr Ser Lys Ser Tyr Met Ala
            500                 505                 510

Ala Thr Ala Leu
        515


<210> SEQ ID NO 93
<211> LENGTH: 585
<212> TYPE: PRT
<213> ORGANISM: Arabidopsis thaliana

<400> SEQUENCE: 93

Met Lys Pro Phe Val Ile Arg Asn Leu Pro Arg Phe Gln Ser Thr Leu
1               5                   10                  15

Arg Ser Ser Leu Leu Tyr Thr Asn His Arg Pro Ser Ser Arg Phe Ser
            20                  25                  30
```

```
Leu Ser Thr Arg Arg Phe Thr Thr Gly Ala Thr Tyr Ile Arg Arg Trp
        35                  40                  45

Lys Ala Thr Ala Ala Gln Thr Leu Lys Leu Ser Ala Val Asn Ser Thr
    50                  55                  60

Val Met Met Lys Pro Ala Lys Ile Ala Leu Asp Gln Phe Ile Ala Ser
65                  70                  75                  80

Leu Phe Thr Phe Leu Leu Leu Tyr Ile Leu Arg Arg Ser Ser Asn Lys
                85                  90                  95

Asn Lys Lys Asn Arg Gly Leu Val Val Ser Gln Asn Asp Thr Val Ser
            100                 105                 110

Lys Asn Leu Glu Thr Glu Val Asp Ser Gly Thr Asp Val Ile Ile Val
        115                 120                 125

Gly Ala Gly Val Ala Gly Ser Ala Leu Ala His Thr Leu Gly Lys Glu
    130                 135                 140

Gly Arg Arg Val His Val Ile Glu Arg Asp Phe Ser Glu Gln Asp Arg
145                 150                 155                 160

Ile Val Gly Glu Leu Leu Gln Pro Gly Gly Tyr Leu Lys Leu Ile Glu
                165                 170                 175

Leu Gly Leu Glu Asp Cys Val Lys Lys Ile Asp Ala Gln Arg Val Leu
            180                 185                 190

Gly Tyr Val Leu Phe Lys Asp Gly Lys His Thr Lys Leu Ala Tyr Pro
        195                 200                 205

Leu Glu Thr Phe Asp Ser Asp Val Ala Gly Arg Ser Phe His Asn Gly
    210                 215                 220

Arg Phe Val Gln Arg Met Arg Glu Lys Ala Leu Thr Leu Ser Asn Val
225                 230                 235                 240

Arg Leu Glu Gln Gly Thr Val Thr Ser Leu Leu Glu Glu His Gly Thr
                245                 250                 255

Ile Lys Gly Val Arg Tyr Arg Thr Lys Glu Gly Asn Glu Phe Arg Ser
            260                 265                 270

Phe Ala Pro Leu Thr Ile Val Cys Asp Gly Cys Phe Ser Asn Leu Arg
        275                 280                 285

Arg Ser Leu Cys Lys Pro Lys Val Asp Val Pro Ser Thr Phe Val Gly
    290                 295                 300

Leu Val Leu Glu Asn Cys Glu Leu Pro Phe Ala Asn His Gly His Val
305                 310                 315                 320

Val Leu Gly Asp Pro Ser Pro Ile Leu Met Tyr Pro Ile Ser Ser Ser
                325                 330                 335

Glu Val Arg Cys Leu Val Asp Val Pro Gly Gln Lys Leu Pro Pro Ile
            340                 345                 350

Ala Asn Gly Glu Met Ala Lys Tyr Leu Lys Thr Arg Val Ala Pro Gln
        355                 360                 365

Val Pro Thr Lys Val Arg Glu Ala Phe Ile Thr Ala Val Glu Lys Gly
    370                 375                 380

Asn Ile Arg Thr Met Pro Asn Arg Ser Met Pro Ala Asp Pro Ile Pro
385                 390                 395                 400

Thr Pro Gly Ala Leu Leu Leu Gly Asp Ala Phe Asn Met Arg His Pro
                405                 410                 415

Leu Thr Gly Gly Gly Met Thr Val Ala Leu Ala Asp Ile Val Val Leu
            420                 425                 430

Arg Asp Leu Leu Arg Pro Ile Arg Asn Leu Asn Asp Lys Glu Ala Leu
        435                 440                 445

Ser Lys Tyr Ile Glu Ser Phe Tyr Thr Leu Arg Lys Pro Val Ala Ser
```

450 455 460

Thr Ile Asn Thr Leu Ala Asp Ala Leu Tyr Lys Val Phe Leu Ala Ser
465 470 475 480

Ser Asp Glu Ala Arg Thr Glu Met Arg Glu Ala Cys Phe Asp Tyr Leu
485 490 495

Ser Leu Gly Gly Val Phe Ser Ser Gly Pro Val Ala Leu Leu Ser Gly
500 505 510

Leu Asn Pro Arg Pro Leu Ser Leu Val Leu His Phe Phe Ala Val Ala
515 520 525

Ile Tyr Ala Val Cys Arg Leu Met Leu Pro Phe Pro Ser Ile Glu Ser
530 535 540

Phe Trp Leu Gly Ala Arg Ile Ile Ser Ser Ala Ser Ser Ile Ile Phe
545 550 555 560

Pro Ile Ile Lys Ala Glu Gly Val Arg Gln Met Phe Phe Pro Arg Thr
565 570 575

Ile Pro Ala Ile Tyr Arg Ala Pro Pro
580 585

<210> SEQ ID NO 94
<211> LENGTH: 525
<212> TYPE: PRT
<213> ORGANISM: Arabidopsis thaliana

<400> SEQUENCE: 94

Met Ala Pro Thr Ile Phe Val Asp His Cys Ile Leu Thr Thr Thr Phe
1 5 10 15

Val Ala Ser Leu Phe Ala Phe Leu Leu Leu Tyr Val Leu Arg Arg Arg
20 25 30

Ser Lys Thr Ile His Gly Ser Val Asn Val Arg Asn Gly Thr Leu Thr
35 40 45

Val Lys Ser Gly Thr Asp Val Asp Ile Ile Ile Val Gly Ala Gly Val
50 55 60

Ala Gly Ala Ala Leu Ala His Thr Leu Gly Lys Glu Gly Arg Arg Val
65 70 75 80

His Val Ile Glu Arg Asp Leu Thr Glu Pro Asp Arg Ile Val Gly Glu
85 90 95

Leu Leu Gln Pro Gly Gly Tyr Leu Lys Leu Ile Glu Leu Gly Leu Glu
100 105 110

Asp Cys Val Lys Asp Ile Asp Ala Gln Arg Val Leu Gly Tyr Ala Leu
115 120 125

Phe Lys Asp Gly Lys His Thr Lys Leu Ser Tyr Pro Leu Asp Gln Phe
130 135 140

Asp Ser Asp Val Ala Gly Arg Ser Phe His Asn Gly Arg Phe Val Gln
145 150 155 160

Arg Met Arg Glu Lys Ala Ser Leu Leu Pro Asn Val Arg Met Glu Gln
165 170 175

Gly Thr Val Thr Ser Leu Val Glu Glu Asn Gly Ile Ile Lys Gly Val
180 185 190

Gln Tyr Lys Thr Lys Asp Gly Gln Glu Leu Lys Ser Phe Ala Pro Leu
195 200 205

Thr Ile Val Cys Asp Gly Cys Phe Ser Asn Leu Arg Arg Ser Leu Cys
210 215 220

Lys Pro Lys Val Glu Val Pro Ser Asn Phe Val Gly Leu Val Leu Glu
225 230 235 240

```
Asn Cys Glu Leu Pro Phe Pro Asn His Gly His Val Val Leu Gly Asp
                245                 250                 255

Pro Ser Pro Ile Leu Phe Tyr Pro Ile Ser Ser Ser Glu Val Arg Cys
            260                 265                 270

Leu Val Asp Val Pro Gly Ser Lys Leu Pro Ser Val Ala Ser Gly Glu
        275                 280                 285

Met Ala His His Leu Lys Thr Met Val Ala Pro Gln Val Pro Pro Gln
    290                 295                 300

Ile Arg Asp Ala Phe Ile Ser Ala Val Glu Lys Gly Asn Ile Arg Thr
305                 310                 315                 320

Met Pro Asn Arg Ser Met Pro Ala Asp Pro Ile His Thr Pro Gly Ala
                325                 330                 335

Leu Leu Leu Gly Asp Ala Phe Asn Met Arg His Pro Leu Thr Gly Gly
            340                 345                 350

Gly Met Thr Val Ala Leu Ser Asp Ile Val Ile Leu Arg Asp Leu Leu
        355                 360                 365

Asn Pro Leu Val Asp Leu Thr Asn Lys Glu Ser Leu Ser Lys Tyr Ile
    370                 375                 380

Glu Ser Phe Tyr Thr Leu Arg Lys Pro Val Ala Ser Thr Ile Asn Thr
385                 390                 395                 400

Leu Ala Gly Ala Leu Tyr Lys Val Phe Leu Ala Ser Pro Asp Asp Ala
                405                 410                 415

Arg Ser Glu Met Arg Arg Ala Cys Phe Asp Tyr Leu Ser Leu Gly Gly
            420                 425                 430

Val Cys Ser Ser Gly Pro Val Ala Leu Leu Ser Gly Leu Asn Pro Arg
        435                 440                 445

Pro Met Ser Leu Val Leu His Phe Phe Ala Val Ala Ile Phe Gly Val
    450                 455                 460

Gly Arg Leu Leu Val Pro Leu Pro Ser Val Lys Arg Leu Trp Leu Gly
465                 470                 475                 480

Ala Arg Leu Ile Ser Ser Ala Ser Gly Ile Ile Phe Pro Ile Ile Lys
                485                 490                 495

Ala Glu Gly Val Arg Gln Met Phe Phe Pro Arg Thr Ile Pro Ala Ile
            500                 505                 510

Tyr Arg Ala Pro Pro Thr Pro Ser Ser Ser Ser Pro Gln
        515                 520                 525
```

<210> SEQ ID NO 95
<211> LENGTH: 506
<212> TYPE: PRT
<213> ORGANISM: Brassica napus

<400> SEQUENCE: 95

```
Met Asp Leu Ala Phe Pro His Val Cys Leu Trp Thr Leu Leu Ala Phe
1               5                   10                  15

Val Leu Thr Trp Thr Val Phe Tyr Val Asn Asn Arg Arg Lys Lys Val
            20                  25                  30

Ala Lys Leu Pro Asp Ala Ala Thr Glu Val Arg Arg Asp Gly Asp Ala
        35                  40                  45

Asp Val Ile Ile Val Gly Ala Gly Val Gly Gly Ser Ala Leu Ala Tyr
    50                  55                  60

Ala Leu Ala Lys Asp Gly Arg Arg Val His Val Ile Glu Arg Asp Met
65                  70                  75                  80

Arg Glu Pro Val Arg Met Met Gly Glu Phe Met Gln Pro Gly Gly Arg
                85                  90                  95
```

-continued

```
Leu Leu Leu Ser Lys Leu Gly Leu Glu Asp Cys Leu Glu Gly Ile Asp
            100                 105                 110

Glu Gln Ile Ala Thr Gly Leu Ala Val Tyr Lys Asp Gly Gln Lys Ala
        115                 120                 125

Leu Val Ser Phe Pro Glu Asp Asn Asp Phe Pro Tyr Glu Pro Thr Gly
    130                 135                 140

Arg Ala Phe Tyr Asn Gly Arg Phe Val Gln Arg Leu Arg Gln Lys Ala
145                 150                 155                 160

Ser Ser Leu Pro Thr Val Gln Leu Glu Glu Gly Thr Val Lys Ser Leu
                165                 170                 175

Ile Glu Glu Lys Gly Val Ile Lys Gly Val Thr Tyr Lys Asn Ser Ala
            180                 185                 190

Gly Glu Glu Thr Thr Ala Phe Ala Pro Leu Thr Val Val Cys Asp Gly
        195                 200                 205

Cys Tyr Ser Asn Leu Arg Arg Ser Val Asn Asp Asn Asn Ala Glu Val
    210                 215                 220

Ile Ser Tyr Gln Val Gly Tyr Val Ser Lys Asn Cys Gln Leu Glu Asp
225                 230                 235                 240

Pro Glu Lys Leu Lys Leu Ile Met Ser Lys Pro Ser Phe Thr Met Leu
                245                 250                 255

Tyr Gln Ile Ser Ser Thr Asp Val Arg Cys Val Met Glu Ile Phe Pro
            260                 265                 270

Gly Asn Ile Pro Ser Ile Ser Asn Gly Glu Met Ala Val Tyr Leu Lys
        275                 280                 285

Asn Thr Met Ala Pro Gln Val Pro Pro Glu Leu Arg Lys Ile Phe Leu
    290                 295                 300

Lys Gly Ile Asp Glu Gly Ala Gln Ile Lys Ala Met Pro Thr Lys Arg
305                 310                 315                 320

Met Glu Ala Thr Leu Ser Glu Lys Gln Gly Val Ile Val Leu Gly Asp
                325                 330                 335

Ala Phe Asn Met Arg His Pro Ala Ile Ala Ser Gly Met Met Val Val
            340                 345                 350

Leu Ser Asp Ile Leu Ile Leu Arg Arg Leu Leu Gln Pro Leu Arg Asn
        355                 360                 365

Leu Ser Asp Ala Asn Lys Val Ser Glu Val Ile Lys Ser Phe Tyr Val
    370                 375                 380

Ile Arg Lys Pro Met Ser Ala Thr Val Asn Thr Leu Gly Asn Ala Phe
385                 390                 395                 400

Ser Gln Val Leu Ile Ala Ser Thr Asp Glu Ala Lys Glu Ala Met Arg
                405                 410                 415

Gln Gly Cys Phe Asp Tyr Leu Ser Ser Gly Gly Phe Arg Thr Ser Gly
            420                 425                 430

Met Met Ala Leu Leu Gly Gly Met Asn Pro Arg Pro Leu Ser Leu Ile
        435                 440                 445

Phe His Leu Cys Gly Ile Thr Leu Ser Ser Ile Gly Gln Leu Leu Ser
    450                 455                 460

Pro Phe Pro Ser Pro Leu Gly Ile Trp His Ser Leu Arg Leu Phe Gly
465                 470                 475                 480

Ala Glu Gly Val Ser Gln Met Leu Ser Pro Ala Tyr Ala Ala Ala Tyr
                485                 490                 495

Arg Lys Ser Tyr Met Thr Ala Thr Ala Leu
            500                 505
```

<210> SEQ ID NO 96
<211> LENGTH: 518
<212> TYPE: PRT
<213> ORGANISM: Brassica napus

<400> SEQUENCE: 96

```
Met Asp Met Ala Phe Val Glu Val Cys Leu Arg Met Leu Leu Val Phe
1               5                   10                  15

Val Leu Ser Trp Thr Ile Phe His Val Asn Asn Arg Lys Lys Lys Lys
            20                  25                  30

Ala Thr Lys Leu Ala Asp Leu Ala Thr Glu Glu Arg Lys Glu Gly Gly
        35                  40                  45

Pro Asp Val Ile Ile Val Gly Ala Gly Val Gly Gly Ser Ala Leu Ala
    50                  55                  60

Tyr Ala Leu Ala Lys Asp Gly Arg Arg Val His Val Ile Glu Arg Asp
65                  70                  75                  80

Met Arg Glu Pro Val Arg Met Met Gly Glu Phe Met Gln Pro Gly Gly
                85                  90                  95

Arg Leu Met Leu Ser Lys Leu Gly Leu Gln Asp Cys Leu Glu Glu Ile
            100                 105                 110

Asp Ala Gln Lys Ser Thr Gly Ile Arg Leu Phe Lys Asp Gly Lys Glu
        115                 120                 125

Thr Val Ala Cys Phe Pro Val Asp Thr Asn Phe Pro Tyr Glu Pro Ser
    130                 135                 140

Gly Arg Phe Phe His Asn Gly Arg Phe Val Gln Arg Leu Arg Gln Lys
145                 150                 155                 160

Ala Ser Ser Leu Pro Asn Val Arg Leu Glu Glu Gly Thr Val Arg Ser
                165                 170                 175

Leu Ile Glu Glu Lys Gly Val Val Lys Gly Val Thr Tyr Lys Asn Ser
            180                 185                 190

Ser Gly Glu Glu Thr Thr Ser Phe Ala Pro Leu Thr Val Val Cys Asp
        195                 200                 205

Gly Cys His Ser Asn Leu Arg Arg Ser Leu Asn Asp Asn Asn Ala Glu
    210                 215                 220

Val Thr Ala Tyr Glu Ile Gly Tyr Ile Ser Arg Asn Cys Arg Leu Glu
225                 230                 235                 240

Gln Pro Asp Lys Leu His Leu Ile Met Ala Lys Pro Ser Phe Ala Met
                245                 250                 255

Leu Tyr Gln Val Ser Ser Thr Asp Val Arg Cys Asn Phe Glu Leu Leu
            260                 265                 270

Ser Lys Asn Leu Pro Ser Val Ser Asn Gly Glu Met Thr Ser Phe Val
        275                 280                 285

Arg Asn Ser Ile Ala Pro Gln Val Pro Leu Lys Leu Arg Lys Thr Phe
    290                 295                 300

Leu Lys Gly Leu Asp Glu Gly Ser His Ile Lys Ile Thr Gln Ala Lys
305                 310                 315                 320

Arg Ile Pro Ala Thr Leu Ser Arg Lys Lys Gly Val Ile Val Leu Gly
                325                 330                 335

Asp Ala Phe Asn Met Arg His Pro Val Ile Ala Ser Gly Met Met Val
            340                 345                 350

Leu Leu Ser Asp Ile Leu Ile Leu Ser Arg Leu Leu Lys Pro Leu Gly
        355                 360                 365

Asn Leu Gly Asp Glu Asn Lys Val Ser Glu Val Met Lys Ser Phe Tyr
    370                 375                 380
```

```
Ala Leu Arg Lys Pro Met Ser Ala Thr Val Asn Thr Leu Gly Asn Ser
385                 390                 395                 400

Phe Trp Gln Val Leu Ile Ala Ser Thr Asp Glu Ala Lys Glu Ala Met
                405                 410                 415

Arg Gln Gly Cys Phe Asp Tyr Leu Ser Ser Gly Gly Phe Arg Thr Ser
            420                 425                 430

Gly Leu Met Ala Leu Ile Gly Gly Met Asn Pro Arg Pro Leu Ser Leu
        435                 440                 445

Phe Tyr His Leu Phe Val Ile Ser Leu Ser Ser Ile Gly Gln Leu Leu
    450                 455                 460

Ser Pro Phe Pro Thr Pro Leu Arg Val Trp His Ser Leu Arg Leu Leu
465                 470                 475                 480

Asp Leu Ser Leu Lys Met Leu Val Pro His Leu Lys Ala Glu Gly Ile
                485                 490                 495

Gly Gln Met Leu Ser Pro Thr Asn Ala Ala Ala Tyr Arg Lys Ser Tyr
            500                 505                 510

Met Ala Ala Thr Val Val
        515


<210> SEQ ID NO 97
<211> LENGTH: 531
<212> TYPE: PRT
<213> ORGANISM: Euphorbia tirucalli

<400> SEQUENCE: 97

Met Glu Val Ile Phe Asp Thr Tyr Ile Phe Gly Thr Phe Phe Ala Ser
1               5                   10                  15

Leu Cys Ala Phe Leu Leu Leu Phe Ile Leu Arg Pro Lys Val Lys Lys
            20                  25                  30

Met Gly Lys Ile Arg Glu Ile Ser Ser Ile Asn Thr Gln Asn Asp Thr
        35                  40                  45

Ala Ile Thr Pro Pro Lys Gly Ser Gly Thr Asp Val Ile Ile Val Gly
    50                  55                  60

Ala Gly Val Ala Gly Ala Ala Leu Ala Cys Thr Leu Gly Lys Asp Gly
65                  70                  75                  80

Arg Arg Val His Val Ile Glu Arg Asp Leu Lys Glu Pro Asp Arg Ile
                85                  90                  95

Val Gly Glu Leu Leu Gln Pro Gly Gly Tyr Leu Lys Leu Val Glu Leu
            100                 105                 110

Gly Leu Gln Asp Cys Val Glu Glu Ile Asp Ala Gln Arg Ile Val Gly
        115                 120                 125

Tyr Ala Leu Phe Met Asp Gly Asn Asn Thr Lys Leu Ser Tyr Pro Leu
    130                 135                 140

Glu Lys Phe Asp Ala Glu Val Ser Gly Lys Ser Phe His Asn Gly Arg
145                 150                 155                 160

Phe Ile Gln Arg Met Arg Glu Lys Ala Ala Ser Leu Pro Asn Val Gln
                165                 170                 175

Leu Glu Gln Gly Thr Val Thr Ser Leu Leu Glu Glu Asn Gly Thr Ile
            180                 185                 190

Lys Gly Val Gln Tyr Lys Thr Lys Asp Gly Gln Glu His Lys Ala Tyr
        195                 200                 205

Ala Pro Leu Thr Val Val Cys Asp Gly Cys Phe Ser Asn Leu Arg Arg
    210                 215                 220

Ser Leu Cys Lys Pro Lys Val Asp Val Pro Ser His Phe Val Gly Leu
```

```
225                 230                 235                 240

Val Leu Glu Asn Cys Asp Leu Pro Phe Ala Asn His Gly His Val Ile
                245                 250                 255

Leu Ala Asp Pro Ser Pro Ile Leu Phe Tyr Pro Ile Ser Ser Thr Glu
            260                 265                 270

Val Arg Cys Leu Val Asp Val Pro Gly Gln Lys Leu Pro Ser Ile Ala
        275                 280                 285

Ser Gly Glu Met Ala Lys Tyr Leu Lys Thr Met Val Ala Lys Gln Ile
    290                 295                 300

Pro Pro Val Leu His Asp Ala Phe Val Ser Ala Ile Asp Lys Gly Asn
305                 310                 315                 320

Ile Arg Thr Met Pro Asn Arg Ser Met Pro Ala Asp Pro Leu Pro Thr
                325                 330                 335

Pro Gly Ala Leu Leu Met Gly Asp Ala Phe Asn Met Arg His Pro Leu
            340                 345                 350

Thr Gly Gly Gly Met Thr Val Ala Leu Ala Asp Ile Val Leu Leu Arg
        355                 360                 365

Asp Leu Leu Lys Pro Leu Arg Asp Leu Asn Asp Ala Pro Ala Leu Ala
    370                 375                 380

Lys Tyr Leu Glu Ser Phe Tyr Thr Leu Arg Lys Pro Val Ala Ser Thr
385                 390                 395                 400

Ile Asn Thr Leu Ala Gly Ala Leu Tyr Lys Val Phe Ser Ala Ser Pro
                405                 410                 415

Asp Glu Ala Arg Lys Glu Met Arg Gln Ala Cys Phe Asp Tyr Leu Ser
            420                 425                 430

Leu Gly Gly Glu Cys Ala Met Gly Pro Val Ser Leu Leu Ser Gly Leu
        435                 440                 445

Asn Pro Ser Pro Leu Thr Leu Val Leu His Phe Phe Gly Val Ala Ile
    450                 455                 460

Tyr Gly Val Gly Arg Leu Leu Ile Pro Phe Pro Thr Pro Lys Gly Met
465                 470                 475                 480

Trp Ile Gly Ala Arg Ile Ile Ser Ser Ala Ser Gly Ile Ile Phe Pro
                485                 490                 495

Ile Ile Lys Ala Glu Gly Val Arg Gln Val Phe Phe Pro Ala Thr Val
            500                 505                 510

Pro Ala Ile Tyr Arg Asn Pro Pro Val Asn Gly Lys Ser Val Glu Val
        515                 520                 525

Pro Lys Ser
    530


<210> SEQ ID NO 98
<211> LENGTH: 519
<212> TYPE: PRT
<213> ORGANISM: Medicago truncatula

<400> SEQUENCE: 98

Met Ile Asp Pro Tyr Gly Phe Gly Trp Ile Thr Cys Thr Leu Ile Thr
1               5                   10                  15

Leu Ala Ala Leu Tyr Asn Phe Leu Phe Ser Arg Lys Asn His Ser Asp
            20                  25                  30

Ser Thr Thr Thr Glu Asn Ile Thr Thr Ala Thr Gly Glu Cys Arg Ser
        35                  40                  45

Phe Asn Pro Asn Gly Asp Val Asp Ile Ile Ile Val Gly Ala Gly Val
    50                  55                  60
```

```
Ala Gly Ser Ala Leu Ala Tyr Thr Leu Gly Lys Asp Gly Arg Arg Val
65                  70                  75                  80

Leu Ile Ile Glu Arg Asp Leu Asn Glu Pro Asp Arg Ile Val Gly Glu
                85                  90                  95

Leu Leu Gln Pro Gly Gly Tyr Leu Lys Leu Ile Glu Leu Gly Leu Asp
            100                 105                 110

Asp Cys Val Glu Lys Ile Asp Ala Gln Lys Val Phe Gly Tyr Ala Leu
        115                 120                 125

Phe Lys Asp Gly Lys His Thr Arg Leu Ser Tyr Pro Leu Glu Lys Phe
    130                 135                 140

His Ser Asp Ile Ala Gly Arg Ser Phe His Asn Gly Arg Phe Ile Leu
145                 150                 155                 160

Arg Met Arg Glu Lys Ala Ala Ser Leu Pro Asn Val Arg Leu Glu Gln
                165                 170                 175

Gly Thr Val Thr Ser Leu Leu Glu Glu Asn Gly Thr Ile Lys Gly Val
            180                 185                 190

Gln Tyr Lys Thr Lys Asp Ala Gln Glu Phe Ser Ala Cys Ala Pro Leu
        195                 200                 205

Thr Ile Val Cys Asp Gly Cys Phe Ser Asn Leu Arg Arg Ser Leu Cys
    210                 215                 220

Asn Pro Lys Val Glu Val Pro Ser Cys Phe Val Gly Leu Val Leu Glu
225                 230                 235                 240

Asn Cys Glu Leu Pro Cys Ala Asp His Gly His Val Ile Leu Gly Asp
                245                 250                 255

Pro Ser Pro Val Leu Phe Tyr Pro Ile Ser Ser Thr Glu Ile Arg Cys
            260                 265                 270

Leu Val Asp Val Pro Gly Gln Lys Val Pro Ser Ile Ser Asn Gly Glu
        275                 280                 285

Met Ala Lys Tyr Leu Lys Thr Val Val Ala Pro Gln Val Pro Pro Glu
    290                 295                 300

Leu His Ala Ala Phe Ile Ala Ala Val Asp Lys Gly His Ile Arg Thr
305                 310                 315                 320

Met Pro Asn Arg Ser Met Pro Ala Asp Pro Tyr Pro Thr Pro Gly Ala
                325                 330                 335

Leu Leu Met Gly Asp Ala Phe Asn Met Arg His Pro Leu Thr Gly Gly
            340                 345                 350

Gly Met Thr Val Ala Leu Ser Asp Ile Val Val Leu Arg Asn Leu Leu
        355                 360                 365

Lys Pro Leu Arg Asp Leu Asn Asp Ala Ser Ser Leu Cys Lys Tyr Leu
    370                 375                 380

Glu Ser Phe Tyr Thr Leu Arg Lys Pro Val Ala Ser Thr Ile Asn Thr
385                 390                 395                 400

Leu Ala Gly Ala Leu Tyr Lys Val Phe Cys Ala Ser Pro Asp Pro Ala
                405                 410                 415

Arg Lys Glu Met Arg Gln Ala Cys Phe Asp Tyr Leu Ser Leu Gly Gly
            420                 425                 430

Leu Phe Ser Glu Gly Pro Val Ser Leu Leu Ser Gly Leu Asn Pro Cys
        435                 440                 445

Pro Leu Ser Leu Val Leu His Phe Phe Ala Val Ala Ile Tyr Gly Val
    450                 455                 460

Gly Arg Leu Leu Leu Pro Phe Pro Ser Pro Lys Arg Leu Trp Ile Gly
465                 470                 475                 480

Ile Arg Leu Ile Ala Ser Ala Ser Gly Ile Ile Leu Pro Ile Ile Lys
```

```
                485                 490                 495

Ala Glu Gly Ile Arg Gln Met Phe Phe Pro Ala Thr Val Pro Ala Tyr
            500                 505                 510

Tyr Arg Ala Pro Pro Asp Ala
        515


<210> SEQ ID NO 99
<211> LENGTH: 526
<212> TYPE: PRT
<213> ORGANISM: Medicago truncatula

<400> SEQUENCE: 99

Met Asp Leu Tyr Asn Ile Gly Trp Ile Leu Ser Ser Val Leu Ser Leu
1               5                   10                  15

Phe Ala Leu Tyr Asn Leu Ile Phe Ala Gly Lys Lys Asn Tyr Asp Val
            20                  25                  30

Asn Glu Lys Val Asn Gln Arg Glu Asp Ser Val Thr Ser Thr Asp Ala
        35                  40                  45

Gly Glu Ile Lys Ser Asp Lys Leu Asn Gly Asp Ala Asp Val Ile Ile
    50                  55                  60

Val Gly Ala Gly Ile Ala Gly Ala Ala Leu Ala His Thr Leu Gly Lys
65                  70                  75                  80

Asp Gly Arg Arg Val His Ile Ile Glu Arg Asp Leu Ser Glu Pro Asp
                85                  90                  95

Arg Ile Val Gly Glu Leu Leu Gln Pro Gly Gly Tyr Leu Lys Leu Val
            100                 105                 110

Glu Leu Gly Leu Gln Asp Cys Val Asp Asn Ile Asp Ala Gln Arg Val
        115                 120                 125

Phe Gly Tyr Ala Leu Phe Lys Asp Gly Lys His Thr Arg Leu Ser Tyr
    130                 135                 140

Pro Leu Glu Lys Phe His Ser Asp Val Ser Gly Arg Ser Phe His Asn
145                 150                 155                 160

Gly Arg Phe Ile Gln Arg Met Arg Glu Lys Ala Ala Ser Leu Pro Asn
                165                 170                 175

Val Asn Met Glu Gln Gly Thr Val Ile Ser Leu Leu Glu Glu Lys Gly
            180                 185                 190

Thr Ile Lys Gly Val Gln Tyr Lys Asn Lys Asp Gly Gln Ala Leu Thr
        195                 200                 205

Ala Tyr Ala Pro Leu Thr Ile Val Cys Asp Gly Cys Phe Ser Asn Leu
    210                 215                 220

Arg Arg Ser Leu Cys Asn Pro Lys Val Asp Asn Pro Ser Cys Phe Val
225                 230                 235                 240

Gly Leu Ile Leu Glu Asn Cys Glu Leu Pro Cys Ala Asn His Gly His
                245                 250                 255

Val Ile Leu Gly Asp Pro Ser Pro Ile Leu Phe Tyr Pro Ile Ser Ser
            260                 265                 270

Thr Glu Ile Arg Cys Leu Val Asp Val Pro Gly Thr Lys Val Pro Ser
        275                 280                 285

Ile Ser Asn Gly Asp Met Thr Lys Tyr Leu Lys Thr Thr Val Ala Pro
    290                 295                 300

Gln Val Pro Pro Glu Leu Tyr Asp Ala Phe Ile Ala Ala Val Asp Lys
305                 310                 315                 320

Gly Asn Ile Arg Thr Met Pro Asn Arg Ser Met Pro Ala Asp Pro Arg
                325                 330                 335
```

Pro Thr Pro Gly Ala Val Leu Met Gly Asp Ala Phe Asn Met Arg His
340 345 350

Pro Leu Thr Gly Gly Gly Met Thr Val Ala Leu Ser Asp Ile Val Val
355 360 365

Leu Arg Asn Leu Leu Lys Pro Met Arg Asp Leu Asn Asp Ala Pro Thr
370 375 380

Leu Cys Lys Tyr Leu Glu Ser Phe Tyr Thr Leu Arg Lys Pro Val Ala
385 390 395 400

Ser Thr Ile Asn Thr Leu Ala Gly Ala Leu Tyr Lys Val Phe Ser Ala
405 410 415

Ser Pro Asp Glu Ala Arg Lys Glu Met Arg Gln Ala Cys Phe Asp Tyr
420 425 430

Leu Ser Leu Gly Gly Leu Phe Ser Glu Gly Pro Ile Ser Leu Leu Ser
435 440 445

Gly Leu Asn Pro Arg Pro Leu Ser Leu Val Leu His Phe Phe Ala Val
450 455 460

Ala Val Phe Gly Val Gly Arg Leu Leu Leu Pro Phe Pro Ser Pro Lys
465 470 475 480

Arg Val Trp Ile Gly Ala Arg Leu Leu Ser Gly Ala Ser Gly Ile Ile
485 490 495

Leu Pro Ile Ile Lys Ala Glu Gly Ile Arg Gln Met Phe Phe Pro Ala
500 505 510

Thr Val Pro Ala Tyr Tyr Arg Ala Pro Pro Val Asn Ala Phe
515 520 525

<210> SEQ ID NO 100
<211> LENGTH: 534
<212> TYPE: PRT
<213> ORGANISM: Ricinus communis

<400> SEQUENCE: 100

Met Ala Asp Asn Tyr Leu Leu Gly Trp Ile Leu Cys Ser Ile Ile Gly
1 5 10 15

Leu Phe Gly Leu Tyr Tyr Met Val Tyr Leu Val Val Lys Arg Glu Glu
20 25 30

Glu Asp Asn Asn Arg Lys Ala Leu Leu Gln Ala Arg Ser Asp Ser Ala
35 40 45

Lys Thr Met Ser Ala Val Ser Gln Asn Gly Glu Cys Arg Ser Asp Asn
50 55 60

Pro Ala Asp Ala Asp Ile Ile Ile Val Gly Ala Gly Val Ala Gly Ser
65 70 75 80

Ala Leu Ala His Thr Leu Gly Lys Asp Gly Arg Arg Val His Val Ile
85 90 95

Glu Arg Asp Leu Thr Glu Pro Asp Arg Ile Val Gly Glu Leu Leu Gln
100 105 110

Pro Gly Gly Tyr Leu Lys Leu Ile Glu Leu Gly Leu Glu Asp Cys Val
115 120 125

Glu Glu Ile Asp Ala Gln Arg Val Phe Gly Tyr Ala Leu Phe Met Asp
130 135 140

Gly Lys His Thr Gln Leu Ser Tyr Pro Leu Glu Lys Phe His Ser Asp
145 150 155 160

Val Ala Gly Arg Ser Phe His Asn Gly Arg Phe Ile Gln Arg Met Arg
165 170 175

Glu Lys Ala Ser Ser Ile Pro Asn Val Arg Leu Glu Gln Gly Thr Val
180 185 190

```
Thr Ser Leu Ile Glu Glu Lys Gly Ile Ile Arg Gly Val Val Tyr Lys
        195                 200                 205

Thr Lys Thr Gly Glu Glu Leu Thr Ala Phe Ala Pro Leu Thr Ile Val
    210                 215                 220

Cys Asp Gly Cys Phe Ser Asn Leu Arg Arg Ser Leu Cys Asn Pro Lys
225                 230                 235                 240

Val Asp Val Pro Ser Cys Phe Val Gly Leu Val Leu Glu Asp Cys Lys
                245                 250                 255

Leu Pro Tyr Gln Tyr His Gly His Val Val Leu Ala Asp Pro Ser Pro
            260                 265                 270

Ile Leu Phe Tyr Gln Ile Ser Ser Thr Glu Val Arg Cys Leu Val Asp
        275                 280                 285

Val Pro Gly Gln Lys Val Pro Ser Ile Ser Asn Gly Glu Met Ala Lys
    290                 295                 300

Tyr Leu Lys Asn Val Val Ala Pro Gln Val Pro Pro Glu Ile Tyr Asp
305                 310                 315                 320

Ser Phe Val Ala Ala Val Asp Lys Gly Asn Ile Arg Thr Met Pro Asn
                325                 330                 335

Arg Ser Met Pro Ala Ser Pro Tyr Pro Thr Pro Gly Ala Leu Leu Met
            340                 345                 350

Gly Asp Ala Phe Asn Met Arg His Pro Leu Thr Gly Gly Gly Met Thr
        355                 360                 365

Val Ala Leu Ser Asp Ile Val Val Leu Arg Glu Leu Leu Lys Pro Leu
    370                 375                 380

Arg Asp Leu His Asp Ala Pro Thr Leu Cys Arg Tyr Leu Glu Ser Phe
385                 390                 395                 400

Tyr Thr Leu Arg Lys Pro Val Ala Ser Thr Ile Asn Thr Leu Ala Gly
                405                 410                 415

Ala Leu Tyr Lys Val Phe Cys Ala Ser Ser Asp Glu Ala Arg Asn Glu
            420                 425                 430

Met Arg Gln Ala Cys Phe Asp Tyr Leu Ser Leu Gly Gly Val Phe Ser
        435                 440                 445

Thr Gly Pro Ile Ser Leu Leu Ser Gly Leu Asn Pro Arg Pro Leu Ser
    450                 455                 460

Leu Val Val His Phe Phe Ala Val Ala Ile Tyr Gly Val Gly Arg Leu
465                 470                 475                 480

Leu Leu Pro Phe Pro Ser Pro Lys Arg Val Trp Val Gly Ala Arg Leu
                485                 490                 495

Ile Ser Gly Ala Ser Gly Ile Ile Phe Pro Ile Ile Lys Ala Glu Gly
            500                 505                 510

Val Arg Gln Met Phe Phe Pro Ala Thr Val Pro Ala Tyr Tyr Arg Ala
        515                 520                 525

Pro Pro Val Glu Cys Asn
    530
```

<210> SEQ ID NO 101
<211> LENGTH: 521
<212> TYPE: PRT
<213> ORGANISM: Ricinus communis

<400> SEQUENCE: 101

```
Met Glu Tyr Lys Leu Ala Val Ala Gly Ile Ile Ala Ser Leu Trp Ala
1               5                   10                  15

Leu Phe Met Leu Cys Ser Leu Lys Arg Lys Lys Asn Ile Thr Arg Ala
```

```
            20                  25                  30

Ser Phe Asn Asn Tyr Thr Asp Glu Thr Leu Lys Ser Ser Ser Lys Glu
        35                  40                  45

Ile Cys Gln Pro Glu Ile Val Ala Ser Pro Asp Ile Ile Ile Val Gly
    50                  55                  60

Ala Gly Val Ala Gly Ala Ala Leu Ala Tyr Ala Leu Gly Glu Asp Gly
65                  70                  75                  80

Arg Gln Val His Val Ile Glu Arg Asp Leu Ser Glu Pro Asp Arg Ile
                85                  90                  95

Val Gly Glu Leu Leu Gln Pro Gly Gly Tyr Leu Lys Leu Ile Glu Leu
            100                 105                 110

Gly Leu Glu Asp Cys Val Glu Lys Ile Asp Ala Gln Gln Val Phe Gly
        115                 120                 125

Tyr Ala Ile Phe Lys Asp Gly Lys Ser Thr Lys Leu Ser Tyr Pro Leu
    130                 135                 140

Asp Gly Phe Gln Thr Asn Val Ser Gly Arg Ser Phe His Asn Gly Arg
145                 150                 155                 160

Phe Ile Gln Arg Met Arg Glu Lys Ala Thr Ser Leu Pro Asn Leu Ile
                165                 170                 175

Leu Gln Gln Gly Thr Val Thr Ser Leu Val Glu Lys Lys Gly Thr Val
            180                 185                 190

Lys Gly Val Asn Tyr Arg Thr Arg Asn Gly Gln Glu Met Thr Ala Tyr
        195                 200                 205

Ala Pro Leu Thr Ile Val Cys Asp Gly Cys Phe Ser Asn Leu Arg Arg
    210                 215                 220

Ser Leu Cys Asn Pro Lys Val Glu Ile Pro Ser Cys Phe Val Ala Leu
225                 230                 235                 240

Val Leu Glu Asn Cys Asp Leu Pro Tyr Ala Asn His Gly His Val Ile
                245                 250                 255

Leu Ala Asp Pro Ser Pro Ile Leu Phe Tyr Pro Ile Ser Ser Thr Glu
            260                 265                 270

Val Arg Cys Leu Val Asp Ile Pro Gly Gln Lys Val Pro Ser Ile Ser
        275                 280                 285

Asn Gly Glu Leu Ala Gln Tyr Leu Lys Ser Thr Val Ala Lys Gln Ile
    290                 295                 300

Pro Ser Glu Leu His Asp Ala Phe Ile Ser Ala Ile Glu Lys Gly Asn
305                 310                 315                 320

Ile Arg Thr Met Pro Asn Arg Ser Met Pro Ala Ser Pro His Pro Thr
                325                 330                 335

Pro Gly Ala Leu Leu Val Gly Asp Ala Phe Asn Met Arg His Pro Leu
            340                 345                 350

Thr Gly Gly Gly Met Thr Val Ala Leu Ser Asp Ile Val Leu Leu Arg
        355                 360                 365

Asn Leu Leu Arg Pro Leu Glu Asn Leu Asn Asp Ala Ser Val Leu Cys
    370                 375                 380

Lys Tyr Leu Glu Ser Phe Tyr Ile Leu Arg Lys Pro Met Ala Ser Thr
385                 390                 395                 400

Ile Asn Thr Leu Ala Gly Ala Leu Tyr Lys Val Phe Ser Ala Ser Thr
                405                 410                 415

Asp Arg Ala Arg Ser Glu Met Arg Gln Ala Cys Phe Asp Tyr Leu Ser
            420                 425                 430

Leu Gly Gly Val Phe Ser Asn Gly Pro Ile Ala Leu Leu Ser Gly Leu
        435                 440                 445
```

Asn Pro Arg Pro Leu Asn Leu Val Leu His Phe Phe Ala Val Ala Val
    450                 455                 460

Tyr Gly Val Gly Arg Leu Ile Leu Pro Phe Pro Ser Pro Lys Ser Ile
465                 470                 475                 480

Trp Asp Gly Val Lys Leu Ile Ser Gly Ala Ser Ser Val Ile Phe Pro
                485                 490                 495

Ile Met Lys Ala Glu Gly Ile Gly Gln Ile Phe Phe Pro Ile Thr Lys
            500                 505                 510

Pro Pro Asn His Lys Ser Gln Thr Trp
        515                 520

<210> SEQ ID NO 102
<211> LENGTH: 458
<212> TYPE: PRT
<213> ORGANISM: Ricinus communis

<400> SEQUENCE: 102

Met Gly Val Ser Arg Glu Glu Asn Ala Arg Asp Glu Lys Cys His Tyr
1               5                   10                  15

Tyr Glu Asn Gly Ile Ser Leu Ser Glu Lys Ser Met Ser Thr Asp Ile
            20                  25                  30

Ile Ile Val Gly Ala Gly Val Ala Gly Ser Ala Leu Ala Tyr Thr Leu
        35                  40                  45

Gly Lys Asp Gly Arg Arg Val His Val Ile Glu Arg Asp Leu Ser Leu
    50                  55                  60

Gln Asp Arg Ile Val Gly Glu Leu Leu Gln Pro Gly Gly Tyr Leu Lys
65                  70                  75                  80

Leu Ile Glu Leu Gly Leu Glu Asp Cys Val Glu Glu Ile Asp Ala Gln
                85                  90                  95

Gln Val Phe Gly Tyr Ala Leu Tyr Lys Asn Gly Arg Ser Thr Lys Leu
            100                 105                 110

Ser Tyr Pro Leu Glu Ser Phe Asp Ser Asp Val Ser Gly Arg Ser Phe
        115                 120                 125

His Asn Gly Arg Phe Ile Gln Arg Met Arg Glu Lys Ala Ala Ser Leu
    130                 135                 140

Pro Asn Val Arg Leu Glu Glu Gly Thr Val Thr Ser Leu Leu Glu Val
145                 150                 155                 160

Lys Gly Thr Ile Lys Gly Val Gln Tyr Lys Thr Lys Asn Gly Glu Glu
                165                 170                 175

Leu Thr Ala Ser Ala Pro Leu Thr Ile Val Cys Asp Gly Cys Phe Ser
            180                 185                 190

Asn Leu Arg Arg Ser Leu Cys Asn Pro Lys Val Asp Ile Pro Ser Cys
        195                 200                 205

Phe Val Ala Leu Ile Leu Glu Asn Ser Gly Gln Lys Leu Pro Ser Ile
    210                 215                 220

Ser Asn Gly Asp Met Ala Asn Tyr Leu Lys Ser Val Val Ala Pro Gln
225                 230                 235                 240

Ile Pro Pro Val Leu Ser Glu Ala Phe Ile Ser Ala Ile Glu Lys Gly
                245                 250                 255

Lys Ile Arg Thr Met Pro Asn Arg Ser Met Pro Ala Ala Pro His Pro
            260                 265                 270

Thr Pro Gly Ala Leu Leu Leu Gly Asp Ala Phe Asn Met Arg His Pro
        275                 280                 285

Leu Thr Gly Gly Gly Met Thr Val Ala Leu Ser Asp Ile Val Val Leu

```
    290                 295                 300

Arg Asn Leu Leu Lys Pro Leu His Asp Leu Thr Asp Ala Ser Ala Leu
305                 310                 315                 320

Cys Glu Tyr Leu Lys Ser Phe Tyr Ser Leu Arg Lys Pro Val Ala Ser
                325                 330                 335

Thr Ile Asn Thr Leu Ala Gly Ala Leu Tyr Lys Val Phe Ser Ala Ser
            340                 345                 350

His Asp Pro Ala Arg Asn Glu Met Arg Gln Ala Cys Phe Asp Tyr Leu
        355                 360                 365

Ser Leu Gly Gly Val Phe Ser Asn Gly Pro Ile Ala Leu Leu Ser Gly
    370                 375                 380

Leu Asn Pro Arg Pro Leu Ser Leu Val Ala His Phe Phe Ala Val Ala
385                 390                 395                 400

Ile Tyr Gly Val Gly Arg Leu Ile Phe Pro Leu Pro Ser Ala Lys Gly
                405                 410                 415

Met Trp Met Gly Ala Arg Met Ile Lys Val Ala Ser Gly Ile Ile Phe
            420                 425                 430

Pro Ile Ile Arg Ala Glu Gly Val Gln His Met Phe Phe Ser Lys Thr
        435                 440                 445

Leu Ser Ala Phe Ser Arg Ser Gln Thr Ser
    450                 455


<210> SEQ ID NO 103
<211> LENGTH: 485
<212> TYPE: PRT
<213> ORGANISM: Ricinus communis

<400> SEQUENCE: 103

Met Glu Tyr Gln Tyr Phe Val Gly Gly Ile Ile Ala Ser Ala Leu Leu
1               5                   10                  15

Phe Val Leu Val Cys Arg Leu Ala Gly Lys Arg Gln Arg Arg Ala Leu
            20                  25                  30

Arg Asp Thr Val Asp Arg Asp Glu Ile Ser Gln Asn Ser Glu Asn Gly
        35                  40                  45

Ile Ser Gln Ser Glu Lys Asn Met Asn Thr Asp Ile Ile Val Gly
    50                  55                  60

Ala Gly Val Ala Gly Ser Thr Leu Ala Tyr Thr Leu Gly Lys Asp Gly
65                  70                  75                  80

Arg Arg Val Arg Val Ile Glu Arg Asp Leu Ser Leu Gln Asp Arg Ile
                85                  90                  95

Val Gly Glu Leu Leu Gln Pro Gly Gly Tyr Leu Lys Leu Ile Glu Leu
            100                 105                 110

Gly Leu Glu Asp Cys Val Glu Glu Ile Asp Ala Leu Gln Val Phe Gly
        115                 120                 125

Tyr Ala Leu Tyr Lys Asn Gly Arg Ser Thr Lys Leu Ser Tyr Pro Leu
    130                 135                 140

Asp Ser Phe Asp Ser Asp Val Ser Gly Arg Ser Phe His Asn Gly Arg
145                 150                 155                 160

Phe Ile Gln Arg Met Arg Glu Lys Ala Ala Ser Leu Pro Asn Val Arg
                165                 170                 175

Met Glu Gly Gly Thr Val Thr Ser Leu Leu Glu Val Lys Gly Thr Ile
            180                 185                 190

Lys Gly Val Gln Tyr Lys Asn Lys Asn Gly Glu Glu Leu Ile Ala Cys
        195                 200                 205
```

Ala Pro Leu Thr Ile Val Cys Asp Gly Cys Phe Ser Asn Leu Arg Arg
    210                 215                 220

Ser Leu Cys Asn Ser Lys Val Asp Ile Pro Phe Cys Phe Val Ala Leu
225                 230                 235                 240

Ile Leu Glu Asn Cys Glu Leu Pro Tyr Pro Asn His Gly His Val Ile
                245                 250                 255

Leu Ala Asp Pro Ser Pro Ile Leu Phe Tyr Arg Ile Ser Ile Ser Glu
            260                 265                 270

Ile Arg Cys Leu Val Asp Ile Pro Ala Gly Gln Lys Leu Pro Ser Ile
        275                 280                 285

Ser Asn Gly Glu Met Ala Asn Tyr Leu Lys Ser Val Val Ala Pro Gln
    290                 295                 300

Ile Pro Pro Glu Leu Ser Asn Ala Phe Leu Ser Ala Ile Glu Lys Gly
305                 310                 315                 320

Lys Ile Arg Thr Met Pro Lys Arg Ser Met Pro Ala Ala Pro His Pro
                325                 330                 335

Thr Pro Gly Ala Leu Leu Leu Gly Asp Ala Phe Asn Met Arg His Pro
            340                 345                 350

Leu Thr Gly Gly Val Met Thr Val Ala Leu Ser Asp Ile Val Val Leu
        355                 360                 365

Arg Ser Leu Leu Arg Pro Leu His Asp Leu Thr Asp Ala Ser Ala Leu
    370                 375                 380

Cys Glu Tyr Leu Lys Ser Phe Tyr Ser Leu Arg Lys Pro Met Val Ser
385                 390                 395                 400

Thr Ile Asn Thr Leu Ala Gly Ala Leu Tyr Arg Val Phe Ser Ala Ser
                405                 410                 415

Gln Asp Pro Ala Arg Asp Glu Met Arg Gln Ala Cys Phe Asp Tyr Leu
            420                 425                 430

Ser Leu Gly Gly Val Phe Ser Asn Gly Pro Ile Ala Leu Leu Ser Gly
        435                 440                 445

Leu Asn Pro Arg Pro Leu Ser Leu Ile Val His Phe Phe Ala Val Ala
    450                 455                 460

Val Tyr Gly Val Gly Arg Leu Ile Phe Pro Leu Pro Ser Ala Lys Arg
465                 470                 475                 480

Met Trp Met Gln Glu
                485

<210> SEQ ID NO 104
<211> LENGTH: 220
<212> TYPE: PRT
<213> ORGANISM: Ricinus communis

<400> SEQUENCE: 104

Met Glu Tyr Gln Tyr Leu Met Gly Gly Gly Ile Met Thr Leu Leu Phe
1               5                   10                  15

Val Leu Ser Tyr Arg Leu Lys Arg Glu Thr Arg Ala Ser Val Glu Asn
            20                  25                  30

Ala Arg Asp Glu Val Leu Gln Asn Ser Glu Asn Gly Ile Ser Gln Ser
        35                  40                  45

Glu Lys Ala Met Asn Thr Asp Ile Lys Leu Leu Leu Glu Gln Ile Val
    50                  55                  60

Gln Lys Ile Ala Met Leu Asn Ser Ile Arg Leu Glu Glu Gly Thr Val
65                  70                  75                  80

Thr Ser Leu Leu Glu Val Lys Arg Asp Ile Lys Gly Val Gln Tyr Lys
                85                  90                  95

```
Thr Lys Asn Gly Glu Glu Leu Thr Ala Cys Ala Pro Leu Thr Ile Val
            100                 105                 110

Ser His Gly Cys Phe Ser Asn Leu Arg Leu His Val Thr Pro Ser Thr
        115                 120                 125

Ser Lys Phe Lys Ser Phe Ile Gly Leu Glu Val Asp Ile Pro Ser Ser
    130                 135                 140

Phe Ala Ala Leu Ile Leu Gly Asn Cys Glu Leu Pro Phe Pro Asn His
145                 150                 155                 160

Gly His Val Ile Leu Ala Asp Pro Ser Ser Ile Leu Phe Tyr Arg Ile
                165                 170                 175

Ser Ser Ser Glu Ile Cys Cys Leu Val Asp Val Pro Ala Gly Gln Lys
            180                 185                 190

Leu Pro Ser Ile Ser Asn Gly Glu Met Ala Asn Tyr Leu Lys Ser Val
        195                 200                 205

Val Ala His Gln Ala Phe Lys Val Gly Leu Ala Tyr
    210                 215                 220


<210> SEQ ID NO 105
<211> LENGTH: 642
<212> TYPE: PRT
<213> ORGANISM: Ricinus communis

<400> SEQUENCE: 105

Met Ser Pro Ile Ser Ile Gln Leu Pro Pro Arg Pro Gln Leu Tyr Arg
1               5                   10                  15

Ser Leu Ile Ser Ser Leu Ser Leu Ser Thr Tyr Lys Gln Pro Pro Ser
            20                  25                  30

Pro Pro Ser Phe Ser Leu Thr Ile Ala Asn Ser Pro Pro Gln Pro Gln
        35                  40                  45

Pro Gln Ala Thr Val Ser Ser Lys Thr Arg Thr Ile Thr Arg Leu Ser
    50                  55                  60

Asn Ser Ser Asn Arg Val Asn Leu Leu Gln Ala Glu Gln His Pro Gln
65                  70                  75                  80

Glu Pro Ser Ser Asp Leu Ser Tyr Ser Ser Ser Pro Pro His Cys Val
                85                  90                  95

Ser Gly Gly Tyr Asn Ile Lys Leu Met Glu Val Gly Thr Asp Asn Tyr
            100                 105                 110

Ala Val Ile Ile Ile Leu Gly Thr Phe Phe Ala Ser Leu Phe Ala Phe
        115                 120                 125

Val Phe Leu Ser Ile Leu Arg Tyr Asn Phe Lys Asn Lys Asn Lys Ala
    130                 135                 140

Lys Ile His Asp Glu Thr Thr Leu Lys Thr Gln Asn Asp Asn Val Arg
145                 150                 155                 160

Leu Pro Asp Asn Gly Ser Gly Asn Asp Val Ile Ile Val Gly Ala Gly
                165                 170                 175

Val Ala Gly Ala Ala Leu Ala Tyr Thr Leu Gly Lys Asp Gly Arg Arg
            180                 185                 190

Val His Val Ile Glu Arg Asp Leu Thr Glu Pro Asp Arg Ile Val Gly
        195                 200                 205

Glu Leu Leu Gln Pro Gly Gly Tyr Leu Lys Leu Ile Glu Leu Gly Leu
    210                 215                 220

Glu Asp Cys Val Gln Glu Ile Asp Ala Gln Arg Val Leu Gly Tyr Ala
225                 230                 235                 240

Leu Phe Lys Asp Gly Lys Asn Thr Arg Leu Ser Tyr Pro Leu Glu Lys
```

-continued

```
                245                 250                 255

Phe His Ala Asp Val Ala Gly Arg Ser Phe His Asn Gly Arg Phe Ile
            260                 265                 270

Gln Arg Met Arg Glu Lys Ala Ala Ser Leu Pro Asn Val Lys Leu Glu
        275                 280                 285

Gln Gly Thr Val Thr Ser Leu Leu Glu Glu Asn Gly Thr Ile Lys Gly
    290                 295                 300

Val Gln Tyr Lys Thr Lys Asp Gly Gln Glu Ile Arg Ala Tyr Ala Pro
305                 310                 315                 320

Leu Thr Ile Val Cys Asp Gly Cys Phe Ser Asn Leu Arg Arg Ser Leu
                325                 330                 335

Cys Asn Pro Lys Val Asp Val Pro Ser Cys Phe Val Gly Leu Val Leu
            340                 345                 350

Glu Asn Cys Gln Leu Pro Phe Ala Asn His Gly His Val Val Leu Ala
        355                 360                 365

Asp Pro Ser Pro Ile Leu Phe Tyr Pro Ile Ser Ser Thr Glu Val Arg
    370                 375                 380

Cys Leu Val Asp Val Pro Gly Gln Lys Val Pro Ser Ile Ala Asn Gly
385                 390                 395                 400

Glu Met Ala Lys Tyr Leu Lys Asn Val Val Ala Pro Gln Ile Pro Pro
                405                 410                 415

Val Leu His Asp Ala Phe Ile Ser Ala Ile Asp Lys Gly Asn Ile Arg
            420                 425                 430

Thr Met Pro Asn Arg Ser Met Pro Ala Asp Pro His Pro Thr Pro Gly
        435                 440                 445

Ala Leu Leu Met Gly Asp Ala Phe Asn Met Arg His Pro Leu Thr Gly
    450                 455                 460

Gly Gly Met Thr Val Ala Leu Ser Asp Ile Val Val Leu Arg Asp Leu
465                 470                 475                 480

Leu Lys Pro Leu Arg Asp Leu Asn Asp Ala Thr Ser Leu Thr Lys Tyr
                485                 490                 495

Leu Glu Ser Phe Tyr Thr Leu Arg Lys Pro Val Ala Ser Thr Ile Asn
            500                 505                 510

Thr Leu Ala Gly Ala Leu Tyr Lys Val Phe Ser Ala Ser Pro Asp Gln
        515                 520                 525

Ala Arg Lys Glu Met Arg Gln Ala Cys Phe Asp Tyr Leu Ser Leu Gly
    530                 535                 540

Gly Ile Phe Ser Ser Gly Pro Val Ala Leu Leu Ser Gly Leu Asn Pro
545                 550                 555                 560

Arg Pro Leu Ser Leu Val Met His Phe Phe Ala Val Ala Ile Tyr Gly
                565                 570                 575

Val Gly Arg Leu Leu Leu Pro Phe Pro Ser Pro Lys Ser Val Trp Ile
            580                 585                 590

Gly Ala Arg Leu Ile Ser Ser Ala Ser Gly Ile Ile Phe Pro Ile Ile
        595                 600                 605

Lys Ala Glu Gly Val Arg Gln Met Phe Phe Pro Ala Thr Ile Pro Ala
    610                 615                 620

Ile Tyr Arg Pro Pro Pro Val Lys Asp Thr Ser Asp Asp Glu Gln Lys
625                 630                 635                 640

Ser Arg
```

METHODS AND MATERIALS FOR BIOSYNTHESIS OF MOGROSIDE COMPOUNDS

BACKGROUND OF THE INVENTION

Field of Invention

The present invention relates to methods and materials for biosynthesis of mogrol precursors, mogrol, and/or mogrosides. More particularly, the present invention relates to methods of using of cucurbitadienol synthase, cytochrome P450, cytochrome P450 reductase, and/or epoxide hydrolase enzymes to produce mogrol precursors and/or mogrol. The present invention also relates to methods of using of uridine-5'-diphospho (UDP) dependent glucosyltransferase (UGT) enzymes to glycosylate mogrol and produce various mogrosides.

Description of Related Art

Mogrosides are a family of triterpene glycosides isolated from fruit of *Siraitia grosvenorii* (*S. grosvenorii*, Swingle), also known as *Momordica grosvenori*. Fruit extracts are commercially used as natural sweeteners. Four major compounds, mogroside V, mogroside IV, siamenoside I, and 11-oxomogroside V (see FIG. 1) have been identified from *S. grosvenorii* as being responsible for the fruit's sweetness. Mogroside V is the most abundant of these four compounds, at approximately 0.57% (w/w) of the dry fruit, followed by mogroside IV and siamenoside I, each of which contains four glucose moieties. 11-oxomogroside V has a ketone group instead of a hydroxyl at C11. See, e.g., Takemoto et al., 1983, *Yakugaku Zasshi* 103: 1151-4; 1155-66; 1167-73; Kasai et al., 1989, *Agric. Biol. Chem.* 53:3347-9; Matsumoto *Chem. Pharm. Bull.*, 1990, 38:2030-2; and Prakash et al., 2011, *J. Carbohydrate Chem.* 30:16-26.

All mogrosides share the same mogrol triterpene core. The aglycone mogrol is glycosylated with different numbers of glucose moieties to form various mogroside compounds. Mogrosides can be synthesized in the following manner: synthesis of cucurbitadienol from the common triterpene precursor oxidosqualene, oxidation of cucurbitadienol to produce mogrol, and glycosylation of mogrol to produce various mogrosides. See, Tang et al., BMC Genomics 12: 343 (2011). Tang et al., 2011, BMC Genomics 12:343 describes seven cytochrome P450s and five UGTs as potential candidates involved in mogroside biosynthesis. However, Tang et al. does not specifically identify any cytochrome P450s or UGTs involved in mogroside biosynthesis. Thus, there remains the need to identify cytochrome P450s and UGTs capable of acting on any *S. grosvenorii* metabolites. Additionally, although mogrosides can be extracted from *S. grosvenorii*, there remains a need for improved production of mogrosides in recombinant hosts for commercial uses.

SUMMARY OF THE INVENTION

It is against the above background that the present invention provides certain advantages and advancements over the prior art.

The present invention provides methods and materials for biosynthesis of mogroside compounds and provides enzymes involved in mogroside biosynthesis.

Although the invention disclosed herein is not limited to specific advantages or functionalities, the invention provides a recombinant host comprising one or more of:

(a) a gene encoding a squalene epoxidase polypeptide;

(b) a gene encoding a cucurbitadienol synthase polypeptide;

(c) a gene encoding a cytochrome P450 polypeptide;

(d) a gene encoding a cytochrome P450 reductase polypeptide;

(e) a gene encoding an epoxide hydrolase polypeptide;

(f) a gene encoding a UGT1576 polypeptide having 60% or greater identity to an amino acid sequence set forth in SEQ ID NO:48;

(g) a gene encoding a UGT430 polypeptide having 45% or greater identity to an amino acid sequence set forth in SEQ ID NO:62;

(h) a gene encoding a UGT1697 polypeptide having 45% or greater identity to an amino acid sequence set forth in SEQ ID NO:68;

(i) a gene encoding a UGT11789 polypeptide having 50% or greater identity to an amino acid sequence set forth in SEQ ID NO:72;

(j) a gene encoding a UGT98 polypeptide having 70% or greater identity to an amino acid sequence set forth in SEQ ID NO:53;

(k) a gene encoding a UGTSK98 polypeptide having 70% or greater identity to an amino acid sequence set forth in SEQ ID NO:50;

wherein at least one of the genes is a recombinant gene;

wherein the host is capable of producing a mogrol precursor, a mogroside precursor, and/or a mogroside compound.

In some aspects of the recombinant host disclosed herein:

(a) the squalene epoxidase polypeptide comprises a polypeptide having 45% or greater identity to an amino acid sequence set forth in SEQ ID NO:54;

(b) the cucurbitadienol synthase polypeptide comprises a polypeptide having 70% or greater identity to an amino acid sequence set forth in SEQ ID NO:43;

(c) the cytochrome P450 polypeptide comprises a CYP5491 polypeptide having 50% or greater identity to an amino acid sequence set forth in SEQ ID NO:44 and/or a CYP1798 polypeptide having 70% or greater identity to an amino acid sequence set forth in SEQ ID NO:74;

(d) the cytochrome P450 reductase polypeptide comprises a CPR4497 polypeptide having 50% or greater identity to an amino acid sequence set forth in SEQ ID NO:46; and/or (e) the epoxide hydrolase polypeptide comprises an epoxide hydrolase 1 polypeptide having 75% or greater identity to an amino acid sequence set forth in SEQ ID NO:38 or an epoxide hydrolase 2 polypeptide having 65% or greater identity to an amino acid sequence set forth in SEQ ID NO:40.

The invention further provides a recombinant host comprising one or more of:

(a) one or more genes encoding one or more enzymes capable of catalyzing conversion of dioxidosqualene to produce 24,25 epoxy cucurbitadienol;

(b) one or more genes encoding one or more enzymes capable of catalyzing conversion of oxidosqualene to produce cucurbitadienol;

(c) one or more genes encoding one or more enzymes capable of catalyzing hydroxylation of 24,25 epoxy cucurbitadienol to produce 11-hydroxy-24,25 epoxy cucurbitadienol;

(d) one or more genes encoding one or more enzymes capable of catalyzing hydroxylation of cucurbitadienol to produce 11-hydroxy-cucurbitadienol;

(e) one or more genes encoding one or more enzymes capable of catalyzing epoxidation of cucurbitadienol to produce 24,25 epoxy cucurbitadienol; or (f) one or more genes encoding one or more enzymes capable of catalyzing epoxidation of 11-hydroxy-cucurbitadienol to produce 11-hydroxy-24,25 epoxy cucurbitadienol;

(g) one or more genes encoding one or more enzymes capable of catalyzing conversion of 11-hydroxy-24,25 epoxy cucurbitadienol to produce mogrol; or (h) one or more genes encoding one or more enzymes capable of catalyzing glycosylation of a mogroside precursor to produce a mogroside compound;

wherein at least one of the genes is a recombinant gene.

In one aspect of the recombinant hosts disclosed herein, the recombinant host further comprises a gene encoding squalene epoxidase polypeptide having 45% or greater identity to an amino acid sequence set forth in SEQ ID NO:54.

In one aspect of the recombinant hosts disclosed herein, the recombinant host has been modified to reduce expression of a lanosterol synthase (ERG7) polypeptide.

In one aspect of the recombinant hosts disclosed herein, the ERG7 polypeptide comprises a polypeptide having an amino acid sequence set forth in SEQ ID NO:55.

The invention further provides a method of producing a mogroside precursor and/or a mogroside compound, comprising:

(a) growing the recombinant host disclosed herein in a culture medium, under conditions in which the genes disclosed herein are expressed;

wherein the mogroside precursor and/or the mogroside compound is synthesized by the recombinant host; and (b) optionally isolating the mogroside precursor and/or the mogroside compound.

In some aspects of the methods disclosed herein, the mogroside precursor is mogrol synthesized by epoxidation of 11-hydroxy-cucurbitadienol to synthesize 11-hydroxy-24,25 epoxy cucurbitadienol and hydrolysis of 11-hydroxy-24,25 epoxy cucurbitadienol to synthesize mogrol.

In some aspects of the methods disclosed herein, the epoxidation of 11-hydroxy-cucurbitadienol to synthesize 11-hydroxy-24,25 epoxy cucurbitadienol is catalyzed by the CYP1798 polypeptide having 70% or greater identity to an amino acid sequence set forth in SEQ ID NO:74.

The invention further provides a method of producing a mogrol precursor in vitro, comprising:

(a) contacting dioxidosqualene with one or more enzymes capable of catalyzing conversion of dioxidosqualene to produce 24,25 epoxy cucurbitadienol; or (b) contacting oxidosqualene with one or more enzymes capable of catalyzing conversion of oxidosqualene to produce cucurbitadienol; or (c) contacting 24,25 epoxy cucurbitadienol with one or more enzymes capable of catalyzing hydroxylation of 24,25 epoxy cucurbitadienol to produce 11-hydroxy-24,25 epoxy cucurbitadienol; or (d) contacting cucurbitadienol with one or more enzymes capable of catalyzing hydroxylation of cucurbitadienol to produce 11-hydroxy-cucurbitadienol; or (e) contacting cucurbitadienol with one or more enzymes capable of catalyzing epoxidation of cucurbitadienol to produce 24,25 epoxy cucurbitadienol; or (f) contacting 11-hydroxy-cucurbitadienol with one or more enzymes capable of catalyzing epoxidation of 11-hydroxy-cucurbitadienol to produce 11-hydroxy-24,25 epoxy cucurbitadienol.

The invention further provides a method of producing a mogrol in vitro, comprising contacting 11-hydroxy-24,25 epoxy cucurbitadienol with one or more enzymes capable of catalyzing conversion of 11-hydroxy-24,25 epoxy cucurbitadienol to produce mogrol.

The invention further provides a method of producing a mogroside compound in vitro, comprising contacting a mogroside precursor with one or more enzymes capable of catalyzing glycosylation of the mogroside precursor to produce a mogroside compound.

In one aspect of the methods disclosed herein, the method further comprises isolating the mogrol precursor, mogrol or the mogroside compound.

In some aspects of the recombinant hosts and methods disclosed herein:

(a) the one or more enzymes capable of catalyzing conversion of dioxidosqualene to produce 24,25 epoxy cucurbitadienol comprise a cucurbitadienol synthase having 70% or greater identity to an amino acid sequence set forth in SEQ ID NO:43;

(b) the one or more enzymes capable of catalyzing conversion of oxidosqualene to produce cucurbitadienol comprise a cucurbitadienol synthase having 70% or greater identity to an amino acid sequence set forth in SEQ ID NO:43;

(c) the one or more enzymes capable of catalyzing conversion of 24,25 epoxy cucurbitadienol to produce 11-hydroxy-24,25 epoxy cucurbitadienol comprise CYP5491 having 50% or greater identity to an amino acid sequence set forth in SEQ ID NO:44;

(d) the one or more enzymes capable of catalyzing conversion of cucurbitadienol to produce 11-hydroxy-cucurbitadienol comprise CYP5491 having 50% or greater identity to an amino acid sequence set forth in SEQ ID NO:44;

(e) the one or more enzymes capable of catalyzing epoxidation of cucurbitadienol to produce 24,25 epoxy cucurbitadienol comprise CYP1798 having 70% or greater identity to an amino acid sequence set forth in SEQ ID NO:74;

(f) the one or more enzymes capable of catalyzing epoxidation of 11-hydroxy-cucurbitadienol to produce 11-hydroxy-24,25 epoxy cucurbitadienol comprise CYP1798 having 70% or greater identity to an amino acid sequence set forth in SEQ ID NO:74;

(g) the one or more enzymes capable of catalyzing conversion of 11-hydroxy-24,25 epoxy cucurbitadienol to produce mogrol comprise a polypeptide comprising epoxide hydrolase 1 having 75% or greater identity to an amino acid sequence set forth in SEQ ID NO:38 or epoxide hydrolase 2 having 65% or greater identity to an amino acid sequence set forth in SEQ ID NO:40; and/or (h) the one or more enzymes capable of catalyzing conversion of the mogroside precursor to a mogroside compound comprise UGT1576 having 60% or greater identity to an amino acid sequence set forth in SEQ ID NO:48; UGT98 having 70% or greater identity to an amino acid sequence set forth in SEQ ID NO:53; UGTSK98 having 70% or greater identity to an amino acid sequence set forth in SEQ ID NO:50; UGT430 having 45% or greater identity to an amino acid sequence set forth in SEQ ID NO:62; UGT1697 having 45% or greater identity to an amino acid sequence set forth in SEQ ID NO:68; or UGT11789 having 50% or greater identity to an amino acid sequence set forth in SEQ ID NO:72.

The invention further provides a method of producing a mogroside compound, comprising contacting a recombinant host expressing one or more of:

(a) a UGT1576 polypeptide having 60% or greater identity to an amino acid sequence set forth in SEQ ID NO:48;

(b) a UGT430 polypeptide having 45% or greater identity to an amino acid sequence set forth in SEQ ID NO:62;

(c) a UGT1697 polypeptide having 45% or greater identity to an amino acid sequence set forth in SEQ ID NO:68;

(d) a UGT11789 polypeptide having 50% or greater identity to an amino acid sequence set forth in SEQ ID NO:72;

(e) a UGT98 polypeptide having 70% or greater identity to an amino acid sequence set forth in SEQ ID NO:53; or (f) a UGTSK98 polypeptide having 70% or greater identity to an amino acid sequence set forth in SEQ ID NO:50 with a mogroside precursor.

In one aspect of the methods disclosed herein, the mogroside precursor is plant-derived or synthetic.

In one aspect of the methods disclosed herein, the method further comprises isolating the mogroside compound.

In some aspects of the recombinant hosts and methods disclosed herein, the mogroside compound is:

(a) mogrol glycosylated at C3 position; or (b) mogrol glycosylated at C24 position; or (c) mogrol glycosylated at C3 position and C24 position.

In some aspects of the recombinant hosts and methods disclosed herein, the mogroside compound is one or more of mogroside I A1, mogroside I E1, mogroside II A, mogroside II A1, mogroside II A2, mogroside II E, mogroside III A1, mogroside III A2, mogroside III, mogroside III E, mogroside IV, mogroside IV A, mogroside V or siamenoside.

In some aspects of the recombinant hosts and methods disclosed herein, the mogrol precursor is one or more of squalene, dioxidosqualene, oxidosqualene, 24,25 epoxy cucurbitadienol, cucurbitadienol, 11-hydroxy-cucurbitadienol, 11-hydroxy 24, 25 epoxy cucurbitadienol or 11-oxo-mogrol.

In some aspects of the recombinant hosts and methods disclosed herein, the mogroside precursor is one or more of mogrol, glycosylated mogrol, di-glycosylated mogrol or tri-glycosylated mogrol.

In some aspects of the recombinant hosts and methods disclosed herein, the recombinant host comprises a microorganism that is a yeast cell, a plant cell, a mammalian cell, an insect cell, a fungal cell, or a bacterial cell.

In some aspects of the recombinant hosts and methods disclosed herein, the bacterial cell comprises *Escherichia* bacteria cells, *Lactobacillus* bacteria cells, *Lactococcus* bacteria cells, *Cornebacterium* bacteria cells, *Acetobacter* bacteria cells, *Acinetobacter* bacteria cells, or *Pseudomonas* bacterial cells.

In some aspects of the recombinant hosts and methods disclosed herein, the yeast cell is a cell from *Saccharomyces cerevisiae, Schizosaccharomyces pombe, Yarrowia lipolytica, Candida glabrata, Ashbya gossypii, Cyberlindnera jadinii, Pichia pastoris, Kluyveromyces lactis, Hansenula polymorpha, Candida boidinii, Arxula adeninivorans, Xanthophyllomyces dendrorhous*, or *Candida albicans* species.

In some aspects of the recombinant hosts and methods disclosed herein, the yeast cell is a Saccharomycete.

In some aspects of the recombinant hosts and methods disclosed herein, the yeast cell is a cell from the *Saccharomyces cerevisiae* species.

In some aspects of the recombinant hosts disclosed herein, one or more of the genes further comprise a nucleotide sequence coding a fusion tag.

In one aspect of the recombinant hosts disclosed herein, the fusion tag is a protein or polypeptide.

In one aspect of the recombinant hosts disclosed herein, the fusion tag is green fluorescent protein (GFP), human influenza hemagglutinin (HA), glutathione S transferase (GST), a polyhistidine-tag (HIS tag), and a FLAG-tag, a chloroplast transit peptide, a mitochondrial transit peptide, an amyloplast peptide, a signal peptide, or a secretion tag.

In one aspect of the recombinant hosts disclosed herein, one or more of the genes are expressed as fusion proteins.

The invention further provides a mogroside composition produced by the recombinant host or the methods disclosed herein, wherein the composition comprises one or more of mogroside I A1, mogroside I E1, mogroside II A, mogroside II E, mogroside III A1, mogroside III A2, mogroside III, mogroside III E, mogroside IV, mogroside V, and siamenoside.

The invention further provides a food or drink product comprising the mogroside composition disclosed herein.

These and other features and advantages of the present invention will be more fully understood from the following detailed description of the invention taken together with the accompanying claims. It is noted that the scope of the claims is defined by the recitations therein and not by the specific discussion of features and advantages set forth in the present description.

BRIEF DESCRIPTION OF THE DRAWINGS

The following detailed description of the embodiments of the present invention can be best understood when read in conjunction with the following drawings, where like structure is indicated with like reference numerals and in which:

FIG. 2B shows production of cucurbitadienol from oxidosqualene using a cucurbitadienol synthase (step A), production of 24,25 epoxy cucurbitadienol from dioxidosqualene using a cucurbitadienol synthase (step B), production of 11-hydroxy-cucurbitadienol from cucurbitadienol using a cytochrome P450 (step C), production of 11-hydroxy 24,25 epoxy cucurbitadienol from 24,25 epoxy cucurbitadienol using a cytochrome P450 (step D), production of 24,25 epoxy cucurbitadienol from cucurbitadienol using a cytochrome P450 (step E), production of 11-hydroxy 24,25 epoxy cucurbitadienol from 11-hydroxy-cucurbitadienol using a cytochrome P450 (step F), production of mogrol from 11-hydroxy 24,25 epoxy cucurbitadienol from using an epoxide hydrolase (step G), production of mogrol from 11-hydroxy-cucurbitadienol using a cytochrome P450 and an epoxide hydrolase (steps F and G), and production of one or more mogroside compounds using one or more UGTs (step H).

FIG. 2C shows production of cucurbitadienol from oxidosqualene using an *S. grosvenorii* cucurbitadienol synthase of SEQ ID NO:43 (step A), production of 24,25 epoxy cucurbitadienol from dioxidosqualene using an *S. grosvenorii* cucurbitadienol synthase of SEQ ID NO:43 (step B), production of 11-hydroxy-cucurbitadienol from cucurbitadienol using CYP5491 of SEQ ID NO:44 (step C), production 11-hydroxy 24,25 epoxy cucurbitadienol from 24,25 epoxy cucurbitadienol using CYP5491 of SEQ ID NO:44 (step D), production of 24,25 epoxy cucurbitadienol from cucurbitadienol using CYP1798 of SEQ ID NO:74 (step E), production of 11-hydroxy 24,25 epoxy cucurbitadienol from 11-hydroxy-cucurbitadienol using CYP1798 of SEQ ID NO:74 (step F), production of mogrol from 11-hydroxy 24,25 epoxy cucurbitadienol from using epoxide hydrolase 1 of SEQ ID NO:38 or epoxide hydrolase 2 of SEQ ID NO:40 (step G), production of mogrol from 11-hydroxy-cucurbitadienol using CYP1798 of SEQ ID NO:74 and epoxide hydrolase 1 of SEQ ID NO:38 or epoxide hydrolase 2 of SEQ ID NO:40 (steps F and G), and production of mogroside compounds using UGT1576 of SEQ ID NO:48, UGT430 of SEQ ID NO:62, UGT1697 of SEQ ID NO:68, UGT98 of SEQ ID NO:53, and/or UGT11789 of SEQ ID NO:72 (step H).

FIGS. 18A, 18B, and 18C show an NMR-elucidated structure, $^{1}H$ NMR spectrum, and $^{1}H$ and $^{13}C$ NMR chemical shifts (in ppm) for mogroside V, mogroside II A2, and mogroside IV A, respectively, as described in Example 16.

DETAILED DESCRIPTION OF THE INVENTION

Before describing the present invention in detail, a number of terms will be defined. As used herein, the singular forms "a," "an," and "the" include plural referents unless the context clearly dictates otherwise. For example, reference to a "nucleic acid" means one or more nucleic acids.

It is noted that terms like "preferably," "commonly," and "typically" are not utilized herein to limit the scope of the claimed invention or to imply that certain features are critical, essential, or even important to the structure or function of the claimed invention. Rather, these terms are merely intended to highlight alternative or additional features that can or cannot be utilized in a particular embodiment of the present invention.

For the purposes of describing and defining the present invention it is noted that the term "substantially" is utilized herein to represent the inherent degree of uncertainty that can be attributed to any quantitative comparison, value, measurement, or other representation. The term "substantially" is also utilized herein to represent the degree by which a quantitative representation can vary from a stated reference without resulting in a change in the basic function of the subject matter at issue.

As used herein, the terms "polynucleotide," "nucleotide," "oligonucleotide," and "nucleic acid" can be used interchangeably to refer to nucleic acid comprising DNA, RNA, derivatives thereof, or combinations thereof.

As used herein, the term "and/or" is utilized to describe multiple components in combination or exclusive of one another. For example, "x, y, and/or z" can refer to "x" alone, "y" alone, "z" alone, "x, y, and z," "(x and y) or z," "x and (y or z)," or "x or y or z." In some embodiments, "and/or" is used to refer to the exogenous nucleic acids that a recombinant cell comprises, wherein a recombinant cell comprises one or more exogenous nucleic acids selected from a group. In some embodiments, "and/or" is used to refer to production of mogrosides, wherein one or more mogrosides is produced. In some embodiments, "and/or" is used to refer to production of mogrosides, wherein one or more mogrosides is produced through one or more of the following steps: culturing a recombinant microorganism, synthesizing one or more mogrosides in a recombinant microorganism, and isolating one or more mogrosides.

Mogrosides and Mogroside Production

As used herein, the terms "mogroside" and "mogroside compound" can be used interchangeably to describe mogrol glycosylated at one or more positions. In particular, a mogroside compound can be mogrol glycosylated with one or more glucose moieties at the positions 1, 3, 11, 24, and 25. Mogrol is a compound of formula I provided below, wherein both $R_1$ and $R_2$ are —H.

Mogrosides can be of the following formula I:

(I)

Figure 1:
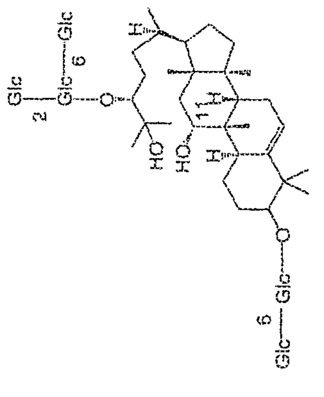
FIG. 1 shows chemical structures of mogroside V, mogroside IV, siamenoside I, and 11-oxomogroside V.
Figure 1:
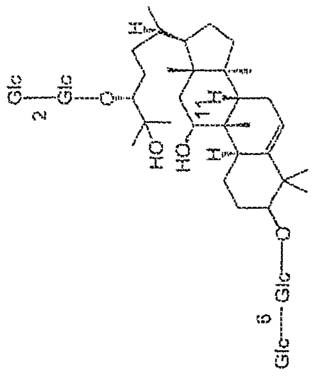
Figure 1:
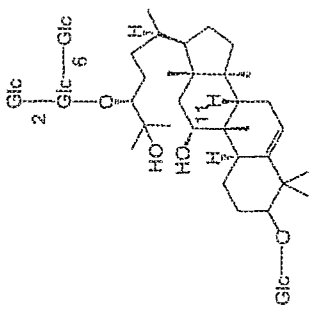
Figure 1:
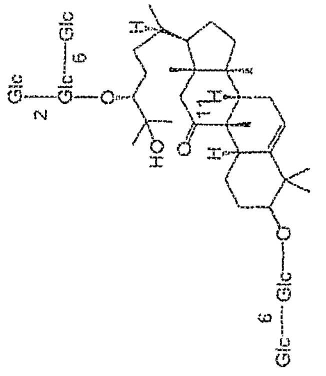

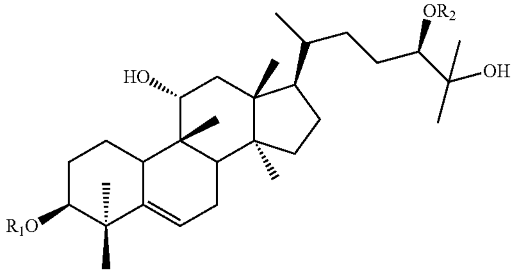

wherein $R_1$ and $R_2$ independently are —H, mono-glucoside, di-glucoside, tri-glucoside, and wherein at least one of $R_1$ and $R_2$ is not —H. In particular, the mogroside can be one of the mogrosides described in Table 1. In Table 1, "Glc" represents glucose, and the 1,6- and 1,2-bonds are indicated. For example, the $R_2$ group of mogroside V comprises 3 glucose molecules linked by one 1,6-bond and one 1,2-bond, a conformation represented as "Glc6-Glc2-Glc-". See FIG. 1 for the structures of mogroside IV, mogroside V, 11-oxo-mogroside V, and siamenoside.

TABLE 1

Mogrosides of formula I. (Glc = glucose)

| Name | $R_1$ | $R_2$ |
|---|---|---|
| mogroside V | Glc6-Glc- | Glc6-Glc2-Glc |
| siamenoside I | Glc- | Glc6-Glc2-Glc- |
| mogroside IV | Glc6-Glc- | Glc2-Glc- |
| mogroside IV A | Glc6-Glc- | Glc6-Glc- |
| mogroside III | Glc- | Glc6-Glc- |
| mogroside III A1 | H | Glc6-Glc2-Glc- |
| mogroside III A2 (mogroside IIIa) | Glc6-Glc- | Glc- |
| mogroside III E | Glc- | Glc2-Glc- |
| mogroside II A | H | Glc2-Glc- |
| mogroside II A1 | H | Glc6-Glc- |
| mogroside II A2 | Glc6-Glc- | H |
| mogroside II E | Glc- | Glc- |
| mogroside I A1 (mogroside Ib) | H | Glc- |
| mogroside I E1 (mogroside Ia) | Glc- | H |

Figure 2A:
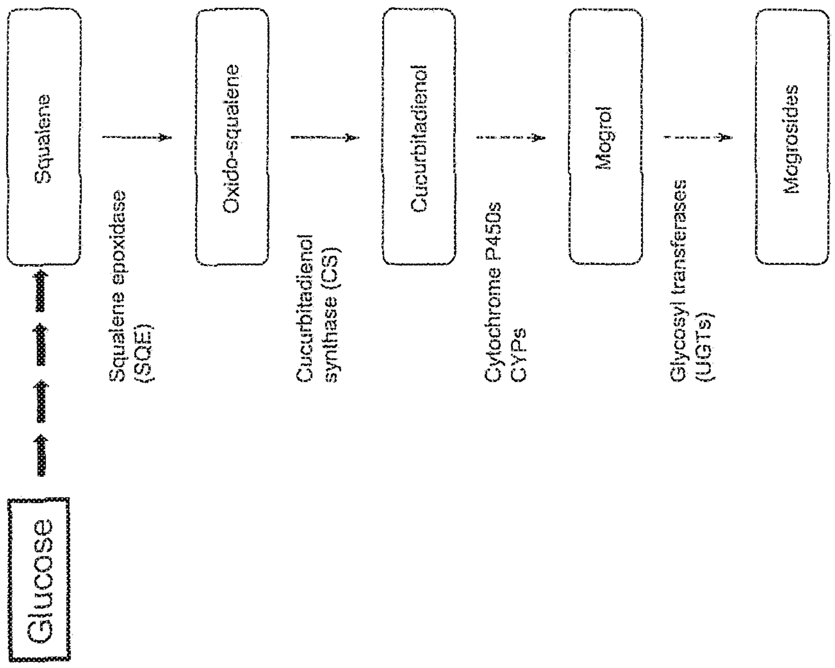
FIG. 2A is a schematic diagram of a pathway for producing mogrosides from glucose.
Figure 4:
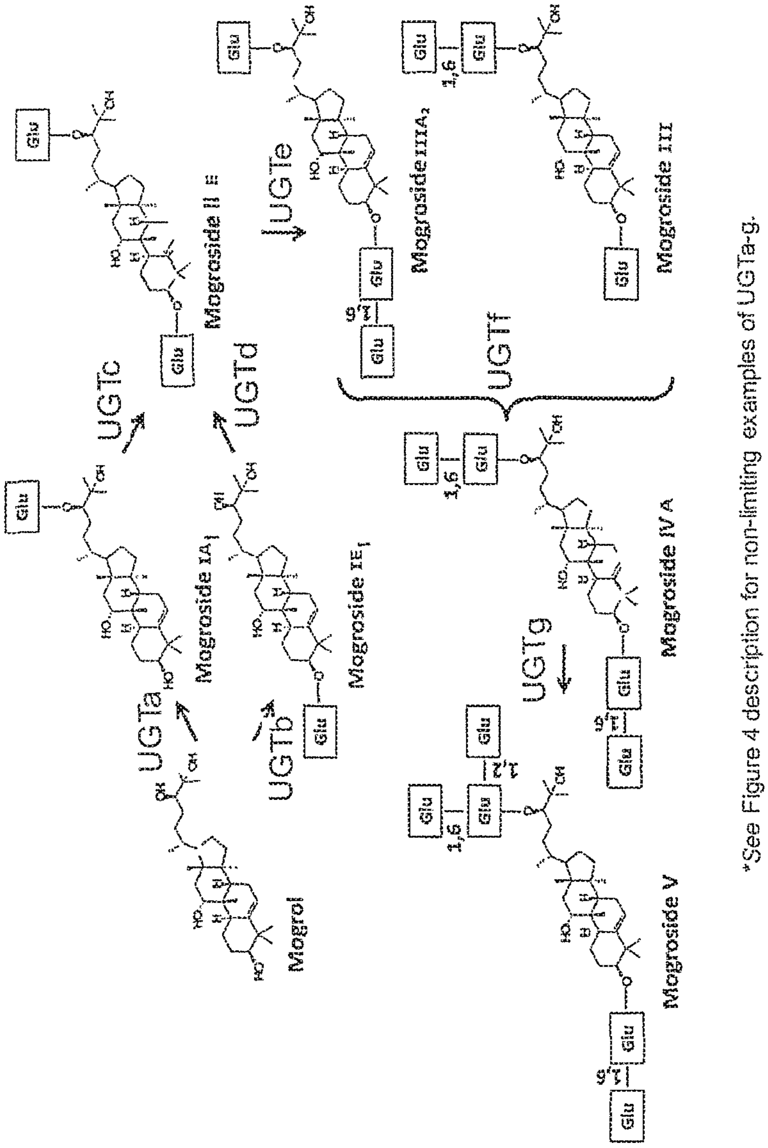
FIG. 4 is schematic diagram of pathways for the biosynthesis of mogroside I E1, mogroside I A1, mogroside II E, mogroside III A2, mogroside III, mogroside IV, and mogroside V from mogrol using UGTs. UGTa of FIG. 4 can be, for example, UGT1576 (SEQ ID NO:48) or UGT1697 (SEQ ID NO:68). UGTb of FIG. 4 can be, for example, UGT430 (SEQ ID NO:62) or UGT1697 (SEQ ID NO:68). UGTc of FIG. 4 can be, for example, UGT430 (SEQ ID NO:62) or UGT1697 (SEQ ID NO:68). UGTd of FIG. 4 can be, for example, UGT1576 (SEQ ID NO:48) or UGT1697 (SEQ ID NO:68). UGTe of FIG. 4 can be, for example, UGT98 (SEQ ID NO:53) or UGT11789 (SEQ ID NO:72). UGTf of FIG. 4 can be, for example, UGT98 (SEQ ID NO:53) or UGT11789 (SEQ ID NO:72). UGTg of FIG. 4 can be, for example, UGT98 (SEQ ID NO:53) or UGT11789 (SEQ ID NO:72).

Mogrosides can be produced from a number of mogroside precursors. In some embodiments, a mogroside precursor is mogrol, glycosylated mogrol, di-glycosylated mogrol or tri-glycosylated mogrol. Mogrol precursors, in turn, include squalene, dioxidosqualene, oxidosqualene, 24,25 epoxy cucurbitadienol, cucurbitadienol, 11-hydroxy-cucurbitadienol, 11-hydroxy 24, 25 epoxy cucurbitadienol, 11-oxo-mogrol. See, e.g., FIGS. 2 and 9. For example, mogroside I A1 is a precursor to the products, mogroside II A and mogroside III A1. See, FIG. 12. In another example, mogroside II E is converted to mogroside V by three enzymatic glycosylations. In one possible route, two glucose moieties are first attached through 1,6-bonds to the two glucose molecules of mogroside II E by a UGT not limited to UGT98 (SEQ ID NO:53) or UGT11789 (SEQ ID NO:72). A third glucose moiety is added to the C24-bound glucose moiety with a 1,2 bond by a UGT not limited to UGT98 (SEQ ID NO:53) or UGT11789 (SEQ ID NO:72). See, FIG. 4.

Figure 3A:
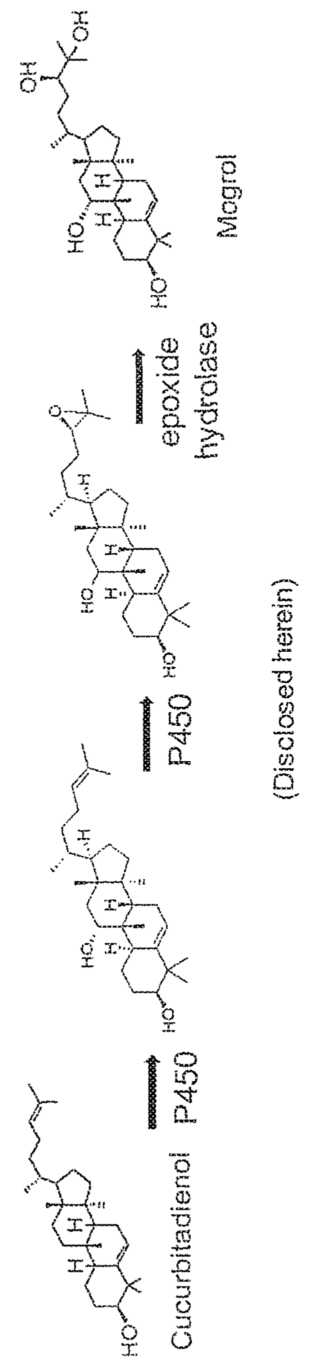
FIG. 3A shows a representative pathway for production of mogrol from cucurbitadienol, as disclosed herein.
Figure 3B:
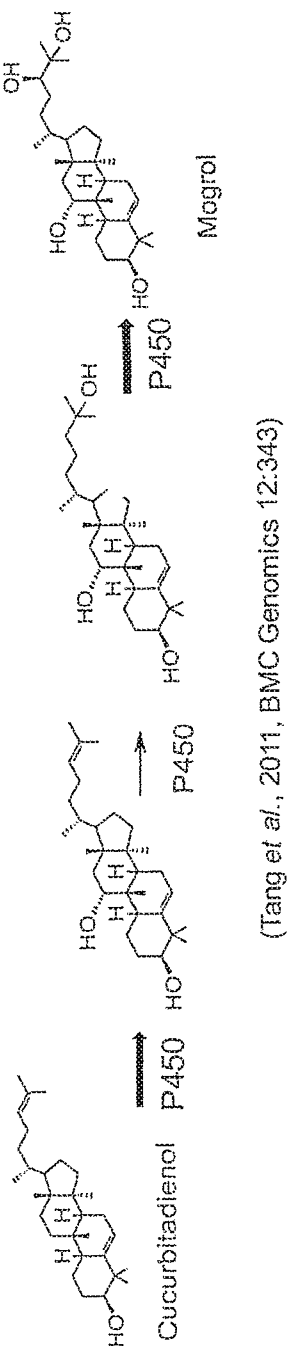
FIG. 3B is a schematic diagram of a pathway for production of mogrol from cucurbitadienol, as proposed in Tang et al., 2011, BMC Genomics 12:343.

A pathway from cucurbitadienol to mogrol was proposed by Tang et al., 2011, *BMC Genomics* 12:343. The precursors, cucurbitadienol and mogrol, have been isolated from *S. grosvenorii*. See Ukiya, et al., 2002, *J. Agric. Food Chem.* 50: 6710-5. Glycoside intermediates exist in both 11-hydroxy and 11-oxo series and gradually change from mogroside I to mogroside V as fruits ripen, indicating that P450 enzymes fully oxidize the triterpene core of a mogrol precursor, such as cucurbitadienol, prior to subsequent glycosylations. According to the scheme proposed by Tang et al., three independent cytochrome P450 enzyme-catalyzed oxidations result in mogrol formation from cucurbitadienol (FIG. 3B). The proposed primary reaction, however, is unlikely, as saturation of the 24-25 double bond would be required prior to two hydroxylation reactions by cytochrome P450 enzymes. As shown in FIG. 3A, epoxidation of cucurbitadienol by one cytochrome P450 enzyme, followed by a spontaneous or enzyme catalyzed hydration, and a second P450 enzyme-catalyzed oxidation can result in production of mogrol. Additional pathways for production of mogrol or 11-oxo-mogrol, as described in Example 11, are shown in FIG. 9.

In some embodiments, one or more mogrol precursors are produced. Mogrol precursors, mogrol, and/or mogrosides can be produced in vivo (i.e., in a recombinant host), in vitro (i.e., enzymatically), or by whole cell bioconversion, as described below. As used herein, the terms "detectable amount," "detectable concentration," "measurable amount," and "measurable concentration" refer to a level of mogrosides and mogroside precursors measured in AUC, μM/$OD_{600}$, mg/L, μM, or mM. Mogroside production (i.e., total, supernatant, and/or intracellular steviol glycoside levels) can be detected and/or analyzed by techniques generally available to one skilled in the art, for example, but not limited to, liquid chromatography-mass spectrometry (LC-MS), thin layer chromatography (TLC), high-performance liquid chromatography (HPLC), ultraviolet-visible spectroscopy/spectrophotometry (UV-Vis), mass spectrometry (MS), and nuclear magnetic resonance spectroscopy (NMR). As used herein, the term "relative abundance" is used to refer to the concentration of a particular ion measured by MS or LC-MS, where the most intense ion is assigned a relative abundance score of 100 and is referred to as the base peak.

Mogroside Production Pathway

In some embodiments, a mogrol precursor (e.g., squalene or oxidosqualene), mogrol, or mogroside is produced, as described herein. Squalene can be produced from farnesyl pyrophosphate using a squalene synthase, and oxidosqualene can be produced from squalene using a squalene epoxidase. The squalene synthase can be any enzyme classified under EC 2.5.1.21. Squalene production can comprise a step of catalyzing conversion of farnesyl pyrophosphate by a squalene synthase in the presence of NADPH. In embodiments of the invention wherein the methods are performed in vivo, the recombinant host can thus comprise a heterologous nucleic acid encoding a squalene synthase. In other aspects, the squalene synthase can be endogenous.

The squalene synthase can be, for example, squalene synthase from *Gynostemma pentaphyllum* (protein accession number C4P9M2), a cucurbitaceae family plant. The squalene synthase can also comprise a squalene synthase from *Arabidopsis thaliana* (protein accession number C4P9M3), *Brassica napus, Citrus macrophylla, Euphorbia tirucalli* (protein accession number B9WZW7), *Glycine max, Glycyrrhiza glabra* (protein accession number Q42760, Q42761), *Glycrrhiza uralensis* (protein accession number D6QX40, D6QX41, D6QX42, D6QX43, D6QX44, D6QX45, D6QX47, D6QX39, D6QX55, D6QX38, D6QX53, D6QX37, D6QX35, B5AID5, B5AID4, B5AID3, C7EDD0, C6KE07, C6KE08, C7EDC9), *Lotus japonicas* (protein accession number Q84LE3), *Medicago truncatula* (protein accessionnumber Q8GSL6), *Pisum sativum, Ricinus communis* (protein accession number B9RHC3), *Prunus mume*, or functional homologs sharing at least 70% identity with any of the squalene synthases described above.

Oxidosqualene can be produced from squalene by squalene epoxidase (also referred to as squalene monoxygenase. See, e.g., Leber et al., 1998, Mol Biol Cell. 9(2): 375-86. The squalene epoxidase can be any enzyme classified under EC 1.4.99.7. Oxidosqualene production can comprise a step of catalyzing conversion of squalene by a squalene epoxidase in the presence of NADPH. See, e.g., Example 8.

The squalene epoxidase can also be the product of the ERG1 gene from *S. cerevisiae*. Thus, the squalene epoxidase can be a polypeptide of SEQ ID NO:54 or a functional homolog thereof sharing at least 45% sequence identity therewith. In some aspects, ERG1 is overexpressed.

The squalene epoxidase can be, for example, squalene epoxidase from *Gynostemma pentaphyllum* (protein accession number C4P9M2; SEQ ID NO: 88). The squalene epoxidase can comprise a squalene epoxidase from *Arabidopsis thaliana* (protein accession number Q9SM02 (SEQ ID NO: 89), O65403 (SEQ ID NO: 90), O65402 (SEQ ID NO: 91), O65404 (SEQ ID NO: 92), O81000 (SEQ ID NO: 93), or Q9T064 (SEQ ID NO: 94)), *Brassica napus* (protein accession number O65727 (SEQ ID NO: 95), O65726 (SEQ ID NO: 96)), *Euphorbia tirucalli* (protein accession number A7VJN1 (SEQ ID NO: 97)), *Medicago truncatula* (protein accession number Q8GSM8 (SEQ ID NO: 98), Q8GSM9 (SEQ ID NO: 99)), *Pisum sativum*, and *Ricinus communis* (protein accession number B9R6V0 (SEQ ID NO: 100), B9S7W5 (SEQ ID NO: 101), B9S6Y2 (SEQ ID NO: 102), B9TOY3 (SEQ ID NO: 103), B9S7T0 (SEQ ID NO: 104), B9SX91 (SEQ ID NO: 105)), or functional homologs sharing at least 70% identity with any of the squalene epoxidases described above.

One or more enzymes capable of catalyzing conversion of oxidosqualene to form cucurbitadienol comprise a cucurbitadienol synthase. See step A of FIGS. 2B and 2C and Example 9. The cucurbitadienol synthase can be, for example, a cucurbitadienol synthase, which has been classified as an oxidosqualene cyclase, such as the oxidosqualene cyclase described by Shibuya, *Tetrahedron,* 60: 6995-7003 (2004).

The amino acid sequence of a cucurbitadienol synthase from *Cucurbita pepo* is provided herein as SEQ ID NO:1. In some embodiments, the cucurbitadienol synthase is a polypeptide of SEQ ID NO:1 or a functional homolog thereof sharing at least 70% sequence identity therewith. In some embodiments, a polypeptide having at least 70% identity to the amino acid sequence set forth in SEQ ID NO:1 includes, but is not limited to, a polypeptide from *Lotus japonicas* (BAE53431), *Populus trichocarpa* (XP_002310905), *Actaea racemosa* (ADC84219), *Betula platyphylla* (BAB83085), *Glycyrrhiza glabra* (BAA76902), *Vitis vinifera* (XP_002264289), *Centella asiatica* (AAS01524), *Panax ginseng* (BAA33460), and *Betula platyphylla* (BAB83086). The cucurbitadienol synthase can be any cucurbitadienol synthase sharing at least 70% identity to a cucurbitadienol synthase described above.

As described in Example 5, the cucurbitadienol synthase from monk fruit was identified herein, and the sequence of the C-terminal portion of the polypeptide determined. The amino acid sequence of the C-terminal portion of the monk fruit polypeptide is provided herein as SEQ ID NO:2. Thus, in some embodiments, the cucurbitadienol synthase is a polypeptide having an amino acid sequence set forth in SEQ ID NO:2.

In other embodiments, the cucurbitadienol synthase is the polypeptide of SEQ ID NO:43 or a functional homolog thereof sharing at least 70% identity therewith.

In some embodiments, 24,25 epoxy cucurbitadienol is produced from dioxidosqualene using one or more enzymes capable of catalyzing conversion of oxidosqualene to form cucurbitadienol. One or more enzymes capable of catalyzing conversion of dioxidosqualene to 24,25 epoxy cucurbitadienol preferably comprises a cucurbitadienol synthase. See step B of FIGS. 2B and 2C and Example 9. The cucurbitadienol synthase can be, for example, a cucurbitadienol synthase as described by Shibuya, *Tetrahedron* 60:6995-7003 (2004) or a cucurbitadienol synthase as described above. In some embodiments, the cucurbitadienol synthase catalyzing conversion of dioxidosqualene to 24,25 epoxy cucurbitadienol is a polypeptide of SEQ ID NO:1 or a functional homolog thereof sharing at least 70% identity therewith.

In some embodiments, 11-hydroxy-cucurbitadienol is produced from cucurbitadienol. In some embodiments, a cytochrome P450 enzyme catalyzes hydroxylation of cucurbitadienol to form 11-hydroxy-cucurbitadienol. In some embodiments, CYP5491 (SEQ ID NO:14, SEQ ID NO:44)

catalyzes conversion of cucurbitadienol to 11-hydroxy-cucurbitadienol. See step C of FIGS. 2B and 2C and Example 10.

As indicated in Examples 6 and 15, one or more of CYP533, CYP937, CYP1798, CYP1994, CYP2048, CYP2740, CYP3404, CYP3968, CYP4112, CYP4149, CYP4491, CYP5491, CYP6479, CYP7604, CYP8224, CYP8728, CYP10020, or CYP10285 (encoded by SEQ ID NOs: 3-20, respectively) can be used to produce mogrol. eYAC technology can be used to assess activity of the cytochrome P450 enzymes, as set forth in Example 8. Alternatively, an in vitro reaction can be used to assess the activity. Thus, in one embodiment of the invention, at least one cytochrome P450 enzyme comprises a polypeptide encoded by the nucleic acid sequence SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20 or a functional homolog thereof sharing at least 70% identity therewith.

In some embodiments, 11-hydroxy-24,25 epoxy cucurbitadienol is produced from 24,25 epoxy cucurbitadienol using one or more enzymes capable of catalyzing hydroxylation of 24,25 epoxy cucurbitadienol to form 11-hydroxy-24,25 epoxy cucurbitadienol. In some embodiments, a cytochrome P450 enzyme catalyzes hydroxylation of 24,25 epoxy cucurbitadienol to form 11-hydroxy-24,25 epoxy cucurbitadienol. In some embodiments, the enzyme capable of catalyzing hydroxylation of 24,25 epoxy cucurbitadienol to form 11-hydroxy-24,25 epoxy cucurbitadienol is CYP5491 (SEQ ID NO:14, SEQ ID NO:44) or a functional homolog sharing at least 50% sequence identity with SEQ ID NO:44. See step D of FIGS. 2B and 2C and Example 9.

In some aspects, 24,25 epoxy cucurbitadienol is produced from cucurbitadienol. In some aspects, a cytochrome P450 catalyzes conversion of cucurbitadienol to 24,25 epoxy cucurbitadienol. The cytochrome P450 can be CYP1798 of SEQ ID NO:74. See step E of FIGS. 2B and 2C. In some aspects, 11-hydroxy 24,25 epoxy cucurbitadienol is produced from 11-hydroxy-cucurbitadienol. In some aspects, a cytochrome P450 catalyzes conversion of 11-hydroxy-cucurbitadienol to produce 11-hydroxy 24,25 epoxy cucurbitadienol. The cytochrome P450 can be CYP1798 of SEQ ID NO:74. See step F of FIGS. 2B and 2C.

In some aspects, mogrol is produced from 11-hydroxy-cucurbitadienol using enzymes capable of catalyzing conversion of 11-hydroxy-cucurbitadienol to form mogrol. Enzymes having cytochrome P450 activity and epoxide hydrolase activity catalyze conversion of 11-hydroxy-cucurbitadienol to mogrol. See steps F and G of FIGS. 2B and 2C. Enzymes with cytochrome P450 activity include polypeptides encoded by the nucleic acid sequence set forth in SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, or a functional homolog thereof sharing at least 70% sequence identity therewith. An enzyme having epoxide hydrolase activity preferably catalyzes production of glycol from epoxide and water. Non-limiting examples of enzymes with epoxide hydrolase activity include *S. grosvenorii* epoxide hydrolase 1 and *S. grosvenorii* epoxide hydrolase 2. Thus, an enzyme with epoxide hydrolase activity can comprise polypeptides having at least 75% sequence identity with the amino acid sequence set forth in SEQ ID NO:38, having at least 65% sequence identity with the amino acid sequence set forth in SEQ ID NO:40, and functional homologs thereof.

In some embodiments, mogrol is produced from 11-hydroxy-24,25 epoxy cucurbitadienol. One or more enzymes capable of catalyzing conversion of 11-hydroxy-24,25 epoxy cucurbitadienol to form mogrol preferably comprise an enzyme with epoxide hydrolase activity. See step G of FIGS. 2B and 2C. Examples of enzymes with epoxide hydrolase activity include *S. grosvenorii* epoxide hydrolase 1 and *S. grosvenorii* epoxide hydrolase 2, as described above. In some embodiments, an enzyme capable of catalyzing conversion of 11-hydroxy-24,25 epoxy cucurbitadienol to produce mogrol comprises a polypeptide having at least 75% sequence identity with the amino acid sequence set forth in SEQ ID NO:38, having at least 65% sequence identity with the amino acid sequence set forth in SEQ ID NO:40, and functional homologs thereof.

Figure 9A:
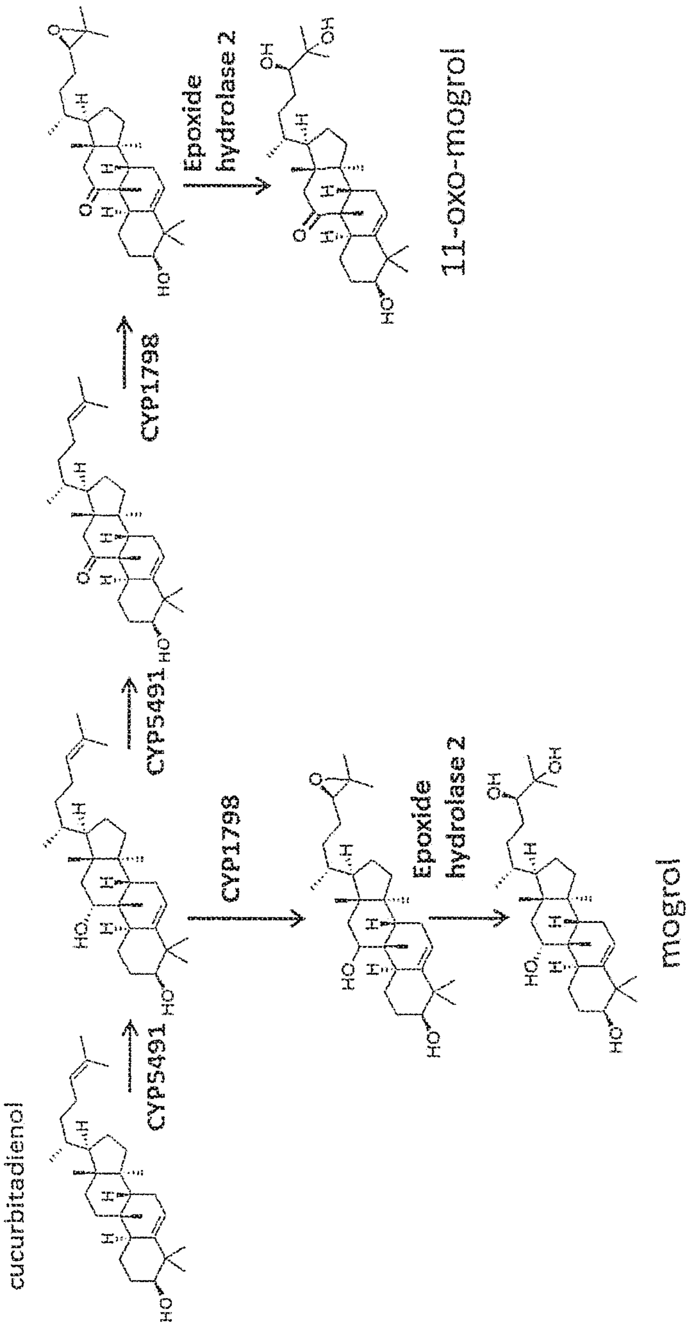
FIGS. 9A and 9B show biosynthetic routes from cucurbitadienol to mogrol and 11-oxo-mogrol with *S. grosvenorii* CYP5491 (SEQ ID NO:14, SEQ ID NO:44), *S. grosvenorii* CYP1798 (SEQ ID NO:5, SEQ ID NO:73, SEQ ID NO:74), and *S. grosvenorii* epoxide hydrolase 2 (SEQ ID NO:39, SEQ ID NO:40).
Figure 9B:
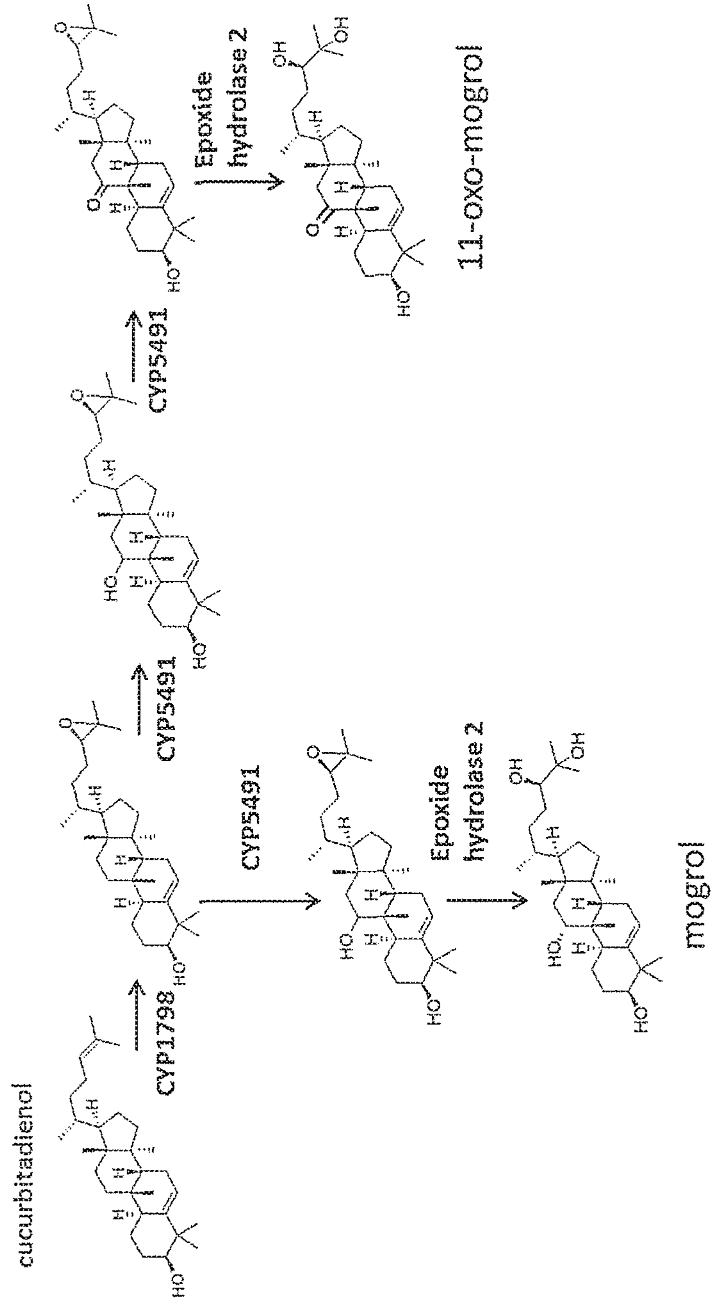
Figure 9C:
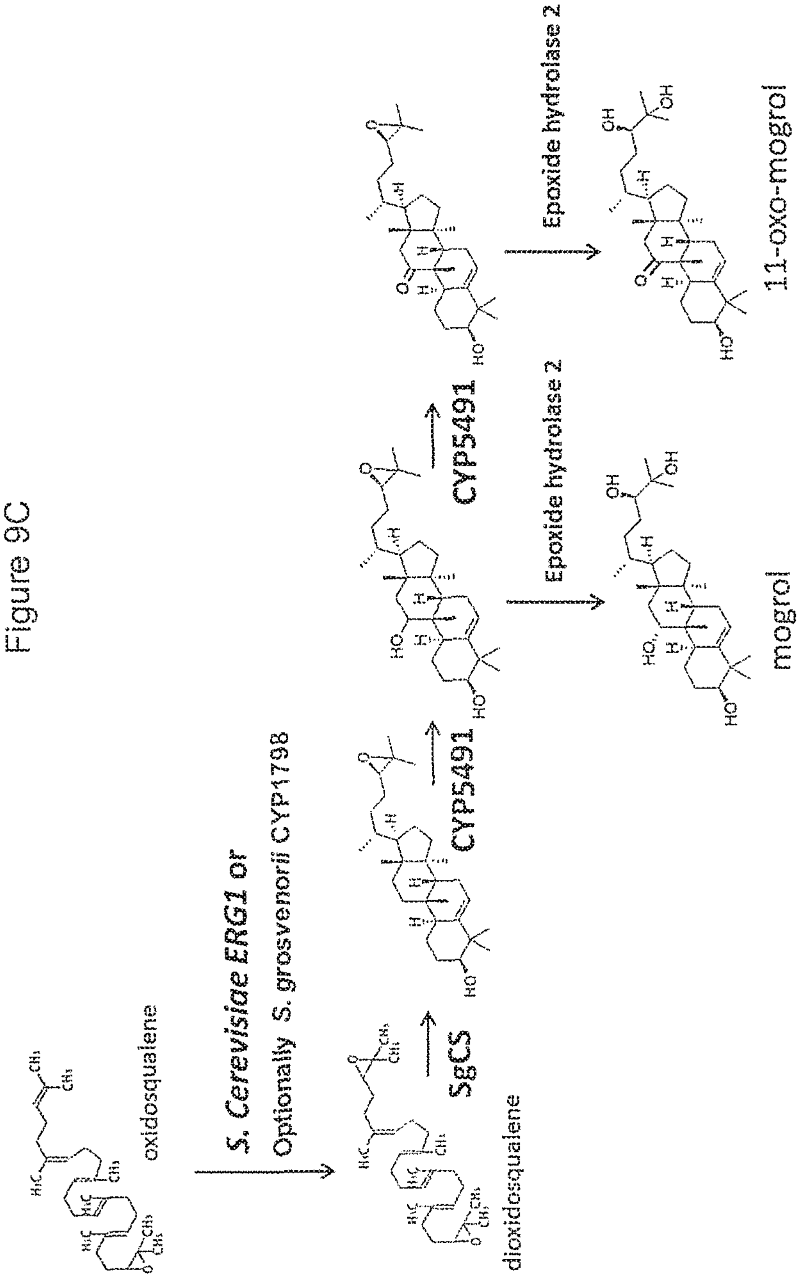
FIG. 9C shows a potential biosynthetic route from oxidosqualene to mogrol and 11-oxo-mogrol with *S. cerevisiae* squalene epoxidase ERG1 (SEQ ID NO:54), *S. grosvenorii* CYP1798 (SEQ ID NO:5, SEQ ID NO:73, SEQ ID NO:74), *S. grosvenorii* cucurbitadienol synthase (SEQ ID NO:42, SEQ ID NO:43), *S. grosvenorii* CYP5491 (SEQ ID NO:14, SEQ ID NO:44), and *S. grosvenorii* epoxide hydrolase 2 (SEQ ID NO:39, SEQ ID NO:40). See Examples 9 and 15.

In some embodiments, CYP1798 (SEQ ID NO:5, SEQ ID NO:73, SEQ ID NO:74) catalyzes the epoxidation of the 24-25 carbon double bonds of cucurbitadienol, 11-hydroxy-cucurbitadienol, or 11-oxo cucurbitadienol. FIGS. 9A and 9B are schematics of mogrol and 11-oxo-mogrol production from cucurbitadienol, and FIG. 9C is a schematic of mogrol and 11-oxo-mogrol production from oxidosqualene. See, also, Example 15.

One or more enzymes capable of catalyzing glycosylation of mogrol preferably comprise a Uridine-5'-diphospho (UDP) dependent glucosyltransferase (UGT). A UGT can catalyze production of a mogroside not limited to mogroside I A1, mogroside I E1, mogroside II A, mogroside II A1, mogroside II A2, mogroside II E, mogroside III A1, mogroside III A2, mogroside III, mogroside III E, mogroside IV, mogroside IV A, or siamenoside. Such UGT can comprise, for example, *Arabidopsis thaliana* UGT73C3 of SEQ ID NO:21, *Arabidopsis thaliana* UGT73C6 of SEQ ID NO:23, *Stevia rebaudiana* UGT85C2 of SEQ ID NO:25, *Arabidopsis thaliana* UGT73C5 of SEQ ID NO:22, *Stevia rebaudiana* UGT73E1 of SEQ ID NO:24, or a functional homolog sharing at least 70% identity with a UGT described above. A UGT can also comprise UGT98 of SEQ ID NO:53, UGT1495 encoded by SEQ ID NO:27, UGT1817 encoded by SEQ ID NO:28, UGT5914 encoded by SEQ ID NO:30, UGT8468 encoded by SEQ ID NO:31, UGT10391 encoded by SEQ ID NO:32, or a functional homolog of any of the UGTs described above. See Examples 4 and 7.

UGT73C3, UGT73C6, UGT85C2, and UGT73E1 are capable of catalyzing glycosylation at the C24 position of mogrol or mogroside. Accordingly, in methods of the invention wherein the mogroside to be produced comprises a glycosylation at the C24 position, at least one UGT can be UGT73C3 of SEQ ID NO:21, UGT73C6 of SEQ ID NO:23, UGT85C2 of SEQ ID NO:25, UGT73E1 of SEQ ID NO:24 or a functional homolog functional homolog sharing at least 70% identity with a UGT described above. See Example 4.

UGT73C5 is capable of catalyzing glycosylation at both the C3-OH of mogrol and mogroside and C24 position. Accordingly, in methods of the invention wherein the mogroside to be produced comprises a glycosylation at the C24 position and/or a glycosylation at the C3-OH position, at least one UGT can be UGT73C5 of SEQ ID NO:22 or a functional homolog sharing at least 60% sequence identity therewith. See Example 4.

In some embodiments, a UGT is UGT1576 of SEQ ID NO:48 or a UGT sharing at least 60% sequence identity with UGT1576 of SEQ ID NO:48. In some embodiments, UGT1576 possesses mogrol C24-OH UDP-glycosyltransferase activity. See Example 11.

In some embodiments, a UGT is UGT98 of SEQ ID NO:53 or a functional homolog thereof sharing at least 70% sequence identity therewith. This is in particular the case in embodiments of the invention wherein the mogroside to be produced comprises a 1,2-glycosylation and a 1,6-glycosylation of the glucose at position C-24 to form mogroside III A1. See Example 11. In some embodiments, UGT98 (SEQ ID NO:53) can be used to convert mogroside II E to mogroside IV, mogroside V, 11-oxo-mogroside V, and/or siamenoside I. See Example 7.

In some embodiments, for example in embodiments wherein the mogroside to be produced comprises a 1,2 glycosylation of the glucose at position C-24 to form mogroside II A, a UGT is UGTSK98 of SEQ ID NO:50 or UGT sharing at least 70% identity with UGTSK98 of SEQ ID NO:50. See Example 11. In some aspects, UGT98 catalyzes 1,2 and 1,6 glucose attachments to convert mogroside II E to mogroside V. See Example 14.

In some embodiments, a UGT is *S. grosvenorii* UGT430 (SEQ ID NO:61, SEQ ID NO:62). UGT430 is a member of UGT family 85A and glycosylates the 3C position of mogrol and particular mogrosides. See Example 12.

In some embodiments, a UGT is *S. grosvenorii* UGT1697 (SEQ ID NO:67, SEQ ID NO:68). UGT1697 is a member of UGT family 85A and glycosylates the 3C and 24C positions of mogrol and particular mogrosides. See Example 13.

In some embodiments, a UGT is *S. grosvenorii* UGT11789 (SEQ ID NO:69, SEQ ID NO:70, SEQ ID NO:71, SEQ ID NO:72). UGT11789 catalyzes 1,2 and/or 1,6 glucose attachments on the 24-O-glucose and/or the 3-O-glucose of mogroside compounds. In some embodiments, UGT11789 glycosylates mogroside I E1, mogroside I A1, mogroside II E, mogroside II A, mogroside III E, mogroside III A2, mogroside III, mogroside IV, or siamenoside. In some embodiments, contacting UGT11789 with mogroside I E1, mogroside I A1, mogroside II E, mogroside II A, mogroside III E, mogroside III A2, mogroside III, mogroside IV, or siamenoside produces mogroside II A1, mogroside II A2, mogroside III, mogroside III A1, mogroside III A2, mogroside IV, mogroside IV A, siamenoside, or mogroside V. See Example 14.

Methods of Producing Mogrosides In Vivo

In some embodiments, a mogrol precursor, mogrol, or mogroside is produced in vivo by a host expressing of one or more nucleic acid molecules encoding one or more enzymes involved in the mogroside pathway. For example, an oxidosqualene-producing recombinant host expressing one or more of a gene encoding a cucurbitadienol synthase polypeptide, a gene encoding a cytochrome P450 polypeptide, a gene encoding a cytochrome P450 reductase polypeptide, a gene encoding an epoxide hydrolase polypeptide, and a gene encoding a UGT polypeptide can produce a mogrol precursor, mogrol, or mogroside in vivo. See Examples 15 and 16.

In some embodiments, more than one host is used to produce a mogrol precursor, mogrol, or mogroside. In a non-limiting example, a host capable of producing mogrol and a host expressing a UGT can be used to produce a mogroside. The methods can also employ a mixture of a recombinant and a non-recombinant host. In embodiments comprising use of two or more hosts, the hosts can be co-cultivated or cultured separately. If the hosts are cultivated separately, the intermediate products can be recovered and optionally purified or partially purified and fed to recombinant hosts using the intermediate products as substrates. Suitable recombinant hosts are described below.

In some aspects, production of a mogrol precursor, mogrol, or mogroside can be performed in vivo and a mogrol precursor, mogrol, or mogroside product can be used as a substrate for subsequent reactions to be performed in vitro, as described below. See WO 2013/076577 and WO 2014/086842.

In some embodiments, a host produces oxidosqualene from glucose via the ergosterol pathway. See, e.g., WO 2014/0027118. In some aspects, host expressing a nucleic acid molecule encoding a squalene synthase polypeptide can produce squalene. In some embodiments, the squalene synthase is ERG9, and the amino acid sequence of ERG9 is set forth in SEQ ID NO:87. In some embodiments, squalene synthase is endogenous to the host. In some embodiments, increased copy numbers of an endogenous squalene synthase and/or squalene epoxidase, expression of a heterologous nucleic acid molecule encoding a squalene synthase and/or squalene epoxidase, or increased expression of an endogenous squalene synthase and/or squalene epoxidase can improve levels of mogrosides produced in a recombinant host.

In one embodiment, the recombinant host comprises a heterologous nucleic acid encoding a squalene epoxidase operably linked to sequence directing high expression of the squalene epoxidase in the host. Thus, the squalene epoxidase can be endogenous to the recombinant host, but the expression level can be increased by additional copies of nucleic acids encoding the squalene epoxidase and/or by use of stronger promoters.

Oxidosqualene serves as a substrate for production of lanosterol. Thus, in some embodiments, the level of oxidosqualene can be increased by reducing lanosterol synthase activity. In recombinant hosts expressing an endogenous lanosterol synthase, this can be achieved by substituting the endogenous promoter-directed expression of lanosterol synthase with a weaker promoter directing expression of a lower level of lanosterol synthase. In yeast, the ERG7 gene encodes lanosterol synthase. Thus, when the recombinant host is yeast, the ERG7 gene promoter can be substituted for another promoter, which directs a level of expression, which is lower than the endogenous expression level of ERG7. The lanosterol synthase can thus be the product of the ERG7 gene of *S. cerevisiae*, the sequence of which is provided herein as SEQ ID NO:55, or a functional homolog thereof sharing at least 50% sequence identity therewith. See Examples 8 and 15.

In addition, expression of a truncated form of the enzyme 3-hydroxy-3-methylglutaryl-CoA reductase (tHMG1, SEQ ID NO:77, SEQ ID NO:78) can also lead enhanced levels of oxidosqualene. A useful truncated form of yeast HMG reductase (tHMG1) is described in Donald et al., 1997, *Appl. Environ. Microbiol.* 63:3341-4.

Dioxidosqualene levels can be enhanced by high expression of a squalene epoxidase. The squalene epoxidase can be the product of the *S. cerevisiae* ERG1 gene. Thus, the squalene epoxidase can be a polypeptide of SEQ ID NO:54 or a functional homolog thereof sharing at least 45% sequence identity therewith. The levels of dioxidosqualene can also be enhanced by reducing lanosterol synthase activity. Dioxidosqualene levels can also be enhanced by expression of a truncated form of 3-hydroxy-3-methylglutaryl-CoA reductase (tHMG1, SEQ ID NO:77, SEQ ID NO:78). See Examples 8 and 15.

In some embodiments, hydroxylation of cucurbitadienol to form 11-hydroxy-cucurbitadienol or hydroxylation of 24,25 epoxy cucurbitadienol to form 11-hydroxy-24,25 epoxy cucurbitadienol can be aided by at least one CYP activator. A recombinant host can co-express heterologous nucleic acids encoding one or more cytochrome P450 enzymes and a heterologous nucleic acid encoding a CYP activator. The CYP activator can be, for example, CPR4497 (SEQ ID NO:45, SEQ ID NO:46) or a functional homolog sharing at least 50% sequence identity with SEQ ID NO:46. See Examples 10, 15, and 16.

In some embodiments, a cucurbitadienol-producing *S. cerevisiae* strain co-expressing *S. grosvenorii* CYP5491 (SEQ ID NO:14, SEQ ID NO:44), *S. grosvenorii* CYP1798 (SEQ ID NO:5, SEQ ID NO:73, SEQ ID NO:74), *S. grosvenorii* CPR4497 (SEQ ID NO:45, SEQ ID NO:46), and an epoxide hydrolase produces mogrol. In some embodiments, the epoxide hydrolase is epoxide hydrolase 2 (SEQ ID NO:39, SEQ ID NO:40). In some embodiments, the cucurbitadienol-producing *S. cerevisiae* strain further overexpresses squalene epoxidase encoded by ERG1 (SEQ ID NO:54), expresses a truncated HMG reductase (tHMG1, SEQ ID NO:77, SEQ ID NO:78), expresses *S. grosvenorii* cucurbitadienol synthase (SEQ ID NO:42, SEQ ID NO:43), is deleted of the TRP1 gene, and comprises a disrupted promoter of the endogenous ERG7 gene (SEQ ID NO:55). See Example 15.

In some embodiments, a mogrol precursor, mogrol, or mogroside is produced in a recombinant host comprising one or more of a gene encoding a squalene epoxidase polypeptide, a gene encoding a cucurbitadienol synthase polypeptide, a gene encoding a cytochrome P450 polypeptide, a gene encoding a cytochrome P450 reductase polypeptide, a gene encoding an epoxide hydrolase polypeptide, and/or a gene encoding a glycosyltransferase. In some aspects, the gene encoding the glycosyltransferase comprises a gene encoding a UGT1576 polypeptide having 60% or greater identity to an amino acid sequence set forth in SEQ ID NO:48, a gene encoding a UGT430 polypeptide having 45% or greater identity to an amino acid sequence set forth in SEQ ID NO:62, a gene encoding a UGT1697 polypeptide having 45% or greater identity to an amino acid sequence set forth in SEQ ID NO:68, a gene encoding a UGT11789 polypeptide having 50% or greater identity to an amino acid sequence set forth in SEQ ID NO:72, and/or a gene encoding a UGT98 polypeptide having 70% or greater identity to an amino acid sequence set forth in SEQ ID NO:53. See Example 16.

In some embodiments, mogroside V is produced in an *S. cerevisiae* strain comprising *S. grosvenorii* cucurbitadienol synthase (SEQ ID NO:42, SEQ ID NO:43), CYP5491 (SEQ ID NO:81, SEQ ID NO:44), CYP1798 (SEQ ID NO:5, SEQ ID NO:74), CYP1798-II (SEQ ID NO:86, SEQ ID NO:74), CPR4497 (SEQ ID NO:82, SEQ ID NO:46), epoxide hydrolase 2 (SEQ ID NO:39, SEQ ID NO:40), UGT1576 (SEQ ID NO:83, SEQ ID NO:48), UGT430 (SEQ ID NO:84, SEQ ID NO:62), UGT1697 (SEQ ID NO:85, SEQ ID NO:68), UGT98 (SEQ ID NO:52, SEQ ID NO:53), and UGT11789 (SEQ ID NO:71, SEQ ID NO:72). In some embodiments, the strain is a Mat alpha derivative of *S. cerevisiae* 288C with a deletion of the *S. cerevisiae* EXG1 gene. In some embodiments, the host further produces mogroside IV A, mogroside II A2, mogroside I E1, and mogrol. See Example 16.

Methods of Producing Mogrosides In Vitro

In some embodiments, a mogroside is produced through contact of a mogrol precursor, mogrol, or glycosylated mogrol with one or more enzymes involved in the mogroside pathway in vitro. For example, contact of mogrol with a UGT polypeptide can result in production of a mogroside in vitro. In some embodiments, a mogrol precursor is produced through contact of an upstream mogroside precursor with one or more enzymes involved in the mogroside pathway in vitro. For example, contact of cucurbitadienol with a cytochrome P450 polypeptide and an epoxide hydrolase can result in production of mogrol in vitro.

In some embodiments, a mogrol precursor is produced by one or more of the following steps:

a. Contacting oxidosqualene with a cucurbitadienol synthase, such as, but not limited to, a cucurbitadienol synthase having 70% or greater identity to an amino acid sequence set forth in SEQ ID NO:43, to produce cucurbitadienol (see step A of FIGS. 2B and 2C); or
b. Contacting dioxidosqualene with a cucurbitadienol synthase, such as, but not limited to, a cucurbitadienol synthase having 70% or greater identity to an amino acid sequence set forth in SEQ ID NO:43, to produce 24,25 epoxy cucurbitadienol (see step B of FIGS. 2B and 2C); or
c. Contacting cucurbitadienol with a cytochrome P450, such as, but not limited to, CYP5491 having 50% or greater identity to an amino acid sequence set forth in SEQ ID NO:44, to produce 11-hydroxy-cucurbitadienol (see step C of FIGS. 2B and 2C); or
d. Contacting 24,25 epoxy cucurbitadienol with a cytochrome P450, such as, but not limited to, CYP5491 having 50% or greater identity to an amino acid sequence set forth in SEQ ID NO:44, to produce 11-hydroxy-24,25 epoxy cucurbitadienol (see step D of FIGS. 2B and 2C); or
e. Contacting cucurbitadienol with a cytochrome P450, such as, but not limited to, CYP1798 having 70% or greater identity to an amino acid sequence set forth in SEQ ID NO:74, to produce 24,25 epoxy cucurbitadienol (see step E of FIGS. 2B and 2C); or
f. Contacting 11-hydroxy-cucurbitadienol with a cytochrome P450, such as, but not limited to, CYP1798 having 70% or greater identity to an amino acid sequence set forth in SEQ ID NO:74, to produce 11-hydroxy-24,25 epoxy cucurbitadienol (see step F of FIGS. 2B and 2C).

Figure 2B:
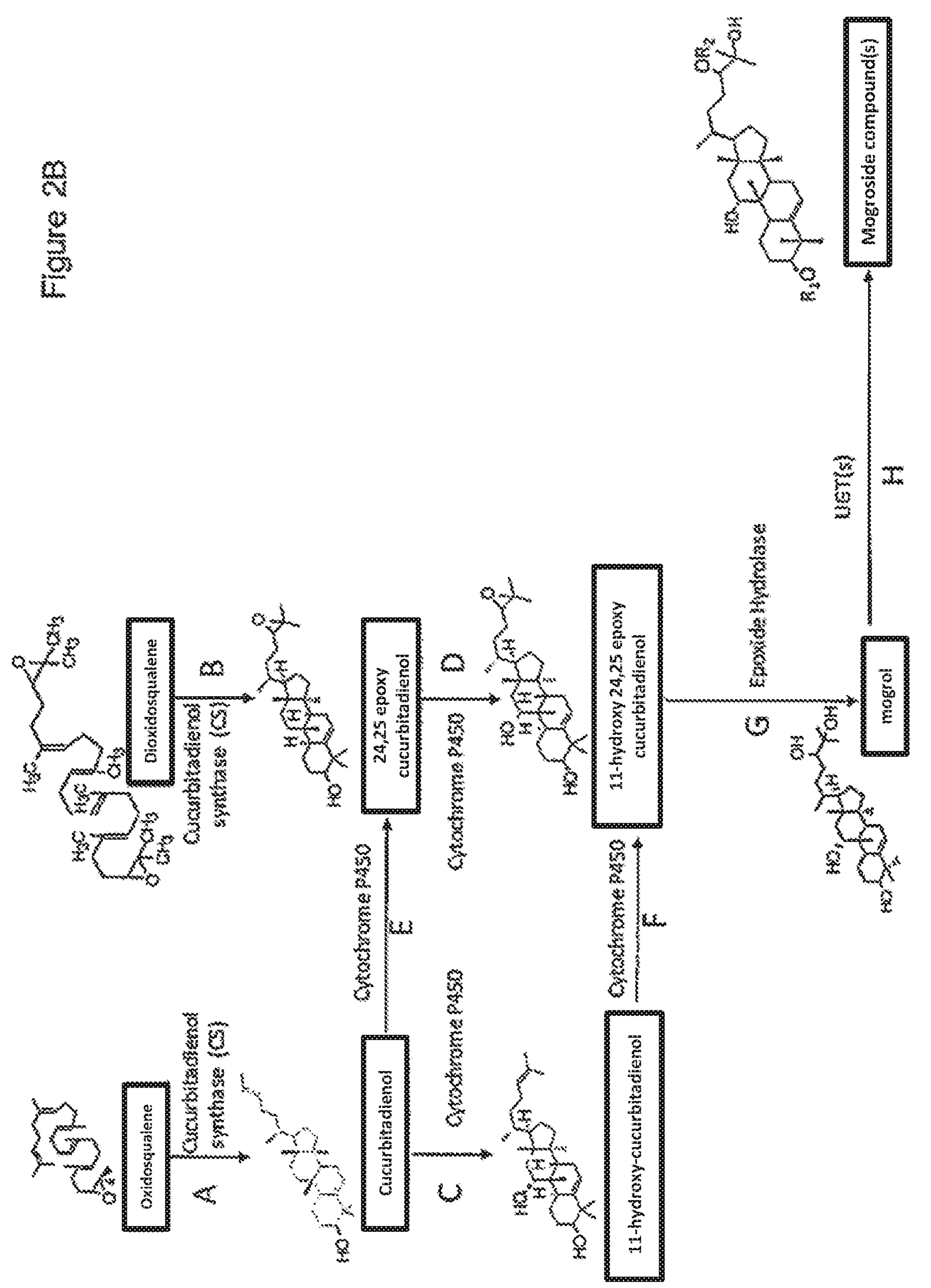
FIG. 2B shows a pathway for production of mogrol precursors, mogrol, and mogrosides.
Figure 2C:
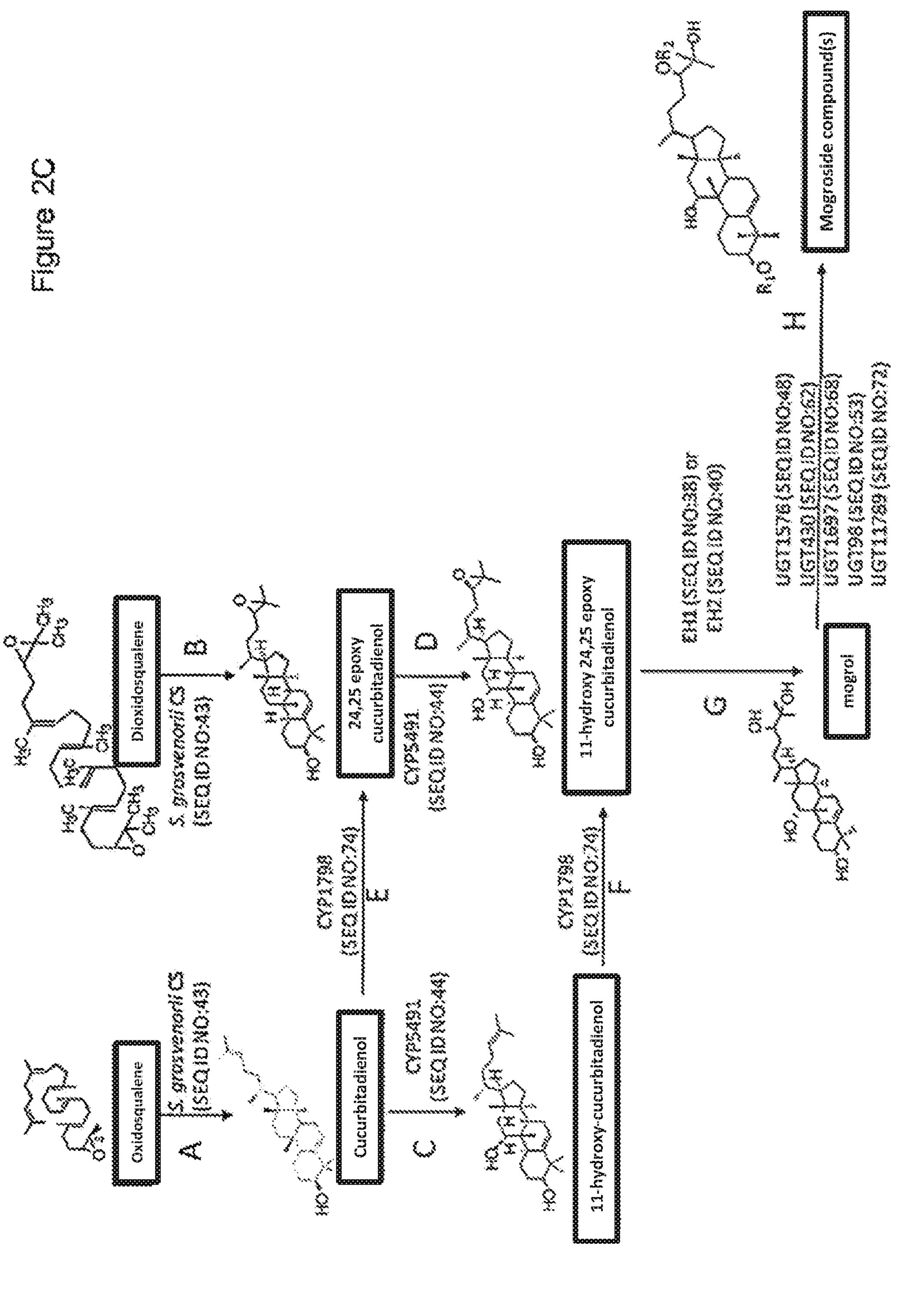
FIG. 2C shows representative enzymes capable of catalyzing the reactions of steps A-H in FIG. 2B.

In some embodiments, mogrol is produced in vitro by contacting 11-hydroxy-24,25 epoxy cucurbitadienol with an epoxide hydrolase, such as, but not limited to, epoxide hydrolase 1 having 75% or greater identity to an amino acid sequence set forth in SEQ ID NO:38 or epoxide hydrolase 2 having 65% or greater identity to an amino acid sequence set forth in SEQ ID NO:40 (see step G of FIGS. 2B and 2C).

In some embodiments, a mogroside (see step H of FIGS. 2B and 2C) is produced in vitro by:

a. Contacting mogrol with UGT73C3 (SEQ ID NO:21), UGT73C6 (SEQ ID NO:23), UGT85C2 (SEQ ID NO:25), and/or UGT1576 (SEQ ID NO:48) to produce mogroside I A1; or
b. Contacting mogrol with UGT73C5 (SEQ ID NO:22) to produce mogroside I E1 and/or mogroside I A1; or
c. Contacting mogrol with UGT73E1 (SEQ ID NO:24) to produce mogroside 1 A1 and/or a mogroside glycosylated on C11-OH; or
d. Contacting mogrol with UGT430 (SEQ ID NO:62) to produce mogroside I E1; or
e. Contacting mogrol with UGT1697 (SEQ ID NO:68) to produce mogroside II E1 and/or mogroside I A1; or f. Contacting mogroside I A1 with UGT98 (SEQ ID NO:53), UGTSK98 (SEQ ID NO:50), and/or UGT11789 (SEQ ID NO:72) to produce mogroside II A; or
g. Contacting mogroside I A1 with UGT430 (SEQ ID NO:62) to produce mogroside II E; or
h. Contacting mogroside I A1 with UGT98 (SEQ ID NO:53) and/or UGT11789 (SEQ ID NO:72) to produce mogroside III A1; or
i. Contacting mogroside I E1 with UGT1576 (SEQ ID NO:48) and/or UGT1697 (SEQ ID NO:68) to produce mogroside II E; or
j. Contacting mogroside II A with UGT98 (SEQ ID NO:53) and/or UGT11789 (SEQ ID NO:72) to produce mogroside III A1; or
k. Contacting mogroside II E with UGT98 (SEQ ID NO:62) and/or UGT11789 (SEQ ID NO:72) to produce mogroside III A1, mogroside III A2, mogroside III E, mogroside III, mogroside IV A, mogroside IV, siamenoside, or mogroside V; or
l. Contacting mogroside III A1 with UGT73C5 (SEQ ID NO:22) to produce siamenoside 1; or
m. Contacting siamenoside 1 with UGT98 (SEQ ID NO:53) and/or UGT11789 (SEQ ID NO:72) to produce mogroside V.

Each of the steps described above can be performed separately. In embodiments wherein at least two steps are performed separately, a product of a step can be purified or partially purified before performing a subsequent step. Alternatively, one or more of the steps can be performed simultaneously within the same mixture.

In some embodiments, a cell lysate is prepared from a host expressing one or more of a gene encoding a squalene epoxidase polypeptide, a gene encoding a cucurbitadienol synthase polypeptide, a gene encoding a cytochrome P450 polypeptide, a gene encoding an epoxide hydrolase polypeptide, and a gene encoding a UGT polypeptide. For example, a cell lysate can be prepared from a host expressing one or more UGTs and used to contact mogrol, such that a mogroside can be produced in vitro.

Methods of Producing Mogrosides by Whole Cell Bioconversion

In some embodiments, a mogrol precursor, mogrol, or mogroside is produced by whole cell bioconversion. For whole cell bioconversion to occur, a host expressing one or more enzymes involved in the mogroside pathway takes up and modifies a mogrol or mogroside precursor in the cell; following modification in vivo, a mogroside is excreted into the culture medium. See Examples 11-14.

In some embodiments, the mogrol precursor is oxidosqualene, dioxidosqualene, cucurbitadienol, 24,25 epoxy cucurbitadienol and the mogroside precursor is mogrol. In a non-limiting example of whole cell bioconversion, a host expressing a gene encoding a UGT polypeptide can take up mogrol and glycosylate mogrol in the cell; following glycosylation in vivo, a mogroside is excreted into the culture medium.

A cell can be fed a mogrol precursor or mogroside precursor during cell growth or after cell growth. The cell can be in suspension or immobilized. The cell can be in fermentation broth or in a reaction buffer. In some embodiments, a permeabilizing agent is used for transfer of a mogrol precursor or mogroside precursor into a cell. In some embodiments, a mogrol precursor or mogroside precursor can be provided in a purified form or as part of a composition or an extract.

In some aspects, a mogrol precursor or mogroside precursor is produced in vitro; thereafter, the mogrol precursor or mogroside precursor is provided to a host capable of catalyzing conversion of the mogrol precursor or mogroside precursor.

In some embodiments, a recombinant host expressing UGT98, UGT1576, and UGT430 converts fed mogrol to mogroside V. See Example 14. In some embodiments, a host expressing UGT11789 catalyzes the conversion of mogroside II E to a tri-glycosylated mogroside. In some embodiments, a host expressing UGT11789, UGT1576, and UGT430 catalyzes the conversion of mogrol to a triglycosylated mogroside. In some embodiments, a recombinant host co-expressing UGT11789, UGT98, UGT1576, and UGT430 converts fed mogrol to mogroside V more efficiently than a recombinant host expressing UGT98, UGT1576, and UGT430. See Example 14.

Recombinant Genes and Functional Homologs

The term "recombinant gene" refers to a gene or DNA sequence that is introduced into a recipient host, regardless of whether the same or a similar gene or DNA sequence can already be present in such a host. "Introduced" or "augmented" in this context is known in the art to mean introduced or augmented by the hand of man. Thus, a recombinant gene can be a DNA sequence from another species, or can be a DNA sequence that originated from or is present in the same species, but has been incorporated into a host by recombinant methods to form a recombinant host. It will be appreciated that a recombinant gene that is introduced into a host can be identical to a DNA sequence that is normally present in the host being transformed, and is introduced to provide one or more additional copies of the DNA to thereby permit overexpression or modified expression of the gene product of that DNA. In a preferred embodiment, the DNA is a cDNA copy of an mRNA transcript of a gene produced in a cell.

In some embodiments, the coding sequence of a polypeptide described herein, such as the coding sequence of a UGT polypeptide, is a heterologous sequence. The phrases "heterologous sequence" and "heterologous coding sequence" are used to describe a sequence derived from a species other than the recombinant host. In some embodiments, the recombinant host is an *S. cerevisiae* cell, and a heterologous sequence is derived from an organism other than *S. cerevisiae*. A heterologous coding sequence, for example, can be from a prokaryotic microorganism, a eukaryotic microorganism, a plant, an animal, an insect, or a fungus different than the recombinant host expressing the heterologous sequence. In some embodiments, a coding sequence is a sequence that is native to the host.

In some aspects of the invention, a squalene epoxidase polypeptide, cucurbitadienol synthase polypeptide, cytochrome P450 polypeptide, cytochrome P450 reductase polypeptide, epoxide hydrolase polypeptide, and/or glycosyltransferase polypeptide is a fusion protein. In some embodiments, a squalene epoxidase polypeptide (including, but not limited to, the squalene epoxidase polypeptide of SEQ ID NO:54, a cucurbitadienol synthase polypeptide (including, but not limited to, the cucurbitadienol synthase polypeptide of SEQ ID NO:43), a cytochrome P450 polypeptide (including, but not limited to, the CYP5491 polypeptide of SEQ ID NO:44), a cytochrome P450 reductase polypeptide (including, but not limited to, the CPR4497 polypeptide of SEQ ID NO:46), an epoxide hydrolase polypeptide (including, but not limited to, the EH1 polypeptide of SEQ ID NO:38 or the EH2 polypeptide of SEQ ID NO:40), and/or a UGT polypeptide (including, but not limited to, UGT1576 of SEQ ID NO:48, UGT430 of SEQ ID NO:62, UGT1697 of SEQ ID NO:68, UGT11789 of SEQ ID NO:72, UGT98 of SEQ ID NO:53, or UGTSK98 of SEQ ID NO:50) is a fusion polypeptide. The terms "chimera," "fusion polypeptide," "fusion protein," "fusion enzyme," "chimeric protein," "chimeric polypeptide," and "chimeric enzyme" can be used interchangeably herein to refer to proteins engineered through the joining of two or more genes that code for different proteins. In some embodiments, a nucleic acid sequence encoding a squalene epoxidase polypeptide, cucurbitadienol synthase polypeptide, cytochrome P450 polypeptide, cytochrome P450 reductase polypeptide, epoxide hydrolase polypeptide, and/or glycosyltransferase polypeptide polypeptide include a tag sequence that encodes a "tag" designed to facilitate subsequent manipulation (e.g., to facilitate purification or detection), secretion, or localization of the encoded polypeptide. Tag sequences can be inserted in the nucleic acid sequence encoding the polypeptide such that the encoded tag is located at either the carboxyl or amino terminus of the polypeptide. Non-limiting examples of encoded tags include green fluorescent protein (GFP), human influenza hemagglutinin (HA), glutathione S transferase (GST), polyhistidine-tag (HIS tag), and Flag™ tag (Kodak, New Haven, Conn.). Other examples of tags include a chloroplast transit peptide, a mitochondrial transit peptide, an amyloplast peptide, signal peptide, or a secretion tag.

In some embodiments, a fusion protein is a protein altered by domain swapping. As used herein, the term "domain swapping" is used to describe the process of replacing a domain of a first protein with a domain of a second protein. In some embodiments, the domain of the first protein and the domain of the second protein are functionally identical or functionally similar. In some embodiments, the structure and/or sequence of the domain of the second protein differs from the structure and/or sequence of the domain of the first protein. In some embodiments, a cytochrome P450 reductase polypeptide is altered by domain swapping. For example, in some aspects, the cytochrome P450 domain or reductase domain of CPR4497 (SEQ ID NO:46) is replaced by the cytochrome P450 domain or reductase domain of a cytochrome P450 reductase other than CPR4497 (SEQ ID NO:46). In other aspects, a UGT polypeptide is altered by domain swapping.

Functional homologs of the polypeptides described above are also suitable for use in producing steviol glycosides in a recombinant host. A functional homolog is a polypeptide that has sequence similarity to a reference polypeptide, and that carries out one or more of the biochemical or physiological function(s) of the reference polypeptide. A functional homolog and the reference polypeptide can be a natural occurring polypeptide, and the sequence similarity can be due to convergent or divergent evolutionary events. As such, functional homologs are sometimes designated in the literature as homologs, or orthologs, or paralogs. Variants of a naturally occurring functional homolog, such as polypeptides encoded by mutants of a wild type coding sequence, can themselves be functional homologs. Functional homologs can also be created via site-directed mutagenesis of the coding sequence for a polypeptide, or by combining domains from the coding sequences for different naturally-occurring polypeptides ("domain swapping"). Techniques for modifying genes encoding functional polypeptides described herein are known and include, inter alia, directed evolution techniques, site-directed mutagenesis techniques and random mutagenesis techniques, and can be useful to increase specific activity of a polypeptide, alter substrate specificity, alter expression levels, alter subcellular location, or modify polypeptide-polypeptide interactions in a desired manner. Such modified polypeptides are considered functional homologs. The term "functional homolog" is sometimes applied to the nucleic acid that encodes a functionally homologous polypeptide.

Functional homologs can be identified by analysis of nucleotide and polypeptide sequence alignments. For example, performing a query on a database of nucleotide or polypeptide sequences can identify homologs of steviol glycoside biosynthesis polypeptides. Sequence analysis can involve BLAST, Reciprocal BLAST, or PSI-BLAST analysis of non-redundant databases using a UGT amino acid sequence as the reference sequence. Amino acid sequence is, in some instances, deduced from the nucleotide sequence. Those polypeptides in the database that have greater than 40% sequence identity are candidates for further evaluation for suitability as a steviol glycoside biosynthesis polypeptide. Amino acid sequence similarity allows for conservative amino acid substitutions, such as substitution of one hydrophobic residue for another or substitution of one polar residue for another. If desired, manual inspection of such candidates can be carried out in order to narrow the number of candidates to be further evaluated. Manual inspection can be performed by selecting those candidates that appear to have domains present in steviol glycoside biosynthesis polypeptides, e.g., conserved functional domains.

Conserved regions can be identified by locating a region within the primary amino acid sequence of a steviol glycoside biosynthesis polypeptide that is a repeated sequence, forms some secondary structure (e.g., helices and beta sheets), establishes positively or negatively charged domains, or represents a protein motif or domain. See, e.g., the Pfam web site describing consensus sequences for a variety of protein motifs and domains on the World Wide Web at sanger.ac.uk/Software/Pfam/and pfam.janelia.org/. The information included at the Pfam database is described in Sonnhammer et al., *Nucl. Acids Res.,* 26:320-322 (1998); Sonnhammer et al., Proteins, 28:405-420 (1997); and Bateman et al., Nucl. Acids Res., 27:260-262 (1999). Conserved regions also can be determined by aligning sequences of the same or related polypeptides from closely related species. Closely related species preferably are from the same family. In some embodiments, alignment of sequences from two different species is adequate to identify such homologs.

Typically, polypeptides that exhibit at least about 40% amino acid sequence identity are useful to identify conserved regions. Conserved regions of related polypeptides exhibit at least 45% amino acid sequence identity (e.g., at least 50%, at least 60%, at least 70%, at least 80%, or at least 90% amino acid sequence identity). In some embodiments, a conserved region exhibits at least 92%, 94%, 96%, 98%, or 99% amino acid sequence identity.

Recombinant Hosts

Recombinant hosts described herein below can be used in methods to produce a mogrol precursor, mogrol, or mogroside. For example, if the recombinant host is a microorganism, the method can include growing the recombinant microorganism in a culture medium under conditions in which one or more of the enzymes catalyzing step(s) of the methods of the invention, e.g., synthases, hydrolases, CYP450s and/or UGTs are expressed. In the present context the terms "microorganism" and "microorganism host" and "recombinant host" can be used interchangeably to refer to microscopic organisms, including bacteria or microscopic fungi, including yeast. The microorganism can be, but not limited to, a eukaryotic cell or immortalized cell.

Exemplary prokaryotic and eukaryotic species are described in more detail below. However, it will be appreciated that other species can be suitable. For example, suitable species can be in a genus including *Agaricus, Aspergillus, Bacillus, Candida, Corynebacterium, Escherichia, Fusarium/Gibberella, Kluyveromyces, Laetiporus, Lentinus, Phaffia, Phanerochaete, Pichia, Physcomitrella, Rhodoturula, Saccharomyces, Schizosaccharomyces, Sphaceloma, Xanthophyllomyces* and *Yarrowia*. Exemplary species from such genera include *Lentinus tigrinus, Laetiporus sulphureus, Phanerochaete chrysosporium, Pichia pastoris, Physcomitrella patens, Rhodoturula glutinis* 32, *Rhodoturula mucilaginosa, Phaffia rhodozyma* UBV-AX, *Xanthophyllomyces dendrorhous, Fusarium fujikuroi/Gibberella fujikuroi, Candida utilis* and *Yarrowia lipolytica*. In some embodiments, a microorganism can be an Ascomycete such as *Gibberella fujikuroi, Kluyveromyces lactis, Schizosaccharomyces pombe, Aspergillus niger*, or *Saccharomyces cerevisiae*. In some embodiments, a microorganism can be a prokaryote such as *Escherichia coli, Rhodobacter sphaeroides*, or *Rhodobacter capsulatus*. It will be appreciated that certain microorganisms can be used to screen and test genes of interest in a high throughput manner, while other microorganisms with desired productivity or growth characteristics can be used for large-scale production of mogrol precursor, mogrol, or mogroside.

In certain embodiments of this invention, microorganisms include, but are not limited to, *S. cerevisiae, A. niger, A. oryzae, E. coli, L. lactis* and *B. subtilis*. The constructed and genetically engineered microorganisms provided by the invention can be cultivated using conventional fermentation processes, including, inter alia, chemostat, batch, fed-batch cultivations, continuous perfusion fermentation, and continuous perfusion cell culture.

Exemplary embodiments comprising bacterial cells include, but are not limited to, cells of species, belonging to the genus *Bacillus*, the genus *Escherichia*, the genus *Lactobacillus*, the genus *Lactobacillus*, the genus *Corynebacterium*, the genus *Acetobacler*, the genus *Acinetobacler*, or the genus *Pseudomonas*.

The microorganism can be a fungus, and more specifically, a filamentous fungus belonging to the genus of *Aspergillus*, e.g., *A. niger, A. awamori, A. oryzae*, or *A. nidulans*, a yeast belonging to the genus of *Saccharomyces*, e.g., *S. cerevisiae, S. kluyveri, S. bayanus, S. exiguus, S. sevazzi*, or *S. uvarum*, a yeast belonging to the genus *Kluyveromyces*, e.g., *K. laclis, K. marxianus* var. *marxianus*, or *K. thermololerans*, a yeast belonging to the genus *Candida*, e.g., *C. ulilis, C. lropicalis, C. albicans, C. lipolylica*, or *C. versalilis*, a yeast belonging to the genus *Pichia*, e.g., *R. slipidis, R. pasloris*, or *P. sorbilophila*, or other yeast genera, e.g., *Cryplococcus, Debaromyces, Hansenula, Pichia, Yarrowia, Zygosaccharomyces*, or *Schizosaccharomyces*. Concerning other microorganisms a non-exhaustive list of suitable filamentous fungi is supplied: a species belonging to the genus *Penicillium, Rhizopus, Fusarium, Fusidium, Gibberella, Mucor, Morlierella*, and *Trichoderma*.

*Saccharomyces cerevisiae*

*Saccharomyces cerevisiae* is a widely used chassis organism in synthetic biology, and can be used as the recombinant microorganism platform. There are libraries of mutants, plasmids, detailed computer models of metabolism and other information available for *S. cerevisiae*, allowing for rational design of various modules to enhance product yield. Methods are known for making recombinant microorganisms.

The genes described herein can be expressed in yeast using any of a number of known promoters. Strains that overproduce phenylpropanoids are known and can be used as acceptor molecules in the production of a mogrol precursor, mogrol, or mogroside.

*Aspergillus* spp.

*Aspergillus* species such as *A. oryzae, A. niger* and *A. sojae* are widely used microorganisms in food production, and can also be used as the recombinant microorganism platform. Nucleotide sequences are available for genomes of *A. nidulans, A. fumigatus, A. oryzae, A. clavatus, A. flavus, A. niger*, and *A. terreus*, allowing rational design and modification of endogenous pathways to enhance flux and increase product yield. Metabolic models have been developed for *Aspergillus*, as well as transcriptomic studies and proteomics studies. *A. niger* is cultured for the industrial production of a number of food ingredients such as citric acid and gluconic acid, and thus species such as *A. niger* are generally suitable for the production of a mogrol precursor, mogrol, or mogroside.

*Escherichia coli*

*Escherichia coli*, another widely used platform organism in synthetic biology, can also be used as the recombinant microorganism platform. Similar to *Saccharomyces*, there are libraries of mutants, plasmids, detailed computer models of metabolism and other information available for *E. coli*, allowing for rational design of various modules to enhance product yield. Methods similar to those described above for *Saccharomyces* can be used to make recombinant *E. coli* microorganisms.

*Agaricus, Gibberella*, and *Phanerochaete* spp.

*Agaricus, Gibberella*, and *Phanerochaete* spp. can be useful because they are known to produce large amounts of gibberellin in culture. Thus, the precursors of terpenes used as acceptor molecules in the production of a mogrol precursor, mogrol, or mogroside are already produced by endogenous genes. Thus, modules containing recombinant genes for biosynthesis of terpenes can be introduced into species from such genera without the necessity of introducing other compounds or pathway genes.

*Arxula adeninivorans* (*Blastobotrys adeninivorans*)

*Arxula adeninivorans* is dimorphic yeast (it grows as budding yeast like the baker's yeast up to a temperature of 42° C., above this threshold it grows in a filamentous form) with unusual biochemical characteristics. It can grow on a wide range of substrates and can assimilate nitrate. It has successfully been applied to the generation of strains that can produce natural plastics or the development of a biosensor for estrogens in environmental samples.

*Yarrowia lipolytica.*

*Yarrowia lipolytica* is dimorphic yeast (see *Arxula adeninivorans*) and belongs to the family Hemiascomycetes. The entire genome of *Yarrowia lipolytica* is known. *Yarrowia* species is aerobic and considered to be non-pathogenic. *Yarrowia* is efficient in using hydrophobic substrates (e.g. alkanes, fatty acids, oils) and can grow on sugars. It has a high potential for industrial applications and is an oleaginous microorganism. *Yarrowia lipolyptica* can accumulate lipid content to approximately 40% of its dry cell weight and is a model organism for lipid accumulation and remobilization. See e.g., Nicaud, 2012, Yeast 29(10):409-18; Beopoulos et al., 2009, *Biochimie* 91(6):692-6; Bankar et al., 2009, *Appl Microbiol Biotechnol.* 84(5):847-65.

*Rhodotorula* sp.

*Rhodotorula* is unicellular, pigmented yeast. The oleaginous red yeast, *Rhodotorula glutinis*, has been shown to produce lipids and carotenoids from crude glycerol (Saenge et al., 2011, *Process Biochemistry* 46(1):210-8). *Rhodotorula* toruloides strains have been shown to be an efficient fed-batch fermentation system for improved biomass and lipid productivity (Li et al., 2007, *Enzyme and Microbial Technology* 41:312-7).

*Rhodosporidium toruloides*

*Rhodosporidium toruloides* is oleaginous yeast and useful for engineering lipid-production pathways (See, e.g., Zhu et al., 2013, *Nature Commun.* 3:1112; Ageitos et al., 2011, *Applied Microbiology and Biotechnology* 90(4):1219-27).

*Candida boidinii*

*Candida boidinii* is methylotrophic yeast (it can grow on methanol). Like other methylotrophic species such as *Hansenula polymorpha* and *Pichia pastoris*, it provides an excellent platform for producing heterologous proteins. Yields in a multigram range of a secreted foreign protein have been reported. A computational method, IPRO, recently predicted mutations that experimentally switched the cofactor specificity of *Candida boidinii* xylose reductase from NADPH to NADH. See, e.g., Mattanovich et al., 2012, *Methods Mol Biol.* 824:329-58; Khoury et al., 2009, *Protein Sci.* 18(10):2125-38.

*Hansenula polymorpha* (*Pichia angusta*)

*Hansenula polymorpha* is methylotrophic yeast (see *Candida boidinii*). It can furthermore grow on a wide range of other substrates; it is thermo-tolerant and can assimilate nitrate (see also *Kluyveromyces lactis*). It has been applied to producing hepatitis B vaccines, insulin and interferon alpha-2a for the treatment of hepatitis C, furthermore to a range of technical enzymes. See, e.g., Xu et al., 2014, *Virol Sin.* 29(6):403-9.

*Kluyveromyces lactis*

*Kluyveromyces lactis* is yeast regularly applied to the production of kefir. It can grow on several sugars, most importantly on lactose which is present in milk and whey. It has successfully been applied among others for producing chymosin (an enzyme that is usually present in the stomach of calves) for producing cheese. Production takes place in fermenters on a 40,000 L scale. See, e.g., van Ooyen et al., 2006, *FEMS Yeast Res.* 6(3):381-92.

*Pichia pastoris*

*Pichia pastoris* is methylotrophic yeast (see *Candida boidinii* and *Hansenula polymorpha*). It provides an efficient platform for producing foreign proteins. Platform elements are available as a kit and it is worldwide used in academia for producing proteins. Strains have been engineered that can produce complex human N-glycan (yeast glycans are similar but not identical to those found in humans). See, e.g., Piirainen et al., 2014, *N Biotechnol.* 31(6):532-7.

*Physcomitrella* spp.

*Physcomitrella* mosses, when grown in suspension culture, have characteristics similar to yeast or other fungal cultures. This genera can be used for producing plant secondary metabolites, which can be difficult to produce in other types of cells.

As will be apparent to one skilled in the art, the particulars of the selection process for specific UGTs capable of glycosylating mogrol and mogrosides depend on the identities of selectable markers. Selection in all cases promotes or permits proliferation of cells comprising the marker while inhibiting or preventing proliferation of cells lacking the marker. If a selectable marker is an antibiotic resistance gene, the transfected host population can be cultured in the presence of an antibiotic to which resistance is conferred by the selectable marker. If a selectable marker is a gene that complements an auxotrophy of the hosts, the transfected host population can be cultivated in the absence of the compound for which the hosts are auxotrophic.

After selection, recombinant hosts can be cloned according to any appropriate method known in the art. For example, recombinant microbial hosts can be plated on solid media under selection conditions, after which single clones can be selected for further selection, characterization, or use. This process can be repeated one or more times to enhance stability of the expression construct within the host. To produce a mogroside pathway polypeptide, recombinant hosts comprising one or more expression vectors can be cultured to expand cell numbers in any appropriate culturing apparatus known in the art, such as a shaken culture flask or a fermenter.

Culture media used for various recombinant hosts are well known in the art. Culture media used to culture recombinant bacterial cells will depend on the identity of the bacteria. Culture media used to culture recombinant yeast cells will depend on the identity of the yeast. Culture media generally comprise inorganic salts and compounds, amino acids, carbohydrates, vitamins and other compounds that are either necessary for the growth of the hosts or improve health or growth or both of the hosts. In particular, culture media typically comprise manganese ($Mn^{2+}$) and magnesium ($Mg^{2+}$) ions, which are co-factors for many, but not all, glycosyltransferases.

As used herein, the term "fed-batch culture" or "semi-batch culture" are used interchangeably to refer to as an operational technique in biotechnological processes where one or more nutrients (substrates) are fed (supplied) to the bioreactor during cultivation and in which the product(s) remain in the bioreactor until the end of the run. In some embodiments, all the nutrients are fed into the bioreactor.

In some embodiments, a recombinant host can be modified in order to reduce glucanase activity, in particular glucanase activity, which can result in deglycosylation of mogrosides. Thus, the recombinant host can for example be modified to reduce of even abolish exo-1,3-beta-Glucanase activity. In embodiments of the invention when the recombinant host is yeast, this can be accomplished by deletion of the EXG1 gene (SEQ ID NO:63, SEQ ID NO:64) and/or of the EXG2 gene (SEQ ID NO:65, SEQ ID NO:66), both of which are encoding an exo-1,3-beta-glucanase.

Table 2 indicates the identities of the sequences utilized herein.

TABLE 2

Sequences used herein.

| | |
|---|---|
| SEQ ID NO: 1 | Amino acid sequence of *C. pepo* cucurbitadienol synthase |
| SEQ ID NO: 2 | Amino acid sequence of C-terminal portion of *S. grosvenorii* cucurbitadienol synthase |
| SEQ ID NO: 3 | Nucleotide sequence encoding CYP533 |
| SEQ ID NO: 4 | Nucleotide sequence encoding CYP937 |
| SEQ ID NO: 5 | Codon-optimized DNA sequence encoding CYP1798 |
| SEQ ID NO: 6 | Nucleotide sequence encoding CYP1994 |
| SEQ ID NO: 7 | Nucleotide sequence encoding CYP2048 |

TABLE 2-continued

| Sequences used herein. | |
|---|---|
| SEQ ID NO: 8 | Nucleotide sequence encoding CYP2740 |
| SEQ ID NO: 9 | Nucleotide sequence encoding CYP3404 |
| SEQ ID NO: 10 | Nucleotide sequence encoding CYP3968 |
| SEQ ID NO: 11 | Nucleotide sequence encoding CYP4112 |
| SEQ ID NO: 12 | Nucleotide sequence encoding CYP4149 |
| SEQ ID NO: 13 | Nucleotide sequence encoding CYP4491 |
| SEQ ID NO: 14 | Nucleotide sequence encoding CYP5491 |
| SEQ ID NO: 15 | Nucleotide sequence encoding CYP6479 |
| SEQ ID NO: 16 | Nucleotide sequence encoding CYP7604 |
| SEQ ID NO: 17 | Nucleotide sequence encoding CYP8224 |
| SEQ ID NO: 18 | Nucleotide sequence encoding CYP8728 |
| SEQ ID NO: 19 | Nucleotide sequence encoding CYP10020 |
| SEQ ID NO: 20 | Nucleotide sequence encoding CYP10285 |
| SEQ ID NO: 21 | Amino acid sequence of UGT73C3 |
| SEQ ID NO: 22 | Amino acid sequence of UGT73C5 |
| SEQ ID NO: 23 | Amino acid sequence of UGT73C6 |
| SEQ ID NO: 24 | Amino acid sequence of UGT73E1 |
| SEQ ID NO: 25 | Amino acid sequence of UGT85C2 |
| SEQ ID NO: 26 | Nucleotide sequence encoding *S. grosvenorii* UGT98 |
| SEQ ID NO: 27 | Nucleotide sequence encoding *S. grosvenorii* UGT1495 |
| SEQ ID NO: 28 | Nucleotide sequence encoding *S. grosvenorii* UGT1817 |
| SEQ ID NO: 29 | Partial nucleotide sequence encoding fragment of *S. grosvenorii* UGT3494 |
| SEQ ID NO: 30 | Nucleotide sequence encoding *S. grosvenorii* UGT5914 |
| SEQ ID NO: 31 | Nucleotide sequence encoding *S. grosvenorii* UGT8468 |
| SEQ ID NO: 32 | Nucleotide sequence encoding *S. grosvenorii* UGT10391 |
| SEQ ID NO: 33 | Partial nucleotide sequence encoding fragment of *S. grosvenorii* UGT11789 |
| SEQ ID NO: 34 | Partial nucleotide sequence encoding fragment of *S. grosvenorii* UGT11999 |
| SEQ ID NO: 35 | Partial nucleotide sequence encoding fragment of *S. grosvenorii* UGT13679 |
| SEQ ID NO: 36 | Partial nucleotide sequence encoding fragment of *S. grosvenorii* UGT15423 |
| SEQ ID NO: 37 | Codon-optimized nucleotide sequence encoding *S. grosvenorii* Epoxide hydrolase 1 |
| SEQ ID NO: 38 | Amino acid sequence of *S. grosvenorii* Epoxide hydrolase 1 |
| SEQ ID NO: 39 | Codon-optimized nucleotide sequence encoding *S. grosvenorii* Epoxide hydrolase 2 |
| SEQ ID NO: 40 | Amino acid sequence of *S. grosvenorii* Epoxide hydrolase 2 |
| SEQ ID NO: 41 | Nucleotide sequence encoding CYP10969 |
| SEQ ID NO: 42 | Codon-optimized nucleotide sequence encoding *S. grosvenorii* cucurbitadienol synthase |
| SEQ ID NO: 43 | Amino acid sequence of *S. grosvenorii* cucurbitadienol synthase |
| SEQ ID NO: 44 | Amino acid sequence of *S. grosvenorii* CYP5491 |
| SEQ ID NO: 45 | Nucleotide sequence encoding *S. grosvenorii* CPR4497 |
| SEQ ID NO: 46 | Amino acid sequence of *S. grosvenorii* CPR4497 |
| SEQ ID NO: 47 | Nucleotide sequence encoding *S. grosvenorii* UGT1576 |
| SEQ ID NO: 48 | Amino acid sequence of *S. grosvenorii* UGT1576 |
| SEQ ID NO: 49 | Nucleotide sequence encoding *S. grosvenorii* UGT SK98 |
| SEQ ID NO: 50 | Amino acid sequence of *S. grosvenorii* UGT SK98 |
| SEQ ID NO: 51 | Nucleotide sequence encoding *S. grosvenorii* UGT98 |
| SEQ ID NO: 52 | Codon-optimized nucleotide sequence encoding *S. grosvenorii* UGT98 |
| SEQ ID NO: 53 | Amino acid sequence of *S. grosvenorii* UGT98 |
| SEQ ID NO: 54 | Amino acid sequence of *S. cerevisiae* squalene epoxidase encoded by the ERG1 gene |
| SEQ ID NO: 55 | Amino acid sequence of *S. cerevisiae* lanosterol synthase encoded by the ERG7 gene |
| SEQ ID NO: 61 | Nucleotide sequence of *S. grosvenorii* UGT430 |
| SEQ ID NO: 62 | Amino acid sequence of *S. grosvenorii* UGT430 |
| SEQ ID NO: 63 | Nucleotide sequence of *S. cerevisiae* EXG1 |
| SEQ ID NO: 64 | Amino acid sequence of *S. cerevisiae* EXG1 |
| SEQ ID NO: 65 | Nucleotide sequence of *S. cerevisiae* EXG2 |
| SEQ ID NO: 66 | Amino acid sequence of *S. cerevisiae* EXG2 |
| SEQ ID NO: 67 | Nucleotide sequence of *S. grosvenorii* UGT1697 |
| SEQ ID NO: 68 | Amino acid sequence of *S. grosvenorii* UGT1697 |
| SEQ ID NO: 69 | Nucleotide sequence encoding *S. grosvenorii* UGT11789 (full-length) |
| SEQ ID NO: 70 | Codon-optimized nucleotide sequence “A” of full-length *S. grosvenorii* UGT11789 |
| SEQ ID NO: 71 | Codon-optimized nucleotide sequence “B” of full-length *S. grosvenorii* UGT11789 |
| SEQ ID NO: 72 | Amino acid sequence of *S. grosvenorii* UGT11789 (full-length) |
| SEQ ID NO: 73 | Nucleotide sequence encoding *S. grosvenorii* CYP1798 |
| SEQ ID NO: 74 | Amino acid sequence of *S. grosvenorii* CYP1798 |
| SEQ ID NO: 75 | Nucleotide sequence encoding *S. cerevisiae* TRP1 |

TABLE 2-continued

| Sequences used herein. | |
|---|---|
| SEQ ID NO: 76 | Amino acid sequence of *S. cerevisiae* TRP1 |
| SEQ ID NO: 77 | Nucleotide sequence encoding *S. cerevisiae* tHMG1 |
| SEQ ID NO: 78 | Amino acid sequence of *S. cerevisiae* tHMG1 |
| SEQ ID NO: 79 | Nucleotide sequence encoding *S. grosvenorii* Epoxide hydrolase 2 |
| SEQ ID NO: 80 | Nucleotide sequence encoding *S. grosvenorii* cucurbitadienol synthase |
| SEQ ID NO: 81 | Codon-optimized nucleotide sequence encoding CYP5491 |
| SEQ ID NO: 82 | Codon-optimized nucleotide sequence encoding CYP4497 |
| SEQ ID NO: 83 | Codon-optimized nucleotide sequence encoding UGT1576 |
| SEQ ID NO: 84 | Codon-optimized nucleotide sequence encoding UGT430 |
| SEQ ID NO: 85 | Codon-optimized nucleotide sequence encoding CYP1697 |
| SEQ ID NO: 86 | Codon-optimized nucleotide sequence encoding CYP1798-II |
| SEQ ID NO: 87 | Amino acid sequence of *S. cerevisiae* ERG9 |
| SEQ ID NO: 88 | Amino acid sequence of *Gynostemma pentaphyllum* Squalene epoxidase |
| SEQ ID NO: 89 | Amino acid sequence of *Arabidopsis thaliana* Squalene epoxidase 1 |
| SEQ ID NO: 90 | Amino acid sequence of *Arabidopsis thaliana* Squalene epoxidase 4 |
| SEQ ID NO: 91 | Amino acid sequence of *Arabidopsis thaliana* Squalene epoxidase 6 |
| SEQ ID NO: 92 | Amino acid sequence of *Arabidopsis thaliana* Squalenel epoxidase 5 |
| SEQ ID NO: 93 | Amino acid sequence of *Arabidopsis thaliana* Squalene epoxidase 2 |
| SEQ ID NO: 94 | Amino acid sequence of *Arabidopsis thaliana* Squalene epoxidase 3 |
| SEQ ID NO: 95 | Amino acid sequence of *Brassica napus* Squalene monooxygenase 1,1 |
| SEQ ID NO: 96 | Amino acid sequence of *Brassica napus* Squalene monooxygenase 1,2 |
| SEQ ID NO: 97 | Amino acid sequence of *Euphorbia tirucalli* Squalene epoxidase |
| SEQ ID NO: 98 | Amino acid sequence of *Medicago truncatula* Squalene epoxidase |
| SEQ ID NO: 99 | Amino acid sequence of *Medicago truncatula* Squalene monooxygenase |
| SEQ ID NO: 100 | Amino acid sequence of *Ricinus communis* Squalene monooxygenase |
| SEQ ID NO: 101 | Amino acid sequence of *Ricinus communis* Squalene monooxygenase |
| SEQ ID NO: 102 | Amino acid sequence of *Ricinus communis* Squalene monooxygenase |
| SEQ ID NO: 103 | Amino acid sequence of *Ricinus communis* Squalene monooxygenase |
| SEQ ID NO: 104 | Amino acid sequence of *Ricinus communis* Squalene monooxygenase |
| SEQ ID NO: 105 | Amino acid sequence of *Ricinus communis* Squalene monooxygenase |

The invention will be further described in the following examples, which do not limit the scope of the invention described in the claims.

EXAMPLES

The Examples that follow are illustrative of specific embodiments of the invention and various uses thereof. They are set forth for explanatory purposes only and are not to be taken as limiting the invention.

Example 1: Purification of Mogroside V

Mogroside V was purified from commercially available monk fruit extracts (PureLo®, Swanson). Three bottles of PureLo® (240 g) were dissolved in water (900 mL) and loaded on a column of HP-20 resin (400 g resin). The column was washed with water (2.5 liters) and further washed with 20% methanol in water. The product was eluted with methanol. After solvent evaporation and drying under high vacuum, mogroside V (2.5 g) was obtained. The product was approximately 80% pure, with 11-oxomogroside V being the largest impurity.

Example 2: Enzymatic Synthesis of Mogrol from Mogroside V

Figure 5:
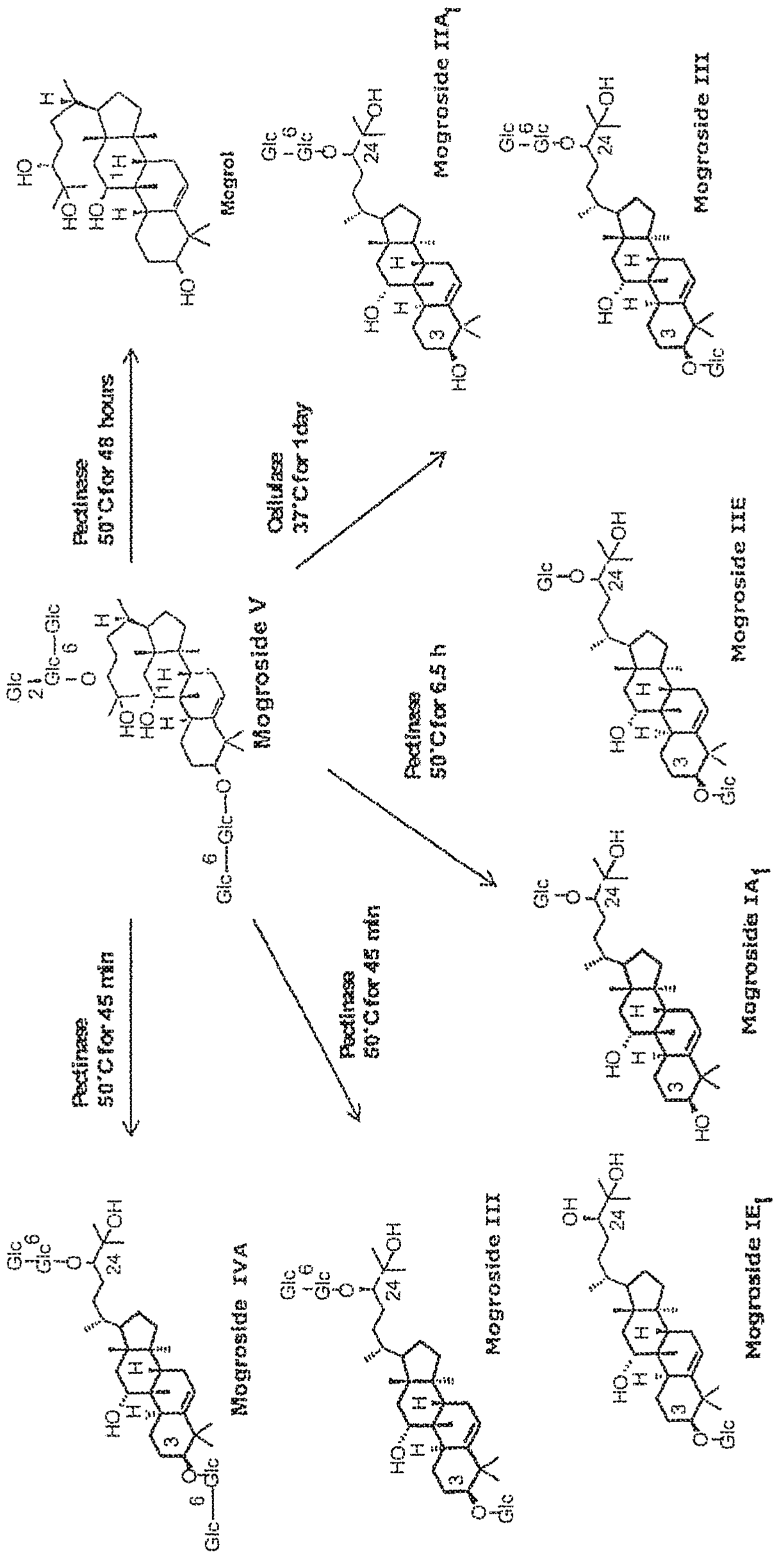
FIG. 5 is a schematic diagram showing enzymatic production of mogroside IV A, mogroside III, mogroside I E1, mogroside I A1, mogroside II E, mogroside II A1, and mogrol from mogroside V.

Mogroside V (300 mg) was dissolved in 0.1 M sodium acetate buffer (pH 4.5, 100 mL), and crude pectinase from *Aspergillus niger* (25 mL, Sigma P2736) was added. The mixture was stirred at 50° C. for 48 h. The reaction mixture was extracted with ethyl acetate (2×100 mL). The organic extract was dried under vacuum and subsequently purified with preparative HPLC. Pure mogrol (40 mg) was obtained, and its structure was confirmed by NMR and mass spectroscopy. See FIG. 5.

Example 3: Enzymatic Synthesis of Mogrol 3-O-glucoside (Mogroside I E1) and Mogrol 24-O-glucoside (Mogroside I A1) from Mogroside V Mogroside V (300 mg) was dissolved in 0.1 M sodium acetate buffer (pH 4.5, 100 mL), and crude pectinase from

*Aspergillus niger* (25 mL, Sigma P2736) was added. The mixture was stirred at 50° C. for 6.5 h and subsequently extracted with ethyl acetate (2×100 mL). The organic extract was dried under vacuum and purified with preparative HPLC. Pure mogroside I E1 (11.0 mg) and mogroside I A1 (8.0 mg) were obtained. Their structures were confirmed by NMR and mass spectroscopy. See FIG. 5.

Example 4: In Vitro UGT Screening and Reactions

UGT73C3 (SEQ ID NO:21), UGT73C5 (SEQ ID NO:22), UGT73C6 (SEQ ID NO:23), UGT73E1 (SEQ ID NO:24), and UGT85C2 (SEQ ID NO:25) were found to glycosylate mogrol in vitro. The reaction mixtures included 4× Tris buffer, mogrol (250 μM), UDP-glucose (750 μM), and 1% alkaline phosphatase. 5 μL of each partially purified UGT enzyme or crude enzyme extract was added to the reaction, and the reaction volume brought to 50 μL with water. The reactions were incubated overnight at 30° C. and performed in sterilized 96 well plates. 25 μL of DMSO were subsequently added into each reaction, and the reaction plates were centrifuged for 5 min. 40 μL samples were taken from each well and filtered to be used for LC-MS analysis.

UGT73C3 (SEQ ID NO:21), UGT73C6 (SEQ ID NO:23) and UGT85C2 (SEQ ID NO:25) were found to convert the entire mogrol substrate to mogroside I A1. UGT73C5 (SEQ ID NO:22) produced both mogroside I E1 and mogroside I A1. UGT73E1 (SEQ ID NO:24) converted mogrol to mogroside 1 A1 (major product) and a glycosylated mogrol that was neither mogroside I E1 nor mogroside I A1. The product was caused by a glycosylation event on C11-OH; the exact mass was shown as a mogroside I.

Example 5: Monk Fruit Cucurbitadienol Synthase

The CirCS gene codes for cucurbitadienol synthase in monk fruit, and the partial gene sequence covering 338 of the supposedly 764 amino acid sequence was identified by doing a tBLASTn (translated nucleotide database) analysis of the assembled data with a query cucurbitadienol synthase from *Cucurbita pepo* (accession number BAD34645.1, SEQ ID NO:1). The partial CirCS is 97.5% identical to the *C. pepo* gene at the protein level (SEQ ID NO:2; from residues 515 to 764 of SEQ ID NO:1).

Example 6: Monk Fruit Genes Encoding P450 Enzymes Catalyzing Formation of Mogrol from Cucurbitadienol To identify P450 enzymes catalyzing formation of mogrol from cucurbitadienol, a tBLASTn (translated nucleotide database) analysis was performed using reassembled sequencing reads of an *S. grosvenorii* transcriptome (see Tang et al., *BMC Genomics* 12: 343 (2011)). E values of 10E-10 or lower were used to identify sequences homologous to the database query sequences.

18 full-length or near full-length genes were identified. The assembled genes were designated CYP533, CYP937, CYP1798, CYP1994, CYP2048, CYP2740, CYP3404, CYP3968, CYP4112, CYP4149, CYP4491, CYP5491, CYP6479, CYP7604, CYP8224, CYP8728, CYP10020, and CYP10285 (see Table 2, SEQ ID NOs: 3-20).

Full-length synthetic *S. grosvenorii* gene sequences of CYP533 (SEQ ID NO:3), CYP937 (SEQ ID NO:4), CYP1798 (SEQ ID NO:5), CYP1994 (SEQ ID NO:6), CYP2740 (SEQ ID NO:8), CYP4112 (SEQ ID NO:11), CYP4149 (SEQ ID NO:12), CYP4491 (SEQ ID NO:13), CYP5491 (SEQ ID NO:14, SEQ ID NO:44), CYP7604 (SEQ ID NO:16), CYP8224 (SEQ ID NO:17), and CYP10285 (SEQ ID NO:20) were cloned into yeast expression vectors.

Example 7: Monk Fruit Genes Encoding Enzymes Catalyzing Glycosylation of Mogroside II E To identify monk fruit gene sequences encoding UGTs capable of converting mogroside II E into mogroside V, a tBLASTn (translated nucleotide database) analysis was performed using reassembled sequencing reads of an *S. grosvenorii* transcriptome (see Tang et al., *BMC Genomics* 12: 343 (2011)). The genes identified were UGT98 (SEQ ID NO:26), UGT1495 (SEQ ID NO:27), UGT1817 (SEQ ID NO:28), UGT3494 (SEQ ID NO:29), UGT5914 (SEQ ID NO:30), UGT8468 (SEQ ID NO:31), UGT10391 (SEQ ID NO:32), UGT11789 (SEQ ID NO:33), UGT11999 (SEQ ID NO:34), UGT13679 (SEQ ID NO:35), and UGT15423 (SEQ ID NO:36).

Of these, UGT98 (SEQ ID NO:26), UGT1495 (SEQ ID NO:27), UGT1817 (SEQ ID NO:28), UGT5914 (SEQ ID NO:30), UGT8468 (SEQ ID NO:31), and UGT10391 (SEQ ID NO:32) were synthesized based on contigs made from the publically-available sequence reads (Tang et al., *BMC Genomics* 12: 343 (2011)). The genes were inserted into yeast expression vectors.

Example 8: Boosting Mogrol Pathway Precursor Availability

To increase the availability of oxidosqualene and dioxidosqualene in yeast, the promoter of the endogenous ERG7 gene (SEQ ID NO:55) was displaced by a PCR fragment comprising the Nurseothricin marker (NatMX) and the CUP1 copper inducible promoter. ERG7 expression was thereby decreased when the yeast strain was grown in normal SC medium. ERG7 encodes lanosterol synthase and lowered expression is known to result in accumulation of oxidosqualene and dioxidosqualene in baker's yeast. Oxidosqualene is generally the precursor of triterpenoids. To further increase oxidosqualene and dioxidosqualene availability, the squalene epoxidase encoded by ERG1 (SEQ ID NO:54) was overexpressed, and a truncated copy of the yeast HMG reductase (tHMG1, SEQ ID NO:77, SEQ ID NO:78) was expressed.

Figure 6:
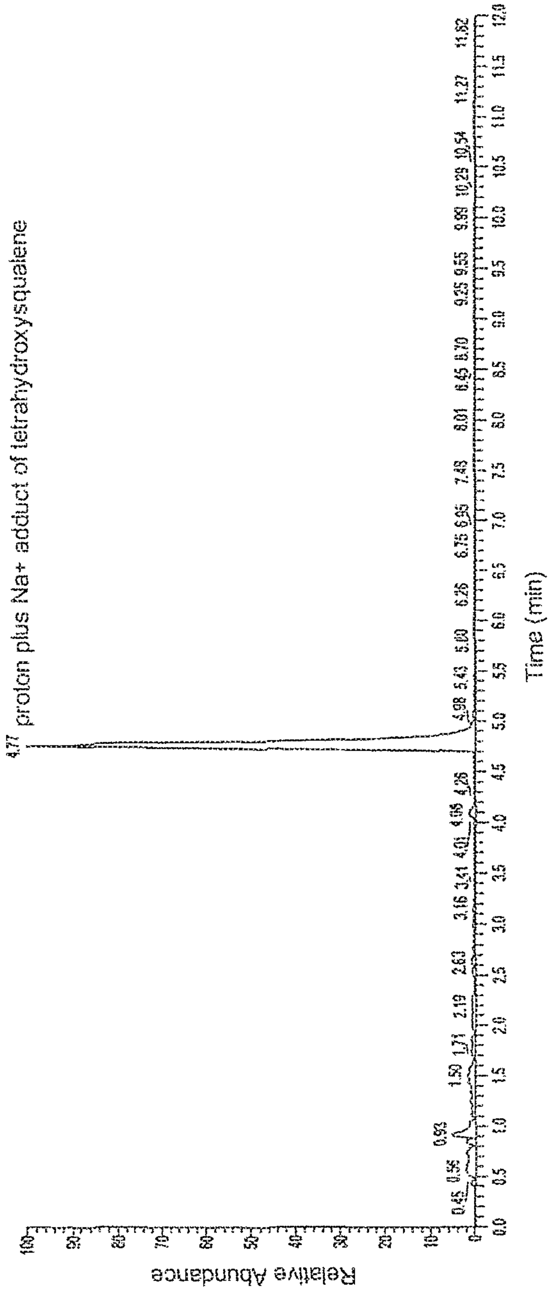
FIG. 6 shows the LC-MS mass peak 501 corresponding to the proton plus Na+ adduct of tetrahydroxysqualene in a sample from a yeast strain transformed with a plasmid expressing *S. grosvenorii* epoxide hydrolase 2 (SEQ ID NO:39, SEQ ID NO:40), as described in Example 8.

Successful boosting of oxidosqualene and dioxidosqualene production in yeast was demonstrated by production of tetrahydroxysqualene when either one of two soluble *S. grosvenorii* epoxide hydrolases was expressed in this strain. The *S. grosvenorii* epoxide hydrolase 1 is set forth in SEQ ID NO:38, and the codon-optimized *S. grosvenorii* epoxide hydrolase 1 is set forth in SEQ ID NO:37. The *S. grosvenorii* epoxide hydrolase 2 is set forth in SEQ ID NO:40, and the codon-optimized *S. grosvenorii* epoxide hydrolase 2 is set forth in SEQ ID NO:39. FIG. 6 shows the LC-MS mass peak 501 corresponding to the proton plus Na+ adduct of tetrahydroxysqualene in a sample from a yeast strain transformed with a plasmid expressing *S. grosvenorii* epoxide hydrolase 2. Tetrahydroxysqualene is produced by hydrolysis of 2,3- and 22,23-epoxide bonds of dioxidosqualene. No accumulation of tetrahydroxysqualene was detected in the background yeast strain. Samples were made by boiling culture aliquots in 50% DMSO and then pelleting of cell material by centrifugation. Supernatants were then measured by ESI LC-MS.

Example 9: Production of Cucurbitadienol in Yeast Strain

Figure 7A:
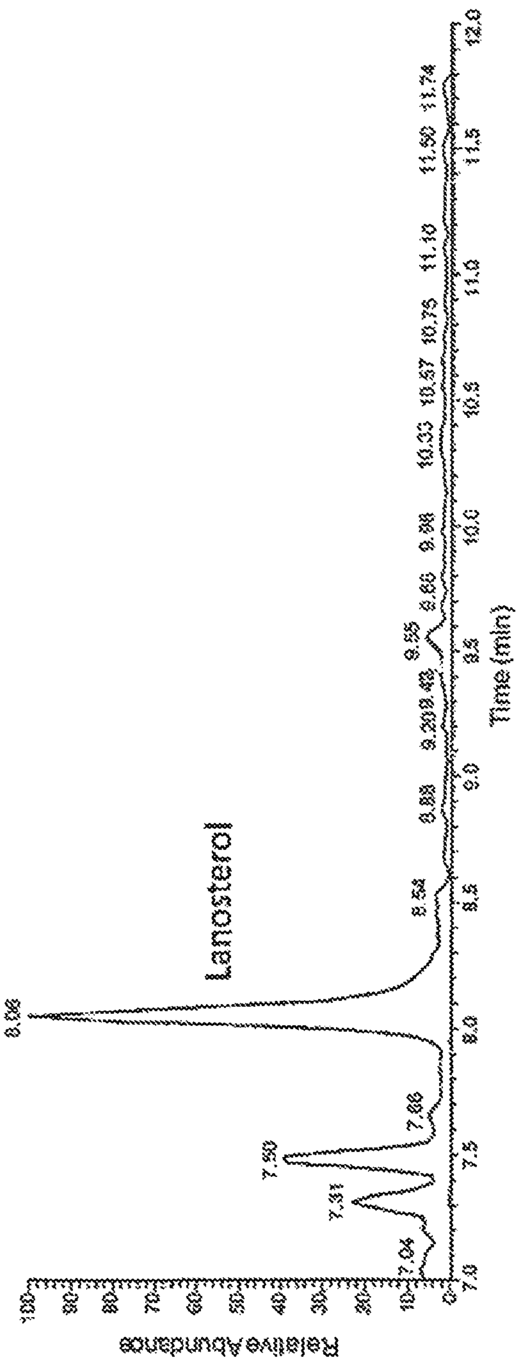
FIG. 7A show an LC-MS chromatogram indicating lanosterol production in a yeast strain that does not express a cucurbitadienol synthase.
Figure 7B:
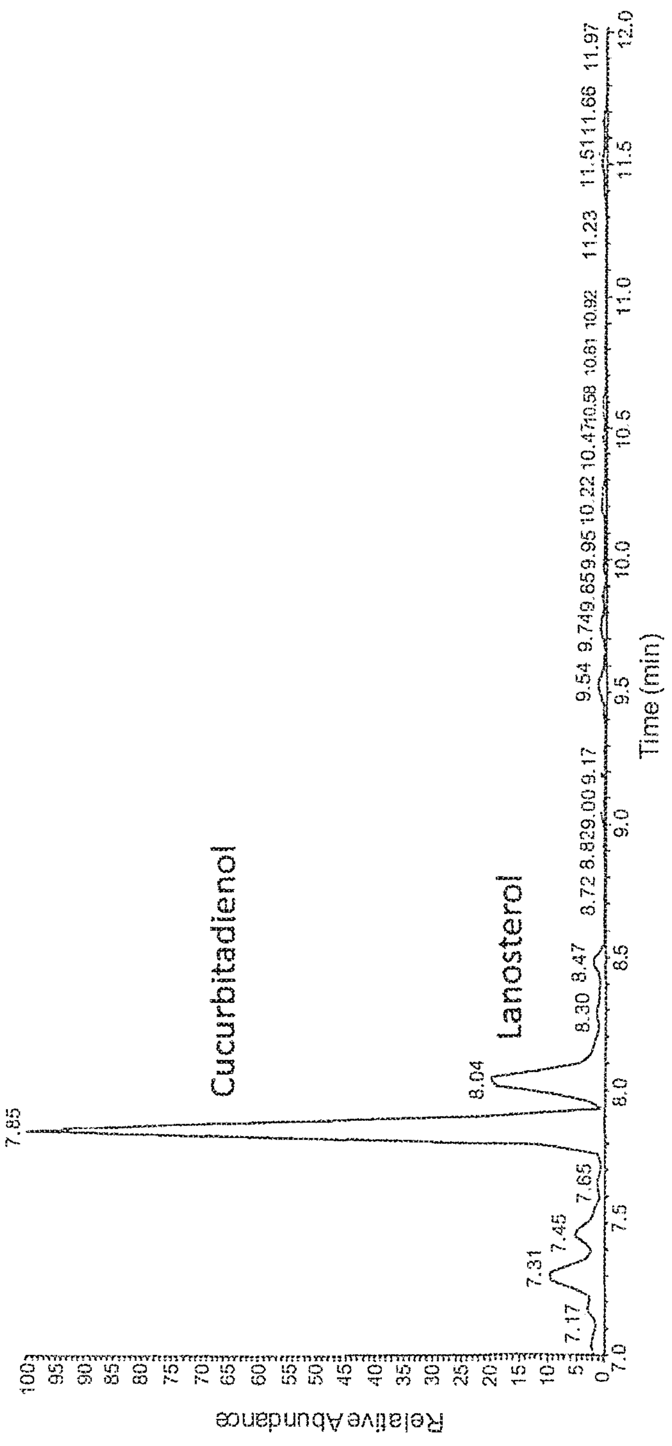
FIG. 7B shows an LC-MS chromatogram indicating cucurbitadienol and lanosterol production in a yeast strain expressing cucurbitadienol synthase (SEQ ID NO:42, SEQ ID NO:43), as described in Example 9.

Integration of a codon-optimized gene copy of the *S. grosvenorii* cucurbitadienol synthase set forth in SEQ ID NO:42 and SEQ ID NO:43 in *S. cerevisiae* resulted in production of cucurbitadienol (see FIG. 7B). The yeast strain was grown at 30° C. for 5 days in SC medium comprising 2% glucose. Cucurbitadienol was extracted by boiling a culture sample in 50% ethanol/20% KOH for 5 min followed by extraction with an equal volume of hexane. The samples were then evaporated with hexane, and the dried extract was resuspended in methanol.

FIGS. 7A and 7B show LC-MS chromatograms of samples of yeast expressing the cucurbitadienol synthase set forth in SEQ ID NO:42 and SEQ ID NO:43. FIG. 7A shows lanosterol peaks, and FIG. 7B shows cucurbitadienol and lanosterol peaks. The peak corresponding to lanosterol shows a retention time of ~8.05, whereas the peak corresponding to cucurbitadienol has a retention time of 7.85. Both lanosterol and cucurbitadienol show a mass in the LC-MS chromatogram of 409.4 (proton adduct minus mass of one $H_2O$ molecule).

Example 10: Modification of Cucurbitadienol in *S. cerevisiae* by CYP5491

Figure 8:
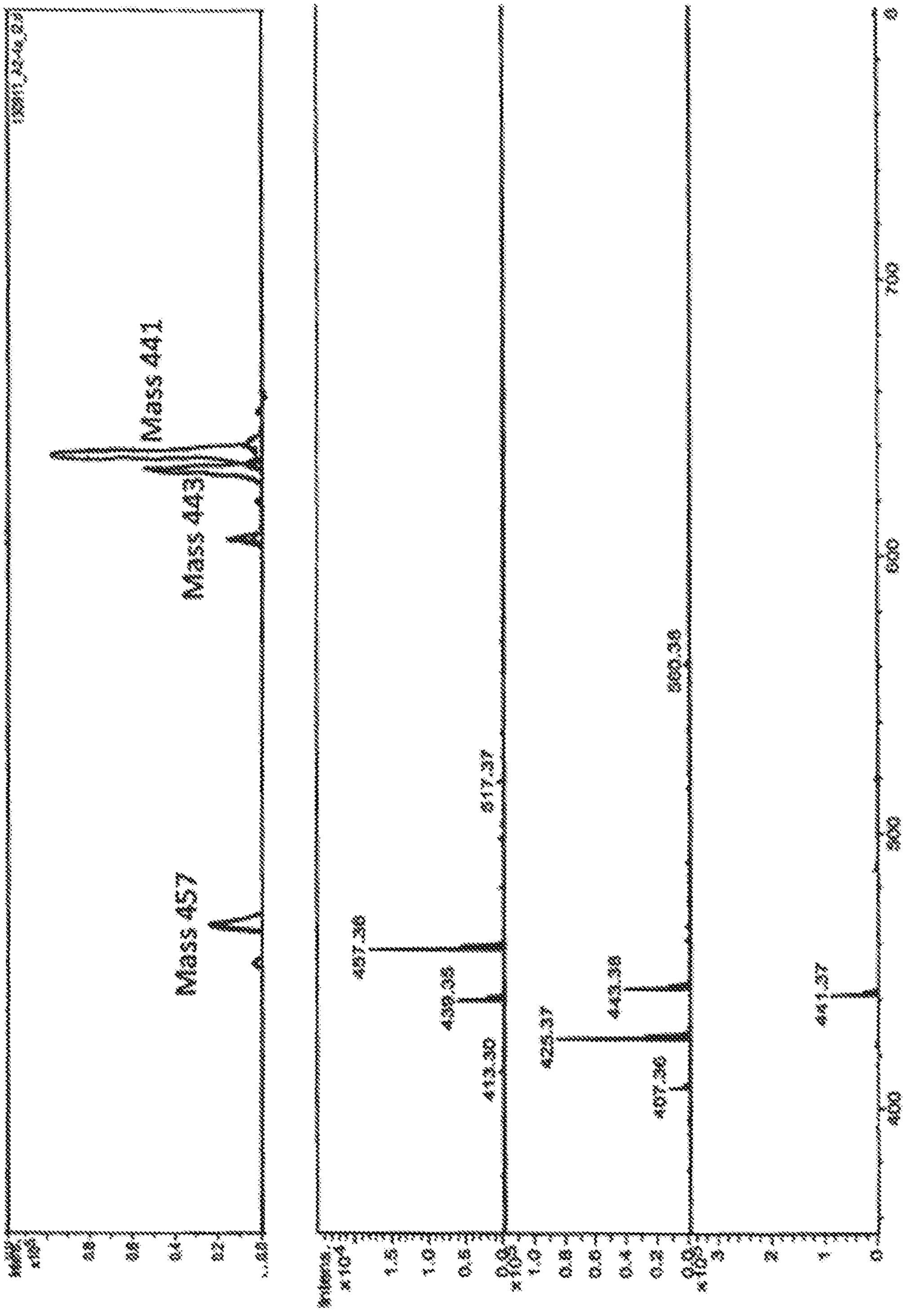
FIG. 8 shows an LC-MS chromatogram with three peaks resulting upon expression of CYP5491 (SEQ ID NO:14, SEQ ID NO:44) and CPR4497 (SEQ ID NO:45, SEQ ID NO:46) in yeast (upper panel), as described in Example 10; the three lower panels show the fragmentation spectrum of these three peaks. The masses of the 3 peaks (443.38, 441.37 and 457.36) correspond in weight to proton adducts of hydroxylated cucurbitadienol, oxo cucurbitadienol, and hydroxy plus oxo cucurbitadienol, respectively.

Upon transformation of a cucurbitadienol-producing yeast strain (see Example 9) with a plasmid comprising the *S. grosvenorii* CYP5491 gene (SEQ ID NO:14, SEQ ID NO:44) and a plasmid comprising the *S. grosvenorii* CPR4497 gene (SEQ ID NO:45, SEQ ID NO:46), three peaks were visible with LC-MS (see FIG. 8). The upper frame in FIG. 8 shows the LC-MS chromatogram with these three peaks, while the three lower frames show the fragmentation spectrum of these three peaks. The masses of the 3 peaks (443.38, 441.37 and 457.36) correspond in weight to proton adducts of hydroxylated cucurbitadienol, oxo cucurbitadienol and hydroxy plus oxo cucurbitadienol respectively. The hydroxylated cucurbitadienol (protonated mass 443.38) and oxidized cucurbitadienol (protonated mass 441.37) were 11-hydroxy-cucurbitadienol and 11-oxo-cucurbitadienol, respectively, as confirmed by NMR (FIG. 9).

Example 11: Glycosylation of Mogrol in *S. cerevisiae* by Expression of *S. grosvenorii* UGT98, UGTSK98, and UGT1576

UGT98, UGTSK98 and UGT1576 genes were synthesized based on contigs made from publically-available sequence reads (Tang et al., 2011, *BMC Genomics* 12:343). The nucleotide and amino acid sequences of UGT98 are set forth herein as SEQ ID NO:51 and SEQ ID NO:53, respectively, whereas SEQ ID NO:52 corresponds to a codon-optimized version of UGT98. The nucleotide and amino acid sequences of UGTSK98 are set forth herein as SEQ ID NO:49 and SEQ ID NO:50, respectively, and the nucleotide and amino acid sequences of UGT1576 are set forth herein as SEQ ID NO:47 and SEQ ID NO:48, respectively.

Figure 10A:
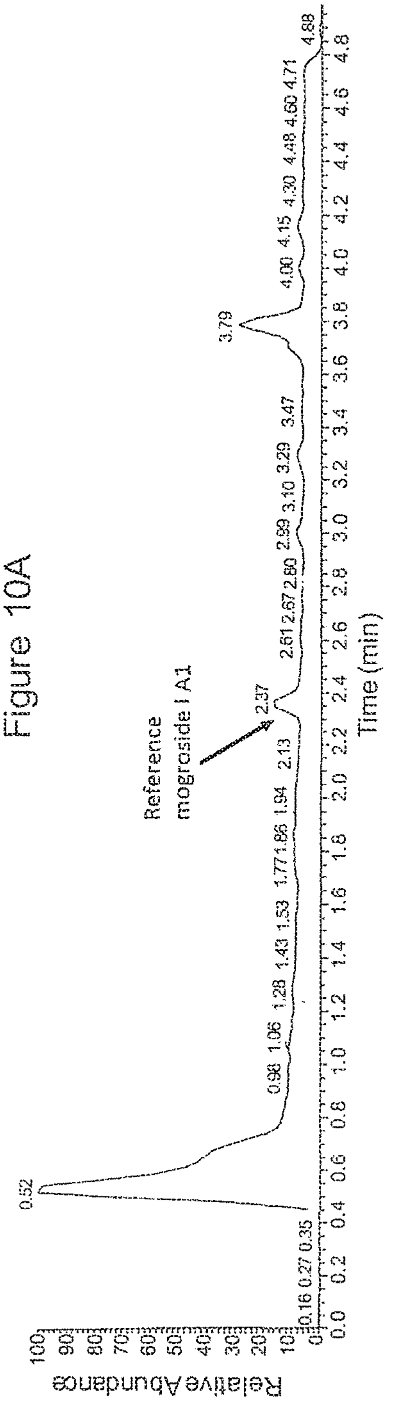
FIG. 10A shows an LC-MS chromatogram of reference mogroside I A1.
Figure 10B:
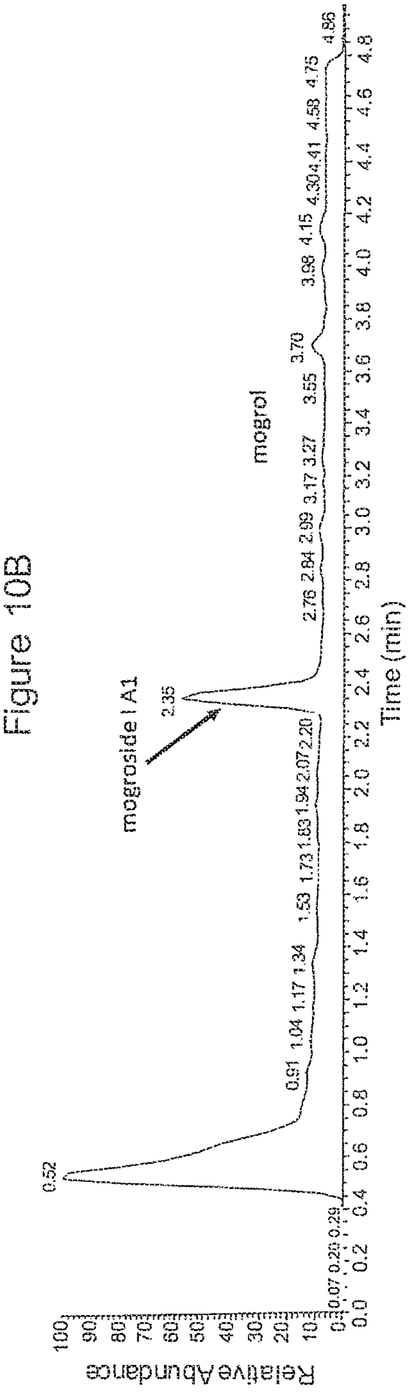
FIG. 10B shows an LC-MS chromatogram of a sample of yeast strain expressing UGT1576 (SEQ ID NO:47, SEQ ID NO:48) in a culture fed 50 μM mogrol, as described in Example 11.
Figure 11A:
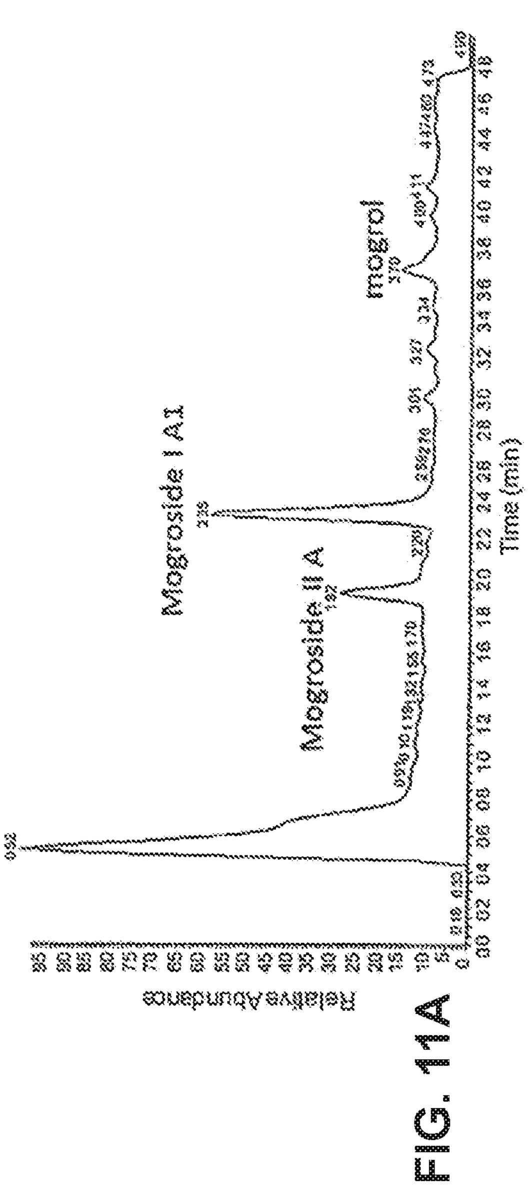
FIG. 11A shows LC-MS chromatograms of samples from a yeast strain co-expressing UGT SK98 with UGT1576 and shows production of di-glycosylated mogrol (mogroside II A) as described in Example 11.
Figure 11B:
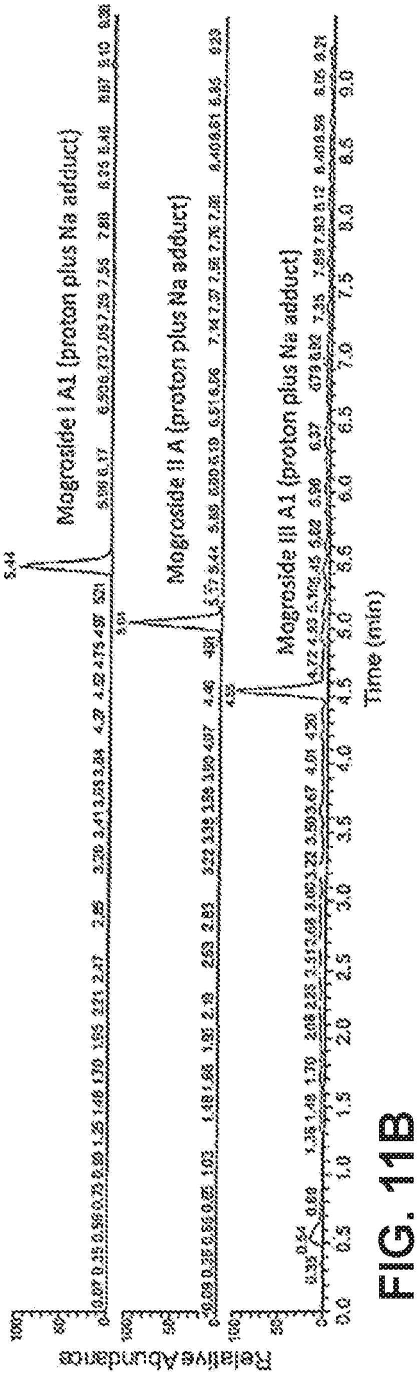
FIG. 11B shows LC-MS chromatograms of samples from a yeast strain co-expressing UGT98 with UGT1576 and shows production of di- and tri-glycosylated mogrol (middle and lower frames), as described in Example 11.

When a yeast strain deleted of the exo-1,3-beta glucanases EXG1 and EXG2 (to prevent de-glycosylation of produced mogrosides) was fed mogrol (10-100 μM) and transformed with a plasmid expressing UGT1576 (SEQ ID NO:47 and SEQ ID NO:48), mogroside I A1 was formed (FIG. 11B). Samples were prepared by mixing a culture aliquot 1:1 with DMSO followed by boiling (80° C.) for 5 min and pelleting by centrifugation. The supernatants were then subjected to ESI LC-MS. FIG. 10A shows the LC-MS chromatogram of reference mogroside I A1, while FIG. 10B shows the peak from a yeast sample expressing UGT1576 in a culture fed with 50 μM mogrol. These data show that the UGT1576 gene encodes a glycosyltransferase with mogrol C24-OH UDP-glycosyltransferase activity.

When UGT98 (SEQ ID NO:51, SEQ ID NO:52, SEQ ID NO:53) and UGTSK98 (SEQ ID NO:49, SEQ ID NO:50) were cloned into yeast expression plasmids and subsequently transformed into a yeast strain deleted of the exo-1,3-beta glucanases EXG1 and EXG2, no conversion of fed mogrol was detected. In contrast, co-expression of UGT98 (SEQ ID NO:51, SEQ ID NO:52, SEQ ID NO:53) or UGT SK98 (SEQ ID NO:49, SEQ ID NO:50) with UGT1576 (SEQ ID NO:47 and SEQ ID NO:48) in yeast fed with mogrol resulted in further glycosylation of mogroside I A1. UGTSK98 co-expressed with UGT1576 resulted in production of di-glycosylated mogrol (mogroside II A, FIG. 11A), while co-expression with UGT98 resulted in di- and tri-glycosylated mogrol (middle and lower frames, FIG. 11B). The di-glycosylated mogrol that was formed by both UGT98 and UGTSK98 had a different retention time than mogroside II E and mogroside II A1 during LC-MS.

Figure 12:
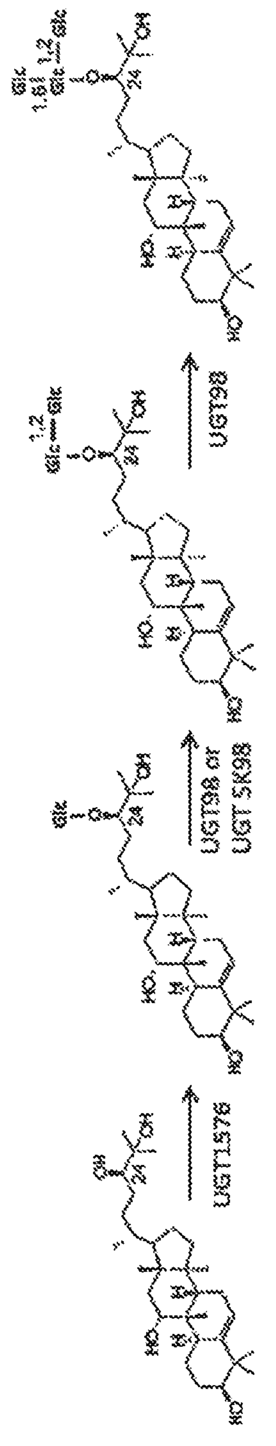
FIG. 12 shows a biosynthetic route from mogrol to mogroside III A1 provided herein, as described in Example 11.

Thus, both UGT98 and UGTSK98 were found to be able to catalyze 1,2-glycosylation of the glucose of mogroside I A1. UGT98 was found to be multifunctional, catalyzing 1,2-glycosylation of mogroside I A1, resulting in production of mogroside II A, followed by a 1,6-glycosylation of mogroside II A to form mogroside III A1 (FIG. 11B). UGT98 and UGTSK98 belong to the UGT91 family of UDP-glucose glycosyltransferases, and members of this family are known to be 1,2- and 1,6-glycosyltransferases. FIG. 12 schematically summarizes the glycosylation reactions from mogrol to mogroside III A1.

Example 12: Glycosylation of Mogrol in *S. cerevisiae* by Expression of *S. grosvenorii* UGT430

UGT430 (SEQ ID NO:61, SEQ ID NO:62) of the 85A UGT family was cloned from synthetic DNA to obtain a sequence identical to that of *S. grosvenorii* UGT430. The cloned gene was transformed into a yeast strain deleted of EXG1 and EXG2 (to prevent de-glycosylation of produced mogrosides). The yeast strain was grown in SC medium minus tryptophan for selection of plasmid maintenance, and comprising 10 μM mogrol. Cells were grown for 2 days at 30° C. with shaking at 140 rpm. After 2 days, 300 μL culture samples were mixed with 300 μL of 96% ethanol and incubated for 10 min at 80° C. Then, samples were centrifuged, and the supernatant was analyzed by LC-MS.

LC-MS analyses were performed using a Waters Acquity I-Class UPLC (Waters Corporation, Milford, Mass.) with Waters Acquity UPLC®BEH C18 column (2.1×50 mm, 1.7 μm particles, 130 Å pore size) coupled to a Waters Xevo TQD triple quadropole mass spectrometer with electrospray ionization (ESI) in negative mode. Compound separation was achieved by a gradient of the two mobile phases A (water with 0.1% formic acid) and B (MeCN with 0.1% formic acid) by increasing from 20% to 50% B between 0.3 to 2.0 min, increasing to 100% B at 2.01 min, holding 100% B for 0.6 min and re-equilibrating for another 0.6 min. The flow rate was 0.6 mL/min, and the column temperature 55° C. Mogroside I E1 (m/z 683.5; $[M+FA]^-$) was monitored using SIR (Single Ion Recording) and compared with a standard.

Figure 13A:
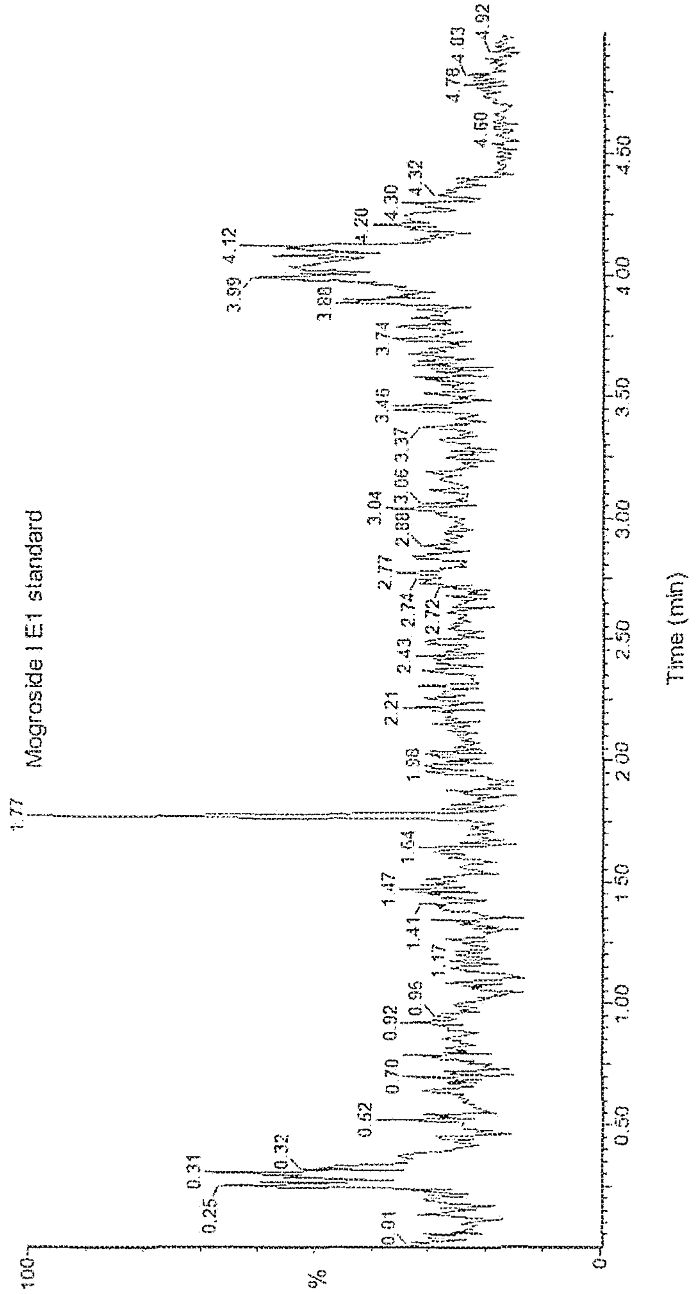
FIG. 13A shows elution of a mogroside I E1 standard.
Figure 13B:
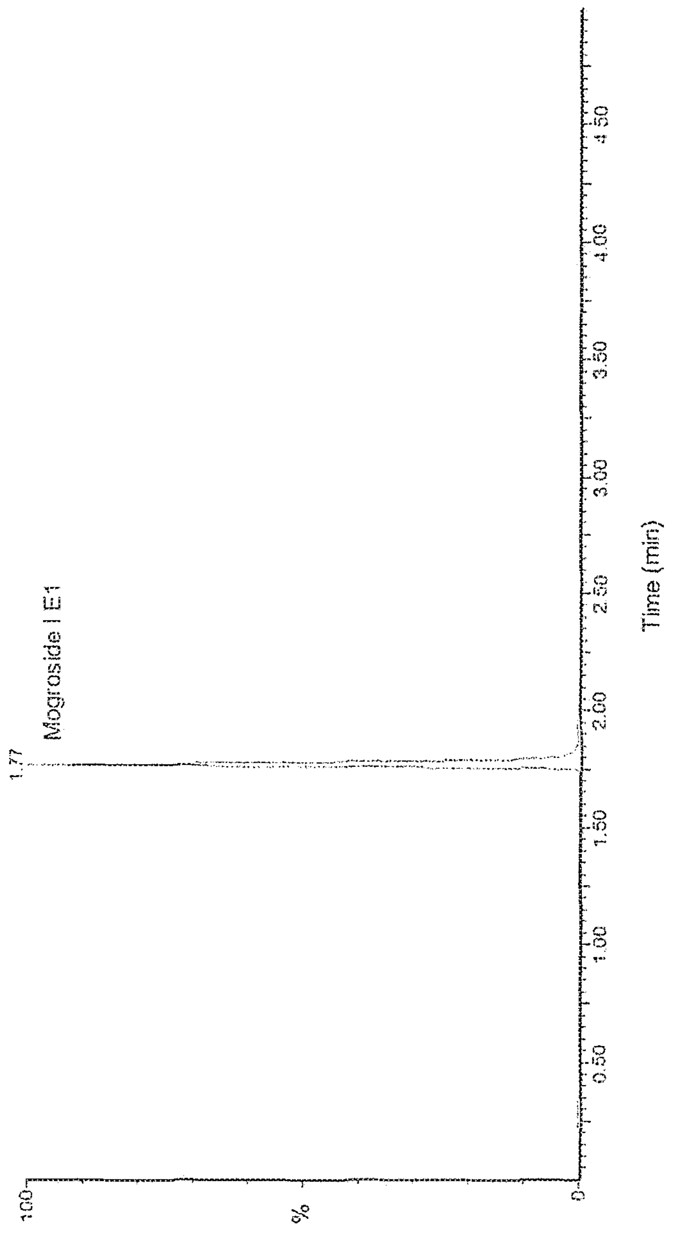
FIG. 13B shows mogroside I E1 produced by UGT430 (SEQ ID NO:61, SEQ ID NO:62), as described in Example 12.

Resulting LC-MS chromatograms are shown in FIG. 13. One large peak belonging to a compound of MW=683.5 was formed by UGT430 (FIG. 13B). The mass of this peak corresponds to a formic acid adduct of mono-glycosylated mogrol. This product has the identical retention time of the mogroside I E1 reference compound shown in FIG. 13A. UGT430 glycosylated mogrol efficiently and completely since no fed mogrol remained after the 2-day growth period of yeast expressing UGT430. Thus, the *S. grosvenorii* UGT430 is the UGT responsible for glycosylation of the hydroxy group on C-3 position of the mogrol molecule in the *S. grosvenorii* mogroside biosynthetic pathway.

Example 13: Glycosylation of Mogrol in *S. cerevisiae* by Expression of *S. grosvenorii* UGT1697

UGT1697 (SEQ ID NO:67, SEQ ID NO:68) of the 85A UGT family was cloned from synthetic DNA to obtain a sequence identical to that of *S. grosvenorii* UGT1697. The cloned gene was transformed into a yeast strain deleted of EXG1 and EXG2 (to prevent de-glycosylation of produced mogrosides. The yeast strain was grown in SC medium minus histidine for selection of plasmid maintenance, and comprising 10 μM mogrol. Cells were grown for 2 days at 30° C. with shaking at 140 rpm. After 2 days, 300 μL culture samples were mixed with 300 μL of 96% ethanol and incubated for 10 min at 80° C. Then, samples were centrifuged, and the supernatant was analyzed by LC-MS.

LC-MS analyses were performed using a Waters Acquity I-Class UPLC (Waters Corporation, Milford, Mass.) with Waters Acquity UPLC®BEH C18 column (2.1×50 mm, 1.7 μm particles, 130 Å pore size) coupled to a Waters Xevo TQD triple quadropole mass spectrometer with electrospray ionization (ESI) in negative mode. Compound separation was achieved by a gradient of the two mobile phases A (water with 0.1% formic acid) and B (MeCN with 0.1% formic acid) by increasing from 20% to 50% B between 0.3 to 2.0 min, increasing to 100% B at 2.01 min, holding 100% B for 0.6 min and re-equilibrating for another 0.6 min. The flow rate was 0.6 mL/min, and the column temperature 55° C. Mogroside I $E_1$ (m/z 683.5; $[M+FA]^-$) was monitored using SIR (Single Ion Recording) and compared with a standard.

Figures 14A, 14B:
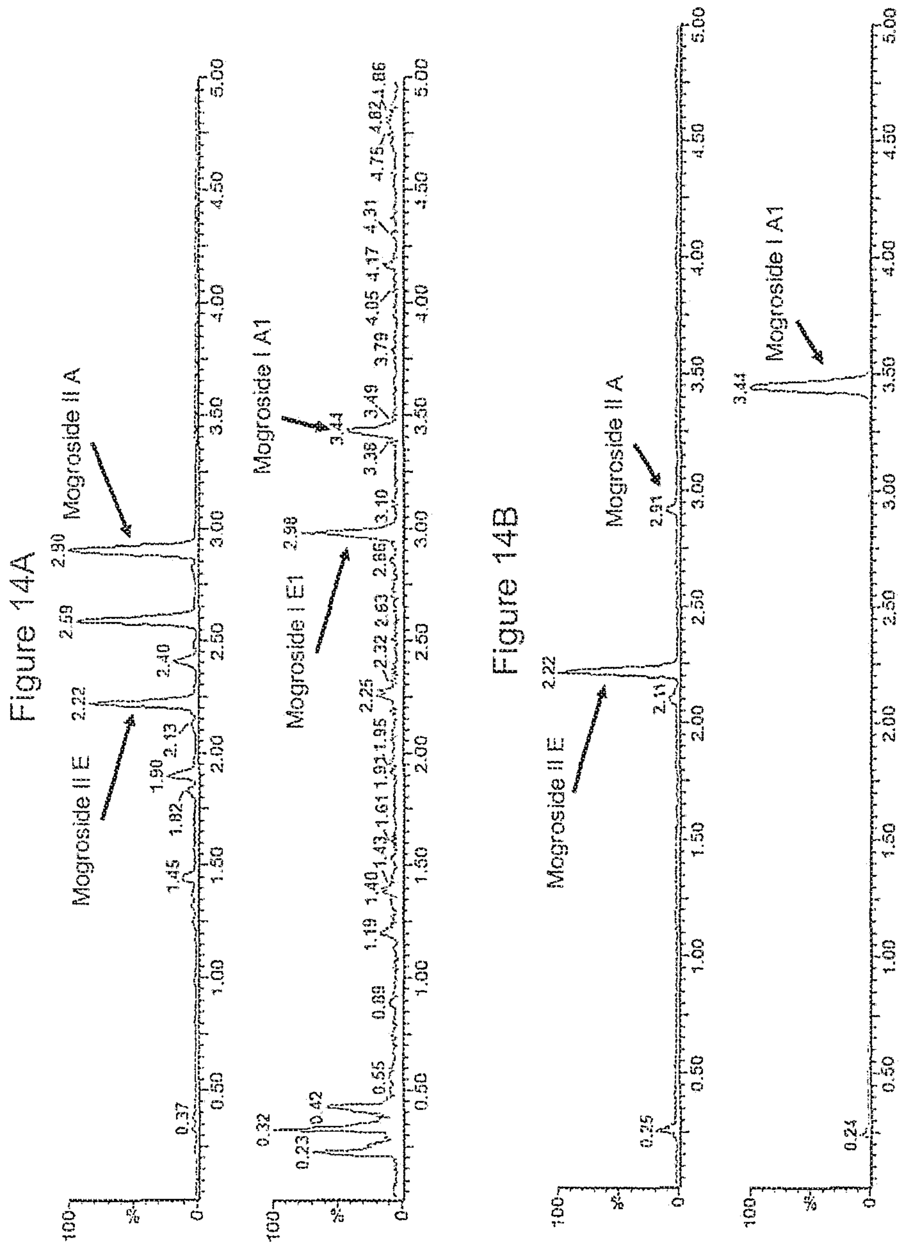
FIG. 14A shows elution of mogroside II E1, mogroside II A, mogroside I E1, and mogroside I A1 standards.
FIG. 14B shows mogroside I A1, mogroside II A, and mogroside II E1 produced by UGT1697 (SEQ ID NO:67, SEQ ID NO:68), as described in Example 13.

Resulting LC-MS chromatograms are shown in FIG. 14. One large peak belonging to a compound of MW=683.5 was formed by UGT1697 (FIG. 14B). The mass of this peak corresponds to a formic acid adduct of mono-glycosylated mogrol. The peak corresponds to mogroside I A1. See FIG. 14A. This result shows that the *S. grosvenorii* UGT1697 glycosylates the hydroxy group at the C-24 position of mogrol. UGT1576 also exhibits C-24 glycosylation of mogrol, as shown in Example 11.

Moreover, UGT1697 acts on the C-3 position as well, since the presence of mogroside II E (containing one glucose on position C-24 and one on C-3) was detected, as depicted in FIG. 14B (retention time of 2.22 min). Thus, UGT1697 glycosylates the C-3 and C-24 position on mogrol and is part of the *S. grosvenorii* mogroside biosynthetic pathway.

Example 14: Glycosylation of Mogrol and Mogrosides in *S. cerevisiae* by Expression of *S. grosvenorii* UGT11789, UGT98, UGT430, and UGT1576

The full-length sequence for UGT11789 (SEQ ID NO:69, SEQ ID NO:70, SEQ ID NO:71, SEQ ID NO:72) was cloned from synthetic DNA to obtain a sequence identical to that of *S. grosvenorii* UGT11789. A yeast strain deleted of EXG1 and EXG2 was co-transformed with UGT11789 (SEQ ID NO:69, SEQ ID NO:70, SEQ ID NO:71, SEQ ID NO:72), UGT430 (SEQ ID NO:61, SEQ ID NO:62), UGT1576 (SEQ ID NO:47, SEQ ID NO:48), and UGT98 (SEQ ID NO:51, SEQ ID NO:52, SEQ ID NO:53). Separately, a yeast strain deleted of EXG1 and EXG2 was co-transformed with UGT430 (SEQ ID NO:61, SEQ ID NO:62), UGT1576 (SEQ ID NO:47, SEQ ID NO:48), and UGT98 (SEQ ID NO:51, SEQ ID NO:52, SEQ ID NO:53). The yeast strains were grown in SC medium minus histidine, uracil, tryptophan, and leucine for selection of plasmid maintenance and comprising 10 μM mogrol. Cells were grown for 2 days at 30° C. with shaking at 140 rpm. After 2 days, 300 μL culture samples were mixed with 300 μL of 96% ethanol and incubated for 10 min at 80° C. Then, samples were centrifuged, and the supernatant was analyzed by LC-MS.

LC-MS analyses were performed using a Waters Acquity I-Class UPLC (Waters Corporation, Milford, Mass.) with Waters Acquity UPLC®BEH C18 column (2.1×50 mm, 1.7 μm particles, 130 Å pore size) coupled to a Waters Xevo TQD triple quadropole mass spectrometer with electrospray ionization (ESI) in negative mode. Compound separation was achieved by gradient I or gradient II. For gradient I, the initial buffer concentration of 80% mobile phase A (water with 0.1% formic acid) and 20% mobile phase B (MeCN with 0.1% formic acid) was increased from to 20% to 40% B between 0.3 to 2.0 min, increased to 100% B at 2.01 min, held at 100% B for 0.6 min, and re-equilibrated for another 0.6 min. For gradient II, the initial buffer concentration of 80% mobile phase A (water with 0.1% formic acid) and 20% mobile phase B (MeCN with 0.1% formic acid) was increased from to 20% to 50% B between 0.3 to 2.0 min, increased to 100% B at 2.01 min, held at 100% B for 0.6 min, and re-equilibrated for another 0.6 min. For both gradient I and gradient II, the flow rate was 0.6 mL/min, and the column temperature 55° C. Mogrol and mogrosides were monitored using SIR (Single Ion Recording) and compared with a commercially available mogroside mixture from plant extract (3W botanical extract. Inc.). The SIR traces were as follows: mogrol (m/z 521.4; $[M+FA-H]^-$), mogrol+1Glucose (m/z 683.5; $[M+FA-H]^-$), mogrol+2Glucose (m/z 799.5; $[M-H]^-$), mogrol+3Glucose (m/z 961.6; $[M-H]^-$), mogrol+4Glucose (m/z 1123.6; $[M-H]^-$) and mogrol+5Glucose (m/z 1285.66; $[M-H]^-$). Resulting LC-MS chromatograms are shown in FIG. 15.

Figure 15A:
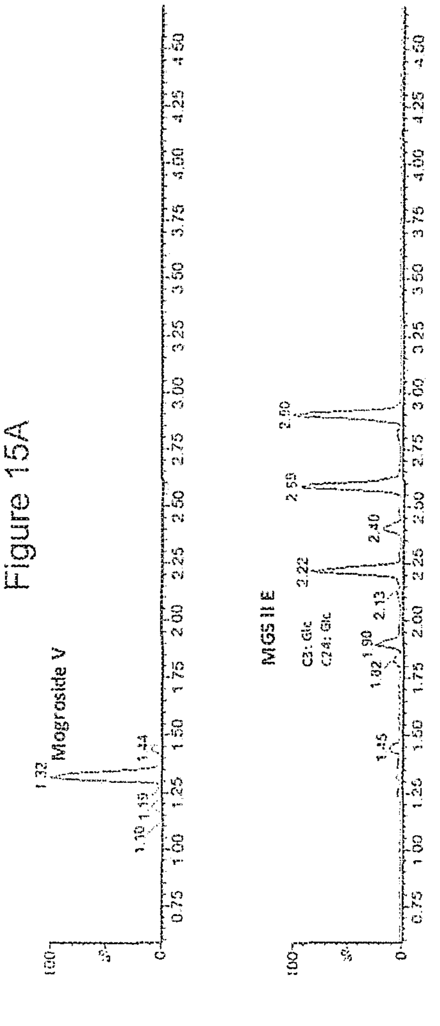
FIG. 15A shows elution of reference compounds mogroside V (top panel) and mogroside II E (bottom panel).
Figure 15B:
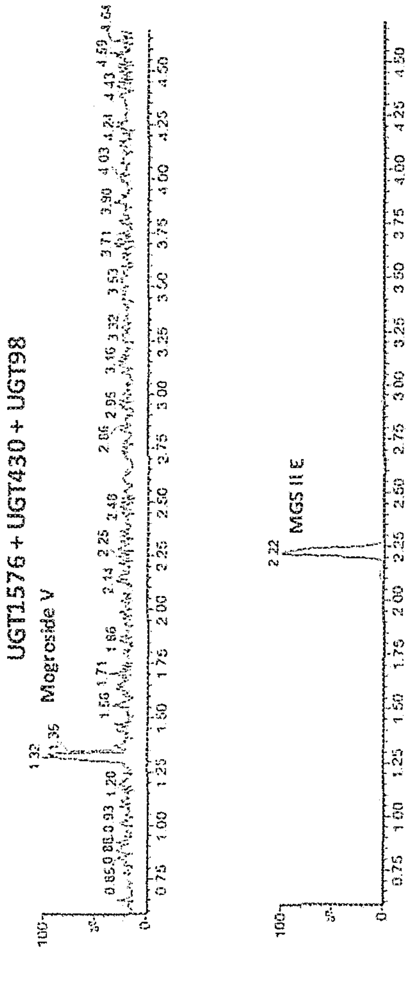
FIG. 15B shows production of mogroside V (top panel) and mogroside II E (bottom panel) in a yeast cell co-expressing UGT1576, UGT430, and UGT98.

FIG. 15A shows mogroside reference standards and indicates peaks corresponding to mogroside V and mogroside II E. Comparison of FIG. 15B and FIG. 15C demonstrates the effect of expression of the UGT11789 codon-optimized sequence A (SEQ ID NO:70, SEQ ID NO:72). FIG. 15B shows that mogroside II E produced upon co-expression of *S. grosvenorii* UGT1576 (SEQ ID NO:47, SEQ ID NO:48) and UGT430 (SEQ ID NO:61, SEQ ID NO:62) in an *S. cerevisiae* strain that was fed mogrol was converted to mogroside V by co-expression of the multifunctional UGT98 (SEQ ID NO:51, SEQ ID NO:52, SEQ ID NO:53). The intensity of the mogroside V peak in FIG. 15B was measured to be 8.65E3 (peak ion intensity in an LC-MS chromatogram). Co-expression of *S. grosvenorii* UGT1576 (SEQ ID NO:47, SEQ ID NO:48), UGT430 (SEQ ID NO:61, SEQ ID NO:62), UGT98 (SEQ ID NO:51, SEQ ID NO:52, SEQ ID NO:53) and UGT11789 (SEQ ID NO:70, SEQ ID NO:72) in an *S. cerevisiae* strain more efficiently converts fed mogrol to mogroside V, as shown in FIG. 15C.

Figure 15C:
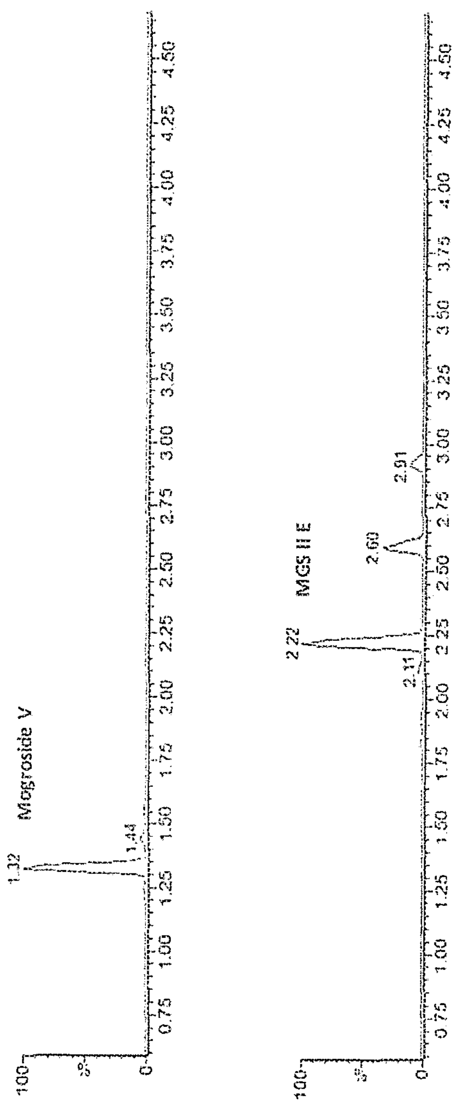
FIG. 15C shows production of mogroside V (top panel) and mogroside II E (bottom panel) in a yeast cell co-expressing UGT1576, UGT430, UGT98, and UGT11789, as described in Example 14.

The intensity of the mogroside V peak in FIG. 15C was measured to be 2.22E5 (peak ion intensity in an LC-MS chromatogram).

Figure 15D:
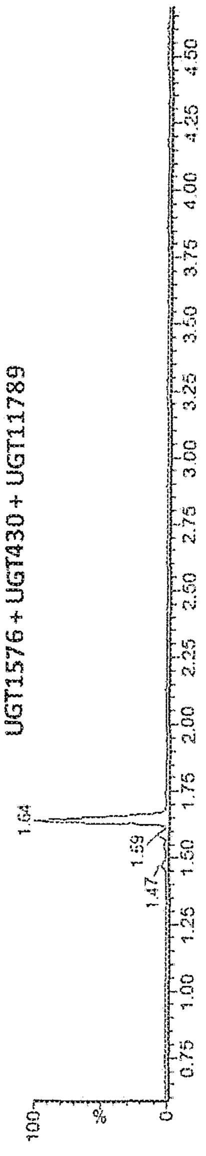
FIG. 15D shows production of a tri-glycosylated mogroside in a yeast cell co-expressing UGT1576, UGT430, and UGT11789, as described in Example 14.

This experiment shows that co-expressed *S. grosvenorii* UGT98 (SEQ ID NO:51, SEQ ID NO:52, SEQ ID NO:53) and UGT11789 (SEQ ID NO:69, SEQ ID NO:70, SEQ ID NO:71, SEQ ID NO:72) catalyze each of the glucose-glucose 1,2- and 1,6-attachments necessary for efficient mogroside V production in yeast. Mogroside II E can be glycosylated by UGT11789 to form a mogroside with 3 glucoses attached (FIG. 15D). Since UGT11789 is of the UGT91 family and cannot glycosylate the mogrol core, this glycosylation of mogroside IIE is by a 1,2-bond or 1,6-bond, and the product of UGT11789 is therefore mogroside III or mogroside IIIA2.

Example 15: Production of Mogrol in *S. cerevisiae* by Expression of *S. grosvenorii* CYP1798

CYP1798 was cloned from synthetic DNA to obtain sequence identical to that of *S. grosvenorii* CYP1798 (SEQ ID NO:5, SEQ ID NO:74). The nucleotide sequence was codon-optimized for expression in *S. cerevisiae* (SEQ ID NO:5). To increase the availability of oxidosqualene, the promoter of the endogenous ERG7 gene (SEQ ID NO:55) was disrupted to lower lanosterol synthase expression in an *S. cerevisiae* strain deleted of the TRP1 gene. To further increase oxidosqualene availability in *S. cerevisiae*, the squalene epoxidase encoded by ERG1 (SEQ ID NO:54) was overexpressed, and a truncated HMG reductase (tHMG1, SEQ ID NO:77, SEQ ID NO:78) was expressed. Integration of a codon-optimized optimized gene encoding *S. grosvenorii* cucurbitadienol synthase (SEQ ID NO:42, SEQ ID NO:43) and of a gene encoding *S. grosvenorii* CPR4497 (SEQ ID NO:45, SEQ ID NO:46) into the genome of the *S. cerevisiae* strain resulted in production of cucurbitadienol detectable by ESI LC-MS (FIG. 7B).

Subsequently, the cucurbitadienol-producing *S. cerevisiae* strain was transformed with plasmids carrying *S. grosvenorii* CYP5491 (SEQ ID NO:14, SEQ ID NO:44), *S. grosvenorii* CYP1798 (SEQ ID NO:5, SEQ ID NO:73, SEQ ID NO:74), and *S. grosvenorii* epoxide hydrolase 2 (SEQ ID NO:39, SEQ ID NO:40) and grown in SC medium minus uracil, leucin, histidine, and tryptophan for plasmid maintenance. Cells were grown for 4 days at 30° C. with shaking at 140 rpm. After 4 days, 300 μL of culture samples were mixed with 300 μL of 96% ethanol and incubated for 10 min at 80° C. Samples were then centrifuged, and the supernatant was analyzed by LC-MS. LC-MS analyses were performed using a Waters Acquity I-Class UPLC (Waters Corporation, Milford, Mass.) with Waters Acquity UPLC®BEH C18 column (2.1×50 mm, 1.7 μm particles, 130 Å pore size) coupled to a Waters Xevo TQD triple quadropole mass spectrometer with electrospray ionization (ESI) in negative mode. Compound separation was achieved by a gradient of the two mobile phases A (water with 0.1% formic acid) and B (MeCN with 0.1% formic acid) by increasing from 20% to 40% B between 0.3 to 3.5 min, increasing to 100% B within 1.0 min, holding 100% B for 1.0 min, and re-equilibrating for another 0.6 min. The flow rate was 0.6 mL/min, and the column temperature 55° C. Mogrol (m/z 521.4; $[M+FA-H]^-$) was monitored using SIR (Single Ion Recording) and compared with a standard.

Figure 16A:
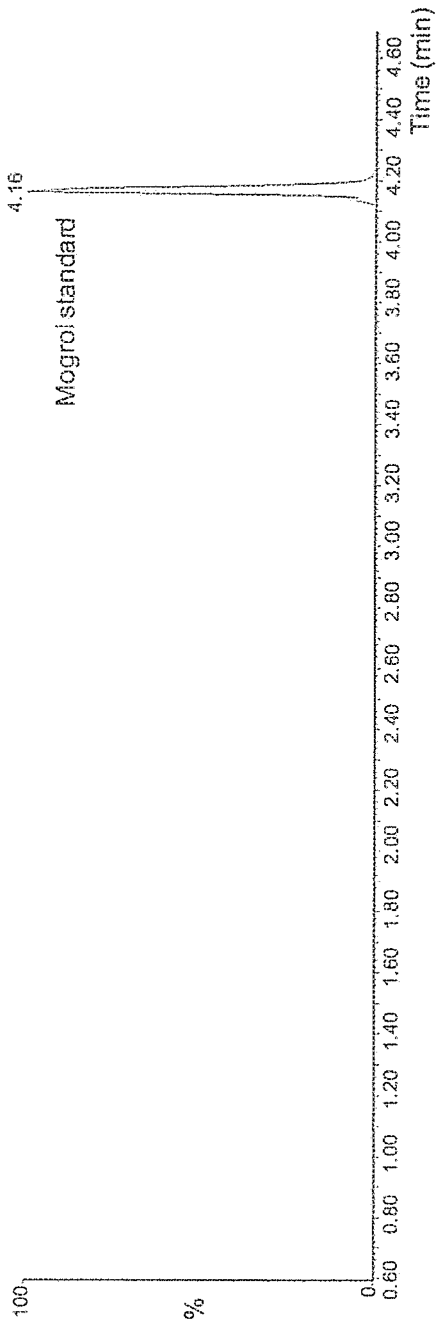
FIG. 16A shows elution of a mogrol standard.
Figure 16B:
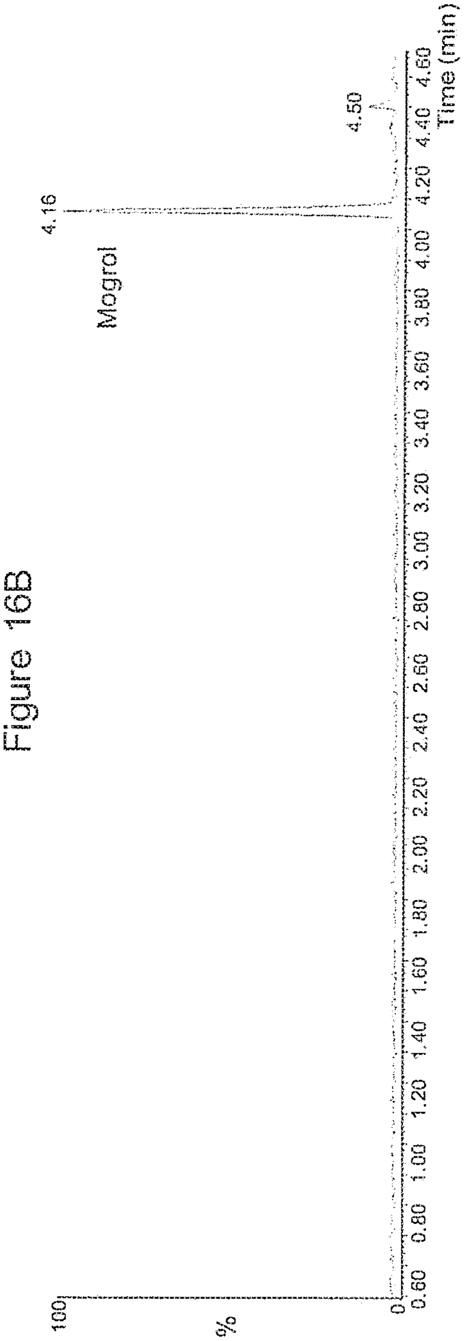
FIG. 16B shows mogrol produced in a cucurbitadienol-producing host expressing CYP5491 (SEQ ID NO:14, SEQ ID NO:44), CPR4497 (SEQ ID NO:45, SEQ ID NO:46), CYP1798 (SEQ ID NO:5, SEQ ID NO:73, SEQ ID NO:74), and an epoxide hydrolase, as described in Example 15.

Expression of *S. grosvenorii* cucurbitadienol synthase (SEQ ID NO:42, SEQ ID NO:43), CYP5491, CYP1798 (SEQ ID NO:5, SEQ ID NO:74), CPR4497 (SEQ ID NO:45, SEQ ID NO:46), and epoxide hydrolase 2 (SEQ ID NO:39, SEQ ID NO:40) resulted in production of mogrol (FIG. 16). Expression of CYP5491 alone in cucurbitadienol producing strain is shown in FIG. 8. Peaks of 11-hydroxy-cucurbitadienol (mass 443) and 11-oxo-cucurbitadienol (mass 441) are shown. Mogrol was only efficiently produced upon co-expression of CYP1798 with epoxide hydrolase 2. Thus, CYP1798 catalyzes the epoxidation of the 24-25 carbon double bonds of cucurbitadienol and/or 11-hydroxy-cucurbitadienol.

Example 16: Production of Mogroside V in *S. cerevisiae*

Mogroside V was produced in an EXG1 (SEQ ID NO:63, SEQ ID NO:64) knockout, Mat alpha derivative of *S. cerevisiae* S288C. *S. grosvenorii* cucurbitadienol synthase (SEQ ID NO:42, SEQ ID NO:43), CYP5491 (SEQ ID NO:81, SEQ ID NO:44), CYP1798 (SEQ ID NO:5, SEQ ID NO:74), CYP1798-II (SEQ ID NO:86, SEQ ID NO:74), CPR4497 (SEQ ID NO:82, SEQ ID NO:46), epoxide hydrolase 2 (SEQ ID NO:39, SEQ ID NO:40), UGT1576 (SEQ ID NO:83, SEQ ID NO:48), UGT430 (SEQ ID NO:84, SEQ ID NO:62), UGT1697 (SEQ ID NO:85, SEQ ID NO:68), UGT98 (SEQ ID NO:52, SEQ ID NO:53), and UGT11789 (SEQ ID NO:71, SEQ ID NO:72) were integrated in expression cassettes flanked by growth selection markers into the *S. cerevisiae* strain by homologous recombination in actively transcribed chromosomal regions. Codon-optimized *S. grosvenorii* cucurbitadienol synthase (SEQ ID NO:42, SEQ ID NO:43), CYP1798 (SEQ ID NO:5, SEQ ID NO:74), CPR4497 (SEQ ID NO:81, SEQ ID NO:46), and UGT98 (SEQ ID NO:52, SEQ ID NO:53) were synthesized by Genscript. Codon-optimized CYP5491 (SEQ ID NO:81, SEQ ID NO:44), UGT1576 (SEQ ID NO:83, SEQ ID NO:48), UGT430 (SEQ ID NO:84, SEQ ID NO:62), and UGT11789 (SEQ ID NO:71, SEQ ID NO:72) were synthesized as *S. cerevisiae* gBlocks® gene fragments (Integrated DNA Technologies). Codon-optimized CYP1798-H (SEQ ID NO:86, SEQ ID NO:74) and UGT1697 (SEQ ID NO:85, SEQ ID NO:68) and native CPR4497 (SEQ ID NO:45, SEQ ID NO:46) were synthesized as GeneArt® Strings™ DNA Fragments (Life Technologies). Codon-optimized epoxide hydrolase 1 (SEQ ID NO:37, SEQ ID NO:38) and epoxide hydroase 2 (SEQ ID NO:39, SEQ ID NO:40) were synthesized by DNA2.0.

Figure 17:
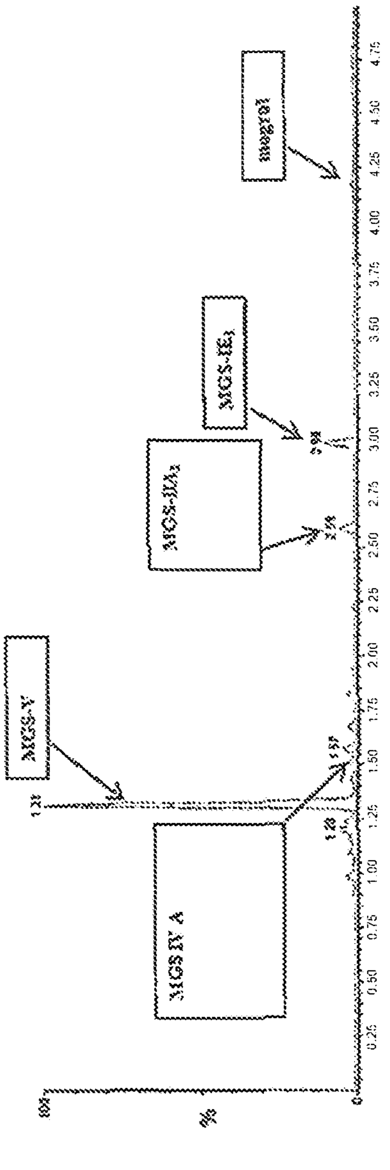
FIG. 17 shows a representative LC-MS chromatogram of a crude isolate of a mogroside V-producing *S. cerevisiae* strain, as described in Example 16.

The *S. cerevisiae* strain was grown for 5 days in SC medium at 30° C. The culture was then frozen with liquid nitrogen, and the residue was concentrated to near dryness. The residue was re-suspended in 50% (v/v) ethanol and heated to 55° C. for approximately 30 min. Afterwards, the suspension was centrifuged for 15 min at 4400 rpm and 4° C. The supernatant was filtered using a 0.22 μm SterilFlip filter (Millipore). FIG. 17 shows an LC-MS chromatogram of the mogroside V-producing strain after filtration. The crude product was then separated on a semi-preparative Agilent 1200 HPLC system. The system was equipped with a Synergi 4u Hydro RP 80 Å column (Phenomenex: column dimension 250×21.2 mm, 4 micron). Elution was carried out using a mobile phase of eluent B (Acetonitrile with 0.02% trifluoroacetic acid) and eluent A (water with 0.02% trifluoroacetic acid) by increasing the gradient linearly from 5% to 8% B from min 0.0 to 2.0, increasing linearly from 8% to 25% B from min 2.0 to 12.0, 25% to 50% B from min 12.0 to 20.0, 50% to 100% B from min 20.0 to 32.0, and finally washing with 100% B and re-equilibrating. A flow rate of 15 mL/min was used for the separation, which was conducted at room temperature. All fractions were analyzed by LC-MS, and fractions comprising a single mogroside compound were pooled and dried under vacuum.

Figure 18A:
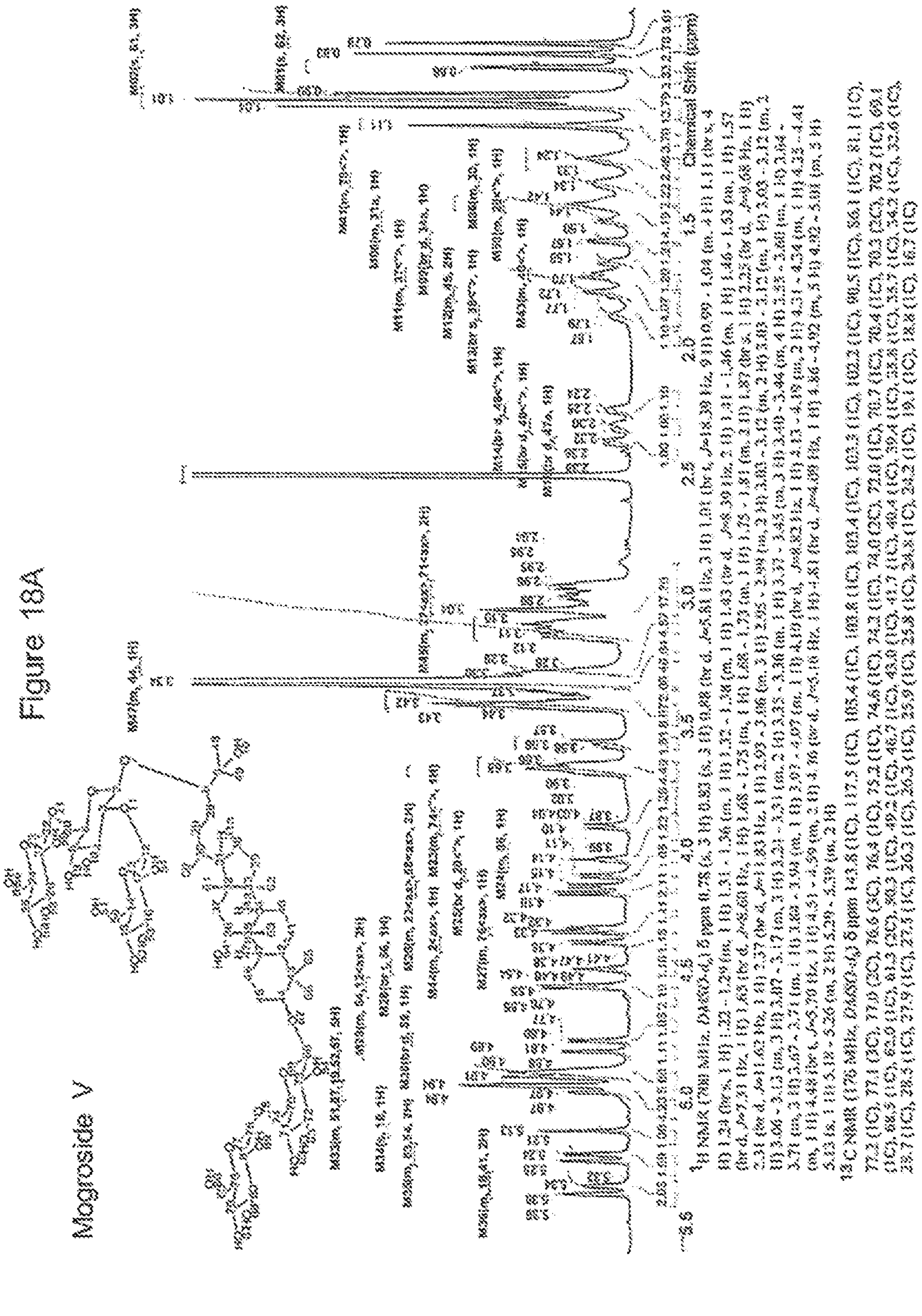
Figure 18B:
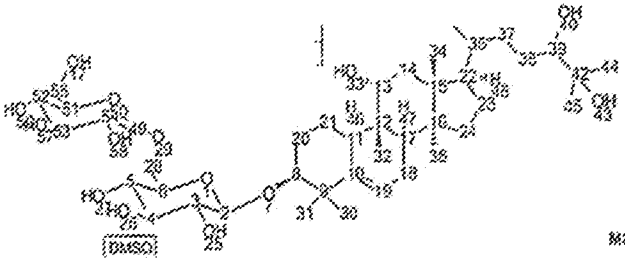
Figure 18B:
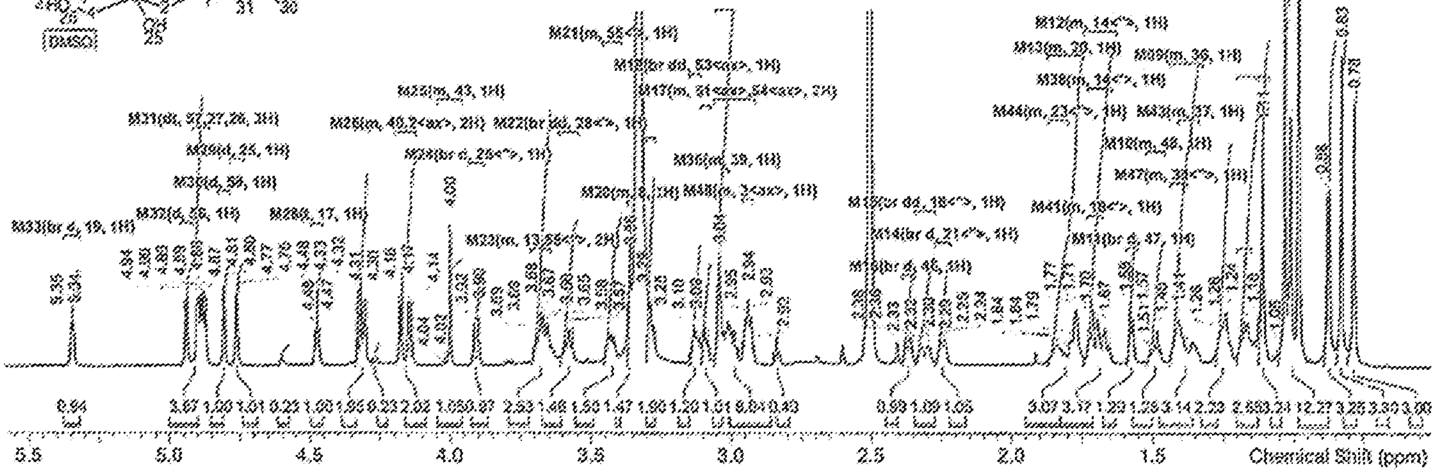
Figure 18D:
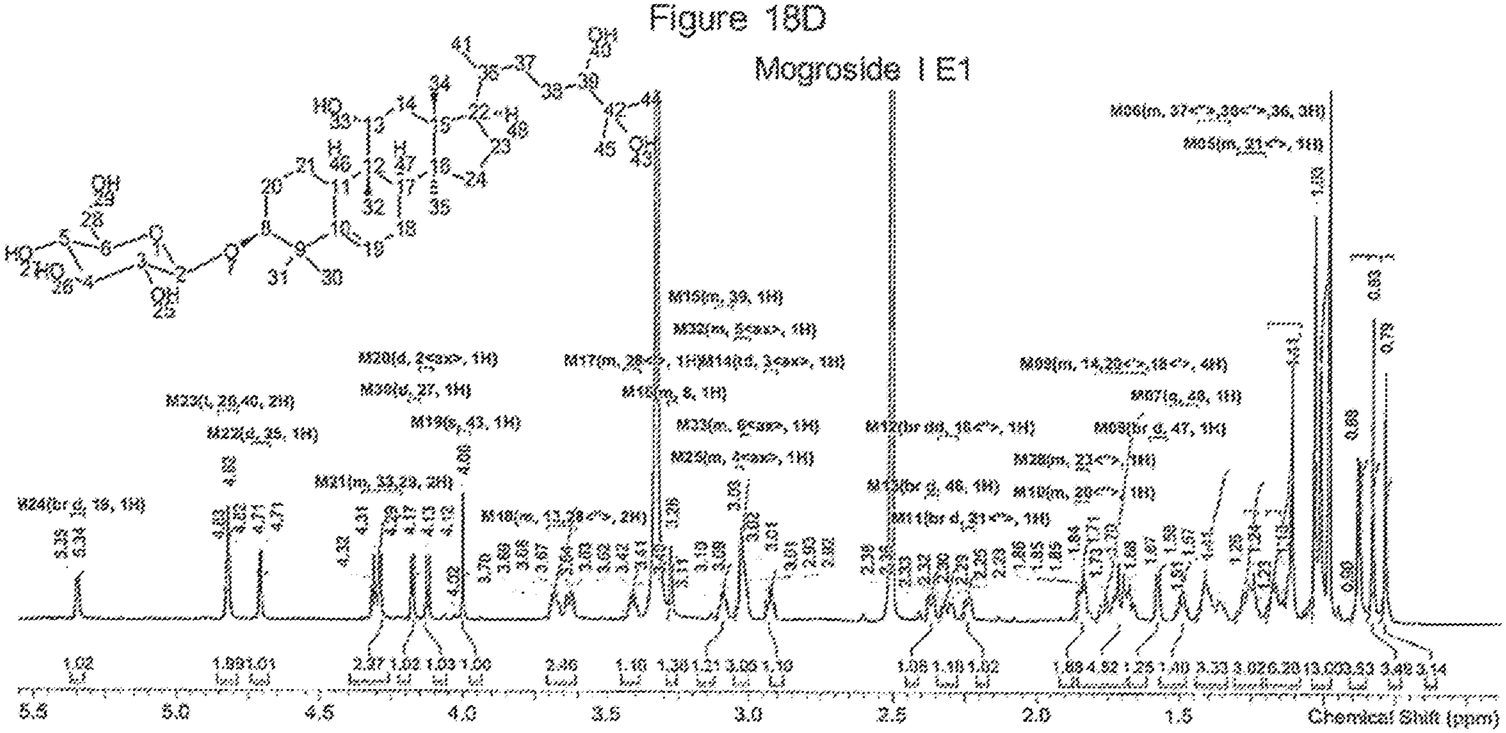
FIG. 18D shows an NMR-elucidated structure, $^{1}H$ NMR spectrum, and $^{1}H$ NMR chemical shifts (in ppm) for mogroside I E1, as described in Example 16.

The combined fractions were utilized for NMR analysis. All NMR experiments were performed in DMSO-d6 at 25° C. using a Bruker Avance III 600 MHz NMR spectrometer equipped with a 1.7 mm cryogenic TCI probe. The structures were solved by standard homo- and heteronuclear multipulse NMR experiments, namely $^{1}H,^{1}H$-COSY, $^{1}H,^{13}C$-HSQC, and $^{1}H,^{13}C$-HMBC experiments. Purified mogroside peaks from the *S. cerevisiae* production strain were confirmed to be mogroside I E1, mogroside II A2, mogroside IV A, and the major product, mogroside V. FIG. 18A shows an NMR-elucidated structure, $^{1}H$ NMR spectrum, and $^{1}H$ and $^{13}C$ NMR chemical shifts (in ppm) for mogroside V. FIG. 18B shows an NMR-elucidated structure, $^{1}H$ NMR spectrum, and $^{1}H$ and $^{13}C$ NMR chemical shifts (in ppm) for mogroside II A2. FIG. 18C shows an NMR-elucidated structure, $^{1}H$ NMR spectrum, and $^{1}H$ and $^{13}C$ NMR chemical shifts (in ppm) for mogroside IV A. FIG. 18D shows an NMR-elucidated structure, $^{1}H$ NMR spectrum, and $^{1}H$ chemical shifts (in ppm) for mogroside I E1.

TABLE 3

| Sequences disclosed herein (see also Table 2). |
|---|
| SEQ ID NO: 1 |
| *Cucurbita pepo* protein sequence |
| Met Trp Arg Leu Lys Val Gly Ala Glu Ser Val Gly Glu Glu Asp Glu |
| 1 5 10 15 |
| Lys Trp Val Lys Ser Val Ser Asn His Leu Gly Arg Gln Val Trp Glu |
| 20 25 30 |
| Phe Cys Ala Asp Ala Ala Ala Asp Thr Pro His Gln Leu Leu Gln Ile |
| 35 40 45 |
| Gln Asn Ala Arg Asn His Phe His His Asn Arg Phe His Arg Lys Gln |
| 50 55 60 |
| Ser Ser Asp Leu Phe Leu Ala Ile Gln Tyr Glu Lys Glu Ile Ala Lys |
| 65 70 75 80 |
| Gly Ala Lys Gly Gly Ala Val Lys Val Lys Glu Gly Glu Glu Val Gly |
| 85 90 95 |
| Lys Glu Ala Val Lys Ser Thr Leu Glu Arg Ala Leu Gly Phe Tyr Ser |
| 100 105 110 |
| Ala Val Gln Thr Arg Asp Gly Asn Trp Ala Ser Asp Leu Gly Gly Pro |
| 115 120 125 |
| Leu Phe Leu Leu Pro Gly Leu Val Ile Ala Leu His Val Thr Gly Val |
| 130 135 140 |
| Leu Asn Ser Val Leu Ser Lys His His Arg Val Glu Met Cys Arg Tyr |
| 145 150 155 160 |
| Leu Tyr Asn His Gln Asn Glu Asp Gly Gly Trp Gly Leu His Ile Glu |
| 165 170 175 |
| Gly Thr Ser Thr Met Phe Gly Ser Ala Leu Asn Tyr Val Ala Leu Arg |
| 180 185 190 |
| Leu Leu Gly Glu Asp Ala Asp Gly Gly Asp Gly Gly Ala Met Thr Lys |
| 195 200 205 |
| Ala Arg Ala Trp Ile Leu Glu Arg Gly Gly Ala Thr Ala Ile Thr Ser |
| 210 215 220 |
| Trp Gly Lys Leu Trp Leu Ser Val Leu Gly Val Tyr Glu Trp Ser Gly |
| 225 230 235 240 |
| Asn Asn Pro Leu Pro Pro Glu Phe Trp Leu Leu Pro Tyr Ser Leu Pro |
| 245 250 255 |
| Phe His Pro Gly Arg Met Trp Cys His Cys Arg Met Val Tyr Leu Pro |
| 260 265 270 |
| Met Ser Tyr Leu Tyr Gly Lys Arg Phe Val Gly Pro Ile Thr Pro Lys |
| 275 280 285 |
| Val Leu Ser Leu Arg Gln Glu Leu Tyr Thr Ile Pro Tyr His Glu Ile |
| 290 295 300 |
| Asp Trp Asn Lys Ser Arg Asn Thr Cys Ala Lys Glu Asp Leu Tyr Tyr |
| 305 310 315 320 |
| Pro His Pro Lys Met Gln Asp Ile Leu Trp Gly Ser Ile Tyr His Val |
| 325 330 335 |

TABLE 3-continued

| Sequences disclosed herein (see also Table 2). |
|---|

Tyr Glu Pro Leu Phe Thr Arg Trp Pro Gly Lys Arg Leu Arg Glu Lys
340 345 350

Ala Leu Gln Ala Ala Met Lys His Ile His Tyr Glu Asp Glu Asn Ser
355 360 365

Arg Tyr Ile Cys Leu Gly Pro Val Asn Lys Val Leu Asn Met Leu Cys
370 375 380

Cys Trp Val Glu Asp Pro Tyr Ser Asp Ala Phe Lys Leu His Leu Gln
385 390 395 400

Arg Val His Asp Tyr Leu Trp Val Ala Glu Asp Gly Met Arg Met Gln
405 410 415

Gly Tyr Asn Gly Ser Gln Leu Trp Asp Thr Ala Phe Ser Ile Gln Ala
420 425 430

Ile Val Ala Thr Lys Leu Val Asp Ser Tyr Ala Pro Thr Leu Arg Lys
435 440 445

Ala His Asp Phe Val Lys Asp Ser Gln Ile Gln Glu Asp Cys Pro Gly
450 455 460

Asp Pro Asn Val Trp Phe Arg His Ile His Lys Gly Ala Trp Pro Leu
465 470 475 480

Ser Thr Arg Asp His Gly Trp Leu Ile Ser Asp Cys Thr Ala Glu Gly
485 490 495

Leu Lys Ala Ser Leu Met Leu Ser Lys Leu Pro Ser Thr Met Val Gly
500 505 510

Glu Pro Leu Glu Lys Asn Arg Leu Cys Asp Ala Val Asn Val Leu Leu
515 520 525

Ser Leu Gln Asn Asp Asn Gly Gly Phe Ala Ser Tyr Glu Leu Thr Arg
530 535 540

Ser Tyr Pro Trp Leu Glu Leu Ile Asn Pro Ala Glu Thr Phe Gly Asp
545 550 555 560

Ile Val Ile Asp Tyr Pro Tyr Val Glu Cys Thr Ala Ala Thr Met Glu
565 570 575

Ala Leu Thr Leu Phe Lys Lys Leu His Pro Gly His Arg Thr Lys Glu
580 585 590

Ile Asp Thr Ala Ile Gly Lys Ala Ala Asn Phe Leu Glu Lys Met Gln
595 600 605

Arg Ala Asp Gly Ser Trp Tyr Gly Cys Trp Gly Val Cys Phe Thr Tyr
610 615 620

Ala Gly Trp Phe Gly Ile Lys Gly Leu Val Ala Ala Gly Arg Thr Tyr
625 630 635 640

Asn Ser Cys Leu Ala Ile Arg Lys Ala Cys Glu Phe Leu Leu Ser Lys
645 650 655

Glu Leu Pro Gly Gly Gly Trp Gly Glu Ser Tyr Leu Ser Cys Gln Asn
660 665 670

Lys Val Tyr Thr Asn Leu Glu Gly Asn Lys Pro His Leu Val Asn Thr
675 680 685

Ala Trp Val Leu Met Ala Leu Ile Glu Ala Gly Gln Gly Glu Arg Asp
690 695 700

Pro Ala Pro Leu His Arg Ala Ala Arg Leu Leu Met Asn Ser Gln Leu
705 710 715 720

Glu Asn Gly Asp Phe Val Gln Gln Glu Ile Met Gly Val Phe Asn Lys
725 730 735

Asn Cys Met Ile Thr Tyr Ala Ala Tyr Arg Asn Ile Phe Pro Ile Trp
740 745 750

TABLE 3-continued

Sequences disclosed herein (see also Table 2).

```
Ala Leu Gly Glu Tyr Cys His Arg Val Leu Thr Glu
        755                 760

SEQ ID NO: 2
```
*Siraitia grosvenorii* protein sequence

```
Leu Glu Arg Asn Arg Leu Cys Asp Ala Val Asn Val Leu Leu Ser Leu

1               5                   10                  15
Gln Asn Asp Asn Gly Gly Phe Ala Ser Tyr Glu Leu Thr Arg Ser Tyr

            20                  25                  30
Pro Trp Leu Glu Leu Ile Asn Pro Ala Glu Thr Phe Gly Asp Ile Val

        35                  40                  45
Ile Asp Tyr Pro Tyr Val Glu Cys Thr Ser Ala Thr Met Glu Ala Leu

    50                  55                  60
Thr Leu Phe Lys Lys Leu His Pro Gly His Arg Thr Lys Glu Ile Asp

65                  70                  75                  80
Thr Ala Ile Val Arg Ala Ala Asn Phe Leu Glu Asn Met Gln Arg Thr

                85                  90                  95
Asp Gly Ser Trp Tyr Gly Cys Trp Gly Val Cys Phe Thr Tyr Ala Gly

            100                 105                 110
Trp Phe Gly Ile Lys Gly Leu Val Ala Ala Gly Arg Thr Tyr Asn Asn

        115                 120                 125
Cys Leu Ala Ile Arg Lys Ala Cys Asp Phe Leu Leu Ser Lys Glu Leu

    130                 135                 140
Pro Gly Gly Gly Trp Gly Glu Ser Tyr Leu Ser Cys Gln Asn Lys Val

145                 150                 155                 160
Tyr Thr Asn Leu Glu Gly Asn Arg Pro His Leu Val Asn Thr Ala Trp

                165                 170                 175
Val Leu Met Ala Leu Ile Glu Ala Gly Gln Ala Glu Arg Asp Pro Thr

            180                 185                 190
Pro Leu His Arg Ala Ala Arg Leu Leu Ile Asn Ser Gln Leu Glu Asn

        195                 200                 205
Gly Asp Phe Pro Gln Gln Glu Ile Met Gly Val Phe Asn Lys Asn Cys

    210                 215                 220
Met Ile Thr Tyr Ala Ala Tyr Arg Asn Ile Phe Pro Ile Trp Ala Leu

225                 230                 235                 240
Gly Glu Tyr Cys His Arg Val Leu Thr Glu

                245                 250

SEQ ID NO: 3
```
*Siraitia grosvenorii* nucleotide sequence

```
atggaactct tctctaccaa aactgcagcc gagatcatcg ctgttgtctt gtttttctac     60
gctctcatcc ggctattatc tggaagattc agctctcaac agaagagact gccacctgaa    120
gccggtggcg cctggccact gatcggccat ctccatctcc taggtgggtc ggaacctgca    180
cataaaacct tggcgaacat ggcggacgcc tacggaccag tttttacgtt gaaactgggc    240
atgcatacag ctttggttat gagcagttgg gaaatagcga gagagtgctt tactaaaaac    300
gacagaatct ttgcctcccg ccccatagtc actgcctcaa agcttctcac ctataaccat    360
accatgtttg ggttcagcca atatggtcca ttctggcgcc atatgcgcaa aatagccacg    420
cttcaactcc tctcaaacca ccgcctcgag cagctccaac acatcagaat atcggaggtc    480
cagacttcga ttaagaaact gtacgagttg tgggtcaaca gcagaaataa tggaggcgag    540
aaagtgttgg tggagatgaa gacgtggttc ggaggcataa ccttgaacac catattcagg    600
atggtggtcg gaaagcgatt ctcgactgct ttcgaaggca gtggtggcga acggtatcgg    660
aaggcgttga gggattctct tgaatggttt ggggcattcg ttccgtcaga ttcattcccg    720
tttttaagat ggttggattt gggaggatat gagaaggcga tgaagaagac ggcgagtgtg    780
ctggacgagg tgcttgataa atggctcaaa gagcatcagc agaggagaaa ctccggtgaa    840
ctggagacgg aggagcacga cttcatgcac gtgatgctgt ctattgttaa ggatgatgaa    900
gaactatccg gctacgatgc cgatacagtc acaaaagcta catgtttgaa tttaatagtt    960
ggtggattcg acactacaca agtaactatg acatgggctc tttctttgct tctcaacaat   1020
gaagaggtat taaaaaaggc ccaacttgaa ctagacgaac aagttggaag agagaggttt   1080
gtggaagagt ccgatgttaa aaatctgtta tatctccagg ccatcgtgaa ggaaactttg   1140
cgtttgtacc cttcagcgcc aatctcgaca tttcatgagg ccatggaaga ttgcactgtt   1200
tctggctacc acatcttttc agggacgcgt ttgatggtga atcttcaaaa gcttcaaaga   1260
```

TABLE 3-continued

Sequences disclosed herein (see also Table 2).

```
gatccacttg catgggagga tccatgtgac tttcgaccgg agagatttct gacaactcat  1320
aaggatttcg atcttagagg acatagtcct caattgatac catttgggag tggtcgaaga  1380
atatgccctg gcatctcgtt tgccattcaa gttttgcatc ttacgcttgc aaatctactt  1440
catgggtttg acattggaag gccatctcat gaaccaatcg atatgcagga gagtaaagga  1500
ctaacgagta ttaaaacaac tccacttgag gttgttttag ctccacgcct tgctgctcaa  1560
gtttatgagt ga                                                      1572
```

SEQ ID NO: 4
*Siraitia grosvenorii* nucleotide SEQUENCE

```
atgccgatcg cagaaggtgc agtctctgat ttgtttggtc gcccactctt ctttgcacta    60
tatgattggt tcttagagca tggatctgtt tataaacttg cctttggacc aaaagccttt   120
gttgttgtat cagatcccat tgtggcaaga tatattcttc gagaaaatgc atttggttat   180
gacaagggag tgcttgctga tattttagaa ccgataatgg gtaaaggact aataccagct   240
gaccttggca cttggaagca gaggagacga gttattgctc caggattcca tgccttgtac   300
ttggaagcta tgaccaaagt atttgccaat tgttcagaac gatcaatatt gaaattggag   360
aagcttctag gagaaggtga actacaggag aataaaacca ttgagttgga tatggaagca   420
gagttttcaa gtttggctct tgatatcatt ggactcggtg ttttcaacta tgattttggt   480
tctgtaacca aagaatctcc ggtgattaag gctgtatatg ggactctttt tgaagcagag   540
catagatcga ctttctatat cccatattgg aaagtacctt tggcaaggtg gatagtccca   600
aggcagcgta aattccatgg tgaccttaag gttattaatg agtgtcttga tggcctaata   660
cgcaacgcaa gagaaacccg agacgaaacg gatgttgaga aattgcagca aagggactac   720
ttaaatctca aggatgccag tcttttgcgt ttcttagttg atatgcgggg agctgatgtt   780
gatgatcgcc agcttaggga cgatctgatg acgatgctta ttgctggcca tgaaacaact   840
gctgctgtgc ttacatgggc tgtttttttg cttgcacaaa atccttcaaa aatgaaaaaa   900
gcgcaagcag agattgattt ggttcttggc atggggaggc caacttttga atcatttaaa   960
gcattgaagt acatcagact tatcgttgca gagactcttc gtttgtttcc tcagcctcca  1020
ttgctgataa gacgagctct caaatcagat atattaccag gaggatacaa tggtgacaaa  1080
actggatatg caattcctgc agggactgac atcttcatct ctgtttacaa tctccacaga  1140
tctccctact tctgggataa tcctcaagaa tttgaaccag agagatttca agtaaagagg  1200
gcaagcgagg gaattgaagg atgggatggt ttcgacccat ctagaagccc tggagctcta  1260
tacccgaatg agattgtagc agacttttcc ttcttaccat ttggtggagg ccctagaaaa  1320
tgtgtgggag atcaatttgc tctaatggag tcaactatag cattggccat gttactgcag  1380
aagtttgatg tggagctaaa aggaagtcca gaatctgtag aactagttac tggagccaca  1440
atacatacca aaagtgggtt gtggtgcaaa ctgagaagaa gatcacaagt aaactga     1497
```

SEQ ID NO: 5
Codon-optimized DNA sequence encoding CYP1798

```
atggaaatgt cctcaagtgt cgcagccaca atcagtatct ggatggtcgt cgtatgtatc    60
gtaggtgtag gttggagagt cgtaaattgg gtttggttga gaccaaagaa attggaaaag   120
agattgagag aacaaggttt ggccggtaat tcttacagat tgttgttcgg tgacttgaag   180
gaaagagctg caatggaaga acaagcaaat tcaaagccta taaacttctc ccatgacatc   240
ggtccaagag ttttcccttc aatgtacaag accatccaaa actacggtaa aaactcctac   300
atgtggttag gtccataccc tagagtccac atcatggatc cacaacaatt gaagaccgtt   360
tttactttgg tctacgacat tcaaaagcca aatttgaacc ctttgattaa attcttgtta   420
gatggtatcg ttacacatga aggtgaaaag tgggctaagc acagaaagat tattaaccca   480
gcattccatt tggaaaagtt gaaggatatg atacctgctt tctttcactc atgtaatgaa   540
atcgtcaacg aatgggaaag attgatttca aaagaaggtt cctgcgaatt ggatgtaatg   600
ccttatttgc aaaatttggc cgctgacgcc atttcaagaa ccgcttttgg ttcttcatac   660
gaagaaggta aaatgatctt ccaattgttg aaggaattga ctgatttggt tgtcaaggta   720
gcttttggtg tttatattcc aggttggaga ttcttgccta caaagagtaa caacaaaatg   780
aaggaaatta atagaaaaat caagtctttg ttgttgggta tcattaacaa gagacaaaag   840
gcaatggaag aaggtgaagc cggtcaatct gatttgttgg gtatattaat ggaaagtaat   900
tctaacgaaa tccaaggtga aggtaataac aaggaagatg gcatgtctat tgaagacgtc   960
atcgaagagt gtaaggtatt ttatataggt ggtcaagaaa ctacagcaag attattgatc  1020
tggactatga tattgttgtc cagtcataca gaatggcaag aaagagccag aaccgaagtc  1080
ttgaaggtat ttggtaataa gaaaccagat ttcgacggtt tgtcaagatt gaaggtagtt  1140
actatgatct tgaacgaagt tttaagattg tacccacctg cttccatgtt gacaagaatc  1200
atccaaaagg aaacaagagt tggtaaatta accttgccag caggtgttat cttgataatg  1260
cctatcatct tgatacatag agatcacgac ttgtggggtg aagatgctaa cgagtttaaa  1320
ccagaaagat tcagtaaagg tgtttctaag gcagccaaag tccaaccagc ctttttccct  1380
tttggttggg gtcctagaat ttgcatgggt caaaacttcg ctatgatcga agctaagatg  1440
gcattgagtt tgatcttgca aagattttct ttcgaattgt cttcatccta cgttcatgca  1500
ccaactgtcg tcttcactac acaaccacaa cacggtgccc acatcgtttt gagaaagtta  1560
tga                                                                1563
```

SEQ ID NO: 6
*Siraitia grosvenorii* nucleotide sequence

```
atggaaccac aaccaagtgc ggaattcaac tggaatcaca gcctaagcac cgtcgctatc    60
ggtgtcattg ccattatttt cttccgtttt ctcgtcaaaa gagtcaccgg cgccggtgag   120
cgaaagggtc cgaagccgcc aaaagtagcc ggagggtggc ctctaattgg ccacctccct   180
ctcctcggag gacctgaact gccccatgtc aaactgggtg gtttggctga taaatatggt   240
ccaatcttct cgatccggct gggtgtccac tccgccgtcg tgataaacag ttgggaggcg   300
gcgaaacagt tattaaccaa ccatgacgtc gccgtctctt cccgccccca aatgctcggc   360
ggaaaactcc tgggctacaa ctacgccgtg tttggtttcg gaccctacgg ctcttactgg   420
cgcaacatgc gcaagataac cacgcaagag cttctatcca atagcagaat ccagctccta   480
agagacgttc gagcgtcaga agtgaaccaa ggcataaaag agctctacca gcactggaaa   540
gaaagaagag acggtcacga ccaagccttg gtggaactgc agcagtgggt cggggacttg   600
actatgaatc tgattctcgg agtcatcgcc gggaaaaggt tctttggagc tgcagcaacg   660
```

TABLE 3-continued

Sequences disclosed herein (see also Table 2).

```
gtagacgagg aagaggcgcg acggagccat aaagcattga aggagttgtt acattatatg   720
gggctttttc tactgggtga tgctgttcca tatctaggat ggttggacgt cggcggccat   780
gtgaaggcga tgaagaaaac ttcaaaagaa ttggaccgta tgttaacaca gtggttggag   840
gagcacaaga aggaaggacc caagaaagat cataaagact tcatggacgt gatgctttca   900
gttctcaatg aaacatccga tgttctttca gataagaccc atggcttcga tgctgatacc   960
atcatcaaag ctacatgtat gacgatggtt ttaggaggga gtgatacgac ggcggtggtt  1020
gtgatatggg caatctcgct gctgctgaat aatcgccctg cgttgagaaa agtgcaagaa  1080
gaactggaag cccatatcgg ccgagacaga gaactggagg aatcggatct cggtaagcta  1140
gtgtatttgc aggcagtcgt gaaggagaca ttgcggctgt acggagccgg aggccttttc  1200
tttcgtgaaa ccacagagga tgtcaccatc gacggattcc atgtcgagaa agggacatgg  1260
ctgttcgtga acgtggggaa gatccacaga gatgggaagg tgtggccgga gccaacggag  1320
ttcaaaccgg agaggtttct gacgacccac aaagatttgg atctgaaggg ccagcggttt  1380
gagctcatcc ctttcggggg aggaagaaga tcgtgccctg gaatgtcttt tgggctccaa  1440
atgctacagc ttattttggg taaactgctt caggcttttg atatatcgac gccgggggac  1500
gccgccgttg atatgaccgg atccattgga ctgacgaaca tgaaagccac tccattggaa  1560
gtgctcatca ccccgcgctt gcctctttcg ctttacgatt ga                     1602
```

SEQ ID NO: 7
*Siraitia grosvenorii* DNA sequence

```
atggagactc ttcttcttca tcttcaatcg ttatttcatc caatttcctt cactggtttc    60
gttgtcctct ttagcttcct gttcctgctc cagaaatggt tactgacacg tccaaactct   120
tcatcagaag cctcaccccc ttctccacca aagcttccca tcttcggaca ccttctaaac   180
ctgggtctgc atccccacat caccctcgga gcctacgctc gccgctatgg ccctctcttc   240
ctcctccact tcggcagcaa gcccaccatc gtcgtctctt ctgccgaaat cgctcgcgat   300
atcatgaaga cccacgacct cgtcttcgcc aaccgtccta aatcaagcat cagcgaaaag   360
attctttacg gctccaaaga tttagccgca tctccttacg gcgaatactg gaggcagatg   420
aaaagcgttg gcgtgcttca tcttttgagc aacaaaaggg ttcaatcctt tcgctctgtc   480
agagaagaag aagtcgaact gatgatccag aagatccaac agaacccccct atcagttaat   540
ttaagcgaaa tattctctgg actgacgaac gacatagttt gcagggtggc tttagggaga   600
aagtatggcg tgggagaaga cggaaagaag ttccggtctc ttctgctgga gtttggggaa   660
gtattgggaa gtttcagtac gagagacttc atcccgtggc tgggttggat tgatcgtatc   720
agtgggctgg acgccaaagc cgagagggta gccaaagagc tcgatgcttt ctttgacaga   780
gtgatcgaag atcacatcca tctaaacaag agagagaata atcccgatga gcagaaggac   840
ttggtggatg tgctgctttg tgtacagaga gaagactcca tcgggtttcc ccttgagatg   900
gatagcataa aagctttaat cttggacatg tttgctgcag gcacagacac gacatacacg   960
gtgttggagt gggcaatgtc ccaactgttg agacacccag aagcgatgaa gaaactgcag  1020
agggaggtca gagaaatagc aggtgagaaa gaacacgtaa gtgaggatga tttagaaaag  1080
atgcattact tgaaggcagt aatcaaagaa acgctgcggc tacacccacc aatcccactc  1140
ctcgtcccca gagaatcaac ccaagacatc aggttgaggg ggtacgatat cagaggcggc  1200
acccgggtta tgatcaatgc atgggccatc ggaaga                            1236
```

SEQ ID NO: 8
*Siraitia grosvenorii* DNA sequence

```
atgtcgatga gtagtgaaat tgaaagcctc tgggttttcg cgctggcttc taaatgctct    60
gctttaacta aagaaaacat cctctggtct ttactcttct ttttcctaat ctgggtttct   120
gtttccattc tccactgggc ccatccgggc ggcccggctt ggggccgcta ctggtggcgc   180
cgccgccgca gcaattccac cgccgctgct attcccggcc cgagaggcct ccccctcgtc   240
ggcagcatgg gcttgatggc cgacttggcc caccaccgga ttgccgccgt ggctgactcc   300
ttaaacgcca cccgcctcat ggccttttcg ctcggcgaca ctcgcgtgat cgtcacatgc   360
aaccccgacg tcgccaaaga gattctcaac agctccctct tcgccgaccg ccccgttaag   420
gagtccgctt actccttgat gttcaaccgc gccattgggt tcgcccccta tggcctttac   480
tggcggaccc tccgccgcat cgcttcccac cacctcttct gccccaagca aatcaagtcc   540
tcccagtccc agcgccgcca aatcgcttcc caaatggtcg caatgttcgc aaaccgcgat   600
gccacacaga gcctctgcgt tcgcgactct ctcaagcggg cttctctcaa caacatgatg   660
ggctctgttt tcggccgagt ttacgacctc tctgactcgg ctaacaatga cgtccaagaa   720
ctccagagcc tcgtcgacga aggctacgac ttgctgggcc tcctcaactg gtccgaccat   780
ctcccatggc tcgccgactt cgactctcag aaaatccggt tcagatgctc ccgactcgtc   840
cccaaggtga accacttcgt cggccggatc atcgccgaac accgcgccaa atccgacaac   900
caagtcctag atttcgtcga cgttttgctc tctctccaag aagccgacaa actctctgac   960
tccgatatga tcgccgttct ttgggaaatg atttttcgtg ggacggacac ggtggcagtt  1020
ttaatcgagt ggatactggc caggatggta cttcacaacg atatccaaag gaaagttcaa  1080
gaggagctag ataacgtggt tgggagtaca cgcgccgtcg cggaatccga cattccgtcg  1140
ctggtgtatc taacggctgt ggttaaggaa gttctgaggt tacatccgcc gggcccactc  1200
ctgtcgtggg cccgcctagc catcactgat acaatcatcg atgggcatca cgtgccccgg  1260
gggaccaccg ctatggttaa catgtggtcg atagcgcggg acccacaggt ctggtcggac  1320
ccactcgaat ttatgcccca gaggtttgtg tccgaccccg gtgacgtgga gttctcggtc  1380
atgggttcgg atctccggct ggctccgttc gggtcgggca gaaggacctg ccccgggaag  1440
gccttcgcct ggacaactgt caccttctgg gtggccacgc ttttacacga cttcaaatgg  1500
tcgccgtccg atcaaaacga cgccgtcgac ttgtcggagg tcctcaagct ctcctgcgag  1560
atggccaatc ccctcaccgt taaagtacac ccaaggcgca gtttaagctt ttaa        1614
```

SEQ ID NO: 9
*Siraitia grosvenorii* DNA sequence

```
atggatggtt ttcttccaac agtggcggcg agcgtgcctg tgggagtggg tgcaatattg    60
ttcacggcgt tgtgcgtcgt cgtgggaggg gttttggttt atttctatgg accttactgg   120
ggagtgagaa gggtgcctgg tccaccagct attccactgg tcggacatct tcccttgctg   180
gctaagtacg gcccagacgt tttctctgtc cttgccaccc aatatggccc tatcttcagg   240
ttccatatgg gtaggcagcc attgataatt atagcagacc ctgagctttg taaagaagct   300
```

TABLE 3-continued

Sequences disclosed herein (see also Table 2).

ggtattaaga aattcaagga catcccaaat agaagtgtcc cttctccaat atcagcttcc 360
cctcttcatc agaagggtct tttcttcaca agggatgcaa gatggtcgac aatgcggaac 420
acgatattat cggtctatca gtcctcccat ctagcgagac taatacctac tatgcaatca 480
atcattgaaa ctgcaactca aaatctccat tcctctgtcc aggaagacat ccctttctcc 540
aatctctccc tcaaattgac caccgatgtg attggaacag cagccttcgg tgtcaacttt 600
gggctctcta atccacaggc aaccaaaact tgtgctacca acggccaaga caacaaaaat 660
gacgaagttt cagacttcat caatcaacac atctactcca caacgcagct caagatggat 720
ttatcaggtt ccttctcaat catacttgga ctgcttgtcc ctatactcca agaaccattt 780
agacaagtcc taaagagaat accattcacc atggactgga aagtggaccg gacaaatcag 840
aaattaagtg gtcggcttaa tgagattgtg gagaagagaa tgaagtgtaa cgatcaaggt 900
tcaaaagact tcttatcgct cattttgaga gcaagagagt cagagacagt atcaaggaat 960
gtcttcactc cagactacat cagtgcagtt acgtatgaac acctacttgc tgggtcggct 1020
accacggcgt ttacgttgtc ttctattgta tatttagttg ctgggcatcc agaagtcgag 1080
aagaagttgc tagaagagat tgacaacttt ggtccatccg atcagatacc aacagctaat 1140
gatcttcatc agaagtttcc atatcttgat caggtgatta aagaggctat gaggttctac 1200
actgtttccc ctctagtagc cagagaaaca gctaaagatg tggagattgg tggatatctt 1260
cttccaaagg ggacatgggt ttggttagca cttggagttc ttgccaagga tccaaagaac 1320
tttccagaac cagataaatt caaaccagag aggtttgatc caaatgaaga agaggagaaa 1380
caaaggcatc cttatgcttt aatccccttt ggaattggtc ctcgagcatg cattggtaaa 1440
aaattcgccc ttcaggagtt gaagctctcg ttgattcatt tgtacaggaa gtttgtattt 1500
cggcat 1506

SEQ ID NO: 10
*Siraitia grosvenorii* DNA sequence
atggaaatca ttttatcata tctcaacagc tccatagctg gactcttcct cttgcttctc 60
ttctcgtttt ttgttttgaa aaaggctaga acctgtaaac gcagacagcc tcctgaagca 120
gccggcggat ggccgatcat cggccacctg agactgctcg gggttcgca acttccccat 180
gaaaccttgg gagccatggc cgacaagtat ggaccaatct tcagcatccg agttggtgtc 240
cacccatctc ttgttataag cagttgggaa gtggctaaag agtgctacac caccctcgac 300
tcagttgtct cttctcgtcc caagagtttg ggtggaaagt tgttgggcta caacttcgcc 360
gcttttgggt tcaggcctta tgattccttt taccggagta tccgcaaaac catagcctcc 420
gaggtgctgt cgaaccgccg tctggagttg cagagacaca ttcgagtttc tgaggtgaag 480
agatcggtga aggagcttta caatctgtgg acgcagagag aggaaggctc agaccacata 540
cttattgatg cggatgaatg gattggtaat attaatttga acgtgattct gatgatggtt 600
tgtgggaagc ggtttcttgg cggttctgcc agcgatgaga aggagatgag gcggtgtctc 660
aaagtctcga gagatttctt cgatttgaca gggcagttta cggtgggaga tgccattcct 720
ttcctgcgat ggctggattt gggtggatat gcgaaggcga tgaagaaaac tgcaaaagaa 780
atggactgtc tcgttgagga atggctggaa gaacaccgcc ggaagagaga ctccggcgcc 840
accgacggtg aacgtgactt catggatgtg atgctttcga ttcttgaaga gatggacctt 900
gctggctacg acgctgacac agtcaacaaa gccacatgcc tgagcattat ttctgggga 960
atcgatacta taacgctaac tctgacatgg gcgatctcgt tattgctgaa caatcgagag 1020
gcactgcgaa gggttcaaga ggaggtggac atccatgtcg gaaacaaaag gcttgtggat 1080
gaatcagact tgagcaagct ggtgtatctc caagccgtcg tgaaagagac attaaggttg 1140
tacccagcag ggccgctgtc gggagctcga gagttcagtc gggactgcac ggtcggaggg 1200
tatgacgtgg ccgccggcac acggctcatc acaaaccttt ggaagataca gacggaccct 1260
cgggtgtggc cggagccact tgagttcagg ccggagaggt ttctgagcag ccaccagcag 1320
ttggatgtga agggccagaa ctttgaactg gccccatttg gttgtggaag aagagtgtgc 1380
cctggggcgg ggcttggggt tcagatgacg cagttggtgc tggcgagtct gattcattcg 1440
gtggaacttg gaactcgctc cgatgaagcg gtggacatgg ctgctaagtt tggactcaca 1500
atgtacagag ccacccctct tcaggctctc gtcaagccac gcctccaagc cggtgcttat 1560
tcatga 1566

SEQ ID NO: 11
*Siraitia grosvenorii* DNA sequence
atgggtgtat tgtccatttt attattcaga tattccgtca agaagaagcc attaagatgc 60
ggtcacgatc aaagaagtac cacagatagt ccacctggtt caagaggttt gccattgata 120
ggtgaaactt tgcaattcat ggctgctatt aattctttga acggtgtata cgatttcgtt 180
agaataagat gtttgagata cggtagatgc tttaagacaa gaatcttcgg tgaaacccat 240
gtttttgtct caactacaga atccgctaag ttgatcttga aggatggtgg tgaaaaattc 300
accaaaaagt acatcagatc aatcgctgaa ttggttggtg acagaagttt gttatgtgca 360
tctcatttgc aacacaagag attgagaggt ttgttgacta atttgttttc tgccacattc 420
ttggcttctt tcgtaactca attcgatgaa caaatcgttg aagcttttag atcatgggaa 480
tccggtagta ccataatcgt tttgaacgaa gcattgaaga tcacttgtaa ggccatgtgc 540
aaaatggtca tgtccttaga aagagaaaac gaattggaag ctttgcaaaa ggaattgggt 600
catgtttgtg aagctatgtt ggcatttcca tgcagattcc ctggtacaag atttcacaat 660
ggtttgaagg caagaagaag aatcattaaa gttgtcgaaa tggccattag agaaagaaga 720
agatctgaag ctcctagaga agatttcttg caaagattgt tgacagaaga aaaggaagaa 780
gaagacggtg gtggtgtttt aagtgatgcc gaaattggtg acaacatatt gacaatgatg 840
atcgcaggtc aagataccac tgcctctgct attacctgga tggtcaagtt tttggaagaa 900
aaccaagatg tattgcaaaa cttaagagac gaacaattcg aaatcatggg taaacaagaa 960
ggttgtggtt catgcttctt gacattagaa gatttgggta atatgtccta tggtgcaaaa 1020
gtagttaagg aatcattgag attagcctcc gtcgtaccat ggtttcctag attggtttta 1080
caagattctt tgatccaagg ttacaaaatt aaaaagggtt ggaacgtcaa catagacgta 1140
agatctttac attcagatcc atccttgtat aatgacccaa caaagtttaa ccctagtaga 1200
ttcgatgacg aagctaaacc ttactcattt ttggcattcg gtatgggtgg tagacaatgt 1260
ttgggtatga acatggcaaa ggccatgatg ttggttttct tgcacagatt ggtcacctca 1320
ttcagatgga aggttataga ttccgactct tcaatcgaaa aatgggcttt gttctctaag 1380
ttgaagtcag gttgccctat cgtagttacc cacatcggtt cctaa 1425

TABLE 3-continued

Sequences disclosed herein (see also Table 2).

SEQ ID NO: 12
*Siraitia grosvenorii* DNA sequence
```
atggatttct actggatctg tgttcttctg ctttgcttcg catggttttc cattttatcc    60
cttcactcga gaacaaacag cagcggcact tccaaacttc ctcccggacc gaaacccttg   120
ccgatcatcg gaagcctttt ggctctcggc cacgagcccc acaagtcttt ggctaatctc   180
gctaaatctc atggccctct tatgacctta aagctcggcc aaatcaccac cgtcgtagtt   240
tcctccgctg ccatggctaa gcaagttctc caaacgcacg accagtttct gtccagcagg   300
accgttccag acgcaatgac ctctcacaac cacgatgctt tcgcactccc atggattccg   360
gtttcacccc tctggcgaaa ccttcgacga atatgcaaca accagttgtt tgccggcaag   420
attctcgacg ccaacgagaa tctccggcga accaaagtgg ccgagctcgt atccgatatc   480
tcgagaagtg cattgaaagg tgagatggtg gattttggaa acgtggtgtt cgtcacttcg   540
ctcaatctgc tttccaatac gattttctcg gtggatttct tcgacccaaa ttctgaaatt   600
gggaaagagt tcaggcacgc agtacgaggc ctcatggaag aagctgccaa accaaatttg   660
ggggattatt tccctctgct gaagaagata gatcttcaag gaataaagag gagacagacc   720
acttacttcg atcgggtttt taatgttttg gagcacatga tcgaccagcg tcttcagcag   780
cagaagacga cgtctggttc tacctccaac aacaacaacg acttactgca ctaccttctc   840
aacctcagca acgaaaatag cgacatgaaa ttgggggaaac ttgagctgaa acacttctta   900
ttggtgctat tcgtcgctgg gactgaaacg agttctgcaa cactgcaatg ggcaatggca   960
gaactactaa gaaacccaga aaagttagca aaagctcaag cggagaccag gcgggtgatt  1020
gggaaaggga acccaattga agaatcagac atttcgaggc tgccttatct gcaagcagtg  1080
gtgaaagaaa ctttcagatt gcacacacca gcgccatttc tactgccgcg caaagcacta  1140
caggacgtgg aaattgcagg tttcacagtc ccaaaggacg ctcaggtact ggtaaattta  1200
tgggctatga gcagagattc aagcatctgg gagaacccag agtggttcga gccagaaagg  1260
tttttggagt cggagctgga cgttagaggg agagattttg agctgatccc gttcggcggt  1320
gggcggagga tttgccccgg tctgccgttg gcgatgagaa tgttgcattt gattttgggt  1380
tctctcatcc acttctttga ttggaagctt gaagatgggt gtcggccgga agacgtgaaa  1440
atggacgaaa agcttggcct cactctggag ttggcttttc ccctcacagc cttgcctgtc  1500
cttgtctaa                                                          1509
```

SEQ ID NO: 13
*Siraitia grosvenorii* DNA sequence
```
atgtcctcct gcggtggtcc aactcctttg aatgttatcg gtatcttatt acaatcagaa    60
tcctccagag cctgcaactc agacgaaaac tcaagaattt tgagagattt cgtaacaaga   120
gaagttaacg ctttcttatg gttgtccttg atcactatca cagcagtttt gatcagtaaa   180
gttgtcggtt tgtttagatt gtggtctaag gcaaagcaat tgagaggtcc accttgtcca   240
tcattctacg gtcattctaa gatcatctca agacaaaatt tgactgattt gttatatgac   300
tcccacaaaa agtacggtcc agtagttaaa ttgtggttag gtcctatgca attgttagtc   360
tccgtaaagg aaccaagttt gttgaaggaa atattggtta aagctgagga taagttgcct   420
ttaacaggta gagcctttag attggctttc ggtagatctt cattatttgc atccagtttc   480
gaaaaggttc aaaacagaag acaaagattg gccgaaaagt tgaataagat cgcattccaa   540
agagccaaca tcattccaga aaaggccgta gcttgtttca tgggtagagt tcaagatttg   600
atgatagaag aatctgtcga ctgtaataag gtttctcaac atttggcttt tactttgtta   660
ggttgcacat tgtttggtga cgccttctta ggttggtcta aggctacaat ctatgaagaa   720
ttgttgatga tgatcgctaa ggacgcatcc ttttgggcta gttatagagt taccccaatc   780
tggaagcaag gtttctggag ataccaaaga ttgtgtatga agttgaagtg cttgactcaa   840
gatatcgttc aacaatacag aaagcattac aagttgtttt ctcactcaca aaaccaaaac   900
ttacacaacg aaaccaagtc aactggtgtt gaagtcgctt ttgatattcc accttgtcct   960
gctgcagacg ttagaaattc ttgctttttc tacggtttga acgatcatgt taacccaaac  1020
gaagaacctt gtggtaatat tatgggtgtc atgtttcacg gttgcttgac tacaacctct  1080
ttgatcgcat caatcttgga aagattggcc actaacccag aaatccaaga aaagattaat  1140
tctgaattga acttagttca aaagggtcca gtcaaggatc atagaaagaa tgttgacaac  1200
atgcctttgt tattggcaac aatctatgaa tcagctagat tattgccagc aggtccttta  1260
ttgcaaagat gtcctttgaa gcaagatttg gttttgaaaa caggtatcac cattccagct  1320
ggtaccttgg tcgtagttcc tattaaattg gttcaaatgg atgactcttc atggggttca  1380
gatgccaatg agtttaatcc atacagattc ttgtccatgg cttgtaatgg tattgacatg  1440
atacaaagaa ccccttttagc tggtgaaaac attggtgacc aaggtgaagg ttcatttgtc  1500
ttgaatgacc caattggtaa cgtaggtttc ttaccttttg gtttcggtgc aagagcctgc  1560
gttggtcaaa agtttataat ccaaggtgtc gctactttgt tcgcaagttt gttggcccat  1620
tacgaaatta aattgcaatc cgagagtaag aatgattcta aaccatccag taacacctct  1680
gccagtcaaa tcgtcccaaa ctcaaaaatc gtattcgtaa gaagaaactc ataa        1734
```

SEQ ID NO: 14
*Siraitia grosvenorii* DNA sequence
```
atgtggactg tcgtgctcgg tttggcgacg ctgtttgtcg cctactacat ccattggatt    60
aacaaatgga gagattccaa gttcaacgga gttctgccgc cgggcaccat gggtttgccg   120
ctcatcggag agacgattca actgagtcga cccagtgact ccctcgacgt tcaccctttc   180
atccagaaaa aagttgaaag atacgggccg atcttcaaaa catgtctggc cggaaggccg   240
gtggtggtgt cggcggacgc agagttcaac aactacataa tgctgcagga aggaagagca   300
gtggaaatgt ggtatttgga tacgctctcc aaatttttcg gcctcgacac cgagtggctc   360
aaagctctgg gcctcatcca caagtacatc agaagcatta ctctcaatca cttcggcgcc   420
gaggccctgc gggagagatt tcttcctttt attgaagcat cctccatgga agcccttcac   480
tcctggtcta ctcaacctag cgtcgaagtc aaaaatgcct ccgctctcat ggtttttagg   540
acctcggtga ataagatgtt cggtgaggat gcgaagaagc tatcgggaaa tatccctggg   600
aagttcacga agcttctagg aggatttctc agtttaccac tgaatttccc cggcaccacc   660
taccacaaat gcttgaagga tatgaaggaa atccagaaga agctaagaga ggttgtagac   720
gatagattgg ctaatgtggg ccctgatgtg gaagatttct tggggcaagc ccttaaagat   780
aaggaatcag agaagttcat ttcagaggag ttcatcatcc aactgttgtt ttctatcagt   840
```

TABLE 3-continued

Sequences disclosed herein (see also Table 2).

```
tttgctagct ttgagtccat ctccaccact cttactttga ttctcaagct ccttgatgaa   900
cacccagaag tagtgaaaga gttggaagct gaacacgagg cgattcgaaa agctagagca   960
gatccagatg gaccaattac ttgggaagaa tacaaatcca tgacttttac attacaagtc  1020
atcaatgaaa ccctaaggtt ggggagtgtc acacctgcct tgttgaggaa aacagttaaa  1080
gatcttcaag taaaaggata cataatcccg gaaggatgga caataatgct tgtcaccgct  1140
tcacgtcaca gagacccaaa agtctataag gaccctcata tcttcaatcc atggcgttgg  1200
aaggacttgg actcaattac catccaaaag aacttcatgc cttttggggg aggcttaagg  1260
cattgtgctg gtgctgagta ctctaaagtc tacttgtgca ccttcttgca catcctctgt  1320
accaaatacc gatggaccaa acttggggga ggaaggattg caagagctca tatattgagt  1380
tttgaagatg ggttacatgt gaagttcaca cccaaggaat ga                     1422
```

SEQ ID NO: 15
*Siraitia grosvenorii* DNA sequence

```
atgaagatga agatggaatc catgcgcacc tccctggata tctccgacca tgacatactt    60
ccaagggttt atcctcatgt tcacctatgg atcaacaaat atgggaaaaa cttcattcag   120
tggaatggca acgtagctca gttgattgtt tcggatcctg acacgatcaa ggagatactc   180
caaaaccgag aacaagctgt tcccaaaata gatctcagcg gagatgcacg gaggatattc   240
gggaatgggc tttcgacttc tgacggtgaa aaatgggcta aggctcgaag aatcgctgat   300
tacgctttcc acggggatct cctaagaaat atggggccaa ccatggtttc ctgtgctgag   360
gcaatggtgg aaaagtggaa gcatcatcaa ggcaaagagc ttgatttgtt cgaagagttt   420
aaggtgctca cttcagatat cattgcacat acagcctttg gaagcagtta tttggaaggg   480
aaagttattt ttcagactct aagtaagctg agcatgatat tatttaagaa tcagttcaaa   540
cgaaggattc ctgttatcag caagttcttc agatcaaagg atgcgaggga gggagaggag   600
ctggaaagaa ggttgaaaaa ttccataatt tcaataatgg aaaagagaga agagaaggtg   660
ataagtggtg aagcagataa ctatggtaat gattttcttg gattactttt gaaggcaaag   720
aatgagcctg accagaggca gaggatttct gttgatgatg tagtggatga atgcaaaaca   780
gtttacttcg ctgggcaaga aactacaagt gttttgcttg cttggaccgc ctttctttta   840
gcaactcatg agcattggca agaagaagca agaaaggaag tgctgaatat gtttggcaac   900
aagaatccaa ctttagaagg catcacaaaa ttaaagatta tgagcatgat catcaaggaa   960
tctctaagat tatatcctcc agccccgccc atgtcaagga aggttaaaaa ggaagtcaga  1020
ttggggaagc tggttctccc ccccaacatt caagtaagca tctcaactat tgcagttcat  1080
catgatactg caatatgggg tgaagatgcc catgtattca aaccagaaag attttctgaa  1140
ggaacagcta aagatatccc atcagctgca tacatcccat ttggctttgg tcctcgaaac  1200
tgcatcggca atatcttggc catcaacgaa actaagattg cactgtcgat gattctacaa  1260
cgatttttctt tcaccatctc cccggcctac gtccacgcac ctttccagtt cctcactatc  1320
tgcccccaac acggggttca ggtaaagctt cagtccctat taagtgaaag gtga        1374
```

SEQ ID NO: 16
*Siraitia grosvenorii* DNA sequence

```
atggaagctg aatttggtgc cggtgctact atggtattat ccgttgtcgc aatcgtcttc    60
tttttcacat ttttacactt gtttgaatct ttctttttga agccagatag attgagatct   120
aagttgagaa agcaaggtat tggtggtcca tctccttcat ttttgttggg taatttgtca   180
gaaattaaat ccatcagagc tttgtcttca caagctaaga acgcagaaga tgcctctgct   240
ggtggtggtg gtggttccgc cagtatagct catggttgga cttcaaattt gtttcctcac   300
ttagaacaat ggagaaacag atatggtcca attttcgtat actccagtgg tacaatccaa   360
atcttgtgta tcacagaaat ggaaaccgtt aaggaaatct ctttgtcaac ctccttgagt   420
ttaggtaaac ctgctcattt gtctaaggat agaggtccat tgttaggttt gggtatctta   480
gcctcttcag gtcctatttg ggttcaccaa agaaagatca tcgctccaca attgtatttg   540
gataaagtaa agggtatgac ctcattgatg gttgaaagtg caaattctat gttaagatcc   600
tgggaaacta aagttgaaaa tcatggtggt caagccgaaa ttaacgtcga tggtgacttg   660
agagcattaa gtgccgatat catttctaag gcttgctttg gttcaaacta ttccgaaggt   720
gaagaaattt tcttgaagtt gagagcattg caagttgtca tgagtaaggg ttctattggt   780
atacctggtt ttagatacat accaactaaa aataacagag aaatgtggaa gttggaaaag   840
gaaatcgaat caatgatctt gaaggttgcc aacgaaagaa cacaacattc cagtcacgaa   900
caagatttgt tgcaaatgat tttggaaggt gcaaagtctt tgggtgaaga caataagagt   960
atgaacatat caagagacaa gtttattgtt gacaattgta agaacatcta tttcgctggt  1020
catgaaacta cagctataac cgcatcttgg tgcttgatgt tgttagctgc acaccctgat  1080
tggcaagcaa gagccagatc tgaagtttta caatgttgcg atgacagacc aatcgatgca  1140
gacacagtca aaaatatgaa gaccttgact atggtaattc aagaaacttt gagattgtac  1200
ccacctgctg tattcgttac aagacaagca ttagaagata tcagattcaa aaacatcaca  1260
ataccaaagg gtatgaactt tcatatacca atccctatgt tgcaacaaga cttccactta  1320
tggggtcctg atgcttgttc atttgaccca caaagattct ccaatggtgt cttaggtgca  1380
tgcaaaaacc cacaagccta tatgcctttt ggtgttggtc caagagtctg tgccggtcaa  1440
catttcgcta tgatcgaatt gaaagtcatc gtatcattgg ttttgtccag attcgaattt  1500
tctttgtcac cttcctacaa gcattcacca gccttcagat tagttgtcga accagaaaac  1560
ggtgtcatat tgcatgtcag aaagttgtga                                   1590
```

SEQ ID NO: 17
*Siraitia grosvenorii* DNA sequence

```
atggaagtgg atatcaatat cttcaccgtc ttttccttcg tattatgcac agtcttcctc    60
ttctttctat ccttcttgat cctcctcctc ctccgaacgc tcgccggaaa atccataacg   120
agctccgagt acacgccagt gtacggcacc gtctacggtc aggctttcta tttcaacaac   180
ctgtacgatc atctaacgga ggtggccaag agacatcgaa ccttccggct gcttgcgccg   240
gcatacagcg agatatacac gaccgatccg agaaacatcg agcatatgtt gaagacgaaa   300
ttcgataagt attcgaaagg aagcaaggat caagaaatcg ttggggatct gtttggagag   360
gggatatttg cagtcgatgg agataagtgg aagcagcaga ggaagctggc tagctatgaa   420
ttctcgacga ggattcttag ggattttagc tgctcggttt tcagacgaag tgctgctaaa   480
cttgttggag ttgtttcgga gttttccagc atgggtcggg tttttgatat ccaggatttg   540
```

TABLE 3-continued

Sequences disclosed herein (see also Table 2).

```
ctaatgcggt gcgctttgga ctccattttc aaagtggggt tcggggttga tttgaattgc   600
ttggaggaat caagcaaaga agggagcgat ttcatgaaag ccttcgatga ttctagcgct   660
cagatttttt ggcgctatat cgatcccttc tggaaattga agagattgct taacatcggt   720
tccgaagctt cgtttaggaa caacataaaa accatagatg cttttgtgca ccagttgatc   780
agagacaaga gaaaattgct tcagcaaccg aatcacaaga atgacaaaga ggacatactt   840
tggaggtttc tgatggaaag tgagaaggat ccaacaagaa tgaatgatca atatctaagg   900
gatatagtcc tcaatttcat gttggctggc aaagattcaa gtggaggaac tctgtcctgg   960
ttcttctaca tgctatgcaa gaacccttta atacaggaaa aagttgcaga agaagtgagg  1020
caaattgttg cgtttgaagg ggaagaagtt gacatcaatt tgttcataca aaacttaact  1080
gattcagctc ttgacaaaat gcattatctt catgcagcat tgaccgagac tctgaggcta  1140
tatcctgcag tccctttgga tggaaggact gcagaaatag atgacattct tcctgatggc  1200
tataaactaa gaaaagggga tggagtatac tacatggcct attccatggg caggatgtcc  1260
tccctttggg gagaagatgc tgaagatttt aaacccgaaa gatggcttga aagtggaact  1320
tttcaacccg aatcaccttt caaattcatc gcttttcatg cgggtcctcg aatgtgtttg  1380
ggaaaagagt ttgcttatcg acaaatgaag atagtatctg ctgctttgct tcaatttttt  1440
cgattcaaag tagctgatac aacgaggaat gtgacttata ggatcatgct tacccttcac  1500
attgatggag gtctccctct tcttgcaatt ccgagaatta gaaaatttac ctaa        1554
```

SEQ ID NO: 18

*Siraitia grosvenorii* DNA sequence

```
ttggatagtg gagttaaaag agtgaaacgg ctagttgaag agaaacggcg agcagaattg    60
tctgcccgga ttgcctctgg agaattcaca gtcgaaaaag ctggttttcc atctgtattg   120
aggagtggct tatcaaagat gggtgttccc agtgagattc tggacatatt atttggtttc   180
gttgatgctc aagaagaata tcccaagatt cccgaagcaa aaggatcagt aaatgcaatt   240
cgtagtgagg ccttcttcat acctctctat gagctttatc tcacatatgg tggaatattt   300
aggttgactt ttgggccaaa gtcattcttg atagtttctg atccttccat tgctaaacat   360
atactgaagg ataatccgag gaattattct aagggtatct tagctgaaat tctagagttt   420
gtcatgggga agggacttat accagctgac gagaagatat ggcgtgtacg aaggcgggct   480
atagtcccat ctttgcatct gaagtatgta ggtgctatga ttaatctttt tggagaagct   540
gcagataggc tttgcaagaa gctagatgct gcagcatctg atggggttga tgtggaaatg   600
gagtccctgt tctcccgttt gactttagat atcattggca aggcagtttt taactatgac   660
tttgattcac ttacaaatga cactggcata gttgaggctg tttacactgt gctaagagaa   720
gcagaggatc gcagtgttgc accaattcca gtatgggaaa ttccaatttg gaaggatatt   780
tcaccacggc aaaaaaaggt ctctaaagcc ctcaaattga tcaacgacac cctcgatcaa   840
ctaattgcta tatgcaagag gatggttgat gaggaggagc tgcagtttca tgaggaatac   900
atgaatgagc aagatccaag catccttcat ttccttttgg catcaggaga tgatgtttca   960
agcaagcagc ttcgtgatga cttgatgact atgcttatag ctgggcatga aacatctgct  1020
gcagttttaa catggacctt ttatcttctt tccaaggagc cgaggatcat gtccaagctc  1080
caggaggagg ttgattcagt ccttggggat cggtttccaa ctattgaaga tatgaagaac  1140
ctcaaatatg ccacacgaat aattaacgaa tccttgaggc tttacccaca gccaccagtt  1200
ttaatacgtc gatctcttga caatgatatg ctcgggaagt accccattaa aaagggtgag  1260
gacatattca tttctgtttg gaacttgcat cgcagtccaa aactctggga tgatgcggat  1320
aaatttaatc ctgaaaggtg gcctctggat ggacccaatc caaatgagac aaatcaaaat  1380
ttcagatatt taccttttgg tggcggacca cggaaatgtg tgggagacat gtttgcttcg  1440
tacgagactg ttgtagcact tgcaatgctt gttcggcgat ttgacttcca aatggcactt  1500
ggagcacctc ctgtaaaaat gacaactgga gctacaattc acacaacaga tggattgaaa  1560
atgacagtta cacgaagaat gagacctcca atcataccca cattagagat gcctgcagtg  1620
gtcgttgact cgtctgtcgt ggactcgtcc gtcgccattt tgaaagaaga aacacaaatt  1680
ggttag                                                             1686
```

SEQ ID NO: 19

*Siraitia grosvenorii* DNA sequence

```
cagttcctct cctggtcctc ccagtttggc aagaggttca tcttctggaa tgggatcgag    60
cccagaatgt gcctcaccga gaccgatttg atcaaagagc ttctctctaa gtacagcgcc   120
gtctccggta agtcatggct tcagcaacag ggctccaagc acttcatcgg ccgcggtctc   180
ttaatggcca acggccaaaa ctggtaccac cagcgtcaca tcgtcgcgcc ggccttcatg   240
ggagacagac tcaagagtta cgccgggtac atggtggaat gcacaaagga gatgcttcag   300
tcaattgaaa acgaggtcaa ctcggggcga tccgagttcg aaatcggtga gtatatgacc   360
agactcaccg ccgatataat atcacgaacc gagttcgaaa gcagctacga aaagggaaag   420
caaattttcc atttgctcac cgttttacag catctctgcg ctcaggcgag ccgccacctc   480
tgccttcctg gaagccggtt ttttccgagt aaatacaaca gagagataaa ggcattgaag   540
acgaaggtgg aggggttgtt aatggagata atacagagca gaagagactg tgtggaggtg   600
gggaggagca gttcgtatgg aaatgatctg ttgggaatgt tgctgaatga gatgcagaag   660
aagaaagatg ggaatgggtt gagcttgaat ttgcagatta taatggatga atgcaagacc   720
ttcttcttcg ccggccatga aaccactgct cttttgctca cttggactgt aatgttattg   780
gccagcaacc cttcttggca acacaaggtt cgagccgaag ttatggccgt ctgcaatgga   840
ggaactctct ctcttgaaca tctctccaag ctctctctgt tgagtatggt gataaatgaa   900
tcgttgaggc tatacccgcc agcaagtatt cttccaagaa tggcatttga agatataaag   960
ctgggagatc ttgagatccc aaaagggctg tcgatatgga tcccagtgct tgcaattcac  1020
cacagtgaag agctatgggg caaagatgca aatgagttca acccagaaag atttgcaaat  1080
tcaaaagcct tcacttcggg gagattcatt ccctttgctt ctggccctcg caactgcgtt  1140
ggccaatcat ttgctctcat ggaaaccaag atcattttgg ctatgctcat ctccaagttt  1200
tccttcacca tctctgacaa ttatcgccat gcacccgtgg tcgtcctcac tataaaaccc  1260
aaatacggag tccaagtttg cttgaagcct ttcaattaa                         1299
```

TABLE 3-continued

Sequences disclosed herein (see also Table 2).

SEQ ID NO: 20
*Siraitia grosvenorii* DNA sequence

```
atggaagaca ccttcctact ctatccttcc ctctctcttc tctttcttct ttttgctttc    60
aagctcatcc gtcgatccgg aggagttcgc aggaacttac cgccgagtcc gccctctctt   120
ccggttatcg gccacctcca tctcttgaaa aagccactcc accggacttt ccagaaactt   180
tccgccaaat atggtcctgt tatgtccctc cgcctcgggt ctcgcctcgc agtcattgta   240
tcgtcgtcgt cggcggtgga cgagtgtttc actaaaaacg acgtcgtgct cgccaaccgt   300
cctcgtttgc taattggcaa acacctcggc tacaactaca ctaccatggt tggggctccc   360
tacggcgacc actggcgtag cctccgccgc atcggtgccc tcgaaatctt ctcttcatct   420
cgcctcaaca aattcgccga catccgaagg gatgaagtag agggattgct tcgcaaactc   480
tcacgcaatt cgctccatca attctcgaaa gtggaagttc aatcggcctt gtcggagctg   540
acgttcaaca tctcgatgag aatggcggca gggaaacggt attacggaga tgacgtgacg   600
gacgaggaag aggcgagaaa gttcagagag ttaattaaac agatagtggc gctgggcgga   660
gtatcaaatc caggggattt cgtcccgatt ctgaattgga ttccgaacgg tttcgagagg   720
aagttgatcg agtgtgggaa gaagacggat gcgttcttgc aggggctgat cgaggaccac   780
cggagaaaga aggaagaggg taggaacacg atgatcgatc acctgctctc tctgcaagaa   840
tcggagcctg ctcactacgg agaccaaata atcaaaggat ttatactggt gttactgacg   900
gcggggaccg atacatcggc cgtgacaatg gagtgggcgc tatctcatct cctgaacaat   960
cctgaagtgc taaagaaggc aagagatgag gtcgacactg aaattggaca agaacgactt  1020
gtcgaagaat cagacgtagt atctaagtta ccctatcttc aagggatcat ctccgagact  1080
ctccggctga atcccgccgc tccgatgttg ttgccccatt acgcctcgga cgactgcacg  1140
atatgtggat acgacgtgcc acgtgacaca atcgtaatgg tcaatgcatg ggccatacat  1200
agggatccaa acgaatggga ggagcccacg tgtttcagac cagaacgata tgaaaagtcg  1260
tcgtcggaag cggaggtaca caagtcggtg agtttcgggg tgggaaggcg agcttgtcct  1320
gggtctggca tggcgcagag ggtgatgggc ttgactttgg cggcactggt tcagtgcttc  1380
gagtgggaga gagttggaga agaagaagtg gacatgaacg aaggctcagg tgccacaatg  1440
cccaagatgg tgccattgga ggccatgtgc agagctcgtc ccatcgtcca caaccttctt  1500
tactga                                                              1506
```

SEQ ID NO: 21
*Arabidopsis thaliana* protein sequence

```
Met Ala Thr Glu Lys Thr His Gln Phe His Pro Ser Leu His Phe Val
1               5                   10                  15

Leu Phe Pro Phe Met Ala Gln Gly His Met Ile Pro Met Ile Asp Ile
            20                  25                  30

Ala Arg Leu Leu Ala Gln Arg Gly Val Thr Ile Thr Ile Val Thr Thr
        35                  40                  45

Pro His Asn Ala Ala Arg Phe Lys Asn Val Leu Asn Arg Ala Ile Glu
    50                  55                  60

Ser Gly Leu Ala Ile Asn Ile Leu His Val Lys Phe Pro Tyr Gln Glu
65                  70                  75                  80

Phe Gly Leu Pro Glu Gly Lys Glu Asn Ile Asp Ser Leu Asp Ser Thr
                85                  90                  95

Glu Leu Met Val Pro Phe Phe Lys Ala Val Asn Leu Leu Glu Asp Pro
            100                 105                 110

Val Met Lys Leu Met Glu Glu Met Lys Pro Arg Pro Ser Cys Leu Ile
        115                 120                 125

Ser Asp Trp Cys Leu Pro Tyr Thr Ser Ile Ile Ala Lys Asn Phe Asn
    130                 135                 140

Ile Pro Lys Ile Val Phe His Gly Met Gly Cys Phe Asn Leu Leu Cys
145                 150                 155                 160

Met His Val Leu Arg Arg Asn Leu Glu Ile Leu Glu Asn Val Lys Ser
                165                 170                 175

Asp Glu Glu Tyr Phe Leu Val Pro Ser Phe Pro Asp Arg Val Glu Phe
            180                 185                 190

Thr Lys Leu Gln Leu Pro Val Lys Ala Asn Ala Ser Gly Asp Trp Lys
        195                 200                 205

Glu Ile Met Asp Glu Met Val Lys Ala Glu Tyr Thr Ser Tyr Gly Val
    210                 215                 220

Ile Val Asn Thr Phe Gln Glu Leu Glu Pro Pro Tyr Val Lys Asp Tyr
225                 230                 235                 240

Lys Glu Ala Met Asp Gly Lys Val Trp Ser Ile Gly Pro Val Ser Leu
                245                 250                 255
```

TABLE 3-continued

Sequences disclosed herein (see also Table 2).

```
Cys Asn Lys Ala Gly Ala Asp Lys Ala Glu Arg Gly Ser Lys Ala Ala
            260                 265                 270

Ile Asp Gln Asp Glu Cys Leu Gln Trp Leu Asp Ser Lys Glu Glu Gly
        275                 280                 285

Ser Val Leu Tyr Val Cys Leu Gly Ser Ile Cys Asn Leu Pro Leu Ser
    290                 295                 300

Gln Leu Lys Glu Leu Gly Leu Gly Leu Glu Glu Ser Arg Arg Ser Phe
305                 310                 315                 320

Ile Trp Val Ile Arg Gly Ser Glu Lys Tyr Lys Glu Leu Phe Glu Trp
                325                 330                 335

Met Leu Glu Ser Gly Phe Glu Glu Arg Ile Lys Glu Arg Gly Leu Leu
            340                 345                 350

Ile Lys Gly Trp Ala Pro Gln Val Leu Ile Leu Ser His Pro Ser Val
        355                 360                 365

Gly Gly Phe Leu Thr His Cys Gly Trp Asn Ser Thr Leu Glu Gly Ile
    370                 375                 380

Thr Ser Gly Ile Pro Leu Ile Thr Trp Pro Leu Phe Gly Asp Gln Phe
385                 390                 395                 400

Cys Asn Gln Lys Leu Val Val Gln Val Leu Lys Ala Gly Val Ser Ala
                405                 410                 415

Gly Val Glu Glu Val Met Lys Trp Gly Glu Glu Asp Lys Ile Gly Val
            420                 425                 430

Leu Val Asp Lys Glu Gly Val Lys Lys Ala Val Glu Glu Leu Met Gly
        435                 440                 445

Asp Ser Asp Asp Ala Lys Glu Arg Arg Arg Arg Val Lys Glu Leu Gly
    450                 455                 460

Glu Leu Ala His Lys Ala Val Glu Lys Gly Gly Ser Ser His Ser Asn
465                 470                 475                 480

Ile Thr Leu Leu Leu Gln Asp Ile Met Gln Leu Ala Gln Phe Lys Asn
                485                 490                 495
```

SEQ ID NO: 22
*Arabidopsis thaliana* protein sequence

```
Met Val Ser Glu Thr Thr Lys Ser Ser Pro Leu His Phe Val Leu Phe
1               5                   10                  15

Pro Phe Met Ala Gln Gly His Met Ile Pro Met Val Asp Ile Ala Arg
            20                  25                  30

Leu Leu Ala Gln Arg Gly Val Ile Ile Thr Ile Val Thr Thr Pro His
        35                  40                  45

Asn Ala Ala Arg Phe Lys Asn Val Leu Asn Arg Ala Ile Glu Ser Gly
    50                  55                  60

Leu Pro Ile Asn Leu Val Gln Val Lys Phe Pro Tyr Leu Glu Ala Gly
65                  70                  75                  80

Leu Gln Glu Gly Gln Glu Asn Ile Asp Ser Leu Asp Thr Met Glu Arg
                85                  90                  95

Met Ile Pro Phe Phe Lys Ala Val Asn Phe Leu Glu Glu Pro Val Gln
            100                 105                 110

Lys Leu Ile Glu Glu Met Asn Pro Arg Pro Ser Cys Leu Ile Ser Asp
        115                 120                 125

Phe Cys Leu Pro Tyr Thr Ser Lys Ile Ala Lys Lys Phe Asn Ile Pro
    130                 135                 140

Lys Ile Leu Phe His Gly Met Gly Cys Phe Cys Leu Leu Cys Met His
145                 150                 155                 160
```

TABLE 3-continued

Sequences disclosed herein (see also Table 2).

```
Val Leu Arg Lys Asn Arg Glu Ile Leu Asp Asn Leu Lys Ser Asp Lys
                165                 170                 175

Glu Leu Phe Thr Val Pro Asp Phe Pro Asp Arg Val Glu Phe Thr Arg
            180                 185                 190

Thr Gln Val Pro Val Glu Thr Tyr Val Pro Ala Gly Asp Trp Lys Asp
        195                 200                 205

Ile Phe Asp Gly Met Val Glu Ala Asn Glu Thr Ser Tyr Gly Val Ile
    210                 215                 220

Val Asn Ser Phe Gln Glu Leu Glu Pro Ala Tyr Ala Lys Asp Tyr Lys
225                 230                 235                 240

Glu Val Arg Ser Gly Lys Ala Trp Thr Ile Gly Pro Val Ser Leu Cys
                245                 250                 255

Asn Lys Val Gly Ala Asp Lys Ala Glu Arg Gly Asn Lys Ser Asp Ile
            260                 265                 270

Asp Gln Asp Glu Cys Leu Lys Trp Leu Asp Ser Lys Lys His Gly Ser
        275                 280                 285

Val Leu Tyr Val Cys Leu Gly Ser Ile Cys Asn Leu Pro Leu Ser Gln
    290                 295                 300

Leu Lys Glu Leu Gly Leu Gly Leu Glu Glu Ser Gln Arg Pro Phe Ile
305                 310                 315                 320

Trp Val Ile Arg Gly Trp Glu Lys Tyr Lys Glu Leu Val Glu Trp Phe
                325                 330                 335

Ser Glu Ser Gly Phe Glu Asp Arg Ile Gln Asp Arg Gly Leu Leu Ile
            340                 345                 350

Lys Gly Trp Ser Pro Gln Met Leu Ile Leu Ser His Pro Ser Val Gly
        355                 360                 365

Gly Phe Leu Thr His Cys Gly Trp Asn Ser Thr Leu Glu Gly Ile Thr
    370                 375                 380

Ala Gly Leu Pro Leu Leu Thr Trp Pro Leu Phe Ala Asp Gln Phe Cys
385                 390                 395                 400

Asn Glu Lys Leu Val Val Glu Val Leu Lys Ala Gly Val Arg Ser Gly
                405                 410                 415

Val Glu Gln Pro Met Lys Trp Gly Glu Glu Glu Lys Ile Gly Val Leu
            420                 425                 430

Val Asp Lys Glu Gly Val Lys Lys Ala Val Glu Glu Leu Met Gly Glu
        435                 440                 445

Ser Asp Asp Ala Lys Glu Arg Arg Arg Arg Ala Lys Glu Leu Gly Asp
    450                 455                 460

Ser Ala His Lys Ala Val Glu Glu Gly Gly Ser Ser His Ser Asn Ile
465                 470                 475                 480

Ser Phe Leu Leu Gln Asp Ile Met Glu Leu Ala Glu Pro Asn Asn
                485                 490                 495
```

SEQ ID NO: 23
*Arabidopsis thaliana* protein sequence

```
Met Ala Phe Glu Lys Asn Asn Glu Pro Phe Pro Leu His Phe Val Leu
1               5                   10                  15

Phe Pro Phe Met Ala Gln Gly His Met Ile Pro Met Val Asp Ile Ala
            20                  25                  30

Arg Leu Leu Ala Gln Arg Gly Val Leu Ile Thr Ile Val Thr Thr Pro
        35                  40                  45

His Asn Ala Ala Arg Phe Lys Asn Val Leu Asn Arg Ala Ile Glu Ser
    50                  55                  60

Gly Leu Pro Ile Asn Leu Val Gln Val Lys Phe Pro Tyr Gln Glu Ala
```

TABLE 3-continued

Sequences disclosed herein (see also Table 2).

```
65                  70                  75                  80

Gly Leu Gln Glu Gly Gln Glu Asn Met Asp Leu Leu Thr Thr Met Glu
                85                  90                  95

Gln Ile Thr Ser Phe Phe Lys Ala Val Asn Leu Leu Lys Glu Pro Val
            100                 105                 110

Gln Asn Leu Ile Glu Glu Met Ser Pro Arg Pro Ser Cys Leu Ile Ser
        115                 120                 125

Asp Met Cys Leu Ser Tyr Thr Ser Glu Ile Ala Lys Lys Phe Lys Ile
    130                 135                 140

Pro Lys Ile Leu Phe His Gly Met Gly Cys Phe Cys Leu Leu Cys Val
145                 150                 155                 160

Asn Val Leu Arg Lys Asn Arg Glu Ile Leu Asp Asn Leu Lys Ser Asp
                165                 170                 175

Lys Glu Tyr Phe Ile Val Pro Tyr Phe Pro Asp Arg Val Glu Phe Thr
            180                 185                 190

Arg Pro Gln Val Pro Val Glu Thr Tyr Val Pro Ala Gly Trp Lys Glu
        195                 200                 205

Ile Leu Glu Asp Met Val Glu Ala Asp Lys Thr Ser Tyr Gly Val Ile
    210                 215                 220

Val Asn Ser Phe Gln Glu Leu Glu Pro Ala Tyr Ala Lys Asp Phe Lys
225                 230                 235                 240

Glu Ala Arg Ser Gly Lys Ala Trp Thr Ile Gly Pro Val Ser Leu Cys
                245                 250                 255

Asn Lys Val Gly Val Asp Lys Ala Glu Arg Gly Asn Lys Ser Asp Ile
            260                 265                 270

Asp Gln Asp Glu Cys Leu Glu Trp Leu Asp Ser Lys Glu Pro Gly Ser
        275                 280                 285

Val Leu Tyr Val Cys Leu Gly Ser Ile Cys Asn Leu Pro Leu Ser Gln
    290                 295                 300

Leu Leu Glu Leu Gly Leu Gly Leu Glu Glu Ser Gln Arg Pro Phe Ile
305                 310                 315                 320

Trp Val Ile Arg Gly Trp Glu Lys Tyr Lys Glu Leu Val Glu Trp Phe
                325                 330                 335

Ser Glu Ser Gly Phe Glu Asp Arg Ile Gln Asp Arg Gly Leu Leu Ile
            340                 345                 350

Lys Gly Trp Ser Pro Gln Met Leu Ile Leu Ser His Pro Ser Val Gly
        355                 360                 365

Gly Phe Leu Thr His Cys Gly Trp Asn Ser Thr Leu Glu Gly Ile Thr
    370                 375                 380

Ala Gly Leu Pro Met Leu Thr Trp Pro Leu Phe Ala Asp Gln Phe Cys
385                 390                 395                 400

Asn Glu Lys Leu Val Val Gln Ile Leu Lys Val Gly Val Ser Ala Glu
                405                 410                 415

Val Lys Glu Val Met Lys Trp Gly Glu Glu Glu Lys Ile Gly Val Leu
            420                 425                 430

Val Asp Lys Glu Gly Val Lys Lys Ala Val Glu Glu Leu Met Gly Glu
        435                 440                 445

Ser Asp Asp Ala Lys Glu Arg Arg Arg Arg Ala Lys Glu Leu Gly Glu
    450                 455                 460

Ser Ala His Lys Ala Val Glu Glu Gly Gly Ser Ser His Ser Asn Ile
465                 470                 475                 480

Thr Phe Leu Leu Gln Asp Ile Met Gln Leu Ala Gln Ser Asn Asn
```

TABLE 3-continued

Sequences disclosed herein (see also Table 2).

```
                485                 490                 495

SEQ ID NO: 24
Stevia rebaudiana protein sequence
Met Ser Pro Lys Met Val Ala Pro Pro Thr Asn Leu His Phe Val Leu
1               5                   10                  15

Phe Pro Leu Met Ala Gln Gly His Leu Val Pro Met Val Asp Ile Ala
            20                  25                  30

Arg Ile Leu Ala Gln Arg Gly Ala Thr Val Thr Ile Ile Thr Thr Pro
        35                  40                  45

Tyr His Ala Asn Arg Val Arg Pro Val Ile Ser Arg Ala Ile Ala Thr
    50                  55                  60

Asn Leu Lys Ile Gln Leu Leu Glu Leu Gln Leu Arg Ser Thr Glu Ala
65                  70                  75                  80

Gly Leu Pro Glu Gly Cys Glu Ser Phe Asp Gln Leu Pro Ser Phe Glu
                85                  90                  95

Tyr Trp Lys Asn Ile Ser Thr Ala Ile Asp Leu Leu Gln Gln Pro Ala
            100                 105                 110

Glu Asp Leu Leu Arg Glu Leu Ser Pro Pro Pro Asp Cys Ile Ile Ser
        115                 120                 125

Asp Phe Leu Phe Pro Trp Thr Thr Asp Val Ala Arg Arg Leu Asn Ile
    130                 135                 140

Pro Arg Leu Val Phe Asn Gly Pro Gly Cys Phe Tyr Leu Leu Cys Ile
145                 150                 155                 160

His Val Ala Ile Thr Ser Asn Ile Leu Gly Glu Asn Glu Pro Val Ser
                165                 170                 175

Ser Asn Thr Glu Arg Val Val Leu Pro Gly Leu Pro Asp Arg Ile Glu
            180                 185                 190

Val Thr Lys Leu Gln Ile Val Gly Ser Ser Arg Pro Ala Asn Val Asp
        195                 200                 205

Glu Met Gly Ser Trp Leu Arg Ala Val Glu Ala Glu Lys Ala Ser Phe
    210                 215                 220

Gly Ile Val Val Asn Thr Phe Glu Glu Leu Glu Pro Glu Tyr Val Glu
225                 230                 235                 240

Glu Tyr Lys Thr Val Lys Asp Lys Lys Met Trp Cys Ile Gly Pro Val
                245                 250                 255

Ser Leu Cys Asn Lys Thr Gly Pro Asp Leu Ala Glu Arg Gly Asn Lys
            260                 265                 270

Ala Ala Ile Thr Glu His Asn Cys Leu Lys Trp Leu Asp Glu Arg Lys
        275                 280                 285

Leu Gly Ser Val Leu Tyr Val Cys Leu Gly Ser Leu Ala Arg Ile Ser
    290                 295                 300

Ala Ala Gln Ala Ile Glu Leu Gly Leu Gly Leu Glu Ser Ile Asn Arg
305                 310                 315                 320

Pro Phe Ile Trp Cys Val Arg Asn Glu Thr Asp Glu Leu Lys Thr Trp
                325                 330                 335

Phe Leu Asp Gly Phe Glu Glu Arg Val Arg Asp Arg Gly Leu Ile Val
            340                 345                 350

His Gly Trp Ala Pro Gln Val Leu Ile Leu Ser His Pro Thr Ile Gly
        355                 360                 365

Gly Phe Leu Thr His Cys Gly Trp Asn Ser Thr Ile Glu Ser Ile Thr
    370                 375                 380

Ala Gly Val Pro Met Ile Thr Trp Pro Phe Phe Ala Asp Gln Phe Leu
385                 390                 395                 400
```

TABLE 3-continued

Sequences disclosed herein (see also Table 2).

```
Asn Glu Ala Phe Ile Val Glu Val Leu Lys Ile Gly Val Arg Ile Gly
                405                 410                 415

Val Glu Arg Ala Cys Leu Phe Gly Glu Glu Asp Lys Val Gly Val Leu
            420                 425                 430

Val Lys Lys Glu Asp Val Lys Lys Ala Val Glu Cys Leu Met Asp Glu
        435                 440                 445

Asp Glu Asp Gly Asp Gln Arg Arg Lys Arg Val Ile Glu Leu Ala Lys
    450                 455                 460

Met Ala Lys Ile Ala Met Ala Glu Gly Gly Ser Ser Tyr Glu Asn Val
465                 470                 475                 480

Ser Ser Leu Ile Arg Asp Val Thr Glu Thr Val Arg Ala Pro His
                485                 490                 495
```

SEQ ID NO: 25
*Stevia rebaudiana* protein sequence

```
Met Asp Ala Met Ala Thr Thr Glu Lys Lys Pro His Val Ile Phe Ile
1               5                   10                  15

Pro Phe Pro Ala Gln Ser His Ile Lys Ala Met Leu Lys Leu Ala Gln
            20                  25                  30

Leu Leu His His Lys Gly Leu Gln Ile Thr Phe Val Asn Thr Asp Phe
        35                  40                  45

Ile His Asn Gln Phe Leu Glu Ser Ser Gly Pro His Cys Leu Asp Gly
    50                  55                  60

Ala Pro Gly Phe Arg Phe Glu Thr Ile Pro Asp Gly Val Ser His Ser
65                  70                  75                  80

Pro Glu Ala Ser Ile Pro Ile Arg Glu Ser Leu Leu Arg Ser Ile Glu
                85                  90                  95

Thr Asn Phe Leu Asp Arg Phe Ile Asp Leu Val Thr Lys Leu Pro Asp
            100                 105                 110

Pro Pro Thr Cys Ile Ile Ser Asp Gly Phe Leu Ser Val Phe Thr Ile
        115                 120                 125

Asp Ala Ala Lys Lys Leu Gly Ile Pro Val Met Met Tyr Trp Thr Leu
    130                 135                 140

Ala Ala Cys Gly Phe Met Gly Phe Tyr His Ile His Ser Leu Ile Glu
145                 150                 155                 160

Lys Gly Phe Ala Pro Leu Lys Asp Ala Ser Tyr Leu Thr Asn Gly Tyr
                165                 170                 175

Leu Asp Thr Val Ile Asp Trp Val Pro Gly Met Glu Gly Ile Arg Leu
            180                 185                 190

Lys Asp Phe Pro Leu Asp Trp Ser Thr Asp Leu Asn Asp Lys Val Leu
        195                 200                 205

Met Phe Thr Thr Glu Ala Pro Gln Arg Ser His Lys Val Ser His His
    210                 215                 220

Ile Phe His Thr Phe Asp Glu Leu Glu Pro Ser Ile Ile Lys Thr Leu
225                 230                 235                 240

Ser Leu Arg Tyr Asn His Ile Tyr Thr Ile Gly Pro Leu Gln Leu Leu
                245                 250                 255

Leu Asp Gln Ile Pro Glu Glu Lys Lys Gln Thr Gly Ile Thr Ser Leu
            260                 265                 270

His Gly Tyr Ser Leu Val Lys Glu Glu Pro Glu Cys Phe Gln Trp Leu
        275                 280                 285

Gln Ser Lys Glu Pro Asn Ser Val Val Tyr Val Asn Phe Gly Ser Thr
    290                 295                 300
```

TABLE 3-continued

Sequences disclosed herein (see also Table 2).

```
Thr Val Met Ser Leu Glu Asp Met Thr Glu Phe Gly Trp Gly Leu Ala
305                 310                 315                 320

Asn Ser Asn His Tyr Phe Leu Trp Ile Ile Arg Ser Asn Leu Val Ile
                325                 330                 335

Gly Glu Asn Ala Val Leu Pro Pro Glu Leu Glu Glu His Ile Lys Lys
            340                 345                 350

Arg Gly Phe Ile Ala Ser Trp Cys Ser Gln Glu Lys Val Leu Lys His
        355                 360                 365

Pro Ser Val Gly Gly Phe Leu Thr His Cys Gly Trp Gly Ser Thr Ile
    370                 375                 380

Glu Ser Leu Ser Ala Gly Val Pro Met Ile Cys Trp Pro Tyr Ser Trp
385                 390                 395                 400

Asp Gln Leu Thr Asn Cys Arg Tyr Ile Cys Lys Glu Trp Glu Val Gly
                405                 410                 415

Leu Glu Met Gly Thr Lys Val Lys Arg Asp Glu Val Lys Arg Leu Val
            420                 425                 430

Gln Glu Leu Met Gly Glu Gly Gly His Lys Met Arg Asn Lys Ala Lys
        435                 440                 445

Asp Trp Lys Glu Lys Ala Arg Ile Ala Ile Ala Pro Asn Gly Ser Ser
    450                 455                 460

Ser Leu Asn Ile Asp Lys Met Val Lys Glu Ile Thr Val Leu Ala Arg
465                 470                 475                 480

Asn
```

SEQ ID NO: 26
*Siraitia grosvenorii* DNA sequence

```
atggatgccc agcgaggtca caccaccacc attttgatgc ttccatgggt cggctacggc    60
catctcttgc ctttcctcga gctggccaaa agcctctcca ggaggaaatt attccacatc   120
tacttctgtt caacgtctgt tagcctcgac gccattaaac caaagcttcc tccttctatc   180
tcttctgatg attccatcca acttgtggaa cttcgtctcc cttcttctcc tgagttacct   240
cctcatcttc acacaaccaa cggccttccc tctcacctca tgcccgctct ccaccaagcc   300
ttcgtcatgg ccgcccaaca ctttcaggtc attttacaaa cacttgcccc gcatctcctc   360
atttatgaca ttctccaacc ttgggctcct caagtggctt catccctcaa cattccagcc   420
atcaacttca gtactaccgg agcttcaatg ctttctcgaa cgcttcaccc tactcactac   480
ccaagttcta aattcccaat ctcagagttt gttcttcaca atcactggag agccatgtac   540
accaccgccg atggggctct tacagaagaa ggccacaaaa ttgaagaaac acttgcgaat   600
tgcttgcata cttcttgcgg ggtagttttg gtcaatagtt tcagagagct tgagacgaaa   660
tatatcgatt atctctctgt tctcttgaac aagaaagttg ttccggtcgg tcctttggtt   720
tacgaaccga atcaagaagg ggaagatgaa ggttattcaa gcatcaaaaa ttggcttgac   780
aaaaaggaac cgtcctcaac cgtcttcgtt tcatttggaa ccgaatactt cccgtcaaag   840
gaagaaatgg aagagatagc gtatgggtta gagctgagcg aggttaattt catctgggtc   900
cttagatttc ctcaaggaga cagcaccagc accattgaag acgccttgcc gaaggggttt   960
ctggagagag cgggagagag ggcgatggtg gtgaagggtt gggctcctca ggcgaagata  1020
ctgaagcatt ggagcacagg ggggcttgtg agtcactgtg gatggaactc gatgatggag  1080
ggcatgatgt ttggcgtacc cataatagcg gtcccgatgc atctggacca gccctttaac  1140
gccggactct tggaagaagc tggcgtcggc gtggaagcca agcgaggttc ggacggcaaa  1200
attcaaagag aagaagttgc aaagtcgatc aaagaagtgg tgattgagaa aaccagggaa  1260
gacgtgagga agaaagcaag agaaatgggt gagattttga ggagtaaagg agatgagaaa  1320
attgatgagt tggtggctga aatttctctt ttgcgcaaaa aggctccatg ttcaatttaa  1380
```

SEQ ID NO: 27
*Siraitia grosvenorii* DNA sequence

```
atgcttccat ggctggctca cggccatgtc tccccttttct tcgagctcgc caagttgctc    60
gccgctagaa acttccacat attcttctgc tccaccgccg taaacctccg ctccgtcgaa   120
ccaaaactct ctcagaagct ctcctcccac gtggagctgg tggagctcaa cctaccgccc   180
tcgccggagc tccctccgca ccgccacacc accgccggcc ttccaccgca cctcatgttc   240
tcgctcaagc gagctttcga catggccgct cccgccttcg ccgccatcct ccgcgacctg   300
aacccggact tgctcatcta cgacttcctg cagccgtggg cggcggcgga ggctctgtcg   360
gcggatattc cggccgtgat gttcaaaagc acgggtgcgc tcatggcggc catggtcgcg   420
tacgagctga cgtttccgaa ctctgatttt ttctcgcttt tccctgagat tcgtctctcc   480
gagtgcgaga ttaaacagct gaagaacttg tttcaatgtt ctgtgaatga tgcgaaagac   540
aagcaaagga ttaagggatg ttatgagaga tcttgcggca tgattttggt gaaatctttc   600
agagaaatcg aaggcaaata tattgatttt ctctctactc tgctgggcaa gaaggttgtt   660
ccagttggtc cacttgttca acaaacagaa gacgacgtcg tatcaggaag ttttgacgaa   720
tggctaaatg gaaaagatag atcgtcttcc atactcgtgt ctttcggaag cgagttctac   780
ctgtccagag aagacatgga agagatcgcg catggcttag agctgagcca ggtgaacttc   840
atatgggtcg tcaggtttcc ggcgggagga gagagaaaca cgacaaaggt ggaagaagaa   900
```

TABLE 3-continued

Sequences disclosed herein (see also Table 2).

ctgccaaaag ggtttctaga gagagttaga gagagaggga tggtggtgga gggctgggcg 960
ccgcaggctc agatcttgaa acatccaagc gtcggcggat tcctcagcca ctgcgggtgg 1020
agctccgtcg tggagagcat gaaattcggc gttccgatca tcgccatgcc gatgcacctc 1080
gaccagccgc tgaattcccg gctggtcgag cggctcggcg tcggcgtagt ggtggagaga 1140
gacggccgcc tccggggaga ggtggagaga gttgtcagag aggtggtggt ggagaaaagt 1200
ggagagagag tgaggaagaa ggtggaggag tttgcagaga tcatgaagaa gaaaaaagac 1260
aatgaagaga tggacgtagt cgtggaagag ttggtgacgc tctgcaggaa gaagaagaag 1320
gaggaggatt tacagagtaa ttattggtgc agaaccgcca ttgatgacca ttgttctgaa 1380
gtcgtgaaga ttgaagatgc tgcagcagcc gacgaggagc ctctttgcaa ataa 1434

SEQ ID NO: 28
*Siraitia grosvenorii* DNA sequence
atggctgtca cttacagcct gcacatagca atgtaccctt ggtttgcttt cggccacttg 60
actccatttc tccaagtctc caacaagctt gccaaggaag gccacaaaat ctccttcttc 120
atcccaacga aaacgctaac caaattgcag cctttcaatc tctttccaga tctcattacc 180
tttgtcccca tcactgttcc tcatgttgat ggtctccctc ttggagctga gactactgct 240
gatgtttctc acccttcaca gctcagtctc atcatgactg ctatggattg cacccaaccc 300
gaaatcgagt gtcttcttcg agacataaaa cctgatgcca tcttcttcga tttcgcgcac 360
tgggtgccaa aattggcatg tggattgggc attaagtcga ttgattacag tgtctgttct 420
gcagtatcaa ttggttatgt tttgccccta ttaaggaaag tttgtggaca agatttatta 480
actgaagatg attttatgca gccatctcct ggctacccga gttccaccat caatcttcaa 540
gctcatgagg ctcgatattt tgcatctctg agccgctgga ggtttggcag tgatgtccct 600
ttctttagtc gccatcttac tgcacttaat gaatgcaatg ctttagcatt caggtcatgt 660
agggagattg aagggccttt tatagactat ccagaaagtg aattaaaaaa gcctgtgttg 720
ctttccggag cagtggatct acaaccgcca accacaactg tagaagaaag atgggcaaaa 780
tggctatcag ggttcaacac cgactcggtc gtatattgtg catttggaag tgagtgtacc 840
ttagcaaaag accaattcca agaactgctg ttgggttttg agctttcaaa tatgccattc 900
tttgctgcac ttaaaccacc ttttggtgtt gactcggttg aagcagcctt gcctgaaggt 960
tttgaacaga gagttcaggg aagaggggtg gtctatgggg gatgggtcca acagcagctc 1020
attttggagc acccatcaat tggatgcttt gttacacatt gtggatcagg ctccttatca 1080
gaggcgttag tgaagaagtg tcaattagtg ttgttacctc gtatcggtga ccactttttc 1140
cgagcaagaa tgttgagcaa ttatttgaaa gttggtgtgg aggtagagaa aggagaagga 1200
gatggatctt ttacaaagga aagtgtgtgg aaggcagtga agacagtgat ggatgaagag 1260
aatgaaactg ggaaagagtt cagagcgaac cgtgccaaga taagagagct attgctcgac 1320
gaagatctcg aggagtctta tatcaacaat ttcatccaca gcctgcatac tttgaatgca 1380
tga 1383

SEQ ID NO: 29
Artificial sequence; Partial nucleotide sequence
from *Siraitia grosvenori*
atggcggatc ggaaagagag cgttgtgatg ttcccgttca tggggcaggg ccatatcatc 60
ccttttctag ctttggccct ccagattgag cacagaaaca gaaactacgc catatacttg 120
gtaaatactc ctctcaacgt taagaaaatg agatcttctc tccctccaga ttga 174

SEQ ID NO: 30
*Siraitia grosvenorii* DNA sequence
atggaagcta agaactgcaa aaaggttctg atgttcccat ggctggcgca tggtcacata 60
tcaccatttg tagagctggc caagaagctc acagacaaca acttcgccgt tttctatgt 120
tcttcccctg caaatcttca aaacgtcaag ccaaaactcc cccatcacta ctctgattcc 180
attgaactcg tggagctcaa ccttccatcg tcgccggagc ttcccctca tatgcacacc 240
accaatggcc tccctttgca tttagttccc accctcgttg acgccttgga catggccgct 300
ccgcacttct ccgccatttt acaggaactg aatccagatt ttctcatatt cgacatcttc 360
caaccctggg cggctgaaat cgcttcctcc ttcggcgttc ctgctatttt gttgcttatc 420
gttggatctg ctataaccgc tttaggggtt catttgtcc ggagctccgg tacggaattc 480
ccctttcccg agcttactaa atcattcaag aaggaggacg accgaaaacc tccaggagat 540
tccggcaacg atagaggaaa acggctattc aaatgtctgc tggacctgga acattcttca 600
gagactattt tggtgaacag ttttacagag atagagggca aatatatgga ctatctctcg 660
gtcttactga agaagaagat ccttccgatt ggtcctttgg ttcagaaaat tggctccgat 720
gacgatgaat cgggaatcct ccggtggctt gacaagaaga aaccgaattc aactgtgtac 780
gtttcgttcg ggagtgagta ctatttgagc aaagaagaca tagcagagct tgcgcatggt 840
ctggaaatca gcggcgtcaa tttcatctgg attgttcggt ttccaaaggg agagaaaatc 900
gccattgaag aggcattacc agatgaattt cttgaaagag tcggagagag aggcgtcgtc 960
gttgatggat gggcgccgca gatgaaaata ttagggcatt cgagcgtcgg cgggtttctg 1020
tctcactgcg gatggaactc tgtgctggag agtctggtgc tcggcgtgcc gatcatatcc 1080
ctgccgatac acctcgaaca gccgtggaac gccttggtag cggagcacgt cggcgtttgt 1140
gtgagggcga agagagacga cggaggaaat cttcaaagag agttggtggc ggaggccatt 1200
aaagaagtgg tggttgagga aacaggagcg gaactgagaa gcaaagcaag agtaattagt 1260
gaaatcttga aaaataaaga agctgaaaca atacaagatt tggtggctga gcttcaccgg 1320
ctttctgacg caagaagagc ttgttga 1347

SEQ ID NO: 31
*Siraitia grosvenorii* DNA sequence
atggaaaaaa atcttcacat agtgatgctt ccatggtcgg cgttcggcca tctcatacca 60
ttttttcacc tctccatagc cttagccaaa gccaaagttt atatctcctt cgtctccact 120
ccaagaaata ttcagagact yccccaaatc ccgccggact tagcttcttt catagatttg 180
gtggccattc ccttgccgag actcgacgac gatctgttgc tagaatctgc agaggccact 240
tctgatattc cgatcgacaa gattcagtat ttgaagcgag ccgtcgacct cctccgccac 300
cccttcaaga agtttgtcgc cgaacaatcg ccggactggg tcgtcgttga ttttcatgct 360

TABLE 3-continued

Sequences disclosed herein (see also Table 2).

```
tattgggccg gcgagatcta ccaggagttt caagttcccg tcgcctactt ctgtattttc   420
tcggccatct gtttgcttta tcttggacct ccagacgtgt attcgaagga tcctcagatc   480
atggcacgaa tatctcccgt taccatgacg gtgccgccgg agtgggtcgg ttttccgtcc   540
gccgtagcct acaacttgca tgaggcgacg gtcatgtact ctgctctcta tgaaacaaat   600
gggtctggaa taagcgactg cgagaggatt cgccggctcg tcctttcctg tcaagccgtg   660
gccattcgaa gctgcgagga gattgaaggc gaatacctta ggttatgtaa gaaactgatt   720
ccaccgcagg ggattgccgt cggcttgctt ccgccggaaa agccaccaaa atcagatcac   780
gagctcatca aatggcttga cgagcaaaag ctccgattcg tcgtgtacgt gacattcggc   840
agcgaatgca acctgacgaa ggaccaagtt cacgagatag cccacgggct ggaactgtcg   900
gagctgccat ttttatgggc actgaggaaa cccagctggg cagctgagga agacgatggg   960
ctgccgtctg ggtttcgtga gagaacgtcc gggagagggg tggtgagcat ggagtgggtg  1020
ccgcagttgg agattctggc gcaccaggcc atcggcgtct ctttagttca cgggggctgg  1080
ggctctatta tcgagtcgct acaagctggg cactgtctgg ttgtgctgcc gtttatcatc  1140
gaccagccgc tgaactcaaa gcttttggtg gagaaaggga tggcgcttga gatcagaagg  1200
aacggttctg atggatggtt tagtagagaa gacatcgccg gaactttgag agaagctatg  1260
cggtcgtctg aggaaggcgg gcagctgagg agccgtgcaa aagaggcggc ggccatcgtt  1320
ggagatgaga agctgcagtg ggaacaatac ttcggcgcgt tcgtacagtt tctgagggac  1380
aagtcttga                                                          1389
```

SEQ ID NO: 32
*Siraitia grosvenorii* DNA sequence

```
atgtccgagg agaaaggcag agggcacagc tcgtcgacgg agagacacac tgctgccgcc    60
atgaacgccg agaaacgaag caccaaaatc ttgatgctcc catggctggc tcacggccac   120
atatctccat acttcgagct cgccaagagg ctcaccaaga aaaactgcca cgtttacttg   180
tgttcttcgc ctgtaaatct ccaaggcatc aagccgaaac tctctgaaaa ttactcttcc   240
tccattgaac ttgtggagct tcatcttcca tctctccccg accttcctcc ccatatgcac   300
acgaccaaag gcatccctct acatctacaa tccaccctca tcaaagcctt cgacatggcc   360
gcccctgatt tttccgacct gttgcagaaa ctcgagccgg atctcgtcat ttccgatctc   420
ttccagccat gggcagttca attagcgtcg tctcggaaca ttcccgtcgt caatttcgtt   480
gtcaccggag tcgctgttct tagtcgtttg gctcacgtgt tttgcaactc cgttaaggaa   540
ttccctttcc cggaactcga tctaaccgac cattggatct ccaagagccg ccgcaaaacg   600
tccgacgaat taggtcgcga gtgcgcgatg cgatttttca actgcatgaa acaatcttca   660
aacatcactc tagccaacac tttccccgag ttcgaagaaa aatacatcga ttatctctct   720
tcctcgttta agaaaaagat tcttccggtt gctcctctag ttcctgaaat cgacgcagac   780
gacgagaaat cggaaattat cgagtggctt gacaagaaga aaccgaaatc gactgtttac   840
gtttcgtttg ggagtgagta ttatctgacg aaagaagaca gggaagagct cgcccatggc   900
ttagaaaaga gcggcgtgaa tttcatctgg gttattaggt ttccaaaggg cgagaagatc   960
accattgaag aggctttacc agaaggattt ctcgagagag taggggacag gggagtgatt  1020
atcgacgggt gggcgccgca gttgaaaata ttgaggcatt caagcgtggg cgggttcgtg  1080
tgccactgcg ggtggaactc tgtggtggag agcgtggtgt ttggggtgcc gatcatagcc  1140
ttgccgatgc agctcgatca gccatggcat gcgaaggtgg cggaggacgg cggcgtctgt  1200
gcggaggcga agagagacgt tgaagggagc gttcagagag aagaggtggc gaaggccatt  1260
aaagaggtgg tgtttgagaa gaagggggggg gttctgagtg gaaaagcaag agagatcagc  1320
gaggccttga gaaagaggga aggggaaatc atagaggaat tggttgctga gtttcaccag  1380
ctctgtgaag cttga                                                   1395
```

SEQ ID NO: 33
Artificial sequence; Partial nucleotide sequence
from *Siraitia grosvenorii*

```
ttctgctcca cgcctgtaaa tttggaagcc attaaaccaa agctttccaa aagctactct    60
gattcgatcc aactaatgga ggttcctctc gaatcgacgc cggagcttcc tcctcactat   120
catacagcca aaggccttcc gccgcattta atgcccaaac tcatgaatgc ctttaaaatg   180
gttgctccca atctcgaatc gatcctaaaa accctaaacc cagatctgct catcgtcgac   240
attctccttc catggatgct tccactcgct tcatcgctca aaattccgat ggtttcttc    300
actattttcg gtgccatggc catctccttt atgatttata atcgaaccgt ctcgaacgag   360
cttccatttc cagaatttga acttcacgag tgctggaaat cgaagtgccc ctatttgttc   420
aaggaccaag cggaaagtca atcgttctta gaatacttgg atcaatcttc aggcgtaatt   480
ttgatcaaaa cttccagaga gattgaggct aagtatgtag actttctcac ttcgtcgttt   540
acgaagaagg ttgtgaccac cggtcccctg gttcagcaac cttcttccgg cgaagacgag   600
aagcagtact ccgatatcat cgaatggcta gacaagaagg agccgttatc gacggtgctc   660
gtttcgtttg ggagcgagta ttatctgtca aaggaagaga tggaagaaat cgcctacggg   720
ctggagagcg ccagcgaggt gaatttcatc tggattgtta ggtttccgat gggacaggaa   780
acggaggtcg aggcggcgct gccggagggg ttcatccaga gggcaggaga gagagggaaa   840
gtggtcgagg gctgggctcc gcaggcgaaa atattggcgc atccgagcac cggcggccat   900
gtgagccaca acgggtggag ctcgattgtg gagtgcttga tgtccggtgt accggtgatc   960
ggcgcgccga tgcaacttga cgggccaatc gtcgcaaggc tggtggagga gatcggcgtg  1020
ggtttggaaa tcaagagaga tgaggaaggg agaatcacga ggggcgaagt tgccgatgca  1080
atcaagacgg tggcggtggg caaaaccggg gaagatttta gaaggaaagc aaaaaaaatc  1140
agcagcattt tgaagatgaa agatgaagaa gaggttgaca ctttggcaat ggaattagtg  1200
aggttatgcc aaatgaaaag agggcaggag tctcaggact aa                     1242
```

SEQ ID NO: 34
Artificial sequence; Partial nucleotide sequence
from *Siraitia grosvenorii*

```
tcccggtcaa cggtagagga cttcacggag cttcgagagt ggatgccttc tggatcgaac    60
atggtctacc ggtaccacga gattaaaaaa tccttagatg gagcaaccgg caacgaatcg   120
gggacgtctg attcggtccg attcggaatt gtgattgagg agagtgttgc tgtggctgta   180
agaagctccc ctgaactgga accggaatgg ttcgatttgc tcgcgaagct ttaccagaag   240
```

TABLE 3-continued

Sequences disclosed herein (see also Table 2).

```
ccagttgttc cggtaggatt tctacctcca gtaattgaag atgcggaaga attgagcagc   300
gatatcaagg aatggttaga caaacagagc tcaaactcgg tcctttacgt cgcattcggg   360
accgaggcga ctctgagtca agatgacgtc actgagttag ccatggggct tgagcaatct   420
gggataccat ttttctgggt actgagaacc tcacctcggg acgagtcaga catgttaccg   480
gccgggttca aggagcgagt cgaaggtcga ggaagtgttc acgtgggatg ggtctcgcag   540
gtgaagatac tgagtcacga ctcggttggc ggttgtttga cacactgtgg atggaactcg   600
atcatagagg ggctcggatt cgggcgcgtt atggtattgt ttccagtcgt gaacgaccag   660
ggattgaacg ctagattgtt gggggagaag aagctcggga tagagataga aagggacgag   720
cgagatggat cgttcacacg cgactcggtg tcggaatcgg tgaggtcggc aatggcggaa   780
agttcaggcg aggccttgag agtgagggcc agggaaatga aggggttgtt tggaaacgga   840
gatgagaacg agcatcaact gaacaagttt gtacaatttc tcgaggcaaa caggaatagg   900
cagtccgagt aa                                                       912
```

SEQ ID NO: 35
Artificial sequence; Partial nucleotide sequence
from *Siraitia grosvenorii*

```
ctgctgccga ttccgctgcc gaaaccggcc gccgatctct tgccggaagg tgcagaggcg    60
acggtggata ttccgtccga caagattccg tatctgaaat tggccctcga tctcgccgag   120
cagccgtttc ggaagttcgt cgttgatcgt ccgccggatt ggatgatcgt cgattttaat   180
gctacttggg tctgcgatat ttctcgggag cttcaaatcc caatcgtttt ctttcgtgtt   240
ctttcgcctg gatttcttgc tttctttgcg catgttcttg ggagtggtct gccgctgtcg   300
gagatcgaaa gcctgatgac tccgccggtg atcgacgggt cgacggtggc gtaccgccgg   360
catgaagctg ccgttatttg tgctgggttt tttgagaaga acgcttctgg tatgagtgat   420
cgcgatcggg taaccaaaat tctctctgcc agtcaagcaa tcgcagttcg ttcttgctac   480
gaatttgacg ttgagtattt gaaattgtac gagaaatatt gtggaaaaag agtgattcct   540
ctagggtttc tccctccaga aaagccccaa aagtccgagt tcgccgccga ttcgccatgg   600
aaaccgacct tcgagtggct tgacaaacaa aagccccgat cagtggtgtt cgtcggattc   660
ggcagcgaat gcaaactcac gaaagatgat gtttacgaga tagcgcgcgg ggtggagctg   720
tcggagctgc catttttgtg ggctctgaga aaaccgatct gggcggcggc ggacgattcc   780
gacgctctgc ctgccggatt cctcgagcgg acggcggaga gagggattgt gagcatgggg   840
tgggcgccgc agatggagat tttaacgcac ccgtcgattg gcggctctct gtttcacgcc   900
gggtggggat ccgccattga agctctgcaa ttcgggcatt gccttgttct gttgccattc   960
atcgtggatc agccactgaa tgcaaggctt ctggtggaga agggtgttgc agtcgaagtt  1020
ggaagaaagg aagacgggtc ttttagtgga gaagacatag ctaaagctct gagagaagct  1080
atggtttcag aagaaggtga gcagatgagg aggcaagcga gaaag                  1125
```

SEQ ID NO: 36
Artificial sequence; Partial nucleotide sequence
from *Siraitia grosvenorii*

```
atggaaaacg acggcgtttt gcacgtggtg gtattcccat ggctagcctt gggtcatctc    60
attcctttcg ctcgactcgc cacctgctta gcccacaagg gtctcagggt ttcgttcgta   120
tcaaccacaa ggaacctgag cagaattccc aaaatacccc cacatctctc ctcctccgtc   180
aacctcgtcg gctttcctct gccccacgtc gacggccttc cggacgccgc cgaggcttcc   240
tccgacgtgc cttacaacaa gcaacagtta ctgaagaagg ccttcgactc tctggaatca   300
ccgctcgccg atttgcttcg tgatttgaat cccgattgga ttatctacga ttacgcctct   360
cattggcttc cgcagctcgc ggcggagctc cgtatctcgt ctgttttctt cagcctcttc   420
accgcggcgt ttcttgcttt tcttggccca ccgtcggcgt tgtccggcga cggcagttcc   480
cggtga                                                              486
```

SEQ ID NO: 37
Artificial Sequence; Codon-optimized nucleotide sequence
encoding Epoxide Hydrolase 1

```
atggacgcga ttgaacatag aaccgtaagt gttaatggta tcaatatgca tgtggcagaa    60
aagggagagg gacctgtcgt gttgttgctt catggtttcc cagaattgtg gtacagttgg   120
agacatcaaa tattggctct ttcctcttta ggttacagag ctgtcgcacc agacttacga   180
ggctacgggg atacagatgc cccagggtca atttcatcat acacatgctt tcacatcgta   240
ggagatctcg tggctctagt tgagtctctg ggtatggaca gggtttttgt tgtagcccac   300
gattggggtg ccatgatcgc ttggtgtttg tgtctgttta gacctgaaat ggttaaagct   360
tttgtttgtc tctccgtccc attcagacag agaaaccccta agatgaaacc agttcaaagt   420
atgagagcct ttttcggcga tgattactat atttgcagat ttcaaaatcc tggggaaatc   480
gaagaggaga tggctcaagt gggtgcaagg gaagtcttaa gaggaattct aacatctcgt   540
cgtcctggac caccaatctt accaaaaggg caagctttta gagcaagacc aggagcatcc   600
actgcattgc catcttggct atctgaaaaa gatctgtcat ttttcgcttc taagtatgat   660
caaaagggct ttacaggccc actaaactac tacagagcca tggatcttaa ttgggaattg   720
actgcgtcat ggactggtgt ccaagttaaa gtacctgtca aatacatcgt gggtgacgtt   780
gacatggttt ttacgactcc tggtgtaaag gaatatgtca acggcggtgg tttcaaaaag   840
gacgttccat ttttacagga agtggtaatc atggaaggcg ttggtcattt cattaatcag   900
gaaaaacctg aggagatttc atctcatata cacgatttca taagcaaatt ctaa         954
```

SEQ ID NO: 38
*Siraitia grosvenorii* protein sequence

```
Met Asp Ala Ile Glu His Arg Thr Val Ser Val Asn Gly Ile Asn Met
1               5                   10                  15

His Val Ala Glu Lys Gly Glu Gly Pro Val Val Leu Leu Leu His Gly
            20                  25                  30

Phe Pro Glu Leu Trp Tyr Ser Trp Arg His Gln Ile Leu Ala Leu Ser
```

TABLE 3-continued

Sequences disclosed herein (see also Table 2).

```
        35                  40                  45

Ser Leu Gly Tyr Arg Ala Val Ala Pro Asp Leu Arg Gly Tyr Gly Asp
    50                  55                  60

Thr Asp Ala Pro Gly Ser Ile Ser Ser Tyr Thr Cys Phe His Ile Val
65                  70                  75                  80

Gly Asp Leu Val Ala Leu Val Glu Ser Leu Gly Met Asp Arg Val Phe
                85                  90                  95

Val Val Ala His Asp Trp Gly Ala Met Ile Ala Trp Cys Leu Cys Leu
            100                 105                 110

Phe Arg Pro Glu Met Val Lys Ala Phe Val Cys Leu Ser Val Pro Phe
        115                 120                 125

Arg Gln Arg Asn Pro Lys Met Lys Pro Val Gln Ser Met Arg Ala Phe
    130                 135                 140

Phe Gly Asp Asp Tyr Tyr Ile Cys Arg Phe Gln Asn Pro Gly Glu Ile
145                 150                 155                 160

Glu Glu Glu Met Ala Gln Val Gly Ala Arg Glu Val Leu Arg Gly Ile
                165                 170                 175

Leu Thr Ser Arg Arg Pro Gly Pro Pro Ile Leu Pro Lys Gly Gln Ala
            180                 185                 190

Phe Arg Ala Arg Pro Gly Ala Ser Thr Ala Leu Pro Ser Trp Leu Ser
        195                 200                 205

Glu Lys Asp Leu Ser Phe Phe Ala Ser Lys Tyr Asp Gln Lys Gly Phe
    210                 215                 220

Thr Gly Pro Leu Asn Tyr Tyr Arg Ala Met Asp Leu Asn Trp Glu Leu
225                 230                 235                 240

Thr Ala Ser Trp Thr Gly Val Gln Val Lys Val Pro Val Lys Tyr Ile
                245                 250                 255

Val Gly Asp Val Asp Met Val Phe Thr Thr Pro Gly Val Lys Glu Tyr
            260                 265                 270

Val Asn Gly Gly Gly Phe Lys Lys Asp Val Pro Phe Leu Gln Glu Val
        275                 280                 285

Val Ile Met Glu Gly Val Gly His Phe Ile Asn Gln Glu Lys Pro Glu
    290                 295                 300

Glu Ile Ser Ser His Ile His Asp Phe Ile Ser Lys Phe
305                 310                 315
```

SEQ ID NO: 39
Artificial Sequence; Codon-optimized nucleotide sequence
encoding Epoxide Hydrolase 2

```
atggatgaaa tcgaacatat taccatcaat acaaatggaa tcaaaatgca tattgcgtca    60
gtcggcacag gaccagttgt tctcttgcta cacggctttc cagaattatg gtactcttgg   120
agacaccaac tactttacct gtcctccgtt gggtacagag caatagctcc agatttgaga   180
ggctatggcg atactgacag tccagctagt cctacctctt atactgctct tcatattgta   240
ggtgacctgg tcggcgcatt agacgaattg ggaatagaaa aggtcttttt agtgggtcat   300
gactggggtg ctattatcgc atggtacttt tgtttgttta gaccagatag aattaaagca   360
cttgtgaatt tgtctgtcca gtttatccca cgtaacccag caataccttt tatagaaggt   420
ttcagaacag cttttggtga tgacttctac atttgtagat ttcaagtacc tggggaagct   480
gaagaggatt tcgcgtctat cgatactgct caattgttta aaacttcatt atgcaataga   540
agctcagccc ctccttgttt gcctaaagag attggtttta gggctatccc accaccagaa   600
aatctgccat cttggctcac agaggaagat atcaacttct acgcagccaa gtttaaacaa   660
actggtttta ctggtgccct taactattat agagcattcg acttgacatg ggaattaaca   720
gccccatgga caggagccca gatccaagtt cctgtaaagt tcatagttgg tgattcagat   780
ctcacgtacc atttccctgg tgctaaggaa tacatccaca acggagggtt taaaagagat   840
gtgccactat tagaggaagt tgttgtggta aaagatgcct gccacttcat taaccaagag   900
cgaccacaag agattaatgc tcatattcat gacttcatca ataagttcta a            951
```

TABLE 3-continued

| Sequences disclosed herein (see also Table 2). |
|---|

SEQ ID NO: 40
*Siraitia grosvenorii* protein sequence
Met Asp Glu Ile Glu His Ile Thr Ile Asn Thr Asn Gly Ile Lys Met
1 5 10 15

His Ile Ala Ser Val Gly Thr Gly Pro Val Val Leu Leu Leu His Gly
20 25 30

Phe Pro Glu Leu Trp Tyr Ser Trp Arg His Gln Leu Leu Tyr Leu Ser
35 40 45

Ser Val Gly Tyr Arg Ala Ile Ala Pro Asp Leu Arg Gly Tyr Gly Asp
50 55 60

Thr Asp Ser Pro Ala Ser Pro Thr Ser Tyr Thr Ala Leu His Ile Val
65 70 75 80

Gly Asp Leu Val Gly Ala Leu Asp Glu Leu Gly Ile Glu Lys Val Phe
85 90 95

Leu Val Gly His Asp Trp Gly Ala Ile Ile Ala Trp Tyr Phe Cys Leu
100 105 110

Phe Arg Pro Asp Arg Ile Lys Ala Leu Val Asn Leu Ser Val Gln Phe
115 120 125

Ile Pro Arg Asn Pro Ala Ile Pro Phe Ile Glu Gly Phe Arg Thr Ala 130 135 140
Phe Gly Asp Asp Phe Tyr Ile Cys Arg Phe Gln Val Pro Gly Glu Ala 145 150 155 160
Glu Glu Asp Phe Ala Ser Ile Asp Thr Ala Gln Leu Phe Lys Thr Ser 165 170 175
Leu Cys Asn Arg Ser Ser Ala Pro Pro Cys Leu Pro Lys Glu Ile Gly
180 185 190

Phe Arg Ala Ile Pro Pro Pro Glu Asn Leu Pro Ser Trp Leu Thr Glu
195 200 205

Glu Asp Ile Asn Phe Tyr Ala Ala Lys Phe Lys Gln Thr Gly Phe Thr
210 215 220

Gly Ala Leu Asn Tyr Tyr Arg Ala Phe Asp Leu Thr Trp Glu Leu Thr
225 230 235 240

Ala Pro Trp Thr Gly Ala Gln Ile Gln Val Pro Val Lys Phe Ile Val
245 250 255

Gly Asp Ser Asp Leu Thr Tyr His Phe Pro Gly Ala Lys Glu Tyr Ile
260 265 270

His Asn Gly Gly Phe Lys Arg Asp Val Pro Leu Leu Glu Glu Val Val
275 280 285

Val Val Lys Asp Ala Cys His Phe Ile Asn Gln Glu Arg Pro Gln Glu
290 295 300

Ile Asn Ala His Ile His Asp Phe Ile Asn Lys Phe
305 310 315

SEQ ID NO: 41
*Siraitia grosvenorii* DNA sequence
gtggggccgt cgtctgttga agctcctcag cggacgattt cgaagcctga acagagggag 60
ctaccgttga ggaagattcc cggggactat gggccgccgt tgttgggtcc gattaaggac 120
cgacaagact atttttacaa tcaggggagg gaggagttcc tgagatcacg catgaacagg 180
tacgaatcaa ctgtgtacag aactaatatg ccaccaggtc cctttatctc ctccgattct 240
cgtgtcatcg ttttactcga cggcaagagc ttccctgtac tcttcgacgt ttctaaagtt 300
ctgaaacaag acgtcttcac cggaacttat atgcccttaa cggagctcac tggcggctac 360
cgagttcttt cttatctcga cccctccgag cccgatcacg agaagcttaa acagttcctc 420
ttctacctcc tcaagtaccg tcgcgacaag attctgccgg agtttcactc taccttttcg 480
gagctgtttg agactctgga gaaggaggtg gctgccgccg gtagagcaga ttataatgat 540
cccggtgaac aggcggcgtt taacttcttg gctcggtctc tgttcggcgc caacccgccc 600
gacaccaaac tgggaaacga cgctccgagt ttaatatcca aatgggtgct gttccagctg 660
ggtccggttc tcactcttgg tcttcccaag cctgtcgagg agcttctcct gcgaaccgtc 720
cggctgccac cggcgcttgt gaaatcggat taccagcggc tgtacgattt cttttacgag 780
gcgtcggagg ctgtgtttgc ggaggcggat agattgggca ttgcgagaga ggaagcgtgt 840

TABLE 3-continued

Sequences disclosed herein (see also Table 2).

```
cacaacttgg tcttcgccac gtgcttcaat tccttcggag ggatgaagat cctcttcccc   900
aatatgataa aatggatcgg acgtgccgga gtgaatctcc atacggagct cgcacgggag   960
ataagatccg ccgtcaaagc ccacggcggc aagatcacga tggcggctat ggaacagatg  1020
ccgctgatga agtccgtagt gtacgaaacg ctcagaatcg aaccccccggt tcctgcgcaa  1080
tacgggcgag cgaaggagga cctggtgatc gagagccacg acgccgcttt cgagatcaaa  1140
gaaggggaaa tgttgtgtgg gtaccagcca ttcgccacta gagatccgaa aatattcgag  1200
agatccgaag aattcgtacc ggatcggttc accggcgacg gcgaggagtt gctgaagcac  1260
gtgctctggt caaacggacc ggagactcaa tccccaaccg ttaaagacaa gcagtgcgct  1320
ggcaaagact tcatagtctt cgtctcccgc ctcctcgtcg tcgaactctt cctccgatac  1380
gactccttcg acattgaagt cgcagcttcg ccgttgggcg ccgccgtcac cataacttcc  1440
ctgaagaagg caagctttta a                                            1461
```

SEQ ID NO: 42
Artificial Sequence; Codon-optimized nucleotide sequence encoding cucurbitadienol synthase

```
atgtggagat tgaaagtagg tgctgaatcc gtaggtgaaa acgacgaaaa gtggttgaaa    60
agtataagta atcatttggg tagacaagtc tgggaatttt gtccagatgc aggtacacaa   120
caacaattgt tgcaagtaca taaggctaga aaggcatttc atgatgacag attccacaga   180
aagcaatctt cagatttgtt catcaccatc caatacggca aggaagtaga aaacggtggc   240
aagactgctg gtgttaaatt gaaggaaggt gaagaagtta gaaaagaagc agttgaatcc   300
agtttggaaa gagccttgtc tttctactct tcaatccaaa cctctgatgg taattgggca   360
tcagacttgg gtggtccaat gttcttgtta cctggtttgg tcattgcctt gtacgtaact   420
ggtgttttga actctgtatt gtcaaagcat cacagacaag aaatgtgtag atacgtttac   480
aaccatcaaa acgaagatgg tggttggggt ttgcacattg aaggtccatc cactatgttt   540
ggtagtgcat tgaattatgt cgccttaaga ttgttaggtg aagatgcaaa cgccggtgct   600
atgcctaagg caagagcctg gatattagac catggtggtg ctactggtat cacatcctgg   660
ggtaaattgt ggttaagtgt cttaggtgta tatgaatggt ctggtaataa cccattgcca   720
cctgaatttt ggttgttccc ttactttta ccattccatc ctggtagaat gtggtgtcac   780
tgcagaatgg tttacttgcc aatgtcttac ttgtacggca agagattcgt tggtccaata   840
acacctatcg tcttgtcatt gagaaaggaa ttgtacgcag ttccttacca tgaaatcgat   900
tggaacaagt ccagaaacac ctgtgctaag gaagatttgt attacccaca ccctaaaatg   960
caagacattt tgtggggtag tttacatcac gtttacgaac cattatttac tagatggcct  1020
gctaaaagat tgagagaaaa ggcattacaa acagccatgc aacatatcca ctacgaagat  1080
gaaaacacca gatacatctg cttgggtcca gttaacaagg tcttgaactt gttgtgttgc  1140
tgggttgaag atccttattc tgacgctttc aagttgcatt tgcaaagagt acacgattac  1200
ttgtgggttg cagaagacgg tatgaaaatg caaggttaca atggttcaca attgtgggat  1260
acagcttttt ccattcaagc aatagtcagt actaagttgg tagataacta cggtccaaca  1320
ttaagaaaag ctcatgactt cgtaaagtcc agtcaaatac aacaagattg tccaggtgac  1380
cctaatgttt ggtatagaca tatccacaaa ggtgcatggc cattttctac cagagatcat  1440
ggttggttga tttcagactg tactgctgaa ggtttgaagg ctgcattgat gttgtctaag  1500
ttgccatcag aaactgttgg tgaatccttg gaaagaaata gattatgcga tgccgttaac  1560
gtcttgttga gtttgcaaaa cgacaacggt ggtttcgctt cttacgaatt gactagatca  1620
tacccatggt tggaattaat taatcctgct gaaacattcg gtgatatcgt cattgactat  1680
ccatacgtag aatgtacctc cgctactatg gaagcattga ccttgttcaa gaagttgcat  1740
cctggtcaca gaacaaagga aatcgatacc gcaattgtta gagccgctaa tttcttggaa  1800
aacatgcaaa gaacagacgg ttcttggtat ggttgttggg gtgtttgctt tacctacgct  1860
ggttggttcg gtattaaagg tttagtcgca gccggtagaa catacaataa ctgtttggcc  1920
ataagaaaag cttgcgattt cttgttatct aaggaattac caggtggtgg ttggggtgaa  1980
tcctacttga gttgtcaaaa caaggtttac actaatttgg aaggcaacag acctcattta  2040
gttaacacag cctgggtctt gatggcttta atcgaagccg gtcaagctga aagagatcca  2100
actcctttgc atagagctgc aagattgttg atcaactcac aattggaaaa cggtgatttt  2160
ccacaacaag aaatcatggg tgttttcaac aagaactgca tgataacata tgccgcttac  2220
agaaacattt ttcctatatg ggctttgggt gaatactgcc acagagtctt gaccgaataa  2280
```

SEQ ID NO: 43
*Siraitia grosvenorii* protein sequence

```
Met Trp Arg Leu Lys Val Gly Ala Glu Ser Val Gly Glu Asn Asp Glu
1               5                   10                  15

Lys Trp Leu Lys Ser Ile Ser Asn His Leu Gly Arg Gln Val Trp Glu
            20                  25                  30

Phe Cys Pro Asp Ala Gly Thr Gln Gln Gln Leu Leu Gln Val His Lys
        35                  40                  45

Ala Arg Lys Ala Phe His Asp Asp Arg Phe His Arg Lys Gln Ser Ser
    50                  55                  60

Asp Leu Phe Ile Thr Ile Gln Tyr Gly Lys Glu Val Glu Asn Gly Gly
65                  70                  75                  80

Lys Thr Ala Gly Val Lys Leu Lys Glu Gly Glu Glu Val Arg Lys Glu
                85                  90                  95

Ala Val Glu Ser Ser Leu Glu Arg Ala Leu Ser Phe Tyr Ser Ser Ile
            100                 105                 110

Gln Thr Ser Asp Gly Asn Trp Ala Ser Asp Leu Gly Gly Pro Met Phe
```

TABLE 3-continued

Sequences disclosed herein (see also Table 2).

```
        115                 120                 125

Leu Leu Pro Gly Leu Val Ile Ala Leu Tyr Val Thr Gly Val Leu Asn
    130                 135                 140

Ser Val Leu Ser Lys His His Arg Gln Glu Met Cys Arg Tyr Val Tyr
145                 150                 155                 160

Asn His Gln Asn Glu Asp Gly Gly Trp Gly Leu His Ile Glu Gly Pro
                165                 170                 175

Ser Thr Met Phe Gly Ser Ala Leu Asn Tyr Val Ala Leu Arg Leu Leu
            180                 185                 190

Gly Glu Asp Ala Asn Ala Gly Ala Met Pro Lys Ala Arg Ala Trp Ile
        195                 200                 205

Leu Asp His Gly Gly Ala Thr Gly Ile Thr Ser Trp Gly Lys Leu Trp
    210                 215                 220

Leu Ser Val Leu Gly Val Tyr Glu Trp Ser Gly Asn Asn Pro Leu Pro
225                 230                 235                 240

Pro Glu Phe Trp Leu Phe Pro Tyr Phe Leu Pro Phe His Pro Gly Arg
                245                 250                 255

Met Trp Cys His Cys Arg Met Val Tyr Leu Pro Met Ser Tyr Leu Tyr
            260                 265                 270

Gly Lys Arg Phe Val Gly Pro Ile Thr Pro Ile Val Leu Ser Leu Arg
        275                 280                 285

Lys Glu Leu Tyr Ala Val Pro Tyr His Glu Ile Asp Trp Asn Lys Ser
    290                 295                 300

Arg Asn Thr Cys Ala Lys Glu Asp Leu Tyr Tyr Pro His Pro Lys Met
305                 310                 315                 320

Gln Asp Ile Leu Trp Gly Ser Leu His His Val Tyr Glu Pro Leu Phe
                325                 330                 335

Thr Arg Trp Pro Ala Lys Arg Leu Arg Glu Lys Ala Leu Gln Thr Ala
            340                 345                 350

Met Gln His Ile His Tyr Glu Asp Glu Asn Thr Arg Tyr Ile Cys Leu
        355                 360                 365

Gly Pro Val Asn Lys Val Leu Asn Leu Leu Cys Cys Trp Val Glu Asp
    370                 375                 380

Pro Tyr Ser Asp Ala Phe Lys Leu His Leu Gln Arg Val His Asp Tyr
385                 390                 395                 400

Leu Trp Val Ala Glu Asp Gly Met Lys Met Gln Gly Tyr Asn Gly Ser
                405                 410                 415

Gln Leu Trp Asp Thr Ala Phe Ser Ile Gln Ala Ile Val Ser Thr Lys
            420                 425                 430

Leu Val Asp Asn Tyr Gly Pro Thr Leu Arg Lys Ala His Asp Phe Val
        435                 440                 445

Lys Ser Ser Gln Ile Gln Gln Asp Cys Pro Gly Asp Pro Asn Val Trp
    450                 455                 460

Tyr Arg His Ile His Lys Gly Ala Trp Pro Phe Ser Thr Arg Asp His
465                 470                 475                 480

Gly Trp Leu Ile Ser Asp Cys Thr Ala Glu Gly Leu Lys Ala Ala Leu
                485                 490                 495

Met Leu Ser Lys Leu Pro Ser Glu Thr Val Gly Glu Ser Leu Glu Arg
            500                 505                 510

Asn Arg Leu Cys Asp Ala Val Asn Val Leu Leu Ser Leu Gln Asn Asp
        515                 520                 525

Asn Gly Gly Phe Ala Ser Tyr Glu Leu Thr Arg Ser Tyr Pro Trp Leu
```

TABLE 3-continued

Sequences disclosed herein (see also Table 2).

```
    530                 535                 540

Glu Leu Ile Asn Pro Ala Glu Thr Phe Gly Asp Ile Val Ile Asp Tyr
545                 550                 555                 560

Pro Tyr Val Glu Cys Thr Ser Ala Thr Met Glu Ala Leu Thr Leu Phe
                565                 570                 575

Lys Lys Leu His Pro Gly His Arg Thr Lys Glu Ile Asp Thr Ala Ile
            580                 585                 590

Val Arg Ala Ala Asn Phe Leu Glu Asn Met Gln Arg Thr Asp Gly Ser
        595                 600                 605

Trp Tyr Gly Cys Trp Gly Val Cys Phe Thr Tyr Ala Gly Trp Phe Gly
    610                 615                 620

Ile Lys Gly Leu Val Ala Ala Gly Arg Thr Tyr Asn Asn Cys Leu Ala
625                 630                 635                 640

Ile Arg Lys Ala Cys Asp Phe Leu Leu Ser Lys Glu Leu Pro Gly Gly
                645                 650                 655

Gly Trp Gly Glu Ser Tyr Leu Ser Cys Gln Asn Lys Val Tyr Thr Asn
            660                 665                 670

Leu Glu Gly Asn Arg Pro His Leu Val Asn Thr Ala Trp Val Leu Met
        675                 680                 685

Ala Leu Ile Glu Ala Gly Gln Ala Glu Arg Asp Pro Thr Pro Leu His
    690                 695                 700

Arg Ala Ala Arg Leu Leu Ile Asn Ser Gln Leu Glu Asn Gly Asp Phe
705                 710                 715                 720

Pro Gln Gln Glu Ile Met Gly Val Phe Asn Lys Asn Cys Met Ile Thr
                725                 730                 735

Tyr Ala Ala Tyr Arg Asn Ile Phe Pro Ile Trp Ala Leu Gly Glu Tyr
            740                 745                 750

Cys His Arg Val Leu Thr Glu
        755
```

SEQ ID NO: 44
*Siraitia grosvenorii* protein sequence

```
Met Trp Thr Val Val Leu Gly Leu Ala Thr Leu Phe Val Ala Tyr Tyr
1               5                   10                  15

Ile His Trp Ile Asn Lys Trp Arg Asp Ser Lys Phe Asn Gly Val Leu
            20                  25                  30

Pro Pro Gly Thr Met Gly Leu Pro Leu Ile Gly Glu Thr Ile Gln Leu
        35                  40                  45

Ser Arg Pro Ser Asp Ser Leu Asp Val His Pro Phe Ile Gln Lys Lys
    50                  55                  60

Val Glu Arg Tyr Gly Pro Ile Phe Lys Thr Cys Leu Ala Gly Arg Pro
65                  70                  75                  80

Val Val Val Ser Ala Asp Ala Glu Phe Asn Asn Tyr Ile Met Leu Gln
                85                  90                  95

Glu Gly Arg Ala Val Glu Met Trp Tyr Leu Asp Thr Leu Ser Lys Phe
            100                 105                 110

Phe Gly Leu Asp Thr Glu Trp Leu Lys Ala Leu Gly Leu Ile His Lys
        115                 120                 125

Tyr Ile Arg Ser Ile Thr Leu Asn His Phe Gly Ala Glu Ala Leu Arg
    130                 135                 140

Glu Arg Phe Leu Pro Phe Ile Glu Ala Ser Ser Met Glu Ala Leu His
145                 150                 155                 160

Ser Trp Ser Thr Gln Pro Ser Val Glu Val Lys Asn Ala Ser Ala Leu
                165                 170                 175
```

TABLE 3-continued

| Sequences disclosed herein (see also Table 2). |
|---|

```
Met Val Phe Arg Thr Ser Val Asn Lys Met Phe Gly Glu Asp Ala Lys
            180                 185                 190

Lys Leu Ser Gly Asn Ile Pro Gly Lys Phe Thr Lys Leu Leu Gly Gly
        195                 200                 205

Phe Leu Ser Leu Pro Leu Asn Phe Pro Gly Thr Thr Tyr His Lys Cys
    210                 215                 220

Leu Lys Asp Met Lys Glu Ile Gln Lys Lys Leu Arg Glu Val Val Asp
225                 230                 235                 240

Asp Arg Leu Ala Asn Val Gly Pro Asp Val Glu Asp Phe Leu Gly Gln
                245                 250                 255

Ala Leu Lys Asp Lys Glu Ser Glu Lys Phe Ile Ser Glu Glu Phe Ile
            260                 265                 270

Ile Gln Leu Leu Phe Ser Ile Ser Phe Ala Ser Phe Glu Ser Ile Ser
        275                 280                 285

Thr Thr Leu Thr Leu Ile Leu Lys Leu Leu Asp Glu His Pro Glu Val
    290                 295                 300

Val Lys Glu Leu Glu Ala Glu His Glu Ala Ile Arg Lys Ala Arg Ala
305                 310                 315                 320

Asp Pro Asp Gly Pro Ile Thr Trp Glu Glu Tyr Lys Ser Met Thr Phe
                325                 330                 335

Thr Leu Gln Val Ile Asn Glu Thr Leu Arg Leu Gly Ser Val Thr Pro
            340                 345                 350

Ala Leu Leu Arg Lys Thr Val Lys Asp Leu Gln Val Lys Gly Tyr Ile
        355                 360                 365

Ile Pro Glu Gly Trp Thr Ile Met Leu Val Thr Ala Ser Arg His Arg
    370                 375                 380

Asp Pro Lys Val Tyr Lys Asp Pro His Ile Phe Asn Pro Trp Arg Trp
385                 390                 395                 400

Lys Asp Leu Asp Ser Ile Thr Ile Gln Lys Asn Phe Met Pro Phe Gly
                405                 410                 415

Gly Gly Leu Arg His Cys Ala Gly Ala Glu Tyr Ser Lys Val Tyr Leu
            420                 425                 430

Cys Thr Phe Leu His Ile Leu Cys Thr Lys Tyr Arg Trp Thr Lys Leu
        435                 440                 445

Gly Gly Gly Arg Ile Ala Arg Ala His Ile Leu Ser Phe Glu Asp Gly
    450                 455                 460

Leu His Val Lys Phe Thr Pro Lys Glu
465                 470
```

SEQ ID NO: 45
*Siraitia grosvenorii* DNA sequence

```
atgaaggtct ctccatttga gttcatgtcg gcaataatta agggcaggat ggacccgtcc     60
aattcttcat ttgagtcgac tggcgaggtt gcctcagtta ttttcgagaa ccgtgagctg    120
gttgcgatct taaccacctc gatcgccgtc atgattggct gcttcgttgt tctcatgtgg    180
cgaagagccg gcagtcggaa agttaagaac gtggagctac ctaagccgtt gattgtgcac    240
gagccggagc ccgaagttga agacggcaag aagaaggttt caatcttctt cggtacacag    300
acaggcaccg ccgaaggatt tgcaaaggct ctagctgacg aggcgaaagc acgatacgag    360
aaggccacat ttagagttgt tgatttggat gattatgcag ctgatgacga tcagtatgaa    420
gagaagttga agaacgagtc tttcgctgtc ttcttattgg caacgtatgg cgatggagag    480
cccactgata atgccgcaag attctataaa tggttcgcgg aggggaaaga gagaggggag    540
tggcttcaga accttcatta tgcggtcttt ggccttggca accgacagta cgagcatttt    600
aataagattg caaaggtggc agatgagctg cttgaggcac agggaggcaa ccgccttgtt    660
aaagttggtc ttggagatga cgatcagtgc atagaggatg acttcagtgc ctggagagaa    720
tcattgtggc ctgagttgga tatgttgctt cgagatgagg atgatgcaac aacagtgacc    780
accccttaca cagctgccgt attagaatat cgagttgtat tccatgattc tgcagatgta    840
gctgctgagg acaagagctg gatcaatgca aacggtcatg ctgtacatga tgctcagcat    900
cccttcagat ctaatgtggt tgtgaggaag gagctccata cgtccgcatc tgatcgctcc    960
tgtagtcatc tagaatttaa tatttctggg tctgcactca attatgaaac aggggatcat   1020
gtcggtgttt actgtgaaaa cttaactgag actgtggacg aggcactaaa cttattgggt   1080
```

TABLE 3-continued

Sequences disclosed herein (see also Table 2).

```
ttgtctcctg aaacgtattt ctccatatat actgataacg aggatggcac tccacttggt  1140
ggaagctctt taccacctcc ttttccatcc tgcaccctca gaacagcatt gactcgatat  1200
gcagatctct tgaattcacc caagaagtca gctttgcttg cattagcagc acatgcttca  1260
aatccagtag aggctgaccg attaagatat cttgcatcac ctgccgggaa ggatgaatac  1320
gcccagtctg tgattggtag ccagaaaagc cttcttgagg tcatggctga atttccttct  1380
gccaagcccc cacttggtgt cttcttcgca gctgttgcac cgcgcttgca gcctcgattc  1440
tactccatat catcatctcc aaggatggct ccatctagaa ttcatgttac ttgtgcttta  1500
gtctatgaca aaatgccaac aggacgtatt cataaaggag tgtgctcaac ttggatgaag  1560
aattctgtgc ccatggagaa aagccatgaa tgcagttggg ctccaatttt cgtgagacaa  1620
tcaaacttca agcttcctgc agagagtaaa gtgcccatta tcatggttgg tcctggaact  1680
ggattggctc ctttcagagg tttcttacag gaaagattag ctttgaagga atctggagta  1740
gaattggggc cttccatatt gttctttgga tgcagaaacc gtaggatgga ttacatatac  1800
gaggatgagc tgaacaactt tgttgagact ggtgctctct ctgagttggt tattgccttc  1860
tcacgcgaag ggccaactaa ggaatatgtg cagcataaaa tggcagagaa ggcttcggat  1920
atctggaatt tgatatcaga aggggcttac ttatatgtat gtggtgatgc aaagggcatg  1980
gctaaggatg tccaccgaac tctccatact atcatgcaag agcagggatc tcttgacagc  2040
tcaaaagctg agagcatggt gaagaatctg caaatgaatg gaaggtatct gcgtgatgtc  2100
tggtga                                                            2106
```

SEQ ID NO: 46
*Siraitia grosvenorii* protein sequence

```
Met Lys Val Ser Pro Phe Glu Phe Met Ser Ala Ile Ile Lys Gly Arg
1               5                   10                  15

Met Asp Pro Ser Asn Ser Ser Phe Glu Ser Thr Gly Glu Val Ala Ser
            20                  25                  30

Val Ile Phe Glu Asn Arg Glu Leu Val Ala Ile Leu Thr Thr Ser Ile
        35                  40                  45

Ala Val Met Ile Gly Cys Phe Val Val Leu Met Trp Arg Arg Ala Gly
    50                  55                  60

Ser Arg Lys Val Lys Asn Val Glu Leu Pro Lys Pro Leu Ile Val His
65                  70                  75                  80

Glu Pro Glu Pro Glu Val Glu Asp Gly Lys Lys Lys Val Ser Ile Phe
                85                  90                  95

Phe Gly Thr Gln Thr Gly Thr Ala Glu Gly Phe Ala Lys Ala Leu Ala
            100                 105                 110

Asp Glu Ala Lys Ala Arg Tyr Glu Lys Ala Thr Phe Arg Val Val Asp
        115                 120                 125

Leu Asp Asp Tyr Ala Ala Asp Asp Asp Gln Tyr Glu Glu Lys Leu Lys
    130                 135                 140

Asn Glu Ser Phe Ala Val Phe Leu Leu Ala Thr Tyr Gly Asp Gly Glu
145                 150                 155                 160

Pro Thr Asp Asn Ala Ala Arg Phe Tyr Lys Trp Phe Ala Glu Gly Lys
                165                 170                 175

Glu Arg Gly Glu Trp Leu Gln Asn Leu His Tyr Ala Val Phe Gly Leu
            180                 185                 190

Gly Asn Arg Gln Tyr Glu His Phe Asn Lys Ile Ala Lys Val Ala Asp
        195                 200                 205

Glu Leu Leu Glu Ala Gln Gly Gly Asn Arg Leu Val Lys Val Gly Leu
    210                 215                 220

Gly Asp Asp Asp Gln Cys Ile Glu Asp Asp Phe Ser Ala Trp Arg Glu
225                 230                 235                 240

Ser Leu Trp Pro Glu Leu Asp Met Leu Leu Arg Asp Glu Asp Asp Ala
                245                 250                 255

Thr Thr Val Thr Thr Pro Tyr Thr Ala Ala Val Leu Glu Tyr Arg Val
            260                 265                 270

Val Phe His Asp Ser Ala Asp Val Ala Ala Glu Asp Lys Ser Trp Ile
        275                 280                 285

Asn Ala Asn Gly His Ala Val His Asp Ala Gln His Pro Phe Arg Ser
    290                 295                 300
```

TABLE 3-continued

Sequences disclosed herein (see also Table 2).

```
Asn Val Val Val Arg Lys Glu Leu His Thr Ser Ala Ser Asp Arg Ser
305                 310                 315                 320

Cys Ser His Leu Glu Phe Asn Ile Ser Gly Ser Ala Leu Asn Tyr Glu
                325                 330                 335

Thr Gly Asp His Val Gly Val Tyr Cys Glu Asn Leu Thr Glu Thr Val
            340                 345                 350

Asp Glu Ala Leu Asn Leu Leu Gly Leu Ser Pro Glu Thr Tyr Phe Ser
        355                 360                 365

Ile Tyr Thr Asp Asn Glu Asp Gly Thr Pro Leu Gly Gly Ser Ser Leu
    370                 375                 380

Pro Pro Pro Phe Pro Ser Cys Thr Leu Arg Thr Ala Leu Thr Arg Tyr
385                 390                 395                 400

Ala Asp Leu Leu Asn Ser Pro Lys Lys Ser Ala Leu Leu Ala Leu Ala
                405                 410                 415

Ala His Ala Ser Asn Pro Val Glu Ala Asp Arg Leu Arg Tyr Leu Ala
            420                 425                 430

Ser Pro Ala Gly Lys Asp Glu Tyr Ala Gln Ser Val Ile Gly Ser Gln
        435                 440                 445

Lys Ser Leu Leu Glu Val Met Ala Glu Phe Pro Ser Ala Lys Pro Pro
    450                 455                 460

Leu Gly Val Phe Phe Ala Ala Val Ala Pro Arg Leu Gln Pro Arg Phe
465                 470                 475                 480

Tyr Ser Ile Ser Ser Ser Pro Arg Met Ala Pro Ser Arg Ile His Val
                485                 490                 495

Thr Cys Ala Leu Val Tyr Asp Lys Met Pro Thr Gly Arg Ile His Lys
            500                 505                 510

Gly Val Cys Ser Thr Trp Met Lys Asn Ser Val Pro Met Glu Lys Ser
        515                 520                 525

His Glu Cys Ser Trp Ala Pro Ile Phe Val Arg Gln Ser Asn Phe Lys
    530                 535                 540

Leu Pro Ala Glu Ser Lys Val Pro Ile Ile Met Val Gly Pro Gly Thr
545                 550                 555                 560

Gly Leu Ala Pro Phe Arg Gly Phe Leu Gln Glu Arg Leu Ala Leu Lys
                565                 570                 575

Glu Ser Gly Val Glu Leu Gly Pro Ser Ile Leu Phe Phe Gly Cys Arg
            580                 585                 590

Asn Arg Arg Met Asp Tyr Ile Tyr Glu Asp Glu Leu Asn Asn Phe Val
        595                 600                 605

Glu Thr Gly Ala Leu Ser Glu Leu Val Ile Ala Phe Ser Arg Glu Gly
    610                 615                 620

Pro Thr Lys Glu Tyr Val Gln His Lys Met Ala Glu Lys Ala Ser Asp
625                 630                 635                 640

Ile Trp Asn Leu Ile Ser Glu Gly Ala Tyr Leu Tyr Val Cys Gly Asp
                645                 650                 655

Ala Lys Gly Met Ala Lys Asp Val His Arg Thr Leu His Thr Ile Met
            660                 665                 670

Gln Glu Gln Gly Ser Leu Asp Ser Ser Lys Ala Glu Ser Met Val Lys
        675                 680                 685

Asn Leu Gln Met Asn Gly Arg Tyr Leu Arg Asp Val Trp
    690                 695                 700
```

TABLE 3-continued

Sequences disclosed herein (see also Table 2).

SEQ ID NO: 47
*Siraitia grosvenorii* DNA sequence
```
atggcttctc ctcgccacac tcctcacttt ctgctcttcc ctttcatggc tcaaggccac    60
atgatcccca tgattgacct tgccaggctt ctggctcagc gaggagttat catcactatt   120
atcaccacgc cccacaatgc tgctcgctac cactctgttc ttgctcgcgc catcgattct   180
gggttacaca tccatgtcct ccaactgcag tttccatgta aggaaggtgg gctgccagaa   240
gggtgcgaga atgtggactt gctaccttca cttgcttcca tacccagatt ctacagagca   300
gcaagtgatc tcctttacga accatctgaa aaactgtttg aggaactcat cccccggccg   360
acctgcataa tctccgatat gtgcctgccc tggaccatgc gaattgctct gaaatatcac   420
gtcccaaggc tcgttttcta cagtttgagc tgcttctttc ttctctgtat gcggagttta   480
aaaaacaatc tagcgcttat aagctccaag tctgattctg agttcgtaac tttctctgac   540
ttgcctgatc cagtcgagtt tctcaagtcg gagctaccta aatccaccga tgaagacttg   600
gtgaagttta gttatgaaat gggggaggcc gatcggcagt catacggcgt tattttaaat   660
ctatttgagg agatggaacc aaagtatctt gcagaatatg aaaaggaaag agaatcgccg   720
gaaagagtct ggtgcgtcgg cccagtttcg ctttgcaacg acaacaaact cgacaaagct   780
gaaagaggca acaaagcctc catcgacgaa tacaaatgca tcaggtggct cgacgggcag   840
cagccatctt cggtggttta cgtctcttta ggaagcttgt gcaatctggt gacggcgcag   900
atcatagagc tgggtttggg tttggaggca tcaaagaaac ccttcatttg ggtcataaga   960
agaggaaaca taacagagga gttacagaaa tggcttgtgg agtacgattt cgaggagaaa  1020
attaaaggga gagggctggt gattcttggc tgggctcccc aagttctgat actgtcacac  1080
cctgcaatcg gatgcttttt gacgcactgc ggttggaact caagcatcga agggatatcg  1140
gccggcgtgc caatggtcac ctggccgctt tttgcggatc aagtcttcaa cgagaagcta  1200
attgtacaaa tactcagaat cggcgtaagt gtaggcacgg aaactactat gaactgggga  1260
gaggaagagg agaaaggggt ggttgtgaag agagagaaag tgagggaagc catagaaata  1320
gtgatggatg gagatgagag agaagagagg agagagagat gcaaagagct tgctgaaacg  1380
gcgaagagag ctatagaaga agggggctcg tctcaccgga acctcacgat gttgattgaa  1440
gatataattc atggaggagg tttgagttat gagaaaggaa gttgtcgctg a           1491
```

SEQ ID NO: 48
*Siraitia grosvenorii* protein sequence
```
Met Ala Ser Pro Arg His Thr Pro His Phe Leu Leu Phe Pro Phe Met
1               5                   10                  15

Ala Gln Gly His Met Ile Pro Met Ile Asp Leu Ala Arg Leu Leu Ala
            20                  25                  30

Gln Arg Gly Val Ile Ile Thr Ile Ile Thr Thr Pro His Asn Ala Ala
        35                  40                  45

Arg Tyr His Ser Val Leu Ala Arg Ala Ile Asp Ser Gly Leu His Ile
    50                  55                  60

His Val Leu Gln Leu Gln Phe Pro Cys Lys Glu Gly Gly Leu Pro Glu
65                  70                  75                  80

Gly Cys Glu Asn Val Asp Leu Leu Pro Ser Leu Ala Ser Ile Pro Arg
                85                  90                  95

Phe Tyr Arg Ala Ala Ser Asp Leu Leu Tyr Glu Pro Ser Glu Lys Leu
            100                 105                 110

Phe Glu Glu Leu Ile Pro Arg Pro Thr Cys Ile Ile Ser Asp Met Cys
        115                 120                 125

Leu Pro Trp Thr Met Arg Ile Ala Leu Lys Tyr His Val Pro Arg Leu
    130                 135                 140

Val Phe Tyr Ser Leu Ser Cys Phe Phe Leu Leu Cys Met Arg Ser Leu
145                 150                 155                 160

Lys Asn Asn Leu Ala Leu Ile Ser Ser Lys Ser Asp Ser Glu Phe Val
                165                 170                 175

Thr Phe Ser Asp Leu Pro Asp Pro Val Glu Phe Leu Lys Ser Glu Leu
            180                 185                 190

Pro Lys Ser Thr Asp Glu Asp Leu Val Lys Phe Ser Tyr Glu Met Gly
        195                 200                 205

Glu Ala Asp Arg Gln Ser Tyr Gly Val Ile Leu Asn Leu Phe Glu Glu
    210                 215                 220

Met Glu Pro Lys Tyr Leu Ala Glu Tyr Glu Lys Glu Arg Glu Ser Pro
225                 230                 235                 240

Glu Arg Val Trp Cys Val Gly Pro Val Ser Leu Cys Asn Asp Asn Lys
                245                 250                 255
```

TABLE 3-continued

Sequences disclosed herein (see also Table 2).

Leu Asp Lys Ala Glu Arg Gly Asn Lys Ala Ser Ile Asp Glu Tyr Lys
260 265 270

Cys Ile Arg Trp Leu Asp Gly Gln Gln Pro Ser Ser Val Val Tyr Val
275 280 285

Ser Leu Gly Ser Leu Cys Asn Leu Val Thr Ala Gln Ile Ile Glu Leu
290 295 300

Gly Leu Gly Leu Glu Ala Ser Lys Lys Pro Phe Ile Trp Val Ile Arg
305 310 315 320

Arg Gly Asn Ile Thr Glu Glu Leu Gln Lys Trp Leu Val Glu Tyr Asp
325 330 335

Phe Glu Glu Lys Ile Lys Gly Arg Gly Leu Val Ile Leu Gly Trp Ala
340 345 350

Pro Gln Val Leu Ile Leu Ser His Pro Ala Ile Gly Cys Phe Leu Thr
355 360 365

His Cys Gly Trp Asn Ser Ser Ile Glu Gly Ile Ser Ala Gly Val Pro
370 375 380

Met Val Thr Trp Pro Leu Phe Ala Asp Gln Val Phe Asn Glu Lys Leu
385 390 395 400

Ile Val Gln Ile Leu Arg Ile Gly Val Ser Val Gly Thr Glu Thr Thr
405 410 415

Met Asn Trp Gly Glu Glu Glu Glu Lys Gly Val Val Val Lys Arg Glu
420 425 430

Lys Val Arg Glu Ala Ile Glu Ile Val Met Asp Gly Asp Glu Arg Glu
435 440 445

Glu Arg Arg Glu Arg Cys Lys Glu Leu Ala Glu Thr Ala Lys Arg Ala
450 455 460

Ile Glu Glu Gly Gly Ser Ser His Arg Asn Leu Thr Met Leu Ile Glu
465 470 475 480

Asp Ile Ile His Gly Gly Gly Leu Ser Tyr Glu Lys Gly Ser Cys Arg
485 490 495

SEQ ID NO: 49
*Siraitia grosvenorii* DNA sequence
atggatgccc agcgaggtca caccaccacc attttgatgc ttccatgggt cggctacggc 60
catctcttgc ctttcctcga gctggccaaa agcctctcca ggaggaaatt attccacatc 120
tacttctgtt caacgtctgt tagcctcgac gccattaaac caaagcttcc tccttctatc 180
tcttctgatg attccatcca acttgtggaa cttcgtctcc cttcttctcc tgagttacct 240
cctcatcttc acacaaccaa cggccttccc tctcacctca tgcccgctct ccaccaagcc 300
ttcgtcatgg ccgcccaaca ctttcaggtc attttacaaa cacttgcccc gcatctcctc 360
atttatgaca ttctccaacc ttgggctcct caagtggctt catccctcaa cattccagcc 420
atcaacttca gtactaccgg agcttcaatg ctttctcgaa cgcttcaccc tactcactac 480
ccaagttcta aattcccaat ctcagagttt gttcttcaca atcactggag agccatgtac 540
accaccgccg atggggctct tacagaagaa ggccacaaaa ttgaagaaac acttgcgaat 600
tgcttgcata cttcttgcgg ggtagttttg gtcaatagtt tcagagagct tgagacgaaa 660
tatatcgatt atctctctgt tctcttgaac aagaaagttg ttccggtcgg tcctttggtt 720
tacgaaccga atcaagaagg ggaagatgaa ggttattcaa gcatcaaaaa ttggcttgac 780
aaaaaggaac cgtcctcaac cgtcttcgtt tcatttggaa ccgaatactt cccgtcaaag 840
gaagaaatgg aagagatagc gtatgggtta gagctgagcg aggttaattt catctgggtc 900
cttagatttc ctcaaggaga cagcaccagc accattgaag acgccttgcc gaaggggttt 960
ctggagagag cgggagagag ggcgatggtg gtgaagggtt gggctcctca ggcgaagata 1020
ctgaagcatt ggagcacagg ggggcttgtg agtcactgtg gatggaactc gatgatggag 1080
ggcatgatgt ttggcgtacc cataatagcg gtcccgatgc atctggacca gccctttaac 1140
gccggactct tggaagaagc tggcgtcggc gtggaagcca agcgaggttc ggacggcaaa 1200
attcaaagag aagaagttgc aaagtcgatc aaagaagtgg tgattgagaa aaccagggaa 1260
gacgtgagga agaaagcaag agaaatgggt gagattttga ggagtaaagg agatgagaaa 1320
attgatgagt tggtggctga aatttctctt ttgcgcaaaa aggctccatg ttcaatttaa 1380

SEQ ID NO: 50
*Siraitia grosvenorii* protein sequence
Met Asp Ala Gln Arg Gly His Thr Thr Thr Ile Leu Met Leu Pro Trp
1 5 10 15

Val Gly Tyr Gly His Leu Leu Pro Phe Leu Glu Leu Ala Lys Ser Leu
20 25 30

TABLE 3-continued

Sequences disclosed herein (see also Table 2).

```
Ser Arg Arg Lys Leu Phe His Ile Tyr Phe Cys Ser Thr Ser Val Ser
        35                  40                  45

Leu Asp Ala Ile Lys Pro Lys Leu Pro Pro Ser Ile Ser Ser Asp Asp
    50                  55                  60

Ser Ile Gln Leu Val Glu Leu Arg Leu Pro Ser Ser Pro Glu Leu Pro
65                  70                  75                  80

Pro His Leu His Thr Thr Asn Gly Leu Pro Ser His Leu Met Pro Ala
                85                  90                  95

Leu His Gln Ala Phe Val Met Ala Ala Gln His Phe Gln Val Ile Leu
            100                 105                 110

Gln Thr Leu Ala Pro His Leu Leu Ile Tyr Asp Ile Leu Gln Pro Trp
        115                 120                 125

Ala Pro Gln Val Ala Ser Ser Leu Asn Ile Pro Ala Ile Asn Phe Ser
    130                 135                 140

Thr Thr Gly Ala Ser Met Leu Ser Arg Thr Leu His Pro Thr His Tyr
145                 150                 155                 160

Pro Ser Ser Lys Phe Pro Ile Ser Glu Phe Val Leu His Asn His Trp
                165                 170                 175

Arg Ala Met Tyr Thr Thr Ala Asp Gly Ala Leu Thr Glu Glu Gly His
            180                 185                 190

Lys Ile Glu Glu Thr Leu Ala Asn Cys Leu His Thr Ser Cys Gly Val
        195                 200                 205

Val Leu Val Asn Ser Phe Arg Glu Leu Glu Thr Lys Tyr Ile Asp Tyr
    210                 215                 220

Leu Ser Val Leu Leu Asn Lys Lys Val Val Pro Val Gly Pro Leu Val
225                 230                 235                 240

Tyr Glu Pro Asn Gln Glu Gly Glu Asp Glu Gly Tyr Ser Ser Ile Lys
                245                 250                 255

Asn Trp Leu Asp Lys Lys Glu Pro Ser Ser Thr Val Phe Val Ser Phe
            260                 265                 270

Gly Thr Glu Tyr Phe Pro Ser Lys Glu Glu Met Glu Glu Ile Ala Tyr
        275                 280                 285
Gly Leu Glu Leu Ser Glu Val Asn Phe Ile Trp Val Leu Arg Phe Pro

    290                 295                 300
Gln Gly Asp Ser Thr Ser Thr Ile Glu Asp Ala Leu Pro Lys Gly Phe

305                 310                 315                 320
Leu Glu Arg Ala Gly Glu Arg Ala Met Val Val Lys Gly Trp Ala Pro

                325                 330                 335
Gln Ala Lys Ile Leu Lys His Trp Ser Thr Gly Gly Leu Val Ser His

            340                 345                 350
Cys Gly Trp Asn Ser Met Met Glu Gly Met Met Phe Gly Val Pro Ile

        355                 360                 365

Ile Ala Val Pro Met His Leu Asp Gln Pro Phe Asn Ala Gly Leu Leu
    370                 375                 380

Glu Glu Ala Gly Val Gly Val Glu Ala Lys Arg Gly Ser Asp Gly Lys
385                 390                 395                 400

Ile Gln Arg Glu Glu Val Ala Lys Ser Ile Lys Glu Val Val Ile Glu
                405                 410                 415

Lys Thr Arg Glu Asp Val Arg Lys Lys Ala Arg Glu Met Gly Glu Ile
            420                 425                 430

Leu Arg Ser Lys Gly Asp Glu Lys Ile Asp Glu Leu Val Ala Glu Ile
        435                 440                 445
```

TABLE 3-continued

Sequences disclosed herein (see also Table 2).

Ser Leu Leu Arg Lys Lys Ala Pro Cys Ser Ile
450 455

SEQ ID NO: 51
*Siraitia grosvenorii* DNA sequence
atggatgccc agcgaggtca caccacaacc attttgatgt ttccatggct cggctatggc 60
catctttcgg ctttcctaga gttggccaaa agcctctcaa ggaggaactt ccatatctac 120
ttctgttcaa cctctgttaa cctcgacgcc attaaaccaa agcttccttc ttcttcctct 180
tctgattcca tccaacttgt ggaactttgt cttccatctt ctcctgatca gctccctcct 240
catcttcaca caaccaacgc cctccccct cacctcatgc ccactctcca ccaagccttc 300
tccatggctg cccaacactt tgctgccatt ttacacacac ttgctccgca tctcctcatt 360
tacgactctt tccaaccttg ggctcctcaa ctagcttcat ccctcaacat tccagccatc 420
aacttcaata ctacgggagc ttcagtcctg acccgaatgc ttcacgctac tcactaccca 480
agttctaaat tcccaatttc agagtttgtt ctccacgatt attggaaagc catgtacagc 540
gccgccggtg ggctgttac aaaaaaagac cacaaaattg gagaaacact tgcgaattgc 600
ttgcatgctt cttgtagtgt aattctaatc aatagtttca gagagctcga ggagaaatat 660
atggattatc tctccgttct cttgaacaag aaagttgttc cggttggtcc tttggtttac 720
gaaccgaatc aagacgggga agatgaaggt tattcaagca tcaaaaattg gcttgacaaa 780
aaggaaccgt cctccaccgt cttcgtttca tttggaagcg aatacttccc gtcaaaggaa 840
gaaatggaag agatagccca tgggttagag gcgagcgagg ttcatttcat ctgggtcgtt 900
aggtttcctc aaggagacaa caccagcgcc attgaagatg ccttgccgaa ggggtttctg 960
gagagggtgg gagagagagg gatggtggtg aagggttggg ctcctcaggc gaagatactg 1020
aagcattgga gcacaggggg attcgtgagc cactgtggat ggaactcggt gatggaaagc 1080
atgatgtttg gcgttcccat aataggggtt ccgatgcatc tggaccagcc ctttaacgcc 1140
ggactcgcgg aagaagctgg cgtcggcgtg gaagccaagc gagattcgga cggcaaaatt 1200
caaagagaag aagttgcaaa gtcgatcaaa gaagtggtga ttgagaaaac cagggaagac 1260
gtgaggaaga aagcaagaga aatgggtgag attttgagga gtaaaggaga tgagaaaatt 1320
gatgagttgg tggctgaaat ttctcttttg cgcaaaaagg ctccatgttc aatttaa 1377

SEQ ID NO: 52
Artificial Sequence; Codon-optimized nucleotide sequence
encoding UGT98
atggatgctc aaagaggtca taccactacc attttgatgt ttccatggtt gggttacggt 60
catttgtctg ctttttgga attggccaag tccttgtcta gaagaaactt ccatatctac 120
ttttgctcca cctccgttaa tttggatgct attaagccaa agttgccatc ctcttcatcc 180
tccgattcta ttcaattggt tgaattgtgc ttgccatctt ccccagatca attgccacca 240
cacttgcata caactaatgc tttaccacca catttgatgc caacattgca tcaagctttt 300
tctatggctg ctcaacattt tgctgctatc ttgcatactt tggctcctca tttgttgatc 360
tacgattctt ttcaaccatg ggctccacaa ttggcttcat ctttgaatat tccagccatc 420
aacttcaaca ctactggtgc ttcagttttg accagaatgt tgcatgctac tcattaccca 480
tcttccaagt tcccaatttc tgaattcgtc ttgcatgatt actggaaggc tatgtattct 540
gctgctggtg gtgctgttac aaaaaaggat cataagattg gtgaaacctt ggccaactgt 600
ttacatgctt cttgctctgt tatcttgatc aactccttca gagaattgga agaaaagtac 660
atggactact tgtccgtctt gttgaacaaa aaggttgttc cagttggtcc attggtctac 720
gaacctaatc aagatggtga agatgaaggt tactcctcca ttaagaattg gttggacaag 780
aaagaaccat cctctaccgt ttttgtttcc ttcggttctg aatacttccc atccaaagaa 840
gaaatggaag aaatcgctca tggtttggaa gcttcagaag ttcatttcat ctgggttgtt 900
agattccctc aaggtgataa cacttccgct attgaagatg ctttgccaaa aggtttcttg 960
gaaagagtcg gtgaaagagg tatggttgtt aagggttggg ctcctcaagc taagattttg 1020
aaacattggt caaccggtgg tttcgtttct cattgtggtt ggaattctgt catggaatct 1080
atgatgttcg gtgttccaat tattggtgtc ccaatgcatt tggatcaacc attcaatgct 1140
ggtttggctg aagaagctgg tgttggtgtt gaagctaaaa gagattctga cggtaagatc 1200
caaagagaag aagttgccaa gtccatcaaa gaagttgtta tcgaaaagac cagagaagat 1260
gtcagaaaga aagctagaga aatgggtgaa atcttgagat ctaaaggtga cgaaaagatc 1320
gatgaattgg tcgccgaaat ttccttgttg agaaaaaaag ctccatgctc tatttga 1377

SEQ ID NO: 53
*Siraitia grosvenorii* protein sequence
Met Asp Ala Gln Arg Gly His Thr Thr Thr Ile Leu Met Phe Pro Trp
1 5 10 15

Leu Gly Tyr Gly His Leu Ser Ala Phe Leu Glu Leu Ala Lys Ser Leu
20 25 30

Ser Arg Arg Asn Phe His Ile Tyr Phe Cys Ser Thr Ser Val Asn Leu
35 40 45

Asp Ala Ile Lys Pro Lys Leu Pro Ser Ser Ser Ser Ser Asp Ser Ile
50 55 60

Gln Leu Val Glu Leu Cys Leu Pro Ser Ser Pro Asp Gln Leu Pro Pro
65 70 75 80

His Leu His Thr Thr Asn Ala Leu Pro Pro His Leu Met Pro Thr Leu
85 90 95

His Gln Ala Phe Ser Met Ala Ala Gln His Phe Ala Ala Ile Leu His

TABLE 3-continued

| Sequences disclosed herein (see also Table 2). |
|---|
| 100 105 110<br><br>Thr Leu Ala Pro His Leu Leu Ile Tyr Asp Ser Phe Gln Pro Trp Ala<br>115 120 125<br><br>Pro Gln Leu Ala Ser Ser Leu Asn Ile Pro Ala Ile Asn Phe Asn Thr<br>130 135 140<br><br>Thr Gly Ala Ser Val Leu Thr Arg Met Leu His Ala Thr His Tyr Pro<br>145 150 155 160<br><br>Ser Ser Lys Phe Pro Ile Ser Glu Phe Val Leu His Asp Tyr Trp Lys<br>165 170 175<br><br>Ala Met Tyr Ser Ala Ala Gly Gly Ala Val Thr Lys Lys Asp His Lys<br>180 185 190<br><br>Ile Gly Glu Thr Leu Ala Asn Cys Leu His Ala Ser Cys Ser Val Ile<br>195 200 205<br><br>Leu Ile Asn Ser Phe Arg Glu Leu Glu Glu Lys Tyr Met Asp Tyr Leu<br>210 215 220<br><br>Ser Val Leu Leu Asn Lys Lys Val Val Pro Val Gly Pro Leu Val Tyr<br>225 230 235 240<br><br>Glu Pro Asn Gln Asp Gly Glu Asp Glu Gly Tyr Ser Ser Ile Lys Asn<br>245 250 255<br><br>Trp Leu Asp Lys Lys Glu Pro Ser Ser Thr Val Phe Val Ser Phe Gly<br>260 265 270<br><br>Ser Glu Tyr Phe Pro Ser Lys Glu Glu Met Glu Glu Ile Ala His Gly<br>275 280 285<br><br>Leu Glu Ala Ser Glu Val His Phe Ile Trp Val Val Arg Phe Pro Gln<br>290 295 300<br><br>Gly Asp Asn Thr Ser Ala Ile Glu Asp Ala Leu Pro Lys Gly Phe Leu<br>305 310 315 320<br><br>Glu Arg Val Gly Glu Arg Gly Met Val Val Lys Gly Trp Ala Pro Gln<br>325 330 335<br><br>Ala Lys Ile Leu Lys His Trp Ser Thr Gly Gly Phe Val Ser His Cys<br>340 345 350<br><br>Gly Trp Asn Ser Val Met Glu Ser Met Met Phe Gly Val Pro Ile Ile<br>355 360 365<br><br>Gly Val Pro Met His Leu Asp Gln Pro Phe Asn Ala Gly Leu Ala Glu<br>370 375 380<br><br>Glu Ala Gly Val Gly Val Glu Ala Lys Arg Asp Ser Asp Gly Lys Ile<br>385 390 395 400<br><br>Gln Arg Glu Glu Val Ala Lys Ser Ile Lys Glu Val Val Ile Glu Lys<br>405 410 415<br><br>Thr Arg Glu Asp Val Arg Lys Lys Ala Arg Glu Met Gly Glu Ile Leu<br>420 425 430<br><br>Arg Ser Lys Gly Asp Glu Lys Ile Asp Glu Leu Val Ala Glu Ile Ser<br>435 440 445<br><br>Leu Leu Arg Lys Lys Ala Pro Cys Ser Ile<br>450 455<br><br>SEQ ID NO: 54<br>*Saccharomyces cerevisiae* protein sequence<br>Met Ser Ala Val Asn Val Ala Pro Glu Leu Ile Asn Ala Asp Asn Thr<br>1 5 10 15<br><br>Ile Thr Tyr Asp Ala Ile Val Ile Gly Ala Gly Val Ile Gly Pro Cys<br>20 25 30<br><br>Val Ala Thr Gly Leu Ala Arg Lys Gly Lys Lys Val Leu Ile Val Glu<br>35 40 45 |

TABLE 3-continued

Sequences disclosed herein (see also Table 2).

```
Arg Asp Trp Ala Met Pro Asp Arg Ile Val Gly Glu Leu Met Gln Pro
    50                  55                  60

Gly Gly Val Arg Ala Leu Arg Ser Leu Gly Met Ile Gln Ser Ile Asn
65                  70                  75                  80

Asn Ile Glu Ala Tyr Pro Val Thr Gly Tyr Thr Val Phe Phe Asn Gly
                85                  90                  95

Glu Gln Val Asp Ile Pro Tyr Pro Tyr Lys Ala Asp Ile Pro Lys Val
            100                 105                 110

Glu Lys Leu Lys Asp Leu Val Lys Asp Gly Asn Asp Lys Val Leu Glu
        115                 120                 125
Asp Ser Thr Ile His Ile Lys Asp Tyr Glu Asp Asp Glu Arg Glu Arg

    130                 135                 140
Gly Val Ala Phe Val His Gly Arg Phe Leu Asn Asn Leu Arg Asn Ile

145                 150                 155                 160
Thr Ala Gln Glu Pro Asn Val Thr Arg Val Gln Gly Asn Cys Ile Glu

                165                 170                 175

Ile Leu Lys Asp Glu Lys Asn Glu Val Val Gly Ala Lys Val Asp Ile
            180                 185                 190

Asp Gly Arg Gly Lys Val Glu Phe Lys Ala His Leu Thr Phe Ile Cys
        195                 200                 205

Asp Gly Ile Phe Ser Arg Phe Arg Lys Glu Leu His Pro Asp His Val
    210                 215                 220

Pro Thr Val Gly Ser Ser Phe Val Gly Met Ser Leu Phe Asn Ala Lys
225                 230                 235                 240

Asn Pro Ala Pro Met His Gly His Val Ile Leu Gly Ser Asp His Met
                245                 250                 255

Pro Ile Leu Val Tyr Gln Ile Ser Pro Glu Glu Thr Arg Ile Leu Cys
            260                 265                 270

Ala Tyr Asn Ser Pro Lys Val Pro Ala Asp Ile Lys Ser Trp Met Ile
        275                 280                 285

Lys Asp Val Gln Pro Phe Ile Pro Lys Ser Leu Arg Pro Ser Phe Asp
    290                 295                 300

Glu Ala Val Ser Gln Gly Lys Phe Arg Ala Met Pro Asn Ser Tyr Leu
305                 310                 315                 320

Pro Ala Arg Gln Asn Asp Val Thr Gly Met Cys Val Ile Gly Asp Ala
                325                 330                 335

Leu Asn Met Arg His Pro Leu Thr Gly Gly Gly Met Thr Val Gly Leu
            340                 345                 350

His Asp Val Val Leu Leu Ile Lys Lys Ile Gly Asp Leu Asp Phe Ser
        355                 360                 365

Asp Arg Glu Lys Val Leu Asp Glu Leu Leu Asp Tyr His Phe Glu Arg
    370                 375                 380

Lys Ser Tyr Asp Ser Val Ile Asn Val Leu Ser Val Ala Leu Tyr Ser
385                 390                 395                 400

Leu Phe Ala Ala Asp Ser Asp Asn Leu Lys Ala Leu Gln Lys Gly Cys
                405                 410                 415

Phe Lys Tyr Phe Gln Arg Gly Gly Asp Cys Val Asn Lys Pro Val Glu
            420                 425                 430

Phe Leu Ser Gly Val Leu Pro Lys Pro Leu Gln Leu Thr Arg Val Phe
        435                 440                 445

Phe Ala Val Ala Phe Tyr Thr Ile Tyr Leu Asn Met Glu Glu Arg Gly
    450                 455                 460
```

TABLE 3-continued

Sequences disclosed herein (see also Table 2).

```
Phe Leu Gly Leu Pro Met Ala Leu Leu Glu Gly Ile Met Ile Leu Ile
465                 470                 475                 480

Thr Ala Ile Arg Val Phe Thr Pro Phe Leu Phe Gly Glu Leu Ile Gly
                485                 490                 495
```

SEQ ID NO: 55
*Saccharomyces cerevisiae* protein sequence

```
Met Thr Glu Phe Tyr Ser Asp Thr Ile Gly Leu Pro Lys Thr Asp Pro
1               5                   10                  15

Arg Leu Trp Arg Leu Arg Thr Asp Glu Leu Gly Arg Glu Ser Trp Glu
            20                  25                  30

Tyr Leu Thr Pro Gln Gln Ala Ala Asn Asp Pro Pro Ser Thr Phe Thr
        35                  40                  45

Gln Trp Leu Leu Gln Asp Pro Lys Phe Pro Gln Pro His Pro Glu Arg
    50                  55                  60

Asn Lys His Ser Pro Asp Phe Ser Ala Phe Asp Ala Cys His Asn Gly
65                  70                  75                  80

Ala Ser Phe Phe Lys Leu Leu Gln Glu Pro Asp Ser Gly Ile Phe Pro
                85                  90                  95

Cys Gln Tyr Lys Gly Pro Met Phe Met Thr Ile Gly Tyr Val Ala Val
            100                 105                 110

Asn Tyr Ile Ala Gly Ile Glu Ile Pro Glu His Glu Arg Ile Glu Leu
        115                 120                 125

Ile Arg Tyr Ile Val Asn Thr Ala His Pro Val Asp Gly Gly Trp Gly
    130                 135                 140

Leu His Ser Val Asp Lys Ser Thr Val Phe Gly Thr Val Leu Asn Tyr
145                 150                 155                 160

Val Ile Leu Arg Leu Leu Gly Leu Pro Lys Asp His Pro Val Cys Ala
                165                 170                 175

Lys Ala Arg Ser Thr Leu Leu Arg Leu Gly Gly Ala Ile Gly Ser Pro
            180                 185                 190

His Trp Gly Lys Ile Trp Leu Ser Ala Leu Asn Leu Tyr Lys Trp Glu
        195                 200                 205

Gly Val Asn Pro Ala Pro Pro Glu Thr Trp Leu Leu Pro Tyr Ser Leu
    210                 215                 220

Pro Met His Pro Gly Arg Trp Trp Val His Thr Arg Gly Val Tyr Ile
225                 230                 235                 240

Pro Val Ser Tyr Leu Ser Leu Val Lys Phe Ser Cys Pro Met Thr Pro
                245                 250                 255

Leu Leu Glu Glu Leu Arg Asn Glu Ile Tyr Thr Lys Pro Phe Asp Lys
            260                 265                 270

Ile Asn Phe Ser Lys Asn Arg Asn Thr Val Cys Gly Val Asp Leu Tyr
        275                 280                 285

Tyr Pro His Ser Thr Thr Leu Asn Ile Ala Asn Ser Leu Val Val Phe
    290                 295                 300

Tyr Glu Lys Tyr Leu Arg Asn Arg Phe Ile Tyr Ser Leu Ser Lys Lys
305                 310                 315                 320

Lys Val Tyr Asp Leu Ile Lys Thr Glu Leu Gln Asn Thr Asp Ser Leu
                325                 330                 335

Cys Ile Ala Pro Val Asn Gln Ala Phe Cys Ala Leu Val Thr Leu Ile
            340                 345                 350

Glu Glu Gly Val Asp Ser Glu Ala Phe Gln Arg Leu Gln Tyr Arg Phe
        355                 360                 365
```

TABLE 3-continued

Sequences disclosed herein (see also Table 2).

```
Lys Asp Ala Leu Phe His Gly Pro Gln Gly Met Thr Ile Met Gly Thr
    370                 375                 380

Asn Gly Val Gln Thr Trp Asp Cys Ala Phe Ala Ile Gln Tyr Phe Phe
385                 390                 395                 400

Val Ala Gly Leu Ala Glu Arg Pro Glu Phe Tyr Asn Thr Ile Val Ser
                405                 410                 415

Ala Tyr Lys Phe Leu Cys His Ala Gln Phe Asp Thr Glu Cys Val Pro
            420                 425                 430

Gly Ser Tyr Arg Asp Lys Arg Lys Gly Ala Trp Gly Phe Ser Thr Lys
        435                 440                 445

Thr Gln Gly Tyr Thr Val Ala Asp Cys Thr Ala Glu Ala Ile Lys Ala
    450                 455                 460

Ile Ile Met Val Lys Asn Ser Pro Val Phe Ser Glu Val His His Met
465                 470                 475                 480

Ile Ser Ser Glu Arg Leu Phe Glu Gly Ile Asp Val Leu Leu Asn Leu
                485                 490                 495

Gln Asn Ile Gly Ser Phe Glu Tyr Gly Ser Phe Ala Thr Tyr Glu Lys
            500                 505                 510

Ile Lys Ala Pro Leu Ala Met Glu Thr Leu Asn Pro Ala Glu Val Phe
        515                 520                 525

Gly Asn Ile Met Val Glu Tyr Pro Tyr Val Glu Cys Thr Asp Ser Ser
    530                 535                 540

Val Leu Gly Leu Thr Tyr Phe His Lys Tyr Phe Asp Tyr Arg Lys Glu
545                 550                 555                 560

Glu Ile Arg Thr Arg Ile Arg Ile Ala Ile Glu Phe Ile Lys Lys Ser
                565                 570                 575

Gln Leu Pro Asp Gly Ser Trp Tyr Gly Ser Trp Gly Ile Cys Phe Thr
            580                 585                 590

Tyr Ala Gly Met Phe Ala Leu Glu Ala Leu His Thr Val Gly Glu Thr
        595                 600                 605

Tyr Glu Asn Ser Ser Thr Val Arg Lys Gly Cys Asp Phe Leu Val Ser
    610                 615                 620

Lys Gln Met Lys Asp Gly Gly Trp Gly Glu Ser Met Lys Ser Ser Glu
625                 630                 635                 640

Leu His Ser Tyr Val Asp Ser Glu Lys Ser Leu Val Val Gln Thr Ala
                645                 650                 655

Trp Ala Leu Ile Ala Leu Leu Phe Ala Glu Tyr Pro Asn Lys Glu Val
            660                 665                 670

Ile Asp Arg Gly Ile Asp Leu Leu Lys Asn Arg Gln Glu Glu Ser Gly
        675                 680                 685

Glu Trp Lys Phe Glu Ser Val Glu Gly Val Phe Asn His Ser Cys Ala
    690                 695                 700

Ile Glu Tyr Pro Ser Tyr Arg Phe Leu Phe Pro Ile Lys Ala Leu Gly
705                 710                 715                 720

Met Tyr Ser Arg Ala Tyr Glu Thr His Thr Leu
                725                 730
```

SEQ ID NO: 56
*Arabidopsis thaliana* protein sequence

```
Met Ala Thr Glu Lys Thr His Gln Phe His Pro Ser Leu His Phe Val
1               5                   10                  15

Leu Phe Pro Phe Met Ala Gln Gly His Met Ile Pro Met Ile Asp Ile
            20                  25                  30

Ala Arg Leu Leu Ala Gln Arg Gly Val Thr Ile Thr Ile Val Thr Thr
```

TABLE 3-continued

Sequences disclosed herein (see also Table 2).

```
        35                  40                  45

Pro His Asn Ala Ala Arg Phe Lys Asn Val Leu Asn Arg Ala Ile Glu
    50                  55                  60

Ser Gly Leu Ala Ile Asn Ile Leu His Val Lys Phe Pro Tyr Gln Glu
65                  70                  75                  80

Phe Gly Leu Pro Glu Gly Lys Glu Asn Ile Asp Ser Leu Asp Ser Thr
                85                  90                  95

Glu Leu Met Val Pro Phe Phe Lys Ala Val Asn Leu Leu Glu Asp Pro
            100                 105                 110

Val Met Lys Leu Met Glu Glu Met Lys Pro Arg Pro Ser Cys Leu Ile
        115                 120                 125

Ser Asp Trp Cys Leu Pro Tyr Thr Ser Ile Ile Ala Lys Asn Phe Asn
    130                 135                 140

Ile Pro Lys Ile Val Phe His Gly Met Gly Cys Phe Asn Leu Leu Cys
145                 150                 155                 160

Met His Val Leu Arg Arg Asn Leu Glu Ile Leu Glu Asn Val Lys Ser
                165                 170                 175

Asp Glu Glu Tyr Phe Leu Val Pro Ser Phe Pro Asp Arg Val Glu Phe
            180                 185                 190

Thr Lys Leu Gln Leu Pro Val Lys Ala Asn Ala Ser Gly Asp Trp Lys
        195                 200                 205

Glu Ile Met Asp Glu Met Val Lys Ala Glu Tyr Thr Ser Tyr Gly Val
    210                 215                 220

Ile Val Asn Thr Phe Gln Glu Leu Glu Pro Pro Tyr Val Lys Asp Tyr
225                 230                 235                 240

Lys Glu Ala Met Asp Gly Lys Val Trp Ser Ile Gly Pro Val Ser Leu
                245                 250                 255

Cys Asn Lys Ala Gly Ala Asp Lys Ala Glu Arg Gly Ser Lys Ala Ala
            260                 265                 270

Ile Asp Gln Asp Glu Cys Leu Gln Trp Leu Asp Ser Lys Glu Glu Gly
        275                 280                 285

Ser Val Leu Tyr Val Cys Leu Gly Ser Ile Cys Asn Leu Pro Leu Ser
    290                 295                 300

Gln Leu Lys Glu Leu Gly Leu Gly Leu Glu Glu Ser Arg Arg Ser Phe
305                 310                 315                 320

Ile Trp Val Ile Arg Gly Ser Glu Lys Tyr Lys Glu Leu Phe Glu Trp
                325                 330                 335

Met Leu Glu Ser Gly Phe Glu Glu Arg Ile Lys Glu Arg Gly Leu Leu
            340                 345                 350

Ile Lys Gly Trp Ala Pro Gln Val Leu Ile Leu Ser His Pro Ser Val
        355                 360                 365

Gly Gly Phe Leu Thr His Cys Gly Trp Asn Ser Thr Leu Glu Gly Ile
    370                 375                 380

Thr Ser Gly Ile Pro Leu Ile Thr Trp Pro Leu Phe Gly Asp Gln Phe
385                 390                 395                 400

Cys Asn Gln Lys Leu Val Val Gln Val Leu Lys Ala Gly Val Ser Ala
                405                 410                 415

Gly Val Glu Glu Val Met Lys Trp Gly Glu Glu Asp Lys Ile Gly Val
            420                 425                 430

Leu Val Asp Lys Glu Gly Val Lys Lys Ala Val Glu Glu Leu Met Gly
        435                 440                 445

Asp Ser Asp Asp Ala Lys Glu Arg Arg Arg Arg Val Lys Glu Leu Gly
```

TABLE 3-continued

Sequences disclosed herein (see also Table 2).

```
    450                 455                 460

Glu Leu Ala His Lys Ala Val Glu Lys Gly Gly Ser Ser His Ser Asn
465                 470                 475                 480

Ile Thr Leu Leu Leu Gln Asp Ile Met Gln Leu Ala Gln Phe Lys Asn
                485                 490                 495
```

SEQ ID NO: 57
*Arabidopsis thaliana* protein sequence

```
Met Val Ser Glu Thr Thr Lys Ser Ser Pro Leu His Phe Val Leu Phe
1               5                   10                  15

Pro Phe Met Ala Gln Gly His Met Ile Pro Met Val Asp Ile Ala Arg
            20                  25                  30

Leu Leu Ala Gln Arg Gly Val Ile Ile Thr Ile Val Thr Thr Pro His
        35                  40                  45

Asn Ala Ala Arg Phe Lys Asn Val Leu Asn Arg Ala Ile Glu Ser Gly
    50                  55                  60

Leu Pro Ile Asn Leu Val Gln Val Lys Phe Pro Tyr Leu Glu Ala Gly
65                  70                  75                  80

Leu Gln Glu Gly Gln Glu Asn Ile Asp Ser Leu Asp Thr Met Glu Arg
                85                  90                  95

Met Ile Pro Phe Phe Lys Ala Val Asn Phe Leu Glu Glu Pro Val Gln
            100                 105                 110

Lys Leu Ile Glu Glu Met Asn Pro Arg Pro Ser Cys Leu Ile Ser Asp
        115                 120                 125

Phe Cys Leu Pro Tyr Thr Ser Lys Ile Ala Lys Lys Phe Asn Ile Pro
    130                 135                 140

Lys Ile Leu Phe His Gly Met Gly Cys Phe Cys Leu Leu Cys Met His
145                 150                 155                 160

Val Leu Arg Lys Asn Arg Glu Ile Leu Asp Asn Leu Lys Ser Asp Lys
                165                 170                 175

Glu Leu Phe Thr Val Pro Asp Phe Pro Asp Arg Val Glu Phe Thr Arg
            180                 185                 190

Thr Gln Val Pro Val Glu Thr Tyr Val Pro Ala Gly Asp Trp Lys Asp
        195                 200                 205

Ile Phe Asp Gly Met Val Glu Ala Asn Glu Thr Ser Tyr Gly Val Ile
    210                 215                 220

Val Asn Ser Phe Gln Glu Leu Glu Pro Ala Tyr Ala Lys Asp Tyr Lys
225                 230                 235                 240

Glu Val Arg Ser Gly Lys Ala Trp Thr Ile Gly Pro Val Ser Leu Cys
                245                 250                 255

Asn Lys Val Gly Ala Asp Lys Ala Glu Arg Gly Asn Lys Ser Asp Ile
            260                 265                 270

Asp Gln Asp Glu Cys Leu Lys Trp Leu Asp Ser Lys Lys His Gly Ser
        275                 280                 285

Val Leu Tyr Val Cys Leu Gly Ser Ile Cys Asn Leu Pro Leu Ser Gln
    290                 295                 300

Leu Lys Glu Leu Gly Leu Gly Leu Glu Glu Ser Gln Arg Pro Phe Ile
305                 310                 315                 320

Trp Val Ile Arg Gly Trp Glu Lys Tyr Lys Glu Leu Val Glu Trp Phe
                325                 330                 335

Ser Glu Ser Gly Phe Glu Asp Arg Ile Gln Asp Arg Gly Leu Leu Ile
            340                 345                 350

Lys Gly Trp Ser Pro Gln Met Leu Ile Leu Ser His Pro Ser Val Gly
        355                 360                 365
```

TABLE 3-continued

Sequences disclosed herein (see also Table 2).

```
Gly Phe Leu Thr His Cys Gly Trp Asn Ser Thr Leu Glu Gly Ile Thr
    370                 375                 380

Ala Gly Leu Pro Leu Leu Thr Trp Pro Leu Phe Ala Asp Gln Phe Cys
385                 390                 395                 400

Asn Glu Lys Leu Val Val Glu Val Leu Lys Ala Gly Val Arg Ser Gly
                405                 410                 415

Val Glu Gln Pro Met Lys Trp Gly Glu Glu Glu Lys Ile Gly Val Leu
            420                 425                 430

Val Asp Lys Glu Gly Val Lys Lys Ala Val Glu Glu Leu Met Gly Glu
        435                 440                 445

Ser Asp Asp Ala Lys Glu Arg Arg Arg Arg Ala Lys Glu Leu Gly Asp
    450                 455                 460

Ser Ala His Lys Ala Val Glu Glu Gly Gly Ser Ser His Ser Asn Ile
465                 470                 475                 480

Ser Phe Leu Leu Gln Asp Ile Met Glu Leu Ala Glu Pro Asn Asn
                485                 490                 495
```

SEQ ID NO: 58
*Arabidopsis thaliana* protein sequence

```
Met Ala Phe Glu Lys Asn Asn Glu Pro Phe Pro Leu His Phe Val Leu
1               5                   10                  15

Phe Pro Phe Met Ala Gln Gly His Met Ile Pro Met Val Asp Ile Ala
            20                  25                  30

Arg Leu Leu Ala Gln Arg Gly Val Leu Ile Thr Ile Val Thr Thr Pro
        35                  40                  45

His Asn Ala Ala Arg Phe Lys Asn Val Leu Asn Arg Ala Ile Glu Ser
    50                  55                  60

Gly Leu Pro Ile Asn Leu Val Gln Val Lys Phe Pro Tyr Gln Glu Ala
65                  70                  75                  80

Gly Leu Gln Glu Gly Gln Glu Asn Met Asp Leu Leu Thr Thr Met Glu
                85                  90                  95

Gln Ile Thr Ser Phe Phe Lys Ala Val Asn Leu Leu Lys Glu Pro Val
            100                 105                 110

Gln Asn Leu Ile Glu Glu Met Ser Pro Arg Pro Ser Cys Leu Ile Ser
        115                 120                 125

Asp Met Cys Leu Ser Tyr Thr Ser Glu Ile Ala Lys Lys Phe Lys Ile
    130                 135                 140

Pro Lys Ile Leu Phe His Gly Met Gly Cys Phe Cys Leu Leu Cys Val
145                 150                 155                 160

Asn Val Leu Arg Lys Asn Arg Glu Ile Leu Asp Asn Leu Lys Ser Asp
                165                 170                 175

Lys Glu Tyr Phe Ile Val Pro Tyr Phe Pro Asp Arg Val Glu Phe Thr
            180                 185                 190

Arg Pro Gln Val Pro Val Glu Thr Tyr Val Pro Ala Gly Trp Lys Glu
        195                 200                 205

Ile Leu Glu Asp Met Val Glu Ala Asp Lys Thr Ser Tyr Gly Val Ile
    210                 215                 220

Val Asn Ser Phe Gln Glu Leu Glu Pro Ala Tyr Ala Lys Asp Phe Lys
225                 230                 235                 240

Glu Ala Arg Ser Gly Lys Ala Trp Thr Ile Gly Pro Val Ser Leu Cys
                245                 250                 255

Asn Lys Val Gly Val Asp Lys Ala Glu Arg Gly Asn Lys Ser Asp Ile
            260                 265                 270
```

TABLE 3-continued

Sequences disclosed herein (see also Table 2).

```
Asp Gln Asp Glu Cys Leu Glu Trp Leu Asp Ser Lys Glu Pro Gly Ser
        275                 280                 285

Val Leu Tyr Val Cys Leu Gly Ser Ile Cys Asn Leu Pro Leu Ser Gln
    290                 295                 300

Leu Leu Glu Leu Gly Leu Gly Leu Glu Glu Ser Gln Arg Pro Phe Ile
305                 310                 315                 320

Trp Val Ile Arg Gly Trp Glu Lys Tyr Lys Glu Leu Val Glu Trp Phe
                325                 330                 335
Ser Glu Ser Gly Phe Glu Asp Arg Ile Gln Asp Arg Gly Leu Leu Ile

            340                 345                 350
Lys Gly Trp Ser Pro Gln Met Leu Ile Leu Ser His Pro Ser Val Gly
        355                 360                 365

Gly Phe Leu Thr His Cys Gly Trp Asn Ser Thr Leu Glu Gly Ile Thr
    370                 375                 380

Ala Gly Leu Pro Met Leu Thr Trp Pro Leu Phe Ala Asp Gln Phe Cys
385                 390                 395                 400

Asn Glu Lys Leu Val Val Gln Ile Leu Lys Val Gly Val Ser Ala Glu
                405                 410                 415

Val Lys Glu Val Met Lys Trp Gly Glu Glu Glu Lys Ile Gly Val Leu
            420                 425                 430

Val Asp Lys Glu Gly Val Lys Lys Ala Val Glu Glu Leu Met Gly Glu
        435                 440                 445

Ser Asp Asp Ala Lys Glu Arg Arg Arg Arg Ala Lys Glu Leu Gly Glu
    450                 455                 460

Ser Ala His Lys Ala Val Glu Glu Gly Gly Ser Ser His Ser Asn Ile
465                 470                 475                 480

Thr Phe Leu Leu Gln Asp Ile Met Gln Leu Ala Gln Ser Asn Asn
                485                 490                 495
```

SEQ ID NO: 59
*Stevia rebaudian* protein sequence

```
Met Ser Pro Lys Met Val Ala Pro Pro Thr Asn Leu His Phe Val Leu
1               5                   10                  15

Phe Pro Leu Met Ala Gln Gly His Leu Val Pro Met Val Asp Ile Ala
            20                  25                  30

Arg Ile Leu Ala Gln Arg Gly Ala Thr Val Thr Ile Ile Thr Thr Pro
        35                  40                  45

Tyr His Ala Asn Arg Val Arg Pro Val Ile Ser Arg Ala Ile Ala Thr
    50                  55                  60

Asn Leu Lys Ile Gln Leu Leu Glu Leu Gln Leu Arg Ser Thr Glu Ala
65                  70                  75                  80

Gly Leu Pro Glu Gly Cys Glu Ser Phe Asp Gln Leu Pro Ser Phe Glu
                85                  90                  95

Tyr Trp Lys Asn Ile Ser Thr Ala Ile Asp Leu Leu Gln Gln Pro Ala
            100                 105                 110

Glu Asp Leu Leu Arg Glu Leu Ser Pro Pro Pro Asp Cys Ile Ile Ser
        115                 120                 125

Asp Phe Leu Phe Pro Trp Thr Thr Asp Val Ala Arg Arg Leu Asn Ile
    130                 135                 140

Pro Arg Leu Val Phe Asn Gly Pro Gly Cys Phe Tyr Leu Leu Cys Ile
145                 150                 155                 160

His Val Ala Ile Thr Ser Asn Ile Leu Gly Glu Asn Glu Pro Val Ser
                165                 170                 175

Ser Asn Thr Glu Arg Val Val Leu Pro Gly Leu Pro Asp Arg Ile Glu
            180                 185                 190
```

TABLE 3-continued

Sequences disclosed herein (see also Table 2).

```
Val Thr Lys Leu Gln Ile Val Gly Ser Ser Arg Pro Ala Asn Val Asp
        195                 200                 205

Glu Met Gly Ser Trp Leu Arg Ala Val Glu Ala Glu Lys Ala Ser Phe
    210                 215                 220

Gly Ile Val Val Asn Thr Phe Glu Glu Leu Glu Pro Glu Tyr Val Glu
225                 230                 235                 240

Glu Tyr Lys Thr Val Lys Asp Lys Lys Met Trp Cys Ile Gly Pro Val
                245                 250                 255

Ser Leu Cys Asn Lys Thr Gly Pro Asp Leu Ala Glu Arg Gly Asn Lys
            260                 265                 270

Ala Ala Ile Thr Glu His Asn Cys Leu Lys Trp Leu Asp Glu Arg Lys
        275                 280                 285

Leu Gly Ser Val Leu Tyr Val Cys Leu Gly Ser Leu Ala Arg Ile Ser
    290                 295                 300

Ala Ala Gln Ala Ile Glu Leu Gly Leu Gly Leu Glu Ser Ile Asn Arg
305                 310                 315                 320

Pro Phe Ile Trp Cys Val Arg Asn Glu Thr Asp Glu Leu Lys Thr Trp
                325                 330                 335

Phe Leu Asp Gly Phe Glu Glu Arg Val Arg Asp Arg Gly Leu Ile Val
            340                 345                 350

His Gly Trp Ala Pro Gln Val Leu Ile Leu Ser His Pro Thr Ile Gly
        355                 360                 365

Gly Phe Leu Thr His Cys Gly Trp Asn Ser Thr Ile Glu Ser Ile Thr
    370                 375                 380

Ala Gly Val Pro Met Ile Thr Trp Pro Phe Phe Ala Asp Gln Phe Leu
385                 390                 395                 400

Asn Glu Ala Phe Ile Val Glu Val Leu Lys Ile Gly Val Arg Ile Gly
                405                 410                 415

Val Glu Arg Ala Cys Leu Phe Gly Glu Glu Asp Lys Val Gly Val Leu
            420                 425                 430

Val Lys Lys Glu Asp Val Lys Lys Ala Val Glu Cys Leu Met Asp Glu
        435                 440                 445

Asp Glu Asp Gly Asp Gln Arg Arg Lys Arg Val Ile Glu Leu Ala Lys
    450                 455                 460

Met Ala Lys Ile Ala Met Ala Glu Gly Gly Ser Ser Tyr Glu Asn Val
465                 470                 475                 480

Ser Ser Leu Ile Arg Asp Val Thr Glu Thr Val Arg Ala Pro His
                485                 490                 495
```

SEQ ID NO: 60
*Stevia rebaudian* protein sequence

```
Met Asp Ala Met Ala Thr Thr Glu Lys Lys Pro His Val Ile Phe Ile

1               5                   10                  15
Pro Phe Pro Ala Gln Ser His Ile Lys Ala Met Leu Lys Leu Ala Gln

            20                  25                  30
Leu Leu His His Lys Gly Leu Gln Ile Thr Phe Val Asn Thr Asp Phe

        35                  40                  45
Ile His Asn Gln Phe Leu Glu Ser Ser Gly Pro His Cys Leu Asp Gly

    50                  55                  60
Ala Pro Gly Phe Arg Phe Glu Thr Ile Pro Asp Gly Val Ser His Ser

65                  70                  75                  80
Pro Glu Ala Ser Ile Pro Ile Arg Glu Ser Leu Leu Arg Ser Ile Glu

                85                  90                  95
```

TABLE 3-continued

Sequences disclosed herein (see also Table 2).

```
Thr Asn Phe Leu Asp Arg Phe Ile Asp Leu Val Thr Lys Leu Pro Asp

            100                 105                 110
Pro Pro Thr Cys Ile Ile Ser Asp Gly Phe Leu Ser Val Phe Thr Ile

        115                 120                 125
Asp Ala Ala Lys Lys Leu Gly Ile Pro Val Met Met Tyr Trp Thr Leu

    130                 135                 140
Ala Ala Cys Gly Phe Met Gly Phe Tyr His Ile His Ser Leu Ile Glu

145                 150                 155                 160
Lys Gly Phe Ala Pro Leu Lys Asp Ala Ser Tyr Leu Thr Asn Gly Tyr

                165                 170                 175
Leu Asp Thr Val Ile Asp Trp Val Pro Gly Met Glu Gly Ile Arg Leu

            180                 185                 190
Lys Asp Phe Pro Leu Asp Trp Ser Thr Asp Leu Asn Asp Lys Val Leu

        195                 200                 205
Met Phe Thr Thr Glu Ala Pro Gln Arg Ser His Lys Val Ser His His

    210                 215                 220
Ile Phe His Thr Phe Asp Glu Leu Glu Pro Ser Ile Ile Lys Thr Leu

225                 230                 235                 240
Ser Leu Arg Tyr Asn His Ile Tyr Thr Ile Gly Pro Leu Gln Leu Leu

                245                 250                 255

Leu Asp Gln Ile Pro Glu Glu Lys Lys Gln Thr Gly Ile Thr Ser Leu
            260                 265                 270

His Gly Tyr Ser Leu Val Lys Glu Glu Pro Glu Cys Phe Gln Trp Leu

        275                 280                 285
Gln Ser Lys Glu Pro Asn Ser Val Val Tyr Val Asn Phe Gly Ser Thr
    290                 295                 300

Thr Val Met Ser Leu Glu Asp Met Thr Glu Phe Gly Trp Gly Leu Ala
305                 310                 315                 320

Asn Ser Asn His Tyr Phe Leu Trp Ile Ile Arg Ser Asn Leu Val Ile
                325                 330                 335

Gly Glu Asn Ala Val Leu Pro Pro Glu Leu Glu Glu His Ile Lys Lys
            340                 345                 350

Arg Gly Phe Ile Ala Ser Trp Cys Ser Gln Glu Lys Val Leu Lys His
        355                 360                 365

Pro Ser Val Gly Gly Phe Leu Thr His Cys Gly Trp Gly Ser Thr Ile
    370                 375                 380

Glu Ser Leu Ser Ala Gly Val Pro Met Ile Cys Trp Pro Tyr Ser Trp
385                 390                 395                 400

Asp Gln Leu Thr Asn Cys Arg Tyr Ile Cys Lys Glu Trp Glu Val Gly
                405                 410                 415

Leu Glu Met Gly Thr Lys Val Lys Arg Asp Glu Val Lys Arg Leu Val
            420                 425                 430

Gln Glu Leu Met Gly Glu Gly Gly His Lys Met Arg Asn Lys Ala Lys
        435                 440                 445

Asp Trp Lys Glu Lys Ala Arg Ile Ala Ile Ala Pro Asn Gly Ser Ser
    450                 455                 460

Ser Leu Asn Ile Asp Lys Met Val Lys Glu Ile Thr Val Leu Ala Arg
465                 470                 475                 480

Asn
```

SEQ ID NO: 61

*Siraitia grosvenorii* DNA sequence

```
atggagcaag ctcatgatct tcttcacgtc ctcctttttc cgtatccggc gaagggccac   60
```

TABLE 3-continued

Sequences disclosed herein (see also Table 2).

```
atcaagccct tcctctgcct cgccgagctc ctctgcaacg ccggtctcaa cgtcaccttc   120
ctcaacaccg actacaacca ccgccgcctc cacaatctcc atctcctcgc cgcctgcttt   180
ccctctcttc atttcgagtc catttccgac ggcctccagc ccgatcagcc tcgagatata   240
ctggacccca agttttatat atccatctgt caagtcacta aacccctttt ccgggagctc   300
ctcctttcct acaaacgaac ttccagtgtc cagaccggcc gcccgccaat aacttgcgtt   360
attacagatg tgatttttcg ttttccgatc gacgtagctg aagaactgga tattcctgtg   420
tttagtttct gtactttcag tgcccgtttc atgtttcttt acttctggat tcccaagctc   480
attgaagatg gccagcttcc atacccaaac ggcaatatca accagaaact ctacggtgtt   540
gctcctgagg cggaaggcct tttaagatgt aaagatttgc cgggacattg ggctttcgca   600
gacgaactaa aagatgatca acttaacttt gtggaccaga caacggcgtc acttcgatcc   660
tccggtctca ttctcaacac attcgacgac ctcgaagctc catttctggg gcgtctctcc   720
accatcttta agaaaatcta cgccgttgga cccatccacg ctctgttgaa ctcccaccac   780
tgtggtcttt ggaaagaaga tcacagttgc ctggcgtggc tcgactcccg ggcggcgaga   840
tccgtcgtgt tcgtcagctt cgggagcttg gtgaagataa caagtaggca gctgatggag   900
ttttggcatg gcttgctcaa cagtggaacg tcgttcctct tcgtgttgag atctgacgta   960
gttgagggcg atggtgaaaa acaagtcgtc aaagaaattt acgagacgaa ggcagagggg  1020
aaatggttgg ttgtggggtg ggctccgcaa gagaaggtgt tagcccatga agctgttggt  1080
ggatttctga cccattcggg ctggaactcc attttagaga gcattgctgc tggggttcct  1140
atgatctcct gccccaaaat tggagaccag tccagtaact gtacgtggat cagtaaagta  1200
tggaaaattg ggctcgaaat ggaggaccaa tacgaccggg ccacggtcga ggcaatggtt  1260
aggtctataa tgaaacatga aggagaaaaa attcaaaaga caattgcaga gttagcaaaa  1320
cgagccaagt ataaagttag taaagatggg acatcgtatc gaaatttaga aattttaatt  1380
gaggatatta aaaaaattaa accaaattaa                                   1410
```

SEQ ID NO: 62

*Siraitia grosvenorii* protein sequence

```
Met Glu Gln Ala His Asp Leu Leu His Val Leu Leu Phe Pro Tyr Pro
1               5                   10                  15
Ala Lys Gly His Ile Lys Pro Phe Leu Cys Leu Ala Glu Leu Leu Cys
            20                  25                  30
Asn Ala Gly Leu Asn Val Thr Phe Leu Asn Thr Asp Tyr Asn His Arg
        35                  40                  45
Arg Leu His Asn Leu His Leu Leu Ala Ala Cys Phe Pro Ser Leu His
    50                  55                  60
Phe Glu Ser Ile Ser Asp Gly Leu Gln Pro Asp Gln Pro Arg Asp Ile
65                  70                  75                  80
Leu Asp Pro Lys Phe Tyr Ile Ser Ile Cys Gln Val Thr Lys Pro Leu
                85                  90                  95
Phe Arg Glu Leu Leu Leu Ser Tyr Lys Arg Thr Ser Ser Val Gln Thr
            100                 105                 110
Gly Arg Pro Pro Ile Thr Cys Val Ile Thr Asp Val Ile Phe Arg Phe
        115                 120                 125
Pro Ile Asp Val Ala Glu Glu Leu Asp Ile Pro Val Phe Ser Phe Cys
    130                 135                 140
Thr Phe Ser Ala Arg Phe Met Phe Leu Tyr Phe Trp Ile Pro Lys Leu
145                 150                 155                 160
Ile Glu Asp Gly Gln Leu Pro Tyr Pro Asn Gly Asn Ile Asn Gln Lys
                165                 170                 175
Leu Tyr Gly Val Ala Pro Glu Ala Glu Gly Leu Leu Arg Cys Lys Asp
            180                 185                 190
Leu Pro Gly His Trp Ala Phe Ala Asp Glu Leu Lys Asp Asp Gln Leu
        195                 200                 205
Asn Phe Val Asp Gln Thr Thr Ala Ser Leu Arg Ser Ser Gly Leu Ile
    210                 215                 220
Leu Asn Thr Phe Asp Asp Leu Glu Ala Pro Phe Leu Gly Arg Leu Ser
225                 230                 235                 240
Thr Ile Phe Lys Lys Ile Tyr Ala Val Gly Pro Ile His Ala Leu Leu
                245                 250                 255
Asn Ser His His Cys Gly Leu Trp Lys Glu Asp His Ser Cys Leu Ala
            260                 265                 270
```

TABLE 3-continued

Sequences disclosed herein (see also Table 2).

Trp Leu Asp Ser Arg Ala Ala Arg Ser Val Val Phe Val Ser Phe Gly
275 280 285

Ser Leu Val Lys Ile Thr Ser Arg Gln Leu Met Glu Phe Trp His Gly
290 295 300

Leu Leu Asn Ser Gly Thr Ser Phe Leu Phe Val Leu Arg Ser Asp Val
305 310 315 320

Val Glu Gly Asp Gly Glu Lys Gln Val Val Lys Glu Ile Tyr Glu Thr
325 330 335

Lys Ala Glu Gly Lys Trp Leu Val Val Gly Trp Ala Pro Gln Glu Lys
340 345 350

Val Leu Ala His Glu Ala Val Gly Gly Phe Leu Thr His Ser Gly Trp
355 360 365

Asn Ser Ile Leu Glu Ser Ile Ala Ala Gly Val Pro Met Ile Ser Cys
370 375 380

Pro Lys Ile Gly Asp Gln Ser Ser Asn Cys Thr Trp Ile Ser Lys Val
385 390 395 400

Trp Lys Ile Gly Leu Glu Met Glu Asp Gln Tyr Asp Arg Ala Thr Val
405 410 415

Glu Ala Met Val Arg Ser Ile Met Lys His Glu Gly Glu Lys Ile Gln
420 425 430

Lys Thr Ile Ala Glu Leu Ala Lys Arg Ala Lys Tyr Lys Val Ser Lys
435 440 445

Asp Gly Thr Ser Tyr Arg Asn Leu Glu Ile Leu Ile Glu Asp Ile Lys
450 455 460

Lys Ile Lys Pro Asn
465

SEQ ID NO: 63
*Saccharomyces cerevisiae* DNA sequence
atgctttcgc ttaaaacgtt actgtgtacg ttgttgactg tgtcatcagt actcgctacc 60
ccagtccctg caagagaccc ttcttccatt caatttgttc atgaggagaa caagaaaaga 120
tactacgatt atgaccacgg ttccctcgga gaaccaatcc gtggtgtcaa cattggtggt 180
tggttacttc ttgaaccata cattactcca tctttgttcg aggctttccg tacaaatgat 240
gacaacgacg aaggaattcc tgtcgacgaa tatcacttct gtcaatattt aggtaaggat 300
ttggctaaaa gccgtttaca gagccattgg tctactttct accaagaaca agatttcgct 360
aatattgctt cccaaggttt caaccttgtc agaattccta tcggttactg ggctttccaa 420
actttggacg atgatcctta tgttagcggc ctacaggaat cttacctaga ccaagccatc 480
ggttgggcta gaaacaacag cttgaaagtt tgggttgatt tgcatggtgc cgctggttcg 540
cagaacgggt ttgataactc tggtttgaga gattcataca agtttttgga agacagcaat 600
ttggccgtta ctacaaatgt cttgaactac atattgaaaa aatactctgc ggaggaatac 660
ttggacactg ttattggtat cgaattgatt aatgagccat tgggtcctgt tctagacatg 720
gataaaatga agaatgacta cttggcacct gcttacgaat acttgagaaa caacatcaag 780
agtgaccaag ttatcatcat ccatgacgct ttccaaccat acaattattg ggatgacttc 840
atgactgaaa acgatggcta ctggggtgtc actatcgacc atcatcacta ccaagtcttt 900
gcttctgatc aattggaaag atccattgat gaacatatta aagtagcttg tgaatggggt 960
accggagttt tgaatgaatc ccactggact gtttgtggtg agtttgctgc cgctttgact 1020
gattgtacaa aatggttgaa tagtgttggc ttcggcgcta gatacgacgg ttcttgggtc 1080
aatggtgacc aaacatcttc ttacattggc tcttgtgcta acaacgatga tatagcttac 1140
tggtctgacg aaagaaagga aaacacaaga cgttatgtgg aggcacaact agatgccttt 1200
gaaatgagag gggttggat tatctggtgt tacaagacag aatctagttt ggaatgggat 1260
gctcaaagat tgatgttcaa tggtttattc cctcaaccat tgactgacag aaagtatcca 1320
aaccaatgtg gcacaatttc taactaa 1347

SEQ ID NO: 64
*Saccharomyces cerevisiae* protein sequence
Met Leu Ser Leu Lys Thr Leu Leu Cys Thr Leu Leu Thr Val Ser Ser
1 5 10 15

Val Leu Ala Thr Pro Val Pro Ala Arg Asp Pro Ser Ser Ile Gln Phe
20 25 30

Val His Glu Glu Asn Lys Lys Arg Tyr Tyr Asp Tyr Asp His Gly Ser
35 40 45

Leu Gly Glu Pro Ile Arg Gly Val Asn Ile Gly Gly Trp Leu Leu Leu
50 55 60

TABLE 3-continued

| Sequences disclosed herein (see also Table 2). |
|---|
| Glu Pro Tyr Ile Thr Pro Ser Leu Phe Glu Ala Phe Arg Thr Asn Asp<br>65 70 75 80<br><br>Asp Asn Asp Glu Gly Ile Pro Val Asp Glu Tyr His Phe Cys Gln Tyr<br>85 90 95<br><br>Leu Gly Lys Asp Leu Ala Lys Ser Arg Leu Gln Ser His Trp Ser Thr<br>100 105 110<br><br>Phe Tyr Gln Glu Gln Asp Phe Ala Asn Ile Ala Ser Gln Gly Phe Asn<br>115 120 125<br><br>Leu Val Arg Ile Pro Ile Gly Tyr Trp Ala Phe Gln Thr Leu Asp Asp<br>130 135 140<br><br>Asp Pro Tyr Val Ser Gly Leu Gln Glu Ser Tyr Leu Asp Gln Ala Ile<br>145 150 155 160<br><br>Gly Trp Ala Arg Asn Asn Ser Leu Lys Val Trp Val Asp Leu His Gly<br>165 170 175<br><br>Ala Ala Gly Ser Gln Asn Gly Phe Asp Asn Ser Gly Leu Arg Asp Ser<br>180 185 190<br><br>Tyr Lys Phe Leu Glu Asp Ser Asn Leu Ala Val Thr Thr Asn Val Leu<br>195 200 205<br><br>Asn Tyr Ile Leu Lys Lys Tyr Ser Ala Glu Glu Tyr Leu Asp Thr Val<br>210 215 220<br><br>Ile Gly Ile Glu Leu Ile Asn Glu Pro Leu Gly Pro Val Leu Asp Met<br>225 230 235 240<br><br>Asp Lys Met Lys Asn Asp Tyr Leu Ala Pro Ala Tyr Glu Tyr Leu Arg<br>245 250 255<br><br>Asn Asn Ile Lys Ser Asp Gln Val Ile Ile His Asp Ala Phe Gln<br>260 265 270<br><br>Pro Tyr Asn Tyr Trp Asp Asp Phe Met Thr Glu Asn Asp Gly Tyr Trp<br>275 280 285<br><br>Gly Val Thr Ile Asp His His His Tyr Gln Val Phe Ala Ser Asp Gln<br>290 295 300<br><br>Leu Glu Arg Ser Ile Asp Glu His Ile Lys Val Ala Cys Glu Trp Gly<br>305 310 315 320<br><br>Thr Gly Val Leu Asn Glu Ser His Trp Thr Val Cys Gly Glu Phe Ala<br>325 330 335<br><br>Ala Ala Leu Thr Asp Cys Thr Lys Trp Leu Asn Ser Val Gly Phe Gly<br>340 345 350<br><br>Ala Arg Tyr Asp Gly Ser Trp Val Asn Gly Asp Gln Thr Ser Ser Tyr<br>355 360 365<br><br>Ile Gly Ser Cys Ala Asn Asn Asp Asp Ile Ala Tyr Trp Ser Asp Glu<br>370 375 380<br><br>Arg Lys Glu Asn Thr Arg Arg Tyr Val Glu Ala Gln Leu Asp Ala Phe<br>385 390 395 400<br><br>Glu Met Arg Gly Gly Trp Ile Ile Trp Cys Tyr Lys Thr Glu Ser Ser<br>405 410 415<br><br>Leu Glu Trp Asp Ala Gln Arg Leu Met Phe Asn Gly Leu Phe Pro Gln<br>420 425 430<br><br>Pro Leu Thr Asp Arg Lys Tyr Pro Asn Gln Cys Gly Thr Ile Ser Asn<br>435 440 445<br><br>SEQ ID NO: 65<br>*Saccharomyces cerevisiae* DNA sequence<br>atgcctttga agtcgttttt tttttcagca tttctagttt tatgcctgtc taaattcacg 60<br>caaggcgttg gcaccacaga gaaggaagaa tcgttatcgc ctttggaact aaatatttta 120<br>caaaacaaat tcgcctccta ctatgcaaac gacactatca ccgtgaaagg tattactatt 180 |

TABLE 3-continued

Sequences disclosed herein (see also Table 2).

```
ggcggctggc tagtaacaga accttatatc acgccatcat tatatcgtaa tgctacgtca   240
ctggcaaaac agcaaaactc ttccagcaat atctccattg tcgacgaatt tactctttgt   300
aaaaccttag gatataacac ctctctaact ttattggata atcacttcaa aacttggatt   360
acagaggatg attttgaaca aatcaaaacc aacggtttca atttagttag gatccccatc   420
ggatattggg cgtggaaaca aaatactgat aaaaacttgt acatcgataa cataactttc   480
aatgatccat acgtaagtga tggattacaa ctgaaatatt taaataatgc tctcgaatgg   540
gcgcaaaagt acgaactaaa tgtatggtta gatctacatg gtgctcctgg atcccagaat   600
ggattcgata attccggtga aagaatactc tatggcgatt taggctggtt aaggttgaat   660
aatactaaag aactgactct ggctatttgg agagatatgt tccagacatt tttaaataaa   720
ggtgacaaaa gtcctgtggt gggtattcaa atcgtcaacg aaccgcttgg tggcaaaatc   780
gatgtttcag acataacgga gatgtattac gaagcatttg acttgctcaa gaaaaatcag   840
aattcgagtg acaacactac gtttgttatt catgacggtt ttcaaggaat cggtcactgg   900
aacttggagc taaacccaac ctaccagaat gtatcgcatc attatttcaa tttgactggt   960
gcaaattaca gctctcaaga tatattggtc gaccatcatc attatgaagt gtttactgat  1020
gcgcaattgg ccgaaactca gtttgcacgt attgaaaaca ttatcaatta tggggactct  1080
atccacaaag aactttcttt tcacccagca gtagtcggag aatggtcagg cgctattact  1140
gattgtgcaa cctggctaaa tggtgttggg gtgggtgcac gttacgatgg atcatactac  1200
aatacaacgt tgtttaccac caacgacaag ccagttggaa catgtatatc ccaaaatagc  1260
ttagctgatt ggacgcaaga ttaccgtgac cgtgtgagac aattcattga ggcacagcta  1320
gccacttatt cgtcaaaaac aacgggatgg attttttgga attggaagac cgaagacgcc  1380
gtagaatggg attatttgaa gctaaaagaa gctaaccttt tcccttcccc tttcgacaac  1440
tacacgtact tcaaagcaga tggatctatc gaagaaaaat tctcatcctc tttatcagca  1500
caggcatttc caagaacaac gtcatcggtt ttgtcctcca ctacgacttc caggaagagt  1560
aagaatgctg caatttctaa taaactaaca acttcgcagc tattaccaat caaaaaatatg  1620
agtttgacct ggaaagcgag cgtatgcgca ctcgctatca ccattgccgc tctttgcgct  1680
tctctttaa                                                          1689
```

SEQ ID NO: 66
*Saccharomyces cerevisiae* protein sequence

```
Met Pro Leu Lys Ser Phe Phe Phe Ser Ala Phe Leu Val Leu Cys Leu
1               5                   10                  15

Ser Lys Phe Thr Gln Gly Val Gly Thr Thr Glu Lys Glu Glu Ser Leu
            20                  25                  30

Ser Pro Leu Glu Leu Asn Ile Leu Gln Asn Lys Phe Ala Ser Tyr Tyr
        35                  40                  45

Ala Asn Asp Thr Ile Thr Val Lys Gly Ile Thr Ile Gly Gly Trp Leu
    50                  55                  60

Val Thr Glu Pro Tyr Ile Thr Pro Ser Leu Tyr Arg Asn Ala Thr Ser
65                  70                  75                  80

Leu Ala Lys Gln Gln Asn Ser Ser Ser Asn Ile Ser Ile Val Asp Glu
                85                  90                  95

Phe Thr Leu Cys Lys Thr Leu Gly Tyr Asn Thr Ser Leu Thr Leu Leu
            100                 105                 110

Asp Asn His Phe Lys Thr Trp Ile Thr Glu Asp Asp Phe Glu Gln Ile
        115                 120                 125

Lys Thr Asn Gly Phe Asn Leu Val Arg Ile Pro Ile Gly Tyr Trp Ala
    130                 135                 140

Trp Lys Gln Asn Thr Asp Lys Asn Leu Tyr Ile Asp Asn Ile Thr Phe
145                 150                 155                 160

Asn Asp Pro Tyr Val Ser Asp Gly Leu Gln Leu Lys Tyr Leu Asn Asn
                165                 170                 175

Ala Leu Glu Trp Ala Gln Lys Tyr Glu Leu Asn Val Trp Leu Asp Leu
            180                 185                 190

His Gly Ala Pro Gly Ser Gln Asn Gly Phe Asp Asn Ser Gly Glu Arg
        195                 200                 205

Ile Leu Tyr Gly Asp Leu Gly Trp Leu Arg Leu Asn Asn Thr Lys Glu
    210                 215                 220

Leu Thr Leu Ala Ile Trp Arg Asp Met Phe Gln Thr Phe Leu Asn Lys
225                 230                 235                 240

Gly Asp Lys Ser Pro Val Val Gly Ile Gln Ile Val Asn Glu Pro Leu
                245                 250                 255

Gly Gly Lys Ile Asp Val Ser Asp Ile Thr Glu Met Tyr Tyr Glu Ala
```

TABLE 3-continued

Sequences disclosed herein (see also Table 2).

```
            260                 265                 270

Phe Asp Leu Leu Lys Lys Asn Gln Asn Ser Ser Asp Asn Thr Thr Phe
        275                 280                 285

Val Ile His Asp Gly Phe Gln Gly Ile Gly His Trp Asn Leu Glu Leu
    290                 295                 300

Asn Pro Thr Tyr Gln Asn Val Ser His His Tyr Phe Asn Leu Thr Gly
305                 310                 315                 320

Ala Asn Tyr Ser Ser Gln Asp Ile Leu Val Asp His His His Tyr Glu
                325                 330                 335

Val Phe Thr Asp Ala Gln Leu Ala Glu Thr Gln Phe Ala Arg Ile Glu
            340                 345                 350

Asn Ile Ile Asn Tyr Gly Asp Ser Ile His Lys Glu Leu Ser Phe His
        355                 360                 365

Pro Ala Val Val Gly Glu Trp Ser Gly Ala Ile Thr Asp Cys Ala Thr
    370                 375                 380

Trp Leu Asn Gly Val Gly Val Gly Ala Arg Tyr Asp Gly Ser Tyr Tyr
385                 390                 395                 400

Asn Thr Thr Leu Phe Thr Thr Asn Asp Lys Pro Val Gly Thr Cys Ile
                405                 410                 415

Ser Gln Asn Ser Leu Ala Asp Trp Thr Gln Asp Tyr Arg Asp Arg Val
            420                 425                 430

Arg Gln Phe Ile Glu Ala Gln Leu Ala Thr Tyr Ser Ser Lys Thr Thr
        435                 440                 445

Gly Trp Ile Phe Trp Asn Trp Lys Thr Glu Asp Ala Val Glu Trp Asp
    450                 455                 460

Tyr Leu Lys Leu Lys Glu Ala Asn Leu Phe Pro Ser Pro Phe Asp Asn
465                 470                 475                 480

Tyr Thr Tyr Phe Lys Ala Asp Gly Ser Ile Glu Glu Lys Phe Ser Ser
                485                 490                 495

Ser Leu Ser Ala Gln Ala Phe Pro Arg Thr Thr Ser Ser Val Leu Ser
            500                 505                 510

Ser Thr Thr Thr Ser Arg Lys Ser Lys Asn Ala Ala Ile Ser Asn Lys
        515                 520                 525

Leu Thr Thr Ser Gln Leu Leu Pro Ile Lys Asn Met Ser Leu Thr Trp
    530                 535                 540

Lys Ala Ser Val Cys Ala Leu Ala Ile Thr Ile Ala Ala Leu Cys Ala
545                 550                 555                 560

Ser Leu
```

SEQ ID NO: 67

*Siraitia grosvenorii* DNA sequence

```
atggtgcaac ctcgggtact gctgtttcct ttcccggcac tgggccacgt gaagcccttc     60
ttatcactgg cggagctgct ttccgacgcc ggcatagacg tcgtcttcct cagcaccgag    120
tataaccacc gtcggatctc caacactgaa gccctagcct cccgcttccc gacgcttcat    180
ttcgaaacta taccggatgg cctgccgcct aatgagtcgc gcgctcttgc cgacggccca    240
ctgtatttct ccatgcgtga gggaactaaa ccgagattcc ggcaactgat tcaatctctt    300
aacgacggtc gttggcccat cacctgcatt atcactgaca tcatgttatc ttctccgatt    360
gaagtagcgg aagaatttgg gattccagta attgccttct gcccctgcag tgctcgctac    420
ttatcgattc actttttat accgaagctc gttgaggaag gtcaaattcc atacgcagat     480
gacgatccga ttggagagat ccaggggtg cccttgttcg aaggtctttt gcgacggaat     540
catttgcctg gttcttggtc tgataaatct gcagatatat ctttctcgca tggcttgatt    600
aatcagaccc ttgcagctgg tcgagcctcg gctcttatac tcaacacctt cgacgagctc    660
gaagctccat ttctgaccca tctctcttcc attttcaaca aaatctacac cattggaccc    720
ctccatgctc tgtccaaatc aaggctcggc gactcctcct cctccgcttc tgccctctcc    780
ggattctgga aagaggatag agcctgcatg tcctggctcg actgtcagcc gccgagatct    840
gtggttttcg tcagtttcgg gagtacgatg aagatgaaag ccgatgaatt gagagagttc    900
tggtatgggt tggtgagcag cgggaaaccg ttcctctgcg tgttgagatc cgacgttgtt    960
tccggcggag aagcggcgga attgatcgaa cagatggcgg aggaggaggg agctggaggg   1020
aagctgggaa tggtagtgga gtgggcagcg caagagaagg tcctgagcca ccctgccgtc   1080
```

TABLE 3-continued

Sequences disclosed herein (see also Table 2).

```
ggtgggtttt tgacgcactg cgggtggaac tcaacggtgg aaagcattgc cgcgggagtt  1140
ccgatgatgt gctggccgat tctcggcgac caacccagca acgccacttg gatcgacaga  1200
gtgtggaaaa ttggggttga aaggaacaat cgtgaatggg acaggttgac ggtggagaag  1260
atggtgagag cattgatgga aggccaaaag agagtggaga ttcagagatc aatggagaag  1320
ctttcaaagt tggcaaatga gaaggttgtc aggggtgggt tgtcttttga taacttggaa  1380
gttctcgttg aagacatcaa aaaattgaaa ccatataaat tttaa                  1425
```

SEQ ID NO: 68
*Siraitia grosvenorii* protein sequence

```
Met Val Gln Pro Arg Val Leu Leu Phe Pro Phe Pro Ala Leu Gly His
1               5                   10                  15

Val Lys Pro Phe Leu Ser Leu Ala Glu Leu Leu Ser Asp Ala Gly Ile
            20                  25                  30

Asp Val Val Phe Leu Ser Thr Glu Tyr Asn His Arg Arg Ile Ser Asn
        35                  40                  45

Thr Glu Ala Leu Ala Ser Arg Phe Pro Thr Leu His Phe Glu Thr Ile
    50                  55                  60

Pro Asp Gly Leu Pro Pro Asn Glu Ser Arg Ala Leu Ala Asp Gly Pro
65                  70                  75                  80

Leu Tyr Phe Ser Met Arg Glu Gly Thr Lys Pro Arg Phe Arg Gln Leu
                85                  90                  95

Ile Gln Ser Leu Asn Asp Gly Arg Trp Pro Ile Thr Cys Ile Ile Thr
            100                 105                 110

Asp Ile Met Leu Ser Ser Pro Ile Glu Val Ala Glu Glu Phe Gly Ile
        115                 120                 125

Pro Val Ile Ala Phe Cys Pro Cys Ser Ala Arg Tyr Leu Ser Ile His
    130                 135                 140

Phe Phe Ile Pro Lys Leu Val Glu Glu Gly Gln Ile Pro Tyr Ala Asp
145                 150                 155                 160

Asp Asp Pro Ile Gly Glu Ile Gln Gly Val Pro Leu Phe Glu Gly Leu
                165                 170                 175

Leu Arg Arg Asn His Leu Pro Gly Ser Trp Ser Asp Lys Ser Ala Asp
            180                 185                 190

Ile Ser Phe Ser His Gly Leu Ile Asn Gln Thr Leu Ala Ala Gly Arg
        195                 200                 205

Ala Ser Ala Leu Ile Leu Asn Thr Phe Asp Glu Leu Glu Ala Pro Phe
    210                 215                 220

Leu Thr His Leu Ser Ser Ile Phe Asn Lys Ile Tyr Thr Ile Gly Pro
225                 230                 235                 240

Leu His Ala Leu Ser Lys Ser Arg Leu Gly Asp Ser Ser Ser Ser Ala
                245                 250                 255

Ser Ala Leu Ser Gly Phe Trp Lys Glu Asp Arg Ala Cys Met Ser Trp
            260                 265                 270

Leu Asp Cys Gln Pro Pro Arg Ser Val Val Phe Val Ser Phe Gly Ser
        275                 280                 285

Thr Met Lys Met Lys Ala Asp Glu Leu Arg Glu Phe Trp Tyr Gly Leu
    290                 295                 300

Val Ser Ser Gly Lys Pro Phe Leu Cys Val Leu Arg Ser Asp Val Val
305                 310                 315                 320

Ser Gly Gly Glu Ala Ala Glu Leu Ile Glu Gln Met Ala Glu Glu Glu
                325                 330                 335

Gly Ala Gly Gly Lys Leu Gly Met Val Val Glu Trp Ala Ala Gln Glu
            340                 345                 350

Lys Val Leu Ser His Pro Ala Val Gly Gly Phe Leu Thr His Cys Gly
        355                 360                 365
```

TABLE 3-continued

Sequences disclosed herein (see also Table 2).

```
Trp Asn Ser Thr Val Glu Ser Ile Ala Ala Gly Val Pro Met Met Cys
    370                 375                 380

Trp Pro Ile Leu Gly Asp Gln Pro Ser Asn Ala Thr Trp Ile Asp Arg
385                 390                 395                 400

Val Trp Lys Ile Gly Val Glu Arg Asn Asn Arg Glu Trp Asp Arg Leu
                405                 410                 415

Thr Val Glu Lys Met Val Arg Ala Leu Met Glu Gly Gln Lys Arg Val
            420                 425                 430

Glu Ile Gln Arg Ser Met Glu Lys Leu Ser Lys Leu Ala Asn Glu Lys
        435                 440                 445

Val Val Arg Gly Gly Leu Ser Phe Asp Asn Leu Glu Val Leu Val Glu
    450                 455                 460

Asp Ile Lys Lys Leu Lys Pro Tyr Lys Phe
465                 470
```

SEQ ID NO: 69
*Siraitia grosvenorii* DNA sequence

```
atggatgcaa aagaagaaag cttgaaagtt tttatgcttc catggttggc ccatggtcat    60
atatcgccct acctagagct agccaagagg cttgcaaaga gaaaatttct tgtttatttc   120
tgctccacgc ctgtaaattt ggaagccatt aaaccaaagc tttccaaaag ctactctgat   180
tcgatccaac taatggaggt tcctctcgaa tcgacgccgg agcttcctcc tcactatcat   240
acagccaaag gccttccgcc gcatttaatg cccaaactca tgaatgcctt taaaatggtt   300
gctcccaatc tcgaatcgat cctaaaaacc ctaaacccag atctgctcat cgtcgacatt   360
ctccttccat ggatgcttcc actcgcttca tcgctcaaaa ttccgatggt tttcttcact   420
attttcggtg ccatggccat ctcctttatg atttataatc gaaccgtctc gaacgagctt   480
ccatttccag aatttgaact tcacgagtgc tggaaatcga agtgccccta tttgttcaag   540
gaccaagcgg aaagtcaatc gttcttagaa tacttggatc aatcttcagg cgtaattttg   600
atcaaaactt ccagagagat tgaggctaag tatgtagact ttctcacttc gtcgtttacg   660
aagaaggttg tgaccaccgg tcccctggtt cagcaacctt cttccggcga agacgagaag   720
cagtactccg atatcatcga atggctagac aagaaggagc cgttatcgac ggtgctcgtt   780
tcgtttggga gcgagtatta tctgtcaaag gaagagatgg aagaaatcgc ctacgggctg   840
gagagcgcca gcgaggtgaa tttcatctgg attgttaggt ttccgatggg acaggaaacg   900
gaggtcgagg cggcgctgcc ggaggggttc atccagaggg caggagagag agggaaagtg   960
gtcgagggct gggctccgca ggcgaaaata ttggcgcatc cgagcaccgg cggccatgtg  1020
agccacaacg ggtggagctc gattgtggag tgcttgatgt ccggtgtacc ggtgatcggc  1080
gcgccgatgc aacttgacgg gccaatcgtc gcaaggctgg tggaggagat cggcgtgggt  1140
ttggaaatca agagagatga ggaagggaga atcacgaggg gcgaagttgc cgatgcaatc  1200
aagacggtgg cggtgggcaa aaccggggaa gatttttagaa ggaaagcaaa aaaaatcagc  1260
agcattttga agatgaaaga tgaagaagag gttgacactt tggcaatgga attagtgagg  1320
ttatgccaaa tgaaaagagg gcaggagtct caggactaa                          1359
```

SEQ ID NO: 70
Artificial Sequence; Codon-optimized nucleotide sequence A encoding UGT11789

```
atggacgcca aagaagaatc cttgaaggtt tttatgttgc catggttggc tcatggtcat    60
atttctccat atttggaatt ggctaagaga ttggccaaga gaaagttctt ggtttacttc   120
tgttctaccc cagttaactt ggaagctatt aagccaaagt tgtccaagtc ctactccgat   180
tctattcaat tgatggaagt cccattggaa tccactccag aattgccacc acattatcat   240
actgctaaag gtttgccacc tcatttgatg ccaaaattga tgaacgcttt caagatggtt   300
gctccaaact tggaatcaat cttgaaaacc ttgaacccag acttgttgat cgttgatatt   360
ttgttgcctt ggatgttgcc tttggcctcc tctttgaaaa ttcctatggt tttcttcacc   420
atcttcggtg ctatggctat ttctttcatg atctacaaca gaaccgtttc caacgaattg   480
ccatttccag aatttgaatt gcacgaatgc tggaagtcta agtgtccata cttgtttaag   540
gatcaagccg aatcccaatc cttcttggaa tatttggatc aatcctccgg tgtcattttg   600
atcaagacct ctagagaaat tgaagccaag tacgttgatt tcttgacctc ttcattcacc   660
aagaaggttg ttactactgg tccattggtt caacaaccat catctggtga agatgaaaag   720
caatactccg atatcattga atggttggac aagaaagaac cattgtccac tgttttggtt   780
tctttcggtt ccgaatatta cttgtctaaa gaagaaatgg aagaaatcgc ctacggtttg   840
gaatctgctt ctgaagttaa tttcatctgg atcgtcagat tcccaatggg tcaagaaact   900
gaagttgaag ctgctttgcc agaaggtttt attcaaagag ctggtgaaag aggtaaagtt   960
gttgaaggtt gggctccaca agctaagatt ttggctcatc catctactgg tggtcacgtt  1020
tctcataatg gttggtcatc tatcgttgaa tgcttgatgt ctggtgttcc agttattggt  1080
gctccaatgc aattggatgg tccaatagtt gctagattgg tcgaagaaat tggtgttggt  1140
ttggaaatca agagagatga agaaggtaga atcaccagag gtgaagttgc tgatgctatt  1200
aagactgttg ctgttggtaa aaccggtgaa gatttttagaa gaaaggccaa gaagatctcc  1260
tccattttaa agatgaagga cgaagaagaa gttgacacct tggctatgga attggttaga  1320
ttgtgtcaaa tgaagagagg tcaagaatcc caagactga                          1359
```

SEQ ID NO: 71
Artificial Sequence; Codon-optimized nucleotide sequence B encoding UGT11789

```
atggatgcta aggaagaatc tttgaaagtc tttatgctgc cttggttggc tcacggtcat    60
```

TABLE 3-continued

Sequences disclosed herein (see also Table 2).

```
atttccccgt atttggaatt ggcaaaaaga ctggccaaga gaaaattctt agtgtatttc   120
tgttcaactc cagtgaattt ggaagccatc aaaccaaaat tgtctaagtc atattctgac   180
tctatacaac tgatggaagt tcctttggaa agtacaccgg aactgccacc ccattatcat   240
acagctaaag ggttacccccc acacttgatg cccaagctaa tgaatgcatt taagatggtc   300
gcaccaaatc tggaaagtat acttaagacg ctaaaccctg atttattaat tgtagatatc   360
cttctaccat ggatgttgcc cttagcttca tctttaaaaa ttccgatggt ttttttcact   420
atctttggag ccatggcaat ttcctttatg atttacaata gaacagtctc aaatgagtta   480
cctttcccag agtttgaatt acatgaatgc tggaaatcta aatgtccata tttgttcaaa   540
gaccaagcag aatcccaatc tttcttagaa tacttagatc agagttccgg agttatcttg   600
atcaagacat ctagggaaat tgaagcaaag tatgtggact ttttgacctc cagttttact   660
aagaaagtcg taacaacggg tcctctagtc caacaaccta gttcaggaga ggatgagaaa   720
caatatagcg atataatcga atggttagat aaaaaagagc cattgagtac cgttctagtg   780
tcctttggtt cagaatatta tttgtctaaa gaagagatgg aagagattgc ctacggctta   840
gaatcagctt ccgaagtaaa ctttatatgg attgtcagat ttcccatggg acaagaaacc   900
gaggtcgaag cagctttgcc cgaaggtttt attcaacgtg ccggcgaaag aggaaaagta   960
gtggaaggtt gggctccaca agccaaaatt ctagctcacc cgtccactgg tggtcatgtc  1020
tctcataacg gatggagttc aattgttgaa tgtttgatga gtggtgttcc agtgatagga  1080
gctcctatgc agctggacgg tccaatagtc gccaggttag tcgaagaaat tggtgttggt  1140
ttagaaataa agagagacga agaaggtaga attactagag gtgaagtagc agatgcaatt  1200
aaaactgttg ctgtcggcaa gactggagag gattttcgta gaaaagccaa aaaaatatca  1260
tctatactaa aaatgaaaga cgaagaggag gttgatacgc tggcgatgga actagttaga  1320
ttgtgtcaga tgaagcgtgg tcaggaaagt caagactaa                         1359
```

SEQ ID NO: 72
*Siraitia grosvenorii* protein sequence

```
Met Asp Ala Lys Glu Glu Ser Leu Lys Val Phe Met Leu Pro Trp Leu
1               5                   10                  15

Ala His Gly His Ile Ser Pro Tyr Leu Glu Leu Ala Lys Arg Leu Ala
            20                  25                  30

Lys Arg Lys Phe Leu Val Tyr Phe Cys Ser Thr Pro Val Asn Leu Glu
        35                  40                  45

Ala Ile Lys Pro Lys Leu Ser Lys Ser Tyr Ser Asp Ser Ile Gln Leu
    50                  55                  60

Met Glu Val Pro Leu Glu Ser Thr Pro Glu Leu Pro Pro His Tyr His
65                  70                  75                  80

Thr Ala Lys Gly Leu Pro Pro His Leu Met Pro Lys Leu Met Asn Ala
                85                  90                  95

Phe Lys Met Val Ala Pro Asn Leu Glu Ser Ile Leu Lys Thr Leu Asn
            100                 105                 110

Pro Asp Leu Leu Ile Val Asp Ile Leu Leu Pro Trp Met Leu Pro Leu
        115                 120                 125

Ala Ser Ser Leu Lys Ile Pro Met Val Phe Phe Thr Ile Phe Gly Ala
    130                 135                 140

Met Ala Ile Ser Phe Met Ile Tyr Asn Arg Thr Val Ser Asn Glu Leu
145                 150                 155                 160

Pro Phe Pro Glu Phe Glu Leu His Glu Cys Trp Lys Ser Lys Cys Pro
                165                 170                 175

Tyr Leu Phe Lys Asp Gln Ala Glu Ser Gln Ser Phe Leu Glu Tyr Leu
            180                 185                 190

Asp Gln Ser Ser Gly Val Ile Leu Ile Lys Thr Ser Arg Glu Ile Glu
        195                 200                 205

Ala Lys Tyr Val Asp Phe Leu Thr Ser Ser Phe Thr Lys Lys Val Val
    210                 215                 220

Thr Thr Gly Pro Leu Val Gln Gln Pro Ser Ser Gly Glu Asp Glu Lys
225                 230                 235                 240

Gln Tyr Ser Asp Ile Ile Glu Trp Leu Asp Lys Lys Glu Pro Leu Ser
                245                 250                 255

Thr Val Leu Val Ser Phe Gly Ser Glu Tyr Tyr Leu Ser Lys Glu Glu
            260                 265                 270

Met Glu Glu Ile Ala Tyr Gly Leu Glu Ser Ala Ser Glu Val Asn Phe
        275                 280                 285
```

TABLE 3-continued

Sequences disclosed herein (see also Table 2).

```
Ile Trp Ile Val Arg Phe Pro Met Gly Gln Glu Thr Glu Val Glu Ala
    290                 295                 300

Ala Leu Pro Glu Gly Phe Ile Gln Arg Ala Gly Glu Arg Gly Lys Val
305                 310                 315                 320

Val Glu Gly Trp Ala Pro Gln Ala Lys Ile Leu Ala His Pro Ser Thr
                325                 330                 335

Gly Gly His Val Ser His Asn Gly Trp Ser Ser Ile Val Glu Cys Leu
            340                 345                 350

Met Ser Gly Val Pro Val Ile Gly Ala Pro Met Gln Leu Asp Gly Pro
        355                 360                 365

Ile Val Ala Arg Leu Val Glu Glu Ile Gly Val Gly Leu Glu Ile Lys
    370                 375                 380

Arg Asp Glu Glu Gly Arg Ile Thr Arg Gly Glu Val Ala Asp Ala Ile
385                 390                 395                 400

Lys Thr Val Ala Val Gly Lys Thr Gly Glu Asp Phe Arg Arg Lys Ala
                405                 410                 415

Lys Lys Ile Ser Ser Ile Leu Lys Met Lys Asp Glu Glu Glu Val Asp
            420                 425                 430

Thr Leu Ala Met Glu Leu Val Arg Leu Cys Gln Met Lys Arg Gly Gln
        435                 440                 445

Glu Ser Gln Asp
    450
```

SEQ ID NO: 73
*Siraitia grosvenorii* DNA sequence

```
atggaaatgt cgtcgtctgt tgcagctacg atttcaatat ggatggttgt ggtgtgcata    60
gtgggagtgg gatggagagt tgtgaactgg gtttggttga ggccgaagaa gcttgagaag   120
cggctgagag agcaaggcct cgccggaaac tcttaccggc ttctgttcgg agacttgaag   180
gagagggcgg cgatggagga gcaggccaac tccaagccca tcaacttctc ccatgatatc   240
ggaccacgtg tcttcccctc catgtacaaa accatccaga attatggtaa gaattcgtac   300
atgtggcttg gcccatatcc aagagtgcac atcatggacc ctcagcaact taaaactgtt   360
tttactctag tctatgatat ccaaaagcca aatttgaacc cccttatcaa gtttcttttg   420
gatggaatag taactcatga aggagaaaaa tgggctaaac acagaaagat aatcaaccct   480
gcatttcatt tggaaaagtt gaaggatatg ataccagcat tctttcatag ttgtaatgag   540
atagttaacg aatgggaaag attaatctcg aaagagggtt cgtgtgagtt ggatgttatg   600
ccatatctgc aaaatttggc agctgatgcc atttctcgaa ctgcatttgg gagtagctat   660
gaagaaggaa aaatgatctt ccaactttta aaagaactaa ctgatttggt ggttaaagtt   720
gcatttggag tttatattcc cggatggagg tttctaccaa ctaagtcaaa caataaaatg   780
aaagaaataa atagaaaaat taaaagtttg cttttgggta ttataaacaa aaggcaaaag   840
gctatggaag aaggtgaagc tggacaaagt gatttattag gcattctcat ggaatccaat   900
tcaaacgaaa ttcaaggaga aggaaacaat aaagaagatg gaatgagcat agaagatgtt   960
attgaagaat gcaaggtttt ctatattggt ggccaagaaa ccacagccag attactgatt  1020
tggaccatga ttttgttgag ttcacacacg gaatggcaag agcgagcaag aactgaggta  1080
ttaaaagtat ttggtaacaa gaagccagat tttgatggtt tgagtcgact aaaagttgta  1140
actatgattt tgaacgaggt tctcaggtta tacccaccag caagtatgct tactcgtatt  1200
attcaaaagg aaacaagagt tggaaaattg actctaccag ctggtgtgat attgatcatg  1260
ccaattattc ttatccatcg tgatcatgac ctatggggtg aagatgcaaa cgaatttaaa  1320
ccagaaagat tttctaaggg agtctctaaa gcagcaaaag ttcaacccgc tttcttccca  1380
tttggatggg gtcctcgaat atgcatgggg cagaactttg cgatgattga agcaaaaatg  1440
gcattatcat taattctaca acgcttctca tttgagcttt cttcgtcgta tgttcatgct  1500
cctaccgtcg ttttcactac tcaacctcaa catggagctc atatcgtcct gcgcaaactg  1560
tag                                                                1563
```

SEQ ID NO: 74
*Siraitia grosvenorii* protein sequence

```
Met Glu Met Ser Ser Ser Val Ala Ala Thr Ile Ser Ile Trp Met Val
1               5                   10                  15

Val Val Cys Ile Val Gly Val Gly Trp Arg Val Val Asn Trp Val Trp
            20                  25                  30

Leu Arg Pro Lys Lys Leu Glu Lys Arg Leu Arg Glu Gln Gly Leu Ala
        35                  40                  45

Gly Asn Ser Tyr Arg Leu Leu Phe Gly Asp Leu Lys Glu Arg Ala Ala
    50                  55                  60
```

TABLE 3-continued

Sequences disclosed herein (see also Table 2).

Met Glu Glu Gln Ala Asn Ser Lys Pro Ile Asn Phe Ser His Asp Ile
65 70 75 80

Gly Pro Arg Val Phe Pro Ser Met Tyr Lys Thr Ile Gln Asn Tyr Gly
85 90 95

Lys Asn Ser Tyr Met Trp Leu Gly Pro Tyr Pro Arg Val His Ile Met
100 105 110

Asp Pro Gln Gln Leu Lys Thr Val Phe Thr Leu Val Tyr Asp Ile Gln
115 120 125

Lys Pro Asn Leu Asn Pro Leu Ile Lys Phe Leu Leu Asp Gly Ile Val
130 135 140

Thr His Glu Gly Glu Lys Trp Ala Lys His Arg Lys Ile Ile Asn Pro
145 150 155 160

Ala Phe His Leu Glu Lys Leu Lys Asp Met Ile Pro Ala Phe Phe His
165 170 175

Ser Cys Asn Glu Ile Val Asn Glu Trp Glu Arg Leu Ile Ser Lys Glu
180 185 190

Gly Ser Cys Glu Leu Asp Val Met Pro Tyr Leu Gln Asn Leu Ala Ala
195 200 205

Asp Ala Ile Ser Arg Thr Ala Phe Gly Ser Ser Tyr Glu Glu Gly Lys
210 215 220

Met Ile Phe Gln Leu Leu Lys Glu Leu Thr Asp Leu Val Val Lys Val
225 230 235 240

Ala Phe Gly Val Tyr Ile Pro Gly Trp Arg Phe Leu Pro Thr Lys Ser
245 250 255

Asn Asn Lys Met Lys Glu Ile Asn Arg Lys Ile Lys Ser Leu Leu Leu
260 265 270

Gly Ile Ile Asn Lys Arg Gln Lys Ala Met Glu Glu Gly Glu Ala Gly
275 280 285

Gln Ser Asp Leu Leu Gly Ile Leu Met Glu Ser Asn Ser Asn Glu Ile
290 295 300

Gln Gly Glu Gly Asn Asn Lys Glu Asp Gly Met Ser Ile Glu Asp Val
305 310 315 320

Ile Glu Glu Cys Lys Val Phe Tyr Ile Gly Gly Gln Glu Thr Thr Ala
325 330 335

Arg Leu Leu Ile Trp Thr Met Ile Leu Leu Ser Ser His Thr Glu Trp
340 345 350

Gln Glu Arg Ala Arg Thr Glu Val Leu Lys Val Phe Gly Asn Lys Lys
355 360 365

Pro Asp Phe Asp Gly Leu Ser Arg Leu Lys Val Val Thr Met Ile Leu
370 375 380

Asn Glu Val Leu Arg Leu Tyr Pro Pro Ala Ser Met Leu Thr Arg Ile
385 390 395 400

Ile Gln Lys Glu Thr Arg Val Gly Lys Leu Thr Leu Pro Ala Gly Val
405 410 415

Ile Leu Ile Met Pro Ile Ile Leu Ile His Arg Asp His Asp Leu Trp
420 425 430

Gly Glu Asp Ala Asn Glu Phe Lys Pro Glu Arg Phe Ser Lys Gly Val
435 440 445

Ser Lys Ala Ala Lys Val Gln Pro Ala Phe Phe Pro Phe Gly Trp Gly
450 455 460

Pro Arg Ile Cys Met Gly Gln Asn Phe Ala Met Ile Glu Ala Lys Met
465 470 475 480

TABLE 3-continued

Sequences disclosed herein (see also Table 2).

```
Ala Leu Ser Leu Ile Leu Gln Arg Phe Ser Phe Glu Leu Ser Ser Ser
                485                 490                 495

Tyr Val His Ala Pro Thr Val Val Phe Thr Thr Gln Pro Gln His Gly
            500                 505                 510

Ala His Ile Val Leu Arg Lys Leu
        515                 520
```

SEQ ID NO: 75
*Saccharomyces cerevisiae* DNA sequence

```
atgtctgtta ttaatttcac aggtagttct ggtccattgg tgaaagtttg cggcttgcag    60
agcacagagg ccgcagaatg tgctctagat tccgatgctg acttgctggg tattatatgt   120
gtgcccaata gaaagagaac aattgacccg gttattgcaa ggaaaatttc aagtcttgta   180
aaagcatata aaaatagttc aggcactccg aaatacttgg ttggcgtgtt tcgtaatcaa   240
cctaaggagg atgttttggc tctggtcaat gattacggca ttgatatcgt ccaactgcat   300
ggagatgagt cgtggcaaga ataccaagag ttcctcggtt tgccagttat taaaagactc   360
gtatttccaa aagactgcaa catactactc agtgcagctt cacagaaacc tcattcgttt   420
attcccttgt ttgattcaga agcaggtggg acaggtgaac ttttggattg gaactcgatt   480
tctgactggg ttggaaggca agagagcccc gaaagcttac attttatgtt agctggtgga   540
ctgacgccag aaaatgttgg tgatgcgctt agattaaatg gcgttattgg tgttgatgta   600
agcggaggtg tggagacaaa tggtgtaaaa gactctaaca aaatagcaaa tttcgtcaaa   660
aatgctaaga aatag                                                     675
```

SEQ ID NO: 76
*Saccharomyces cerevisiae* protein sequence

```
Met Ser Val Ile Asn Phe Thr Gly Ser Ser Gly Pro Leu Val Lys Val
1               5                   10                  15

Cys Gly Leu Gln Ser Thr Glu Ala Ala Glu Cys Ala Leu Asp Ser Asp
            20                  25                  30

Ala Asp Leu Leu Gly Ile Ile Cys Val Pro Asn Arg Lys Arg Thr Ile
        35                  40                  45

Asp Pro Val Ile Ala Arg Lys Ile Ser Ser Leu Val Lys Ala Tyr Lys
    50                  55                  60

Asn Ser Ser Gly Thr Pro Lys Tyr Leu Val Gly Val Phe Arg Asn Gln
65                  70                  75                  80

Pro Lys Glu Asp Val Leu Ala Leu Val Asn Asp Tyr Gly Ile Asp Ile
                85                  90                  95

Val Gln Leu His Gly Asp Glu Ser Trp Gln Glu Tyr Gln Glu Phe Leu
            100                 105                 110

Gly Leu Pro Val Ile Lys Arg Leu Val Phe Pro Lys Asp Cys Asn Ile
        115                 120                 125

Leu Leu Ser Ala Ala Ser Gln Lys Pro His Ser Phe Ile Pro Leu Phe
    130                 135                 140

Asp Ser Glu Ala Gly Gly Thr Gly Glu Leu Leu Asp Trp Asn Ser Ile
145                 150                 155                 160

Ser Asp Trp Val Gly Arg Gln Glu Ser Pro Glu Ser Leu His Phe Met
                165                 170                 175

Leu Ala Gly Gly Leu Thr Pro Glu Asn Val Gly Asp Ala Leu Arg Leu
            180                 185                 190

Asn Gly Val Ile Gly Val Asp Val Ser Gly Gly Val Glu Thr Asn Gly
        195                 200                 205

Val Lys Asp Ser Asn Lys Ile Ala Asn Phe Val Lys Asn Ala Lys Lys
    210                 215                 220
```

SEQ ID NO: 77
*Saccharomyces cerevisiae* DNA sequence

```
atggcagctg accaattggt gaaaactgaa gtcaccaaga agtcttttac tgctcctgta    60
caaaaggctt ctacaccagt tttaaccaat aaaacagtca tttctggatc gaaagtcaaa   120
agtttatcat ctgcgcaatc gagctcatca ggaccttcat catctagtga ggaagatgat   180
tcccgcgata ttgaaagctt ggataagaaa atacgtcctt tagaagaatt agaagcatta   240
ttaagtagtg gaaatacaaa acaattgaag aacaaagagg tcgctgcctt ggttattcac   300
ggtaagttac ctttgtacgc tttggagaaa aaattaggtg atactacgag agcggttgcg   360
gtacgtagga aggctctttc aattttggca gaagctcctg tattagcatc tgatcgttta   420
ccatataaaa attatgacta cgaccgcgta tttggcgctt gttgtgaaaa tgttataggt   480
```

TABLE 3-continued

Sequences disclosed herein (see also Table 2).

```
tacatgcctt tgcccgttgg tgttataggc cccttggtta tcgatggtac atcttatcat   540
ataccaatgg caactacaga gggttgtttg gtagcttctg ccatgcgtgg ctgtaaggca   600
atcaatgctg gcggtggtgc aacaactgtt ttaactaagg atggtatgac aagaggccca   660
gtagtccgtt tcccaacttt gaaaagatct ggtgcctgta agatatggtt agactcagaa   720
gagggacaaa acgcaattaa aaaagctttt aactctacat caagatttgc acgtctgcaa   780
catattcaaa cttgtctagc aggagattta ctcttcatga gatttagaac aactactggt   840
gacgcaatgg gtatgaatat gatttctaaa ggtgtcgaat actcattaaa gcaaatggta   900
gaagagtatg gctgggaaga tatggaggtt gtctccgttt ctggtaacta ctgtaccgac   960
aaaaaaccag ctgccatcaa ctggatcgaa ggtcgtggta agagtgtcgt cgcagaagct  1020
actattcctg gtgatgttgt cagaaaagtg ttaaaaagtg atgtttccgc attggttgag  1080
ttgaacattg ctaagaattt ggttggatct gcaatggctg ggtctgttgg tggatttaac  1140
gcacatgcag ctaatttagt gacagctgtt ttcttggcat taggacaaga tcctgcacaa  1200
aatgttgaaa gttccaactg tataacattg atgaaagaag tggacggtga tttgagaatt  1260
tccgtatcca tgccatccat cgaagtaggt accatcggtg gtggtactgt tctagaacca  1320
caaggtgcca tgttggactt attaggtgta agaggcccgc atgctaccgc tcctggtacc  1380
aacgcacgtc aattagcaag aatagttgcc tgtgccgtct tggcaggtga attatcctta  1440
tgtgctgccc tagcagccgg ccatttggtt caaagtcata tgacccacaa caggaaacct  1500
gctgaaccaa caaaacctaa caatttggac gccactgata taaatcgttt gaaagatggg  1560
tccgtcacct gcattaaatc ctaa                                         1584
```

SEQ ID NO: 78
*Saccharomyces cerevisiae* protein sequence

```
Met Ala Ala Asp Gln Leu Val Lys Thr Glu Val Thr Lys Lys Ser Phe
1               5                   10                  15

Thr Ala Pro Val Gln Lys Ala Ser Thr Pro Val Leu Thr Asn Lys Thr
            20                  25                  30

Val Ile Ser Gly Ser Lys Val Lys Ser Leu Ser Ser Ala Gln Ser Ser
        35                  40                  45

Ser Ser Gly Pro Ser Ser Ser Ser Glu Glu Asp Asp Ser Arg Asp Ile
    50                  55                  60

Glu Ser Leu Asp Lys Lys Ile Arg Pro Leu Glu Glu Leu Glu Ala Leu
65                  70                  75                  80

Leu Ser Ser Gly Asn Thr Lys Gln Leu Lys Asn Lys Glu Val Ala Ala
                85                  90                  95

Leu Val Ile His Gly Lys Leu Pro Leu Tyr Ala Leu Glu Lys Lys Leu
            100                 105                 110

Gly Asp Thr Thr Arg Ala Val Ala Val Arg Arg Lys Ala Leu Ser Ile
        115                 120                 125

Leu Ala Glu Ala Pro Val Leu Ala Ser Asp Arg Leu Pro Tyr Lys Asn
    130                 135                 140

Tyr Asp Tyr Asp Arg Val Phe Gly Ala Cys Cys Glu Asn Val Ile Gly
145                 150                 155                 160

Tyr Met Pro Leu Pro Val Gly Val Ile Gly Pro Leu Val Ile Asp Gly
                165                 170                 175

Thr Ser Tyr His Ile Pro Met Ala Thr Thr Glu Gly Cys Leu Val Ala
            180                 185                 190

Ser Ala Met Arg Gly Cys Lys Ala Ile Asn Ala Gly Gly Gly Ala Thr
        195                 200                 205

Thr Val Leu Thr Lys Asp Gly Met Thr Arg Gly Pro Val Val Arg Phe
    210                 215                 220

Pro Thr Leu Lys Arg Ser Gly Ala Cys Lys Ile Trp Leu Asp Ser Glu
225                 230                 235                 240

Glu Gly Gln Asn Ala Ile Lys Lys Ala Phe Asn Ser Thr Ser Arg Phe
                245                 250                 255

Ala Arg Leu Gln His Ile Gln Thr Cys Leu Ala Gly Asp Leu Leu Phe
            260                 265                 270

Met Arg Phe Arg Thr Thr Thr Gly Asp Ala Met Gly Met Asn Met Ile
        275                 280                 285

Ser Lys Gly Val Glu Tyr Ser Leu Lys Gln Met Val Glu Glu Tyr Gly
    290                 295                 300
```

TABLE 3-continued

Sequences disclosed herein (see also Table 2).

```
Trp Glu Asp Met Glu Val Val Ser Val Ser Gly Asn Tyr Cys Thr Asp
305                 310                 315                 320

Lys Lys Pro Ala Ala Ile Asn Trp Ile Glu Gly Arg Gly Lys Ser Val
                325                 330                 335

Val Ala Glu Ala Thr Ile Pro Gly Asp Val Val Arg Lys Val Leu Lys
            340                 345                 350

Ser Asp Val Ser Ala Leu Val Glu Leu Asn Ile Ala Lys Asn Leu Val
        355                 360                 365

Gly Ser Ala Met Ala Gly Ser Val Gly Gly Phe Asn Ala His Ala Ala
    370                 375                 380

Asn Leu Val Thr Ala Val Phe Leu Ala Leu Gly Gln Asp Pro Ala Gln
385                 390                 395                 400

Asn Val Glu Ser Ser Asn Cys Ile Thr Leu Met Lys Glu Val Asp Gly
                405                 410                 415

Asp Leu Arg Ile Ser Val Ser Met Pro Ser Ile Glu Val Gly Thr Ile
            420                 425                 430

Gly Gly Gly Thr Val Leu Glu Pro Gln Gly Ala Met Leu Asp Leu Leu
        435                 440                 445

Gly Val Arg Gly Pro His Ala Thr Ala Pro Gly Thr Asn Ala Arg Gln
    450                 455                 460

Leu Ala Arg Ile Val Ala Cys Ala Val Leu Ala Gly Glu Leu Ser Leu
465                 470                 475                 480

Cys Ala Ala Leu Ala Ala Gly His Leu Val Gln Ser His Met Thr His
                485                 490                 495

Asn Arg Lys Pro Ala Glu Pro Thr Lys Pro Asn Asn Leu Asp Ala Thr
            500                 505                 510

Asp Ile Asn Arg Leu Lys Asp Gly Ser Val Thr Cys Ile Lys Ser
        515                 520                 525
```

SEQ ID NO: 79

*Siraitia grosvenorii* DNA sequence

```
atggacgaga ttgagcatat caccatcaac accaatggca tcaaaatgca cattgcctct    60
gtagggacgg gcccagtagt tcttcttctc catggcttcc cggagctctg gtactcatgg   120
cgccaccagc ttctgtatct ttcttccgta ggatatcgag ctattgcgcc ggacctccgc   180
ggctatggcg acacggactc gccggcgtct cctacctcct acaccgcgct ccacatcgtc   240
ggcgatttgg ttggggctct ggacgagctt gggatcgaga aggtgttcct ggtcggacat   300
gactgggggg cgatcatcgc ctggtacttt tgcttgttca ggcccgatag aatcaaggcg   360
ctggtgaatc tgagcgtcca gttcataccc agaaacccag cgattccttt catcgagggt   420
ttcagaactg cgttcggtga tgacttctat atttgcaggt ttcaggttcc aggagaggca   480
gaagaagatt ttgcctccat cgacacagct cagctgttca agacatcatt atgtaataga   540
agttctgcac ctccatgctt gcctaaagaa attggatttc gtgcgatccc acctccagag   600
aaccttcctt cttggctgac agaagaagat atcaactttt atgctgccaa atttaagcag   660
acaggcttca ccggagcgtt gaactactat cgagcttttg acctaacttg ggagctcacg   720
gcgccatgga cgggagcaca gattcaggta ccggtgaagt tcatcgtcgg ggattcggat   780
ctaacttacc attttccggg agccaaggaa tatatccata atggcggatt caaaagggac   840
gtgccgttgc tggaggaagt agttgtagta aaagatgctt gtcacttcat caaccaagaa   900
aggccacaag aaatcaatgc tcacatccat gacttcatca ataaattctg a            951
```

SEQ ID NO: 80

*Siraitia grosvenorii* DNA sequence

```
atgtggaggt taaaggtcgg agcagaaagc gttggggaga atgatgagaa atggttgaag    60
agcataagca atcacttggg acgccaggtg tgggagttct gtccggatgc cggcacccaa   120
caacagctct tgcaagtcca caaagctcgt aaagctttcc acgatgaccg tttccaccga   180
aagcaatctt ccgatctctt tatcactatt cagtatggaa aggaagtaga aaatggtgga   240
aagacagcgg gagtgaaatt gaaagaaggg gaagaggtga ggaaagaggc agtagagagt   300
agcttagaga gggcattaag tttctactca agcatccaga caagcgatgg gaactgggct   360
tcggatcttg gggggcccat gtttttactt ccgggtctgg tgattgccct ctacgttaca   420
ggcgtcttga attctgtttt atccaagcac caccggcaag agatgtgcag atatgtttac   480
aatcaccaga atgaagatgg ggggtggggt ctccacatcg agggcccaag caccatgttt   540
ggttccgcac tgaattatgt tgcactcagg ctgcttggag aagacgccaa cgccggggca   600
atgccaaaag cacgtgcttg gatcttggac cacggtggcg ccaccggaat cacttcctgg   660
ggcaaattgt ggctttctgt acttggagtc tacgaatgga gtggcaataa tcctcttcca   720
cccgaatttt ggttatttcc ttacttccta ccatttcatc caggaagaat gtggtgccat   780
tgtcgaatgg tttatctacc aatgtcatac ttatatggaa agagatttgt tgggccaatc   840
```

TABLE 3-continued

Sequences disclosed herein (see also Table 2).

```
acacccatag ttctgtctct cagaaaagaa ctctacgcag ttccatatca tgaaatagac   900
tggaataaat ctcgcaatac atgtgcaaag gaggatctgt actatccaca tcccaagatg   960
caagatattc tgtggggatc tctccaccac gtgtatgagc ccttgtttac tcgttggcct  1020
gccaaacgcc tgagagaaaa ggctttgcag actgcaatgc aacatattca ctatgaagat  1080
gagaataccc gatatatatg ccttggccct gtcaacaagg tactcaatct gctttgttgt  1140
tgggttgaag atccctactc cgacgccttc aaacttcatc ttcaacgagt ccatgactat  1200
ctctgggttg ctgaagatgg catgaaaatg cagggttata atgggagcca gttgtgggac  1260
actgctttct ccatccaagc aatcgtatcc accaaacttg tagacaacta tggcccaacc  1320
ttaagaaagg cacacgactt cgttaaaagt tctcagattc agcaggactg tcctggggat  1380
cctaatgttt ggtaccgtca cattcataaa ggtgcatggc cattttcaac tcgagatcat  1440
ggatggctca tctctgactg tacagcagag ggattaaagg ctgctttgat gttatccaaa  1500
cttccatccg aaacagttgg ggaatcatta gaacggaatc gcctttgcga tgctgtaaac  1560
gttctccttt ctttgcaaaa cgataatggt ggctttgcat catatgagtt gacaagatca  1620
tacccttggt tggagttgat caaccccgca gaaacgtttg gagatattgt cattgattat  1680
ccgtatgtgg agtgcacctc agccacaatg gaagcactga cgttgtttaa gaaattacat  1740
cccggccata ggaccaaaga aattgatact gctattgtca gggcggccaa cttccttgaa  1800
aatatgcaaa ggacggatgg ctcttggtat ggatgttggg ggtttgcttt cacgtatgcg  1860
gggtggtttg gcataaaggg attggtggct gcaggaagga catataataa ttgccttgcc  1920
attcgcaagg cttgcgattt tttactatct aaagagctgc ccggcggtgg atggggagag  1980
agttaccttt catgtcagaa taaggtatac acaaatcttg aaggaaacag accgcacctg  2040
gttaacacgg cctgggtttt aatggccctc atagaagctg gccaggctga gagagaccca  2100
acaccattgc atcgtgcagc aaggttgtta atcaattccc agttggagaa tggtgatttc  2160
ccccaacagg agatcatggg agtctttaat aaaaattgca tgatcacata tgctgcatac  2220
cgaaacattt ttcccatttg ggctcttgga gagtattgcc atcgggtttt gactgaataa  2280
```

SEQ ID NO: 81
Artificial Sequence; Codon-optimized nucleotide sequence encoding CYP5491

```
atgtggactg ttgttttggg tttggctact ttgtttgttg cctactacat tcactggatc    60
aacaagtgga gagactctaa gtttaatggt gttttgccac caggtactat gggtttgcca   120
ttgattggtg aaaccatcca attgtcaaga ccatccgatt ctttggatgt tcatccattc   180
atccaaaaaa aggtcgaaag atacggtcca atcttcaaga cttgtttggc tggtagacca   240
gttgttgttt ctgctgatgc tgaatttaac aactacatca tgttgcaaga aggtagagct   300
gttgaaatgt ggtacttgga tactttgtct aagttcttcg gtttggatac cgaatggttg   360
aaggctttgg gtttaatcca taagtacatc agatccatca ccttgaatca ttttggtgct   420
gaagccttga gagaaagatt cttgcctttt attgaagcct cttctatgga agccttgcat   480
tcttggtcta ctcaaccatc tgttgaagtt aagaatgctt ccgctttgat ggttttcaga   540
acctctgtta acaagatgtt tggtgaagat gccaagaagt tgtctggtaa tattccaggt   600
aagttcacca agttgttggg tggttttttg tctttgcctt tgaatttccc aggtacaacc   660
taccataagt gcttgaaaga tatgaaggaa atccaaaaga agttgagaga agtcgttgat   720
gatagattgg ctaatgttgg tccagatgtc gaagattttt tgggtcaagc cttgaaggac   780
aaagaatccg aaaagttcat ctccgaagaa tttatcattc aattgttgtt ctctatctcc   840
ttcgcctcct tcgaatctat ttctactact ttgaccttga tcttgaagtt gttagacgaa   900
catccagaag tcgtcaaaga attggaagct gaacatgaag ctattagaaa ggctagagct   960
gatccagatg gtccaattac ttgggaagaa tacaagtcta tgaccttcac cttgcaagtt  1020
atcaacgaaa ctttgagatt gggttctgtt actccagctt tgttgagaaa aactgtcaag  1080
gacttacaag tcaagggtta cattattcct gaaggttgga ccattatgtt ggttactgct  1140
tcaagacata gagatccaaa ggtttacaaa gacccacata ttttcaatcc ttggagatgg  1200
aaggatttgg actccattac tattcaaaag aacttcatgc cattcggtgg tggtttgaga  1260
cattgtgctg gtgcagaata ctctaaggtt tacttgtgta ctttcttgca catcttgtgc  1320
actaagtaca gatggacaaa attgggtggt ggtagaattg ctagagccca tatttgtca   1380
ttcgaagatg gtttacatgt caagttcacc ccaaaagaat ga                     1422
```

SEQ ID NO: 82
Artificial Sequence; Codon-optimized nucleotide sequence encoding CYP4497

```
atgaaggtca gtccattcga attcatgtcc gctattatca agggtagaat ggacccatct    60
aactcctcat ttgaatctac tggtgaagtt gcctccgtta tctttgaaaa cagagaattg   120
gttgccatct tgaccacttc tattgctggt atgattggtt gcttcgttgt cttgatgtgg   180
agaagagctg gttctagaaa ggttaagaat gtcgaattgc caaagccatt gattgtccat   240
gaaccagaac ctgaagttga agatggtaag aagaaggttt ccatcttctt cggtactcaa   300
actggtactg ctgaaggttt tgctaaggct ttggctgatg aagctaaagc tagatacgaa   360
aaggctacct tcagagttgt tgatttggat gattatgctg ccgatgatga ccaatacgaa   420
gaaaaattga agaacgaatc cttcgccgtt ttcttgttgg ctacttatgg tgatggtgaa   480
cctactgata atgctgctag attttacaag tggttcgccg aaggtaaaga aagaggtgaa   540
tggttgcaaa acttgcacta tgctgttttt ggtttgggta acagacaata cgaacacttc   600
aacaagattg ctaaggttgc cgacgaatta ttggaagctc aaggtggtaa tagattggtt   660
aaggttggtt taggtgatga cgatcaatgc atcgaagatg atttttctgc ttggagagaa   720
tctttgtggc cagaattgga tatgttgttg agagatgaag atgatgctac tactgttact   780
actccatata ctgctgctgt cttggaatac agagttgtct ttcatgattc tgctgatgtt   840
gctgctgaag ataagtcttg gattaacgct aatggtcatg ctgttcatga tgctcaacat   900
ccattcagat ctaacgttgt cgtcagaaaa gaattgcata cttctgcctc tgatagatcc   960
tgttctcatt tggaattcaa catttccggt tccgctttga attacgaaac tggtgatcat  1020
gttggtgtct actgtgaaaa cttgactgaa actgttgatg aagccttgaa cttgttgggt  1080
ttgtctccag aaacttactt ctctatctac accgataacg aagatggtac tccattgggt  1140
ggttcttcat tgccaccacc atttccatca tgtactttga gaactgcttt gaccagatac  1200
gctgatttgt tgaactctcc aaaaaagtct gctttgttgg ctttagctgc tcatgcttct  1260
aatccagttg aagctgatag attgagatac ttggcttctc cagctggtaa agatgaatat  1320
```

TABLE 3-continued

Sequences disclosed herein (see also Table 2).

```
gcccaatctg ttatcggttc ccaaaagtct ttgttggaag ttatggctga attcccatct  1380
gctaaaccac cattaggtgt ttttttgct gctgttgctc caagattgca acctagattc  1440
tactccattt catcctctcc aagaatggct ccatctagaa tccatgttac ttgtgctttg  1500
gtttacgata agatgccaac tggtagaatt cataagggtg tttgttctac ctggatgaag  1560
aattctgttc caatggaaaa gtcccatgaa tgttcttggg ctccaatttt cgttagacaa  1620
tccaatttta agttgccagc cgaatccaag gttccaatta tcatggttgg tccaggtact  1680
ggtttggctc cttttagagg ttttttacaa gaaagattgg ccttgaaaga atccggtgtt  1740
gaattgggtc catccatttt gtttttcggt tgcagaaaca gaagaatgga ttacatctac  1800
gaagatgaat tgaacaactt cgttgaaacc ggtgctttgt ccgaattggt tattgctttt  1860
tctagagaag gtcctaccaa agaatacgtc caacataaga tggctgaaaa ggcttctgat  1920
atctggaact tgatttctga aggtgcttac ttgtacgttt gtggtgatgc taaaggtatg  1980
gctaaggatg ttcatagaac cttgcatacc atcatgcaag aacaaggttc tttggattct  2040
tccaaagctg aatccatggt caagaacttg caaatgaatg gtagatactt aagagatgtt  2100
tggtaa                                                             2106
```

SEQ ID NO: 83
Artificial Sequence; Codon-optimized nucleotide sequence
encoding UGT1576

```
atggcgtcac ctagacatac tcctcatttc ttgttatttc catttatggc tcaaggacat    60
atgataccta tgattgatct ggctaggcta ctagcacaaa gaggtgttat tatcactatt   120
attactactc cacataatgc agctcgttat catagtgttt tagctcgtgc cattgactct   180
ggtttacata tccacgtttt acaactacaa ttcccttgca aagaaggcgg actaccggaa   240
ggttgtgaga acgtagactt acttccatcc ttagcgagca ttccaagatt ttacagagct   300
gcctctgatc tactatatga acctagcgaa aaacttttcg aagagttgat accgagacca   360
acttgtatca tttctgatat gtgtttacca tggactatga gaattgcctt aaagtatcat   420
gtgcccagac ttgttttcta ctctttgtct tgcttttttc tgctgtgcat gagaagctta   480
aagaacaatt tagcattaat ttctagcaag tcagattccg agttcgtaac tttctctgat   540
ttacccgatc cagttgaatt tttgaagtct gagcttccta agtccacaga cgaagacttg   600
gttaaatttt catatgaaat gggtgaggca gacagacaat catatggcgt tatactaaac   660
ttgtttgaag aaatggagcc caaatatttg gcagagtatg aaaaagaaag agaaagtccc   720
gaaagagttt ggtgtgttgg tccagtatct ttgtgcaacg ataacaaatt agataaagca   780
gagaggggta acaaagcatc aattgacgaa tataagtgta ttagatggtt agatgggcaa   840
caacctagca gtgttgttta tgttagtctt ggatcattat gcaacttggt tactgctcaa   900
attattgaat tggggttggg gttggaagct tctaaaaagc cattcatttg ggttattagg   960
aggggcaaca taacagaaga actacaaaaa tggctggttg aatatgactt tgaggagaag  1020
attaagggac gtggattagt catattaggg tgggcgcccc aagtacttat tctatctcat  1080
ccagctattg gttgcttctt aactcattgc ggttggaatt cctctatcga aggtatttcc  1140
gccggtgttc ctatggttac ctggcctcta tttgcagatc aggttttcaa cgaaaaatta  1200
atagttcaaa tcttgagaat cggagttagc gttggtacag aaacaaccat gaactggggt  1260
gaggaagaag aaaaaggtgt ggtggtcaaa agggagaaag tgagagaggc gatagagatc  1320
gtaatggatg gcgacgaaag agaagaaaga agagaaaggt gtaaagaact agcagaaact  1380
gccaaacgtg ctatcgagga aggtggtagc agtcatagaa atttgaccat gctaattgaa  1440
gatattatcc acggtggtgg cttatcttac gagaaagggt cctgcaggta g           1491
```

SEQ ID NO: 84
Artificial Sequence; Codon-optimized nucleotide sequence
encoding UGT430

```
atggaacaag cccacgattt gctgcatgtt ttactttttc catatccagc taaagggcat    60
attaagccct tttgtgtct tgcggaactt ttatgcaacg caggtcttaa tgttacgttt   120
ttgaataccg attataatca cagaagatta cacaatctgc acctattagc ggcttgtttt   180
cctagtttgc attttgaaag tatcagtgat ggtttgcagc cagatcaacc tagagatatc   240
ttggacccaa agttttacat ctctatttgc caagttacca agccattatt cagagaattg   300
ttattatcct ataaaaggac atcctcagta caaaccggca ggccgccaat aacttgtgtt   360
ataacagatg ttatatttcg ttttccaatc gatgtagccg aggaattaga tatccctgtt   420
ttttctttct gtacttttag cgcgcgtttt atgtttcttt acttctggat cccaaagctt   480
atcgaggatg ggcaattgcc ttacccaaac ggtaacataa atcagaaact gtatggtgtt   540
gcacctgaag cagaaggatt attaaggtgt aaggatttac cgggacactg ggctttcgct   600
gatgagttaa aagacgatca gttgaacttt gttgatcaaa ctaccgccag tttgagatca   660
tctggtttga tcttaaacac tttcgacgat ttggaagctc cattcctggg acgtttgtca   720
acaatattta agaagatcta cgctgttggg ccaatacatg cgttgctaaa cagtcaccat   780
tgcggtttat ggaaagaaga ccacagctgt ttggcctggt tagatagtag agcggcacgt   840
tctgtcgtgt tcgtcagttt cggttctttg gttaagatca cttctaggca attgatggaa   900
ttctggcatg gattgttgaa tagcgggaca agctttttgt ttgtcttgag aagtgatgtt   960
gtagaaggtg atggggaaaa gcaagttgtc aaagaaatct acgaaacgaa agcagagggt  1020
aaatggttag ttgttggttg ggctccacaa gaaaaagtat tggcacatga agccgttgga  1080
ggtttcttaa ctcattccgg ttggaactca atcttagagt ctatagccgc aggtgtacct  1140
atgataagtt gcccaaaaat aggagaccaa tcttctaatt gtacctggat tagtaaagtt  1200
tggaagattg gtttagaaat ggaagaccag tatgacagag caactgtgga agctatggtg  1260
agatcaatta tgaaacacga aggtgagaag atacaaaaga ctattgcgga acttgcaaaa  1320
agagcaaaat ataaagtttc caaggacggc acttcatata gaaatctgga aattttgatc  1380
gaagatatca agaagatcaa gccgaattag                                  1410
```

SEQ ID NO: 85
Artificial Sequence; Codon-optimized nucleotide sequence
encoding UGT1697

```
atggttcaac ctagggtctt attgtttccc ttccctgctt tgggacatgt caaacccttt    60
ctgtcactgg cagaattact ttccgatgct gggatagacg ttgtatttct tagtacagaa   120
tacaatcata ggaggattag taacacggag gctctggcct caagatttcc aaccttgcat   180
```

TABLE 3-continued

Sequences disclosed herein (see also Table 2).

```
tttgaaacaa taccagatgg tcttccacct aacgagagca gggctttggc agacggccct   240
ttgtacttta gcatgcgtga ggggacaaaa cccagattca gacagctgat acagagcctg   300
aacgatggca gatggcctat cacgtgtatc attaccgata tcatgttgag tagccccatc   360
gaagtagctg aggagtttgg aattccagta attgcctttt gtccctgctc cgctagatac   420
ttgtctattc atttttcat acccaagttg gttgaagagg gtcagatccc ttatgcagat   480
gatgatccaa tcggtgaaat tcaaggtgtg ccacttttcg aagggcttct gaggagaaat   540
catttgccag gcagctggag tgataagtct gcagacatct cattttccca tggtttgatc   600
aaccaaacat tagcagccgg tagagcttct gcattaatct tgaatacgtt tgatgagttg   660
gaagctccat ttctgactca tctttctagt atttttaata agatttatac aattggtcct   720
ttgcatgcct tatctaagtc aaggttagga gactcctcat ctagtgctag tgcacttagt   780
ggattctgga aggaagatag ggcttgtatg tcttggttgg attgtcaacc tcctagatct   840
gttgttttcg tctcttttgg cagtactatg aaaatgaagg cggacgaact aagagaattt   900
tggtatggat tagtatcttc aggaaaacca tttttatgcg ttttaagatc cgatgtagtc   960
tcaggcggag aagctgcgga gttaattgaa caaatggcag aagaggaagg tgccgggggt  1020
aagttgggca tggttgttga atgggcagct caggagaagg tacttagcca tccagcggtt  1080
ggtggatttt tgacgcattg cgggtggaat agcactgtgg aaagtatagc agcaggggtc  1140
ccgatgatgt gttggccaat cttgggagat caaccatcca acgcgacctg gatcgataga  1200
gtttggaaaa tcggtgtaga aagaaataat agagaatggg atagattaac tgttgaaaaa  1260
atggttagag ccttgatgga aggacagaaa agagttgaaa ttcagcgttc aatggaaaag  1320
ctatcaaagt tggccaatga aaaagtagtt aggggggggtc tttcatttga taatcttgaa  1380
gttcttgtcg aagatattaa aaagttaaag ccgtacaagt tttaa                  1425
```

SEQ ID NO: 86
Artificial Sequence; Codon-optimized nucleotide sequence
encoding CYP1798

```
atggaaatgt cctcttctgt tgctgccacc atttctattt ggatggttgt tgtatgtatc    60
gttggtgttg gttggagagt tgttaattgg gtttggttaa gaccaaagaa gttggaaaag   120
agattgagag aacaaggttt ggctggtaac tcttacagat tgttgttcgg tgacttgaaa   180
gaaagagctg ctatggaaga acaagctaac tctaagccaa tcaacttctc ccatgatatt   240
ggtccaagag ttttcccatc tatgtacaag accattcaaa actacggtaa gaactcctat   300
atgtggttgg gtccataccc aagagttcat attatggatc cacaacaatt gaaaaccgtc   360
tttaccttgg tttacgacat ccaaaagcca aacttgaacc cattgatcaa gttcttgttg   420
gatggtattg tcacccatga aggtgaaaaa tgggctaaac atagaaagat tatcaaccca   480
gccttccact tggaaaagtt gaaagatatg attccagcct tcttccactc ttgcaacgaa   540
atagttaatg aatgggaaag attgatctcc aaagaaggtt cttgcgaatt ggatgttatg   600
ccatacttgc aaaatttggc tgctgatgct atttctagaa ctgcttttgg ttcctcttac   660
gaagaaggta agatgatctt ccaattattg aaagaattga ccgacttggt tgttaaggtt   720
gctttcggtg tttacattcc aggttggaga tttttgccaa ctaagtccaa caacaagatg   780
aaggaaatca acagaaagat caagtctttg ttgttaggta tcatcaacaa gagacaaaag   840
gccatggaag aaggtgaagc tggtcaatct gatttgttgg gtattttgat ggaatccaac   900
tccaacgaaa ttcaaggtga aggtaacaac aaagaagatg gtatgtccat cgaagatgtt   960
atcgaagaat gcaaggtttt ctacatcggt ggtcaagaaa ctaccgccag attattgatt  1020
tggaccatga tcttgttgag ttcccatact gaatggcaag aaagagcaag aactgaagtc  1080
ttgaaggttt tcggtaacaa aaagccagat ttcgacggtt tgtctagatt gaaggttgtc  1140
accatgattt tgaacgaagt tttgagatta tacccaccag cttctatgtt gaccagaatc  1200
attcaaaaag aaaccagagt cggtaagttg actttgccag ctggtgttat tttgatcatg  1260
ccaatcatct tgatccacag agatcatgat ttgtggggtg aagatgctaa tgaattcaag  1320
ccagaaagat tctccaaggg tgtttctaaa gctgctaaag ttcaaccagc tttctttcca  1380
tttggttggg gtccaagaat atgtatgggt caaaatttcg ctatgatcga agctaagatg  1440
gccttgtctt tgatcttgca aagattttcc ttcgaattgt cctcctcata tgttcatgct  1500
ccaactgttg ttttcaccac tcaaccacaa catggtgctc atatcgtttt gagaaagttg  1560
taa                                                                1563
```

SEQ ID NO: 87
*Saccharomyces cerevisiae* protein sequence

```
Met Gly Lys Leu Leu Gln Leu Ala Leu His Pro Val Glu Met Lys Ala
1               5                   10                  15

Ala Leu Lys Leu Lys Phe Cys Arg Thr Pro Leu Phe Ser Ile Tyr Asp
            20                  25                  30

Gln Ser Thr Ser Pro Tyr Leu Leu His Cys Phe Glu Leu Leu Asn Leu
        35                  40                  45

Thr Ser Arg Ser Phe Ala Ala Val Ile Arg Glu Leu His Pro Glu Leu
    50                  55                  60

Arg Asn Cys Val Thr Leu Phe Tyr Leu Ile Leu Arg Ala Leu Asp Thr
65                  70                  75                  80

Ile Glu Asp Asp Met Ser Ile Glu His Asp Leu Lys Ile Asp Leu Leu
                85                  90                  95

Arg His Phe His Glu Lys Leu Leu Leu Thr Lys Trp Ser Phe Asp Gly
            100                 105                 110

Asn Ala Pro Asp Val Lys Asp Arg Ala Val Leu Thr Asp Phe Glu Ser
        115                 120                 125
```

TABLE 3-continued

Sequences disclosed herein (see also Table 2).

```
Ile Leu Ile Glu Phe His Lys Leu Lys Pro Glu Tyr Gln Glu Val Ile
    130                 135                 140

Lys Glu Ile Thr Glu Lys Met Gly Asn Gly Met Ala Asp Tyr Ile Leu
145                 150                 155                 160

Asp Glu Asn Tyr Asn Leu Asn Gly Leu Gln Thr Val His Asp Tyr Asp
                165                 170                 175

Val Tyr Cys His Tyr Val Ala Gly Leu Val Gly Asp Gly Leu Thr Arg
            180                 185                 190

Leu Ile Val Ile Ala Lys Phe Ala Asn Glu Ser Leu Tyr Ser Asn Glu
        195                 200                 205

Gln Leu Tyr Glu Ser Met Gly Leu Phe Leu Gln Lys Thr Asn Ile Ile
    210                 215                 220

Arg Asp Tyr Asn Glu Asp Leu Val Asp Gly Arg Ser Phe Trp Pro Lys
225                 230                 235                 240

Glu Ile Trp Ser Gln Tyr Ala Pro Gln Leu Lys Asp Phe Met Lys Pro
                245                 250                 255

Glu Asn Glu Gln Leu Gly Leu Asp Cys Ile Asn His Leu Val Leu Asn
            260                 265                 270

Ala Leu Ser His Val Ile Asp Val Leu Thr Tyr Leu Ala Gly Ile His
        275                 280                 285

Glu Gln Ser Thr Phe Gln Phe Cys Ala Ile Pro Gln Val Met Ala Ile
    290                 295                 300

Ala Thr Leu Ala Leu Val Phe Asn Asn Arg Glu Val Leu His Gly Asn
305                 310                 315                 320

Val Lys Ile Arg Lys Gly Thr Thr Cys Tyr Leu Ile Leu Lys Ser Arg
                325                 330                 335

Thr Leu Arg Gly Cys Val Glu Ile Phe Asp Tyr Tyr Leu Arg Asp Ile
            340                 345                 350

Lys Ser Lys Leu Ala Val Gln Asp Pro Asn Phe Leu Lys Leu Asn Ile
        355                 360                 365

Gln Ile Ser Lys Ile Glu Gln Phe Met Glu Glu Met Tyr Gln Asp Lys
    370                 375                 380

Leu Pro Pro Asn Val Lys Pro Asn Glu Thr Pro Ile Phe Leu Lys Val
385                 390                 395                 400

Lys Glu Arg Ser Arg Tyr Asp Asp Glu Leu Val Pro Thr Gln Gln Glu
                405                 410                 415

Glu Glu Tyr Lys Phe Asn Met Val Leu Ser Ile Ile Leu Ser Val Leu
            420                 425                 430

Leu Gly Phe Tyr Tyr Ile Tyr Thr Leu His Arg Ala
        435                 440
```

SEQ ID NO: 88
*Gynostemma pentaphyllum* Squalene epoxidase protein sequence

```
Met Val Asp Gln Phe Ser Leu Ala Phe Ile Phe Ala Ser Val Leu Gly
1               5                   10                  15

Ala Val Ala Phe Tyr Tyr Leu Phe Leu Arg Asn Arg Ile Phe Arg Val
            20                  25                  30

Ser Arg Glu Pro Arg Arg Glu Ser Leu Lys Asn Ile Ala Thr Thr Asn
        35                  40                  45

Gly Glu Cys Lys Ser Ser Tyr Ser Asp Gly Asp Ile Ile Ile Val Gly
    50                  55                  60

Ala Gly Val Ala Gly Ser Ala Leu Ala Tyr Thr Leu Gly Lys Asp Gly
65                  70                  75                  80
```

TABLE 3-continued

| Sequences disclosed herein (see also Table 2). |
|---|
| Arg Arg Val His Val Ile Glu Arg Asp Leu Thr Glu Pro Asp Arg Thr<br>85 90 95 |
| Val Gly Glu Leu Leu Gln Pro Gly Gly Tyr Leu Lys Leu Thr Glu Leu<br>100 105 110 |
| Gly Leu Glu Asp Cys Val Asn Glu Ile Asp Ala Gln Arg Val Tyr Gly<br>115 120 125 |
| Tyr Ala Leu Phe Lys Asp Gly Lys Asp Thr Lys Leu Ser Tyr Pro Leu<br>130 135 140 |
| Glu Lys Phe His Ser Asp Val Ser Gly Arg Ser Phe His Asn Gly Arg<br>145 150 155 160 |
| Phe Ile Gln Arg Met Arg Glu Lys Ala Ala Thr Leu Pro Asn Val Arg<br>165 170 175 |
| Leu Glu Gln Gly Thr Val Thr Ser Leu Leu Glu Glu Asn Gly Ile Ile<br>180 185 190 |
| Lys Gly Val Gln Tyr Lys Ser Lys Thr Gly Gln Glu Met Thr Ala Tyr<br>195 200 205 |
| Ala Pro Leu Thr Ile Val Cys Asp Gly Cys Phe Ser Asn Leu Arg Arg<br>210 215 220 |
| Ser Leu Cys Asn Pro Lys Val Asp Val Pro Ser Cys Phe Val Ala Leu<br>225 230 235 240 |
| Val Leu Glu Asn Cys Glu Leu Pro His Ala Asn Tyr Gly His Val Ile<br>245 250 255 |
| Leu Ala Asp Pro Ser Pro Ile Leu Phe Tyr Pro Ile Ser Ser Thr Glu<br>260 265 270 |
| Val Arg Cys Leu Val Asp Val Pro Gly Gln Lys Val Pro Ser Ile Ser<br>275 280 285 |
| Asn Gly Glu Met Ala Asn Tyr Leu Lys Ser Val Val Ala Pro Gln Ile<br>290 295 300 |
| Pro Pro Gln Ile Tyr Asp Ala Leu Arg Ser Cys Tyr Asp Lys Gly Asn<br>305 310 315 320 |
| Ile Arg Thr Met Pro Asn Arg Ser Met Pro Ala Asp Pro Tyr Pro Thr<br>325 330 335 |
| Pro Gly Ala Leu Leu Met Gly Asp Ala Phe Asn Met Arg His Pro Leu<br>340 345 350 |
| Thr Gly Gly Gly Met Thr Val Ala Leu Ser Asp Ile Val Val Leu Arg<br>355 360 365 |
| Asp Leu Leu Lys Pro Leu Arg Asp Leu His Asp Ala Pro Ile Leu Ser<br>370 375 380 |
| Asn Tyr Leu Glu Ala Phe Tyr Thr Leu Arg Lys Pro Val Ala Ser Thr<br>385 390 395 400 |
| Ile Asn Thr Leu Ala Gly Ala Leu Tyr Lys Val Phe Cys Ala Ser Pro<br>405 410 415 |
| Asp Gln Ala Arg Arg Glu Met Arg Gln Ala Cys Phe Asp Tyr Leu Ser<br>420 425 430 |
| Leu Gly Gly Val Phe Ser Asn Gly Pro Val Ser Leu Leu Ser Gly Leu<br>435 440 445 |
| Asn Pro Arg Pro Leu Ser Leu Val Leu His Phe Phe Ala Val Ala Ile<br>450 455 460 |
| Tyr Gly Val Gly Arg Leu Leu Ile Pro Phe Pro Ser Pro Arg Arg Val<br>465 470 475 480 |
| Trp Ile Gly Ala Arg Leu Ile Ser Gly Ala Ser Gly Ile Ile Phe Pro<br>485 490 495 |

TABLE 3-continued

Sequences disclosed herein (see also Table 2).

```
Ile Ile Lys Ala Glu Gly Val Arg Gln Ile Phe Phe Pro Ala Thr Leu
            500                 505                 510

Pro Ala Tyr Tyr Arg Ala Pro Pro Leu Val Arg Gly Arg
        515                 520                 525
```

SEQ ID NO: 89
*Arabidopsis thaliana* Squalene epoxidase 1 protein sequence

```
Met Glu Ser Gln Leu Trp Asn Trp Ile Leu Pro Leu Leu Ile Ser Ser
1               5                   10                  15

Leu Leu Ile Ser Phe Val Ala Phe Tyr Gly Phe Phe Val Lys Pro Lys
            20                  25                  30

Arg Asn Gly Leu Arg His Asp Arg Lys Thr Val Ser Thr Val Thr Ser
        35                  40                  45

Asp Val Gly Ser Val Asn Ile Thr Gly Asp Thr Val Ala Asp Val Ile
    50                  55                  60

Val Val Gly Ala Gly Val Ala Gly Ser Ala Leu Ala Tyr Thr Leu Gly
65                  70                  75                  80

Lys Asp Lys Arg Arg Val His Val Ile Glu Arg Asp Leu Ser Glu Pro
                85                  90                  95

Asp Arg Ile Val Gly Glu Leu Leu Gln Pro Gly Gly Tyr Leu Lys Leu
            100                 105                 110

Leu Glu Leu Gly Ile Glu Asp Cys Val Glu Glu Ile Asp Ala Gln Arg
        115                 120                 125

Val Tyr Gly Tyr Ala Leu Phe Lys Asn Gly Lys Arg Ile Arg Leu Ala
    130                 135                 140

Tyr Pro Leu Glu Lys Phe His Glu Asp Val Ser Gly Arg Ser Phe His
145                 150                 155                 160

Asn Gly Arg Phe Ile Gln Arg Met Arg Glu Lys Ala Ala Ser Leu Pro
                165                 170                 175

Asn Val Gln Leu Glu Gln Gly Thr Val Leu Ser Leu Leu Glu Glu Asn
            180                 185                 190

Gly Thr Ile Lys Gly Val Arg Tyr Lys Asn Lys Ala Gly Glu Glu Gln
        195                 200                 205

Thr Ala Phe Ala Ala Leu Thr Ile Val Cys Asp Gly Cys Phe Ser Asn
    210                 215                 220

Leu Arg Arg Ser Leu Cys Asn Pro Gln Val Glu Val Pro Ser Cys Phe
225                 230                 235                 240

Val Gly Leu Val Leu Glu Asn Cys Asn Leu Pro Tyr Ala Asn His Gly
                245                 250                 255

His Val Val Leu Ala Asp Pro Ser Pro Ile Leu Met Tyr Pro Ile Ser
            260                 265                 270

Ser Thr Glu Val Arg Cys Leu Val Asp Val Pro Gly Gln Lys Val Pro
        275                 280                 285

Ser Ile Ala Asn Gly Glu Met Lys Asn Tyr Leu Lys Thr Val Val Ala
    290                 295                 300

Pro Gln Met Pro His Glu Val Tyr Asp Ser Phe Ile Ala Ala Val Asp
305                 310                 315                 320

Lys Gly Asn Ile Lys Ser Met Pro Asn Arg Ser Met Pro Ala Ser Pro
                325                 330                 335

Tyr Pro Thr Pro Gly Ala Leu Leu Met Gly Asp Ala Phe Asn Met Arg
            340                 345                 350

His Pro Leu Thr Gly Gly Gly Met Thr Val Ala Leu Ala Asp Ile Val
        355                 360                 365

Val Leu Arg Asn Leu Leu Arg Pro Leu Arg Asp Leu Ser Asp Gly Ala
```

TABLE 3-continued

Sequences disclosed herein (see also Table 2).

```
    370                 375                 380

Ser Leu Cys Lys Tyr Leu Glu Ser Phe Tyr Thr Leu Arg Lys Pro Val
385                 390                 395                 400

Ala Ala Thr Ile Asn Thr Leu Ala Asn Ala Leu Tyr Gln Val Phe Cys
                405                 410                 415

Ser Ser Glu Asn Glu Ala Arg Asn Glu Met Arg Glu Ala Cys Phe Asp
            420                 425                 430

Tyr Leu Gly Leu Gly Gly Met Cys Thr Ser Gly Pro Val Ser Leu Leu
        435                 440                 445

Ser Gly Leu Asn Pro Arg Pro Leu Thr Leu Val Cys His Phe Phe Ala
    450                 455                 460

Val Ala Val Tyr Gly Val Ile Arg Leu Leu Ile Pro Phe Pro Ser Pro
465                 470                 475                 480

Lys Arg Ile Trp Leu Gly Ala Lys Leu Ile Ser Gly Ala Ser Gly Ile
                485                 490                 495

Ile Phe Pro Ile Ile Lys Ala Glu Gly Val Arg Gln Met Phe Phe Pro
            500                 505                 510

Ala Thr Val Pro Ala Tyr Tyr Tyr Lys Ala Pro Thr Val Gly Glu Thr
        515                 520                 525

Lys Cys Ser
    530
```

SEQ ID NO: 90

*Arabidopsis thaliana* Squalene epoxidase 4 protein sequence

```
Met Thr Tyr Ala Trp Leu Trp Thr Leu Leu Ala Phe Val Leu Thr Trp
1               5                   10                  15

Met Val Phe His Leu Ile Lys Met Lys Lys Ala Ala Thr Gly Asp Leu
            20                  25                  30

Glu Ala Glu Ala Glu Ala Arg Arg Asp Gly Ala Thr Asp Val Ile Ile
        35                  40                  45

Val Gly Ala Gly Val Ala Gly Ala Ser Leu Ala Tyr Ala Leu Ala Lys
    50                  55                  60

Asp Gly Arg Arg Val His Val Ile Glu Arg Asp Leu Lys Glu Pro Gln
65                  70                  75                  80

Arg Phe Met Gly Glu Leu Met Gln Ala Gly Gly Arg Phe Met Leu Ala
                85                  90                  95

Gln Leu Gly Leu Glu Asp Cys Leu Glu Asp Ile Asp Ala Gln Glu Ala
            100                 105                 110

Lys Ser Leu Ala Ile Tyr Lys Asp Gly Lys His Ala Thr Leu Pro Phe
        115                 120                 125

Pro Asp Asp Lys Ser Phe Pro His Glu Pro Val Gly Arg Leu Leu Arg
    130                 135                 140

Asn Gly Arg Leu Val Gln Arg Leu Arg Gln Lys Ala Ala Ser Leu Ser
145                 150                 155                 160

Asn Val Gln Leu Glu Glu Gly Thr Val Lys Ser Leu Ile Glu Glu Glu
                165                 170                 175

Gly Val Val Lys Gly Val Thr Tyr Lys Asn Ser Ala Gly Glu Glu Ile
            180                 185                 190

Thr Ala Phe Ala Pro Leu Thr Val Val Cys Asp Gly Cys Tyr Ser Asn
        195                 200                 205

Leu Arg Arg Ser Leu Val Asp Asn Thr Glu Glu Val Leu Ser Tyr Met
    210                 215                 220

Val Gly Tyr Val Thr Lys Asn Ser Arg Leu Glu Asp Pro His Ser Leu
225                 230                 235                 240
```

TABLE 3-continued

Sequences disclosed herein (see also Table 2).

```
His Leu Ile Phe Ser Lys Pro Leu Val Cys Val Ile Tyr Gln Ile Thr
                245                 250                 255

Ser Asp Glu Val Arg Cys Val Ala Glu Val Pro Ala Asp Ser Ile Pro
            260                 265                 270

Ser Ile Ser Asn Gly Glu Met Ser Thr Phe Leu Lys Lys Ser Met Ala
        275                 280                 285

Pro Gln Ile Pro Glu Thr Gly Asn Leu Arg Glu Ile Phe Leu Lys Gly
    290                 295                 300

Ile Glu Glu Gly Leu Pro Glu Ile Lys Ser Thr Ala Thr Lys Ser Met
305                 310                 315                 320

Ser Ser Arg Leu Cys Asp Lys Arg Gly Val Ile Val Leu Gly Asp Ala
                325                 330                 335

Phe Asn Met Arg His Pro Ile Ile Ala Ser Gly Met Met Val Ala Leu
            340                 345                 350

Ser Asp Ile Cys Ile Leu Arg Asn Leu Leu Lys Pro Leu Pro Asn Leu
        355                 360                 365

Ser Asn Thr Lys Lys Val Ser Asp Leu Val Lys Ser Phe Tyr Ile Ile
    370                 375                 380

Arg Lys Pro Met Ser Ala Thr Val Asn Thr Leu Ala Ser Ile Phe Ser
385                 390                 395                 400

Gln Val Leu Val Ala Thr Thr Asp Glu Ala Arg Glu Gly Met Arg Gln
                405                 410                 415

Gly Cys Phe Asn Tyr Leu Ala Arg Gly Asp Phe Lys Thr Arg Gly Leu
            420                 425                 430

Met Thr Ile Leu Gly Gly Met Asn Pro His Pro Leu Thr Leu Val Leu
        435                 440                 445

His Leu Val Ala Ile Thr Leu Thr Ser Met Gly His Leu Leu Ser Pro
    450                 455                 460

Phe Pro Ser Pro Arg Arg Phe Trp His Ser Leu Arg Ile Leu Ala Trp
465                 470                 475                 480

Ala Leu Gln Met Leu Gly Ala His Leu Val Asp Glu Gly Phe Lys Glu
                485                 490                 495

Met Leu Ile Pro Thr Asn Ala Ala Ala Tyr Arg Arg Asn Tyr Ile Ala
            500                 505                 510

Thr Thr Thr Val
        515
```

SEQ ID NO: 91

*Arabidopsis thaliana* Squalene epoxidase 6 protein sequence

```
Met Ala Phe Thr His Val Cys Leu Trp Thr Leu Val Ala Phe Val Leu
1               5                   10                  15

Thr Trp Thr Val Phe Tyr Leu Thr Asn Met Lys Lys Lys Ala Thr Asp
            20                  25                  30

Leu Ala Asp Thr Val Ala Glu Asp Gln Lys Asp Gly Ala Ala Asp Val
        35                  40                  45

Ile Ile Val Gly Ala Gly Val Gly Gly Ser Ala Leu Ala Tyr Ala Leu
    50                  55                  60

Ala Lys Asp Gly Arg Arg Val His Val Ile Glu Arg Asp Met Arg Glu
65                  70                  75                  80

Pro Glu Arg Met Met Gly Glu Phe Met Gln Pro Gly Gly Arg Leu Met
                85                  90                  95

Leu Ser Lys Leu Gly Leu Gln Asp Cys Leu Glu Asp Ile Asp Ala Gln
            100                 105                 110
```

TABLE 3-continued

Sequences disclosed herein (see also Table 2).

```
Lys Ala Thr Gly Leu Ala Val Tyr Lys Asp Gly Lys Glu Ala Asp Ala
        115                 120                 125

Pro Phe Pro Val Asp Asn Asn Asn Phe Ser Tyr Glu Pro Ser Ala Arg
    130                 135                 140

Ser Phe His Asn Gly Arg Phe Val Gln Gln Leu Arg Arg Lys Ala Phe
145                 150                 155                 160

Ser Leu Ser Asn Val Arg Leu Glu Glu Gly Thr Val Lys Ser Leu Leu
                165                 170                 175

Glu Glu Lys Gly Val Val Lys Gly Val Thr Tyr Lys Asn Lys Glu Gly
            180                 185                 190

Glu Glu Thr Thr Ala Leu Ala Pro Leu Thr Val Val Cys Asp Gly Cys
        195                 200                 205

Tyr Ser Asn Leu Arg Arg Ser Leu Asn Asp Asp Asn Asn Ala Glu Ile
    210                 215                 220

Met Ser Tyr Ile Val Gly Tyr Ile Ser Lys Asn Cys Arg Leu Glu Glu
225                 230                 235                 240

Pro Glu Lys Leu His Leu Ile Leu Ser Lys Pro Ser Phe Thr Met Val
                245                 250                 255

Tyr Gln Ile Ser Ser Thr Asp Val Arg Cys Gly Phe Glu Val Leu Pro
            260                 265                 270

Glu Asn Phe Pro Ser Ile Ala Asn Gly Glu Met Ser Thr Phe Met Lys
        275                 280                 285

Asn Thr Ile Val Pro Gln Val Pro Pro Lys Leu Arg Lys Ile Phe Leu
    290                 295                 300

Lys Gly Ile Asp Glu Gly Ala His Ile Lys Val Val Pro Ala Lys Arg
305                 310                 315                 320

Met Thr Ser Thr Leu Ser Lys Lys Lys Gly Val Ile Val Leu Gly Asp
                325                 330                 335

Ala Phe Asn Met Arg His Pro Val Val Ala Ser Gly Met Met Val Leu
            340                 345                 350

Leu Ser Asp Ile Leu Ile Leu Arg Arg Leu Leu Gln Pro Leu Ser Asn
        355                 360                 365

Leu Gly Asp Ala Asn Lys Val Ser Glu Val Ile Asn Ser Phe Tyr Asp
    370                 375                 380

Ile Arg Lys Pro Met Ser Ala Thr Val Asn Thr Leu Gly Asn Ala Phe
385                 390                 395                 400

Ser Gln Val Leu Ile Gly Ser Thr Asp Glu Ala Lys Glu Ala Met Arg
                405                 410                 415

Gln Gly Val Tyr Asp Tyr Leu Cys Ser Gly Gly Phe Arg Thr Ser Gly
            420                 425                 430

Met Met Ala Leu Leu Gly Gly Met Asn Pro Arg Pro Leu Ser Leu Val
        435                 440                 445

Tyr His Leu Cys Ala Ile Thr Leu Ser Ser Ile Gly Gln Leu Leu Ser
    450                 455                 460

Pro Phe Pro Ser Pro Leu Arg Ile Trp His Ser Leu Lys Leu Phe Gly
465                 470                 475                 480

Leu Ala Met Lys Met Leu Val Pro Asn Leu Lys Ala Glu Gly Val Ser
                485                 490                 495

Gln Met Leu Phe Pro Ala Asn Ala Ala Ala Tyr His Lys Ser Tyr Met
            500                 505                 510

Ala Ala Thr Thr Leu
        515
```

TABLE 3-continued

Sequences disclosed herein (see also Table 2).

SEQ ID NO: 92
*Arabidopsis thaliana* Squalene epoxidase 5 protein sequence

```
Met Ala Phe Thr Asn Val Cys Leu Trp Thr Leu Leu Ala Phe Met Leu
1               5                   10                  15

Thr Trp Thr Val Phe Tyr Val Thr Asn Arg Gly Lys Lys Ala Thr Gln
            20                  25                  30

Leu Ala Asp Ala Val Val Glu Glu Arg Glu Asp Gly Ala Thr Asp Val
        35                  40                  45

Ile Ile Val Gly Ala Gly Val Gly Gly Ser Ala Leu Ala Tyr Ala Leu
    50                  55                  60

Ala Lys Asp Gly Arg Arg Val His Val Ile Glu Arg Asp Leu Arg Glu
65                  70                  75                  80

Pro Glu Arg Ile Met Gly Glu Phe Met Gln Pro Gly Gly Arg Leu Met
                85                  90                  95

Leu Ser Lys Leu Gly Leu Glu Asp Cys Leu Glu Gly Ile Asp Ala Gln
            100                 105                 110

Lys Ala Thr Gly Met Thr Val Tyr Lys Asp Gly Lys Glu Ala Val Ala
        115                 120                 125

Ser Phe Pro Val Asp Asn Asn Asn Phe Pro Phe Asp Pro Ser Ala Arg
    130                 135                 140

Ser Phe His Asn Gly Arg Phe Val Gln Arg Leu Arg Gln Lys Ala Ser
145                 150                 155                 160

Ser Leu Pro Asn Val Arg Leu Glu Glu Gly Thr Val Lys Ser Leu Ile
                165                 170                 175

Glu Glu Lys Gly Val Ile Lys Gly Val Thr Tyr Lys Asn Ser Ala Gly
            180                 185                 190

Glu Glu Thr Thr Ala Leu Ala Pro Leu Thr Val Val Cys Asp Gly Cys
        195                 200                 205

Tyr Ser Asn Leu Arg Arg Ser Leu Asn Asp Asn Asn Ala Glu Val Leu
    210                 215                 220

Ser Tyr Gln Val Gly Phe Ile Ser Lys Asn Cys Gln Leu Glu Glu Pro
225                 230                 235                 240

Glu Lys Leu Lys Leu Ile Met Ser Lys Pro Ser Phe Thr Met Leu Tyr
                245                 250                 255

Gln Ile Ser Ser Thr Asp Val Arg Cys Val Phe Glu Val Leu Pro Asn
            260                 265                 270

Asn Ile Pro Ser Ile Ser Asn Gly Glu Met Ala Thr Phe Val Lys Asn
        275                 280                 285

Thr Ile Ala Pro Gln Val Pro Leu Lys Leu Arg Lys Ile Phe Leu Lys
    290                 295                 300

Gly Ile Asp Glu Gly Glu His Ile Lys Ala Met Pro Thr Lys Lys Met
305                 310                 315                 320

Thr Ala Thr Leu Ser Glu Lys Lys Gly Val Ile Leu Leu Gly Asp Ala
                325                 330                 335

Phe Asn Met Arg His Pro Ala Ile Ala Ser Gly Met Met Val Leu Leu
            340                 345                 350

Ser Asp Ile Leu Ile Leu Arg Arg Leu Leu Gln Pro Leu Ser Asn Leu
        355                 360                 365

Gly Asn Ala Gln Lys Ile Ser Gln Val Ile Lys Ser Phe Tyr Asp Ile
    370                 375                 380

Arg Lys Pro Met Ser Ala Thr Val Asn Thr Leu Gly Asn Ala Phe Ser
385                 390                 395                 400

Gln Val Leu Val Ala Ser Thr Asp Glu Ala Lys Glu Ala Met Arg Gln
```

TABLE 3-continued

Sequences disclosed herein (see also Table 2).

```
                405                 410                 415

Gly Cys Tyr Asp Tyr Leu Ser Ser Gly Gly Phe Arg Thr Ser Gly Met
            420                 425                 430

Met Ala Leu Leu Gly Gly Met Asn Pro Arg Pro Ile Ser Leu Ile Tyr
        435                 440                 445

His Leu Cys Ala Ile Thr Leu Ser Ser Ile Gly His Leu Leu Ser Pro
    450                 455                 460

Phe Pro Ser Pro Leu Arg Ile Trp His Ser Leu Arg Leu Phe Gly Leu
465                 470                 475                 480

Ala Met Lys Met Leu Val Pro His Leu Lys Ala Glu Gly Val Ser Gln
                485                 490                 495

Met Leu Phe Pro Val Asn Ala Ala Ala Tyr Ser Lys Ser Tyr Met Ala
            500                 505                 510

Ala Thr Ala Leu
        515
```

SEQ ID NO: 93
*Arabidopsis thaliana* Squalene epoxidase 2 protein sequence

```
Met Lys Pro Phe Val Ile Arg Asn Leu Pro Arg Phe Gln Ser Thr Leu
1               5                   10                  15

Arg Ser Ser Leu Leu Tyr Thr Asn His Arg Pro Ser Ser Arg Phe Ser
            20                  25                  30

Leu Ser Thr Arg Arg Phe Thr Thr Gly Ala Thr Tyr Ile Arg Arg Trp
        35                  40                  45

Lys Ala Thr Ala Ala Gln Thr Leu Lys Leu Ser Ala Val Asn Ser Thr
    50                  55                  60

Val Met Met Lys Pro Ala Lys Ile Ala Leu Asp Gln Phe Ile Ala Ser
65                  70                  75                  80

Leu Phe Thr Phe Leu Leu Leu Tyr Ile Leu Arg Arg Ser Ser Asn Lys
                85                  90                  95

Asn Lys Lys Asn Arg Gly Leu Val Val Ser Gln Asn Asp Thr Val Ser
            100                 105                 110

Lys Asn Leu Glu Thr Glu Val Asp Ser Gly Thr Asp Val Ile Ile Val
        115                 120                 125

Gly Ala Gly Val Ala Gly Ser Ala Leu Ala His Thr Leu Gly Lys Glu
    130                 135                 140

Gly Arg Arg Val His Val Ile Glu Arg Asp Phe Ser Glu Gln Asp Arg
145                 150                 155                 160

Ile Val Gly Glu Leu Leu Gln Pro Gly Gly Tyr Leu Lys Leu Ile Glu
                165                 170                 175

Leu Gly Leu Glu Asp Cys Val Lys Lys Ile Asp Ala Gln Arg Val Leu
            180                 185                 190

Gly Tyr Val Leu Phe Lys Asp Gly Lys His Thr Lys Leu Ala Tyr Pro
        195                 200                 205

Leu Glu Thr Phe Asp Ser Asp Val Ala Gly Arg Ser Phe His Asn Gly
    210                 215                 220

Arg Phe Val Gln Arg Met Arg Glu Lys Ala Leu Thr Leu Ser Asn Val
225                 230                 235                 240

Arg Leu Glu Gln Gly Thr Val Thr Ser Leu Leu Glu Glu His Gly Thr
                245                 250                 255

Ile Lys Gly Val Arg Tyr Arg Thr Lys Glu Gly Asn Glu Phe Arg Ser
            260                 265                 270

Phe Ala Pro Leu Thr Ile Val Cys Asp Gly Cys Phe Ser Asn Leu Arg
        275                 280                 285
```

TABLE 3-continued

Sequences disclosed herein (see also Table 2).

Arg Ser Leu Cys Lys Pro Lys Val Asp Val Pro Ser Thr Phe Val Gly
290 295 300

Leu Val Leu Glu Asn Cys Glu Leu Pro Phe Ala Asn His Gly His Val
305 310 315 320

Val Leu Gly Asp Pro Ser Pro Ile Leu Met Tyr Pro Ile Ser Ser Ser
325 330 335

Glu Val Arg Cys Leu Val Asp Val Pro Gly Gln Lys Leu Pro Pro Ile
340 345 350

Ala Asn Gly Glu Met Ala Lys Tyr Leu Lys Thr Arg Val Ala Pro Gln
355 360 365

Val Pro Thr Lys Val Arg Glu Ala Phe Ile Thr Ala Val Glu Lys Gly
370 375 380

Asn Ile Arg Thr Met Pro Asn Arg Ser Met Pro Ala Asp Pro Ile Pro
385 390 395 400

Thr Pro Gly Ala Leu Leu Leu Gly Asp Ala Phe Asn Met Arg His Pro
405 410 415

Leu Thr Gly Gly Gly Met Thr Val Ala Leu Ala Asp Ile Val Val Leu
420 425 430

Arg Asp Leu Leu Arg Pro Ile Arg Asn Leu Asn Asp Lys Glu Ala Leu
435 440 445

Ser Lys Tyr Ile Glu Ser Phe Tyr Thr Leu Arg Lys Pro Val Ala Ser
450 455 460

Thr Ile Asn Thr Leu Ala Asp Ala Leu Tyr Lys Val Phe Leu Ala Ser
465 470 475 480

Ser Asp Glu Ala Arg Thr Glu Met Arg Glu Ala Cys Phe Asp Tyr Leu
485 490 495

Ser Leu Gly Gly Val Phe Ser Ser Gly Pro Val Ala Leu Leu Ser Gly
500 505 510

Leu Asn Pro Arg Pro Leu Ser Leu Val Leu His Phe Phe Ala Val Ala
515 520 525

Ile Tyr Ala Val Cys Arg Leu Met Leu Pro Phe Pro Ser Ile Glu Ser
530 535 540

Phe Trp Leu Gly Ala Arg Ile Ile Ser Ser Ala Ser Ser Ile Ile Phe
545 550 555 560

Pro Ile Ile Lys Ala Glu Gly Val Arg Gln Met Phe Phe Pro Arg Thr
565 570 575

Ile Pro Ala Ile Tyr Arg Ala Pro Pro
580 585

SEQ ID NO: 94
*Arabidopsis thaliana* Squalene epoxidase 3 protein sequence
Met Ala Pro Thr Ile Phe Val Asp His Cys Ile Leu Thr Thr Thr Phe
1 5 10 15

Val Ala Ser Leu Phe Ala Phe Leu Leu Leu Tyr Val Leu Arg Arg Arg
20 25 30

Ser Lys Thr Ile His Gly Ser Val Asn Val Arg Asn Gly Thr Leu Thr
35 40 45

Val Lys Ser Gly Thr Asp Val Asp Ile Ile Ile Val Gly Ala Gly Val
50 55 60

Ala Gly Ala Ala Leu Ala His Thr Leu Gly Lys Glu Gly Arg Arg Val
65 70 75 80

His Val Ile Glu Arg Asp Leu Thr Glu Pro Asp Arg Ile Val Gly Glu
85 90 95

TABLE 3-continued

| Sequences disclosed herein (see also Table 2). |
|---|
| Leu Leu Gln Pro Gly Gly Tyr Leu Lys Leu Ile Glu Leu Gly Leu Glu<br>100 105 110 |
| Asp Cys Val Lys Asp Ile Asp Ala Gln Arg Val Leu Gly Tyr Ala Leu<br>115 120 125 |
| Phe Lys Asp Gly Lys His Thr Lys Leu Ser Tyr Pro Leu Asp Gln Phe<br>130 135 140 |
| Asp Ser Asp Val Ala Gly Arg Ser Phe His Asn Gly Arg Phe Val Gln<br>145 150 155 160 |
| Arg Met Arg Glu Lys Ala Ser Leu Leu Pro Asn Val Arg Met Glu Gln<br>165 170 175 |
| Gly Thr Val Thr Ser Leu Val Glu Glu Asn Gly Ile Ile Lys Gly Val<br>180 185 190 |
| Gln Tyr Lys Thr Lys Asp Gly Gln Glu Leu Lys Ser Phe Ala Pro Leu<br>195 200 205 |
| Thr Ile Val Cys Asp Gly Cys Phe Ser Asn Leu Arg Arg Ser Leu Cys<br>210 215 220 |
| Lys Pro Lys Val Glu Val Pro Ser Asn Phe Val Gly Leu Val Leu Glu<br>225 230 235 240 |
| Asn Cys Glu Leu Pro Phe Pro Asn His Gly His Val Val Leu Gly Asp<br>245 250 255 |
| Pro Ser Pro Ile Leu Phe Tyr Pro Ile Ser Ser Ser Glu Val Arg Cys<br>260 265 270 |
| Leu Val Asp Val Pro Gly Ser Lys Leu Pro Ser Val Ala Ser Gly Glu<br>275 280 285 |
| Met Ala His His Leu Lys Thr Met Val Ala Pro Gln Val Pro Pro Gln<br>290 295 300 |
| Ile Arg Asp Ala Phe Ile Ser Ala Val Glu Lys Gly Asn Ile Arg Thr<br>305 310 315 320 |
| Met Pro Asn Arg Ser Met Pro Ala Asp Pro Ile His Thr Pro Gly Ala<br>325 330 335 |
| Leu Leu Leu Gly Asp Ala Phe Asn Met Arg His Pro Leu Thr Gly Gly<br>340 345 350 |
| Gly Met Thr Val Ala Leu Ser Asp Ile Val Ile Leu Arg Asp Leu Leu<br>355 360 365 |
| Asn Pro Leu Val Asp Leu Thr Asn Lys Glu Ser Leu Ser Lys Tyr Ile<br>370 375 380 |
| Glu Ser Phe Tyr Thr Leu Arg Lys Pro Val Ala Ser Thr Ile Asn Thr<br>385 390 395 400 |
| Leu Ala Gly Ala Leu Tyr Lys Val Phe Leu Ala Ser Pro Asp Asp Ala<br>405 410 415 |
| Arg Ser Glu Met Arg Arg Ala Cys Phe Asp Tyr Leu Ser Leu Gly Gly<br>420 425 430 |
| Val Cys Ser Ser Gly Pro Val Ala Leu Leu Ser Gly Leu Asn Pro Arg<br>435 440 445 |
| Pro Met Ser Leu Val Leu His Phe Phe Ala Val Ala Ile Phe Gly Val<br>450 455 460 |
| Gly Arg Leu Leu Val Pro Leu Pro Ser Val Lys Arg Leu Trp Leu Gly<br>465 470 475 480 |
| Ala Arg Leu Ile Ser Ser Ala Ser Gly Ile Ile Phe Pro Ile Ile Lys<br>485 490 495 |
| Ala Glu Gly Val Arg Gln Met Phe Phe Pro Arg Thr Ile Pro Ala Ile<br>500 505 510 |

TABLE 3-continued

Sequences disclosed herein (see also Table 2).

Tyr Arg Ala Pro Pro Thr Pro Ser Ser Ser Ser Pro Gln
515 520 525

SEQ ID NO: 95
*Brassica napus* Squalene monooxygenase 1,1 protein sequence
Met Asp Leu Ala Phe Pro His Val Cys Leu Trp Thr Leu Leu Ala Phe
1 5 10 15

Val Leu Thr Trp Thr Val Phe Tyr Val Asn Asn Arg Arg Lys Lys Val
20 25 30

Ala Lys Leu Pro Asp Ala Ala Thr Glu Val Arg Arg Asp Gly Asp Ala
35 40 45

Asp Val Ile Ile Val Gly Ala Gly Val Gly Gly Ser Ala Leu Ala Tyr
50 55 60

Ala Leu Ala Lys Asp Gly Arg Arg Val His Val Ile Glu Arg Asp Met
65 70 75 80

Arg Glu Pro Val Arg Met Met Gly Glu Phe Met Gln Pro Gly Gly Arg
85 90 95

Leu Leu Leu Ser Lys Leu Gly Leu Glu Asp Cys Leu Glu Gly Ile Asp
100 105 110

Glu Gln Ile Ala Thr Gly Leu Ala Val Tyr Lys Asp Gly Gln Lys Ala
115 120 125

Leu Val Ser Phe Pro Glu Asp Asn Asp Phe Pro Tyr Glu Pro Thr Gly
130 135 140

Arg Ala Phe Tyr Asn Gly Arg Phe Val Gln Arg Leu Arg Gln Lys Ala
145 150 155 160

Ser Ser Leu Pro Thr Val Gln Leu Glu Glu Gly Thr Val Lys Ser Leu
165 170 175

Ile Glu Glu Lys Gly Val Ile Lys Gly Val Thr Tyr Lys Asn Ser Ala
180 185 190

Gly Glu Glu Thr Thr Ala Phe Ala Pro Leu Thr Val Val Cys Asp Gly
195 200 205

Cys Tyr Ser Asn Leu Arg Arg Ser Val Asn Asp Asn Asn Ala Glu Val
210 215 220

Ile Ser Tyr Gln Val Gly Tyr Val Ser Lys Asn Cys Gln Leu Glu Asp
225 230 235 240

Pro Glu Lys Leu Lys Leu Ile Met Ser Lys Pro Ser Phe Thr Met Leu
245 250 255

Tyr Gln Ile Ser Ser Thr Asp Val Arg Cys Val Met Glu Ile Phe Pro
260 265 270

Gly Asn Ile Pro Ser Ile Ser Asn Gly Glu Met Ala Val Tyr Leu Lys
275 280 285

Asn Thr Met Ala Pro Gln Val Pro Pro Glu Leu Arg Lys Ile Phe Leu
290 295 300

Lys Gly Ile Asp Glu Gly Ala Gln Ile Lys Ala Met Pro Thr Lys Arg
305 310 315 320

Met Glu Ala Thr Leu Ser Glu Lys Gln Gly Val Ile Val Leu Gly Asp
325 330 335

Ala Phe Asn Met Arg His Pro Ala Ile Ala Ser Gly Met Met Val Val
340 345 350

Leu Ser Asp Ile Leu Ile Leu Arg Arg Leu Leu Gln Pro Leu Arg Asn
355 360 365

Leu Ser Asp Ala Asn Lys Val Ser Glu Val Ile Lys Ser Phe Tyr Val
370 375 380

Ile Arg Lys Pro Met Ser Ala Thr Val Asn Thr Leu Gly Asn Ala Phe

TABLE 3-continued

Sequences disclosed herein (see also Table 2).

```
385                 390                 395                 400

Ser Gln Val Leu Ile Ala Ser Thr Asp Glu Ala Lys Glu Ala Met Arg
                405                 410                 415

Gln Gly Cys Phe Asp Tyr Leu Ser Ser Gly Gly Phe Arg Thr Ser Gly
            420                 425                 430

Met Met Ala Leu Leu Gly Gly Met Asn Pro Arg Pro Leu Ser Leu Ile
        435                 440                 445

Phe His Leu Cys Gly Ile Thr Leu Ser Ser Ile Gly Gln Leu Leu Ser
    450                 455                 460

Pro Phe Pro Ser Pro Leu Gly Ile Trp His Ser Leu Arg Leu Phe Gly
465                 470                 475                 480

Ala Glu Gly Val Ser Gln Met Leu Ser Pro Ala Tyr Ala Ala Ala Tyr
                485                 490                 495

Arg Lys Ser Tyr Met Thr Ala Thr Ala Leu
            500                 505
```

SEQ ID NO: 96
*Brassica napus* Squalene monooxygenase 1,2 protein sequence

```
Met Asp Met Ala Phe Val Glu Val Cys Leu Arg Met Leu Leu Val Phe
1               5                   10                  15

Val Leu Ser Trp Thr Ile Phe His Val Asn Asn Arg Lys Lys Lys Lys
            20                  25                  30

Ala Thr Lys Leu Ala Asp Leu Ala Thr Glu Glu Arg Lys Glu Gly Gly
        35                  40                  45

Pro Asp Val Ile Ile Val Gly Ala Gly Val Gly Gly Ser Ala Leu Ala
    50                  55                  60

Tyr Ala Leu Ala Lys Asp Gly Arg Arg Val His Val Ile Glu Arg Asp
65                  70                  75                  80

Met Arg Glu Pro Val Arg Met Met Gly Glu Phe Met Gln Pro Gly Gly
                85                  90                  95

Arg Leu Met Leu Ser Lys Leu Gly Leu Gln Asp Cys Leu Glu Glu Ile
            100                 105                 110

Asp Ala Gln Lys Ser Thr Gly Ile Arg Leu Phe Lys Asp Gly Lys Glu
        115                 120                 125

Thr Val Ala Cys Phe Pro Val Asp Thr Asn Phe Pro Tyr Glu Pro Ser
    130                 135                 140

Gly Arg Phe Phe His Asn Gly Arg Phe Val Gln Arg Leu Arg Gln Lys
145                 150                 155                 160

Ala Ser Ser Leu Pro Asn Val Arg Leu Glu Glu Gly Thr Val Arg Ser
                165                 170                 175

Leu Ile Glu Glu Lys Gly Val Val Lys Gly Val Thr Tyr Lys Asn Ser
            180                 185                 190

Ser Gly Glu Glu Thr Thr Ser Phe Ala Pro Leu Thr Val Val Cys Asp
        195                 200                 205

Gly Cys His Ser Asn Leu Arg Arg Ser Leu Asn Asp Asn Asn Ala Glu
    210                 215                 220

Val Thr Ala Tyr Glu Ile Gly Tyr Ile Ser Arg Asn Cys Arg Leu Glu
225                 230                 235                 240

Gln Pro Asp Lys Leu His Leu Ile Met Ala Lys Pro Ser Phe Ala Met
                245                 250                 255

Leu Tyr Gln Val Ser Ser Thr Asp Val Arg Cys Asn Phe Glu Leu Leu
            260                 265                 270

Ser Lys Asn Leu Pro Ser Val Ser Asn Gly Glu Met Thr Ser Phe Val
        275                 280                 285
```

TABLE 3-continued

Sequences disclosed herein (see also Table 2).

```
Arg Asn Ser Ile Ala Pro Gln Val Pro Leu Lys Leu Arg Lys Thr Phe
    290                 295                 300

Leu Lys Gly Leu Asp Glu Gly Ser His Ile Lys Ile Thr Gln Ala Lys
305                 310                 315                 320

Arg Ile Pro Ala Thr Leu Ser Arg Lys Lys Gly Val Ile Val Leu Gly
                325                 330                 335

Asp Ala Phe Asn Met Arg His Pro Val Ile Ala Ser Gly Met Met Val
            340                 345                 350

Leu Leu Ser Asp Ile Leu Ile Leu Ser Arg Leu Leu Lys Pro Leu Gly
        355                 360                 365

Asn Leu Gly Asp Glu Asn Lys Val Ser Glu Val Met Lys Ser Phe Tyr
    370                 375                 380

Ala Leu Arg Lys Pro Met Ser Ala Thr Val Asn Thr Leu Gly Asn Ser
385                 390                 395                 400

Phe Trp Gln Val Leu Ile Ala Ser Thr Asp Glu Ala Lys Glu Ala Met
                405                 410                 415

Arg Gln Gly Cys Phe Asp Tyr Leu Ser Ser Gly Gly Phe Arg Thr Ser
            420                 425                 430

Gly Leu Met Ala Leu Ile Gly Gly Met Asn Pro Arg Pro Leu Ser Leu
        435                 440                 445

Phe Tyr His Leu Phe Val Ile Ser Leu Ser Ser Ile Gly Gln Leu Leu
    450                 455                 460

Ser Pro Phe Pro Thr Pro Leu Arg Val Trp His Ser Leu Arg Leu Leu
465                 470                 475                 480

Asp Leu Ser Leu Lys Met Leu Val Pro His Leu Lys Ala Glu Gly Ile
                485                 490                 495

Gly Gln Met Leu Ser Pro Thr Asn Ala Ala Ala Tyr Arg Lys Ser Tyr
            500                 505                 510

Met Ala Ala Thr Val Val
        515
```

SEQ ID NO: 97
*Euphorbia tirucalli* Squalene epoxidase protein sequence

```
Met Glu Val Ile Phe Asp Thr Tyr Ile Phe Gly Thr Phe Phe Ala Ser
1               5                   10                  15

Leu Cys Ala Phe Leu Leu Leu Phe Ile Leu Arg Pro Lys Val Lys Lys
            20                  25                  30

Met Gly Lys Ile Arg Glu Ile Ser Ser Ile Asn Thr Gln Asn Asp Thr
        35                  40                  45

Ala Ile Thr Pro Pro Lys Gly Ser Gly Thr Asp Val Ile Ile Val Gly
    50                  55                  60

Ala Gly Val Ala Gly Ala Ala Leu Ala Cys Thr Leu Gly Lys Asp Gly
65                  70                  75                  80

Arg Arg Val His Val Ile Glu Arg Asp Leu Lys Glu Pro Asp Arg Ile
                85                  90                  95

Val Gly Glu Leu Leu Gln Pro Gly Gly Tyr Leu Lys Leu Val Glu Leu
            100                 105                 110

Gly Leu Gln Asp Cys Val Glu Glu Ile Asp Ala Gln Arg Ile Val Gly
        115                 120                 125

Tyr Ala Leu Phe Met Asp Gly Asn Asn Thr Lys Leu Ser Tyr Pro Leu
    130                 135                 140

Glu Lys Phe Asp Ala Glu Val Ser Gly Lys Ser Phe His Asn Gly Arg
145                 150                 155                 160
```

TABLE 3-continued

Sequences disclosed herein (see also Table 2).

```
Phe Ile Gln Arg Met Arg Glu Lys Ala Ala Ser Leu Pro Asn Val Gln
                165                 170                 175

Leu Glu Gln Gly Thr Val Thr Ser Leu Leu Glu Glu Asn Gly Thr Ile
            180                 185                 190

Lys Gly Val Gln Tyr Lys Thr Lys Asp Gly Gln Glu His Lys Ala Tyr
        195                 200                 205

Ala Pro Leu Thr Val Val Cys Asp Gly Cys Phe Ser Asn Leu Arg Arg
    210                 215                 220

Ser Leu Cys Lys Pro Lys Val Asp Val Pro Ser His Phe Val Gly Leu
225                 230                 235                 240

Val Leu Glu Asn Cys Asp Leu Pro Phe Ala Asn His Gly His Val Ile
                245                 250                 255

Leu Ala Asp Pro Ser Pro Ile Leu Phe Tyr Pro Ile Ser Ser Thr Glu
            260                 265                 270

Val Arg Cys Leu Val Asp Val Pro Gly Gln Lys Leu Pro Ser Ile Ala
        275                 280                 285

Ser Gly Glu Met Ala Lys Tyr Leu Lys Thr Met Val Ala Lys Gln Ile
    290                 295                 300

Pro Pro Val Leu His Asp Ala Phe Val Ser Ala Ile Asp Lys Gly Asn
305                 310                 315                 320

Ile Arg Thr Met Pro Asn Arg Ser Met Pro Ala Asp Pro Leu Pro Thr
                325                 330                 335

Pro Gly Ala Leu Leu Met Gly Asp Ala Phe Asn Met Arg His Pro Leu
            340                 345                 350

Thr Gly Gly Gly Met Thr Val Ala Leu Ala Asp Ile Val Leu Leu Arg
        355                 360                 365

Asp Leu Leu Lys Pro Leu Arg Asp Leu Asn Asp Ala Pro Ala Leu Ala
    370                 375                 380

Lys Tyr Leu Glu Ser Phe Tyr Thr Leu Arg Lys Pro Val Ala Ser Thr
385                 390                 395                 400

Ile Asn Thr Leu Ala Gly Ala Leu Tyr Lys Val Phe Ser Ala Ser Pro
                405                 410                 415

Asp Glu Ala Arg Lys Glu Met Arg Gln Ala Cys Phe Asp Tyr Leu Ser
            420                 425                 430

Leu Gly Gly Glu Cys Ala Met Gly Pro Val Ser Leu Leu Ser Gly Leu
        435                 440                 445

Asn Pro Ser Pro Leu Thr Leu Val Leu His Phe Phe Gly Val Ala Ile
    450                 455                 460

Tyr Gly Val Gly Arg Leu Leu Ile Pro Phe Pro Thr Pro Lys Gly Met
465                 470                 475                 480

Trp Ile Gly Ala Arg Ile Ile Ser Ser Ala Ser Gly Ile Ile Phe Pro
                485                 490                 495

Ile Ile Lys Ala Glu Gly Val Arg Gln Val Phe Phe Pro Ala Thr Val
            500                 505                 510

Pro Ala Ile Tyr Arg Asn Pro Pro Val Asn Gly Lys Ser Val Glu Val
        515                 520                 525

Pro Lys Ser
    530
```

SEQ ID NO: 98
*Medicago truncatula* Squalene epoxidase protein sequence

```
Met Ile Asp Pro Tyr Gly Phe Gly Trp Ile Thr Cys Thr Leu Ile Thr
1               5                   10                  15

Leu Ala Ala Leu Tyr Asn Phe Leu Phe Ser Arg Lys Asn His Ser Asp
```

TABLE 3-continued

Sequences disclosed herein (see also Table 2).

```
            20                  25                  30

Ser Thr Thr Thr Glu Asn Ile Thr Thr Ala Thr Gly Glu Cys Arg Ser
        35                  40                  45

Phe Asn Pro Asn Gly Asp Val Asp Ile Ile Ile Val Gly Ala Gly Val
    50                  55                  60

Ala Gly Ser Ala Leu Ala Tyr Thr Leu Gly Lys Asp Gly Arg Arg Val
65                  70                  75                  80

Leu Ile Ile Glu Arg Asp Leu Asn Glu Pro Asp Arg Ile Val Gly Glu
                85                  90                  95

Leu Leu Gln Pro Gly Gly Tyr Leu Lys Leu Ile Glu Leu Gly Leu Asp
            100                 105                 110

Asp Cys Val Glu Lys Ile Asp Ala Gln Lys Val Phe Gly Tyr Ala Leu
        115                 120                 125

Phe Lys Asp Gly Lys His Thr Arg Leu Ser Tyr Pro Leu Glu Lys Phe
    130                 135                 140

His Ser Asp Ile Ala Gly Arg Ser Phe His Asn Gly Arg Phe Ile Leu
145                 150                 155                 160

Arg Met Arg Glu Lys Ala Ala Ser Leu Pro Asn Val Arg Leu Glu Gln
                165                 170                 175

Gly Thr Val Thr Ser Leu Leu Glu Glu Asn Gly Thr Ile Lys Gly Val
            180                 185                 190

Gln Tyr Lys Thr Lys Asp Ala Gln Glu Phe Ser Ala Cys Ala Pro Leu
        195                 200                 205

Thr Ile Val Cys Asp Gly Cys Phe Ser Asn Leu Arg Arg Ser Leu Cys
    210                 215                 220

Asn Pro Lys Val Glu Val Pro Ser Cys Phe Val Gly Leu Val Leu Glu
225                 230                 235                 240

Asn Cys Glu Leu Pro Cys Ala Asp His Gly His Val Ile Leu Gly Asp
                245                 250                 255

Pro Ser Pro Val Leu Phe Tyr Pro Ile Ser Ser Thr Glu Ile Arg Cys
            260                 265                 270

Leu Val Asp Val Pro Gly Gln Lys Val Pro Ser Ile Ser Asn Gly Glu
        275                 280                 285

Met Ala Lys Tyr Leu Lys Thr Val Val Ala Pro Gln Val Pro Pro Glu
    290                 295                 300

Leu His Ala Ala Phe Ile Ala Ala Val Asp Lys Gly His Ile Arg Thr
305                 310                 315                 320

Met Pro Asn Arg Ser Met Pro Ala Asp Pro Tyr Pro Thr Pro Gly Ala
                325                 330                 335

Leu Leu Met Gly Asp Ala Phe Asn Met Arg His Pro Leu Thr Gly Gly
            340                 345                 350

Gly Met Thr Val Ala Leu Ser Asp Ile Val Val Leu Arg Asn Leu Leu
        355                 360                 365

Lys Pro Leu Arg Asp Leu Asn Asp Ala Ser Ser Leu Cys Lys Tyr Leu
    370                 375                 380

Glu Ser Phe Tyr Thr Leu Arg Lys Pro Val Ala Ser Thr Ile Asn Thr
385                 390                 395                 400

Leu Ala Gly Ala Leu Tyr Lys Val Phe Cys Ala Ser Pro Asp Pro Ala
                405                 410                 415

Arg Lys Glu Met Arg Gln Ala Cys Phe Asp Tyr Leu Ser Leu Gly Gly
            420                 425                 430

Leu Phe Ser Glu Gly Pro Val Ser Leu Leu Ser Gly Leu Asn Pro Cys
```

TABLE 3-continued

Sequences disclosed herein (see also Table 2).

```
        435                 440                 445

Pro Leu Ser Leu Val Leu His Phe Phe Ala Val Ala Ile Tyr Gly Val
    450                 455                 460

Gly Arg Leu Leu Leu Pro Phe Pro Ser Pro Lys Arg Leu Trp Ile Gly
465                 470                 475                 480

Ile Arg Leu Ile Ala Ser Ala Ser Gly Ile Ile Leu Pro Ile Ile Lys
                485                 490                 495

Ala Glu Gly Ile Arg Gln Met Phe Phe Pro Ala Thr Val Pro Ala Tyr
            500                 505                 510

Tyr Arg Ala Pro Pro Asp Ala
        515
```

SEQ ID NO: 99
*Medicago truncatula* Squalene monooxygenase protein sequence

```
Met Asp Leu Tyr Asn Ile Gly Trp Ile Leu Ser Ser Val Leu Ser Leu
1               5                   10                  15

Phe Ala Leu Tyr Asn Leu Ile Phe Ala Gly Lys Lys Asn Tyr Asp Val
            20                  25                  30

Asn Glu Lys Val Asn Gln Arg Glu Asp Ser Val Thr Ser Thr Asp Ala
        35                  40                  45

Gly Glu Ile Lys Ser Asp Lys Leu Asn Gly Asp Ala Asp Val Ile Ile
    50                  55                  60

Val Gly Ala Gly Ile Ala Gly Ala Ala Leu Ala His Thr Leu Gly Lys
65                  70                  75                  80

Asp Gly Arg Arg Val His Ile Ile Glu Arg Asp Leu Ser Glu Pro Asp
                85                  90                  95

Arg Ile Val Gly Glu Leu Leu Gln Pro Gly Gly Tyr Leu Lys Leu Val
            100                 105                 110

Glu Leu Gly Leu Gln Asp Cys Val Asp Asn Ile Asp Ala Gln Arg Val
        115                 120                 125

Phe Gly Tyr Ala Leu Phe Lys Asp Gly Lys His Thr Arg Leu Ser Tyr
    130                 135                 140

Pro Leu Glu Lys Phe His Ser Asp Val Ser Gly Arg Ser Phe His Asn
145                 150                 155                 160

Gly Arg Phe Ile Gln Arg Met Arg Glu Lys Ala Ala Ser Leu Pro Asn
                165                 170                 175

Val Asn Met Glu Gln Gly Thr Val Ile Ser Leu Leu Glu Glu Lys Gly
            180                 185                 190

Thr Ile Lys Gly Val Gln Tyr Lys Asn Lys Asp Gly Gln Ala Leu Thr
        195                 200                 205

Ala Tyr Ala Pro Leu Thr Ile Val Cys Asp Gly Cys Phe Ser Asn Leu
    210                 215                 220

Arg Arg Ser Leu Cys Asn Pro Lys Val Asp Asn Pro Ser Cys Phe Val
225                 230                 235                 240

Gly Leu Ile Leu Glu Asn Cys Glu Leu Pro Cys Ala Asn His Gly His
                245                 250                 255

Val Ile Leu Gly Asp Pro Ser Pro Ile Leu Phe Tyr Pro Ile Ser Ser
            260                 265                 270

Thr Glu Ile Arg Cys Leu Val Asp Val Pro Gly Thr Lys Val Pro Ser
        275                 280                 285

Ile Ser Asn Gly Asp Met Thr Lys Tyr Leu Lys Thr Thr Val Ala Pro
    290                 295                 300

Gln Val Pro Pro Glu Leu Tyr Asp Ala Phe Ile Ala Ala Val Asp Lys
305                 310                 315                 320
```

TABLE 3-continued

Sequences disclosed herein (see also Table 2).

```
Gly Asn Ile Arg Thr Met Pro Asn Arg Ser Met Pro Ala Asp Pro Arg
                325                 330                 335

Pro Thr Pro Gly Ala Val Leu Met Gly Asp Ala Phe Asn Met Arg His
            340                 345                 350

Pro Leu Thr Gly Gly Gly Met Thr Val Ala Leu Ser Asp Ile Val Val
        355                 360                 365

Leu Arg Asn Leu Leu Lys Pro Met Arg Asp Leu Asn Asp Ala Pro Thr
    370                 375                 380

Leu Cys Lys Tyr Leu Glu Ser Phe Tyr Thr Leu Arg Lys Pro Val Ala
385                 390                 395                 400

Ser Thr Ile Asn Thr Leu Ala Gly Ala Leu Tyr Lys Val Phe Ser Ala
                405                 410                 415

Ser Pro Asp Glu Ala Arg Lys Glu Met Arg Gln Ala Cys Phe Asp Tyr
            420                 425                 430

Leu Ser Leu Gly Gly Leu Phe Ser Glu Gly Pro Ile Ser Leu Leu Ser
        435                 440                 445

Gly Leu Asn Pro Arg Pro Leu Ser Leu Val Leu His Phe Phe Ala Val
    450                 455                 460

Ala Val Phe Gly Val Gly Arg Leu Leu Leu Pro Phe Pro Ser Pro Lys
465                 470                 475                 480

Arg Val Trp Ile Gly Ala Arg Leu Leu Ser Gly Ala Ser Gly Ile Ile
                485                 490                 495

Leu Pro Ile Ile Lys Ala Glu Gly Ile Arg Gln Met Phe Phe Pro Ala
            500                 505                 510

Thr Val Pro Ala Tyr Tyr Arg Ala Pro Pro Val Asn Ala Phe
        515                 520                 525
```

SEQ ID NO: 100
*Ricinus communis* Squalene monooxygenase protein sequence

```
Met Ala Asp Asn Tyr Leu Leu Gly Trp Ile Leu Cys Ser Ile Ile Gly
1               5                   10                  15

Leu Phe Gly Leu Tyr Tyr Met Val Tyr Leu Val Val Lys Arg Glu Glu
            20                  25                  30

Glu Asp Asn Asn Arg Lys Ala Leu Leu Gln Ala Arg Ser Asp Ser Ala
        35                  40                  45

Lys Thr Met Ser Ala Val Ser Gln Asn Gly Glu Cys Arg Ser Asp Asn
    50                  55                  60

Pro Ala Asp Ala Asp Ile Ile Ile Val Gly Ala Gly Val Ala Gly Ser
65                  70                  75                  80

Ala Leu Ala His Thr Leu Gly Lys Asp Gly Arg Arg Val His Val Ile
                85                  90                  95

Glu Arg Asp Leu Thr Glu Pro Asp Arg Ile Val Gly Glu Leu Leu Gln
            100                 105                 110

Pro Gly Gly Tyr Leu Lys Leu Ile Glu Leu Gly Leu Glu Asp Cys Val
        115                 120                 125

Glu Glu Ile Asp Ala Gln Arg Val Phe Gly Tyr Ala Leu Phe Met Asp
    130                 135                 140

Gly Lys His Thr Gln Leu Ser Tyr Pro Leu Glu Lys Phe His Ser Asp
145                 150                 155                 160

Val Ala Gly Arg Ser Phe His Asn Gly Arg Phe Ile Gln Arg Met Arg
                165                 170                 175

Glu Lys Ala Ser Ser Ile Pro Asn Val Arg Leu Glu Gln Gly Thr Val
            180                 185                 190
```

TABLE 3-continued

Sequences disclosed herein (see also Table 2).

```
Thr Ser Leu Ile Glu Glu Lys Gly Ile Ile Arg Gly Val Val Tyr Lys
        195                 200                 205

Thr Lys Thr Gly Glu Glu Leu Thr Ala Phe Ala Pro Leu Thr Ile Val
    210                 215                 220

Cys Asp Gly Cys Phe Ser Asn Leu Arg Arg Ser Leu Cys Asn Pro Lys
225                 230                 235                 240

Val Asp Val Pro Ser Cys Phe Val Gly Leu Val Leu Glu Asp Cys Lys
                245                 250                 255

Leu Pro Tyr Gln Tyr His Gly His Val Val Leu Ala Asp Pro Ser Pro
            260                 265                 270

Ile Leu Phe Tyr Gln Ile Ser Ser Thr Glu Val Arg Cys Leu Val Asp
        275                 280                 285

Val Pro Gly Gln Lys Val Pro Ser Ile Ser Asn Gly Glu Met Ala Lys
    290                 295                 300

Tyr Leu Lys Asn Val Val Ala Pro Gln Val Pro Pro Glu Ile Tyr Asp
305                 310                 315                 320

Ser Phe Val Ala Ala Val Asp Lys Gly Asn Ile Arg Thr Met Pro Asn
                325                 330                 335

Arg Ser Met Pro Ala Ser Pro Tyr Pro Thr Pro Gly Ala Leu Leu Met
            340                 345                 350

Gly Asp Ala Phe Asn Met Arg His Pro Leu Thr Gly Gly Gly Met Thr
        355                 360                 365

Val Ala Leu Ser Asp Ile Val Val Leu Arg Glu Leu Leu Lys Pro Leu
    370                 375                 380

Arg Asp Leu His Asp Ala Pro Thr Leu Cys Arg Tyr Leu Glu Ser Phe
385                 390                 395                 400

Tyr Thr Leu Arg Lys Pro Val Ala Ser Thr Ile Asn Thr Leu Ala Gly
                405                 410                 415

Ala Leu Tyr Lys Val Phe Cys Ala Ser Ser Asp Glu Ala Arg Asn Glu
            420                 425                 430

Met Arg Gln Ala Cys Phe Asp Tyr Leu Ser Leu Gly Gly Val Phe Ser
        435                 440                 445

Thr Gly Pro Ile Ser Leu Leu Ser Gly Leu Asn Pro Arg Pro Leu Ser
    450                 455                 460

Leu Val Val His Phe Phe Ala Val Ala Ile Tyr Gly Val Gly Arg Leu
465                 470                 475                 480

Leu Leu Pro Phe Pro Ser Pro Lys Arg Val Trp Val Gly Ala Arg Leu
                485                 490                 495

Ile Ser Gly Ala Ser Gly Ile Ile Phe Pro Ile Ile Lys Ala Glu Gly
            500                 505                 510

Val Arg Gln Met Phe Phe Pro Ala Thr Val Pro Ala Tyr Tyr Arg Ala
        515                 520                 525

Pro Pro Val Glu Cys Asn
    530
```

SEQ ID NO: 101
*Ricinus communis* Squalene monooxygenase protein sequence

```
Met Glu Tyr Lys Leu Ala Val Ala Gly Ile Ile Ala Ser Leu Trp Ala
1               5                   10                  15

Leu Phe Met Leu Cys Ser Leu Lys Arg Lys Lys Asn Ile Thr Arg Ala
            20                  25                  30

Ser Phe Asn Asn Tyr Thr Asp Glu Thr Leu Lys Ser Ser Ser Lys Glu
        35                  40                  45

Ile Cys Gln Pro Glu Ile Val Ala Ser Pro Asp Ile Ile Ile Val Gly
```

TABLE 3-continued

Sequences disclosed herein (see also Table 2).

```
    50                  55                  60

Ala Gly Val Ala Gly Ala Ala Leu Ala Tyr Ala Leu Gly Glu Asp Gly
65                  70                  75                  80

Arg Gln Val His Val Ile Glu Arg Asp Leu Ser Glu Pro Asp Arg Ile
                85                  90                  95

Val Gly Glu Leu Leu Gln Pro Gly Gly Tyr Leu Lys Leu Ile Glu Leu
            100                 105                 110

Gly Leu Glu Asp Cys Val Glu Lys Ile Asp Ala Gln Gln Val Phe Gly
        115                 120                 125

Tyr Ala Ile Phe Lys Asp Gly Lys Ser Thr Lys Leu Ser Tyr Pro Leu
    130                 135                 140

Asp Gly Phe Gln Thr Asn Val Ser Gly Arg Ser Phe His Asn Gly Arg
145                 150                 155                 160

Phe Ile Gln Arg Met Arg Glu Lys Ala Thr Ser Leu Pro Asn Leu Ile
                165                 170                 175

Leu Gln Gln Gly Thr Val Thr Ser Leu Val Glu Lys Lys Gly Thr Val
            180                 185                 190

Lys Gly Val Asn Tyr Arg Thr Arg Asn Gly Gln Glu Met Thr Ala Tyr
        195                 200                 205

Ala Pro Leu Thr Ile Val Cys Asp Gly Cys Phe Ser Asn Leu Arg Arg
    210                 215                 220

Ser Leu Cys Asn Pro Lys Val Glu Ile Pro Ser Cys Phe Val Ala Leu
225                 230                 235                 240

Val Leu Glu Asn Cys Asp Leu Pro Tyr Ala Asn His Gly His Val Ile
                245                 250                 255

Leu Ala Asp Pro Ser Pro Ile Leu Phe Tyr Pro Ile Ser Ser Thr Glu
            260                 265                 270

Val Arg Cys Leu Val Asp Ile Pro Gly Gln Lys Val Pro Ser Ile Ser
        275                 280                 285

Asn Gly Glu Leu Ala Gln Tyr Leu Lys Ser Thr Val Ala Lys Gln Ile
    290                 295                 300

Pro Ser Glu Leu His Asp Ala Phe Ile Ser Ala Ile Glu Lys Gly Asn
305                 310                 315                 320

Ile Arg Thr Met Pro Asn Arg Ser Met Pro Ala Ser Pro His Pro Thr
                325                 330                 335

Pro Gly Ala Leu Leu Val Gly Asp Ala Phe Asn Met Arg His Pro Leu
            340                 345                 350

Thr Gly Gly Gly Met Thr Val Ala Leu Ser Asp Ile Val Leu Leu Arg
        355                 360                 365

Asn Leu Leu Arg Pro Leu Glu Asn Leu Asn Asp Ala Ser Val Leu Cys
    370                 375                 380

Lys Tyr Leu Glu Ser Phe Tyr Ile Leu Arg Lys Pro Met Ala Ser Thr
385                 390                 395                 400

Ile Asn Thr Leu Ala Gly Ala Leu Tyr Lys Val Phe Ser Ala Ser Thr
                405                 410                 415

Asp Arg Ala Arg Ser Glu Met Arg Gln Ala Cys Phe Asp Tyr Leu Ser
            420                 425                 430

Leu Gly Gly Val Phe Ser Asn Gly Pro Ile Ala Leu Leu Ser Gly Leu
        435                 440                 445

Asn Pro Arg Pro Leu Asn Leu Val Leu His Phe Phe Ala Val Ala Val
    450                 455                 460

Tyr Gly Val Gly Arg Leu Ile Leu Pro Phe Pro Ser Pro Lys Ser Ile
```

TABLE 3-continued

Sequences disclosed herein (see also Table 2).

```
465                 470                 475                 480

Trp Asp Gly Val Lys Leu Ile Ser Gly Ala Ser Ser Val Ile Phe Pro
                485                 490                 495

Ile Met Lys Ala Glu Gly Ile Gly Gln Ile Phe Phe Pro Ile Thr Lys
            500                 505                 510

Pro Pro Asn His Lys Ser Gln Thr Trp
        515                 520
```

SEQ ID NO: 102
*Ricinus communis* Squalene monooxygenase protein sequence

```
Met Gly Val Ser Arg Glu Glu Asn Ala Arg Asp Glu Lys Cys His Tyr
1               5                   10                  15

Tyr Glu Asn Gly Ile Ser Leu Ser Glu Lys Ser Met Ser Thr Asp Ile
            20                  25                  30

Ile Ile Val Gly Ala Gly Val Ala Gly Ser Ala Leu Ala Tyr Thr Leu
        35                  40                  45

Gly Lys Asp Gly Arg Arg Val His Val Ile Glu Arg Asp Leu Ser Leu
    50                  55                  60

Gln Asp Arg Ile Val Gly Glu Leu Leu Gln Pro Gly Gly Tyr Leu Lys
65                  70                  75                  80

Leu Ile Glu Leu Gly Leu Glu Asp Cys Val Glu Glu Ile Asp Ala Gln
                85                  90                  95

Gln Val Phe Gly Tyr Ala Leu Tyr Lys Asn Gly Arg Ser Thr Lys Leu
            100                 105                 110

Ser Tyr Pro Leu Glu Ser Phe Asp Ser Asp Val Ser Gly Arg Ser Phe
        115                 120                 125

His Asn Gly Arg Phe Ile Gln Arg Met Arg Glu Lys Ala Ala Ser Leu
    130                 135                 140

Pro Asn Val Arg Leu Glu Glu Gly Thr Val Thr Ser Leu Leu Glu Val
145                 150                 155                 160

Lys Gly Thr Ile Lys Gly Val Gln Tyr Lys Thr Lys Asn Gly Glu Glu
                165                 170                 175

Leu Thr Ala Ser Ala Pro Leu Thr Ile Val Cys Asp Gly Cys Phe Ser
            180                 185                 190

Asn Leu Arg Arg Ser Leu Cys Asn Pro Lys Val Asp Ile Pro Ser Cys
        195                 200                 205

Phe Val Ala Leu Ile Leu Glu Asn Ser Gly Gln Lys Leu Pro Ser Ile
    210                 215                 220

Ser Asn Gly Asp Met Ala Asn Tyr Leu Lys Ser Val Val Ala Pro Gln
225                 230                 235                 240

Ile Pro Pro Val Leu Ser Glu Ala Phe Ile Ser Ala Ile Glu Lys Gly
                245                 250                 255

Lys Ile Arg Thr Met Pro Asn Arg Ser Met Pro Ala Ala Pro His Pro
            260                 265                 270

Thr Pro Gly Ala Leu Leu Leu Gly Asp Ala Phe Asn Met Arg His Pro
        275                 280                 285

Leu Thr Gly Gly Gly Met Thr Val Ala Leu Ser Asp Ile Val Val Leu
    290                 295                 300

Arg Asn Leu Leu Lys Pro Leu His Asp Leu Thr Asp Ala Ser Ala Leu
305                 310                 315                 320

Cys Glu Tyr Leu Lys Ser Phe Tyr Ser Leu Arg Lys Pro Val Ala Ser
                325                 330                 335

Thr Ile Asn Thr Leu Ala Gly Ala Leu Tyr Lys Val Phe Ser Ala Ser
            340                 345                 350
```

TABLE 3-continued

Sequences disclosed herein (see also Table 2).

```
His Asp Pro Ala Arg Asn Glu Met Arg Gln Ala Cys Phe Asp Tyr Leu
        355                 360                 365

Ser Leu Gly Gly Val Phe Ser Asn Gly Pro Ile Ala Leu Leu Ser Gly
    370                 375                 380

Leu Asn Pro Arg Pro Leu Ser Leu Val Ala His Phe Phe Ala Val Ala
385                 390                 395                 400

Ile Tyr Gly Val Gly Arg Leu Ile Phe Pro Leu Pro Ser Ala Lys Gly
                405                 410                 415

Met Trp Met Gly Ala Arg Met Ile Lys Val Ala Ser Gly Ile Ile Phe
            420                 425                 430

Pro Ile Ile Arg Ala Glu Gly Val Gln His Met Phe Phe Ser Lys Thr
        435                 440                 445

Leu Ser Ala Phe Ser Arg Ser Gln Thr Ser
    450                 455
```

SEQ ID NO: 103
*Ricinus communis* Squalene monooxygenase protein sequence

```
Met Glu Tyr Gln Tyr Phe Val Gly Gly Ile Ile Ala Ser Ala Leu Leu
1               5                   10                  15

Phe Val Leu Val Cys Arg Leu Ala Gly Lys Arg Gln Arg Arg Ala Leu
            20                  25                  30

Arg Asp Thr Val Asp Arg Asp Glu Ile Ser Gln Asn Ser Glu Asn Gly
        35                  40                  45

Ile Ser Gln Ser Glu Lys Asn Met Asn Thr Asp Ile Ile Ile Val Gly
    50                  55                  60

Ala Gly Val Ala Gly Ser Thr Leu Ala Tyr Thr Leu Gly Lys Asp Gly
65                  70                  75                  80

Arg Arg Val Arg Val Ile Glu Arg Asp Leu Ser Leu Gln Asp Arg Ile
                85                  90                  95

Val Gly Glu Leu Leu Gln Pro Gly Gly Tyr Leu Lys Leu Ile Glu Leu
            100                 105                 110

Gly Leu Glu Asp Cys Val Glu Glu Ile Asp Ala Leu Gln Val Phe Gly
        115                 120                 125

Tyr Ala Leu Tyr Lys Asn Gly Arg Ser Thr Lys Leu Ser Tyr Pro Leu
    130                 135                 140

Asp Ser Phe Asp Ser Asp Val Ser Gly Arg Ser Phe His Asn Gly Arg
145                 150                 155                 160

Phe Ile Gln Arg Met Arg Glu Lys Ala Ala Ser Leu Pro Asn Val Arg
                165                 170                 175

Met Glu Gly Gly Thr Val Thr Ser Leu Leu Glu Val Lys Gly Thr Ile
            180                 185                 190

Lys Gly Val Gln Tyr Lys Asn Lys Asn Gly Glu Glu Leu Ile Ala Cys
        195                 200                 205

Ala Pro Leu Thr Ile Val Cys Asp Gly Cys Phe Ser Asn Leu Arg Arg
    210                 215                 220

Ser Leu Cys Asn Ser Lys Val Asp Ile Pro Phe Cys Phe Val Ala Leu
225                 230                 235                 240

Ile Leu Glu Asn Cys Glu Leu Pro Tyr Pro Asn His Gly His Val Ile
                245                 250                 255

Leu Ala Asp Pro Ser Pro Ile Leu Phe Tyr Arg Ile Ser Ile Ser Glu
            260                 265                 270

Ile Arg Cys Leu Val Asp Ile Pro Ala Gly Gln Lys Leu Pro Ser Ile
        275                 280                 285
```

TABLE 3-continued

Sequences disclosed herein (see also Table 2).

```
Ser Asn Gly Glu Met Ala Asn Tyr Leu Lys Ser Val Val Ala Pro Gln
    290                 295                 300

Ile Pro Pro Glu Leu Ser Asn Ala Phe Leu Ser Ala Ile Glu Lys Gly
305                 310                 315                 320

Lys Ile Arg Thr Met Pro Lys Arg Ser Met Pro Ala Ala Pro His Pro
                325                 330                 335

Thr Pro Gly Ala Leu Leu Leu Gly Asp Ala Phe Asn Met Arg His Pro
            340                 345                 350

Leu Thr Gly Gly Val Met Thr Val Ala Leu Ser Asp Ile Val Val Leu
        355                 360                 365

Arg Ser Leu Leu Arg Pro Leu His Asp Leu Thr Asp Ala Ser Ala Leu
    370                 375                 380

Cys Glu Tyr Leu Lys Ser Phe Tyr Ser Leu Arg Lys Pro Met Val Ser
385                 390                 395                 400

Thr Ile Asn Thr Leu Ala Gly Ala Leu Tyr Arg Val Phe Ser Ala Ser
                405                 410                 415

Gln Asp Pro Ala Arg Asp Glu Met Arg Gln Ala Cys Phe Asp Tyr Leu
            420                 425                 430

Ser Leu Gly Gly Val Phe Ser Asn Gly Pro Ile Ala Leu Leu Ser Gly
        435                 440                 445

Leu Asn Pro Arg Pro Leu Ser Leu Ile Val His Phe Phe Ala Val Ala
    450                 455                 460

Val Tyr Gly Val Gly Arg Leu Ile Phe Pro Leu Pro Ser Ala Lys Arg
465                 470                 475                 480

Met Trp Met Gln Glu
                485
```

SEQ ID NO: 104
*Ricinus communis* Squalene monooxygenase protein sequence

```
Met Glu Tyr Gln Tyr Leu Met Gly Gly Gly Ile Met Thr Leu Leu Phe
1               5                   10                  15

Val Leu Ser Tyr Arg Leu Lys Arg Glu Thr Arg Ala Ser Val Glu Asn
            20                  25                  30

Ala Arg Asp Glu Val Leu Gln Asn Ser Glu Asn Gly Ile Ser Gln Ser
        35                  40                  45

Glu Lys Ala Met Asn Thr Asp Ile Lys Leu Leu Leu Glu Gln Ile Val
    50                  55                  60

Gln Lys Ile Ala Met Leu Asn Ser Ile Arg Leu Glu Glu Gly Thr Val
65                  70                  75                  80

Thr Ser Leu Leu Glu Val Lys Arg Asp Ile Lys Gly Val Gln Tyr Lys
                85                  90                  95

Thr Lys Asn Gly Glu Glu Leu Thr Ala Cys Ala Pro Leu Thr Ile Val
            100                 105                 110

Ser His Gly Cys Phe Ser Asn Leu Arg Leu His Val Thr Pro Ser Thr
        115                 120                 125

Ser Lys Phe Lys Ser Phe Ile Gly Leu Glu Val Asp Ile Pro Ser Ser
    130                 135                 140

Phe Ala Ala Leu Ile Leu Gly Asn Cys Glu Leu Pro Phe Pro Asn His
145                 150                 155                 160

Gly His Val Ile Leu Ala Asp Pro Ser Ser Ile Leu Phe Tyr Arg Ile
                165                 170                 175

Ser Ser Ser Glu Ile Cys Cys Leu Val Asp Val Pro Ala Gly Gln Lys
            180                 185                 190

Leu Pro Ser Ile Ser Asn Gly Glu Met Ala Asn Tyr Leu Lys Ser Val
```

TABLE 3-continued

Sequences disclosed herein (see also Table 2).

```
        195                 200                 205

Val Ala His Gln Ala Phe Lys Val Gly Leu Ala Tyr
    210                 215                 220
```

SEQ ID NO: 105

*Ricinus communis* Squalene monooxygenase protein sequence

```
Met Ser Pro Ile Ser Ile Gln Leu Pro Pro Arg Pro Gln Leu Tyr Arg
1               5                   10                  15

Ser Leu Ile Ser Ser Leu Ser Leu Ser Thr Tyr Lys Gln Pro Pro Ser
            20                  25                  30

Pro Pro Ser Phe Ser Leu Thr Ile Ala Asn Ser Pro Pro Gln Pro Gln
        35                  40                  45

Pro Gln Ala Thr Val Ser Ser Lys Thr Arg Thr Ile Thr Arg Leu Ser
    50                  55                  60

Asn Ser Ser Asn Arg Val Asn Leu Leu Gln Ala Glu Gln His Pro Gln
65                  70                  75                  80

Glu Pro Ser Ser Asp Leu Ser Tyr Ser Ser Ser Pro Pro His Cys Val
                85                  90                  95

Ser Gly Gly Tyr Asn Ile Lys Leu Met Glu Val Gly Thr Asp Asn Tyr
            100                 105                 110

Ala Val Ile Ile Ile Leu Gly Thr Phe Phe Ala Ser Leu Phe Ala Phe
        115                 120                 125

Val Phe Leu Ser Ile Leu Arg Tyr Asn Phe Lys Asn Lys Asn Lys Ala
    130                 135                 140

Lys Ile His Asp Glu Thr Thr Leu Lys Thr Gln Asn Asp Asn Val Arg
145                 150                 155                 160

Leu Pro Asp Asn Gly Ser Gly Asn Asp Val Ile Ile Val Gly Ala Gly
                165                 170                 175

Val Ala Gly Ala Ala Leu Ala Tyr Thr Leu Gly Lys Asp Gly Arg Arg
            180                 185                 190

Val His Val Ile Glu Arg Asp Leu Thr Glu Pro Asp Arg Ile Val Gly
        195                 200                 205

Glu Leu Leu Gln Pro Gly Gly Tyr Leu Lys Leu Ile Glu Leu Gly Leu
    210                 215                 220

Glu Asp Cys Val Gln Glu Ile Asp Ala Gln Arg Val Leu Gly Tyr Ala
225                 230                 235                 240

Leu Phe Lys Asp Gly Lys Asn Thr Arg Leu Ser Tyr Pro Leu Glu Lys
                245                 250                 255

Phe His Ala Asp Val Ala Gly Arg Ser Phe His Asn Gly Arg Phe Ile
            260                 265                 270

Gln Arg Met Arg Glu Lys Ala Ala Ser Leu Pro Asn Val Lys Leu Glu
        275                 280                 285

Gln Gly Thr Val Thr Ser Leu Leu Glu Glu Asn Gly Thr Ile Lys Gly
    290                 295                 300

Val Gln Tyr Lys Thr Lys Asp Gly Gln Glu Ile Arg Ala Tyr Ala Pro
305                 310                 315                 320

Leu Thr Ile Val Cys Asp Gly Cys Phe Ser Asn Leu Arg Arg Ser Leu
                325                 330                 335

Cys Asn Pro Lys Val Asp Val Pro Ser Cys Phe Val Gly Leu Val Leu
            340                 345                 350

Glu Asn Cys Gln Leu Pro Phe Ala Asn His Gly His Val Val Leu Ala
        355                 360                 365

Asp Pro Ser Pro Ile Leu Phe Tyr Pro Ile Ser Ser Thr Glu Val Arg
    370                 375                 380
```

TABLE 3-continued

Sequences disclosed herein (see also Table 2).

```
Cys Leu Val Asp Val Pro Gly Gln Lys Val Pro Ser Ile Ala Asn Gly
385                 390                 395                 400

Glu Met Ala Lys Tyr Leu Lys Asn Val Val Ala Pro Gln Ile Pro Pro
                405                 410                 415

Val Leu His Asp Ala Phe Ile Ser Ala Ile Asp Lys Gly Asn Ile Arg
            420                 425                 430

Thr Met Pro Asn Arg Ser Met Pro Ala Asp Pro His Pro Thr Pro Gly
        435                 440                 445

Ala Leu Leu Met Gly Asp Ala Phe Asn Met Arg His Pro Leu Thr Gly
    450                 455                 460

Gly Gly Met Thr Val Ala Leu Ser Asp Ile Val Val Leu Arg Asp Leu
465                 470                 475                 480

Leu Lys Pro Leu Arg Asp Leu Asn Asp Ala Thr Ser Leu Thr Lys Tyr
                485                 490                 495

Leu Glu Ser Phe Tyr Thr Leu Arg Lys Pro Val Ala Ser Thr Ile Asn
            500                 505                 510

Thr Leu Ala Gly Ala Leu Tyr Lys Val Phe Ser Ala Ser Pro Asp Gln
        515                 520                 525

Ala Arg Lys Glu Met Arg Gln Ala Cys Phe Asp Tyr Leu Ser Leu Gly
    530                 535                 540

Gly Ile Phe Ser Ser Gly Pro Val Ala Leu Leu Ser Gly Leu Asn Pro
545                 550                 555                 560

Arg Pro Leu Ser Leu Val Met His Phe Phe Ala Val Ala Ile Tyr Gly
                565                 570                 575

Val Gly Arg Leu Leu Leu Pro Phe Pro Ser Pro Lys Ser Val Trp Ile
            580                 585                 590

Gly Ala Arg Leu Ile Ser Ser Ala Ser Gly Ile Ile Phe Pro Ile Ile
        595                 600                 605

Lys Ala Glu Gly Val Arg Gln Met Phe Phe Pro Ala Thr Ile Pro Ala
    610                 615                 620

Ile Tyr Arg Pro Pro Pro Val Lys Asp Thr Ser Asp Asp Glu Gln Lys
625                 630                 635                 640

Ser Arg
```

Having described the invention in detail and by reference to specific embodiments thereof, it will be apparent that modifications and variations are possible without departing from the scope of the invention defined in the appended claims. More specifically, although some aspects of the present invention are identified herein as particularly advantageous, it is contemplated that the present invention is not necessarily limited to these particular aspects of the invention.

What is claimed is:

1. A recombinant host cell capable of producing a mogrol precursor, a mogroside precursor, and/or a mogroside compound in a cell culture, comprising:

(a) a gene encoding a polypeptide capable of synthesizing oxidosqualene or dioxidosqualene from squalene;

wherein the polypeptide capable of synthesizing oxidosqualene or dioxidosqualene from squalene comprises a polypeptide having at least 90% sequence identity to the amino acid sequence set forth in SEQ ID NO:54;

(b) a gene encoding a polypeptide capable of synthesizing cucurbitadienol from oxidosqualene, or 24,25-epoxy-cucurbitadienol from dioxidosqualene;

wherein the polypeptide capable of synthesizing cucurbitadienol from oxidosqualene or 24,25-epoxy-cucurbitadienol from dioxidosqualene comprises a polypeptide having at least 90% sequence identity to the amino acid sequence set forth in SEQ ID NO:43;

(c) a gene encoding a polypeptide capable of synthesizing 11-hydroxy-cucurbitadienol from cucurbitadienol, or 11-hydroxy-24,25-epoxy-cucurbitadienol from 24,25-epoxy-cucurbitadienol;

wherein the polypeptide capable of synthesizing 11-hydroxy-cucurbitadienol from cucurbitadienol or 11-hydroxy-24,25-epoxy-cucurbitadienol from 24,25-epoxy-cucurbitadienol comprises a polypeptide having at least 90% sequence identity to the amino acid sequence set forth in SEQ ID NO:44;

(d) a gene encoding a polypeptide capable of synthesizing mogrol from 11-hydroxy-24,25-epoxy-cucurbitadienol;

wherein the polypeptide capable of synthesizing mogrol from 11-hydroxy-24,25-epoxy-cucurbitadienol comprises a polypeptide having at least 90% sequence identity to the amino acid sequence set forth in SEQ ID NO:74;

(e) a gene encoding a polypeptide capable of reducing cytochrome P450 complex; wherein the polypeptide capable of reducing cytochrome P450 complex comprises a polypeptide having at least 90% sequence identity to the amino acid sequence set forth in SEQ ID NO:46; and (f) a gene encoding a polypeptide capable of synthesizing the mogroside precursor from 11-hydroxy-24,25-epoxy-cucurbitadienol;

wherein the polypeptide capable of synthesizing the mogroside precursor from 11-hydroxy-24,25-epoxy-cucurbitadienol comprises a polypeptide having at least 90% sequence identity to the amino acid sequence set forth in SEQ ID NO:38 or 40;

and further comprising:

(g) a gene encoding a polypeptide capable of glycosylating the mogroside precursor and/or the mogroside compound at its C-3 hydroxyl group;

wherein the polypeptide capable of glycosylating the mogroside precursor and/or the mogroside compound at its C-3 hydroxyl group comprises a polypeptide having at least 90% sequence identity to the amino acid sequence set forth in any one of SEQ ID NOs:22, 62, and 68;

(h) a gene encoding a polypeptide capable of glycosylating the mogroside precursor and/or the mogroside compound at its C-24 hydroxyl group;

wherein the polypeptide capable of glycosylating the mogroside precursor and/or the mogroside compound at its C-24 hydroxyl group comprises a polypeptide having at least 90% sequence identity to the amino acid sequence set forth in any one of SEQ ID NOs:21, 22, 23, 24 25, 48, and 68;

(i) a gene encoding a polypeptide capable of glycosylating the mogroside precursor and/or the mogroside compound at its C-3 hydroxyl group and C-24 hydroxyl group;

wherein the polypeptide capable of glycosylating the mogroside precursor and/or the mogroside compound at its C-3 hydroxyl group and C-24 hydroxyl group comprises a polypeptide having at least 90% sequence identity to the amino acid sequence set forth in SEQ ID NO:22 or 68;

(j) a gene encoding a polypeptide capable of glycosylating the mogroside precursor and/or the mogroside compound at its C-11 hydroxyl group;

wherein the polypeptide capable of glycosylating the mogroside precursor and/or the mogroside compound at its C-11 hydroxyl group comprises a polypeptide having at least 90% sequence identity to the amino acid sequence set forth in SEQ ID NO:24;

(k) a gene encoding a polypeptide capable of beta-1,6-glycosylation of the C2' of the 24-O-glucose of the mogroside precursor and/or the mogroside compound;

wherein the polypeptide capable of beta-1,6-glycosylation of the C2' of the 24-O-glucose of the mogroside precursor and/or the mogroside compound comprises a polypeptide having at least 90% sequence identity to the amino acid sequence set forth in any one of SEQ ID NOs:50, 53, 70, and 72; and (l) a gene encoding a polypeptide capable of beta-1,6-glycosylation of the C2' of the 24-O-glucose and/or beta-1,2-glycosylation of the C6' of the 3-O-glucose and/or the 24-O-glucose of the mogroside precursor and/or the mogroside compound;

wherein the polypeptide capable of beta-1,6-glycosylation of the C2' of the 24-O-glucose and/or beta-1,2-glycosylation of the C6' of the 3-O-glucose and/or the 24-O-glucose of the mogroside precursor and/or the mogroside compound comprises a polypeptide having at least 90% sequence identity to the amino acid sequence set forth in SEQ ID NO:70 or 72;

wherein at least one of the genes in items (a)-(l) is a recombinant gene.

2. The recombinant host cell of claim 1, wherein the recombinant host cell has been modified to reduce expression of a lanosterol synthase (ERG7) polypeptide.

3. The recombinant host of claim 2, wherein the ERG7 polypeptide comprises a polypeptide having an amino acid sequence set forth in SEQ ID NO:55.

4. The recombinant host of claim 1, wherein one or more of the genes further comprise a nucleotide sequence coding a fusion tag.

5. The recombinant host of claim 4, wherein the fusion tag is a protein or polypeptide.

6. The recombinant host of claim 5, wherein the fusion tag is green fluorescent protein (GFP), human influenza hemagglutinin (HA), glutathione S transferase (GST), a polyhistidine-tag (HIS tag), and a FLAG-tag, a chloroplast transit peptide, a mitochondrial transit peptide, an amyloplast peptide, a signal peptide, or a secretion tag.

7. The recombinant host of claim 1, wherein one or more of the genes are expressed as fusion proteins.

8. The recombinant host of claim 1, wherein the mogrol precursor is squalene, oxidosqualene, dioxidosqualene, cucurbitadienol, 24,25 epoxy cucurbitadienol, 11-hydroxy-cucurbitadienol, 11-hydroxy 24, 25 epoxy cucurbitadienol or 11-oxo-mogrol.

9. The recombinant host of claim 1, wherein the mogroside precursor is mogrol or a glycosylated, a di-glycosylated, a tri-glycosylated, or a tetra-glycosylated mogrol.

10. The recombinant host cell of claim 9, wherein the tetra-glycosylated mogroside precursor is mogroside IV or siamenoside I.

11. The recombinant host cell of claim 1, wherein the mogroside compound is a glycosylated, a di-glycosylated, a tri-glycosylated, a tetra-glycosylated, or a penta-glycosylated mogroside compound.

12. The recombinant host of claim 11, wherein:
- (a) the glycosylated mogroside compound is mogroside I A1 or mogroside I E1;
- (b) the di-glycosylated mogroside compound is mogroside IIA, mogroside II A1, mogroside II A2, mogroside II E or mogroside II E1;
- (c) the tri-glycosylated mogroside compound is mogroside III A1, mogroside III A2, mogroside III, or mogroside III E;
- (d) the tetra-glycosylated mogroside compound is mogroside IV, mogroside IV A, or siamenoside; and
- (e) the penta-glycosylated mogroside compound is mogroside V.

13. The recombinant host cell of claim 1, wherein the recombinant host cell comprises a plant cell, a mammalian cell, an insect cell, a fungal cell, an algal cell, or a bacterial cell.

14. A method of producing a mogrol precursor, a mogroside precursor, and/or a mogroside compound, comprising growing the recombinant host cell of claim 1 in a culture medium, under conditions in which the genes are expressed;
- wherein the mogrol precursor, the mogroside precursor, and/or the mogroside compound are produced by the recombinant host cell.

15. The method of claim 14, wherein the recombinant host cell is grown in a fermentor at a temperature for a period of time, wherein the temperature and period of time facilitate the production of the mogrol precursor, the mogroside precursor, and/or the mogroside compound.

16. The method of claim 14, further comprising isolating the mogrol precursor, the mogroside precursor, and/or the mogroside compound produced.

17. The method of claim 16, wherein the isolating step comprises:
- (a) providing the cell culture comprising the mogrol precursor, the mogroside precursor, and/or the mogroside compound;
- (b) separating a liquid phase of the cell culture from a solid phase of the cell culture to obtain a supernatant comprising the mogrol precursor, the mogroside precursor, and/or the mogroside compound;
- (c) providing one or more adsorbent resins, comprising providing the adsorbent resins in a packed column; and
- (d) contacting the supernatant of step (b) with the one or more adsorbent resins in order to obtain at least a portion of the mogrol precursor, the mogroside precursor, and/or the mogroside compound, thereby isolating the mogrol precursor, the mogroside precursor, and/or the mogroside compound;

or
- (a) providing the cell culture comprising the mogrol precursor, the mogroside precursor, and/or the mogroside compound;
- (b) separating a liquid phase of the cell culture from a solid phase of the cell culture to obtain a supernatant comprising the mogrol precursor, the mogroside precursor, and/or the mogroside compound;
- (c) providing one or more ion exchange or reversed-phase chromatography columns; and
- (d) contacting the supernatant of step (b) with the one or more ion exchange or reversed-phase chromatography columns in order to obtain at least a portion of the mogrol precursor, the mogroside precursor, and/or the mogroside compound, thereby isolating the mogrol precursor, the mogroside precursor, and/or the mogroside compound; or
- (a) providing the cell culture comprising the mogrol precursor, the mogroside precursor, and/or the mogroside compound;
- (b) separating a liquid phase of the cell culture from a solid phase of the cell culture to obtain a supernatant comprising the mogrol precursor, the mogroside precursor, and/or the mogroside compound;
- (c) crystallizing or extracting the mogrol precursor, the mogroside precursor, and/or the mogroside compound, thereby isolating the mogrol precursor, the mogroside precursor, and/or the mogroside compound.

18. The method of claim 14, further comprising recovering the mogroside precursor and/or the mogroside compound, providing a mogroside composition thereby.

19. The method of claim 18, wherein the recovered mogroside composition is enriched for the mogroside precursor and/or the mogroside compound relative to a mogroside composition from a *S. grosvenorii* plant; and
- wherein the recovered mogroside composition has a reduced level of *S. grosvenorii* plant-derived components relative to a plant-derived *S. grosvenorii* extract.

20. A method of producing mogroside compound, comprising whole cell bioconversion of a plant-derived or a synthetic mogrol precursor or a mogroside precursor in a cell culture medium of the recombinant host cell of claim 1 using:
- (a) the polypeptide capable of synthesizing oxidosqualene or dioxidosqualene from squalene;
  - wherein the polypeptide capable of synthesizing oxidosqualene or dioxidosqualene from squalene comprises a polypeptide having at least 90% sequence identity to the amino acid sequence set forth in SEQ ID NO: 54;
- (b) the polypeptide capable of synthesizing cucurbitadienol from oxidosqualene, or 24,25-epoxy-cucurbitadienol from dioxidosqualene;
  - wherein the polypeptide capable of synthesizing cucurbitadienol from oxidosqualene or 24,25-epoxy-cucurbitadienol from dioxidosqualene comprises a polypeptide having at least 90% sequence identity to the amino acid sequence set forth in SEQ ID NO: 43;
- (c) the polypeptide capable of synthesizing 11-hydroxy-cucurbitadienol from cucurbitadienol, or 11-hydroxy-24,25-epoxy-cucurbitadienol from 24,25-epoxy-cucurbitadienol;
  - wherein the polypeptide capable of synthesizing 11-hydroxy-cucurbitadienol from cucurbitadienol or 11-hydroxy-24,25-epoxy-cucurbitadienol from 24,25-epoxy-cucurbitadienol comprises a polypeptide having at least 90% sequence identity to the amino acid sequence set forth in SEQ ID NO: 44;
- (d) the polypeptide capable of synthesizing mogrol from 11-hydroxy-24,25-epoxy-cucurbitadienol;

wherein the polypeptide capable of synthesizing mogrol from 11-hydroxy-24,25-epoxy-cucurbitadienol comprises a polypeptide having at least 90% sequence identity to the amino acid sequence set forth in SEQ ID NO: 74;

(e) the polypeptide capable of reducing cytochrome P450 complex;

wherein the polypeptide capable of reducing cytochrome P450 complex comprises a polypeptide having at least 90% sequence identity to the amino acid sequence set forth in SEQ ID NO: 46; and (f) the polypeptide capable of synthesizing the mogroside precursor from 11-hydroxy-24,25-epoxy-cucurbitadienol;

wherein the polypeptide capable of synthesizing the mogroside precursor from 11-hydroxy-24,25-epoxy-cucurbitadienol comprises a polypeptide having at least 90% sequence identity to the amino acid sequence set forth in SEQ ID NO: 38 or 40;

and further comprising:

(g) the polypeptide capable of glycosylating the mogroside precursor and/or the mogroside compound at its C-3 hydroxyl group;

wherein the polypeptide capable of glycosylating the mogroside precursor and/or the mogroside compound at its C-3 hydroxyl group comprises a polypeptide having at least 90% sequence identity to the amino acid sequence set forth in any one of SEQ ID NOs:22, 62, and 68;

(h) the polypeptide capable of glycosylating the mogroside precursor and/or the mogroside compound at its C-24 hydroxyl group;

wherein the polypeptide capable of glycosylating the mogroside precursor and/or the mogroside compound at its C-24 hydroxyl group comprises a polypeptide having at least 90% sequence identity to the amino acid sequence set forth in any one of SEQ ID NOs:21, 22, 23, 24 25, 48, and 68;

(i) the polypeptide capable of glycosylating the mogroside precursor and/or the mogroside compound at its C-3 hydroxyl group and C-24 hydroxyl group;

wherein the polypeptide capable of glycosylating the mogroside precursor and/or the mogroside compound at its C-3 hydroxyl group and C-24 hydroxyl group comprises a polypeptide having at least 90% sequence identity to the amino acid sequence set forth in SEQ ID NO:22 or 68;

(j) the polypeptide capable of glycosylating the mogroside precursor and/or the mogroside compound at its C-11 hydroxyl group;

wherein the polypeptide capable of glycosylating the mogroside precursor and/or the mogroside compound at its C-11 hydroxyl group comprises a polypeptide having at least 90% sequence identity to the amino acid sequence set forth in SEQ ID NO:24;

(k) the polypeptide capable of beta-1,6-glycosylation of the C2' of the 24-O-glucose of the mogroside precursor and/or the mogroside compound;

wherein the polypeptide capable of beta-1,6-glycosylation of the C2' of the 24-O-glucose of the mogroside precursor and/or the mogroside compound comprises a polypeptide having at least 90% sequence identity to the amino acid sequence set forth in SEQ ID NO:50, 53, 70, or 72; and (l) the polypeptide capable of beta-1,6-glycosylation of the C2' of the 24-O-glucose and/or beta-1,2-glycosylation of the C6' of the 3-O-glucose and/or the 24-O-glucose of the mogroside precursor and/or the mogroside compound;

wherein the polypeptide capable of beta-1,6-glycosylation of the C2' of the 24-O-glucose and/or beta-1,2-glycosylation of the C6' of the 3-O-glucose and/or the 24-O-glucose of the mogroside precursor and/or the mogroside compound comprises a polypeptide having at least 90% sequence identity to the amino acid sequence set forth in SEQ ID NO:70 or 72;

wherein at least one of the polypeptides in items (a)-(l) is a recombinant polypeptide expressed in the recombinant host cell;

wherein the mogrol precursor is squalene, oxidosqualene, dioxidosqualene, cucurbitadienol, 24,25 epoxy cucurbitadienol, 11-hydroxy-cucurbitadienol, 11-hydroxy 24, 25 epoxy cucurbitadienol or 11-oxo-mogrol; and wherein the mogroside precursor is mogrol or a glycosylated, a di-glycosylated, a tri-glycosylated, or a tetra-glycosylated mogrol;

and producing the mogroside compound.

21. An in vitro method of producing a mogroside compound, comprising adding:

(a) a polypeptide capable of synthesizing oxidosqualene or dioxidosqualene from squalene;

wherein the polypeptide capable of synthesizing oxidosqualene or dioxidosqualene from squalene comprises a polypeptide having at least 90% sequence identity to the amino acid sequence set forth in SEQ ID NO:54;

(b) a polypeptide capable of synthesizing cucurbitadienol from oxidosqualene, or 24,25-epoxy-cucurbitadienol from dioxidosqualene;

wherein the polypeptide capable of synthesizing cucurbitadienol from oxidosqualene or 24,25-epoxy-cucurbitadienol from dioxidosqualene comprises a polypeptide having at least 90% sequence identity to the amino acid sequence set forth in SEQ ID NO:43;

(c) a polypeptide capable of synthesizing 11-hydroxy-cucurbitadienol from cucurbitadienol, or 11-hydroxy-24,25-epoxy-cucurbitadienol from 24,25-epoxy-cucurbitadienol;

wherein the polypeptide capable of synthesizing 11-hydroxy-cucurbitadienol from cucurbitadienol or 11-hydroxy-24,25-epoxy-cucurbitadienol from 24,25-epoxy-cucurbitadienol comprises a polypeptide having at least 90% sequence identity to the amino acid sequence set forth in SEQ ID NO:44;

(d) a polypeptide capable of synthesizing mogrol from 11-hydroxy-24,25-epoxy-cucurbitadienol;

wherein the polypeptide capable of synthesizing mogrol from 11-hydroxy-24,25-epoxy-cucurbitadienol comprises a polypeptide having at least 90% sequence identity to the amino acid sequence set forth in SEQ ID NO:74;

(e) a polypeptide capable of reducing cytochrome P450 complex;

wherein the polypeptide capable of reducing cytochrome P450 complex comprises a polypeptide having at least 90% sequence identity to the amino acid sequence set forth in SEQ ID NO:46; and (f) a polypeptide capable of synthesizing the mogroside precursor from 11-hydroxy-24,25-epoxy-cucurbitadienol;

wherein the polypeptide capable of synthesizing the mogroside precursor from 11-hydroxy-24,25-epoxy-cucurbitadienol comprises a polypeptide having at least 90% sequence identity to the amino acid sequence set forth in SEQ ID NO:38 or 40;

and further comprising:

(g) a polypeptide capable of glycosylating the mogroside precursor and/or the mogroside compound at its C-3 hydroxyl group;
  wherein the polypeptide capable of glycosylating the mogroside precursor and/or the mogroside compound at its C-3 hydroxyl group comprises a polypeptide having at least 90% sequence identity to the amino acid sequence set forth in any one of SEQ ID NOs:22, 62, and 68;

(h) a polypeptide capable of glycosylating the mogroside precursor and/or the mogroside compound at its C-24 hydroxyl group;
  wherein the polypeptide capable of glycosylating the mog roside precursor and/or the mogroside compound at its C-24 hydroxyl group comprises a polypeptide having at least 90% sequence identity to the amino acid sequence set forth in any one of SEQ ID NOs:21, 22, 23, 24 25, 48, and 68;

(i) a polypeptide capable of glycosylating the mogroside precursor and/or the mogroside compound at its C-3 hydroxyl group and C-24 hydroxyl group;
  wherein the polypeptide capable of glycosylating the mogroside precursor and/or the mogroside compound at its C-3 hydroxyl group and C-24 hydroxyl group comprises a polypeptide having at least 90% sequence identity to the amino acid sequence set forth in SEQ ID NO:22 or 68;

(j) a polypeptide capable of glycosylating the mogroside precursor and/or the mogroside compound at its C-11 hydroxyl group;
  wherein the polypeptide capable of glycosylating the mogroside precursor and/or the mogroside compound at its C-11 hydroxyl group comprises a polypeptide having at least 90% sequence identity to the amino acid sequence set forth in SEQ ID NO:24;

(k) a polypeptide capable of beta-1,6-glycosylation of the C2' of the 24-O-glucose of the mogroside precursor and/or the mogroside compound;
  wherein the polypeptide capable of beta-1,6-glycosylation of the C2' of the 24-O-glucose of the mogroside precursor and/or the mogroside compound comprises a polypeptide having at least 90% sequence identity to the amino acid sequence set forth in any one of SEQ ID NOs:50, 53, 70, and 72; and (l) a polypeptide capable of beta-1,6-glycosylation of the C2' of the 24-O-glucose and/or beta-1,2-glycosylation of the C6' of the 3-O-glucose and/or the 24-O-glucose of the mogroside precursor and/or the mogroside compound;
  wherein the polypeptide capable of beta-1,6-glycosylation of the C2' of the 24-O-glucose and/or beta-1, 2-glycosylation of the C6' of the 3-O-glucose and/or the 24-O-glucose of the mogroside precursor and/or the mogroside compound comprises a polypeptide having at least 90% sequence identity to the amino acid sequence set forth in SEQ ID NO:70 or 72;

and a plant-derived ora synthetic mogrol precursor or a mogroside precursor to a reaction mixture;

wherein the mogrol precursor is squalene, oxidosqualene, dioxidosqualene, cucurbitadienol, 24,25 epoxy cucurbitadienol, 11-hydroxy-cucurbitadienol, 11-hydroxy 24,25 epoxy cucurbitadienol or 11-oxo-mogrol;

wherein the mogroside precursor is mogrol or a glycosylated, a di-glycosylated, a tri-glycosylated, or a tetra-glycosylated mogrol; and wherein at least one of the polypeptides in items (a)-(l) is a recombinant polypeptide;

and producing the mogroside compound.

22. A method for transferring a sugar moiety to a C-3 hydroxyl group, a C-24 hydroxyl group, both the C-3 hydroxyl group and the C-24 hydroxyl group, a C2' and/or a C6' position of a 3-O-glucose and/or the 24-O-glucose of a mogroside precursor and/or a mogroside compound, comprising contacting the mogroside precursor and/or the mogroside compound with a recombinant polypeptide capable of glycosylating the mogroside precursor and/or the mogroside compound at the C-3 hydroxyl group, wherein the polypeptide capable of glycosylating the mogroside precursor and/or the mogroside compound at its C-3 hydroxyl group comprises a polypeptide having at least 90% sequence identity to the amino acid sequence set forth in any one of SEQ ID NOs:22, 62, and 68; the C-11 hydroxyl group, wherein the polypeptide capable of glycosylating the mogroside precursor and/or the mogroside compound at its C-11 hydroxyl group comprises a polypeptide having at least 90% sequence identity to the amino acid sequence set forth in SEQ ID NO:24; the C-24 hydroxyl group, wherein the polypeptide capable of glycosylating the mogroside precursor and/or the mogroside compound at its C-24 hydroxyl group comprises a polypeptide having at least 90% sequence identity to the amino acid sequence set forth in any one of SEQ ID NOs:21, 22, 23, 24 25, 48, and 68; both the C-3 hydroxyl group and the C-24 hydroxyl group, wherein the polypeptide capable of glycosylating the mogroside precursor and/or the mogroside compound at its C-3 hydroxyl group and C-24 hydroxyl group comprises a polypeptide having at least 90% sequence identity to the amino acid sequence set forth in SEQ ID NO:22 or 68; beta-1,6-glycosylation of the C2' of the 24-O-glucose, wherein the polypeptide capable of beta-1,6-glycosylation of the C2' of the 24-O-glucose of the mogroside precursor and/or the mogroside compound comprises a polypeptide having at least 90% sequence identity to the amino acid sequence set forth in any one of SEQ ID NOs:50, 53, 70, and 72; and/or beta-1,6-glycosylation of the C2' of the 24-O-glucose and/or beta-1,2-glycosylation of the C6' of the 3-O-glucose and/or the 24-O-glucose, wherein the polypeptide capable of beta-1,6-glycosylation of the C2' of the 24-O-glucose and/or beta-1,2-glycosylation of the C6' of the 3-O-glucose and/or the 24-O-glucose of the mogroside precursor and/or the mogroside compound comprises a polypeptide having at least 90% sequence identity to the amino acid sequence set forth in SEQ ID NO:70 or 72; and a UDP-sugar under suitable reaction conditions for the transfer of the sugar moiety to the mogroside precursor and/or the mogroside compound, wherein the mogroside precursor is mogrol or a glycosylated, a di-glycosylated, a tri-glycosylated or a tetra-glycosylated mogrol; and wherein a glycosylated, a di-glycosylated, a tri-glycosylated, a tetra-glycosylated, or a penta-glycosylated mogroside compound, an isomer thereof, and/or a mogroside composition thereof is produced upon transfer of the sugar moiety.

23. The method of claim 22, wherein:

(a) the sugar moiety is glucose, and mogroside I A1 is produced upon transfer of the glucose moiety to mogrol;

(b) the sugar moiety is glucose, and mogroside I E1 is produced upon transfer of the glucose moiety to mogrol;

(c) the sugar moiety is glucose, and mogroside II E1 is produced upon transfer of the glucose moiety to mogrol;

(d) the mogroside precursor is mogroside I A1, wherein the sugar moiety is glucose, and mogroside II A is produced upon transfer of the glucose moiety;

the mogroside precursor is mogroside I A1, wherein the sugar moiety is glucose, and mogroside II A2 is produced upon transfer of the glucose moiety;

(e) the mogroside precursor is mogroside I A1, wherein the sugar moiety is glucose, and mogroside II E is produced upon transfer of the glucose moiety;

(f) the mogroside precursor is mogroside I A1, wherein the sugar moiety is glucose, and mogroside III A1 is produced upon transfer of the glucose moiety;

(g) the mogroside precursor is mogroside I E1, wherein the sugar moiety is glucose, and mogroside II E is produced upon transfer of the glucose moiety;

the mogroside precursor is mogroside I E1, wherein the sugar moiety is glucose, and mogroside II A1 is produced upon transfer of the glucose moiety;

(h) the mogroside precursor is mogroside II A, wherein the sugar moiety is glucose, and mogroside III A1 is produced upon transfer of the glucose moiety;

(i) the mogroside precursor is mogroside II E, wherein the sugar moiety is glucose, and mogroside III A1 is produced upon transfer of the glucose moiety;

(j) the mogroside precursor is mogroside II E, wherein the sugar moiety is glucose, and mogroside III A2 is produced upon transfer of the glucose moiety;

(k) the mogroside precursor is mogroside II E, wherein the sugar moiety is glucose, and mogroside III E is produced upon transfer of the glucose moiety;

(l) the mogroside precursor is mogroside II E, wherein the sugar moiety is glucose, and mogroside III is produced upon transfer of the glucose moiety;

(m) the mogroside precursor is mogroside II E, wherein the sugar moiety is glucose, and mogroside IV A is produced upon transfer of the glucose moiety;

(n) the mogroside precursor is mogroside II E, wherein the sugar moiety is glucose, and mogroside IV A is produced upon transfer of the glucose moiety;

(o) the mogroside precursor is mogroside II E, wherein the sugar moiety is glucose, and mogroside IV is produced upon transfer of the glucose moiety;

(p) the mogroside precursor is mogroside II E, wherein the sugar moiety is glucose, and mogroside V is produced upon transfer of the glucose moiety;

(q) the mogroside precursor is mogroside III E, wherein the sugar moiety is glucose, and mogroside II A2 is produced upon transfer of the glucose moiety;

(r) the mogroside precursor is mogroside III A2, wherein the sugar moiety is glucose, and mogroside IV is produced upon transfer of the glucose moiety;

(s) the mogroside precursor is mogroside III, wherein the sugar moiety is glucose, and mogroside IVA is produced upon transfer of the glucose moiety;

(t) the mogroside precursor is mogroside III A1, wherein the sugar moiety is glucose, and siamenoside 1 is produced upon transfer of the glucose moiety;

(u) the mogroside precursor is mogroside IV, wherein the sugar moiety is glucose, and siamenoside 1 is produced upon transfer of the glucose moiety; or (v) the mogroside precursor is siamenoside 1, wherein the sugar moiety is glucose, and mogroside V is produced upon transfer of the glucose moiety.

24. The method of claim 22, wherein mogrol or the glycosylated, the di-glycosylated, the tri-glycosylated or the tetra-glycosylated mogrol, the glycosylated, the di-glycosylated, the tri-glycosylated, the tetra-glycosylated or the penta-glycosylated mogroside compound, the isomer thereof, and/or the mogroside composition thereof is produced in a cell culture broth, the method comprising growing a recombinant host cell comprising (i) a gene encoding a polypeptide capable of glycosylating the mogroside precursor and/or the mogroside compound at its C-3 hydroxyl group; wherein the polypeptide capable of glycosylating the mogroside precursor and/or the mogroside compound at its C-3 hydroxyl group comprises a polypeptide having at least 90% sequence identity to the amino acid sequence set forth in any one of SEQ ID NOs:22, 62, and 68; (ii) a gene encoding a polypeptide capable of glycosylating the mogroside precursor and/or the mogroside compound at its C-24 hydroxyl group; wherein the polypeptide capable of glycosylating the mogroside precursor and/or the mogroside compound at its C-24 hydroxyl group comprises a polypeptide having at least 90% sequence identity to the amino acid sequence set forth in any one of SEQ ID NOs:21, 22, 23, 24 25, 48, and 68; (iii) a gene encoding a polypeptide capable of glycosylating the mogroside precursor and/or the mogroside compound at its C-3 hydroxyl group and C-24 hydroxyl group; wherein the polypeptide capable of glycosylating the mogroside precursor and/or the mogroside compound at its C-3 hydroxyl group and C-24 hydroxyl group comprises a polypeptide having at least 90% sequence identity to the amino acid sequence set forth in SEQ ID NO:22 or 68; (iv) a gene encoding a polypeptide capable of glycosylating the mogroside precursor and/or the mogroside compound at its C-11 hydroxyl group; wherein the polypeptide capable of glycosylating the mogroside precursor and/or the mogroside compound at its C-11 hydroxyl group comprises a polypeptide having at least 90% sequence identity to the amino acid sequence set forth in SEQ ID NO:24; (v) a gene encoding a polypeptide capable of beta-1,6-glycosylation of the C2' of the 24-O-glucose of the mogroside precursor and/or the mogroside compound; wherein the polypeptide capable of beta-1,6-glycosylation of the C2' of the 24-O-glucose of the mogroside precursor and/or the mogroside compound comprises a polypeptide having at least 90% sequence identity to the amino acid sequence set forth in any one of SEQ ID NOs:50, 53, 70, and 72; and/or (vi) a gene encoding a polypeptide capable of beta-1,6-glycosylation of the C2' of the 24-O-glucose and/or beta-1,2-glycosylation of the C6' of the 3-O-glucose and/or the 24-O-glucose of the mogroside precursor and/or the mogroside compound; wherein the polypeptide capable of beta-1,6-glycosylation of the C2' of the 24-O-glucose and/or beta-1,2-glycosylation of the C6' of the 3-O-glucose and/or the 24-O-glucose of the mogroside precursor and/or the mogroside compound comprises a polypeptide having at least 90% sequence identity to the amino acid sequence set forth in SEQ ID NO:70 or 72;

wherein at least one of the genes in items (i)-(vi) is a recombinant gene, under conditions in which one or more of the genes are expressed;

wherein contacting the glycosylated, the di-glycosylated, the tri-glycosylated or the tetra-glycosylated mogrol with the recombinant polypeptide comprises contacting the glycosylated, the di-glycosylated, the tri-glycosylated or the tetra-glycosylated mogrol with at least one of the polypeptides produced by the recombinant host cell.

25. A cell culture, comprising the recombinant host cell of claim 1, the cell culture further comprising:

(a) the mogrol precursor, the mogroside precursor, and/or the mogroside compound produced by the recombinant host cell;

(b) glucose, fructose, sucrose, xylose, rhamnose, uridine diphosphate (UDP)-glucose, UDP-rhamnose, UDP-xylose, and/or N-acetyl-glucosamine; and (c) supplemental nutrients comprising trace metals, vitamins, salts, YNB, and/or amino acids;

wherein the mogroside precursor and/or the mogroside compound is present at a concentration of at least 1 mg/liter of the cell culture;

wherein the cell culture is enriched for the mogroside precursor and/or the mogroside compound relative to a mogroside composition from a *S. grosvenorii* plant; and wherein the cell culture has a reduced level of *S. grosvenorii* plant-derived components relative to a plant-derived *S. grosvenorii extract*.

26. A cell lysate from the recombinant host cell of claim 1 grown in the cell culture, wherein the cell lysate comprises:

(a) the mogrol precursor, the mogroside precursor, and/or the mogroside compound produced by the recombinant host cell;

(b) glucose, fructose, sucrose, xylose, rhamnose, uridine diphosphate (UDP)-glucose, UDP-rhamnose, UDP-xylose, and/or N-acetyl-glucosamine; and (c) supplemental nutrients comprising trace metals, vitamins, salts, YNB, and/or amino acids;

wherein the mogroside precursor and/or the mogroside compound is present at a concentration of at least 1 mg/liter of the cell lysate.

27. The recombinant host cell of claim 1, wherein the recombinant host cell is a *Yarrowia lipolytica* cell.

28. The method of claim 20, wherein the mogroside compound is a glycosylated, a di-glycosylated, a tri-glycosylated, a tetra-glycosylated, or a penta-glycosylated mogroside compound, wherein:

(a) the glycosylated mogroside compound is mogroside I A1 or mogroside I E1;

(b) the di-glycosylated mogroside compound is mogroside IIA, mogroside II A1, mogroside II A2, mogroside II E1, or mogroside II E;

(c) the tri-glycosylated mogroside compound is mogroside III A1, mogroside III A2, mogroside III, or mogroside III E;

(d) the tetra-glycosylated mogroside compound is mogroside IV, mogroside IV A, or siamenoside; and (e) the penta-glycosylated mogroside compound is mogroside V.

29. The method of claim 21, wherein the mogroside compound is a glycosylated, a di-glycosylated, a tri-glycosylated, a tetra-glycosylated, or a penta-glycosylated mogroside compound, wherein:

(a) the glycosylated mogroside compound is mogroside I A1 or mogroside I E1;

(b) the di-glycosylated mogroside compound is mogroside IIA, mogroside II A1, mogroside II A2, mogroside II E1, or mogroside II E;

(c) the tri-glycosylated mogroside compound is mogroside III A1, mogroside III A2, mogroside III, or mogroside III E;

(d) the tetra-glycosylated mogroside compound is mogroside IV, mogroside IV A, or siamenoside; and (e) the penta-glycosylated mogroside compound is mogroside V.

* * * * *